(12) United States Patent
Arrington et al.

(10) Patent No.: US 8,765,784 B2
(45) Date of Patent: Jul. 1, 2014

(54) POSITIVE ALLOSTERIC MODULATORS OF MGLUR2

(75) Inventors: Kenneth L. Arrington, Revere, MA (US); Vadim Dudkin, Lansdale, PA (US); Mark E. Layton, Harleysville, PA (US); Joseph E. Pero, Harleysville, PA (US); Alexander J. Reif, Holland, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/701,039

(22) PCT Filed: Jun. 6, 2011

(86) PCT No.: PCT/US2011/039205
§ 371 (c)(1),
(2), (4) Date: Jan. 17, 2013

(87) PCT Pub. No.: WO2011/156245
PCT Pub. Date: Dec. 15, 2011

(65) Prior Publication Data
US 2013/0210768 A1     Aug. 15, 2013

Related U.S. Application Data

(60) Provisional application No. 61/352,918, filed on Jun. 9, 2010.

(51) Int. Cl.
*C07D 471/04* (2006.01)
*A61K 31/415* (2006.01)

(52) U.S. Cl.
USPC .......................................... 514/303; 546/118

(58) Field of Classification Search
USPC .......................................... 546/118; 514/303
See application file for complete search history.

(56) References Cited

U.S. PATENT DOCUMENTS

2007/0213323 A1    9/2007   Imogai et al.

OTHER PUBLICATIONS

Smolyar et al. (Russian Journal of Organic Chemistry (2009), 45(5), 796-797).*
Jullian, et al., "Agonjist Selectivity of mGluR1 and mGlur2 Metabotropic Receptors: A Different Environment but Similar Recognition of an Extended Glutamate Conformation," J. Med. Chem., vol. 42, pp. 1546-1555, 1999.
PCTUS2011093205_SrchRpt.pdf, Nov. 2011.

* cited by examiner

*Primary Examiner* — Bruck Kifle
(74) *Attorney, Agent, or Firm* — John C. Todaro; Keith D. MacMillan

(57) ABSTRACT

The present invention is directed to 5-substituted 1,3-dihydro-2H-imidazo[4,5-b]pyridine-2-one derivatives which are positive allosteric modulators of the mGluR2 receptor, useful in the treatment or prevention of neurological and psychiatric disorders associated with glutamate dysfunction and diseases in which the mGluR2 receptor is involved. The invention is also directed to pharmaceutical compositions comprising these compounds and the use of these compounds and compositions in the prevention or treatment of such diseases in which metabotropic glutamate receptors are involved, such as schizophrenia.

19 Claims, No Drawings

POSITIVE ALLOSTERIC MODULATORS OF MGLUR2

BACKGROUND OF THE INVENTION

The excitatory amino acid L-glutamate (sometimes referred to herein simply as glutamate) through its many receptors mediates most of the excitatory neurotransmission within the mammalian central nervous system (CNS). The excitatory amino acids, including glutamate, are of great physiological importance, playing a role in a variety of physiological processes, such as long-term potentiation (learning and memory), the development of synaptic plasticity, motor control, respiration, cardiovascular regulation, and sensory perception.

Glutamate acts via at least two distinct classes of receptors. One class is composed of the ionotropic glutamate (iGlu) receptors that act as ligand-gated ionic channels. Via activation of the iGlu receptors, glutamate is thought to regulate fast neuronal transmission within the synapse of two connecting neurons in the CNS. The second general type of receptor is the G-protein or second messenger-linked "metabotropic" glutamate (mGluR) receptor. Both types of receptors appear not only to mediate normal synaptic transmission along excitatory pathways, but also participate in the modification of synaptic connections during development and throughout life. Schoepp, Bockaert, and Sladeczek, Trends in Pharmacol. Sci., 11, 508 (1990); McDonald and Johnson, Brain Research Reviews, 15, 41 (1990).

The present invention relates to potentiators of mGlu receptors, in particular mGluR2 receptors. The mGluR receptors belong to the Type III G-protein coupled receptor (GPCR) superfamily. This superfamily of GPCR's including the calcium-sensing receptors, GABAB receptors and pheromone receptors, which are unique in that they are activated by binding of effectors to the amino-terminus portion of the receptor protein. The mGlu receptors are thought to mediate glutamate's demonstrated ability to modulate intracellular signal transduction pathways. Ozawa, Kamiya and Tsuzuski, Prog. Neurobio., 54, 581 (1998). They have been demonstrated to be localized both pre- and post-synaptically where they can regulate neurotransmitter release, either glutamate or other neurotransmitters, or modify the post-synaptic response of neurotransmitters, respectively.

At present, there are eight distinct mGlu receptors that have been positively identified, cloned, and their sequences reported. These are further subdivided based on their amino acid sequence homology, their ability to effect certain signal transduction mechanisms, and their known pharmacological properties. Ozawa, Kamiya and Tsuzuski, Prog. Neurobio., 54, 581 (1998). For instance, the Group I mGluR receptors, which include the mGlu1R and mGlu5R, are known to activate phospholipase C (PLC) via Gαq-proteins thereby resulting in the increased hydrolysis of phosphoinositides and intracellular calcium mobilization. There are several compounds that are reported to activate the Group I mGlu receptors including DHPG, (R/S)-3,5-dihydroxyphenylglycine. Schoepp, Goldworthy, Johnson, Salhoff and Baker, J. Neurochem., 63, 769 (1994); Ito, et al., keurorep., 3, 1013 (1992). The Group II mGlu receptors consist of the two distinct receptors, mGluR2 and mGluR3 receptors. Both have been found to be negatively coupled to adenylate cyclase via activation of Gαi-protein. These receptors can be activated by a selective compound such as 1S,2S,SR,6S-2 aminobicyclo [3.1.0]hexane-2,6-dicarboxylate. Monn, et al., J. Med. Chem., 40, 528 (1997); Schoepp, et al., Neuropharmacol., 36, 1 (1997). This activation leads to inhibition of glutamate release in the synapse (Cartmell et al, J Neurochem 75, 889 (2000)). Similarly, the Group III mGlu receptors, including mGluR4, mGluR6, mGluR7 and mGluR8, are negatively coupled to adenylate cyclase via Gαi and are potently activated by L-AP4 (L-(+)-2-amino-4-phosphonobutyric acid). Schoepp, Neurochem. Int., 24, 439 (1994).

Nonselective mGluR2/mGluR3 receptor agonists (Monn, et al., J. Med. Chem., 43, 4893, (2000)) have shown efficacy in numerous animal models of anxiety and psychosis as well as human clinical trials in schizophrenia patients; Patil et al, Nature Medicine, 13, 1102 (2007). Recent reports indicate that mGluR2 but not the mGluR3 receptor mediates the actions of the dual mGluR2/mGluR3 agonist LY379268 in mouse models predictive of antipsychotic activity. Woolley et al, Psychopharmacology, 196, 431 (2008). Additionally, recent animal studies demonstrate that selective potentiation of the mGluR2 receptor has similar effects to such non-selective agonists (Galici et al, Journal of Pharmacology and Experimental Therapeutics, 315, 1181 (2005)) suggesting an alternative strategy concerning the discovery of selective, positive allosteric modulators (PAMs or allosteric potentiators) of mGluR2 (Johnson et al, J. Med. Chem. 46, 3189, (2003); Pinkerton et al., J. Med. Chem., 47, 4595 (2004). These potentiators act by enabling the receptor to produce an enhanced response to endogenous glutamate. Such allosteric potentiators do not bind at the glutamate binding site also known as the "orthosteric site", and may benefit by binding to a site other than the highly conserved orthosteric site. A potential advantage to this approach includes the opportunity to have a distinct pharmacological profile by enhancing the activity of the endogenous ligand upon its binding to the orthosteric site. The pharmacological distinctions include the potential for pharmacological specificity between related receptor types that share the same endogenous ligand. In addition, positive allosteric modulators of mGluR2 have been shown to potentiate the response of mGluR2 agonists such as LY379268 (Johnson et. Al. Biochemical Soc. Trans. 32, 881 (2004) and this represents an alternative strategy for treatment using mGluR2 selective PAMs.

It has become increasingly clear that there is a link between modulation of excitatory amino acid receptors, including the glutamatergic system, through changes in glutamate release or alteration in postsynaptic receptor activation, and a variety of neurological and psychiatric disorders. e.g. Monaghan, Bridges and Cotman, Ann. Rev. Pharmacol. Toxicol., 29, 365-402 (1989); Schoepp and Sacann, Neurobio. Aging, 15, 261-263 (1994); Meldrum and Garthwaite, Tr. Pharmacol. Sci., 11, 379-387 (1990). The medical consequences of such glutamate dysfunction make the abatement of these neurological processes an important therapeutic goal.

SUMMARY OF THE INVENTION

The present invention is directed to 5-substituted 1,3-dihydro-2H-imidazo[4,5-b]pyridine-2-one derivatives which are positive allosteric modulators of the mGluR2 receptor, useful in the treatment or prevention of neurological and psychiatric disorders associated with glutamate dysfunction and diseases in which the mGluR2 receptor is involved. The invention is also directed to pharmaceutical compositions comprising these compounds and the use of these compounds and compositions in the prevention or treatment of such diseases in which metabotropic glutamate receptors are involved, such as schizophrenia.

DETAILED DESCRIPTION OF THE INVENTION

The invention encompasses a genus of compounds of Formula I

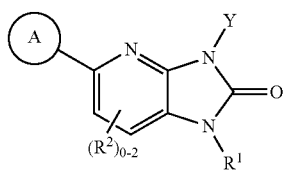

wherein: Y is H, $C_{1-6}$alkyl or $C_{2-6}$alkenyl, said $C_{1-6}$alkyl and $C_{2-6}$alkenyl optionally substituted with 1 to 3 groups selected from: halo and $C_{1-4}$alkoxy; $R^1$ is selected from the group consisting of: (1) $C_{2-8}$alkyl, (2) $C_{2-8}$alkenyl, (3) $C_{2-8}$alkynyl, (4) $C_{3-6}$cycloalkyl-$(CH_2)_p$—, wherein p is 1, 2, 3 or 4, (5) benzyl, (6) biphenyl, and (7) 1-phenyl-1H-pyrazol-4-yl, wherein groups (1) to (7) above are optionally substituted with 1 to 3 $R^2$ groups; each $R^2$ is independently selected from the group consisting of: halo, OH, $C_{1-4}$alkyl, $C_{1-4}$alkoxy, $CF_3$, —$OCF_3$ and —CN; ring A is selected from aryl, heteroaryl and heterocycle, wherein said heterocycle is partially aromatic and the point of attachment is to the aromatic portion, and wherein said aryl, heteroaryl and heterocycle are optionally substituted with one or more $R^3$ groups up to the maximum number of substitutable positions; each $R^3$ is independently selected from the group consisting of: halo, —CN, —$NO_2$, X, —$C(R^4)_2$—N(R)—X, —$C(R^4)_2$—N(R)C(O)—X, —$C(R^4)_2$—N(R)S(O)$_k$—X, —$C(R^4)_2$—N(R)C(O)—O—X, —C(O)—X, —C(O)—O—X, —C(O)—N(R)—X, —S(O)$_k$—X, —S(O)$_k$N(R)—X, —N(R)—X, —O—X, —N(R)C(O)—X, —N(R)S(O)$_k$—X, —N(R)C(O)—O—X, —N(R)C(O)N(R)—X and —N(R)SO$_2$N(R)—X; each X is independently selected from the group consisting of: H, $C_{1-8}$alkyl, $C_{2-6}$alkenyl, $C_{2-6}$alkynyl, $C_{3-6}$cycloalkyl, aryl, heteroaryl, heterocycle, $C_{3-6}$cycloalkyl-$C(R^4)_2$—, aryl-$C(R^4)_2$—, heteroaryl-$C(R^4)_2$— and heterocycle-$C(R^4)_2$—, wherein each member of the group excluding hydrogen is optionally substituted from one up to the maximum number of substitutable positions with one or more substituents independently selected from the group consisting of: CN, halo, $R^5$, —O—$R^5$, —N(R)—$R^5$, —N(R)C(O)—$R^5$, —N(R)S(O)$_2$—$R^5$, —N(R)—C(O)—O—$R^5$, —C(O)—N(R)—$R^5$, —C(O)—O—$R^5$, —C(O)—$R^5$, —C(O)—$C(R^4)_2$—$R^5$, —C(O)—$C(R^4)_2$—S(O)$_2$—$R^5$, —$C(R^4)_2$—N(R)—$R^5$, —SO$_2$—N(R)—$R^5$, —Si$(CH_3)_2(R^5)$, —$C(R^4)_2$—$R^5$ and —SO$_2$—$R^5$; each k is independently 0, 1 or 2; each R is independently selected from the group consisting of: H and $C_{1-4}$alkyl; each $R^4$ is independently selected from the group consisting of: H, OH and $C_{1-4}$alkyl; each $R^5$ is independently selected from the group consisting of: H, $C_{1-4}$alkyl, $C_{2-4}$alkenyl, $C_{2-4}$alkynyl, $C_{3-6}$cycloalkyl, phenyl, heterocycle and heteroaryl, wherein each member of the group excluding hydrogen is optionally substituted with 1 to 3 substituents independently selected from: halogen, cyano, hydroxy and methyl; aryl at each occurrence is independently selected from the group consisting of: phenyl, naphthyl, anthryl and phenanthryl; heteroaryl at each occurrence independently means a 5- or 6-membered monocyclic aromatic or 9- or 10-membered bicyclic aromatic, wherein at least one atom in the aromatic is selected from N(R), O and S, the sulfur optionally oxidized to sulfone or sulfoxide, and the remaining atoms are selected from C, N(R), O and S, the sulfur optionally oxidized to sulfone or sulfoxide; heterocycle at each occurrence independently means a 4- to 7-membered monocyclic non-aromatic ring, an 8- to 11-membered bi-cyclic, including spiro-cyclic, non- or partially-aromatic ring or a 12- to 20-membered tri-cyclic, including spiro-cyclic portions, non- or partially-aromatic ring, each optionally substituted with 1 to 2 oxo groups, wherein at least one atom is selected from N(R), O and S, the sulfur optionally oxidized to sulfone or sulfoxide, and the remaining atoms are selected from C, N(R), O and S, the sulfur optionally oxidized to sulfone or sulfoxide; and pharmaceutically acceptable salts thereof.

Within the genus, the invention encompasses a first sub-genus of compounds of Formula I wherein Y is $C_{1-4}$alkyl. Within this first sub-genus, the invention encompasses compounds of Formula I wherein Y is methyl.

Also within the genus, the invention encompasses a second sub-genus of compounds of Formula I wherein $R^1$ is selected from the group consisting of: cyclopropylmethyl, 2,2-difluorocyclopropylmethyl, 2,2-difluoro-1-methylcyclopropylmethyl, 1-(trifluromethyl)cyclopropylmethyl, 4,4,4-trifluoro-2,2-dimethylbutyl, cyclobutylmethyl, 2,2-dimethylpropyl, prop-2-enyl, biphenyl and benzyl, optionally substituted with methoxy or —$OCF_3$.

Also within the genus, the invention encompasses a third sub-genus of compounds of Formula Ia

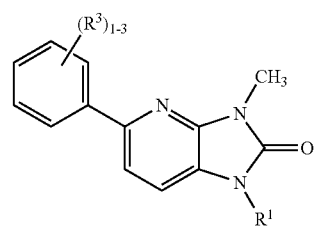

and pharmaceutically acceptable salts thereof.

Within the third sub-genus, the invention encompasses a first class of compounds having Formula Ia wherein $R^3$ is selected from the group consisting of: halo, —CN, —$N(O)_2$, amino, —$N(C_{1-4}$alkyl$)_2$, —C(O)—O—$C_{1-4}$alkyl, —C(O)—$C_{1-4}$alkyl, —S(O)$_2$—$C_{1-4}$alkyl, $C_{3-6}$cycloalkyl, —$C(C_{1-4}$alkyl$)_2$-NHC(O)—O—$C_{1-4}$alkyl and $C_{1-8}$alkyl optionally substituted with 1 to 4 substituents independently selected from hydroxy and halo.

Also within the genus, the invention encompasses a fourth sub-genus of compounds of Formula Ib

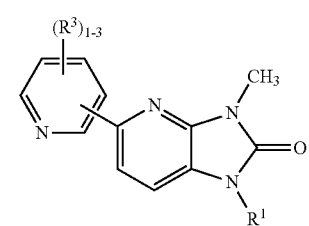

and pharmaceutically acceptable salts thereof.

Within the fourth sub-genus, the invention encompasses a second class of compounds having Formula Ib wherein $R^3$ is selected from the group consisting of: halo, —CN, —$N(O)_2$, amino, —$N(C_{1-4}$alkyl$)_2$, —C(O)—O—$C_{1-4}$alkyl, —C(O)—$C_{1-4}$alkyl, —S(O)$_2$—$C_{1-4}$alkyl, $C_{3-6}$cycloalkyl and $C_{1-8}$alkyl optionally substituted with 1 to 4 substituents independently selected from hydroxy and halo.

Also within the genus, the invention encompasses a fifth sub-genus of compounds of Formula Ic

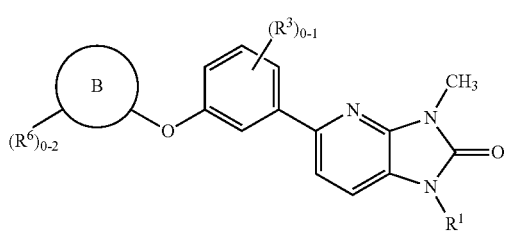

wherein: ring B is heteroaryl; $R^3$ is CN, halo or $C_{1-4}$alkyl, optionally substituted with 1-5 halo atoms; and each $R^6$ is independently selected from the group consisting of: —CN, halo, —N(R)$_2$, $C_{1-4}$alkoxy, —C(O)—O—$C_{1-4}$alkyl, and $C_{1-4}$alkyl, optionally substituted with hydroxy; and pharmaceutically acceptable salts thereof.

Within the fifth sub-genus, the invention encompasses a third class of compounds having Formula Ic wherein ring B is pyridyl.

Also within the genus, the invention encompasses a sixth sub-genus of compounds of Formula Id

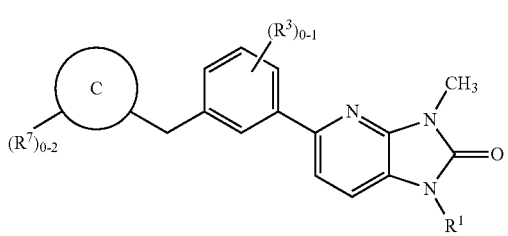

wherein: ring C is heterocycle; $R^3$ is CN, halo or $C_{1-4}$alkyl, optionally substituted with 1-5 halo atoms; and each $R^7$ is independently selected from the group consisting of: OH, acetyl, methylsulfonyl, acetylamine, —C(O)—O—$C_{1-4}$alkyl and $C_{1-4}$alkyl, optionally substituted with 1-3 halo atoms or hydroxy; and pharmaceutically acceptable salts thereof.

Within the sixth sub-genus, the invention encompasses a fourth class of compounds having Formula Id wherein ring C is dioxidothiomorpholin-4-yl.

Also within the sixth sub-genus, the invention encompasses a fifth class of compounds having Formula Id wherein ring C is 6,7-dihydroisoxazolo[4,5-c]pyridine-5(4H)-yl.

Also within the genus, the invention encompasses a seventh sub-genus of compounds of Formula Ie

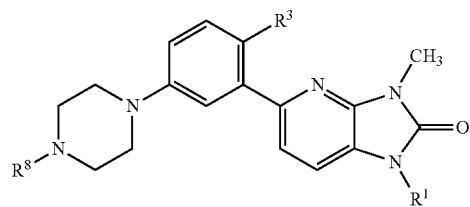

wherein: $R^3$ is CN, halo or $C_{1-4}$alkyl, optionally substituted with 1-5 halo atoms, and $R^8$ is selected from the group consisting of: heteroaryl, heteroarylcarbonyl, methylsulfonyl and $C_{1-6}$alkyl-C(O)—, optionally substituted with 1 to 3 substituents independently selected from halo or hydroxy; and pharmaceutically acceptable salts thereof.

Also within the genus, the invention encompasses a eighth sub-genus of compounds of Formula If

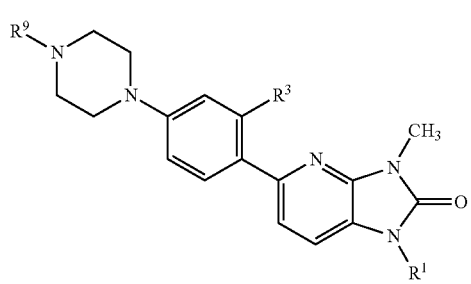

wherein: $R^3$ is CN, halo or $C_{1-4}$alkyl, optionally substituted with 1-5 halo atoms; and $R^9$ is selected from the group consisting of: heteroaryl, heteroarylcarbonyl, methylsulfonyl and $C_{1-6}$alkyl-C(O)—, optionally substituted with 1 to 3 substituents independently selected from halo or hydroxy; and pharmaceutically acceptable salts thereof.

Also within the genus, the invention encompasses a ninth sub-genus of compounds of Formula Ih

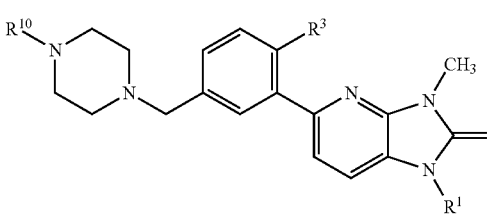

wherein: $R^3$ is CN, halo or $C_{1-4}$alkyl, optionally substituted with 1-5 halo atoms; and $R^{10}$ is selected from the group consisting of: heteroaryl, heteroarylcarbonyl, methylsulfonyl and $C_{1-6}$alkyl-C(O)—, optionally substituted with 1 to 3 substituents independently selected from halo or hydroxy; and pharmaceutically acceptable salts thereof.

Also within the genus, the invention encompasses a tenth sub-genus of compounds of Formula Ii

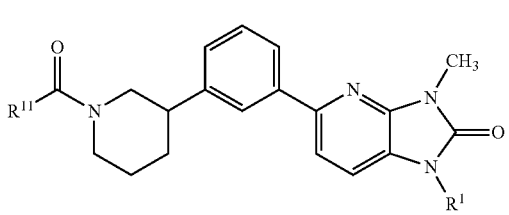

wherein: $R^{11}$ is selected from the group consisting of: heteroaryl and $C_{1-6}$alkyl, optionally substituted with 1 to 3 substituents independently selected from halo or hydroxy; and pharmaceutically acceptable salts thereof.

The invention also encompasses compounds 1-5 to 1-21, 2-2 to 2-4, 3-3, 4-2, 5-1, 6-1, 7-2, 8-2 to 8-6, 9-2 to 9-6, 10-1, 11-2, 12-1, 13-2, 14-2 to 14-96, 15-1 to 15-7, 16-3 to 16-5, 17-3, 18-2 to 18-9, 19-2 to 19-4, 20-1, 21-2 to 21-129, 22-1 to 22-7, 23-2 to 23-7, 24-1, 25-1, 26-1, 27-1, 28-1, 29-1, 30-2, 31-2, 32-1, 33-2, 34-3, 35-1, 36-1, 36-2, 37-3, 38-5, 39-5, 40-5, 41-1, 41-2, 42-3 to 42-7, 43-1, 44-2 to 44-12, 45-2 to 45-14, 46-2, 46-3, 47-1, 47-2, 48-1 to 48-6, 49-1 to 49-5, 50-1, 51-3 to 51-12, 52-2, 53-2 to 53-5, 54-2, 54-3, 55-2 to 55-10, 56-3 to 56-5, 57-1, 58-3 to 58-7, 59-3 to 59-5, 60-1, 61-3 to 61-7, 62-1, 63-3 to 63-5, 64-4, 65-4 to 65-6, 66-3 to 66-33, 67-1, 67-2, 68-1, 68-2, 69-3 to 69-31, 70-1, 71-6 to 71-11, 72-4, 73-2 to 73-13, 74-3 to 74-22, 75-3 to 75-11, 76-1, 77-1, 78-1, 79-2, 79-3, 80-2, 80-3, 81-3 and 82-4 that follow.

The invention also encompasses a pharmaceutical composition comprising a compound of Formula I or a pharmaceutically acceptable salt thereof in combination with a pharmaceutically acceptable carrier.

The invention also encompasses a method for treating a neurological or psychiatric disorder associated with glutamate dysfunction in a patient in need thereof comprising administering to the patient a therapeutically effective amount of a compound of Formula I or a pharmaceutically acceptable salt thereof. The invention also encompasses this method wherein the neurological or psychiatric disorder associated with glutamate dysfunction is schizophrenia.

The invention also encompasses the use of a compound of Formula I for the preparation of a medicament for the treatment of a neurological or psychiatric disorder associated with glutamate dysfunction. The invention also encompasses a compound of Formula I for use in the treatment of a neurological or psychiatric disorder associated with glutamate dysfunction "Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono-, bi- or tri-cyclic structures, optionally combined with linear or branched structures, having the indicated number of carbon atoms. Examples of cycloalkyl groups include cyclopropyl, cyclopentyl, cycloheptyl, adamantyl, cyclododecylmethyl, 2-ethyl-1-bicyclo[4.4.0]decyl, and the like.

"Alkoxy" means alkoxy groups of a straight or branched having the indicated number of carbon atoms. $C_{1-6}$alkoxy, for example, includes methoxy, ethoxy, propoxy, isopropoxy, and the like.

"Cycloalkoxy" means cycloalkyl as defined above bonded to an oxygen atom, such as cyclopropyloxy.

Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, and the like.

"Halogen" and "halo" includes fluorine, chlorine, bromine and iodine.

The point of attachment for heterocycle may be through a carbon or nitrogen atom.

A heteroaryl group may be attached to the remainder of the molecule via a ring carbon or a ring nitrogen, provided that this is consistent with preservation of aromaticity.

The compounds of the present invention are potentiators of metabotropic glutamate (mGluR) receptor function, in particular they are potentiators of mGluR2 receptors. That is, the compounds of the present invention do not appear to bind at the glutamate recognition site on the mGluR receptor, but in the presence of glutamate or a glutamate agonist, the compounds of the present invention increase mGluR receptor response. The present potentiators are expected to have their effect at mGluR receptors by virtue of their ability to increase the response of such receptors to glutamate or glutamate agonists, enhancing the function of the receptors. It is recognized that the compounds of the present invention would be expected to increase the effectiveness of glutamate and glutamate agonists of the mGluR2 receptor. Thus, the potentiators of the present invention are expected to be useful in the treatment of various neurological and psychiatric disorders associated with glutamate dysfunction described to be treated herein and others that can be treated by such potentiators as are appreciated by those skilled in the art.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium (1H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. It will be understood that, as used herein, references to the compounds of Formula I are meant to also include a pharmaceutically acceptable salts.

Exemplifying the invention are compounds 1-5 to 1-21, 2-2 to 2-4, 3-3, 4-2, 5-1, 6-1, 7-2, 8-2 to 8-6, 9-2 to 9-6, 10-1, 11-2, 12-1, 13-2, 14-2 to 14-96, 15-1 to 15-7, 16-3 to 16-5, 17-3, 18-2 to 18-9, 19-2 to 19-4, 20-1, 21-2 to 21-129, 22-1 to 22-7, 23-2 to 23-7, 24-1, 25-1, 26-1, 27-1, 28-1, 29-1, 30-2, 31-2, 32-1, 33-2, 34-3, 35-1, 36-1, 36-2, 37-3, 38-5, 39-5, 40-5, 41-1, 41-2, 42-3 to 42-7, 43-1, 44-2 to 44-12, 45-2 to 45-14, 46-2, 46-3, 47-1, 47-2, 48-1 to 48-6, 49-1 to 49-5, 50-1, 51-3 to 51-12, 52-2, 53-2 to 53-5, 54-2, 54-3, 55-2 to 55-10, 56-3 to 56-5, 57-1, 58-3 to 58-7, 59-3 to 59-5, 60-1, 61-3 to 61-7, 62-1, 63-3 to 63-5, 64-4, 65-4 to 65-6, 66-3 to 66-33, 67-1, 67-2, 68-1, 68-2, 69-3 to 69-31, 70-1, 71-6 to 71-11, 72-4, 73-2 to 73-13, 74-3 to 74-22, 75-3 to 75-11, 76-1, 77-1, 78-1, 79-2, 79-3, 80-2, 80-3, 81-3 and 82-4, described below. The subject compounds are useful in a method of potentiating metabotropic glutamate receptor activity in a patient such as a mammal in need of such inhibition comprising the administration of an effective amount of the compound. The present invention is directed to the use of the subject compounds disclosed herein as potentiators of metabotropic glutamate receptor activity. In addition to primates, especially humans, a variety of other mammals can be treated according to the method of the present invention.

The present invention is further directed to a method for the manufacture of a medicament for potentiating metabotropic glutamate receptor activity in humans and animals comprising combining a compound of the present invention with a pharmaceutical carrier or diluent.

The subject treated in the present methods is generally a mammal, preferably a human being, male or female, in whom potentiation of metabotropic glutamate receptor activity is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as potentiators of metabotropic glutamate receptor activity, in particular mGluR2 activity, may be demonstrated by methodology known in the art. Activity in potentiating the mGluR2 receptor may be determined as follows. The compounds of the present invention are tested in a fluorescence laser imaging plate reader (FLIPR) based assay. This assay is a common functional assay to monitor $Ca^{2+}$ mobilization in whole cells expressing recombinant receptor coupled with a promiscuous G-protein. CHO dhfr-cells stably expressing recombinant human mGluR2 and Gα16 loaded with Fluo-4 AM (Invitrogen, Carlsbad Calif.) are treated with dose responses of compounds and the $Ca^{2+}$ response is monitored on a FLIPR384 (Molecular Devices, Sunnydale Calif.) for agonist activity. The potentiation response is monitored after a subsequent addition of an EC20 concentration of glutamate (900 nM). The maximum calcium response at each concentration of compound for agonist or potentiation are plotted as dose responses and the curves are fitted with a four parameters logistic equation giving EC50 and Hill coefficient using the iterative non linear curve fitting software program.

The compounds of the present invention may also be tested in a $[^{35}S]$-GTPγS assay. The stimulation of $[^{35}S]$-GTPγS binding is a common functional assay to monitor Gαi-coupled receptor in native and recombinant receptor membrane preparation. Membrane from cells stably expressing hmGlu2 CHO-K1 (50 µg) are incubated in a 96 well plate for 1 hour in the presence of GTPγS$^{35}$ (0.05 nM), GDP (5 µM) and compounds. The reaction is stopped by rapid filtration over Unifilter GF/B plate (Packard, Bioscience, Meriden Conn.) using a 96-well cell harvester (Brandel Gaithersburg, Md.). The filter plates are counted using Topcount counter (Packard, Bioscience, Meriden Conn., USA). When compounds are evaluated as potentiators they are tested in the presence of glutamate (1 µM). The activation (agonist) or the potentiation of glutamate (potentiator) curves are fitted with a four parameters logistic equation giving $EC_{50}$ and Hill coefficient using the iterative non linear curve fitting software GraphPad (San Diego Calif., USA).

In particular, compounds I-5 to 1-21, 2-2 to 2-4, 3-3, 4-2, 5-1, 6-1, 7-2, 8-2 to 8-6, 9-2 to 9-6, 10-1, 11-2, 12-1, 13-2, 14-2 to 14-96, 15-1 to 15-7, 16-3 to 16-5, 17-3, 18-2 to 18-9, 19-2 to 19-4, 20-1, 21-2 to 21-129, 22-1 to 22-7, 23-2 to 23-7, 24-1, 25-1, 26-1, 27-1, 28-1, 29-1, 30-2, 31-2, 32-1, 33-2, 34-3, 35-1, 36-1, 36-2, 37-3, 38-5, 39-5, 40-5, 41-1, 41-2, 42-3 to 42-7, 43-1, 44-2 to 44-12, 45-2 to 45-14, 46-2, 46-3, 47-1, 47-2, 48-1 to 48-6, 49-1 to 49-5, 50-1, 51-3 to 51-12, 52-2, 53-2 to 53-5, 54-2, 54-3, 55-2 to 55-10, 56-3 to 56-5, 57-1, 58-3 to 58-7, 59-3 to 59-5, 60-1, 61-3 to 61-7, 62-1, 63-3 to 63-5, 64-4, 65-4 to 65-6, 66-3 to 66-33, 67-1, 67-2, 68-1, 68-2, 69-3 to 69-31, 70-1, 71-6 to 71-11, 72-4, 73-2 to 73-13, 74-3 to 74-22, 75-3 to 75-11, 76-1, 77-1, 78-1, 79-2, 79-3, 80-2, 80-3, 81-3 and 82-4, described below, were tested and demonstrated activity in potentiating the mGluR2 receptor in the FLIPR assay, generally with an $EC_{50}$ of less than about 3 µM. Compounds within the present invention had activity in potentiating the mGluR2 receptor in the FLIPR and GTPγS assays with an $EC_{50}$ of less than about 3 µM. Compounds 1-5 to 1-21, 2-2 to 2-4, 3-3, 4-2, 5-1, 6-1, 7-2, 8-2 to 8-6, 9-2 to 9-6, 10-1, 11-2, 12-1, 13-2, 14-2 to 14-96, 15-1 to 15-7, 16-3 to 16-5, 17-3, 18-2 to 18-9, 19-2 to 19-4, 20-1, 21-2 to 21-129, 22-1 to 22-7, 23-2 to 23-7, 24-1, 25-1, 26-1, 27-1, 28-1, 29-1, 30-2, 31-2, 32-1, 33-2, 34-3, 35-1, 36-1, 36-2, 37-3, 38-5, 39-5, 40-5, 41-1, 41-2, 42-3 to 42-7, 43-1, 44-2 to 44-12, 45-2 to 45-14, 46-2, 46-3, 47-1, 47-2, 48-1 to 48-6, 49-1 to 49-5, 50-1, 51-3 to 51-12, 52-2, 53-2 to 53-5, 54-2, 54-3, 55-2 to 55-10, 56-3 to 56-5, 57-1, 58-3 to 58-7, 59-3 to 59-5, 60-1, 61-3 to 61-7, 62-1, 63-3 to 63-5, 64-4, 65-4 to 65-6, 66-3 to 66-33, 67-1, 67-2, 68-1, 68-2, 69-3 to 69-31, 70-1, 71-6 to 71-11, 72-4, 73-2 to 73-13, 74-3 to 74-22, 75-3 to 75-11, 76-1, 77-1, 78-1, 79-2, 79-3, 80-2, 80-3, 81-3 and 82-4 resulted in a minimum 1.4-fold potentiation of glutamate response in the presence of an EC20 concentration of glutamate (900 nM). Such results are indicative of the intrinsic activity of the compounds in use as potentiators of mGluR2 receptor activity.

Representative FLIPR $EC_{50}$ Values

| Ex. | $IC_{50}$ (nM) | N |
|---|---|---|
| 14-2 | 62 | 103 |
| 16-3 | 8 | 4 |
| 21-11 | 34 | 7 |
| 21-45 | 21 | 2 |
| 21-47 | 74 | 3 |
| 42-3 | 37 | 4 |
| 51-9 | 226 | 3 |
| 51-10 | 26 | 4 |
| 56-4 | 35 | 2 |
| 60-1 | 25 | 4 |
| 61-4 | 11 | 4 |
| 65-6 | 28 | 2 |
| 66-4 | 45 | 2 |
| 81-3 | 43 | 2 |

Metabotropic glutamate receptors including the mGluR2 receptor have been implicated in a wide range of biological functions. This has suggested a potential role for these receptors in a variety of disease processes in humans or other species.

The compounds of the present invention have utility in treating, preventing, ameliorating, controlling or reducing the risk of a variety of neurological and psychiatric disorders associated with glutamate dysfunction, including one or more of the following conditions or diseases: acute neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, substance withdrawal (including, substances such as opiates, nicotine, tobacco products, alcohol, benzodiazepines, cocaine, sedatives, hypnotics, etc.), psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic pain states, severe pain, intractable pain, neuropathic pain, and post-traumatic pain), tardive dyskinesia, sleep disorders (including narcolepsy), autism, autism spectrum disorders, attention deficit/hyperactivity disorder, and conduct disorder.

In an embodiment the present invention provides a method for treating migraine, comprising: administering to a patient in need thereof an effective amount of a compound of Formula I. In another embodiment the present invention provides a method for preventing or treating anxiety, comprising: administering to a patient in need thereof an effective amount of a compound of Formula I. Particular anxiety disorders of the invention are generalized anxiety disorder, panic disorder, and obsessive compulsive disorder. In another embodiment the present invention provides a method for treating schizophrenia, comprising: administering to a patient in need thereof an effective amount of a compound of Formula I. In yet another embodiment the present invention provides a method for treating epilepsy, comprising: administering to a patient in need thereof an effective amount of a compound of Formula I.

In an embodiment, the present invention provides a method for the treatment of schizophrenia comprising: administering to a patient in need thereof an effective amount of a compound of Formula I or a pharmaceutical composition thereof. In one of the available sources of diagnostic tools, The Merck Manual (2006-2007), schizophrenia is characterized by psychosis (loss of contact with reality), hallucinations (false perceptions), delusions (false beliefs), disorganized speech and behavior, flattened affect (restricted range of emotions), cognitive deficits (impaired reasoning and problem solving), and occupational and social dysfunction. The skilled artisan will recognize that there are alternative nomenclatures, nosologies, and classification systems for neurological and psychiatric disorders, including migraine, and that these systems evolve with medical scientific progress Thus, in an embodiment the present invention provides a method for treating migraine, comprising: administering to a patient in need thereof an effective amount of a compound of Formula I or a pharmaceutical composition thereof. In one of the available sources of diagnostic tools, Dorland's Medical Dictionary (23'd Ed., 1982, W.B. Saunders Company, Philadelphia, Pa.), migraine is defined as a symptom complex of periodic headaches, usually temporal and unilateral, often with irritability, nausea, vomiting, constipation or diarrhea, and photophobia. As used herein the term "migraine" includes these periodic headaches, both temporal and unilateral, the associated irritability, nausea, vomiting, constipation or diarrhea, photophobia, and other associated symptoms. The skilled artisan will recognize that there are alternative nomenclatures, nosologies, and classification systems for neurological and psychiatric disorders, including migraine, and that these systems evolve with medical scientific progress.

In another embodiment the present invention provides a method for treating anxiety, comprising: administering to a patient in need thereof an effective amount of a compound of Formula I or a pharmaceutical composition thereof. At present, the fourth edition of the Diagnostic and Statistical Manual of Mental Disorders (DSM-IV) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified. As used herein the term "anxiety" includes treatment of those anxiety disorders and related disorder as described in the DSM-IV. The skilled artisan will recognize that there are alternative nomenclatures, nosologies, and classification systems for neurological and psychiatric disorders, and particular anxiety, and that these systems evolve with medical scientific progress. Thus, the term "anxiety" is intended to include like disorders that are described in other diagnostic sources.

In another embodiment the present invention provides a method for treating depression, comprising: administering to a patient in need thereof an effective amount of a compound of Formula I or a pharmaceutical composition thereof. At present, DSM-IV provides a diagnostic tool including depression and related disorders. Depressive disorders include, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or bipolar disorders or manic depression, for example, bipolar I disorder, bipolar II disorder and cyclothymic disorder. As used herein the term "depression" includes treatment of those depression disorders and related disorder as described in the DSM-IV.

In another embodiment the present invention provides a method for treating epilepsy, comprising: administering to a patient in need thereof an effective amount of a compound of Formula I or a pharmaceutical composition thereof. At present, there are several types and subtypes of seizures associated with epilepsy, including idiopathic, symptomatic, and cryptogenic. These epileptic seizures can be focal (partial) or generalized. They can also be simple or complex. Epilepsy is described in the art, such as Epilepsy: A comprehensive textbook. Ed. by Jerome Engel, Jr. and Timothy A. Pedley. (Lippincott-Raven, Philadelphia, 1997). At present, the International Classification of Diseases, Ninth Revision, (ICD-9) provides a diagnostic tool including epilepsy and related disorders. These include: generalized nonconvulsive epilepsy, generalized convulsive epilepsy, petit mal status epilepticus, grand mal status epilepticus, partial epilepsy with impairment of consciousness, partial epilepsy without impairment of consciousness, infantile spasms, epilepsy partialis continua, other forms of epilepsy, epilepsy, unspecified, NOS. As used herein the term "epilepsy" includes these all types and subtypes. The skilled artisan will recognize that there are alternative nomenclatures, nosologies, and classification systems for neurological and psychiatric disorders, including epilepsy, and that these systems evolve with medical scientific progress.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents, including an mGluR agonist.

The term "potentiated amount" refers to an amount of an mGluR agonist, that is, the dosage of agonist which is effective in treating the neurological and psychiatric disorders described herein when administered in combination with an effective amount of a compound of the present invention. A potentiated amount is expected to be less than the amount that is required to provided the same effect when the mGluR agonist is administered without an effective amount of a compound of the present invention.

A potentiated amount can be readily determined by the attending diagnostician, as one skilled in the art, by the use of conventional techniques and by observing results obtained under analogous circumstances. In determining a potentiated amount, the dose of an mGluR agonist to be administered in combination with a compound of Formula I, a number of factors are considered by the attending diagnostician, including, but not limited to: the mGluR agonist selected to be administered, including its potency and selectivity; the compound of Formula I to be coadministered; the species of mammal; its size, age, and general health; the specific disorder involved; the degree of involvement or the severity of the disorder; the response of the individual patient; the modes of administration; the bioavailability characteristics of the preparations administered; the dose regimens selected; the use of other concomitant medication; and other relevant circumstances.

A potentiated amount of an mGluR agonist to be administered in combination with an effective amount of a compound of Formula I is expected to vary from about 0.1 milligram per kilogram of body weight per day (mg/kg/day) to about 100 mg/kg/day and is expected to be less than the amount that is required to provided the same effect when administered without an effective amount of a compound of Formula I. Preferred amounts of a co-administered mGlu agonist are able to be determined by one skilled in the art.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form may be utilized containing such other drugs and the compound of Formula I. However, the combination therapy may also includes therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention may be utilized. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional nontoxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives.

Pharmaceutical compositions of the present compounds may be in the form of a sterile injectable aqueous or oleageneous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require potentiation of metabotorpic glutamate receptor activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

When treating, preventing, controlling, ameliorating, or reducing the risk of neurological and psychiatric disorders associated with glutamate dysfunction or other diseases for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein. The compounds of the present invention can be prepared in a variety of fashions.

Abbreviations used in the description of the chemistry and in the Examples that follow are: Ac2O (acetic anhydride); AcOH (acetic acid); AEBSF (p-aminoethylbenzenesulfonyl fluoride); Boc (di-tert-butyl carbamate); (Boc)$_2$O (di-tert-butyl dicarbonate); BSA (bovine serum albumin); BuLi (n-Butyl lithium); CDCl3 (chloroform-d); CuI (copper iodide); CuSO4 (copper sulfate); DBU (1,8-DIAZABICYCLO [5.4.0]UNDEC-7-ENE); DCE (dichloroethane); DCM (dichloromethane); DEAD (diethyl azodicarboxylate); DIPEA (diisopropylethylamine); DMBA (1,3-dimethylbarbituric acid); DMF (N,N-dimethylformamide); DMP (Dess-Martin periodinane); DMSO (dimethyl sulfoxide); DPPA (diphenylphosphoryl azide); DTT (dithiothreitol); EDTA (ethylene-diamine-tetra-acetic acid); EGTA (ethylene-glycol-tetra-acetic acid); Et2O (diethylether); EtOAc (ethyl acetate); EtOH (ethanol); HOAc (acetic acid); HPLC (high-performance liquid chromatography); HRMS (high resolution mass spectrum); LAH (lithium aluminum hydride); LCMS (liquid chromatograph-mass spectrometer); LHMDS (lithium bis(trimethylsilyl)amide); LRMS (low resolution mass spectrum); mCPBA (3-chloroperoxybenzoic acid); MeOH (methanol); MOM-Cl (methoxymethyl chloride); MP-B(CN)H3 (Macroporous cyanoborohydride); NaHCO3 (sodium bicarbonate); Na2SO4 (sodium sulfate); Na(OAc)3BH (sodium triacetoxyborohydride); NH4OAc (ammonium acetate); NBS (N-bromosuccinamide); NFSi (N-fluorobenzenesulfonimide); NMP (1-methyl-2-pyrrolidinone); NMR (nuclear magnetic resonance); PBS (phosphate buffered saline); PCR (polymerase chain reaction); Pd(dppf) ([1,1'-bis (diphenylphosphino)ferrocene]palladium); Pd(Ph3)4 (palladium(0)tetrakis-triphenylphosphine); POCl3 (phosphorous oxychloride); PS-DIEA (polystyrene diisopropylethylamine); PS-PPh3 (polystyrene-triphenyl phosphine); PTSA (para-toluene sulfonic acid); Pyr (pyridine); Selectfluor (1-chloromethyl-4-fluoro-1,4-diazoniabicyclo[2.2.2]octane bis(tetrafluoroborate); TBAF (tetrabutylammonium fluoride); T-BuOH (tert-butanol); THF (tetrahydrofuran); Tf (trifluoromethanesulfonyl); TFA (trifluoroacteic acid); and TMSCH2N2 (trimethylsilyldiazomethane).

The compounds of this invention may be prepared by employing reactions as shown in the following schemes and examples that follow, in addition to other standard manipulations that are known in the literature or exemplified in the experimental procedures. The illustrative schemes below, therefore, are not limited by the compounds listed or by any particular substituents employed for illustrative purposes. Substituent numbering as shown in the schemes do not necessarily correlate to that used in the claims and often, for clarity, a single substituent is shown attached to the compound where multiple substituents are optionally allowed under the definitions of Formula I hereinabove. Examples provided are intended to assist in a further understanding of the invention. Particular materials employed, species and conditions are intended to be further illustrative of the invention and not limitative of the reasonable scope thereof. The reagents utilized in synthesizing the compounds depicted in the following tables are either commercially available or are readily prepared by one of ordinary skill in the art.

SCHEME 1

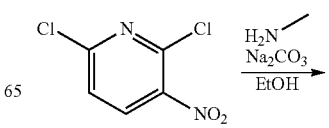

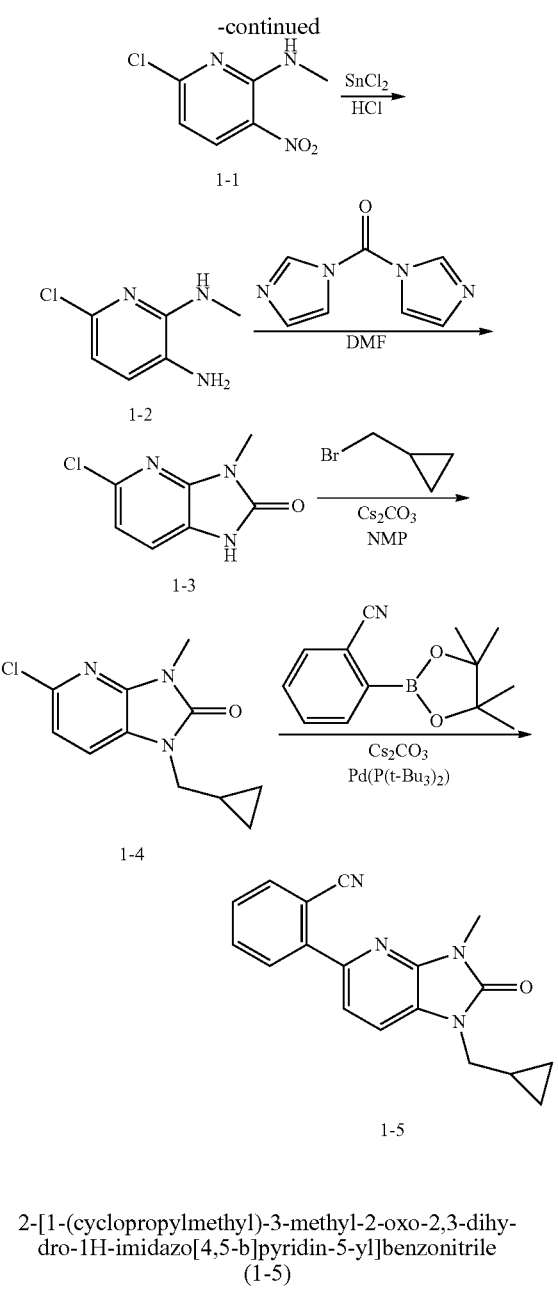

2-[1-(cyclopropylmethyl)-3-methyl-2-oxo-2,3-dihydro-1H-imidazo[4,5-b]pyridin-5-yl]benzonitrile (1-5)

6-chloro-N-methyl-3-nitropyridin-2-amine (1-1)

2,6-Dichloro-3-Nitropyridine (2.0 g, 10 mmol) and sodium carbonate (2.8 g, 26 mmol) were added to a round bottom flask under nitrogen, and suspended in ethanol (100 mL). 2M methylamine in methanol (7.8 mL) was then added and stirred at room temperature for 3 hours. The yellow solution was concentrated, and then redissolved in ethyl acetate followed by washing with sodium bicarbonate and brine. The organic phase was dried over sodium sulfate, filtered, and concentrated. The yellow solid was then redissolved in ethanol and recrystallized to give 6-chloro-N-methyl-3-nitropyridin-2-amine (1-1) as a yellow solid. MS (M+H)$^+$: observed=188.0, calculated=188.6.

6-chloro-N$^2$-methylpyridine-2,3-diamine (1-2)

6-chloro-N-methyl-3-nitropyridin-2-amine (1-1) (10.5 g, 56 mmol) and Tin(II) chloride dihydrate (50 g, 220 mmol) were suspended in concentrated HCl (80 mL) and refluxed overnight. The solution was cooled to room temperature and then added very slowly to a NaOH/Ethyl acetate solution at −78° C., until the solution had a slightly basic pH. The suspension was washed with sodium bicarbonate, brine, dried over sodium sulfate, filtered, and concentrated to produce the black solid 6-chloro-N$^2$-methylpyridine-2,3-diamine(1-2). MS (M+H)$^+$: observed=158.0, calculated=158.6.

5-chloro-3-methyl-1,3-dihydro-2H-imidazo[4,5-b]pyridin-2-one (1-3)

6-chloro-N$^2$-methylpyridine-2,3-diamine (1-2) (35 g, 222 mmol) and 1,1'-Carbonyldiimidazole (63 g, 389 mmol) were added to a round bottom flask and suspended in DMF (150 mL). The solution was heated to 80° C. in an oil bath overnight. The reaction was then suspended in ethyl acetate and sodium bicarbonate. The suspension was washed with sodium bicarbonate, brine (×5), dried over sodium sulfate, filtered, and concentrated to produce the solid 5-chloro-3-methyl-1,3-dihydro-2H-imidazo[4,5-b]pyridin-2-one (1-3). MS (M+H)$^+$: observed=184.2, calculated=184.6.

5-chloro-1-(cyclopropylmethyl)-3-methyl-1,3-dihydro-2H-imidazo[4,5-b]pyridin-2-one (1-4)

5-chloro-3-methyl-1,3-dihydro-2H-imidazo[4,5-b]pyridin-2-one (1-3) (2.97 g, 16.2 mmol) and cesium carbonate (15.8 g, 48.6 mmol) were added to a round bottom flask and suspended in NMP (25 mL) under nitrogen. Cyclopropylmethyl Bromide (4.4, 32.4 mmol) was added to the suspension and then refluxed at 90° C. overnight. The reaction was then cooled to room temperature and suspended in ethyl acetate and sodium bicarbonate. The suspension was washed with sodium bicarbonate, brine (×5), dried over sodium sulfate, filtered, and concentrated. The mixture was purified using normal phase chromatography (0-60% Ethyl Acetate/Hexanes), and the desired fractions were collected to produce the tan solid 5-chloro-1-(cyclopropylmethyl)-3-methyl-1,3-dihydro-2H-imidazo[4,5-b]pyridin-2-one (1-4). MS (M+H)$^+$: observed=237.7, calculated=238.1.

2-[1-(cyclopropylmethyl)-3-methyl-2-oxo-2,3-dihydro-1H-imidazo[4,5b]pyridin-5-yl]benzonitrile (1-5)

5-chloro-1-(cyclopropylmethyl)-3-methyl-1,3-dihydro-2H-imidazo[4,5-b]pyridin-2-one (1-4) (35 mg, 0.138 mmol), 2-cyanophenylboronic acid pinacol ester (79 mg, 0.345 mmol), cesium carbonate (135 mg, 0.414 mmol), and bis(tri-t-butylphosphine)palladium(0) (7 mg, 0.014 mmol) were added to a microwave vial, and purged with nitrogen. Dioxane (1.1 ml) and water (0.3 ml) were added and the suspension was heated at 90° C. overnight. The reaction was cooled to room temperature, diluted with methanol, and passed through a syringe filter. The solution was purified using reverse phase chromatography (10-100%, 0.1% TFA in H$_2$O/Acetonitrile) and the desired fractions were collected and concentrated to produce 2-[1-(cyclopropylmethyl)-3-methyl-2-oxo-2,3-dihydro-1H-imidazo[4,5-b]pyridin-5-yl]benzonitrile (1-5). HRMS (M+H)$^+$: observed=305.1403, calculated=305.1397.

TABLE 1

The following compounds were prepared from 1-4 by a reaction sequence analogous to that illustrated in Scheme 1.

| Cmpd | Structure | IUPAC Name | Exact Mass [M + H]+ |
|---|---|---|---|
| 1-6 | 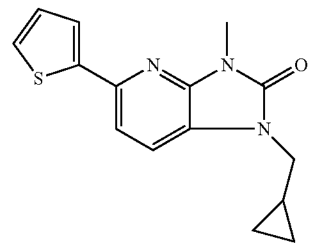 [SMILES: Cn1c(=O)n(CC2CC2)c2ccc(-c3cccs3)nc21] | 1-(cyclopropylmethyl)-3-methyl-5-thiophen-2-yl-1,3-dihydro-2H-imidazo[4,5-b]pyridin-2-one | Calc'd 286.1009, found 286.1014 |
| 1-7 | 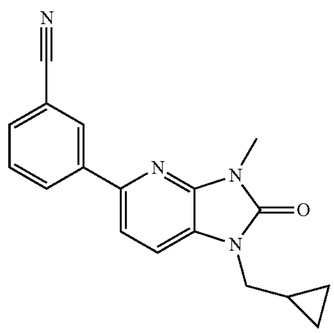 [SMILES: Cn1c(=O)n(CC2CC2)c2ccc(-c3cccc(C#N)c3)nc21] | 3-[1-(cyclopropylmethyl)-3-methyl-2-oxo-2,3-dihydro-1H-imidazo[4,5-b]pyridin-5-yl]benzonitrile | Calc'd 305.1397, found 305.1403 |
| 1-8 | 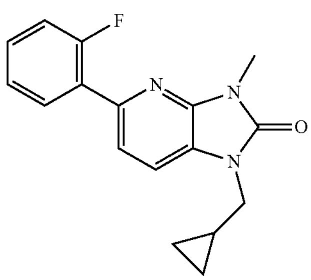 [SMILES: Cn1c(=O)n(CC2CC2)c2ccc(-c3ccccc3F)nc21] | 1-(cyclopropylmethyl)-5-(2-fluorophenyl)-3-methyl-1,3-dihydro-2H-imidazo[4,5-b]pyridin-2-one | Calc'd 298.1350, found 298.1356 |
| 1-9 | 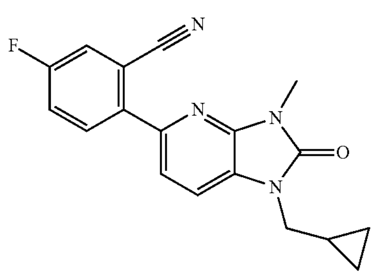 [SMILES: Cn1c(=O)n(CC2CC2)c2ccc(-c3ccc(F)cc3C#N)nc21] | 2-[1-(cyclopropylmethyl)-3-methyl-2-oxo-2,3-dihydro-1H-imidazo[4,5-b]pyridin-5-yl]-5-fluorobenzonitrile | Calc'd 323.1303, found 323.1299 |
| 1-10 | 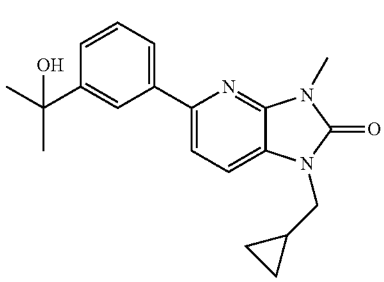 [SMILES: Cn1c(=O)n(CC2CC2)c2ccc(-c3cccc(C(C)(C)O)c3)nc21] | 1-(cyclopropylmethyl)-5-[3-(1-hydroxy-1-methylethyl)phenyl]-3-methyl-1,3-dihydro-2H-imidazo[4,5-b]pyridin-2-one | Calc'd 338.1863, found 338.1862 |

TABLE 1-continued

The following compounds were prepared from 1-4 by a reaction sequence analogous to that illustrated in Scheme 1.

| Cmpd | Structure | IUPAC Name | Exact Mass [M + H]+ |
|---|---|---|---|
| 1-11 | 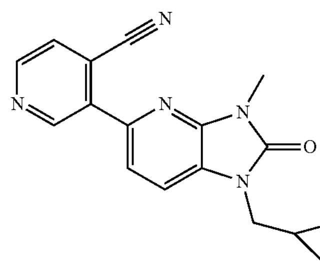 | 3-[1-(cyclopropylmethyl)-3-methyl-2-oxo-2,3-dihydro-1H-imidazo[4,5-b]pyridin-5-yl]pyridine-4-carbonitrile | Calc'd 306.1349, found 306.1349 |
| 1-12 | 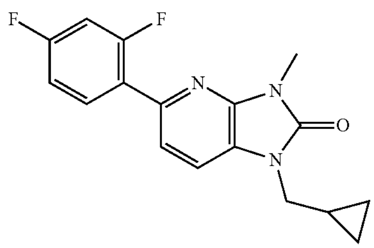 [SMILES: Cn1c(=O)n(CC2CC2)c2ccc(-c3ccc(F)cc3F)nc21] | 1-(cyclopropylmethyl)-5-(2,4-difluorophenyl)-3-methyl-1,3-dihydro-2H-imidazo[4,5-b]pyridin-2-one | Calc'd 316.1256, found 316.1255 |
| 1-13 | 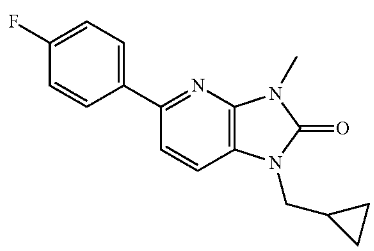 [SMILES: Cn1c(=O)n(CC2CC2)c2ccc(-c3ccc(F)cc3)nc21] | 1-(cyclopropylmethyl)-5-(4-fluorophenyl)-3-methyl-1,3-dihydro-2H-imidazo[4,5-b]pyridin-2-one | Calc'd 298.135, found 298.135 |
| 1-14 | 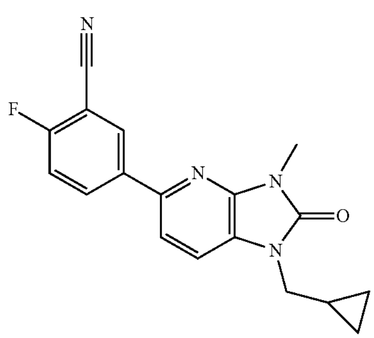 [SMILES: Cn1c(=O)n(CC2CC2)c2ccc(-c3ccc(F)c(C#N)c3)nc21] | 5-[1-(cyclopropylmethyl)-3-methyl-2-oxo-2,3-dihydro-1H-imidazo[4,5-b]pyridin-5-yl]-2-fluorobenzonitrile | Calc'd 323.1303, found 323.1301 |
| 1-15 | 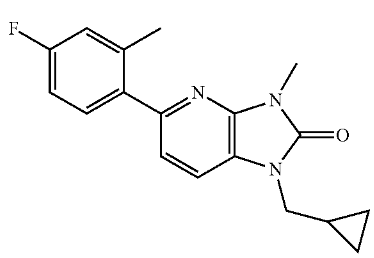 [SMILES: Cc1cc(F)ccc1-c1ccc2c(n1)n(C)c(=O)n2CC1CC1] | 1-(cyclopropylmethyl)-5-(4-fluoro-2-methylphenyl)-3-methyl-1,3-dihydro-2H-imidazo[4,5-b]pyridin-2-one | Calc'd 312.1507, found 312.1505 |

TABLE 1-continued

The following compounds were prepared from 1-4 by a reaction sequence analogous to that illustrated in Scheme 1.

| Cmpd | Structure | IUPAC Name | Exact Mass [M + H]+ |
|---|---|---|---|
| 1-16 | 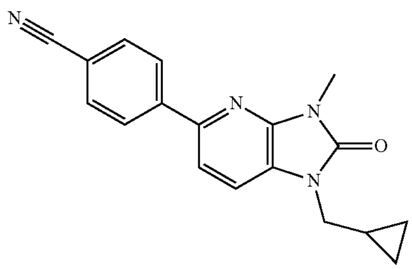 [SMILES: Cn1c(=O)n(CC2CC2)c2ccc(-c3ccc(C#N)cc3)nc21] | 4-[1-(cyclopropylmethyl)-3-methyl-2-oxo-2,3-dihydro-1H-imidazo[4,5-b]pyridin-5-yl]benzonitrile | Calc'd 305.1397, found 305.1395 |
| 1-17 | 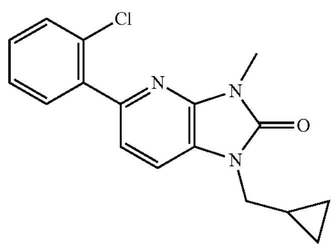 [SMILES: Cn1c(=O)n(CC2CC2)c2ccc(-c3ccccc3Cl)nc21] | 5-(2-chlorophenyl)-1-(cyclopropylmethyl)-3-methyl-1,3-dihydro-2H-imidazo[4,5-b]pyridin-2-one | Calc'd 314.1055, found 314.1054 |
| 1-18 | 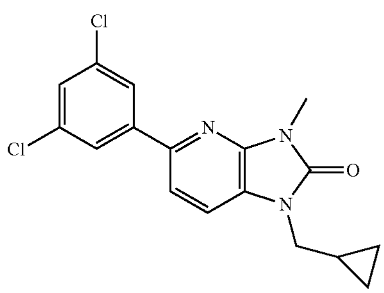 [SMILES: Cn1c(=O)n(CC2CC2)c2ccc(-c3cc(Cl)cc(Cl)c3)nc21] | 1-(cyclopropylmethyl)-5-(3,5-dichlorophenyl)-3-methyl-1,3-dihydro-2H-imidazo[4,5-b]pyridin-2-one | Calc'd 348.0665, found 348.0663 |
| 1-19 | 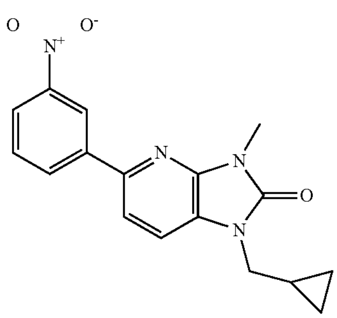 | 1-(cyclopropylmethyl)-3-methyl-5-(3-nitrophenyl)-1,3-dihydro-2H-imidazo[4,5-b]pyridin-2-one | Calc'd 325.1295, found 325.1294 |
| 1-20 | 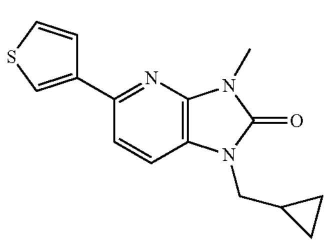 [SMILES: Cn1c(=O)n(CC2CC2)c2ccc(-c3ccsc3)nc21] | 1-(cyclopropylmethyl)-3-methyl-5-thiophen-3-yl-1,3-dihydro-2H-imidazo[4,5-b]pyridin-2-one | Calc'd 286.1009, found 286.1009 |

TABLE 1-continued

The following compounds were prepared from 1-4 by a reaction sequence analogous to that illustrated in Scheme 1.

| Cmpd | Structure | IUPAC Name | Exact Mass [M + H]+ |
|---|---|---|---|
| 1-21 | 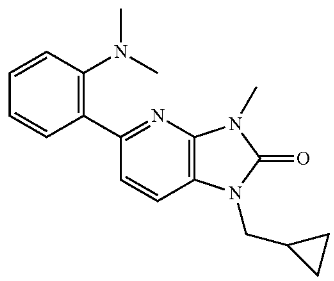 [SMILES: CN(C)c1ccccc1-c1ccc2c(n1)n(C)c(=O)n2CC1CC1] | 1-(cyclopropylmethyl)-5-[2-(dimethylamino)phenyl]-3-methyl-1,3-dihydro-2H-imidazo[4,5-b]pyridin-2-one | Calc'd 323.1866, found 323.1863 |

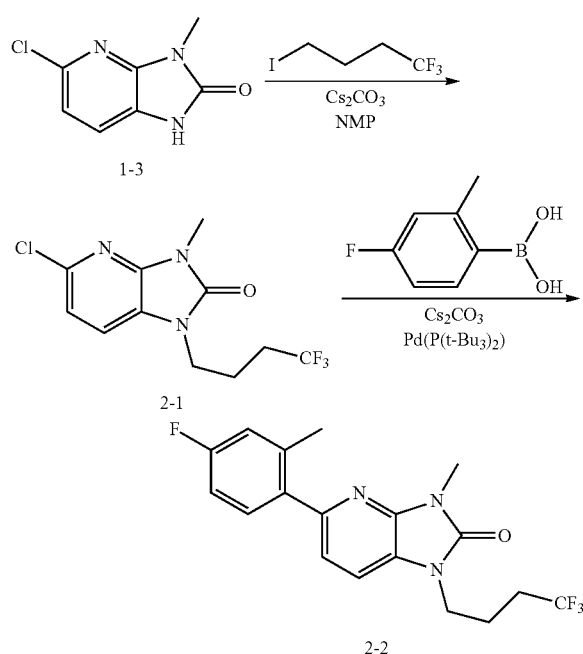

SCHEME 2

5-(4-fluoro-2-methylphenyl)-3-methyl-1-(4,4,4-trifluorobutyl)-1,3-dihydro-2H-imidazo[4,5-b]pyridin-2-one (2-2)

5-chloro-3-methyl-1-(4,4,4-trifluorobutyl)-1,3-dihydro-2H-imidazo[4,5-b]pyridin-2-one (2-1)

Prepared from 1-3 according to the procedures reported in Scheme 1. MS (M+H)+: observed=294.1, calculated=294.7.

5-(4-fluoro-2-methylphenyl)-3-methyl-1-(4,4,4-trifluorobutyl)-1,3-dihydro-2H-imidazo[4,5-b]pyridin-2-one (2-2)

Prepared from 2-1 according to the procedures reported in Scheme 1. HRMS (M+H)+: observed=368.1380, calculated=368.1381.

TABLE 2

The following compounds were prepared from 2-1 by a reaction sequence analogous to that illustrated in Scheme 2.

| Cmpd | Structure | IUPAC Name | Exact Mass [M + H]+ |
|---|---|---|---|
| 2-3 | 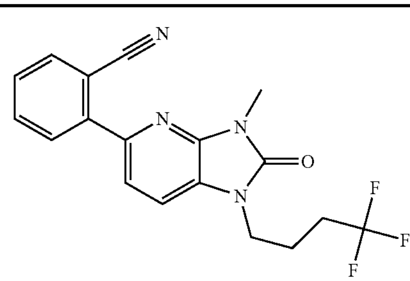 | 2-[3-methyl-2-oxo-1-(4,4,4-trifluorobutyl)-2,3-dihydro-1H-imidazo[4,5-b]pyridin-5-yl]benzonitrile | Calc'd 361.1271, found 361.1275 |

TABLE 2-continued

The following compounds were prepared from 2-1 by a reaction sequence analogous to that illustrated in Scheme 2.

| Cmpd | Structure | IUPAC Name | Exact Mass [M + H]+ |
|---|---|---|---|
| 2-4 | 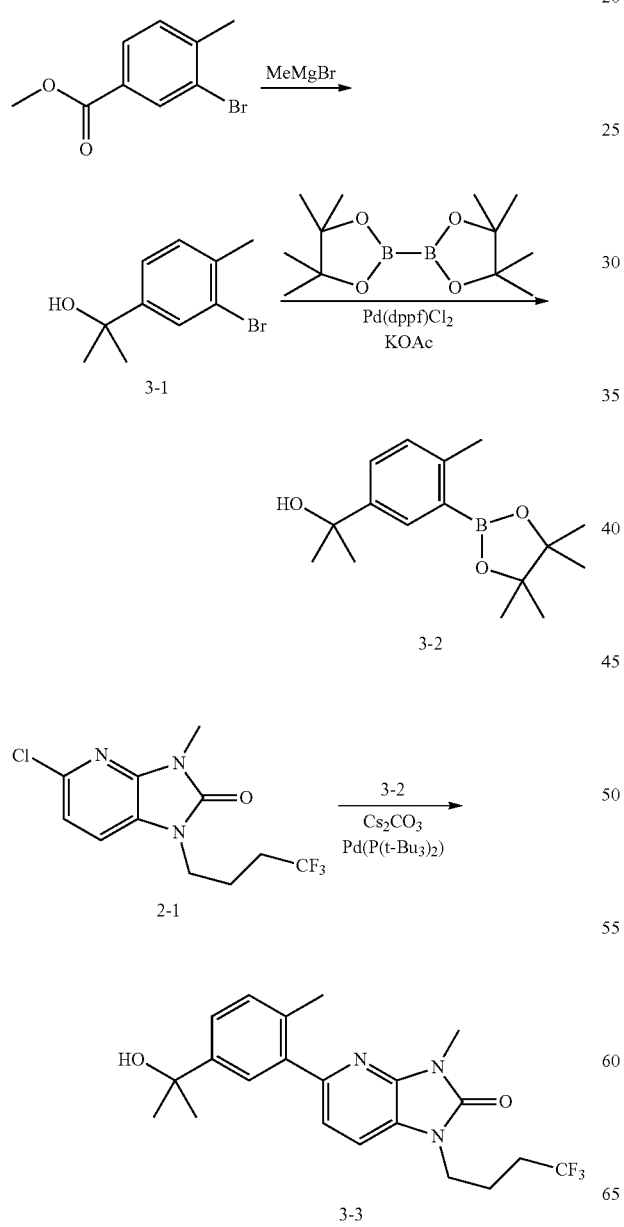 | 5-[3-(1-hydroxy-1-methyl-ethyl)phenyl]-3-methyl-1-(4,4,4-trifluorobutyl)-1,3-dihydro-2H-imidazo[4,5-b]pyridin-2-one | Calc'd 394.1737, found 394.1734 |

5-[5-(1-hydroxy-1-methylethyl)-2-methylphenyl]-3-methyl-1-(4,4,4-trifluorobutyl)-1,3-dihydro-22H-imidazo[4,5-b]pyridin-2-one (3-3)

2-(3-bromo-4-methylphenyl)propan-2-ol (3-1)

To a round bottom flask, Methyl 3-bromo-4-methylbenzoate (25 g, 109 mmol) was added under nitrogen, dissolved in THF (110 mL), and cooled to −78° C. 3M methylmagnesium bromide (85 ml, 251 mmol) was added slowly to the cooled solution and allowed to stir for 30 minutes. The reaction was warmed to room temperature for 30 minutes until complete conversion over starting material. The solution was diluted with ethyl acetate and sodium bicarbonate. Extracted (3×) with ethyl acetate, and washed the combined organic layers with brine, dried over sodium sulfate, filtered, and concentrated to afford the desired 2-(3-bromo-4-methylphenyl)propan-2-ol (3-1). MS (M+H)+: observed=211.0/213.0, calculated=211.1/213.1.

2-[4-methyl-3-(4,4,5,5-tetramethyl-1,3,2-dioxaborolan-2-yl)phenyl]propan-2-ol (3-2)

To a round bottom flask, 2-(3-bromo-4 methylphenyl)propan-2-ol (3-1) (10 g, 43.7 mmol), Bispinacoloto(diboron) (12.2 g, 48 mmol), Potassium Acetate (12.9 g, 131 mmol), and Bis(diphenylphosphino)ferrocene dichloropalladium (2.1 g, 2.85 mmol) was added under nitrogen and suspended in dioxane (44 ml). The mixture was refluxed at 90° C. overnight, and the allowed to cool to room temperature. The suspension was diluted with ethyl acetate and filtered, while the resulting filtrate was then suspended in sodium bicarbonate. Extracted (3×) with ethyl acetate, and washed the combined organic layers with brine, dried over sodium sulfate, filtered, and concentrated to a black tar. The compound was purified using normal phase chromatography (0-80% Ethyl Acetate/Hexanes), and the desired fractions were collected to produce the white solid 2-[4-methyl-3-(4,4,5,5-tetramethyl-1,3,2-dioxaborolan-2-yl)phenyl]propan-2-ol (3-2). MS (M-OH)+: observed=259.2, calculated=259.2.

5-[5-(1-hydroxy-1-methylethyl)-2-methylphenyl]-3-methyl-1-(4,4,4-trifluorobutyl)-1,3-dihydro-2H-imidazo[4,5-b]pyridin-2-one (3-3)

Prepared from 2-1 and 3-2 according to the procedures reported in Scheme 2. HRMS (M+H)+: observed=408.1891, calculated=408.1893.

SCHEME 4

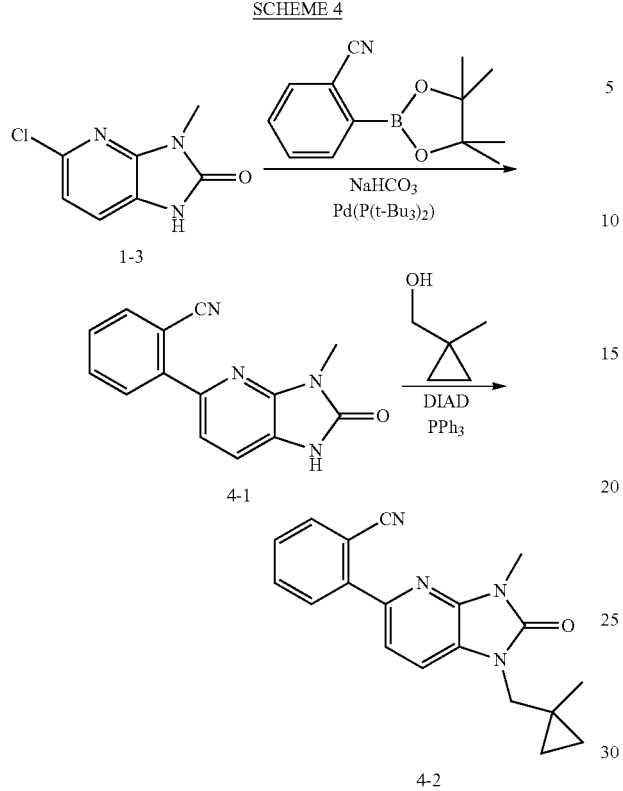

2-{3-methyl-1-[(1-methylcyclopropyl)methyl]-2-oxo-2,3-dihydro-1H-imidazo[4,5-b]pyridin-5-yl}benzonitrile (4-2)

2-(3-methyl-2-oxo-2,3-dihydro-1H-imidazo[4,5-b]pyridin-5-yl)benzonitrile (4-1)

5-chloro-3-methyl-1,3-dihydro-2H-imidazo[4,5-b]pyridin-2-one (1-3) (74 mg, 0.4 mmol), 2-cyanophenylboronic acid pinacol ester (179 mg, 1.2 mmol), sodium bicarbonate (200 mg, 2.4 mmol), and bis(tri-t-butylphosphine)palladium (0) (61 mg, 0.12 mmol) were added to a microwave vial and purged with nitrogen. Dioxane (1.2 mL) was added, the vessel was sealed and the suspension was heated at 100° C. for 12 minutes in a microwave reactor. The cooled reaction was diluted with methanol, and passed through a syringe filter. The solution was purified using reverse phase chromatography (10-100%, 0.1% TFA in H$_2$O/Acetonitrile) and the desired fractions were collected and concentrated to produce 2-(3-methyl-2-oxo-2,3-dihydro-1H-imidazo[4,5-b]pyridin-5-yl)benzonitrile (4-1). MS (M+H)$^+$: observed=251.1, calculated=251.3.

2-{3-methyl-1-[(1-methylcyclopropyl)methyl]-2-oxo-2,3-dihydro-1H-imidazo[4,5-b]pyridin-5-yl}benzonitrile (4-2)

2-(3-methyl-2-oxo-2,3-dihydro-1H-imidazo[4,5-b]pyridin-5-yl)benzonitrile (4-1) (50 mg, 0.2 mmol), 1-methylcyclopropanemethanol (52 mg, 0.6 mmol), Diisopropyl azodicarboxylate (121 mg, 0.6 mmol), and triphenylphosphine (157 mg, 0.6 mmol) were added to a microwave vial under nitrogen and dissolved with DCM (1 mL). The reaction was stirred for one hour, and desired product was observed via LCMS. The mixture was diluted with methanol and purified using reverse phase chromatography (10-100%, 0.1% TFA in H$_2$O/Acetonitrile); the desired fractions were collected and concentrated to produce 2-{3-methyl-1-[(1-methylcyclopropyl)methyl]-2-oxo-2,3-dihydro-1H-imidazo[4,5-b]pyridin-5-yl}benzonitrile (4-2). HRMS (M+H)$^+$: observed=319.1551, calculated=319.1553.

SCHEME 5

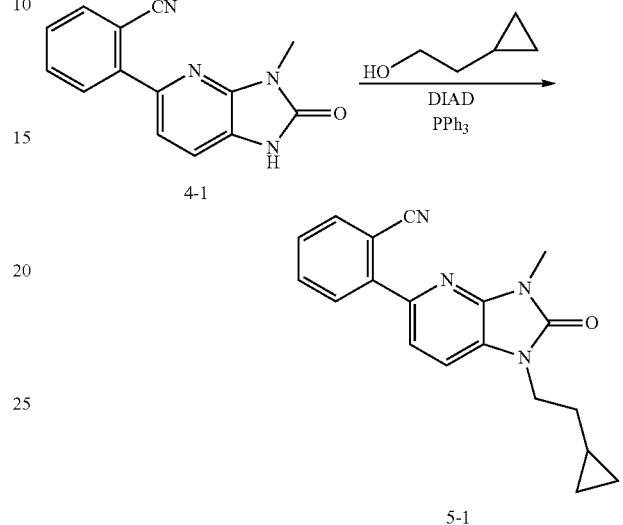

2-[1-(2-cyclopropylethyl)-3-methyl-2-oxo-2,3-dihydro-1H-imidazo[4,5-b]pyridin-5-yl]benzonitrile (5-1)

Prepared from 4-1 according to the procedures reported in Scheme 4. HRMS (M+H)$^+$: observed=319.1554, calculated=319.1553.

SCHEME 6

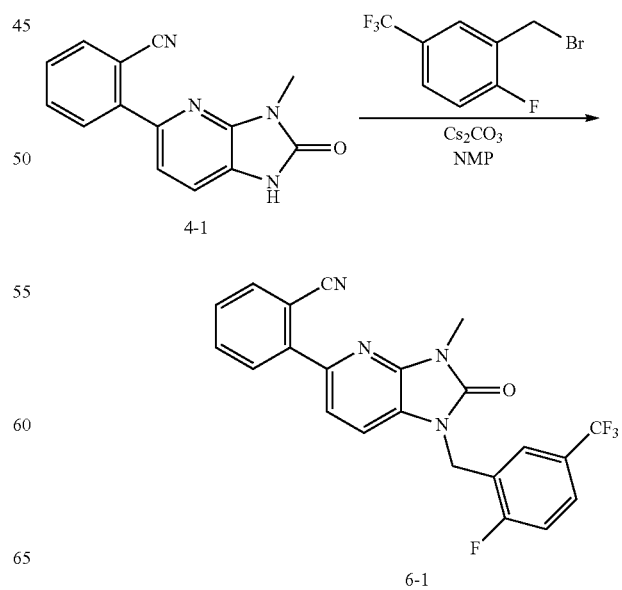

2-{1-[2-fluoro-5-(trifluoromethyl)benzyl]-3-methyl-2-oxo-2,3-dihydro 1H-imidazo[4,5-b]pyridin-5-yl}benzonitrile (6-1)

2-(3-methyl-2-oxo-2,3-dihydro-1H-imidazo[4,5-b]pyridin-5-yl)benzonitrile (4-1) (30 mg, 0.12 mmol) and cesium carbonate (117 mg, 0.36 mmol) were added to a microwave vial and suspended in NMP (0.5 mL) under nitrogen. 2-Fluoro-5-(trifluoromethyl)benzyl bromide (47 mg, 0.18 mmol) was added to the suspension and then heated at 90° C. overnight. The mixture was diluted with methanol and purified using reverse phase chromatography (10-100%, 0.1% TFA in H$_2$O/Acetonitrile); the desired fractions were collected and concentrated to produce 2-{1-[2-fluoro-5-(trifluoromethyl)benzyl]-3-methyl-2-oxo-2,3-dihydro 1H-imidazo[4,5-b]pyridin-5-yl}benzonitrile (6-1). HRMS (M+H)$^+$: observed=427.1179, calculated=427.1177.

SCHEME 7

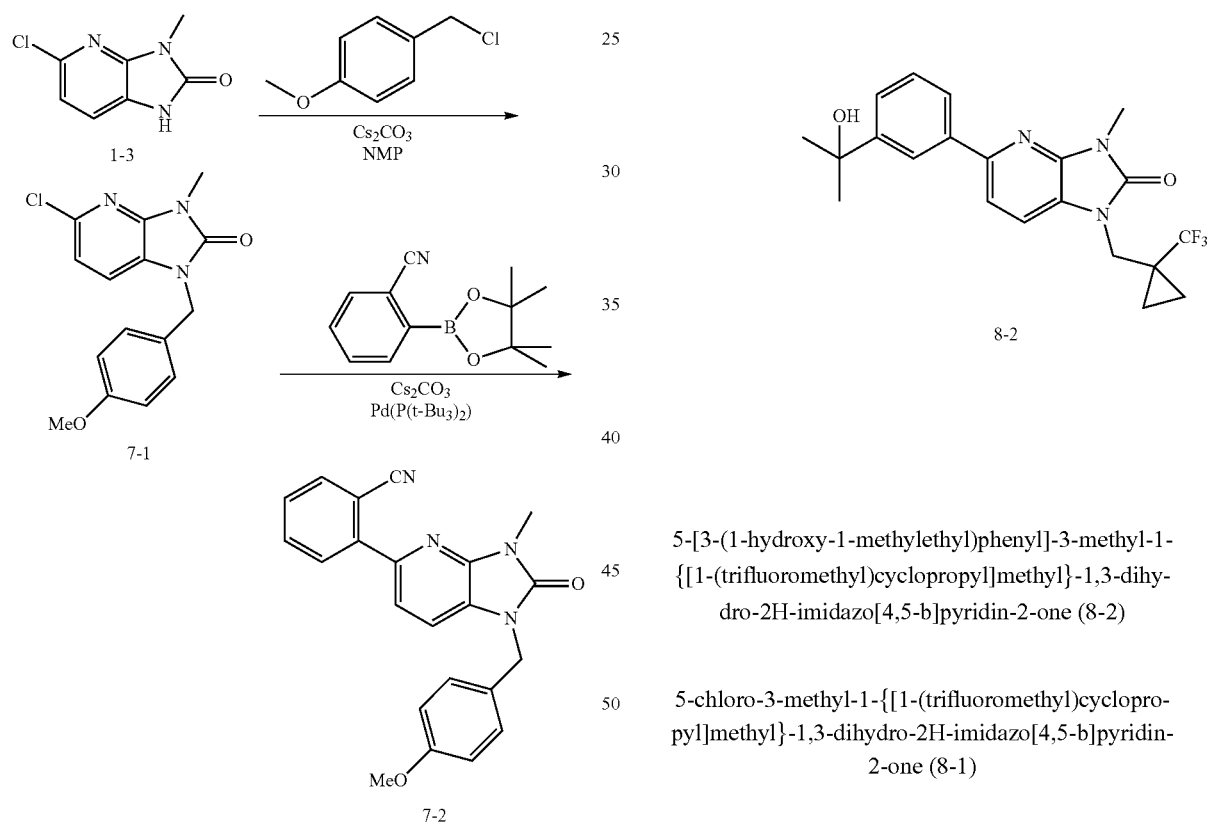

2-[1-(4-methoxybenzyl)-3-methyl-2-oxo-2,3-dihydro-1H-imidazo[4,5-b]pyridin-5-yl]benzonitrile (7-2)

Prepared from 7-2 according to the procedures reported in Scheme 1. HRMS (M+H)$^+$: observed=371.1500, calculated=371.1503.

SCHEME 8

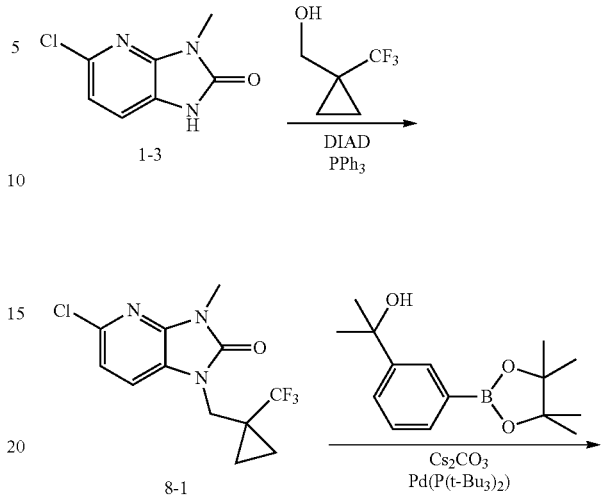

5-[3-(1-hydroxy-1-methylethyl)phenyl]-3-methyl-1-{[1-(trifluoromethyl)cyclopropyl]methyl}-1,3-dihydro-2H-imidazo[4,5-b]pyridin-2-one (8-2)

5-chloro-3-methyl-1-{[1-(trifluoromethyl)cyclopropyl]methyl}-1,3-dihydro-2H-imidazo[4,5-b]pyridin-2-one (8-1)

Prepared from 1-3 according to the procedures reported in Scheme 4. MS (M+H)$^+$: observed=306.1, calculated=306.7.

5-[3-(1-hydroxy-1-methylethyl)phenyl]-3-methyl-1-{[1-(trifluoromethyl)cyclopropyl]methyl}-1,3-dihydro-2H-imidazo[4,5-b]pyridin-2-one (8-2)

Prepared from 8-1 according to the procedures reported in Scheme 1. HRMS (M+H)$^+$: observed=406.1742, calculated=406.1737.

TABLE 3

The following compounds were prepared from 8-1 by a reaction sequence analogous to that illustrated in Scheme 8.

| Cmpd | Structure | IUPAC Name | Exact Mass [M + H]+ |
| --- | --- | --- | --- |
| 8-3 | 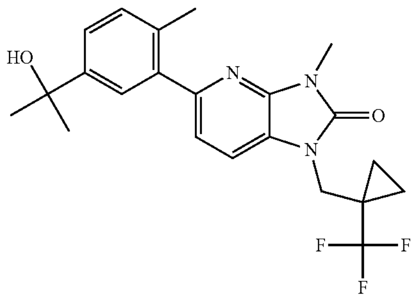 [SMILES: Cc1ccc(C(C)(C)O)cc1-c1ccc2c(n1)n(C)c(=O)n2CC1(C(F)(F)F)CC1] | 5-[5-(1-hydroxy-1-methylethyl)-2-methylphenyl]-3-methyl-1-{[1-(trifluoromethyl)cyclopropyl]methyl}-1,3-dihydro-2H-imidazo[4,5-b]pyridin-2-one | Calc'd 420.1893, found 420.1898 |
| 8-4 | 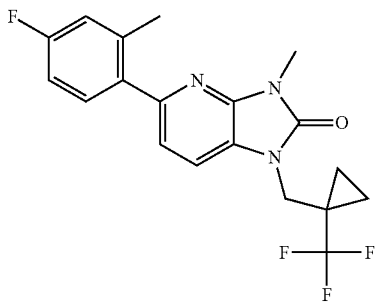 [SMILES: Cc1cc(F)ccc1-c1ccc2c(n1)n(C)c(=O)n2CC1(C(F)(F)F)CC1] | 5-(4-fluoro-2-methylphenyl)-3-methyl-1-{[1-(trifluoromethyl)cyclopropyl]methyl}-1,3-dihydro-2H-imidazo[4,5-b]pyridin-2-one | Calc'd 380.1381, found 380.1380 |
| 8-5 | 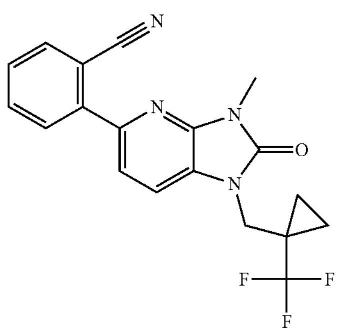 [SMILES: Cn1c(=O)n(CC2(C(F)(F)F)CC2)c2ccc(-c3ccccc3C#N)nc21] | 2-(3-methyl-2-oxo-1-{[1-(trifluoromethyl)cyclopropyl]methyl}-2,3-dihydro-1H-imidazo[4,5-b]pyridin-5-yl)benzonitrile | Calc'd 373.1271, found 373.1277 |
| 8-6 | 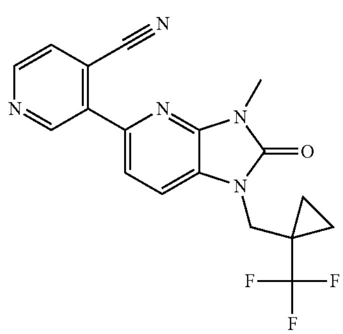 [SMILES: Cn1c(=O)n(CC2(C(F)(F)F)CC2)c2ccc(-c3cnccc3C#N)nc21] | 3-(3-methyl-2-oxo-1-{[1-(trifluoromethyl)cyclopropyl]methyl}-2,3-dihydro-1H-imidazo[4,5-b]pyridin-5-yl)pyridine-4-carbonitrile | Calc'd 374.1223, found 374.1228 |

SCHEME 9

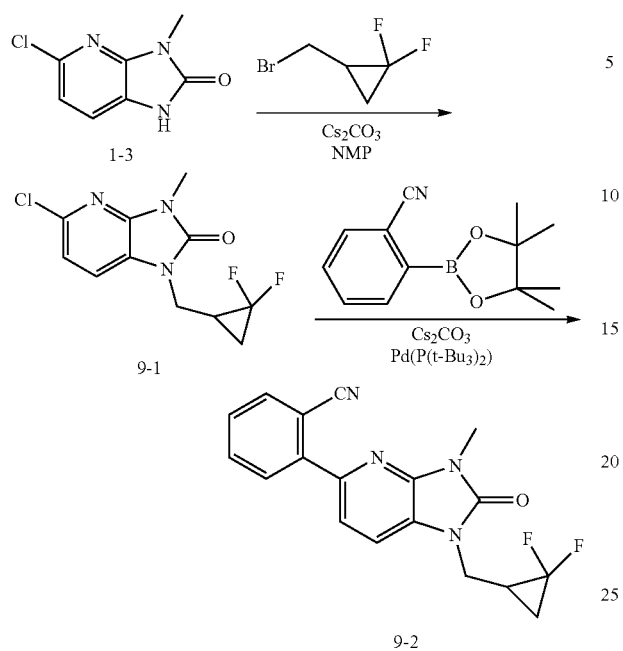

2-(1-{[2,2-difluorocyclopropyl]methyl}-3-methyl-2-oxo-2,3-dihydro-1H-imidazo[4,5-b]pyridin-5-yl)benzonitrile (9-2)

5-chloro-1-[(2,2-difluorocyclopropyl)methyl]-3-methyl-1,3-dihydro-2H-imidazo[4,5-b]pyridin-2-one (9-1)

Prepared from 1-3 according to the procedures reported in Scheme 1. MS (M+H)⁺: observed=274.1, calculated=274.7.

2-(1-{[2,2-difluorocyclopropyl]methyl}-3-methyl-2-oxo-2,3-dihydro-1H-imidazo[4,5-b]pyridin-5-yl)benzonitrile (9-2)

Prepared from 9-1 according to the procedures reported in Scheme 1. HRMS (M+H)⁺: observed=341.1205, calculated=341.1208.

TABLE 4

The following compounds were prepared from 9-1 by a reaction sequence analogous to that illustrated in Scheme 9.

| Cmpd | Structure | IUPAC Name | Exact Mass [M + H]+ |
|---|---|---|---|
| 9-3 | 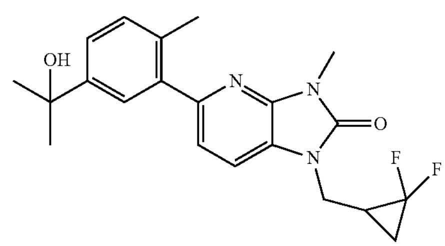 [SMILES: Cc1ccc(C(C)(C)O)cc1-c1ccc2c(n1)n(C)c(=O)n2CC1CC1(F)F] | 1-[(2,2-difluoro cyclopropyl)methyl]-5-[5-(1-hydroxy-1-methyl ethyl)-2-methyl phenyl]-3-methyl-1,3-dihydro-2H-imidazo[4,5-b]pyridin-2-one | Calc'd 388.1831, found 388.1831 |
| 9-4 | 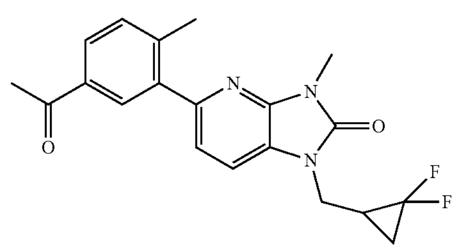 [SMILES: CC(=O)c1ccc(C)c(-c2ccc3c(n2)n(C)c(=O)n3CC2CC2(F)F)c1] | 5-(5-acetyl-2-methyl phenyl)-1-[(2,2-difluoro cyclopropyl)methyl]-3-methyl-1,3-dihydro-2H-imidazo[4,5-b]pyridin-2-one | Calc'd 372.1518, found 372.1519 |
| 9-5 | 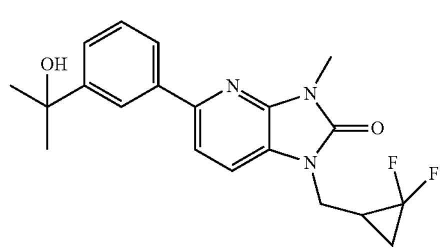 [SMILES: Cn1c(=O)n(CC2CC2(F)F)c2ccc(-c3cccc(C(C)(C)O)c3)nc21] | 1-[(2,2-difluoro cyclopropyl)methyl]-5-[3-(1-hydroxy-1-methylethyl) phenyl]-3-methyl-1,3-dihydro-2H-imidazo[4,5-b]pyridin-2-one | Calc'd 374.1675, found 374.1673 |

TABLE 4-continued

The following compounds were prepared from 9-1 by a reaction sequence analogous to that illustrated in Scheme 9.

| Cmpd | Structure | IUPAC Name | Exact Mass [M + H]+ |
|---|---|---|---|
| 9-6 | 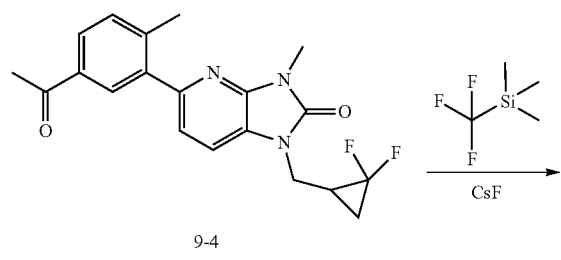 | methyl-3-{1-[(2,2-difluoro cyclopropyl)methyl]-3-methyl-2-oxo-2,3-dihydro-1H-imidazo[4,5-b]pyridin-5-yl}-4-methylbenzene | Calc'd 388.1, found 388.2 |

SCHEME 10

SCHEME 11

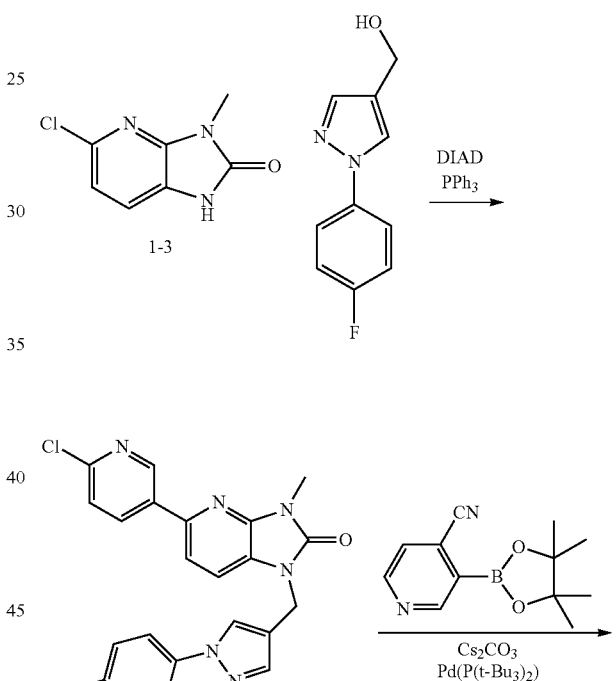

1-[(2,2-difluorocyclopropyl)methyl]-3-methyl-5-[2-methyl-5-(1,1,1-trifluoro-2-hydroxypropan-2-yl)phenyl]-1,3-dihydro-2H-imidazo[4,5-b]pyridin-2-one (10-1)

To a microwave vial, 5-(5-acetyl-2-methylphenyl)-1-{[(1R)-2,2-difluorocyclopropyl]methyl}-3-methyl-1,3-dihydro-2H-imidazo[4,5-b]pyridin-2-one (9-4) (25 mg, 0.067 mmol) and Cesium fluoride (21 mg, 0.135 mmol) were dissolved in DMF (0.35 mL). Trimethyl(trifluoromethyl)silane (54 uL, 0.34 mmol) was added dropwise and allowed to stir at room temperature for 30 minutes. The mixture was diluted with methanol and purified using reverse phase chromatography (10-100%, 0.1% TFA in H$_2$O/Acetonitrile); the desired fractions were collected and concentrated to produce racemic 1-[(2,2-difluorocyclopropyl)methyl]-3-methyl-5-[2-methyl-5-(1,1,1-trifluoro-2-hydroxypropan-2-yl)phenyl]-1,3-dihydro-2H-imidazo[4,5-b]pyridin-2-one (10-1). HRMS (M+H)$^+$: observed=442.1543, calculated=442.1548.

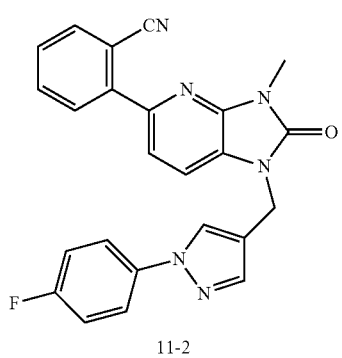

2-(1-{[1-(4-fluorophenyl)-1H-pyrazol-4-yl]methyl}-3-methyl-2-oxo-2,3-dihydro-1H-imidazo[4,5-b]pyridin-5-yl)benzonitrile (11-2)

5-chloro-1-{[1-(4-fluorophenyl)-1H-pyrazol-4-yl]methyl}-3-methyl-1,3-dihydro-2H-imidazo[4,5-b]pyridin-2-one (11-1)

Prepared from 1-3 according to the procedures reported in Scheme 4. MS (M+H)$^+$: observed=358.1, calculated=358.8.

2-(1-{[1-(4-fluorophenyl)-1H-pyrazol-4-yl]methyl}-3-methyl-2-oxo-2,3-dihydro-1H-imidazo[4,5-b]pyridin-5-yl)benzonitrile (11-2)

Prepared from 11-1 according to the procedures reported in Scheme 1. HRMS (M+H)$^+$: observed=425.1525, calculated=425.1521.

SCHEME 12

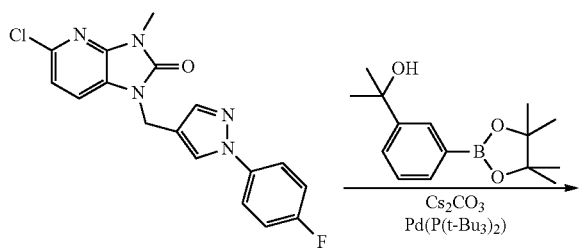

1-{[1-(4-fluorophenyl)-1H-pyrazol-4-yl]methyl}-5-[3-(1-hydroxy-1-methylethyl)phenyl]-3-methyl-1,3-dihydro-2H-imidazo[4,5-b]pyridin-2-one (12-1)

Prepared from 11-1 according to the procedures reported in Scheme 1. HRMS (M+H)$^+$: observed=458.1988, calculated=458.1987.

SCHEME 13

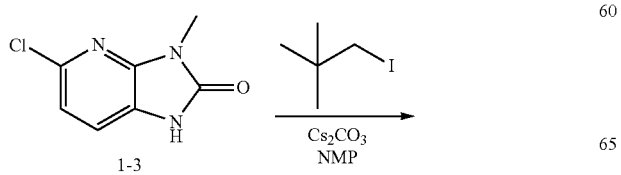

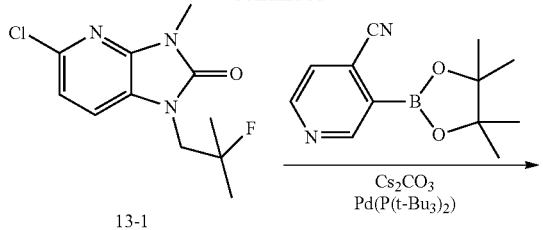

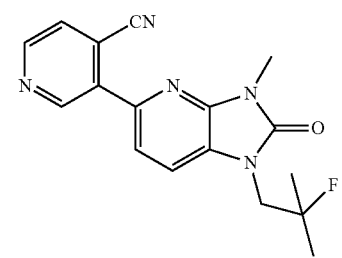

3-[1-(2-fluoro-2-methylpropyl)-3-methyl-2-oxo-2,3-dihydro-1H-imidazo[4,5-b]pyridin-5-yl]pyridine-4-carbonitrile (13-2)

Prepared from 1-3 according to the procedures reported in Scheme 1. MS (M+H)$^+$: observed=326.1, calculated=326.2.

SCHEME 14

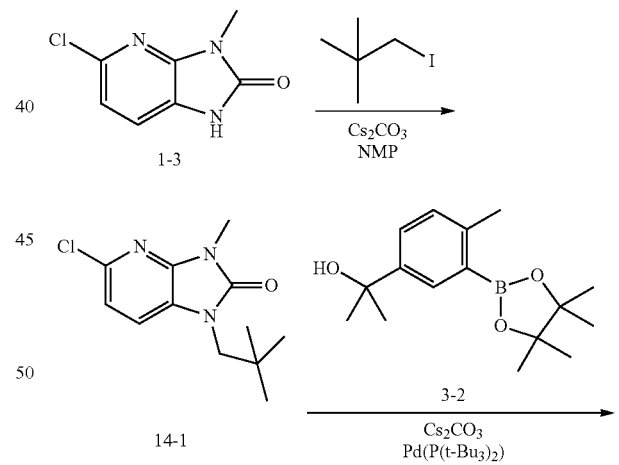

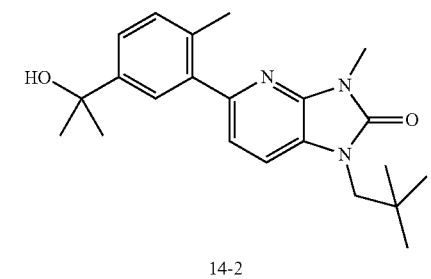

1-(2,2-dimethylpropyl)-5-[5-(1-hydroxy-1-methyl-ethyl)-2-methylphenyl]-3-methyl-1,3-dihydro-2H-imidazo[4,5-b]pyridin-2-one (14-2)

5-chloro-1-(2,2-dimethylpropyl)-3-methyl-1,3-dihydro-2H-imidazo[4,5-b]pyridin-2-one (14-1)

Prepared from 1-3 according to the procedures reported in Scheme 1. MS (M+H)+: observed=254.1, calculated=254.7.

1-(2,2-dimethylpropyl)-5-[5-(1-hydroxy-1-methyl-ethyl)-2-methylphenyl]-3-methyl-1,3-dihydro-2H-imidazo[4,5-b]pyridin-2-one (14-2)

Prepared from 14-1 and 3-2 according to the procedures reported in Scheme 1. HRMS (M+H)+: observed=368.2334, calculated=368.2333. $^1$H NMR (400 MHz, CD$_3$OD): δ 7.57 (d, J=8.0 Hz, 1H); 7.50 (d, J=2.0 Hz, 1H); 7.41 (dd, J=8.0, 2.1 Hz, 1H); 7.24 (d, J=8.0 Hz, 1H); 7.17 (d, J=8.0 Hz, 1H); 3.76 (s, 2H); 3.48 (s, 3H); 2.33 (s, 3H); 1.55 (s, 6H); 1.06 (s, 9H).

TABLE 5

The following compounds were prepared from 14-1 by a reaction sequence analogous to that illustrated in Scheme 14.

| Cmpd | Structure | IUPAC Name | Exact Mass [M + H]+ |
|---|---|---|---|
| 14-3 | 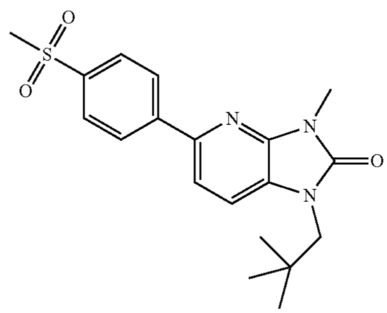 [SMILES: Cn1c(=O)n(CC(C)(C)C)c2ccc(-c3ccc(S(C)(=O)=O)cc3)nc21] | 1-(2,2-dimethylpropyl)-3-methyl-5-[4-(methylsulfonyl)phenyl]-1,3-dihydro-2H-imidazo[4,5-b]pyridin-2-one | Calc'd 374.1533, found 374.1538 |
| 14-4 | 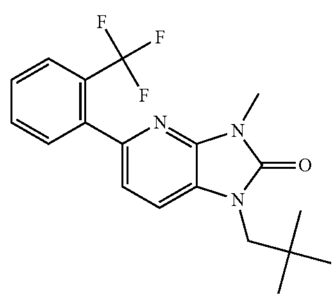 [SMILES: Cn1c(=O)n(CC(C)(C)C)c2ccc(-c3ccccc3C(F)(F)F)nc21] | 1-(2,2-dimethylpropyl)-3-methyl-5-[2-(trifluoromethyl)phenyl]-1,3-dihydro-2H-imidazo[4,5-b]pyridin-2-one | Calc'd 364.1631, found 364.1635 |
| 14-5 | 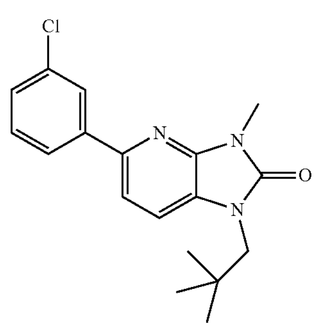 [SMILES: Cn1c(=O)n(CC(C)(C)C)c2ccc(-c3cccc(Cl)c3)nc21] | 5-(3-chlorophenyl)-1-(2,2-dimethylpropyl)-3-methyl-1,3-dihydro-2H-imidazo[4,5-b]pyridin-2-one | Calc'd 330.1368, found 330.1367 |
| 14-6 | 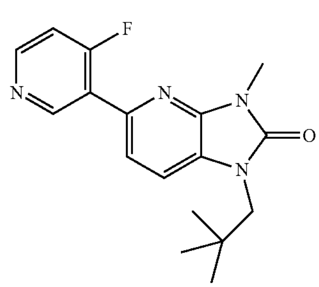 [SMILES: Cn1c(=O)n(CC(C)(C)C)c2ccc(-c3cnccc3F)nc21] | 1-(2,2-dimethylpropyl)-5-(4-fluoropyridin-3-yl)-3-methyl-1,3-dihydro-2H-imidazo[4,5-b]pyridin-2-one | Calc'd 315.1616, found 315.1613 |

TABLE 5-continued

The following compounds were prepared from 14-1 by a reaction sequence analogous to that illustrated in Scheme 14.

| Cmpd | Structure | IUPAC Name | Exact Mass [M + H]+ |
|---|---|---|---|
| 14-7 | 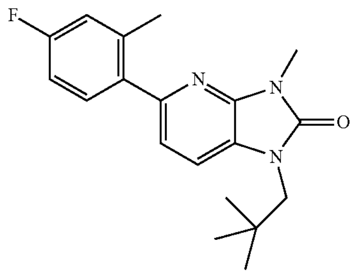 [SMILES: Cc1cc(F)ccc1-c1ccc2c(n1)n(C)c(=O)n2CC(C)(C)C] | 1-(2,2-dimethylpropyl)-5-(4-fluoro-2-methylphenyl)-3-methyl-1,3-dihydro-2H-imidazo[4,5-b]pyridin-2-one | Calc'd 328.1820, found 328.1816 |
| 14-8 | 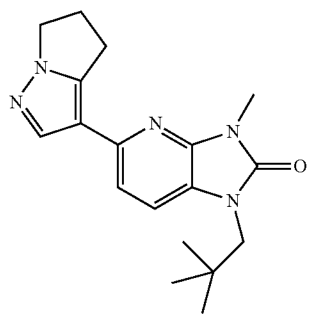 [SMILES: Cn1c(=O)n(CC(C)(C)C)c2ccc(-c3cnn4c3CCC4)nc21] | 5-(5,6-dihydro-4H-pyrrolo[1,2-b]pyrazol-3-yl)-1-(2,2-dimethylpropyl)-3-methyl-1,3-dihydro-2H-imidazo[4,5-b]pyridin-2-one | Calc'd 326.1975, found 326.1978 |
| 14-9 | 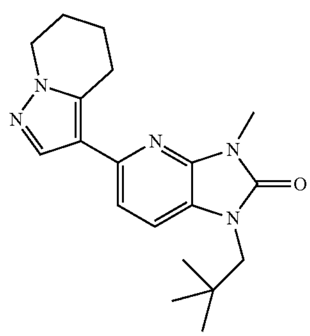 [SMILES: Cn1c(=O)n(CC(C)(C)C)c2ccc(-c3cnn4c3CCCC4)nc21] | 1-(2,2-dimethylpropyl)-3-methyl-5-(4,5,6,7-tetrahydropyrazolo[1,5-a]pyridin-3-yl)-1,3-dihydro-2H-imidazo[4,5-b]pyridin-2-one | Calc'd 340.2132, found 340.2132 |
| 14-10 | 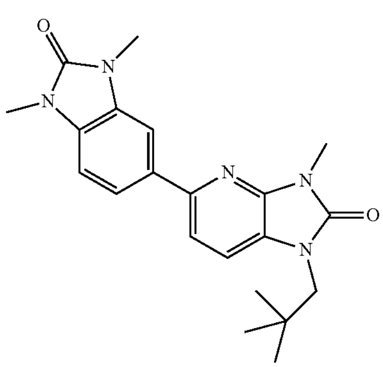 [SMILES: Cn1c(=O)n(C)c2cc(-c3ccc4c(n3)n(C)c(=O)n4CC(C)(C)C)ccc21] | 5-(1,3-dimethyl-2-oxo-2,3-dihydro-1H-benzimidazol-5-yl)-1-(2,2-dimethylpropyl)-3-methyl-1,3-dihydro-2H-imidazo[4,5-b]pyridin-2-one | Calc'd 380.2081, found 380.2082 |

TABLE 5-continued

The following compounds were prepared from 14-1 by a reaction sequence analogous to that illustrated in Scheme 14.

| Cmpd | Structure | IUPAC Name | Exact Mass [M + H]+ |
| --- | --- | --- | --- |
| 14-11 | 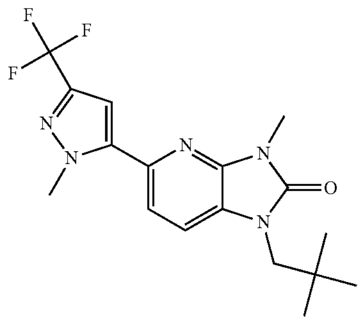 [SMILES: Cn1nc(C(F)(F)F)cc1-c1ccc2c(n1)n(C)c(=O)n2CC(C)(C)C] | 1-(2,2-dimethylpropyl)-3-methyl-5-[1-methyl-3-(trifluoromethyl)-1H-pyrazol-5-yl]-1,3-dihydro-2H-imidazo[4,5-b]pyridin-2-one | Calc'd 368.1693, found 368.1690 |
| 14-12 | 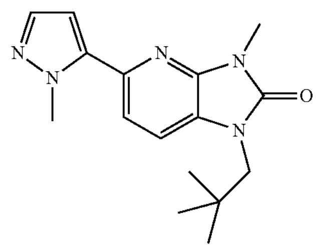 [SMILES: Cn1nccc1-c1ccc2c(n1)n(C)c(=O)n2CC(C)(C)C] | 1-(2,2-dimethylpropyl)-3-methyl-5-(1-methyl-1H-pyrazol-5-yl)-1,3-dihydro-2H-imidazo[4,5-b]pyridin-2-one | Calc'd 300.1819, found 300.1817 |
| 14-13 | 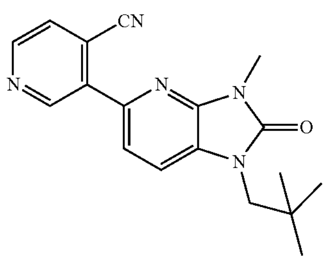 [SMILES: Cn1c(=O)n(CC(C)(C)C)c2ccc(-c3cnccc3C#N)nc21] | 3-[1-(2,2-dimethylpropyl)-3-methyl-2-oxo-2,3-dihydro-1H-imidazo[4,5-b]pyridin-5-yl]pyridine-4-carbonitrile | Calc'd 322.1662, found 322.1662 |
| 14-14 | 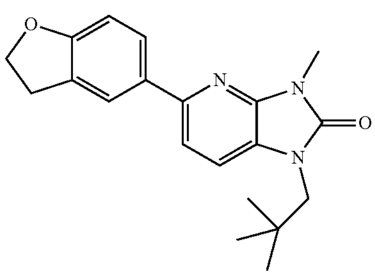 [SMILES: Cn1c(=O)n(CC(C)(C)C)c2ccc(-c3ccc4c(c3)CCO4)nc21] | 5-(2,3-dihydro-1-benzofuran-5-yl)-1-(2,2-dimethylpropyl)-3-methyl-1,3-dihydro-2H-imidazo[4,5-b]pyridin-2-one | Calc'd 338.1863, found 338.1863 |
| 14-15 | 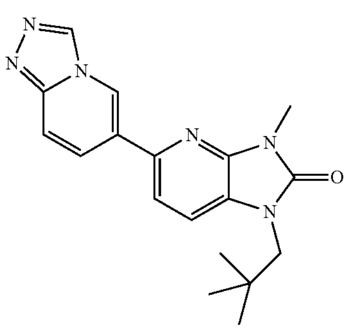 [SMILES: Cn1c(=O)n(CC(C)(C)C)c2ccc(-c3ccc4nncn4c3)nc21] | 1-(2,2-dimethylpropyl)-3-methyl-5-[1,2,4]triazolo[4,3-a]pyridin-6-yl-1,3-dihydro-2H-imidazo[4,5-b]pyridin-2-one | Calc'd 337.1771, found 337.1773 |

TABLE 5-continued

The following compounds were prepared from 14-1 by a reaction sequence analogous to that illustrated in Scheme 14.

| Cmpd | Structure | IUPAC Name | Exact Mass [M + H]+ |
|---|---|---|---|
| 14-16 | 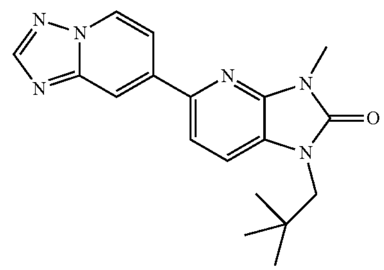 [SMILES: Cn1c(=O)n(CC(C)(C)C)c2ccc(-c3ccn4ncnc4c3)nc21] | 1-(2,2-dimethylpropyl)-3-methyl-5-[1,2,4]triazolo[1,5-a]pyridin-7-yl-1,3-dihydro-2H-imidazo[4,5-b]pyridin-2-one | Calc'd 337.1771, found 337.1773 |
| 14-17 | 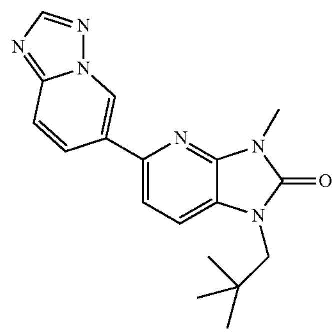 [SMILES: Cn1c(=O)n(CC(C)(C)C)c2ccc(-c3ccc4ncnn4c3)nc21] | 1-(2,2-dimethylpropyl)-3-methyl-5-[1,2,4]triazolo[1,5-a]pyridin-6-yl-1,3-dihydro-2H-imidazo[4,5-b]pyridin-2-one | Calc'd 337.1771, found 337.1772 |
| 14-18 | 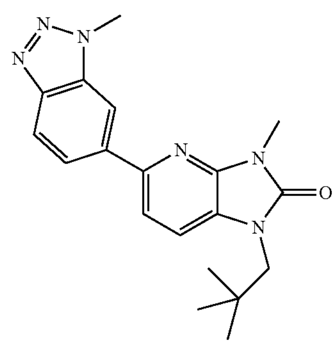 [SMILES: Cn1nnc2ccc(-c3ccc4c(n3)n(C)c(=O)n4CC(C)(C)C)cc21] | 1-(2,2-dimethylpropyl)-3-methyl-5-(1-methyl-1H-benzotriazol-6-yl)-1,3-dihydro-2H-imidazo[4,5-b]pyridin-2-one | Calc'd 351.1928, found 351.1927 |
| 14-19 | 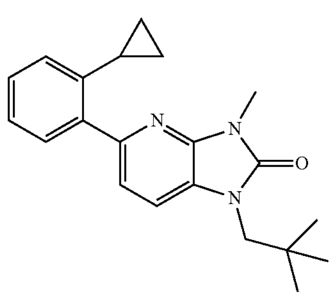 [SMILES: Cn1c(=O)n(CC(C)(C)C)c2ccc(-c3ccccc3C3CC3)nc21] | 5-(2-cyclopropylphenyl)-1-(2,2-dimethylpropyl)-3-methyl-1,3-dihydro-2H-imidazo[4,5-b]pyridin-2-one | Calc'd 336.2070, found 336.2068 |
| 14-20 | 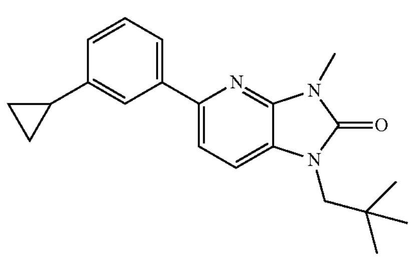 [SMILES: Cn1c(=O)n(CC(C)(C)C)c2ccc(-c3cccc(C4CC4)c3)nc21] | 5-(3-cyclopropylphenyl)-1-(2,2-dimethylpropyl)-3-methyl-1,3-dihydro-2H-imidazo[4,5-b]pyridin-2-one | Calc'd 336.2070, found 336.2069 |

TABLE 5-continued

The following compounds were prepared from 14-1 by a reaction sequence analogous to that illustrated in Scheme 14.

| Cmpd | Structure | IUPAC Name | Exact Mass [M + H]+ |
| --- | --- | --- | --- |
| 14-21 | 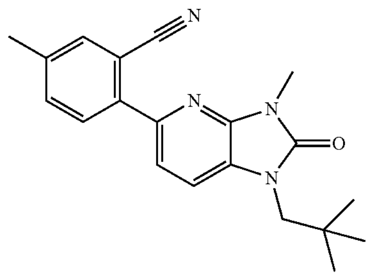 [SMILES: Cc1ccc(-c2ccc3c(n2)n(C)c(=O)n3CC(C)(C)C)c(C#N)c1] | 2-[1-(2,2-dimethylpropyl)-3-methyl-2-oxo-2,3-dihydro-1H-imidazo[4,5-b]pyridin-5-yl]-5-methylbenzonitrile | Calc'd 335.1866, found 335.1863 |
| 14-22 | 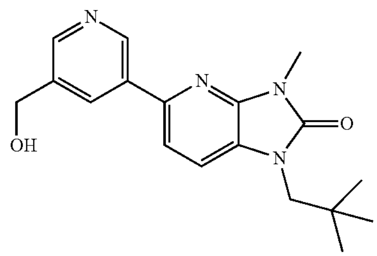 [SMILES: Cn1c(=O)n(CC(C)(C)C)c2ccc(-c3cncc(CO)c3)nc21] | 1-(2,2-dimethylpropyl)-5-[5-(hydroxymethyl)pyridin-3-yl]-3-methyl-1,3-dihydro-2H-imidazo[4,5-b]pyridin-2-one | Calc'd 327.1816, found 327.1814 |
| 14-23 | 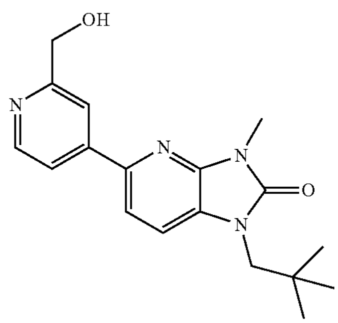 [SMILES: Cn1c(=O)n(CC(C)(C)C)c2ccc(-c3ccnc(CO)c3)nc21] | 1-(2,2-dimethylpropyl)-5-[2-(hydroxymethyl)pyridin-4-yl]-3-methyl-1,3-dihydro-2H-imidazo[4,5-b]pyridin-2-one | Calc'd 327.1816, found 327.1814 |
| 14-24 | 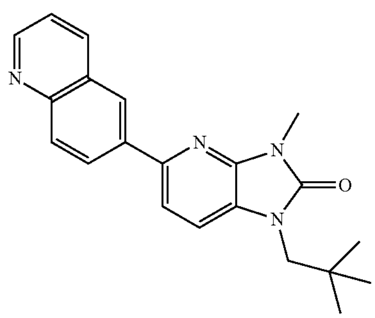 [SMILES: Cn1c(=O)n(CC(C)(C)C)c2ccc(-c3ccc4ncccc4c3)nc21] | 1-(2,2-dimethylpropyl)-3-methyl-5-quinolin-6-yl-1,3-dihydro-2H-imidazo[4,5-b]pyridin-2-one | Calc'd 347.1866, found 347.1864 |
| 14-25 | 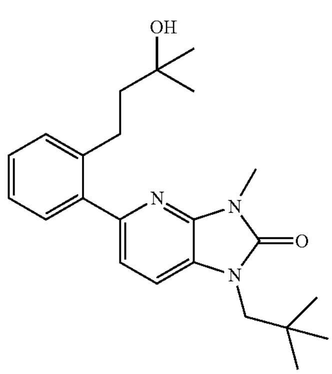 [SMILES: Cn1c(=O)n(CC(C)(C)C)c2ccc(-c3ccccc3CCC(C)(C)O)nc21] | 1-(2,2-dimethylpropyl)-5-[2-(3-hydroxy-3-methylbutyl)phenyl]-3-methyl-1,3-dihydro-2H-imidazo[4,5-b]pyridin-2-one | Calc'd 382.2489, found 382.2483 |

TABLE 5-continued

The following compounds were prepared from 14-1 by a reaction sequence analogous to that illustrated in Scheme 14.

| Cmpd | Structure | IUPAC Name | Exact Mass [M + H]+ |
| --- | --- | --- | --- |
| 14-26 | 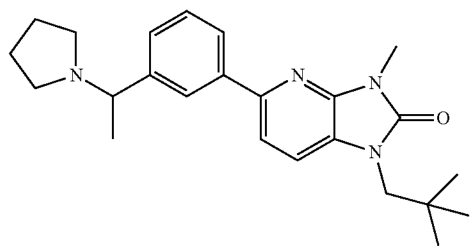 [SMILES: CC(c1cccc(-c2ccc3c(n2)n(C)c(=O)n3CC(C)(C)C)c1)N1CCCC1] | 1-(2,2-dimethylpropyl)-3-methyl-5-[3-(1-pyrrolidin-1-ylethyl)phenyl]-1,3-dihydro-2H-imidazo[4,5-b]pyridin-2-one | Calc'd 393.2648, found 393.2649 |
| 14-27 | 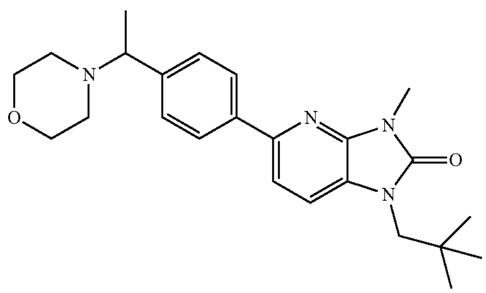 [SMILES: CC(c1ccc(-c2ccc3c(n2)n(C)c(=O)n3CC(C)(C)C)cc1)N1CCOCC1] | 1-(2,2-dimethylpropyl)-3-methyl-5-[4-(1-morpholin-4-ylethyl)phenyl]-1,3-dihydro-2H-imidazo[4,5-b]pyridin-2-one | Calc'd 409.2598, found 409.2597 |
| 14-28 | 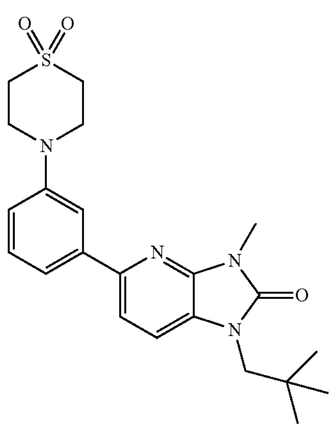 [SMILES: Cn1c(=O)n(CC(C)(C)C)c2ccc(-c3cccc(N4CCS(=O)(=O)CC4)c3)nc21] | 1-(2,2-dimethylpropyl)-5-[3-(1,1-dioxidothiomorpholin-4-yl)phenyl]-3-methyl-1,3-dihydro-2H-imidazo[4,5-b]pyridin-2-one | Calc'd 429.1955, found 429.1948 |
| 14-29 | 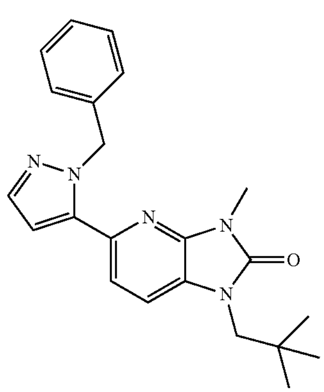 [SMILES: Cn1c(=O)n(CC(C)(C)C)c2ccc(-c3ccnn3Cc3ccccc3)nc21] | 5-(1-benzyl-1H-pyrazol-5-yl)-1-(2,2-dimethylpropyl)-3-methyl-1,3-dihydro-2H-imidazo[4,5-b]pyridin-2-one | Calc'd 376.2132, found 376.2129 |

TABLE 5-continued

The following compounds were prepared from 14-1 by a reaction sequence analogous to that illustrated in Scheme 14.

| Cmpd | Structure | IUPAC Name | Exact Mass [M + H]+ |
| --- | --- | --- | --- |
| 14-30 | 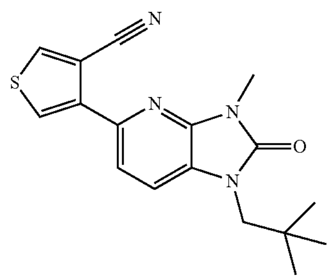 [SMILES: Cn1c(=O)n(CC(C)(C)C)c2ccc(-c3cscc3C#N)nc21] | 4-[1-(2,2-dimethylpropyl)-3-methyl-2-oxo-2,3-dihydro-1H-imidazo[4,5-b]pyridin-5-yl]thiophene-3-carbonitrile | Calc'd 327.1274, found 327.1272 |
| 14-31 | 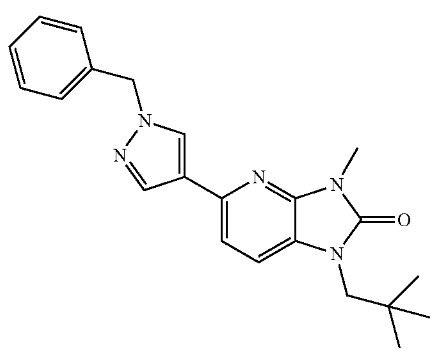 [SMILES: Cn1c(=O)n(CC(C)(C)C)c2ccc(-c3cnn(Cc4ccccc4)c3)nc21] | 5-(1-benzyl-1H-pyrazol-4-yl)-1-(2,2-dimethylpropyl)-3-methyl-1,3-dihydro-2H-imidazo[4,5-b]pyridin-2-one | Calc'd 376.2132, found 376.2128 |
| 14-32 | 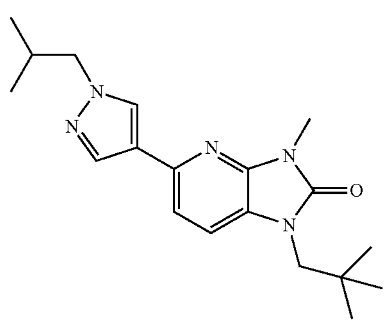 [SMILES: CC(C)Cn1cc(-c2ccc3c(n2)n(C)c(=O)n3CC(C)(C)C)cn1] | 1-(2,2-dimethylpropyl)-3-methyl-5-[1-(2-methylpropyl)-1H-pyrazol-4-yl]-1,3-dihydro-2H-imidazo[4,5-b]pyridin-2-one | Calc'd 342.2288, found 342.2286 |
| 14-33 | 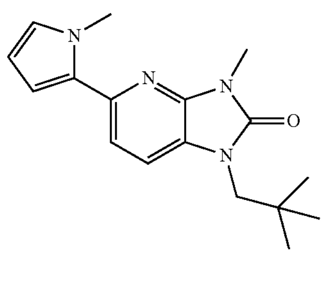 [SMILES: Cn1cccc1-c1ccc2c(n1)n(C)c(=O)n2CC(C)(C)C] | 1-(2,2-dimethylpropyl)-3-methyl-5-(1-methyl-1H-pyrrol-3-yl)-1,3-dihydro-2H-imidazo[4,5-b]pyridin-2-one | Calc'd 299.1866, found 299.1863 |

TABLE 5-continued

The following compounds were prepared from 14-1 by a reaction sequence analogous to that illustrated in Scheme 14.

| Cmpd | Structure | IUPAC Name | Exact Mass [M + H]+ |
|---|---|---|---|
| 14-34 | 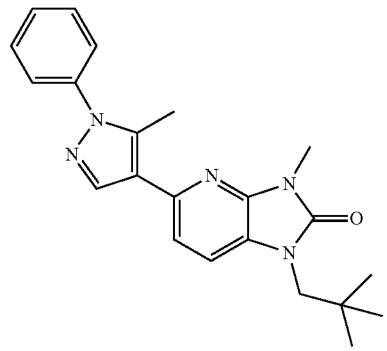 [SMILES: Cc1c(-c2ccc3c(n2)n(C)c(=O)n3CC(C)(C)C)cnn1-c1ccccc1] | 1-(2,2-dimethylpropyl)-3-methyl-5-(5-methyl-1-phenyl-1H-pyrazol-4-yl)-1,3-dihydro-2H-imidazo[4,5-b]pyridin-2-one | Calc'd 376.2132, found 376.2130 |
| 14-35 | 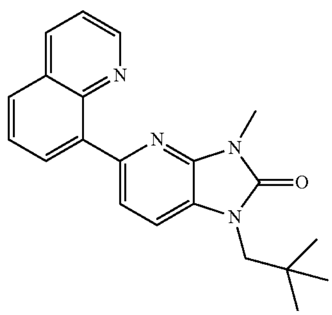 [SMILES: Cn1c(=O)n(CC(C)(C)C)c2ccc(-c3cccc4cccnc34)nc21] | 1-(2,2-dimethylpropyl)-3-methyl-5-quinolin-8-yl-1,3-dihydro-2H-imidazo[4,5-b]pyridin-2-one | Calc'd 347.1866, found 347.1863 |
| 14-36 | 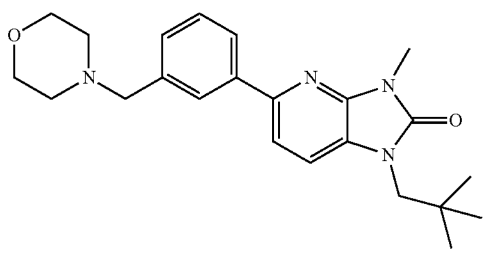 [SMILES: Cn1c(=O)n(CC(C)(C)C)c2ccc(-c3cccc(CN4CCOCC4)c3)nc21] | 1-(2,2-dimethylpropyl)-3-methyl-5-[3-(morpholin-4-ylmethyl)phenyl]-1,3-dihydro-2H-imidazo[4,5-b]pyridin-2-one | Calc'd 395.2442, found 395.2441 |
| 14-37 | 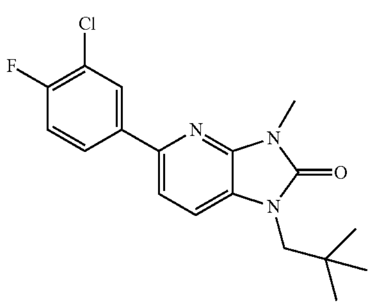 [SMILES: Cn1c(=O)n(CC(C)(C)C)c2ccc(-c3ccc(F)c(Cl)c3)nc21] | 5-(3-chloro-4-fluorophenyl)-1-(2,2-dimethylpropyl)-3-methyl-1,3-dihydro-2H-imidazo[4,5-b]pyridin-2-one | Calc'd 348.1273, found 348.1269 |
| 14-38 | 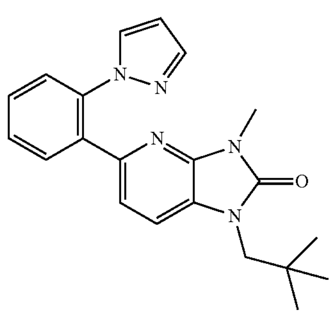 [SMILES: Cn1c(=O)n(CC(C)(C)C)c2ccc(-c3ccccc3-n3cccn3)nc21] | 1-(2,2-dimethylpropyl)-3-methyl-5-[2-(1H-pyrazol-1-yl)phenyl]-1,3-dihydro-2H-imidazo[4,5-b]pyridin-2-one | Calc'd 362.1975, found 362.1972 |

TABLE 5-continued

The following compounds were prepared from 14-1 by a reaction sequence analogous to that illustrated in Scheme 14.

| Cmpd | Structure | IUPAC Name | Exact Mass [M + H]+ |
|---|---|---|---|
| 14-39 | 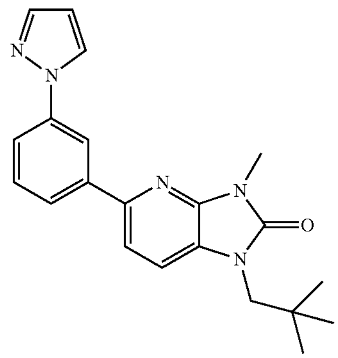 [SMILES: Cn1c(=O)n(CC(C)(C)C)c2ccc(-c3cccc(-n4cccn4)c3)nc21] | 1-(2,2-dimethylpropyl)-3-methyl-5-[3-(1H-pyrazol-1-yl)phenyl]-1,3-dihydro-2H-imidazo[4,5-b]pyridin-2-one | Calc'd 362.1975, found 362.1975 |
| 14-40 | 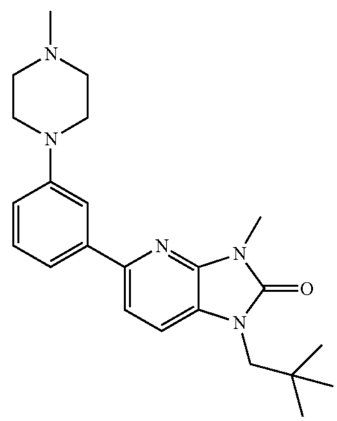 [SMILES: CN1CCN(c2cccc(-c3ccc4c(n3)n(C)c(=O)n4CC(C)(C)C)c2)CC1] | 1-(2,2-dimethylpropyl)-3-methyl-5-[3-(4-methylpiperazin-1-yl)phenyl]-1,3-dihydro-2H-imidazo[4,5-b]pyridin-2-one | Calc'd 394.2601, found 394.2600 |
| 14-41 | 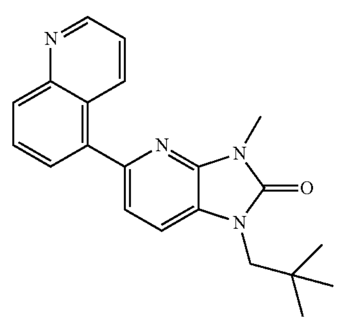 [SMILES: Cn1c(=O)n(CC(C)(C)C)c2ccc(-c3cccc4ncccc34)nc21] | 1-(2,2-dimethylpropyl)-3-methyl-5-quinolin-5-yl-1,3-dihydro-2H-imidazo[4,5-b]pyridin-2-one | Calc'd 347.1866, found 347.1863 |
| 14-42 | 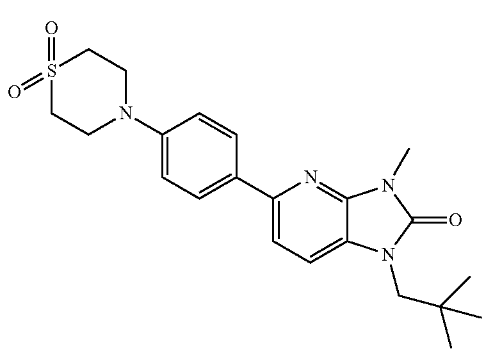 [SMILES: Cn1c(=O)n(CC(C)(C)C)c2ccc(-c3ccc(N4CCS(=O)(=O)CC4)cc3)nc21] | 1-(2,2-dimethylpropyl)-5-[4-(1,1-dioxidothiomorpholin-4-yl)phenyl]-3-methyl-1,3-dihydro-2H-imidazo[4,5-b]pyridin-2-one | Calc'd 429.1955, found 429.1950 |

TABLE 5-continued

The following compounds were prepared from 14-1 by a reaction sequence analogous to that illustrated in Scheme 14.

| Cmpd | Structure | IUPAC Name | Exact Mass [M + H]+ |
|---|---|---|---|
| 14-43 | 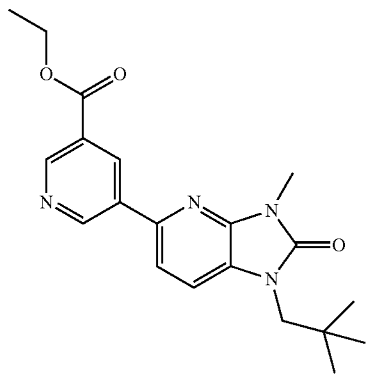 [SMILES: CCOC(=O)c1cncc(-c2ccc3c(n2)n(C)c(=O)n3CC(C)(C)C)c1] | ethyl 5-[1-(2,2-dimethylpropyl)-3-methyl-2-oxo-2,3-dihydro-1H-imidazo[4,5-b]pyridin-5-yl]pyridine-3-carboxylate | Calc'd 369.1921, found 369.1922 |
| 14-44 | 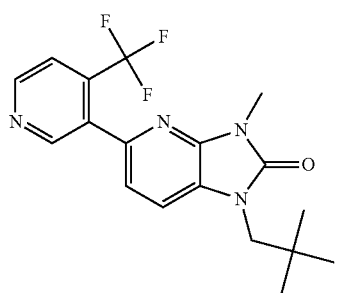 [SMILES: Cn1c(=O)n(CC(C)(C)C)c2ccc(-c3cnccc3C(F)(F)F)nc21] | 1-(2,2-dimethylpropyl)-3-methyl-5-[4-(trifluoromethyl)pyridin-3-yl]-1,3-dihydro-2H-imidazo[4,5-b]pyridin-2-one | Calc'd 365.1584, found 365.1587 |
| 14-45 | 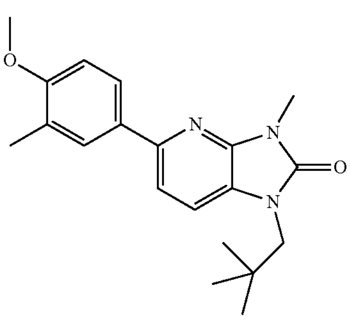 [SMILES: COc1ccc(-c2ccc3c(n2)n(C)c(=O)n3CC(C)(C)C)cc1C] | 1-(2,2-dimethylpropyl)-5-(4-methoxy-3-methylphenyl)-3-methyl-1,3-dihydro-2H-imidazo[4,5-b]pyridin-2-one | Calc'd 340.2020, found 340.2021 |
| 14-46 | 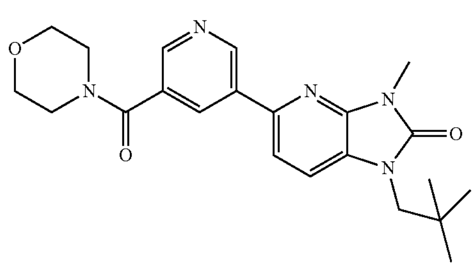 [SMILES: Cn1c(=O)n(CC(C)(C)C)c2ccc(-c3cncc(C(=O)N4CCOCC4)c3)nc21] | 1-(2,2-dimethylpropyl)-3-methyl-5-[5-(morpholin-4-ylcarbonyl)pyridin-3-yl]-1,3-dihydro-2H-imidazo[4,5-b]pyridin-2-one | Calc'd 410.2187, found 410.2195 |

TABLE 5-continued

The following compounds were prepared from 14-1 by a reaction sequence analogous to that illustrated in Scheme 14.

| Cmpd | Structure | IUPAC Name | Exact Mass [M + H]+ |
| --- | --- | --- | --- |
| 14-47 | 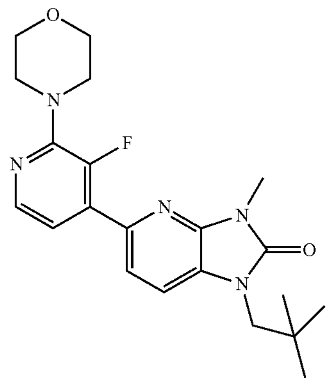 [SMILES: Cn1c(=O)n(CC(C)(C)C)c2ccc(-c3ccnc(N4CCOCC4)c3F)nc21] | 1-(2,2-dimethylpropyl)-5-(3-fluoro-2-morpholin-4-ylpyridin-4-yl)-3-methyl-1,3-dihydro-2H-imidazo[4,5-b]pyridin-2-one | Calc'd 400.2143, found 400.2145 |
| 14-48 | 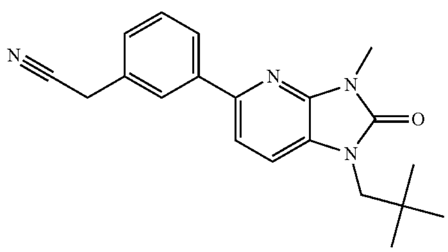 [SMILES: Cn1c(=O)n(CC(C)(C)C)c2ccc(-c3cccc(CC#N)c3)nc21] | {3-[1-(2,2-dimethylpropyl)-3-methyl-2-oxo-2,3-dihydro-1H-imidazo[4,5-b]pyridin-5-yl]phenyl}acetonitrile | Calc'd 335.1866, found 335.1869 |
| 14-49 | 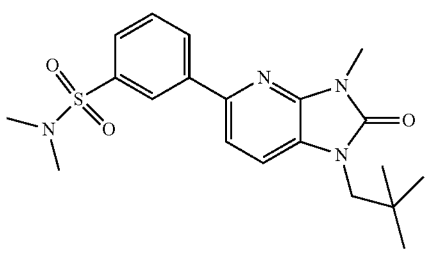 [SMILES: CN(C)S(=O)(=O)c1cccc(-c2ccc3c(n2)n(C)c(=O)n3CC(C)(C)C)c1] | 3-[1-(2,2-dimethylpropyl)-3-methyl-2-oxo-2,3-dihydro-1H-imidazo[4,5-b]pyridin-5-yl]-N,N-dimethylbenzene-sulfonamide | Calc'd 403.1798, found 403.1802 |
| 14-50 | 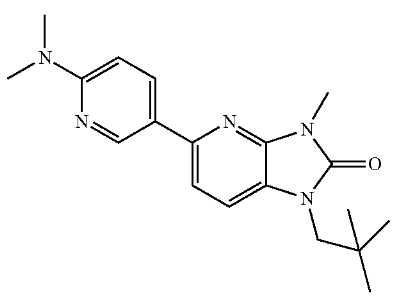 [SMILES: CN(C)c1ccc(-c2ccc3c(n2)n(C)c(=O)n3CC(C)(C)C)cn1] | 5-[6-(dimethylamino)pyridin-3-yl]-1-(2,2-dimethylpropyl)-3-methyl-1,3-dihydro-2H-imidazo[4,5-b]pyridin-2-one | Calc'd 340.2132, found 340.2132 |
| 14-51 | 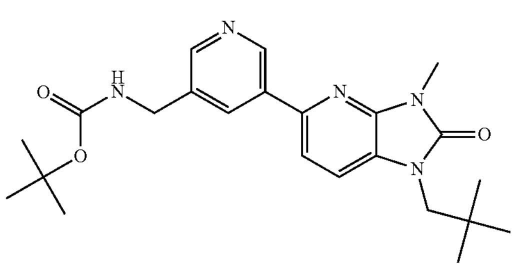 [SMILES: Cn1c(=O)n(CC(C)(C)C)c2ccc(-c3cncc(CNC(=O)OC(C)(C)C)c3)nc21] | tert-butyl ({5-[1-(2,2-dimethylpropyl)-3-methyl-2-oxo-2,3-dihydro-1H-imidazo[4,5-b]pyridin-5-yl]pyridine-3-yl}methyl)carbamate | Calc'd 426.2500, found 426.2501 |

TABLE 5-continued

The following compounds were prepared from 14-1 by a reaction sequence
analogous to that illustrated in Scheme 14.

| Cmpd | Structure | IUPAC Name | Exact Mass [M + H]+ |
| --- | --- | --- | --- |
| 14-52 | 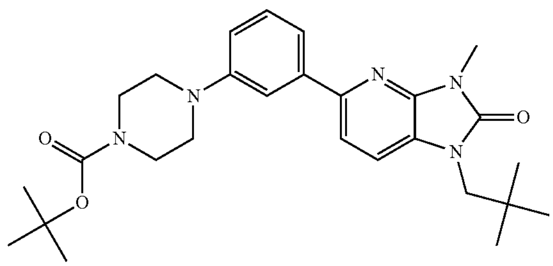 [SMILES: Cn1c(=O)n(CC(C)(C)C)c2ccc(-c3cccc(N4CCN(C(=O)OC(C)(C)C)CC4)c3)nc21] | tert-butyl 4-{3-[1-(2,2-dimethylpropyl)-3-methyl-2-oxo-2,3-dihydro-1H-imidazo[4,5-b]pyridin-5-yl]phenyl}piperazine-1-carboxylate | Calc'd 480.2969, found 480.2972 |
| 14-53 | 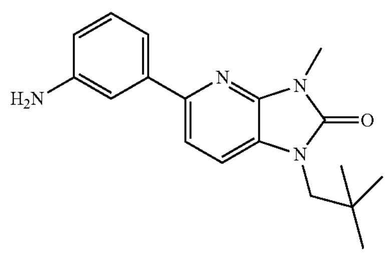 [SMILES: Cn1c(=O)n(CC(C)(C)C)c2ccc(-c3cccc(N)c3)nc21] | 5-(3-aminophenyl)-1-(2,2-dimethylpropyl)-3-methyl-1,3-dihydro-2H-imidazo[4,5-b]pyridin-2-one | Calc'd 311.1866, found 311.1874 |
| 14-54 | 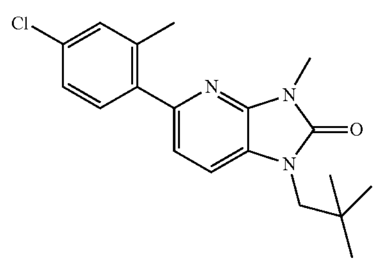 [SMILES: Cc1cc(Cl)ccc1-c1ccc2c(n1)n(C)c(=O)n2CC(C)(C)C] | 5-(4-chloro-2-methylphenyl)-1-(2,2-dimethylpropyl)-3-methyl-1,3-dihydro-2H-imidazo[4,5-b]pyridin-2-one | Calc'd 344.1524, found 344.1528 |
| 14-55 | 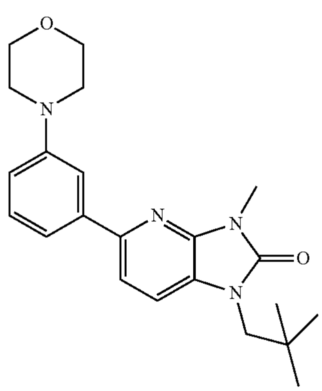 [SMILES: Cn1c(=O)n(CC(C)(C)C)c2ccc(-c3cccc(N4CCOCC4)c3)nc21] | 1-(2,2-dimethylpropyl)-3-methyl-5-(3-morpholin-4-ylphenyl)-1,3-dihydro-2H-imidazo[4,5-b]pyridin-2-one | Calc'd 381.2285, found 381.2290 |

TABLE 5-continued

The following compounds were prepared from 14-1 by a reaction sequence analogous to that illustrated in Scheme 14.

| Cmpd | Structure | IUPAC Name | Exact Mass [M + H]+ |
|---|---|---|---|
| 14-56 | 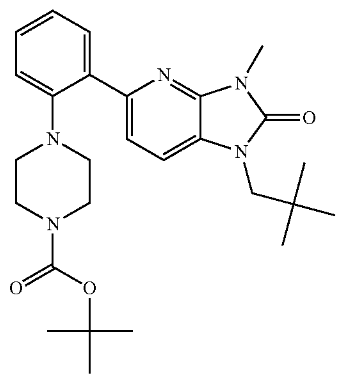 [SMILES: Cn1c(=O)n(CC(C)(C)C)c2ccc(-c3ccccc3N3CCN(C(=O)OC(C)(C)C)CC3)nc21] | tert-butyl 4-{2-[1-(2,2-dimethylpropyl)-3-methyl-2-oxo-2,3-dihydro-1H-imidazo[4,5-b]pyridin-5-yl]phenyl}piperazine-1-carboxylate | Calc'd 480.2969, found 480.2980 |
| 14-57 | 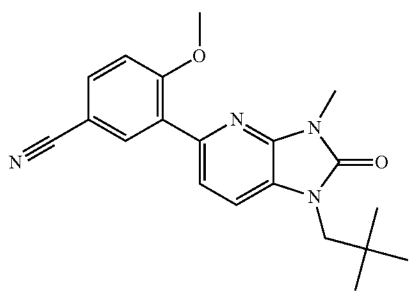 [SMILES: COc1ccc(C#N)cc1-c1ccc2c(n1)n(C)c(=O)n2CC(C)(C)C] | 3-[1-(2,2-dimethylpropyl)-3-methyl-2-oxo-2,3-dihydro-1H-imidazo[4,5-b]pyridin-5-yl]-4-methoxybenzonitrile | Calc'd 351.1816, found 351.1824 |
| 14-58 | 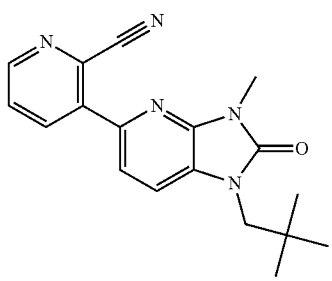 [SMILES: Cn1c(=O)n(CC(C)(C)C)c2ccc(-c3cccnc3C#N)nc21] | 3-[1-(2,2-dimethylpropyl)-3-methyl-2-oxo-2,3-dihydro-1H-imidazo[4,5-b]pyridin-5-yl]pyridine-2-carbonitrile | Calc'd 322.1662, found 322.1657 |
| 14-59 | 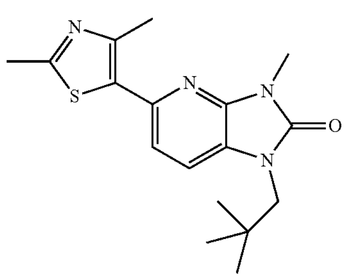 [SMILES: Cc1nc(C)c(-c2ccc3c(n2)n(C)c(=O)n3CC(C)(C)C)s1] | 1-(2,2-dimethylpropyl)-5-(2,4-dimethyl-1,3-thiazol-5-yl)-3-methyl-1,3-dihydro-2H-imidazo[4,5-b]pyridin-2-one | Calc'd 331.1587, found 331.1587 |
| 14-60 | 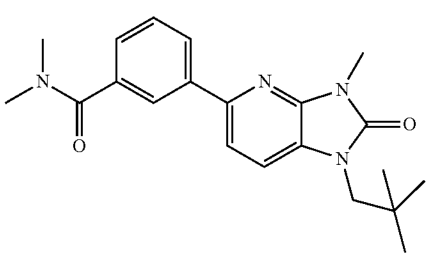 [SMILES: CN(C)C(=O)c1cccc(-c2ccc3c(n2)n(C)c(=O)n3CC(C)(C)C)c1] | 3-[1-(2,2-dimethylpropyl)-3-methyl-2-oxo-2,3-dihydro-1H-imidazo[4,5-b]pyridin-5-yl]-N,N-dimethylbenzamide | Calc'd 367.2129, found 367.2127 |

TABLE 5-continued

The following compounds were prepared from 14-1 by a reaction sequence analogous to that illustrated in Scheme 14.

| Cmpd | Structure | IUPAC Name | Exact Mass [M + H]+ |
|---|---|---|---|
| 14-61 | 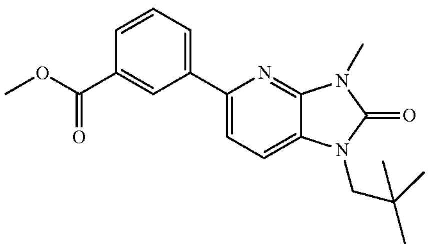 [SMILES: COC(=O)c1cccc(-c2ccc3c(n2)n(C)c(=O)n3CC(C)(C)C)c1] | methyl 3-[1-(2,2-dimethylpropyl)-3-methyl-2-oxo-2,3-dihydro-1H-imidazo[4,5-b]pyridin-5-yl]benzoate | Calc'd 354.1812, found 354.1814 |
| 14-62 | 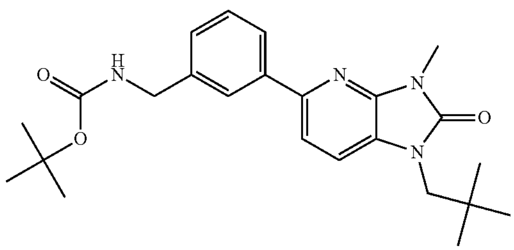 [SMILES: Cn1c(=O)n(CC(C)(C)C)c2ccc(-c3cccc(CNC(=O)OC(C)(C)C)c3)nc21] | tert-butyl {3-[1-(2,2-dimethylpropyl)-3-methyl-2-oxo-2,3-dihydro-1H-imidazo[4,5-b]pyridin-5-yl]benzyl}carbamate | Calc'd 425.2547, found 425.2549 |
| 14-63 | 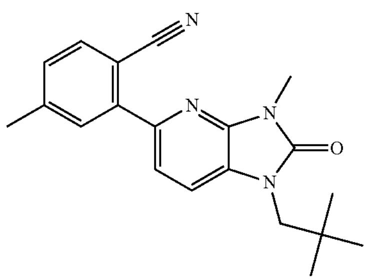 [SMILES: Cc1ccc(C#N)c(-c2ccc3c(n2)n(C)c(=O)n3CC(C)(C)C)c1] | 2-[1-(2,2-dimethylpropyl)-3-methyl-2-oxo-2,3-dihydro-1H-imidazo[4,5-b]pyridin-5-yl]-4-methylbenzonitrile | Calc'd 335.1866, found 335.1866 |
| 14-64 | 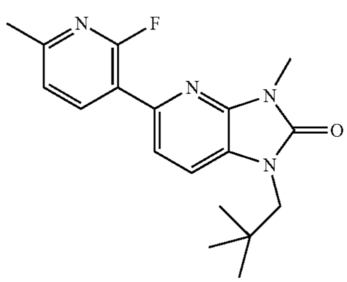 [SMILES: Cc1ccc(-c2ccc3c(n2)n(C)c(=O)n3CC(C)(C)C)c(F)n1] | 1-(2,2-dimethylpropyl)-5-(2-fluoro-6-methylpyridin-3-yl)-3-methyl-1,3-dihydro-2H-imidazo[4,5-b]pyridin-2-one | Calc'd 329.1772, found 329.1771 |
| 14-65 | 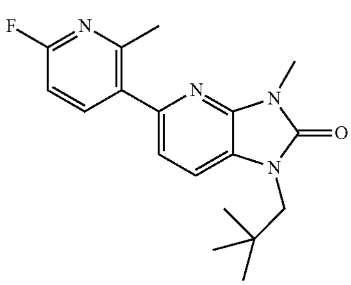 [SMILES: Cc1nc(F)ccc1-c1ccc2c(n1)n(C)c(=O)n2CC(C)(C)C] | 1-(2,2-dimethylpropyl)-5-(6-fluoro-2-methylpyridin-3-yl)-3-methyl-1,3-dihydro-2H-imidazo[4,5-b]pyridin-2-one | Calc'd 329.1772, found 329.1770 |

TABLE 5-continued

The following compounds were prepared from 14-1 by a reaction sequence
analogous to that illustrated in Scheme 14.

| Cmpd | Structure | IUPAC Name | Exact Mass [M + H]+ |
|---|---|---|---|
| 14-66 | 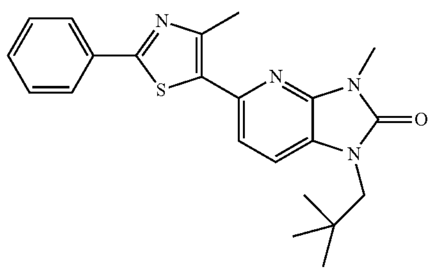 [SMILES: Cc1nc(-c2ccccc2)sc1-c1ccc2c(n1)n(C)c(=O)n2CC(C)(C)C] | 1-(2,2-dimethylpropyl)-3-methyl-5-(4-methyl-2-phenyl-1,3-thiazol-5-yl)-1,3-dihydro-2H-imidazo[4,5-b]pyridin-2-one | Calc'd 393.1744, found 393.1746 |
| 14-67 | 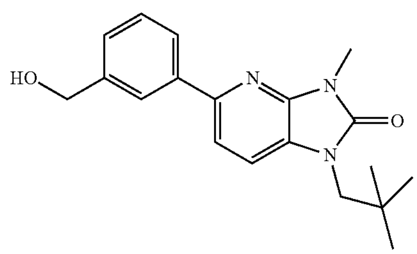 [SMILES: Cn1c(=O)n(CC(C)(C)C)c2ccc(-c3cccc(CO)c3)nc21] | 1-(2,2-dimethylpropyl)-5-[3-(hydroxymethyl)phenyl]-3-methyl-1,3-dihydro-2H-imidazo[4,5-b]pyridin-2-one | Calc'd 326.1863, found 326.1858 |
| 14-68 | 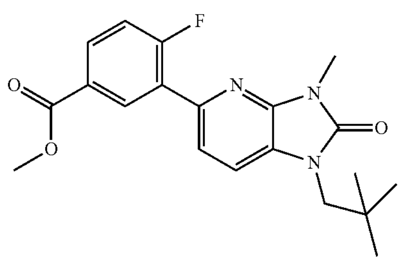 [SMILES: COC(=O)c1ccc(F)c(-c2ccc3c(n2)n(C)c(=O)n3CC(C)(C)C)c1] | methyl 3-[1-(2,2-dimethylpropyl)-3-methyl-2-oxo-2,3-dihydro-1H-imidazo[4,5-b]pyridin-5-yl]-4-fluorobenzoate | Calc'd 372.2, found 371.8 |
| 14-69 | 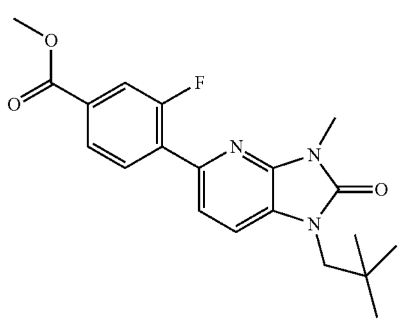 [SMILES: COC(=O)c1ccc(-c2ccc3c(n2)n(C)c(=O)n3CC(C)(C)C)c(F)c1] | methyl 4-[1-(2,2-dimethylpropyl)-3-methyl-2-oxo-2,3-dihydro-1H-imidazo[4,5-b]pyridin-5-yl]-3-fluorobenzoate | Calc'd 372.1718, found 372.1714 |
| 14-70 | 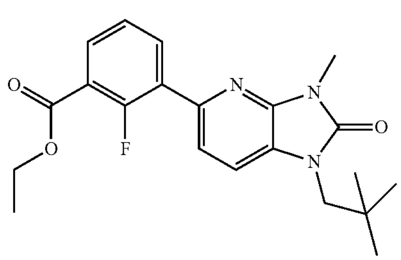 [SMILES: CCOC(=O)c1cccc(-c2ccc3c(n2)n(C)c(=O)n3CC(C)(C)C)c1F] | ethyl 3-[1-(2,2-dimethylpropyl)-3-methyl-2-oxo-2,3-dihydro-1H-imidazo[4,5-b]pyridin-5-yl]-2-fluorobenzoate | Calc'd 386.2, found 385.9 |

TABLE 5-continued

The following compounds were prepared from 14-1 by a reaction sequence analogous to that illustrated in Scheme 14.

| Cmpd | Structure | IUPAC Name | Exact Mass [M + H]+ |
|---|---|---|---|
| 14-71 | 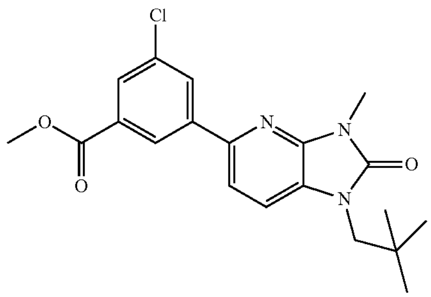 [SMILES: COC(=O)c1cc(Cl)cc(-c2ccc3c(n2)n(C)c(=O)n3CC(C)(C)C)c1] | methyl 3-chloro-5-[1-(2,2-dimethylpropyl)-3-methyl-2-oxo-2,3-dihydro-1H-imidazo[4,5-b]pyridin-5-yl]benzoate | Calc'd 388.1422, found 388.1417 |
| 14-72 | 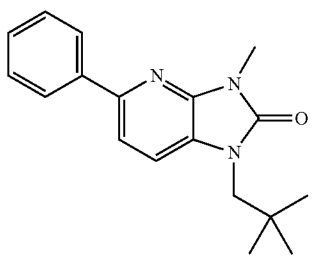 [SMILES: Cn1c(=O)n(CC(C)(C)C)c2ccc(-c3ccccc3)nc21] | 1-(2,2-dimethylpropyl)-3-methyl-5-phenyl-1,3-dihydro-2H-imidazo[4,5-b]pyridin-2-one | Calc'd 296.1757, found 296.1752 |
| 14-73 | 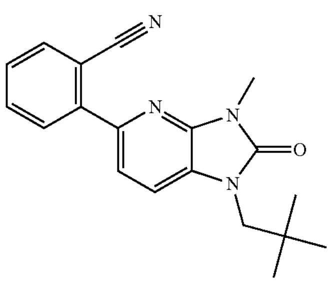 [SMILES: Cn1c(=O)n(CC(C)(C)C)c2ccc(-c3ccccc3C#N)nc21] | 2-[1-(2,2-dimethylpropyl)-3-methyl-2-oxo-2,3-dihydro-1H-imidazo[4,5-b]pyridin-5-yl]benzonitrile | Calc'd 321.1710, found 321.1706 |
| 14-74 | 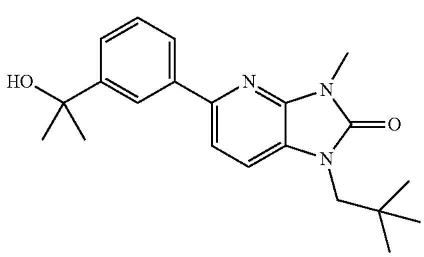 [SMILES: Cn1c(=O)n(CC(C)(C)C)c2ccc(-c3cccc(C(C)(C)O)c3)nc21] | 1-(2,2-dimethylpropyl)-5-[3-(1-hydroxy-1-methylethyl)phenyl]-3-methyl-1,3-dihydro-2H-imidazo[4,5-b]pyridin-2-one | Calc'd 354.2, found 354.3 |
| 14-75 | 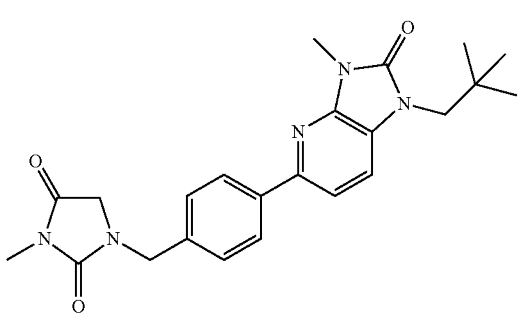 [SMILES: CN1C(=O)CN(Cc2ccc(-c3ccc4c(n3)n(C)c(=O)n4CC(C)(C)C)cc2)C1=O] | 1-{4-[1-(2,2-dimethylpropyl)-3-methyl-2-oxo-2,3-dihydro-1H-imidazo[4,5-b]pyridin-5-yl]benzyl}-3-methyl imidazolidine-2,4-dione | Calc'd 422.2, found 422.1 |

TABLE 5-continued

The following compounds were prepared from 14-1 by a reaction sequence analogous to that illustrated in Scheme 14.

| Cmpd | Structure | IUPAC Name | Exact Mass [M + H]+ |
|---|---|---|---|
| 14-76 | 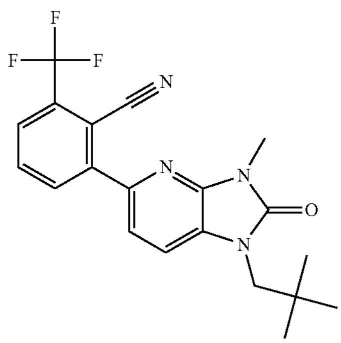 [SMILES: Cn1c(=O)n(CC(C)(C)C)c2ccc(-c3cccc(C(F)(F)F)c3C#N)nc21] | 2-[1-(2,2-dimethylpropyl)-3-methyl-2-oxo-2,3-dihydro-1H-imidazo[4,5-b]pyridin-5-yl]-6-(trifluoromethyl)benzonitrile | Calc'd 389.1771 Found 389.1778 |
| 14-77 | 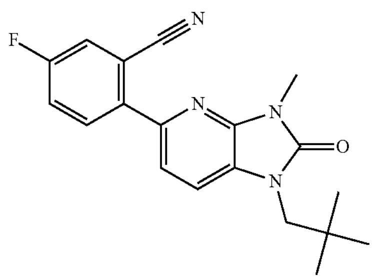 [SMILES: Cn1c(=O)n(CC(C)(C)C)c2ccc(-c3ccc(F)cc3C#N)nc21] | 2-[1-(2,2-dimethylpropyl)-3-methyl-2-oxo-2,3-dihydro-1H-imidazo[4,5-b]pyridin-5-yl]-5-fluorobenzonitrile | Calc'd 389.1567, found 389.1567 |
| 14-78 | 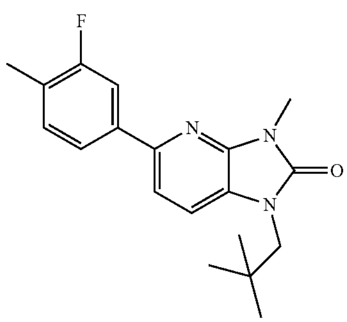 [SMILES: Cc1ccc(-c2ccc3c(n2)n(C)c(=O)n3CC(C)(C)C)cc1F] | 1-(2,2-dimethylpropyl)-5-(3-fluoro-4-methylphenyl)-3-methyl-1,3-dihydro-2H-imidazo[4,5-b]pyridin-2-one | Calc'd 328.0505, found 328.0518 |
| 14-79 | 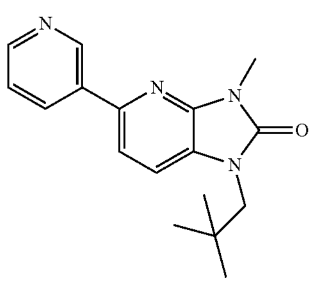 [SMILES: Cn1c(=O)n(CC(C)(C)C)c2ccc(-c3cccnc3)nc21] | 1-(2,2-dimethylpropyl)-3-methyl-5-pyridin-3-yl-1,3-dihydro-2H-imidazo[4,5-b]pyridin-2-one | Calc'd 297.1025, found 297.1027 |
| 14-80 | 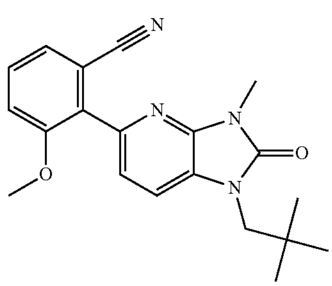 [SMILES: COc1cccc(C#N)c1-c1ccc2c(n1)n(C)c(=O)n2CC(C)(C)C] | 2-[1-(2,2-dimethylpropyl)-3-methyl-2-oxo-2,3-dihydro-1H-imidazo[4,5-b]pyridin-5-yl]-3-methoxybenzonitrile | Calc'd 351.1808, found 351.1835 |

TABLE 5-continued

The following compounds were prepared from 14-1 by a reaction sequence analogous to that illustrated in Scheme 14.

| Cmpd | Structure | IUPAC Name | Exact Mass [M + H]+ |
| --- | --- | --- | --- |
| 14-81 | 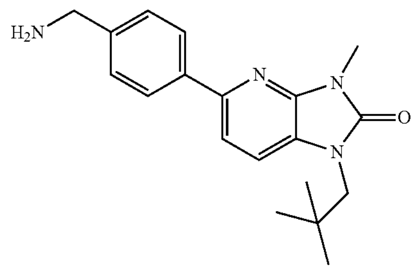 [SMILES: Cn1c(=O)n(CC(C)(C)C)c2ccc(-c3ccc(CN)cc3)nc21] | 5-[4-(aminomethyl)phenyl]-1-(2,2-dimethylpropyl)-3-methyl-1,3-dihydro-2H-imidazo[4,5-b]pyridin-2-one | Calc'd 325.1101, found 325.1103 |
| 14-82 | 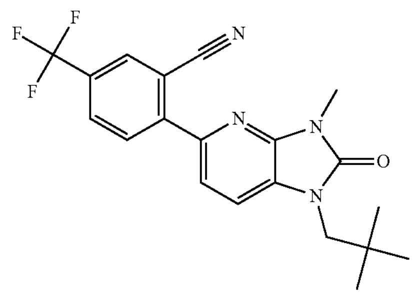 [SMILES: Cn1c(=O)n(CC(C)(C)C)c2ccc(-c3ccc(C(F)(F)F)cc3C#N)nc21] | 2-[1-(2,2-dimethylpropyl)-3-methyl-2-oxo-2,3-dihydro-1H-imidazo[4,5-b]pyridin-5-yl]-5-(trifluoromethyl)benzonitrile | Calc'd 379.103, found 389.1027 |
| 14-83 | 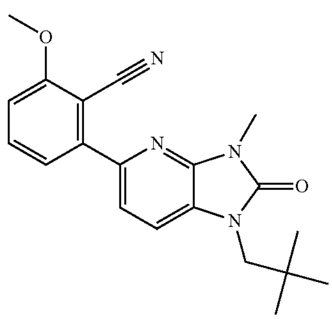 [SMILES: COc1cccc(-c2ccc3c(n2)n(C)c(=O)n3CC(C)(C)C)c1C#N] | 2-[1-(2,2-dimethylpropyl)-3-methyl-2-oxo-2,3-dihydro-1H-imidazo[4,5-b]pyridin-5-yl]-6-methoxybenzonitrile | Calc'd 351.2012, found 351.2008 |
| 14-84 | 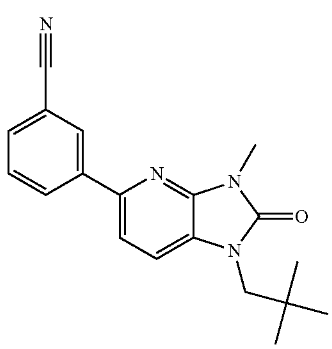 [SMILES: Cn1c(=O)n(CC(C)(C)C)c2ccc(-c3cccc(C#N)c3)nc21] | 3-[1-(2,2-dimethylpropyl)-3-methyl-2-oxo-2,3-dihydro-1H-imidazo[4,5-b]pyridin-5-yl]benzonitrile | Calc'd 321.2067, found 321.2078 |
| 14-85 | 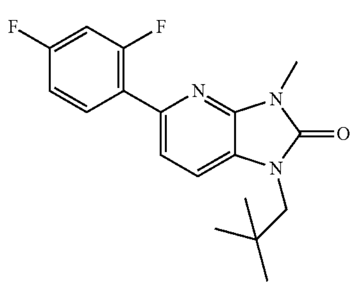 [SMILES: Cn1c(=O)n(CC(C)(C)C)c2ccc(-c3ccc(F)cc3F)nc21] | 5-(2,4-difluorophenyl)-1-(2,2-dimethylpropyl)-3-methyl-1,3-dihydro-2H-imidazo[4,5-b]pyridin-2-one | Calc'd 322.1105, found 322.1103 |

TABLE 5-continued

The following compounds were prepared from 14-1 by a reaction sequence analogous to that illustrated in Scheme 14.

| Cmpd | Structure | IUPAC Name | Exact Mass [M + H]+ |
|---|---|---|---|
| 14-86 | 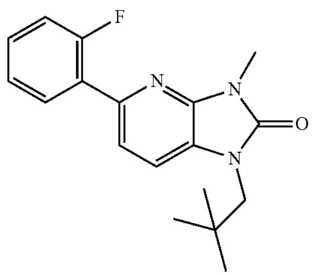 [SMILES: Cn1c(=O)n(CC(C)(C)C)c2ccc(-c3ccccc3F)nc21] | 1-(2,2-dimethylpropyl)-5-(2-fluorophenyl)-3-methyl-1,3-dihydro-2H-imidazo[4,5-b]pyridin-2-one | Calc'd 314.1216, found 314.1215 |
| 14-87 | 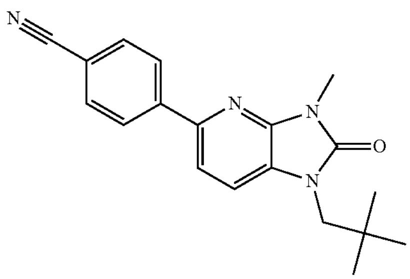 [SMILES: Cn1c(=O)n(CC(C)(C)C)c2ccc(-c3ccc(C#N)cc3)nc21] | 4-[1-(2,2-dimethylpropyl)-3-methyl-2-oxo-2,3-dihydro-1H-imidazo[4,5-b]pyridin-5-yl]benzonitrile | Calc'd 321.1105, found 321.1103 |
| 14-88 | 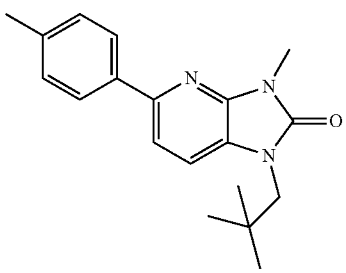 [SMILES: Cc1ccc(-c2ccc3c(n2)n(C)c(=O)n3CC(C)(C)C)cc1] | 1-(2,2-dimethylpropyl)-3-methyl-5-(4-methylphenyl)-1,3-dihydro-2H-imidazo[4,5-b]pyridin-2-one | Calc'd 310.1659, found 310.1661 |
| 14-89 | 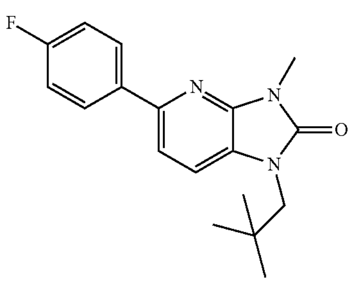 [SMILES: Cn1c(=O)n(CC(C)(C)C)c2ccc(-c3ccc(F)cc3)nc21] | 1-(2,2-dimethylpropyl)-5-(4-fluorophenyl)-3-methyl-1,3-dihydro-2H-imidazo[4,5-b]pyridin-2-one | Calc'd 314.1216, found 314.1215 |
| 14-90 | 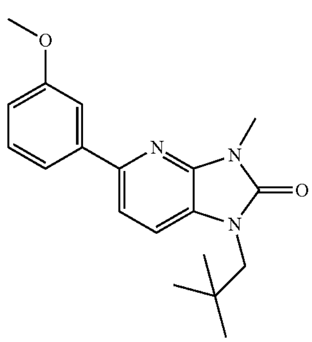 [SMILES: COc1cccc(-c2ccc3c(n2)n(C)c(=O)n3CC(C)(C)C)c1] | 1-(2,2-dimethylpropyl)-5-(3-methoxyphenyl)-3-methyl-1,3-dihydro-2H-imidazo[4,5-b]pyridin-2-one | Calc'd 326.1965, found 326.1972 |

TABLE 5-continued

The following compounds were prepared from 14-1 by a reaction sequence analogous to that illustrated in Scheme 14.

| Cmpd | Structure | IUPAC Name | Exact Mass [M + H]+ |
|---|---|---|---|
| 14-91 | 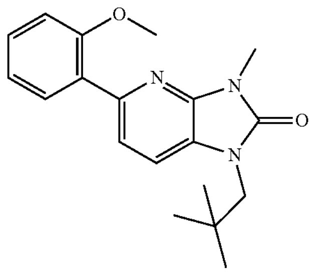 [SMILES: COc1ccccc1-c1ccc2c(n1)n(C)c(=O)n2CC(C)(C)C] | 1-(2,2-dimethylpropyl)-5-(2-methoxyphenyl)-3-methyl-1,3-dihydro-2H-imidazo[4,5-b]pyridin-2-one | Calc'd 326.1965, found 326.1972 |
| 14-92 | 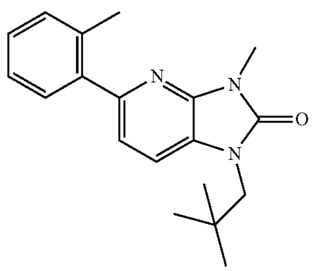 [SMILES: Cc1ccccc1-c1ccc2c(n1)n(C)c(=O)n2CC(C)(C)C] | 1-(2,2-dimethylpropyl)-3-methyl-5-(2-methylphenyl)-1,3-dihydro-2H-imidazo[4,5-b]pyridin-2-one | Calc'd 310.1659, found 310.1661 |
| 14-93 | 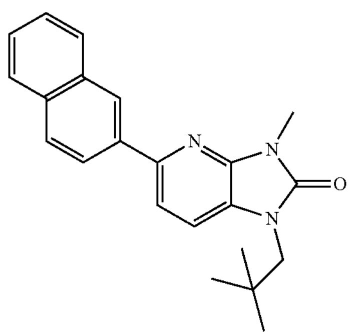 [SMILES: Cn1c(=O)n(CC(C)(C)C)c2ccc(-c3ccc4ccccc4c3)nc21] | 1-(2,2-dimethylpropyl)-3-methyl-5-naphthalen-2-yl-1,3-dihydro-2H-imidazo[4,5-b]pyridin-2-one | Calc'd 346.2071, found 346.2058 |
| 14-94 | 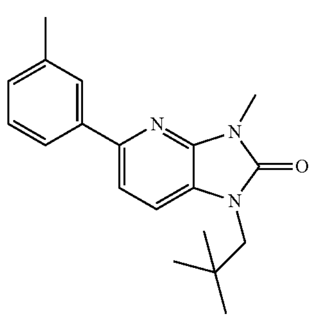 [SMILES: Cc1cccc(-c2ccc3c(n2)n(C)c(=O)n3CC(C)(C)C)c1] | 1-(2,2-dimethylpropyl)-3-methyl-5-(3-methylphenyl)-1,3-dihydro-2H-imidazo[4,5-b]pyridin-2-one | Calc'd 310.1659, found 310.1660 |

TABLE 5-continued

The following compounds were prepared from 14-1 by a reaction sequence analogous to that illustrated in Scheme 14.

| Cmpd | Structure | IUPAC Name | Exact Mass [M + H]+ |
|---|---|---|---|
| 14-95 | 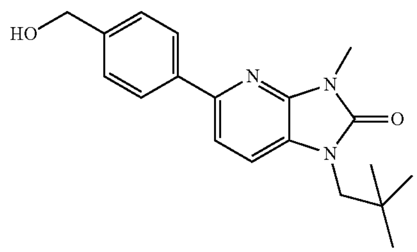 [SMILES: Cn1c(=O)n(CC(C)(C)C)c2ccc(-c3ccc(CO)cc3)nc21] | 1-(2,2-dimethylpropyl)-5-[4-(hydroxymethyl)phenyl]-3-methyl-1,3-dihydro-2H-imidazo[4,5-b]pyridin-2-one | Calc'd 326.1863, found 326.1864 |
| 14-96 | 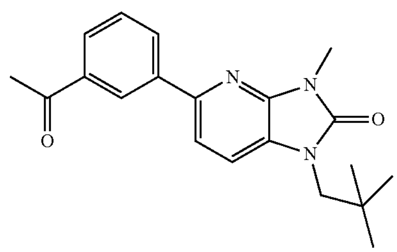 [SMILES: CC(=O)c1cccc(-c2ccc3c(n2)n(C)c(=O)n3CC(C)(C)C)c1] | 5-(3-acetylphenyl)-1-(2,2-dimethylpropyl)-3-methyl-1,3-dihydro-2H-imidazo[4,5-b]pyridin-2-one | Calc'd 338.4, found 338.1 |

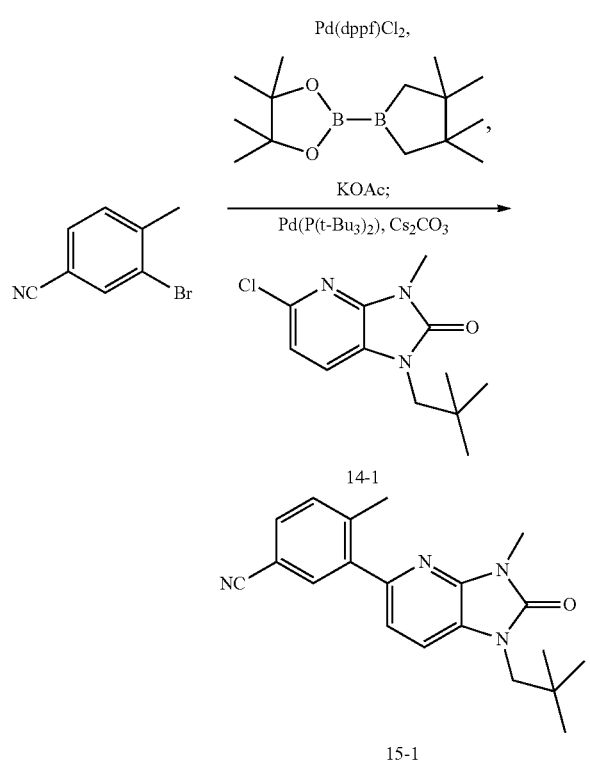

3-[1-(2,2-dimethylpropyl)-3-methyl-2-oxo-2,3-dihydro-1H-imidazo[4,5-b]pyridin-5-yl]-4-methylbenzonitrile (15-1)

To a microwave vial, 3-bromo-4-methylbenzonitrile (250 mg, 1.28 mmol), Bispinnacoloto(diboron) (356 mg, 1.4 mmol), Potassium Acetate (560 mg, 5.74 mmol), and Bis(diphenylphosphino)ferrocene dicholoropalladium (180 mg, 0.25 mmol) was added under nitrogen and suspended in dioxane (2.5 ml). The mixture was refluxed at 90° C. overnight, and showed the intermediate boronic ester. The reaction was cooled to room temperature and to the reaction mixture was added 14-1 (191 mg, 0.76 mmol), cesium carbonate (830 mg, 2.6 mmol), bis(tri-t-butylphosphine)palladium(0) (65 mg, 0.13 mmol) and water (0.7 mL). The mixture was refluxed at 90° C. overnight, at the desired coupled product was observed by LC/MS. The mixture was diluted with methanol and purified using reverse phase chromatography (10-100%, 0.1% TFA in $H_2O$/Acetonitrile); the desired fractions were collected and concentrated to produce 3-[1-(2,2-dimethylpropyl)-3-methyl-2-oxo-2,3-dihydro-1H-imidazo[4,5-b]pyridin-5-yl]-4-methylbenzonitrile (15-1). HRMS (M+H)+: observed=335.1865, calculated=335.1866.

TABLE 6

The following compounds were prepared from 14-1 by a reaction sequence analogous to that illustrated in Scheme 15.

| Cmpd | Structure | IUPAC Name | Exact Mass [M + H]+ |
|---|---|---|---|
| 15-2 | 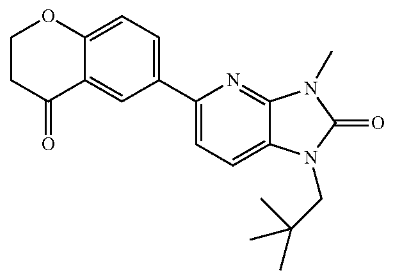 [SMILES: Cn1c(=O)n(CC(C)(C)C)c2ccc(-c3ccc4c(c3)C(=O)CCO4)nc21] | 1-(2,2-dimethylpropyl)-3-methyl-5-(4-oxo-3,4-dihydro-2H-chromen-6-yl)-1,3-dihydro-2H-imidazo[4,5-b]pyridin-2-one | Calc'd 366.1812, found 366.1811 |
| 15-3 | 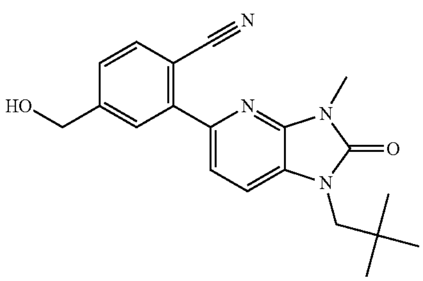 [SMILES: Cn1c(=O)n(CC(C)(C)C)c2ccc(-c3cc(CO)ccc3C#N)nc21] | 2-[1-(2,2-dimethylpropyl)-3-methyl-2-oxo-2,3-dihydro-1H-imidazo[4,5-b]pyridin-5-yl]-4-(hydroxylmethyl)benzonitrile | Calc'd 351.1816, found 351.1812 |
| 15-4 | 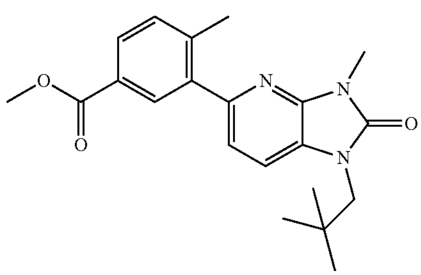 [SMILES: COC(=O)c1ccc(C)c(-c2ccc3c(n2)n(C)c(=O)n3CC(C)(C)C)c1] | methyl 3-[1-(2,2-dimethylpropyl)-3-methyl-2-oxo-2,3-dihydro-1H-imidazo[4,5-b]pyridin-5-yl]-4-methylbenzoate | Calc'd 368.1969, found 368.1971 |
| 15-5 | 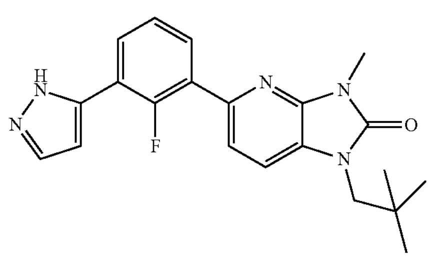 [SMILES: Cn1c(=O)n(CC(C)(C)C)c2ccc(-c3cccc(-c4ccn[nH]4)c3F)nc21] | 1-(2,2-dimethylpropyl)-5-[2-fluoro-3-(1H-pyrazol-5-yl)phenyl]-3-methyl-1,3-dihydro-2H-imidazo[4,5-b]pyridin-2-one | Calc'd 380.1881, found 380.1888 |
| 15-6 | 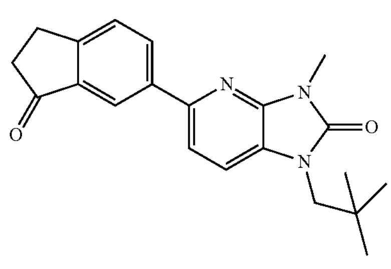 [SMILES: Cn1c(=O)n(CC(C)(C)C)c2ccc(-c3ccc4c(c3)C(=O)CC4)nc21] | 1-(2,2-dimethylpropyl)-3-methyl-5-(3-oxo-2,3-dihydro-1H-inden-5-yl)-1,3-dihydro-2H-imidazo[4,5-b]pyridin-2-one | Calc'd 350.1863, found 350.1866 |

TABLE 6-continued

The following compounds were prepared from 14-1 by a reaction sequence analogous to that illustrated in Scheme 15.

| Cmpd | Structure | IUPAC Name | Exact Mass [M + H]+ |
|---|---|---|---|
| 15-7 | 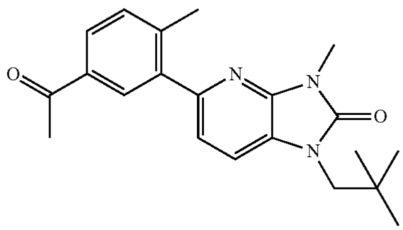 [SMILES: CC(=O)c1ccc(C)c(-c2ccc3c(n2)n(C)c(=O)n3CC(C)(C)C)c1] | 5-(5-acetyl-2-methyl phenyl)-1-(2,2-dimethyl propyl)-3-methyl-1,3-dihydro-2H-imidazo[4,5-b]pyridin-2-one (16-1) | Calc'd 261.1, found 261.2 |

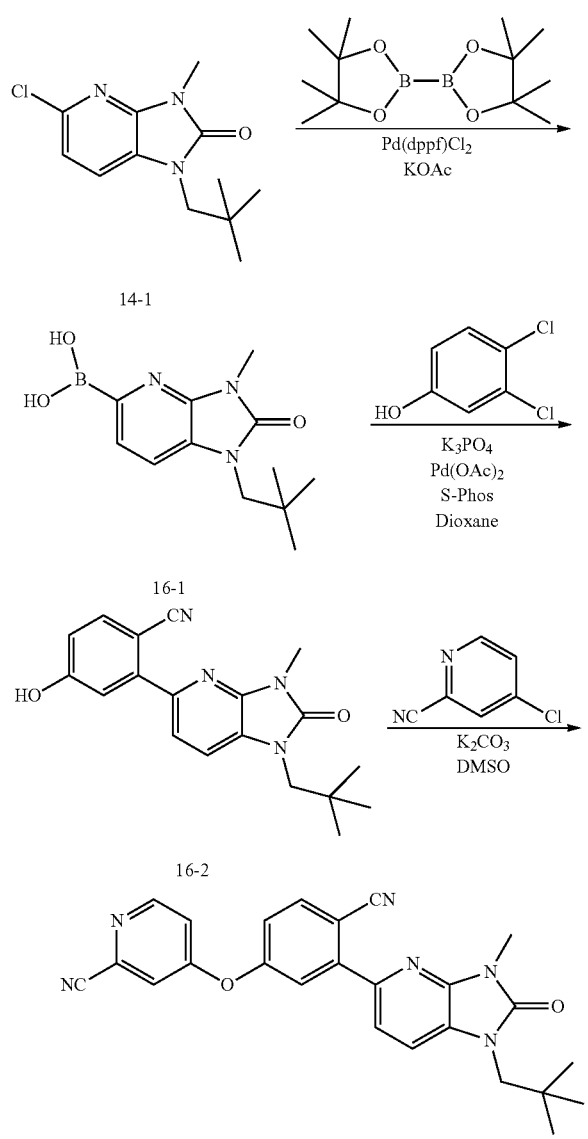

SCHEME 16

4-{4-cyano-3-[1-(2,2-dimethylpropyl)-3-methyl-2-oxo-2,3-dihydro-1H-imidazo[4,5-b]pyridin-5-yl]phenoxy}pyridine-2-carbonitrile (16-3)

[1-(2,2-dimethylpropyl)-3-methyl-2-oxo-2,3-dihydro-1H-imidazo[4,5-b]pyridin-5-yl]boronic acid (16-1)

Prepared from 14-1 according to the procedures reported in Scheme 3. MS (M+H)+: observed=264.1, calculated=264.1.

2-[1-(2,2-dimethylpropyl)-3-methyl-2-oxo-2,3-dihydro-1H-imidazo[4,5-b]pyridin-5-yl]-4-hydroxybenzonitrile (16-2)

To a solution of [1-(2,2-dimethylpropyl)-3-methyl-2-oxo-2,3-dihydro-1H-imidazo[4,5-b]pyridin-5-yl]boronic acid (16-1, 500 mg, 1.90 mmol) in anhydrous THF (15 ml) was added a solution of Potassium phosphate tribasic (807 mg, 3.80 mmol, 2.0 equiv) dissolved in water (2 ml). This mixture was treated with 2-chloro-4-hydroxybenzonitrile (409 mg, 2.66 mmol, 1.40 equiv), deoxygenated, then charged with Pd(OAc)$_2$ (21 mg, 0.10 mmol, 0.05 equiv) and S-Phos (78 mg, 0.19 mmol, 0.10 equiv). The resulting dark mixture was irradiated in a microwave at 125° C. for 15 min. The reaction was 75% complete by LC/MS, so more 2-chloro-4-hydroxybenzonitrile (405 mg, 2.66 mmol, 1.40 equiv), Pd(OAc)$_2$ (21 mg, 0.10 mmol, 0.05 equiv) and S-Phos (78 mg, 0.19 mmol, 0.10 equiv) were introduced, and the reaction mixture was irradiated at 140° C. for 25 min. The completed reaction was partitioned between EtOAc (3×75 ml) and saturated aqueous NaHCO$_3$ (80 ml) and the combined organic layers were dried over MgSO$_4$ and concentrated. The crude oil was purified via flash column chromatography (SiO$_2$: 100% Hex to 50/50 Hex/EtOAc) which afforded the title compound, 2-[1-(2,2-dimethylpropyl)-3-methyl-2-oxo-2,3-dihydro-1H-imidazo[4,5-b]pyridin-5-yl]-4-hydroxybenzonitrile (16-2), as a yellow solid-oil. LRMS m/z: Calc'd for C$_{19}$H$_{20}$N$_4$O$_2$ (M+H) 337.3. found 337.0.

4-{4-cyano-3-[1-(2,2-dimethylpropyl)-3-methyl-2-oxo-2,3-dihydro-1H-imidazo[4,5b]pyridin-5-yl]phenoxy}pyridine-2-carbonitrile (16-3)

A solution of 2-[1-(2,2-dimethylpropyl)-3-methyl-2-oxo-2,3-dihydro-1H-imidazo[4,5-b]pyridin-5-yl]-4-hydroxybenzonitrile (16-2, 100 mg, 0.30 mmol) in DMSO (4 ml) was charged with Potassium carbonate (82 mg, 0.59 mmol, 2.0 equiv) and 4-Chloro-pyridine-2-carbonitrile (82 mg, 0.59 mmol, 2.0 equiv). The reaction was irradiated at 160° C. for 20 min. The dark mixture was purified via reverse-phase HPLC (Acetonitrile/Water gradient with 0.1% TFA present) to afford the title compound, 4-{4-cyano-3-[1-(2,2-dimethyl-propyl)-3-methyl-2-oxo-2,3-dihydro-1H-imidazo[4,5-b]py-ridin-5-yl]phenoxy}pyridine-2-carbonitrile (3), as a pure yellow-tan solid-oil. $^1$H NMR (500 MHz, CDCl$_3$) δ 8.64 (d, 1H, J=5.6 Hz), 7.91 (d, 1H, J=8.3 Hz), 7.62 (bs, 1H), 7.54 (d, 1H, J=8.1 Hz), 7.36-7.33 (m, 2H), 7.21-7.15 (m, 2H), 3.71 (s, 2H), 3.58 (s, 3H), 1.06 (s, 9H). LRMS m/z: Calc'd for C$_{25}$H$_{22}$N$_6$O$_2$ (M+H) 439.0. found 439.1.

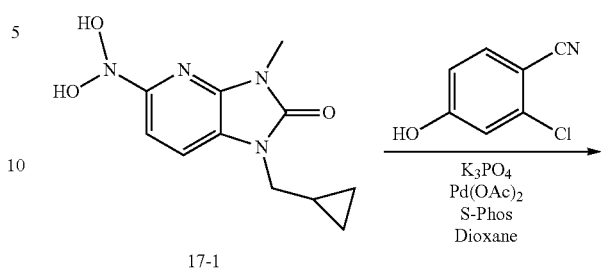

17-1

TABLE 7

The following compounds were prepared from 16-2 by a reaction sequence analogous to that illustrated in Scheme 16.

| Cmpd | Structure | IUPAC Name | Exact Mass [M + H]+ |
|---|---|---|---|
| 16-4 | 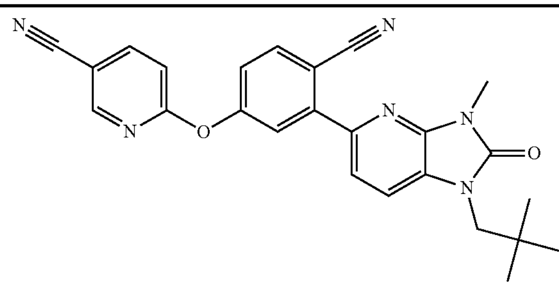 | 6-{4-cyano-3-[1-(2,2-dimethylpropyl)-3-methyl-2-oxo-2,3-dihydro-1H-imidazo[4,5-b]pyridin-5-yl]phenoxy}pyridine-3-carbonitrile | Calc'd 439.1877, found 439.1884 |
| 16-5 | 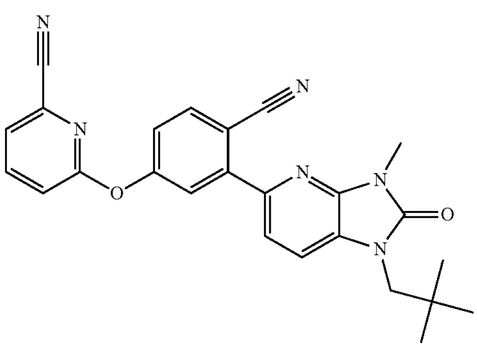 [SMILES: Cn1c(=O)n(CC(C)(C)C)c2ccc(-c3cc(Oc4cccc(C#N)n4)ccc3C#N)nc21] | 6-{4-cyano-3-[1-(2,2-dimethylpropyl)-3-methyl-2-oxo-2,3-dihydro-1H-imidazo[4,5-b]pyridin-5-yl]phenoxy}pyridine-2-carbonitrile | Calc'd 439.1877, found 439.1886 |

SCHEME 17

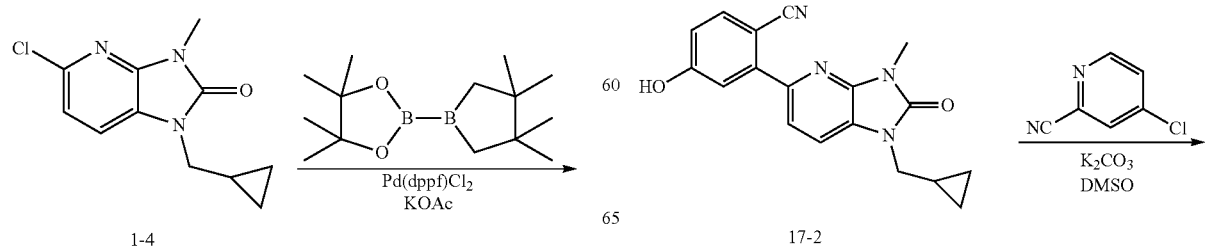

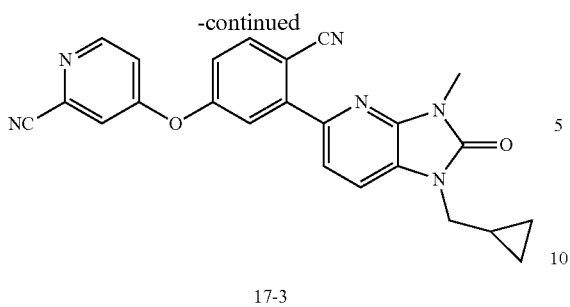

17-3

4-{4-cyano-3-[1-(cyclopropylmethyl)-3-methyl-2-oxo-2,3-dihydro-1H-imidazo[4,5-b]pyridin-5-yl]phenoxy}pyridine-2-carbonitrile (17-3)

Prepared from 1-4 according to the procedures reported in Scheme 16. MS (M+H)$^+$: observed=423.1, calculated=423.2.

SCHEME 18

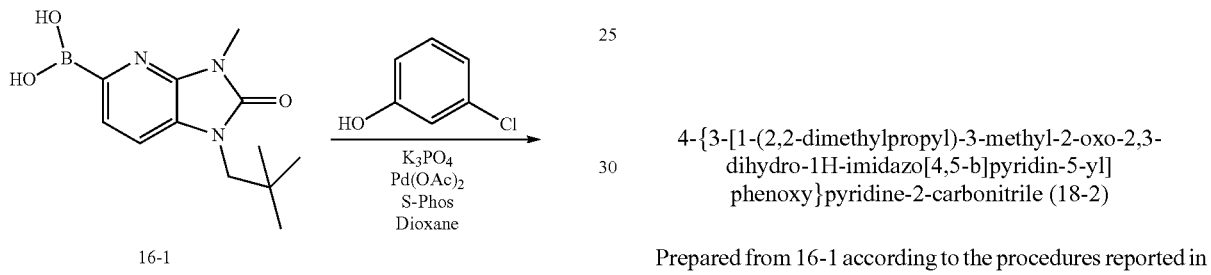

16-1

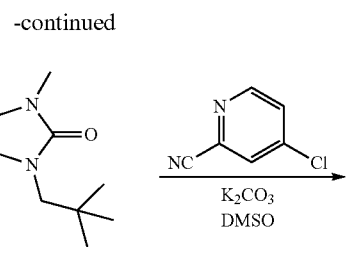

18-1

4-{3-[1-(2,2-dimethylpropyl)-3-methyl-2-oxo-2,3-dihydro-1H-imidazo[4,5-b]pyridin-5-yl]phenoxy}pyridine-2-carbonitrile (18-2)

Prepared from 16-1 according to the procedures reported in Scheme 16. MS (M+H)$^+$: observed=414.0, calculated=414.2.

TABLE 8

The following compounds were prepared from 18-1 by a reaction sequence analogous to that illustrated in Scheme 18.

| Cmpd | Structure | IUPAC Name | Exact Mass [M + H]+ |
|---|---|---|---|
| 18-3 | 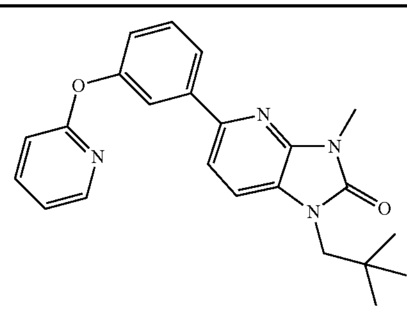 | 1-(2,2-dimethylpropyl)-3-methyl-5-[3-(pyridin-2-yloxy)phenyl]-1,3-dihydro-2H-imidazo[4,5-b]pyridin-2-one | Calc'd 389.2, found 389.0 |
| 18-4 | 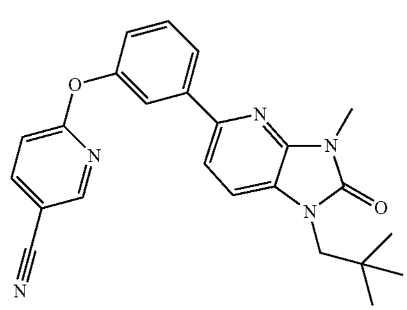 [SMILES: Cn1c(=O)n(CC(C)(C)C)c2ccc(-c3cccc(Oc4ccc(C#N)cn4)c3)nc21] | 6-{3-[1-(2,2-dimethylpropyl)-3-methyl-2-oxo-2,3-dihydro-1H-imidazo[4,5-b]pyridin-5-yl]phenoxy}pyridine-3-carbonitrile | Calc'd 414.2, found 414.2 |

TABLE 8-continued

The following compounds were prepared from 18-1 by a reaction sequence analogous to that illustrated in Scheme 18.

| Cmpd | Structure | IUPAC Name | Exact Mass [M + H]+ |
|---|---|---|---|
| 18-5 | 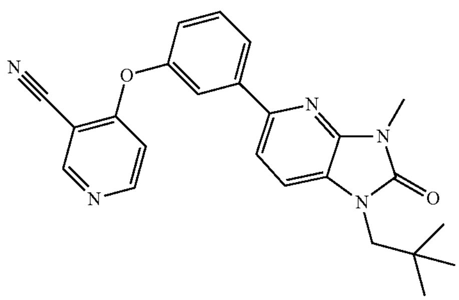 [SMILES: Cn1c(=O)n(CC(C)(C)C)c2ccc(-c3cccc(Oc4ccncc4C#N)c3)nc21] | 4-{3-[1-(2,2-dimethylpropyl)-3-methyl-2-oxo-2,3-dihydro-1H-imidazo[4,5-b]pyridin-5-yl]phenoxy}pyridine-3-carbonitrile | Calc'd 414.2, found 414.2 |
| 18-6 | 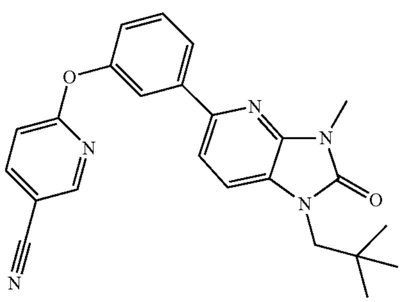 [SMILES: Cn1c(=O)n(CC(C)(C)C)c2ccc(-c3cccc(Oc4ccc(C#N)cn4)c3)nc21] | 6-{3-[1-(2,2-dimethylpropyl)-3-methyl-2-oxo-2,3-dihydro-1H-imidazo[4,5-b]pyridin-5-yl]phenoxy}pyridine-3-carbonitrile | Calc'd 414.1925, found 414.1933 |
| 18-7 | 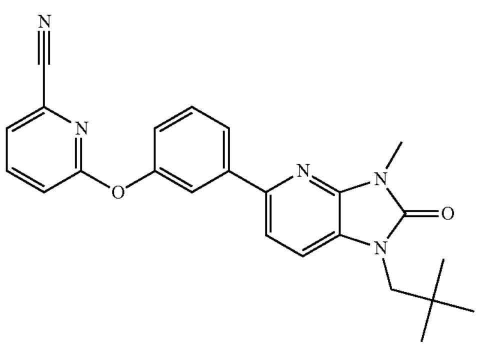 [SMILES: Cn1c(=O)n(CC(C)(C)C)c2ccc(-c3cccc(Oc4cccc(C#N)n4)c3)nc21] | 6-{3-[1-(2,2-dimethylpropyl)-3-methyl-2-oxo-2,3-dihydro-1H-imidazo[4,5-b]pyridin-5-yl]phenoxy}pyridine-2-carbonitrile | Calc'd 414.2, found 414.1 |
| 18-8 | 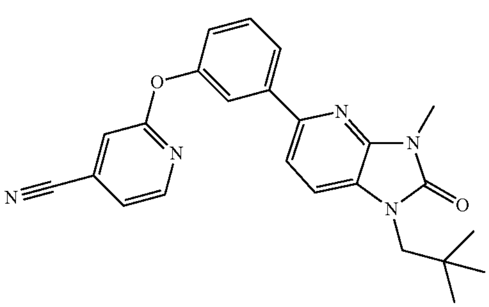 [SMILES: Cn1c(=O)n(CC(C)(C)C)c2ccc(-c3cccc(Oc4cc(C#N)ccn4)c3)nc21] | 2-{3-[1-(2,2-dimethylpropyl)-3-methyl-2-oxo-2,3-dihydro-1H-imidazo[4,5-b]pyridin-5-yl]phenoxy}pyridine-4-carbonitrile | Calc'd 414.2, found 414.2 |

TABLE 8-continued

The following compounds were prepared from 18-1 by a reaction sequence analogous to that illustrated in Scheme 18.

| Cmpd | Structure | IUPAC Name | Exact Mass [M + H]+ |
|---|---|---|---|
| 18-9 | 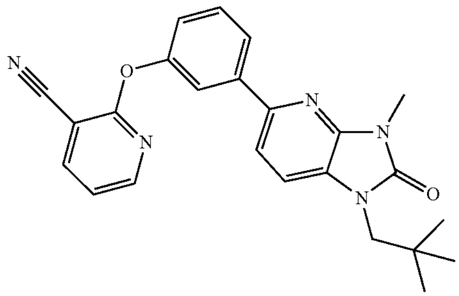 [SMILES: Cn1c(=O)n(CC(C)(C)C)c2ccc(-c3cccc(Oc4ncccc4C#N)c3)nc21] | 2-{3-[1-(2,2-dimethylpropyl)-3-methyl-2-oxo-2,3-dihydro-1H-imidazo[4,5-b]pyridin-5-yl]phenoxy}pyridine-3-carbonitrile | Calc'd 414.2, found 414.2 |

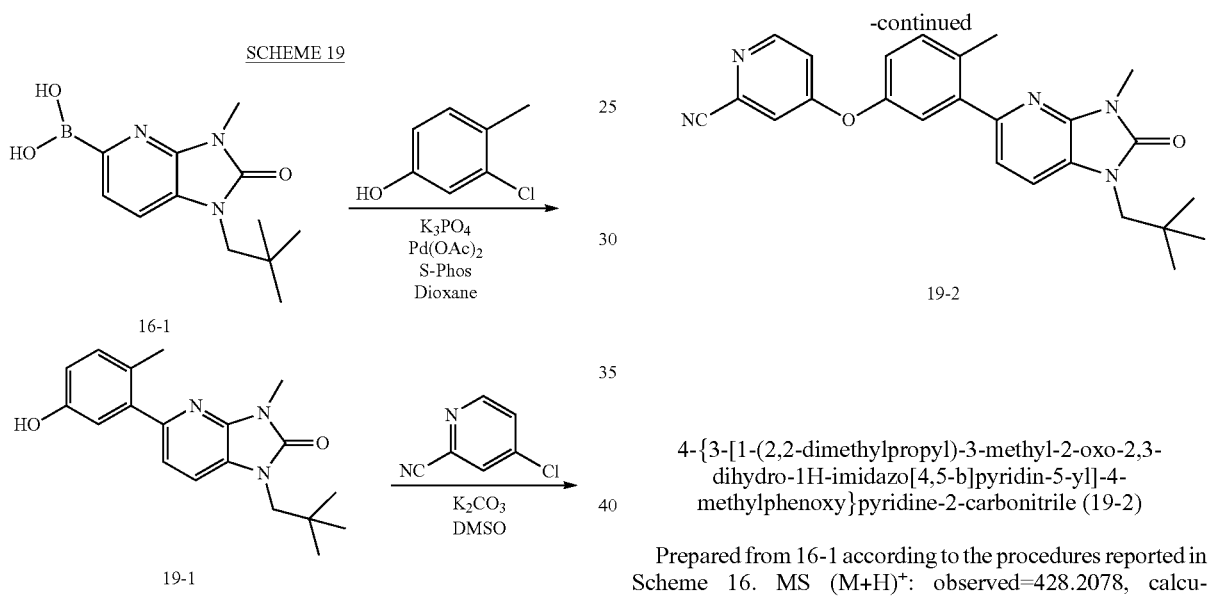

4-{3-[1-(2,2-dimethylpropyl)-3-methyl-2-oxo-2,3-dihydro-1H-imidazo[4,5-b]pyridin-5-yl]-4-methylphenoxy}pyridine-2-carbonitrile (19-2)

Prepared from 16-1 according to the procedures reported in Scheme 16. MS (M+H)+: observed=428.2078, calculated=428.2081.

TABLE 9

The following compounds were prepared from 19-1 by a reaction sequence analogous to that illustrated in Scheme 19.

| Cmpd | Structure | IUPAC Name | Exact Mass [M + H]+ |
|---|---|---|---|
| 19-3 | 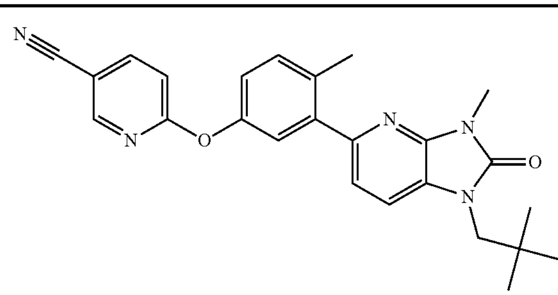 | 6-{3-[1-(2,2-dimethylpropyl)-3-methyl-2-oxo-2,3-dihydro-1H-imidazo[4,5-b]pyridin-5-yl]-4-methylphenoxy}pyridine-3-carbonitrile | Calc'd 428.2081, found 428.2076 |

TABLE 9-continued

The following compounds were prepared from 19-1 by a reaction sequence analogous to that illustrated in Scheme 19.

| Cmpd | Structure | IUPAC Name | Exact Mass [M + H]+ |
|---|---|---|---|
| 19-4 | 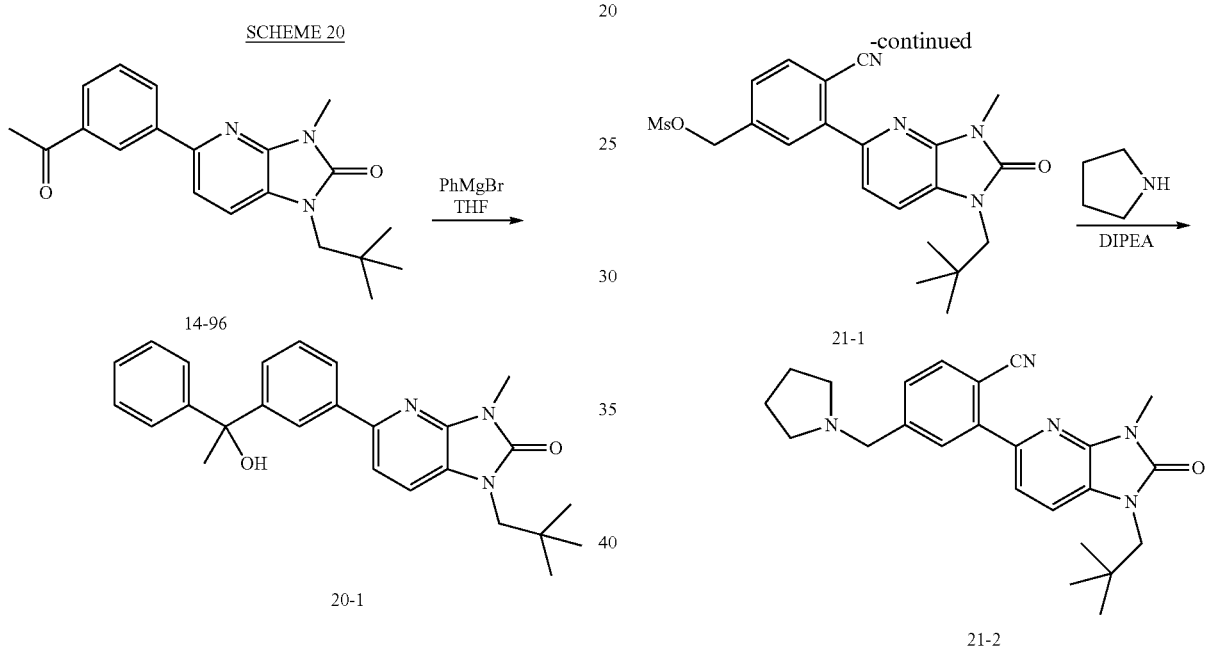 | 4-{3-[1-(2,2-dimethylpropyl)-3-methyl-2-oxo-2,3-dihydro-1H-imidazo[4,5-b]pyridin-5-yl]-4-methylphenoxy}pyridine-3-carbonitrile | Calc'd 428.2081, found 428.2076 |

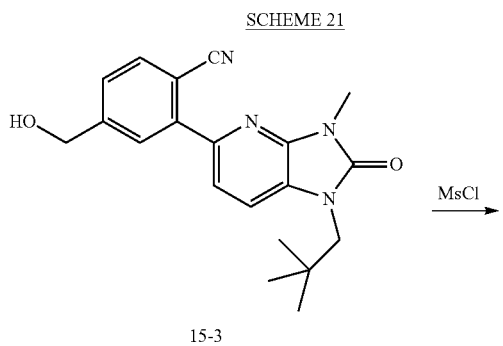

SCHEME 20

1-(2,2-dimethylpropyl)-5-[3-(1-hydroxy-1-phenyl-ethyl)phenyl]-3-methyl-1,3-dihydro-2H-imidazo[4,5-b]pyridin-2-one (20-1)

Prepared from 14-96 according to the procedures reported in Scheme 3. MS (M+H)+: observed=416.0, calculated=416.2.

SCHEME 21

2-[1-(2,2-dimethylpropyl)-3-methyl-2-oxo-2,3-dihydro-1H-imidazo[4,5-b]pyridin-5-yl]-4-(pyrrolidin-1-ylmethyl)benzonitrile (21-2)

4-cyano-3-[1-(2,2-dimethylpropyl)-3-methyl-2-oxo-2,3-dihydro-1H-imidazo[4,5-b]pyridin-5-yl]benzyl methanesulfonate (21-1)

15-3 (95 mg, 0.27 mmol) was added to a round bottom flask under nitrogen, dissolved in DCM (0.7 ml), and cooled to −78° C. Methanesulfonyl chloride (37 mg, 0.325 ml) was then added followed by Diisopropyl ethyl amine (0.10 ml, 0.542 mmol) and allowed to stir for 30 minutes. The solution was diluted with DCM and sodium bicarbonate, and then extracted (3×) with DCM. The organic layers were then was with brine, dried over sodium sulfate, filtered, and concentrate to give the desired solid product, 4-cyano-3-[1-(2,2-dimethylpropyl)-3-methyl-2-oxo-2,3-dihydro-1H-imidazo[4,5-b]pyridin-5-yl]benzyl methanesulfonate (21-1). MS (M+H)+: observed=429.3, calculated=429.5.

2-[1-(2,2-dimethylpropyl)-3-methyl-2-oxo-2,3-dihydro-1H-imidazo[4,5-b]pyridin-5-yl]-4-(pyrrolidin-1-ylmethyl)benzonitrile (21-2)

To a microwave vial, 4-cyano-3-[1-(2,2-dimethylpropyl)-3-methyl-2-oxo-2,3-dihydro-1H-imidazo[4,5-b]pyridin-5-yl]benzyl methanesulfonate (21-1) (20 mg, 0.05 mmol) and pyrrolidine (5 mg, 0.07 mmol) were added and dissolved in NMP (0.25 ml). Diisopropyl ethyl amine (18 mg, 0.14 mmol) was then added and the reaction was heated at 65° C. allowed to stir for 4 hours. The mixture was diluted with methanol and purified using reverse phase chromatography (10-100%, 0.1% TFA in $H_2O$/Acetonitrile); the desired fractions were collected and concentrated to produce 2-[1-(2,2-dimethylpropyl)-3-methyl-2-oxo-2,3-dihydro-1H-imidazo[4,5-b]pyridin-5-yl]-4-(pyrrolidin-1-ylmethyl)benzonitrile (13-2). HRMS (M+H)$^+$: observed=404.2456, calculated=404.2445. $^1$H NMR (400 MHz, $CD_3$ OD): δ 7.91 (s, 1H); 7.83 (d, J=7.9 Hz, 1H); 7.60 (q, J=8.3 Hz, 2H); 7.54 (d, J=8.0 Hz, 1H); 3.82 (s, 2H); 3.77 (s, 2H); 3.55 (s, 3H); 2.64 (m, 4H); 1.85 (m, 4H); 1.06 (s, 9H).

TABLE 10

The following compounds were prepared from 21-1 by a reaction sequence analogous to that illustrated in Scheme 21.

| Cmpd | Structure | IUPAC Name | Exact Mass [M + H]+ |
|---|---|---|---|
| 21-3 | 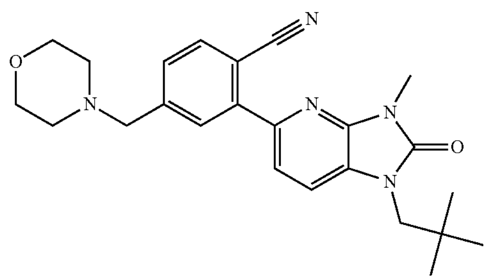 [SMILES: Cn1c(=O)n(CC(C)(C)C)c2ccc(-c3cc(CN4CCOCC4)ccc3C#N)nc21] | 2-[1-(2,2-dimethylpropyl)-3-methyl-2-oxo-2,3-dihydro-1H-imidazo[4,5-b]pyridin-5-yl]-4-(morpholin-4-ylmethyl)benzonitrile | Calc'd 420.2394, found 420.2397 |
| 21-4 | 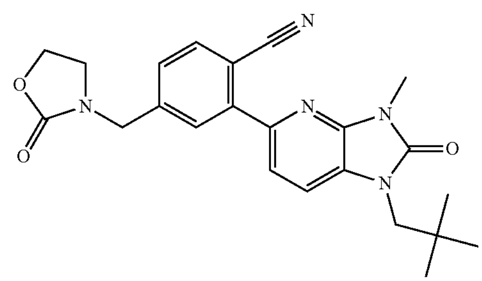 [SMILES: Cn1c(=O)n(CC(C)(C)C)c2ccc(-c3cc(CN4CCOC4=O)ccc3C#N)nc21] | 2-[1-(2,2-dimethylpropyl)-3-methyl-2-oxo-2,3-dihydro-1H-imidazo[4,5-b]pyridin-5-yl]-4-[(2-oxo-1,3-oxazolidin-3-yl)methyl]benzonitrile | Calc'd 420.2030, found 420.2030 |
| 21-5 | 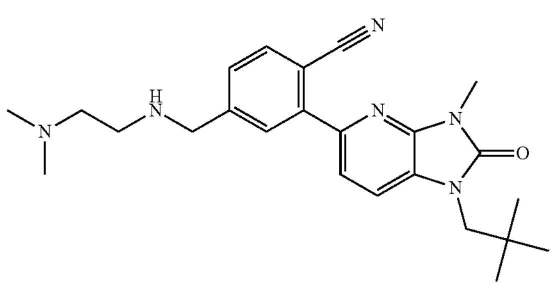 [SMILES: CN(C)CCNCc1ccc(C#N)c(-c2ccc3c(n2)n(C)c(=O)n3CC(C)(C)C)c1] | 4-({[2-(dimethylamino)ethyl]amino}methyl)-2-[1-(2,2-dimethylpropyl)-3-methyl-2-oxo-2,3-dihydro-1H-imidazo[4,5-b]pyridin-5-yl]benzonitrile | Calc'd 421.2710, found 421.2719 |
| 21-6 | 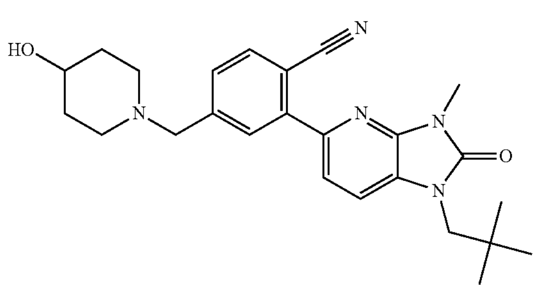 [SMILES: Cn1c(=O)n(CC(C)(C)C)c2ccc(-c3cc(CN4CCC(O)CC4)ccc3C#N)nc21] | 2-[1-(2,2-dimethylpropyl)-3-methyl-2-oxo-2,3-dihydro-1H-imidazo[4,5-b]pyridin-5-yl]-4-[(4-hydroxypiperidin-1-yl)methyl]benzonitrile | Calc'd 434.2551, found 434.2552 |

TABLE 10-continued

The following compounds were prepared from 21-1 by a reaction sequence analogous to that illustrated in Scheme 21.

| Cmpd | Structure | IUPAC Name | Exact Mass [M + H]+ |
|---|---|---|---|
| 21-7 | 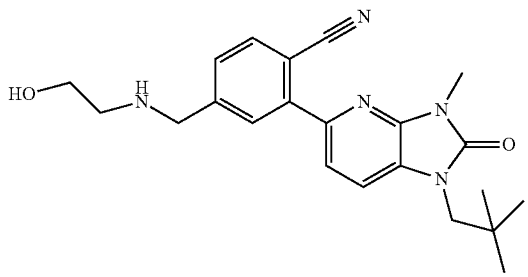 [SMILES: Cn1c(=O)n(CC(C)(C)C)c2ccc(-c3cc(CNCCO)ccc3C#N)nc21] | 2-[1-(2,2-dimethylpropyl)-3-methyl-2-oxo-2,3-dihydro-1H-imidazo[4,5-b]pyridin-5-yl]-4-{[(2-hydroxyethyl)amino]methyl}benzonitrile | Calc'd 394.2238, found 394.2240 |
| 21-8 | 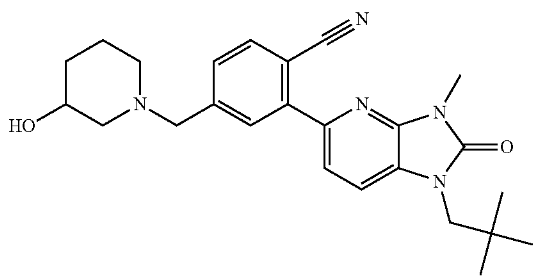 [SMILES: Cn1c(=O)n(CC(C)(C)C)c2ccc(-c3cc(CN4CCCC(O)C4)ccc3C#N)nc21] | 2-[1-(2,2-dimethylpropyl)-3-methyl-2-oxo-2,3-dihydro-1H-imidazo[4,5-b]pyridin-5-yl]-4-[(3-hydroxypiperidin-1-yl)methyl]benzonitrile | Calc'd 434.2551, found 434.2552 |
| 21-9 | 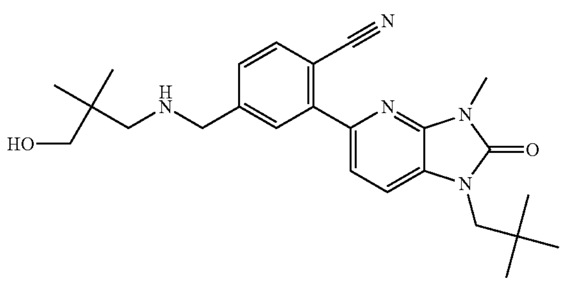 [SMILES: Cn1c(=O)n(CC(C)(C)C)c2ccc(-c3cc(CNCC(C)(C)CO)ccc3C#N)nc21] | 2-[1-(2,2-dimethylpropyl)-3-methyl-2-oxo-2,3-dihydro-1H-imidazo[4,5-b]pyridin-5-yl]-4-{[(3-hydroxy-2,2-dimethylpropyl)amino]methyl}benzonitrile | Calc'd 436.2707, found 436.2720 |
| 21-10 | 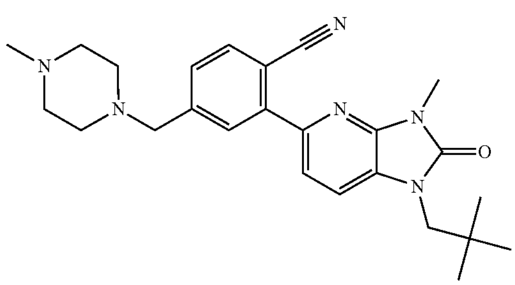 [SMILES: CN1CCN(Cc2ccc(C#N)c(-c3ccc4c(n3)n(C)c(=O)n4CC(C)(C)C)c2)CC1] | 2-[1-(2,2-dimethylpropyl)-3-methyl-2-oxo-2,3-dihydro-1H-imidazo[4,5-b]pyridin-5-yl]-4-[(4-methylpiperazin-1-yl)methyl]benzonitrile | Calc'd 433.2710, found 433.2731 |
| 21-11 | 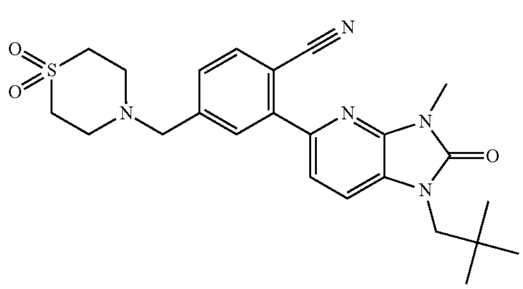 [SMILES: Cn1c(=O)n(CC(C)(C)C)c2ccc(-c3cc(CN4CCS(=O)(=O)CC4)ccc3C#N)nc21] | 2-[1-(2,2-dimethylpropyl)-3-methyl-2-oxo-2,3-dihydro-1H-imidazo[4,5-b]pyridin-5-yl]-4-[(1,1-dioxidothiomorpholin-4-yl)methyl]benzonitrile | Calc'd 468.2064, found 468.2073 |

TABLE 10-continued

The following compounds were prepared from 21-1 by a reaction sequence analogous to that illustrated in Scheme 21.

| Cmpd | Structure | IUPAC Name | Exact Mass [M + H]+ |
|---|---|---|---|
| 21-12 | 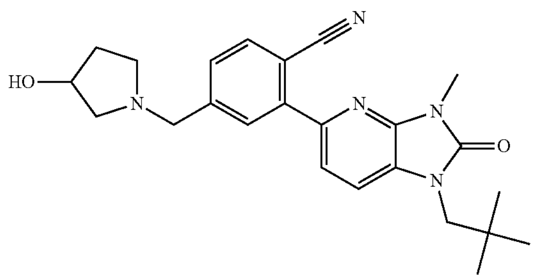 [SMILES: Cn1c(=O)n(CC(C)(C)C)c2ccc(-c3cc(CN4CCC(O)C4)ccc3C#N)nc21] | 2-[1-(2,2-dimethylpropyl)-3-methyl-2-oxo-2,3-dihydro-1H-imidazo[4,5-b]pyridin-5-yl]-4-[(3-hydroxypyrrolidin-1-yl)methyl]benzonitrile | Calc'd 420.2394, found 420.2404 |
| 21-13 | 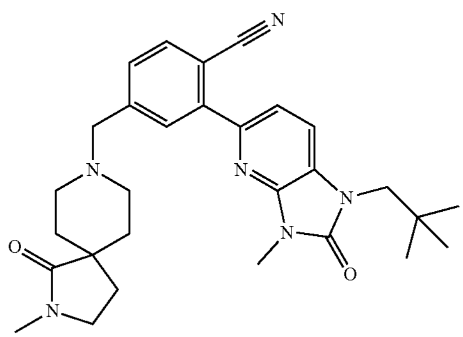 [SMILES: CN1CCC2(CCN(Cc3ccc(C#N)c(-c4ccc5c(n4)n(C)c(=O)n5CC(C)(C)C)c3)CC2)C1=O] | 2-[1-(2,2-dimethylpropyl)-3-methyl-2-oxo-2,3-dihydro-1H-imidazo[4,5-b]pyridin-5-yl]-4-[(2-methyl-1-oxo-2,8-diazaspiro[4.5]dec-8-yl)methyl]benzonitrile | Calc'd 501.2973, found 501.2976 |
| 21-14 | 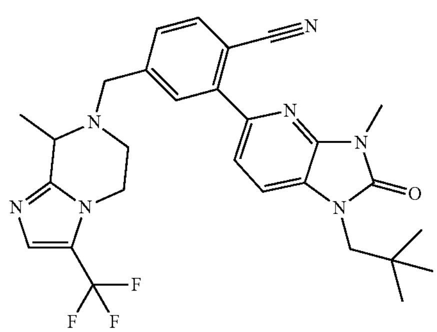 [SMILES: CC1c2ncc(C(F)(F)F)n2CCN1Cc1ccc(C#N)c(-c2ccc3c(n2)n(C)c(=O)n3CC(C)(C)C)c1] | 2-[1-(2,2-dimethylpropyl)-3-methyl-2-oxo-2,3-dihydro-1H-imidazo[4,5-b]pyridin-5-yl]-4-{[8-methyl-3-(trifluoromethyl)-5,6-dihydroimidazo[1,2-a]pyrazin-7(8H)-yl]methyl}benzonitrile | Calc'd 538.2537, found 538.2542 |
| 21-15 | 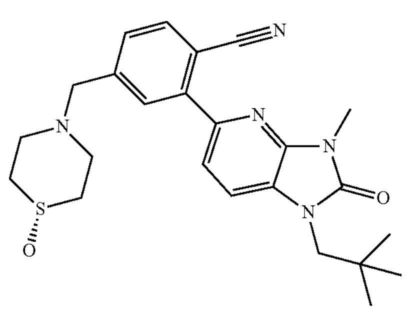 | 2-[1-(2,2-dimethylpropyl)-3-methyl-2-oxo-2,3-dihydro-1H-imidazo[4,5-b]pyridin-5-yl]-4-[(1-oxidothiomorpholin-4-yl)methyl]benzonitrile | Calc'd 452.2115, found 452.2116 |

TABLE 10-continued

The following compounds were prepared from 21-1 by a reaction sequence analogous to that illustrated in Scheme 21.

| Cmpd | Structure | IUPAC Name | Exact Mass [M + H]+ |
|---|---|---|---|
| 21-16 | 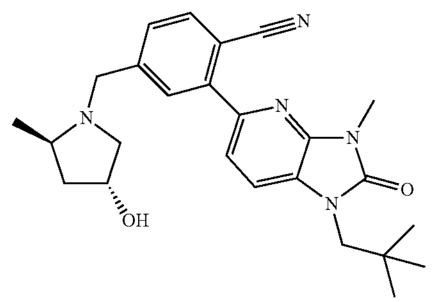 [SMILES: C[C@@H]1C[C@@H](O)CN1Cc1ccc(C#N)c(-c2ccc3c(n2)n(C)c(=O)n3CC(C)(C)C)c1] | 2-[1-(2,2-dimethylpropyl)-3-methyl-2-oxo-2,3-dihydro-1H-imidazo[4,5-b]pyridin-5-yl]-4-{[(2R,4R)-4-hydroxy-2-methylpyrrolidin-1-yl]methyl}benzonitrile | Calc'd 434.2551, found 434.2552 |
| 21-17 | 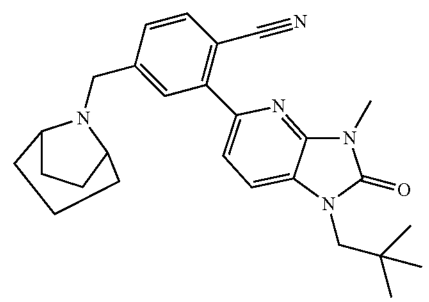 [SMILES: Cn1c(=O)n(CC(C)(C)C)c2ccc(-c3cc(CN4C5CCCC4CC5)ccc3C#N)nc21] | 4-(8-azabicyclo[3.2.1]oct-8-ylmethyl)-2-[1-(2,2-dimethylpropyl)-3-methyl-2-oxo-2,3-dihydro-1H-imidazo[4,5-b]pyridin-5-yl]benzonitrile | Calc'd 444.2758, found 444.2760 |
| 21-18 | 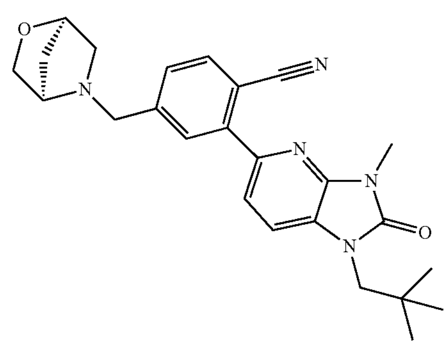 [SMILES: Cn1c(=O)n(CC(C)(C)C)c2ccc(-c3cc(CN4C[C@H]5C[C@@H]4CO5)ccc3C#N)nc21] | 2-[1-(2,2-dimethylpropyl)-3-methyl-2-oxo-2,3-dihydro-1H-imidazo[4,5-b]pyridin-5-yl]-4-[(1R,4R)-2-oxa-5-azabicyclo[2.2.1]hept-5-ylmethyl]benzonitrile | Calc'd 432.2394, found 432.2394 |
| 21-19 | 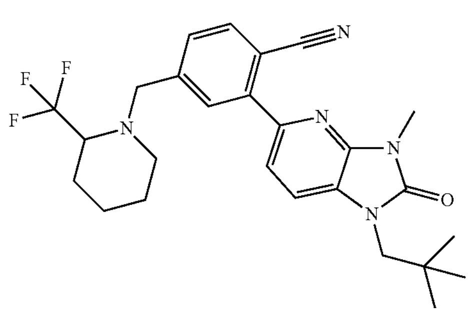 [SMILES: Cn1c(=O)n(CC(C)(C)C)c2ccc(-c3cc(CN4CCCCC4C(F)(F)F)ccc3C#N)nc21] | 2-[1-(2,2-dimethylpropyl)-3-methyl-2-oxo-2,3-dihydro-1H-imidazo[4,5-b]pyridin-5-yl]-4-{[2-(trifluoromethyl)piperidin-1-yl]methyl}benzonitrile | Calc'd 486.2475, found 486.2477 |

TABLE 10-continued

The following compounds were prepared from 21-1 by a reaction sequence analogous to that illustrated in Scheme 21.

| Cmpd | Structure | IUPAC Name | Exact Mass [M + H]+ |
|---|---|---|---|
| 21-20 | 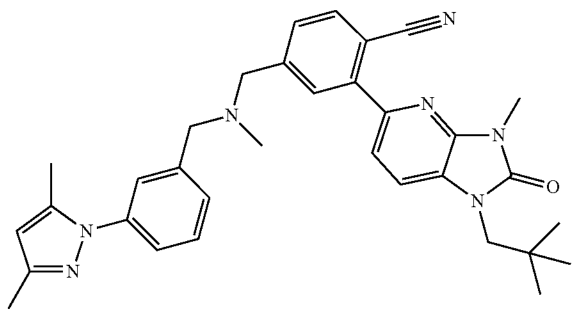 [SMILES: Cc1cc(C)n(-c2cccc(CN(C)Cc3ccc(C#N)c(-c4ccc5c(n4)n(C)c(=O)n5CC(C)(C)C)c3)c2)n1] | 2-[1-(2,2-dimethylpropyl)-3-methyl-2-oxo-2,3-dihydro-1H-imidazo[4,5-b]pyridin-5-yl]-4-({[3-(3,5-dimethyl-1H-pyrazol-1-yl)benzyl](methyl)amino}methyl)benzonitrile | Calc'd 548.3132, found 548.2132 |
| 21-21 | 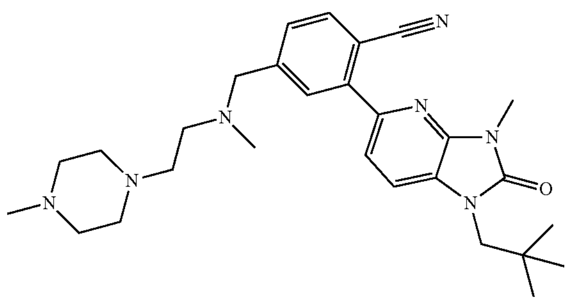 [SMILES: CN1CCN(CCN(C)Cc2ccc(C#N)c(-c3ccc4c(n3)n(C)c(=O)n4CC(C)(C)C)c2)CC1] | 2-[1-(2,2-dimethylpropyl)-3-methyl-2-oxo-2,3-dihydro-1H-imidazo[4,5-b]pyridin-5-yl]-4-({methyl[2-(4-methylpiperazin-1-yl)ethyl]amino}methyl)benzonitrile | Calc'd 490.3289, found 490.3288 |
| 21-22 | 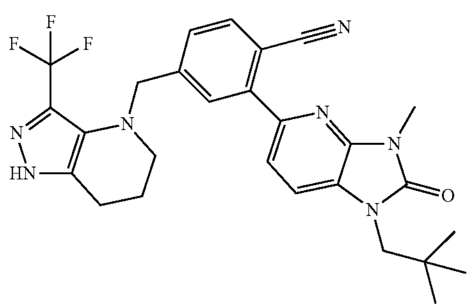 [SMILES: Cn1c(=O)n(CC(C)(C)C)c2ccc(-c3cc(CN4CCCc5[nH]nc(C(F)(F)F)c54)ccc3C#N)nc21] | 2-[1-(2,2-dimethylpropyl)-3-methyl-2-oxo-2,3-dihydro-1H-imidazo[4,5-b]pyridin-5-yl]-4-{[3-(trifluoromethyl)-1,5,6,7-tetrahydro-4H-pyrazolo[4,3-b]pyridin-4-yl]methyl}benzonitrile | Calc'd 524.2380, found 524.2383 |
| 21-23 | 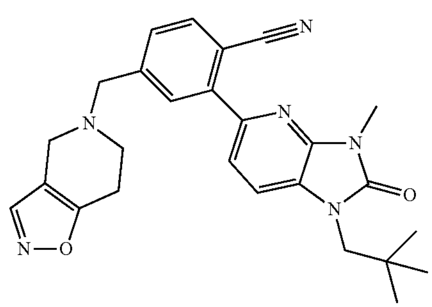 [SMILES: Cn1c(=O)n(CC(C)(C)C)c2ccc(-c3cc(CN4CCc5oncc5C4)ccc3C#N)nc21] | 4-(6,7-dihydroisoxazolo[4,5-c]pyridin-5(4H)-ylmethyl)-2-[1-(2,2-dimethylpropyl)-3-methyl-2-oxo-2,3-dihydro-1H-imidazo[4,5-b]pyridin-5-yl]benzonitrile | Calc'd 457.2347, found 457.2347 |

TABLE 10-continued

The following compounds were prepared from 21-1 by a reaction sequence analogous to that illustrated in Scheme 21.

| Cmpd | Structure | IUPAC Name | Exact Mass [M + H]+ |
|---|---|---|---|
| 21-24 | 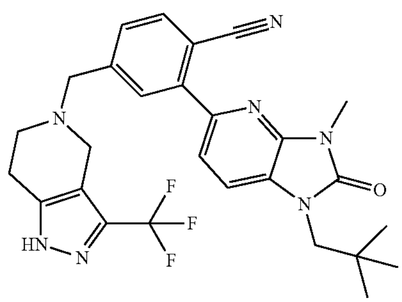 [SMILES: Cn1c(=O)n(CC(C)(C)C)c2ccc(-c3cc(CN4CCc5[nH]nc(C(F)(F)F)c5C4)ccc3C#N)nc21] | 2-[1-(2,2-dimethylpropyl)-3-methyl-2-oxo-2,3-dihydro-1H-imidazo[4,5-b]pyridin-5-yl]-4-{[3-(trifluoromethyl)-1,4,6,7-tetrahydro-5H-pyrazolo[4,3-c]pyridin-5-yl]methyl}benzonitrile | Calc'd 524.2380, found 524.2379 |
| 21-25 | 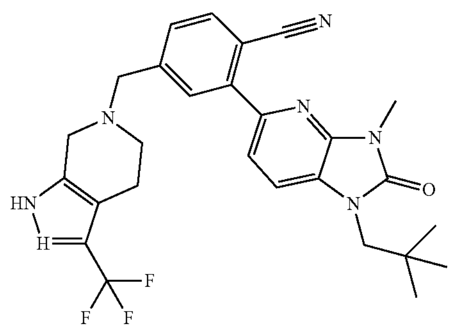 | 2-[1-(2,2-dimethylpropyl)-3-methyl-2-oxo-2,3-dihydro-1H-imidazo[4,5-b]pyridin-5-yl]-4-{[3-(trifluoromethyl)-1,4,5,7-tetrahydro-6H-pyrazolo[3,4-c]pyridin-6-yl]methyl}benzonitrile | Calc'd 524.2380, found 524.2379 |
| 21-26 | 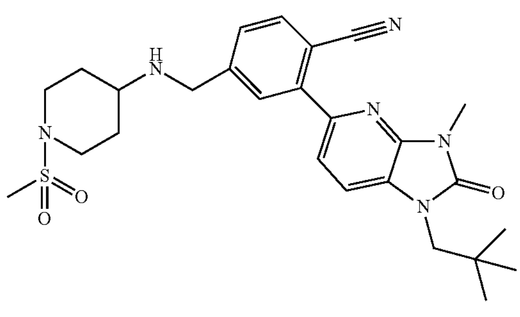 [SMILES: Cn1c(=O)n(CC(C)(C)C)c2ccc(-c3cc(CNC4CCN(S(C)(=O)=O)CC4)ccc3C#N)nc21] | 2-[1-(2,2-dimethylpropyl)-3-methyl-2-oxo-2,3-dihydro-1H-imidazo[4,5-b]pyridin-5-yl]-4-({[1-(methylsulfonyl)piperidin-4-yl]amino}methyl)benzonitrile | Calc'd 511.2486, found 511.2486 |
| 21-27 | 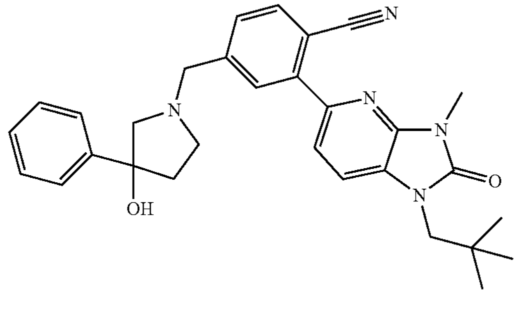 [SMILES: Cn1c(=O)n(CC(C)(C)C)c2ccc(-c3cc(CN4CCC(O)(c5ccccc5)C4)ccc3C#N)nc21] | 2-[1-(2,2-dimethylpropyl)-3-methyl-2-oxo-2,3-dihydro-1H-imidazo[4,5-b]pyridin-5-yl]-4-[(3-hydroxy-3-phenylpyrrolidin-1-yl)methyl]benzonitrile | Calc'd 496.2707, found 496.2707 |

TABLE 10-continued

The following compounds were prepared from 21-1 by a reaction sequence analogous to that illustrated in Scheme 21.

| Cmpd | Structure | IUPAC Name | Exact Mass [M + H]+ |
|---|---|---|---|
| 21-28 | 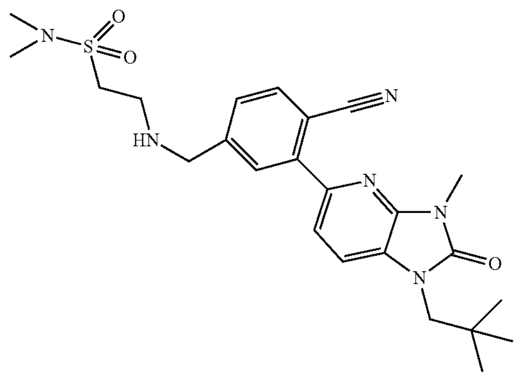 [SMILES: CN(C)S(=O)(=O)CCNCc1ccc(C#N)c(-c2ccc3c(n2)n(C)c(=O)n3CC(C)(C)C)c1] | 2-({4-cyano-3-[1-(2,2-dimethylpropyl)-3-methyl-2-oxo-2,3-dihydro-1H-imidazo[4,5-b]pyridin-5-yl]benzyl}amino)-N,N-dimethylethanesulfonamide | Calc'd 485.2329, found 485.2328 |
| 21-29 | 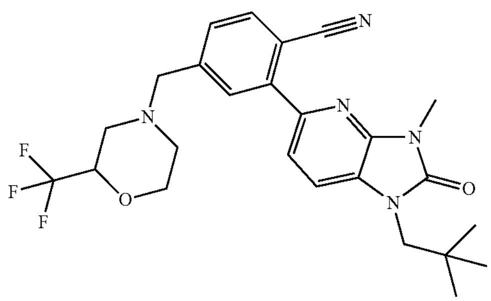 | 2-[1-(2,2-dimethylpropyl)-3-methyl-2-oxo-2,3-dihydro-1H-imidazo[4,5-b]pyridin-5-yl]-4-{[2-(trifluoromethyl)morpholin-4-yl]methyl}benzonitrile | Calc'd 488.2268, found 488.2268 |
| 21-30 | 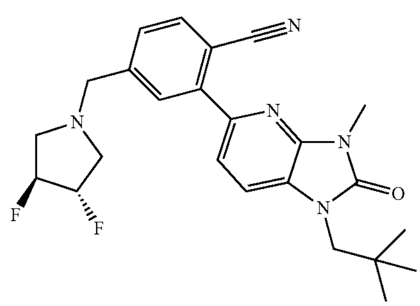 [SMILES: Cn1c(=O)n(CC(C)(C)C)c2ccc(-c3cc(CN4C[C@H](F)[C@@H](F)C4)ccc3C#N)nc21] | 4-{[(3S,4S)-3,4-difluoropyrrolidin-1-yl]methyl}-2-[1-(2,2-dimethylpropyl)-3-methyl-2-oxo-2,3-dihydro-1H-imidazo[4,5-b]pyridin-5-yl]benzonitrile | Calc'd 440.2256, found 440.2256 |
| 21-31 | 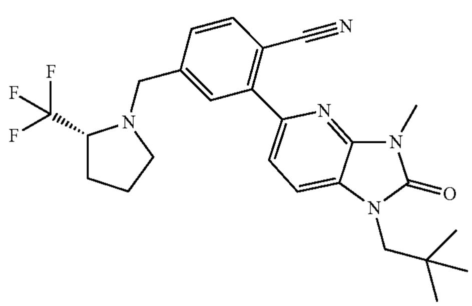 [SMILES: Cn1c(=O)n(CC(C)(C)C)c2ccc(-c3cc(CN4CCC[C@@H]4C(F)(F)F)ccc3C#N)nc21] | 2-[1-(2,2-dimethylpropyl)-3-methyl-2-oxo-2,3-dihydro-1H-imidazo[4,5-b]pyridin-5-yl]-4-{[(2R)-2-(trifluoromethyl)pyrrolidin-1-yl]methyl}benzonitrile | Calc'd 472.2319, found 472.2317 |

TABLE 10-continued

The following compounds were prepared from 21-1 by a reaction sequence analogous to that illustrated in Scheme 21.

| Cmpd | Structure | IUPAC Name | Exact Mass [M + H]+ |
| --- | --- | --- | --- |
| 21-32 | 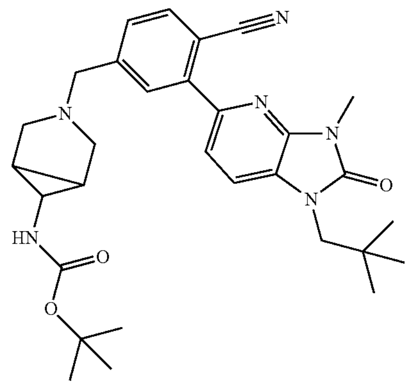 [SMILES: Cn1c(=O)n(CC(C)(C)C)c2ccc(-c3cc(CN4CC5C(C4)C5NC(=O)OC(C)(C)C)ccc3C#N)nc21] | tert-butyl (3-{4-cyano-3-[1-(2,2-dimethylpropyl)-3-methyl-2-oxo-2,3-dihydro-1H-imidazo[4,5-b]pyridin-5-yl]benzyl}-3-azabicyclo[3.1.0]hex-6-yl)carbamate | Calc'd 531.3078, found 531.3078 |
| 21-33 | 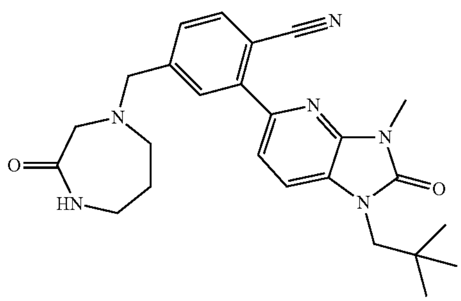 [SMILES: Cn1c(=O)n(CC(C)(C)C)c2ccc(-c3cc(CN4CCCNC(=O)C4)ccc3C#N)nc21] | 2-[1-(2,2-dimethylpropyl)-3-methyl-2-oxo-2,3-dihydro-1H-imidazo[4,5-b]pyridin-5-yl]-4-[(3-oxo 1,4-diazepan-1-yl)methyl]benzonitrile | Calc'd 447.2503, found 447.2503 |
| 21-34 | 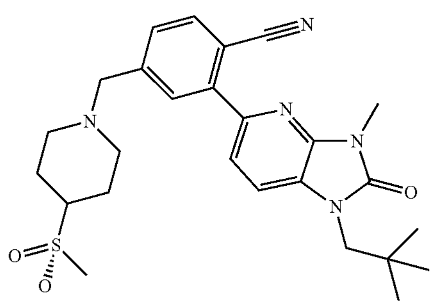 | 2-[1-(2,2-dimethylpropyl)-3-methyl-2-oxo-2,3-dihydro-1H-imidazo[4,5-b]pyridin-5-yl]-4-{[4-(methylsulfonyl)piperidin-1-yl]methyl}benzonitrile | Calc'd 496.2377, found 496.2376 |
| 21-35 | 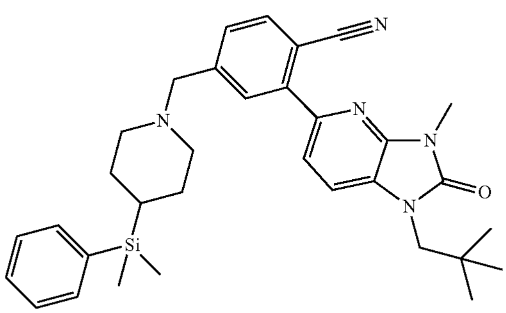 [SMILES: Cn1c(=O)n(CC(C)(C)C)c2ccc(-c3cc(CN4CCC([Si](C)(C)c5ccccc5)CC4)ccc3C#N)nc21] | 4-({4-[dimethyl(phenyl)silyl]piperidin-1-yl}methyl)-2-[1-(2,2-dimethylpropyl)-3-methyl-2-oxo-2,3-dihydro-1H-imidazo[4,5-b]pyridin-5-yl]benzonitrile | Calc'd 552.3153, found 552.3153 |

TABLE 10-continued

The following compounds were prepared from 21-1 by a reaction sequence analogous to that illustrated in Scheme 21.

| Cmpd | Structure | IUPAC Name | Exact Mass [M + H]+ |
|---|---|---|---|
| 21-36 | 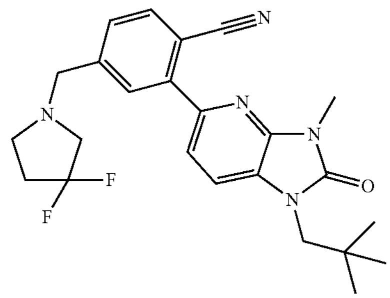 [SMILES: Cn1c(=O)n(CC(C)(C)C)c2ccc(-c3cc(CN4CCC(F)(F)C4)ccc3C#N)nc21] | 4-[(3,3-difluoropyrrolidin-1-yl)methyl]-2-[1-(2,2-dimethylpropyl)-3-methyl-2-oxo-2,3-dihydro-1H-imidazo[4,5-b]pyridin-5-yl]benzonitrile | Calc'd 440.2256, found 440.2256 |
| 21-37 | 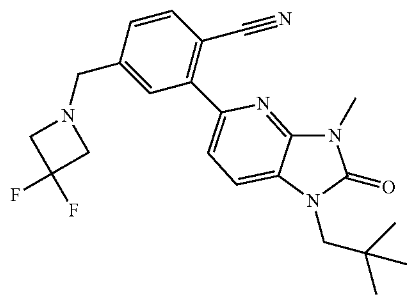 [SMILES: Cn1c(=O)n(CC(C)(C)C)c2ccc(-c3cc(CN4CC(F)(F)C4)ccc3C#N)nc21] | 4-[(3,3-difluoroazetidin-1-yl)methyl]-2-[1-(2,2-dimethylpropyl)-3-methyl-2-oxo-2,3-dihydro-1H-imidazo[4,5-b]pyridin-5-yl]benzonitrile | Calc'd 426.2100, found 426.2101 |
| 21-38 | 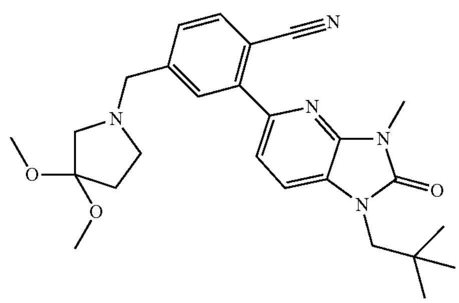 [SMILES: COC1(OC)CCN(Cc2ccc(C#N)c(-c3ccc4c(n3)n(C)c(=O)n4CC(C)(C)C)c2)C1] | 4-[(3,3-dimethoxypyrrolidin-1-yl)methyl]-2-[1-(2,2-dimethylpropyl)-3-methyl-2-oxo-2,3-dihydro-1H-imidazo[4,5-b]pyridin-5-yl]benzonitrile | Calc'd 464.2656, found 464.2657 |
| 21-39 | 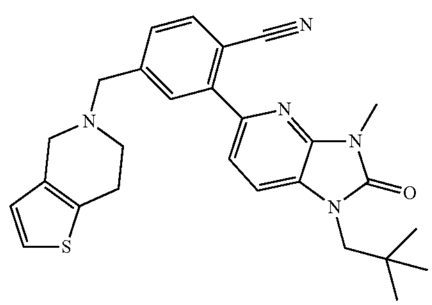 [SMILES: Cn1c(=O)n(CC(C)(C)C)c2ccc(-c3cc(CN4CCc5sccc5C4)ccc3C#N)nc21] | 4-(6,7-dihydrothieno[3,2-c]pyridin-5(4H)-ylmethyl)-2-[1-(2,2-dimethylpropyl)-3-methyl-2-oxo-2,3-dihydro-1H-imidazo[4,5-b]pyridin-5-yl]benzonitrile | Calc'd 472.2166, found 472.2166 |
| 21-40 | 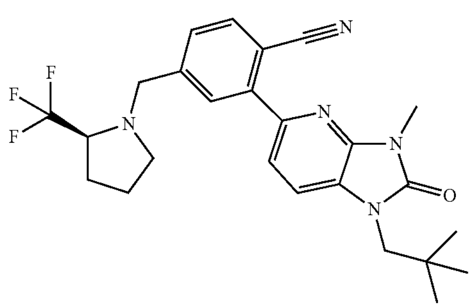 [SMILES: Cn1c(=O)n(CC(C)(C)C)c2ccc(-c3cc(CN4CCC[C@H]4C(F)(F)F)ccc3C#N)nc21] | 2-[1-(2,2-dimethylpropyl)-3-methyl-2-oxo-2,3-dihydro-1H-imidazo[4,5-b]pyridin-5-yl]-4-{[(2S)-2-(trifluoromethyl)pyrrolidin-1-yl]methyl}benzonitrile | Calc'd 472.2319, found 472.2320 |

TABLE 10-continued

The following compounds were prepared from 21-1 by a reaction sequence analogous to that illustrated in Scheme 21.

| Cmpd | Structure | IUPAC Name | Exact Mass [M + H]+ |
| --- | --- | --- | --- |
| 21-41 | 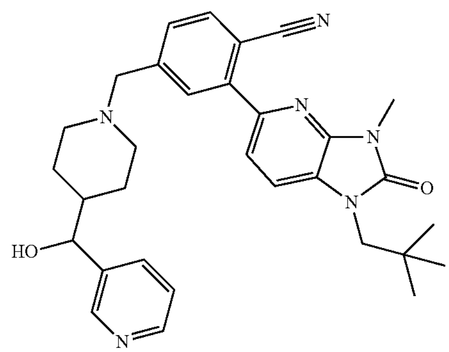 [SMILES: Cn1c(=O)n(CC(C)(C)C)c2ccc(-c3cc(CN4CCC(C(O)c5cccnc5)CC4)ccc3C#N)nc21] | 2-[1-(2,2-dimethylpropyl)-3-methyl-2-oxo-2,3-dihydro-1H-imidazo[4,5-b]pyridin-5-yl]-4-({4-[hydroxy(pyridin-3-yl)methyl]piperidin-1-yl}methyl)benzonitrile | Calc'd 525.2973, found 525.2971 |
| 21-42 | 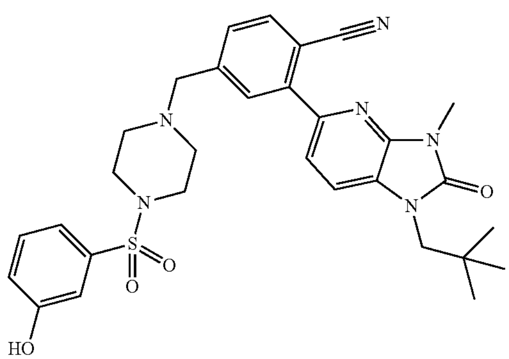 [SMILES: Cn1c(=O)n(CC(C)(C)C)c2ccc(-c3cc(CN4CCN(S(=O)(=O)c5cccc(O)c5)CC4)ccc3C#N)nc21] | 2-[1-(2,2-dimethylpropyl)-3-methyl-2-oxo-2,3-dihydro-1H-imidazo[4,5-b]pyridin-5-yl]-4-({4-[(3-hydroxyphenyl)sulfonyl]piperazin-1-yl}methyl)benzonitrile | Calc'd 575.2435, found 575.2434 |
| 21-43 | 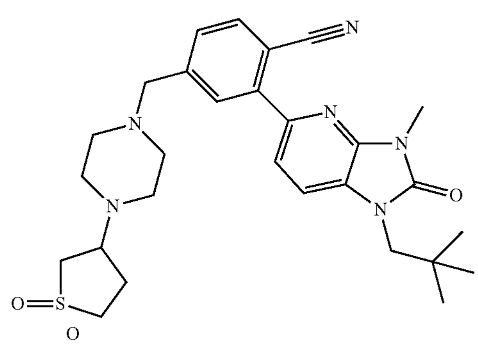 | 2-[1-(2,2-dimethylpropyl)-3-methyl-2-oxo-2,3-dihydro-1H-imidazo[4,5-b]pyridin-5-yl]-4-{[4-(1,1-dioxidotetrahydrothiophen-3-yl)piperazin-1-yl]methyl}benzonitrile | Calc'd 537.2642, found 537.2639 |
| 21-44 | 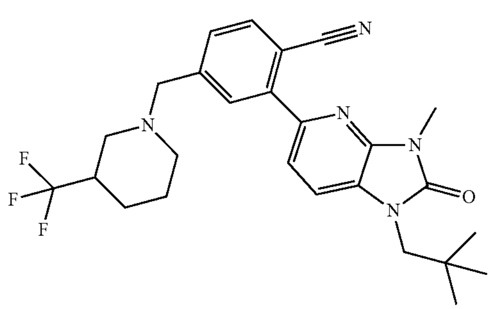 [SMILES: Cn1c(=O)n(CC(C)(C)C)c2ccc(-c3cc(CN4CCCC(C(F)(F)F)C4)ccc3C#N)nc21] | 2-[1-(2,2-dimethylpropyl)-3-methyl-2-oxo-2,3-dihydro-1H-imidazo[4,5-b]pyridin-5-yl]-4-{[3-(trifluoromethyl)piperidin-1-yl]methyl}benzonitrile | Calc'd 486.2475, found 486.2475 |

TABLE 10-continued

The following compounds were prepared from 21-1 by a reaction sequence analogous to that illustrated in Scheme 21.

| Cmpd | Structure | IUPAC Name | Exact Mass [M + H]+ |
|---|---|---|---|
| 21-45 | 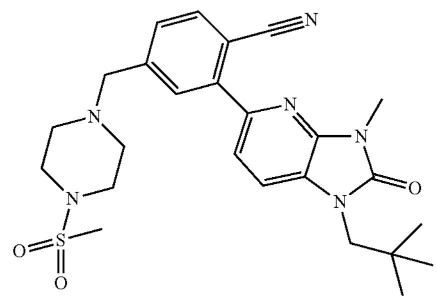 [SMILES: Cn1c(=O)n(CC(C)(C)C)c2ccc(-c3cc(CN4CCN(S(C)(=O)=O)CC4)ccc3C#N)nc21] | 2-[1-(2,2-dimethylpropyl)-3-methyl-2-oxo-2,3-dihydro-1H-imidazo[4,5-b]pyridin-5-yl]-4-{[4-(methylsulfonyl)piperazin-1-yl]methyl}benzonitrile | Calc'd 497.2329, found 497.2330 |
| 21-46 | 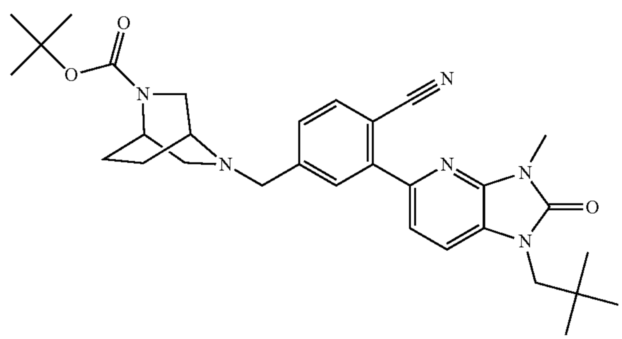 [SMILES: Cn1c(=O)n(CC(C)(C)C)c2ccc(-c3cc(CN4CC5CCC4CN5C(=O)OC(C)(C)C)ccc3C#N)nc21] | tert-butyl 5-{4-cyano-3-[1-(2,2-dimethylpropyl)-3-methyl-2-oxo-2,3-dihydro-1H-imidazo[4,5-b]pyridin-5-yl]benzyl}-2,5-diazabicyclo[2.2.2]octane-2-carboxylate | Calc'd 545.3235, found 545.3226 |
| 21-47 | 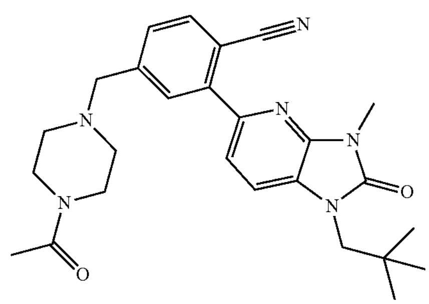 [SMILES: CC(=O)N1CCN(Cc2ccc(C#N)c(-c3ccc4c(n3)n(C)c(=O)n4CC(C)(C)C)c2)CC1] | 4-[(4-acetylpiperazin-1-yl)methyl]-2-[1-(2,2-dimethylpropyl)-3-methyl-2-oxo-2,3-dihydro-1H-imidazo[4,5-b]pyridin-5-yl]benzonitrile | Calc'd 461.2660, found 461.2660 |
| 21-48 | 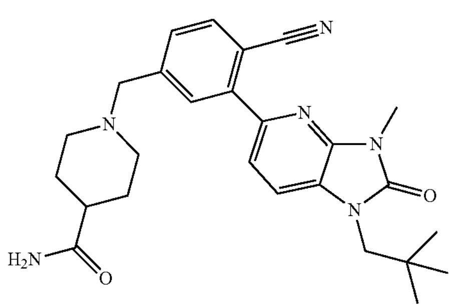 [SMILES: Cn1c(=O)n(CC(C)(C)C)c2ccc(-c3cc(CN4CCC(C(N)=O)CC4)ccc3C#N)nc21] | 1-{4-cyano-3-[1-(2,2-dimethylpropyl)-3-methyl-2-oxo-2,3-dihydro-1H-imidazo[4,5-b]pyridin-5-yl]benzyl}piperidine-4-carboxamide | Calc'd 461.2660, found 461.2660 |

TABLE 10-continued

The following compounds were prepared from 21-1 by a reaction sequence analogous to that illustrated in Scheme 21.

| Cmpd | Structure | IUPAC Name | Exact Mass [M + H]+ |
|---|---|---|---|
| 21-49 | 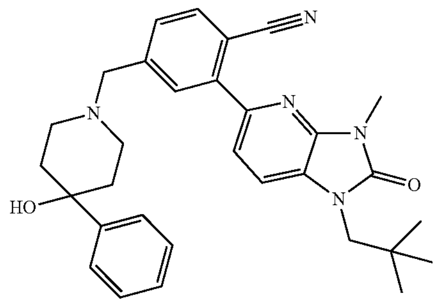 [SMILES: Cn1c(=O)n(CC(C)(C)C)c2ccc(-c3cc(CN4CCC(O)(c5ccccc5)CC4)ccc3C#N)nc21] | 2-[1-(2,2-dimethylpropyl)-3-methyl-2-oxo-2,3-dihydro-1H-imidazo[4,5-b]pyridin-5-yl]-4-[(4-hydroxy-4-phenyl benzonitrile | Calc'd 510.2864, found 510.2861 |
| 21-50 | 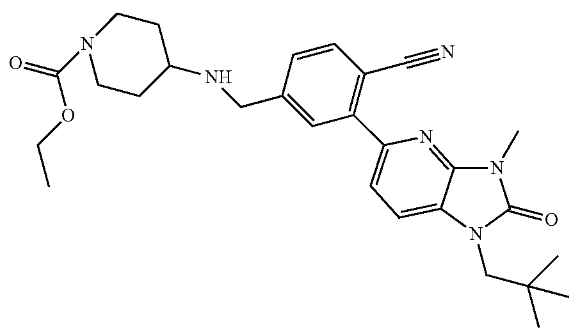 [SMILES: CCOC(=O)N1CCC(NCc2ccc(C#N)c(-c3ccc4c(n3)n(C)c(=O)n4CC(C)(C)C)c2)CC1] | ethyl 4-({4-cyano-3-[1-(2,2-dimethylpropyl)-3-methyl-2-oxo-2,3-dihydro-1H-imidazo[4,5-b]pyridin-5-yl]benzyl}amino) piperidine-1-carboxylate | Calc'd 505.2922, found 505.2921 |
| 21-51 | 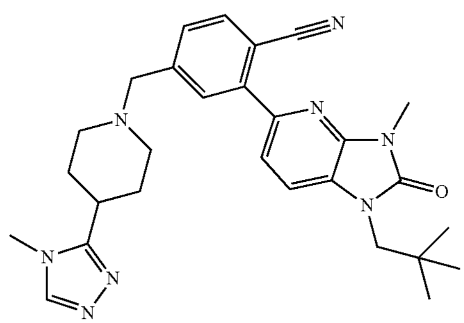 [SMILES: Cn1cnnc1C1CCN(Cc2ccc(C#N)c(-c3ccc4c(n3)n(C)c(=O)n4CC(C)(C)C)c2)CC1] | 2-[1-(2,2-dimethylpropyl)-3-methyl-2-oxo-2,3-dihydro-1H-imidazo[4,5-b]pyridin-5-yl]-4-{[4-(4-methyl-4H-1,2,4-triazol-3-yl)piperidin-1-yl]methyl}benzonitrile | Calc'd 499.2928, found 499.2926 |
| 21-52 | 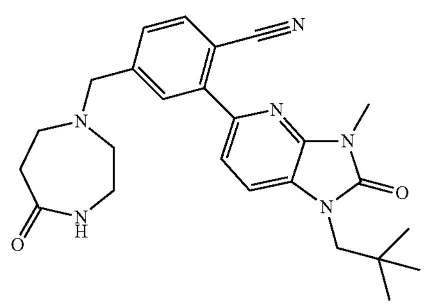 [SMILES: Cn1c(=O)n(CC(C)(C)C)c2ccc(-c3cc(CN4CCNC(=O)CC4)ccc3C#N)nc21] | 2-[1-(2,2-dimethylpropyl)-3-methyl-2-oxo-2,3-dihydro-1H-imidazo[4,5-b]pyridin-5-yl]-4-[(5-oxo-1,4-diazepan-1-yl)methyl]benzonitrile | Calc'd 447.2503, found 447.2503 |

TABLE 10-continued

The following compounds were prepared from 21-1 by a reaction sequence analogous to that illustrated in Scheme 21.

| Cmpd | Structure | IUPAC Name | Exact Mass [M + H]+ |
|---|---|---|---|
| 21-53 | 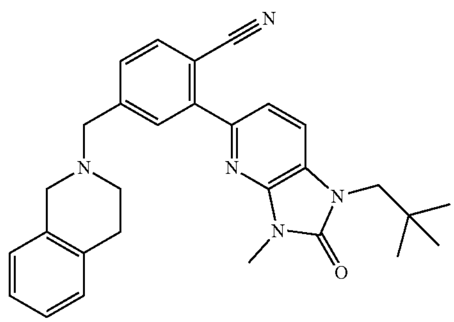 [SMILES: Cn1c(=O)n(CC(C)(C)C)c2ccc(-c3cc(CN4CCc5ccccc5C4)ccc3C#N)nc21] | 4-(3,4-dihydroisoquinolin-2(1H)-ylmethyl)-2-[1-(2,2-dimethylpropyl)-3-methyl-2-oxo-2,3-dihydro-1H-imidazo[4,5-b]pyridin-5-yl]benzomtrile | Calc'd 466.2601, found 466.2605 |
| 21-54 | 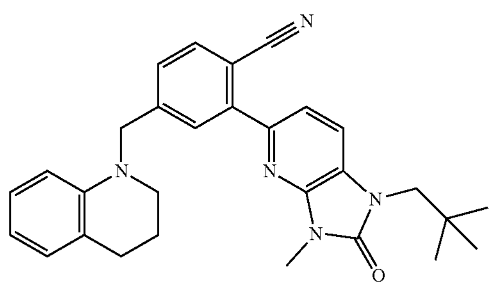 [SMILES: Cn1c(=O)n(CC(C)(C)C)c2ccc(-c3cc(CN4CCCc5ccccc54)ccc3C#N)nc21] | 4-(3,4-dihydroquinolin-1(2H)-ylmethyl)-2-[1-(2,2-dimethylpropyl)-3-methyl-2-oxo-2,3-dihydro-1H-imidazo[4,5-b]pyridin-5-yl]benzonitrile | Calc'd 466.2601, found 466.2602 |
| 21-55 | 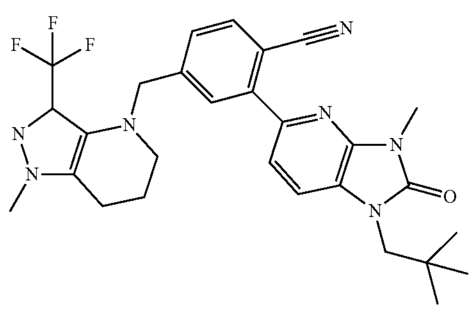 [SMILES: CN1NC(C(F)(F)F)C2=C1CCCN2Cc1ccc(C#N)c(-c2ccc3c(n2)n(C)c(=O)n3CC(C)(C)C)c1] | 2-[1-(2,2-dimethylpropyl)-3-methyl-2-oxo-2,3-dihydro-1H-imidazo[4,5-b]pyridin-5-yl]-4-{[1-methyl-3-(trifluoromethyl)-1,5,6,7-tetrahydo-4H-pyrazolo[4,3-b]pyridin-4-yl]methyl}benzonitrile | Calc'd 538.2537, found 538.2537 |
| 21-56 | 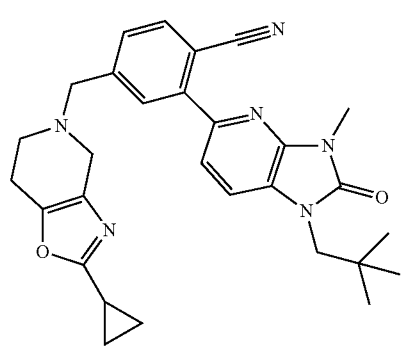 [SMILES: Cn1c(=O)n(CC(C)(C)C)c2ccc(-c3cc(CN4CCc5oc(C6CC6)nc5C4)ccc3C#N)nc21] | 4-[(2-cyclopropyl-6,7-dihydro[1,3]oxazolo[4,5-c]pyridin-5(4H)-yl)methyl]-2-[1-(2,2-dimethylpropyl)-3-methyl-2-oxo-2,3-dihydro-1H-imidazo[4,5-b]pyridin-5-yl]benzonitrile | Calc'd 497.2660, found 497.2665 |

TABLE 10-continued

The following compounds were prepared from 21-1 by a reaction sequence analogous to that illustrated in Scheme 21.

| Cmpd | Structure | IUPAC Name | Exact Mass [M + H]+ |
|---|---|---|---|
| 21-57 | 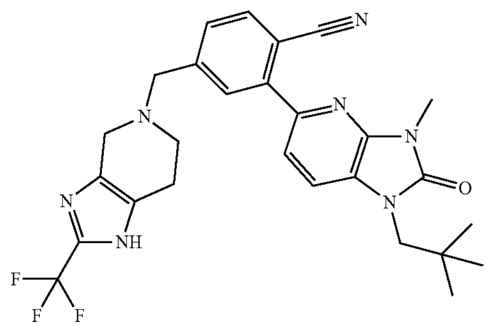 [SMILES: Cn1c(=O)n(CC(C)(C)C)c2ccc(-c3cc(CN4CCc5[nH]c(C(F)(F)F)nc5C4)ccc3C#N)nc21] | 2-[1-(2,2-dimethylpropyl)-3-methyl-2-oxo-2,3-dihydro-1H-imidazo[4,5-b]pyridin-5-yl]-4-{[2-(trifluoromethyl)-1,4,6,7-tetrahydro-5H-imidazo[4,5-c]pyridin-5-yl]methyl}benzonitrile | Calc'd 524.2380, found 524.2391 |
| 21-58 | 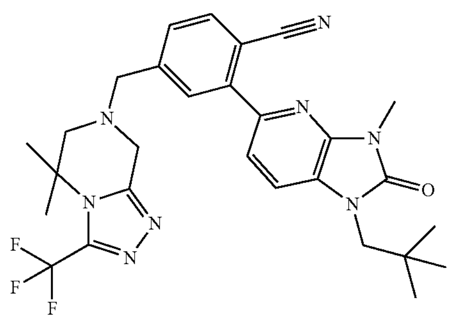 [SMILES: Cn1c(=O)n(CC(C)(C)C)c2ccc(-c3cc(CN4Cc5nnc(C(F)(F)F)n5C(C)(C)C4)ccc3C#N)nc21] | 2-[1-(2,2-dimethylpropyl)-3-methyl-2-oxo-2,3-dihydro-1H-imidazo[4,5-b]pyridin-5-yl]-4-{[5,5-dimethyl-3-(trifluoromethyl)-5,6-dihydro[1,2,4]triazolo[4,3-a]pyrazin-7(8H)-yl]methyl}benzonitrile | Calc'd 553.2646, found 553.2657 |
| 21-59 | 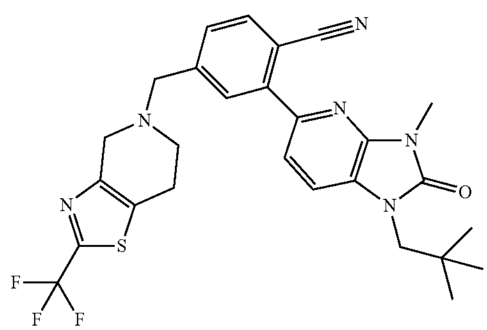 [SMILES: Cn1c(=O)n(CC(C)(C)C)c2ccc(-c3cc(CN4CCc5sc(C(F)(F)F)nc5C4)ccc3C#N)nc21] | 2-[1-(2,2-dimethylpropyl)-3-methyl-2-oxo-2,3-dihydro-1H-imidazo[4,5-b]pyridin-5-yl]-4-{[2-(trifluoromethyl)-6,7-dihydro[1,3]thiazolo[4,5-c]pyridin-5(4H)-yl]methyl}benzonitrile | Calc'd 541.1992, found 541.2003 |
| 21-60 | 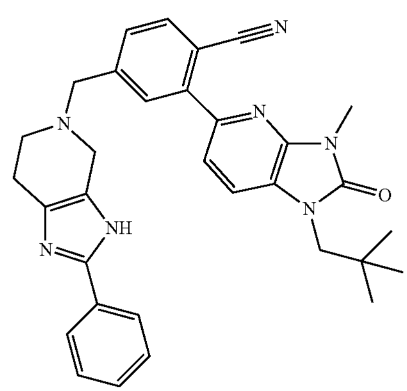 [SMILES: Cn1c(=O)n(CC(C)(C)C)c2ccc(-c3cc(CN4CCc5nc(-c6ccccc6)[nH]c5C4)ccc3C#N)nc21] | 2-[1-(2,2-dimethylpropyl)-3-methyl-2-oxo-2,3-dihydro-1H-imidazo[4,5-b]pyridin-5-yl]-4-[(2-phenyl-3,4,6,7-tetrahydro-5H-imidazo[4,5-c]pyridin-5-yl)methyl]benzonitrile | Calc'd 532.2819, found 532.2822 |

TABLE 10-continued

The following compounds were prepared from 21-1 by a reaction sequence analogous to that illustrated in Scheme 21.

| Cmpd | Structure | IUPAC Name | Exact Mass [M + H]+ |
|---|---|---|---|
| 21-61 | 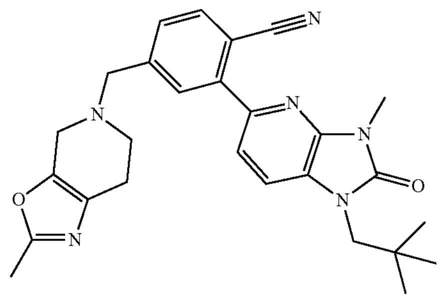 [SMILES: Cc1nc2c(o1)CN(Cc1ccc(C#N)c(-c3ccc4c(n3)n(C)c(=O)n4CC(C)(C)C)c1)CC2] | 2-[1-(2,2-dimethylpropyl)-3-methyl-2-oxo-2,3-dihydro-1H-imidazo[4,5-b]pyridin-5-yl]-4-[(2-methyl-6,7-dihydro[1,3]oxazolo[5,4-c]pyridin-5(4H)-yl)methyl]benzonitrile | Calc'd 471.2503, found 471.2509 |
| 21-62 | 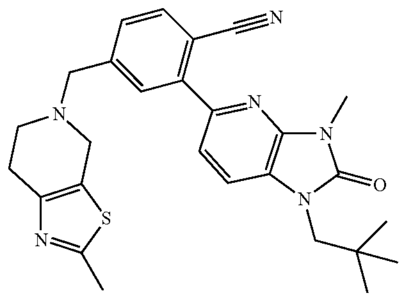 [SMILES: Cc1nc2c(s1)CN(Cc1ccc(C#N)c(-c3ccc4c(n3)n(C)c(=O)n4CC(C)(C)C)c1)CC2] | 2-[1-(2,2-dimethylpropyl)-3-methyl-2-oxo-2,3-dihydro-1H-imidazo[4,5-b]pyridin-5-yl]-4-[(2-methyl-6,7-dihydro[1,3]thiazolo[5,4-c]pyridin-5(4H)-yl)methyl]benzonitrile | Calc'd 487.2275, found 487.2281 |
| 21-63 | 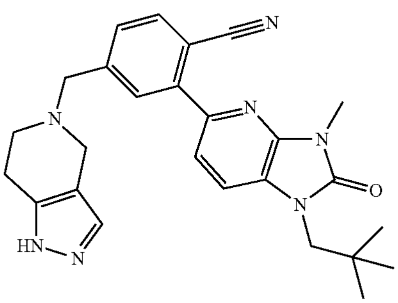 [SMILES: Cn1c(=O)n(CC(C)(C)C)c2ccc(-c3cc(CN4CCc5[nH]ncc5C4)ccc3C#N)nc21] | 2-[1-(2,2-dimethylpropyl)-3-methyl-2-oxo-2,3-dihydro-1H-imidazo[4,5-b]pyridin-5-yl]-4-(1,4,6,7-tetrahydro-5H-pyrazolo[4,3-c]pyridin-5-ylmethyl)benzonitrile | Calc'd 456.2506, found 456.2514 |
| 21-64 | 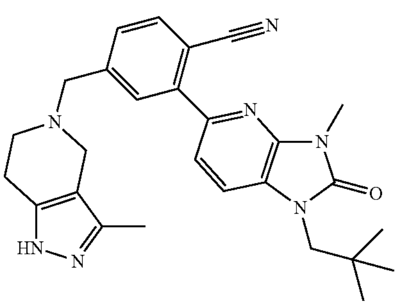 [SMILES: Cc1n[nH]c2c1CN(Cc1ccc(C#N)c(-c3ccc4c(n3)n(C)c(=O)n4CC(C)(C)C)c1)CC2] | 2-[1-(2,2-dimethylpropyl)-3-methyl-2-oxo-2,3-dihydro-1H-imidazo[4,5-b]pyridin-5-yl]-4-[(3-methyl-1,4,6,7-tetrahydro-5H-pyrazolo[4,3-c]pyridin-5-yl)methyl]benzonitrile | Calc'd 470.2663, found 470.2666 |
| 21-65 | 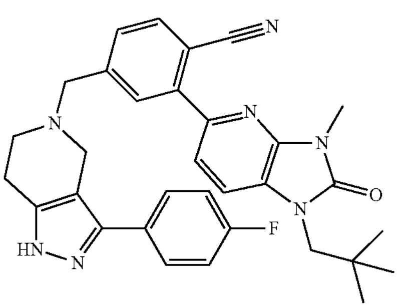 [SMILES: Cn1c(=O)n(CC(C)(C)C)c2ccc(-c3cc(CN4CCc5[nH]nc(-c6ccc(F)cc6)c5C4)ccc3C#N)nc21] | 2-[1-(2,2-dimethylpropyl)-3-methyl-2-oxo-2,3-dihydro-1H-imidazo[4,5-b]pyridin-5-yl]-4-{[3-(4-fluorophenyl)-1,4,6,7-tetrahydro-5H-pyrazolo[4,3-c]pyridin-5-yl]methyl}benzonitrile | Calc'd 550.2725, found 550.2734 |

TABLE 10-continued

The following compounds were prepared from 21-1 by a reaction sequence analogous to that illustrated in Scheme 21.

| Cmpd | Structure | IUPAC Name | Exact Mass [M + H]+ |
|---|---|---|---|
| 21-66 | 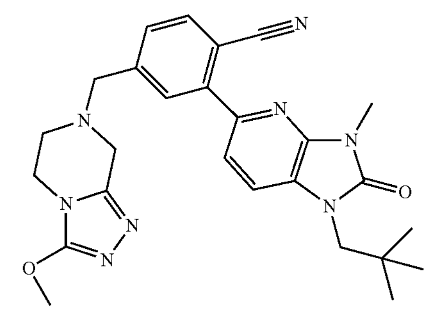 [SMILES: COc1nnc2n1CCN(Cc1ccc(C#N)c(-c3ccc4c(n3)n(C)c(=O)n4CC(C)(C)C)c1)C2] | 2-[1-(2,2-dimethylpropyl)-3-methyl-2-oxo-2,3-dihydro-1H-imidazo[4,5-b]pyridin-5-yl]-4-[(3-methoxy-5,6-dihydro[1,2,4]triazolo[4,3-a]pyrazin-7(8H)-yl)methyl]benzonitrile | Calc'd 487.2564, found 487.2570 |
| 21-67 | 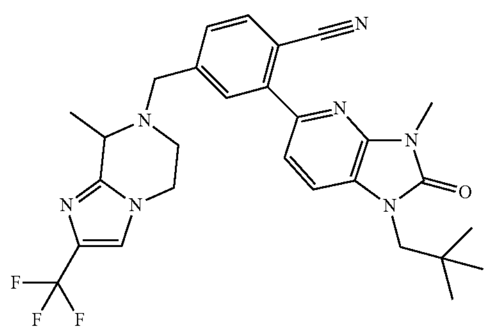 | 2-[1-(2,2-dimethylpropyl)-3-methyl-2-oxo-2,3-dihydro-1H-imidazo[4,5-b]pyridin-5-yl]-4-{[8-methyl-2-(trifluoromethyl)-5,6-dihydroimidazo[1,2-a]pyrazin-7(8H)-yl]methyl}benzonitrile | Calc'd 538.2537, found 538.2542 |
| 21-68 | 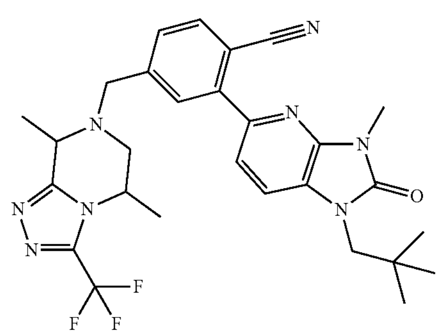 [SMILES: CC1c2nnc(C(F)(F)F)n2C(C)CN1Cc1ccc(C#N)c(-c2ccc3c(n2)n(C)c(=O)n3CC(C)(C)C)c1] | 2-[1-(2,2-dimethylpropyl)-3-methyl-2-oxo-2,3-dihydro-1H-imidazo[4,5-b]pyridin-5-yl]-4-{[5,8-dimethyl-3-(trifluoromethyl)-5,6-dihydro[1,2,4]triazolo[4,3-a]pyrazin-7(8H)-yl]methyl}benzonitrile | Calc'd 553.2646, found 553.2652 |
| 21-69 | 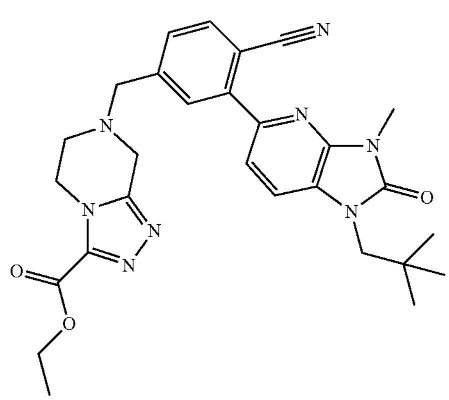 [SMILES: CCOC(=O)c1nnc2n1CCN(Cc1ccc(C#N)c(-c3ccc4c(n3)n(C)c(=O)n4CC(C)(C)C)c1)C2] | ethyl 7-{4-cyano-3-[1-(2,2-dimethylpropyl)-3-methyl-2-oxo-2,3-dihydro-1H-imidazo[4,5-b]pyridin-5-yl]benzyl}-5,6,7,8-tetrahydro[1,2,4]triazolo[4,3-a]pyrazine-3-carboxylate | Calc'd 526.2670, found 529.2666 |

TABLE 10-continued

The following compounds were prepared from 21-1 by a reaction sequence analogous to that illustrated in Scheme 21.

| Cmpd | Structure | IUPAC Name | Exact Mass [M + H]+ |
|---|---|---|---|
| 21-70 | 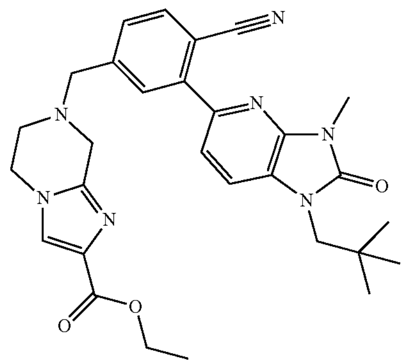 [SMILES: CCOC(=O)c1cn2c(n1)CN(Cc1ccc(C#N)c(-c3ccc4c(n3)n(C)c(=O)n4CC(C)(C)C)c1)CC2] | ethyl 7-{4-cyano-3-[1-(2,2-dimethylpropyl)-3-methyl-2-oxo-2,3-dihydro-1H-imidazo[4,5-b]pyridin-5-yl]benzyl}-5,6,7,8-tetrahydroimidazo[1,2-a]pyrazine-2-carboxylate | Calc'd 528.2718, found 528.2724 |
| 21-71 | 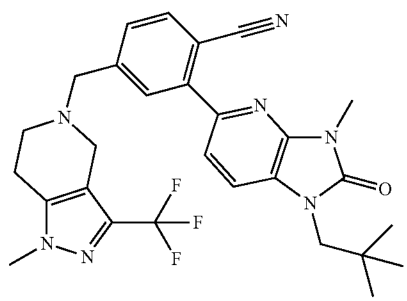 [SMILES: Cn1nc(C(F)(F)F)c2c1CCN(Cc1ccc(C#N)c(-c3ccc4c(n3)n(C)c(=O)n4CC(C)(C)C)c1)C2] | 2-[1-(2,2-dimethylpropyl)-3-methyl-2-oxo-2,3-dihydro-1H-imidazo[4,5-b]pyridin-5-yl]-4-{[1-methyl-3-(trifluoromethyl)-1,4,6,7-tetrahydro-5H-pyrazolo[4,3-c]pyridin-5-yl]methyl}benzonitrile | Calc'd 538.2537, found 538.2547 |
| 21-72 | 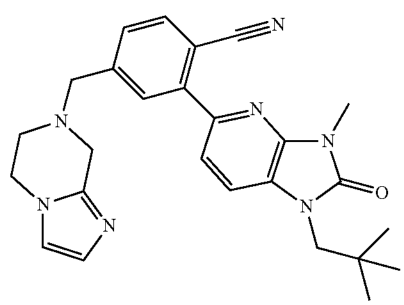 [SMILES: Cn1c(=O)n(CC(C)(C)C)c2ccc(-c3cc(CN4CCn5ccnc5C4)ccc3C#N)nc21] | 4-(5,6-dihydroimidazo[1,2-a]pyrazin-7(8H)-ylmethyl)-2-[1-(2,2-dimethylpropyl)-3-methyl-2-oxo-2,3-dihydro-1H-imidazo[4,5-b]pyridin-5-yl]benzonitrile | Calc'd 456.2506, found 456.2512 |
| 21-73 | 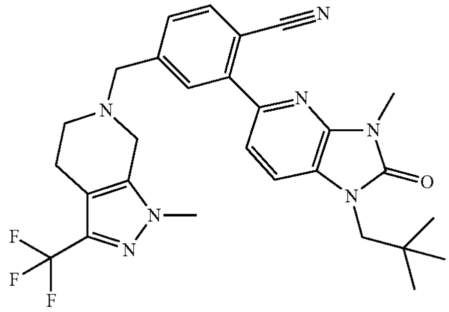 [SMILES: Cn1nc(C(F)(F)F)c2c1CN(Cc1ccc(C#N)c(-c3ccc4c(n3)n(C)c(=O)n4CC(C)(C)C)c1)CC2] | 2-[1-(2,2-dimethylpropyl)-3-methyl-2-oxo-2,3-dihydro-1H-imidazo[4,5-b]pyridin-5-yl]-4-{[1-methyl-3-(trifluoromethyl)-1,4,5,7-tetrahydro-6H-pyrazolo[3,4-c]pyridin-6-yl]methyl}benzonitrile | Calc'd 538.2537, found 538.2546 |

TABLE 10-continued

The following compounds were prepared from 21-1 by a reaction sequence analogous to that illustrated in Scheme 21.

| Cmpd | Structure | IUPAC Name | Exact Mass [M + H]+ |
|---|---|---|---|
| 21-74 | 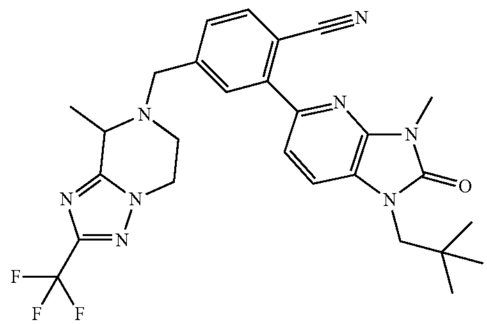 [SMILES: CC1c2nc(C(F)(F)F)nn2CCN1Cc1ccc(C#N)c(-c2ccc3c(n2)n(C)c(=O)n3CC(C)(C)C)c1] | 2-[1-(2,2-dimethylpropyl)-3-methyl-2-oxo-2,3-dihydro-1H-imidazo[4,5-b]pyridin-5-yl]-4-{[8-methyl-2-(trifluoromethyl)-5,6-dihydro[1,2,4]triazolo[1,5-a]pyrazin-7(8H)-yl]methyl}benzonitrile | Calc'd 539.2489, found 539.2493 |
| 21-75 | 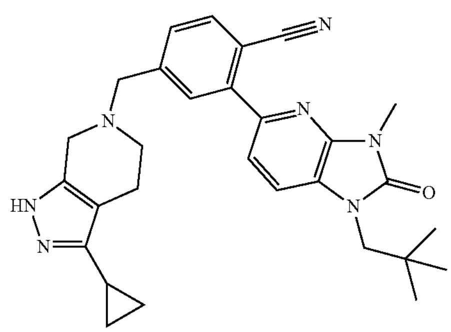 [SMILES: Cn1c(=O)n(CC(C)(C)C)c2ccc(-c3cc(CN4CCc5c(C6CC6)n[nH]c5C4)ccc3C#N)nc21] | 4-[(3-cyclopropyl-1,4,5,7-tetrahydro-6H-pyrazolo[3,4-c]pyridin-6-yl)methyl]-2-[1-(2,2-dimethylpropyl)-3-methyl-2-oxo-2,3-dihydro-1H-imidazo[4,5-b]pyridin-5-yl]benzonitrile | Calc'd 496.2819, found 496.2828 |
| 21-76 | 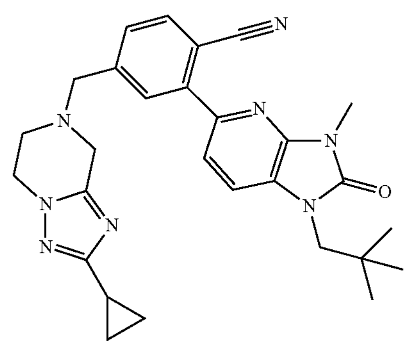 [SMILES: Cn1c(=O)n(CC(C)(C)C)c2ccc(-c3cc(CN4CCn5nc(C6CC6)nc5C4)ccc3C#N)nc21] | 4-[(2-cyclopropyl-5,6-dihydro[1,2,4]triazolo[1,5-a]pyrazin-7(8H)-yl)methyl]-2-[1-(2,2-dimethylpropyl)-3-methyl-2-oxo-2,3-dihydro-1H-imidazo[4,5-b]pyridin-5-yl]benzonitrile | Calc'd 497.2772, found 497.2776 |
| 21-77 | 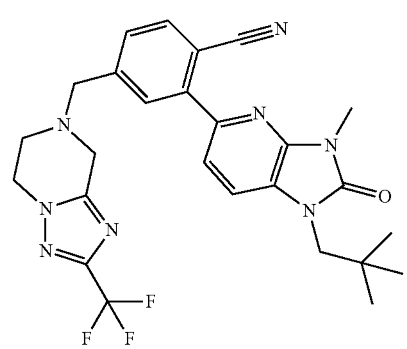 [SMILES: Cn1c(=O)n(CC(C)(C)C)c2ccc(-c3cc(CN4CCn5nc(C(F)(F)F)nc5C4)ccc3C#N)nc21] | 2-[1-(2,2-dimethylpropyl)-3-methyl-2-oxo-2,3-dihydro-1H-imidazo[4,5-b]pyridin-5-yl]-4-{[2-(trifluoromethyl)-5,6-dihydro[1,2,4]triazolo[1,5-a]pyrazin-7(8H)-yl]methyl}benzonitrile | Calc'd 525.2333, found 525.2336 |

TABLE 10-continued

The following compounds were prepared from 21-1 by a reaction sequence analogous to that illustrated in Scheme 21.

| Cmpd | Structure | IUPAC Name | Exact Mass [M + H]+ |
|---|---|---|---|
| 21-78 | 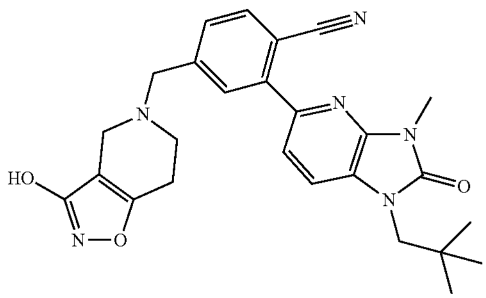 [SMILES: Cn1c(=O)n(CC(C)(C)C)c2ccc(-c3cc(CN4CCc5onc(O)c5C4)ccc3C#N)nc21] | 2-[1-(2,2-dimethylpropyl)-3-methyl-2-oxo-2,3-dihydro-1H-imidazo[4,5-b]pyridin-5-yl]-4-[(3-hydroxy-6,7-dihydroisoxazolo[4,5-c]pyridin-5(4H)-yl)methyl]benzonitrile | Calc'd 473.2296, found 473.2302 |
| 21-79 | 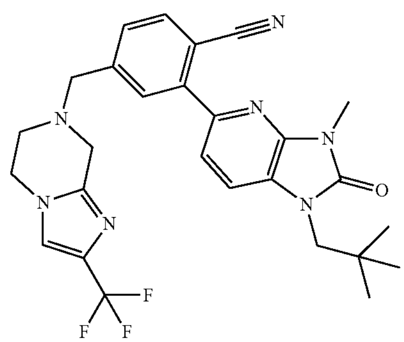 | 2-[1-(2,2-dimethylpropyl)-3-methyl-2-oxo-2,3-dihydro-1H-imidazo[4,5-b]pyridin-5-yl]-4-{[2-(trifluoromethyl)-5,6-dihydroimidazo[1,2-a]pyrazin-7(8H)-yl]methyl}benzonitrile | Calc'd 524.2380, found 524.2387 |
| 21-80 | 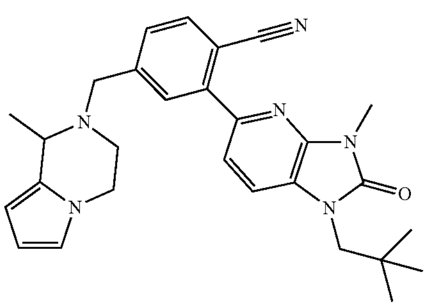 [SMILES: CC1c2cccn2CCN1Cc1ccc(C#N)c(-c2ccc3c(n2)n(C)c(=O)n3CC(C)(C)C)c1] | 2-[1-(2,2-dimethylpropyl)-3-methyl-2-oxo-2,3-dihydro-1H-imidazo[4,5-b]pyridin-5-yl]-4-[(1-methyl-3,4-dihydropyrrolo[1,2-a]pyrazin-2(1H)-yl)methyl]benzonitrile | Calc'd 469.2710, found 469.2717 |
| 21-81 | 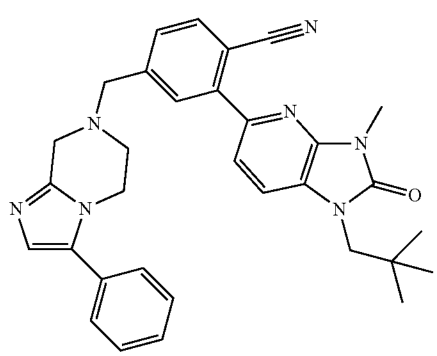 [SMILES: Cn1c(=O)n(CC(C)(C)C)c2ccc(-c3cc(CN4CCn5c(-c6ccccc6)cnc5C4)ccc3C#N)nc21] | 2-[1-(2,2-dimethylpropyl)-3-methyl-2-oxo-2,3-dihydro-1H-imidazo[4,5-b]pyridin-5-yl]-4-[(3-phenyl-5,6-dihydroimidazo[1,2-a]pyrazin-7(8H)-yl)methyl]benzonitrile | Calc'd 532.2819, found 532.2826 |

TABLE 10-continued

The following compounds were prepared from 21-1 by a reaction sequence analogous to that illustrated in Scheme 21.

| Cmpd | Structure | IUPAC Name | Exact Mass [M + H]+ |
|---|---|---|---|
| 21-82 | 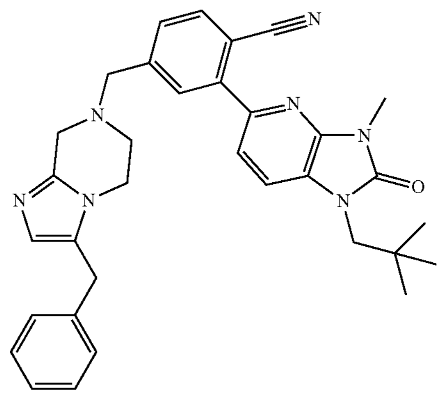 [SMILES: Cn1c(=O)n(CC(C)(C)C)c2ccc(-c3cc(CN4CCn5c(Cc6ccccc6)cnc5C4)ccc3C#N)nc21] | 4-[(3-benzyl-5,6-dihydroimidazo[1,2-a]pyrazin-7(8H)-yl)methyl]-2-[1-(2,2-dimethylpropyl)-3-methyl-2-oxo-2,3-dihydro-1H-imidazo[4,5-b]pyridin-5-yl]benzonitrile | Calc'd 546.2976, found 546.2982 |
| 21-83 | 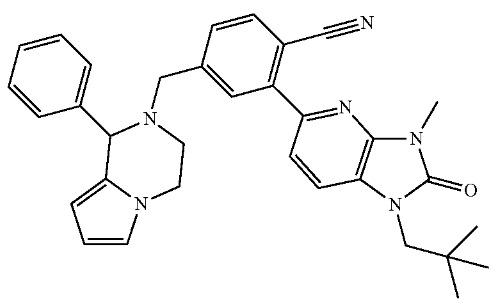 [SMILES: Cn1c(=O)n(CC(C)(C)C)c2ccc(-c3cc(CN4CCn5cccc5C4c4ccccc4)ccc3C#N)nc21] | 2-[1-(2,2-dimethylpropyl)-3-methyl-2-oxo-2,3-dihydro-1H-imidazo[4,5-b]pyridin-5-yl]-4-[(1-phenyl-3,4-dihydropyrrolo[1,2-a]pyrazin-2(1H)-yl)methyl]benzonitrile | Calc'd 531.2867, found 531.2866 |
| 21-84 | 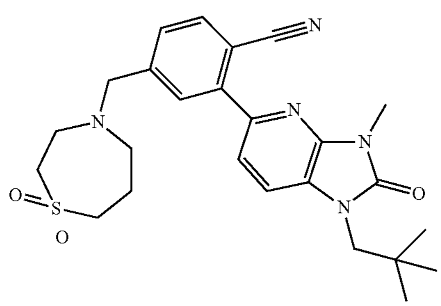 | 2-[1-(2,2-dimethylpropyl)-3-methyl-2-oxo-2,3-dihydro-1H-imidazo[4,5-b]pyridin-5-yl]-4-[(1,1-dioxido-1,4-thiazepan-4-yl)methyl]benzonitrile | Calc'd 482.2220, found 482.2228 |
| 21-85 | 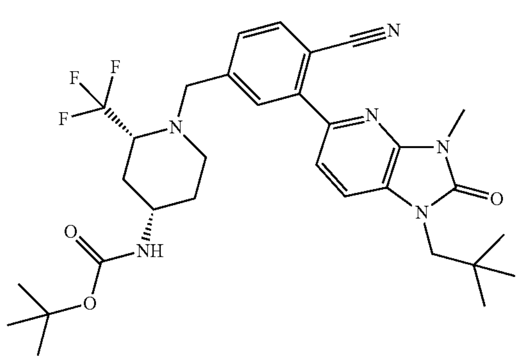 [SMILES: Cn1c(=O)n(CC(C)(C)C)c2ccc(-c3cc(CN4CC[C@H](NC(=O)OC(C)(C)C)C[C@@H]4C(F)(F)F)ccc3C#N)nc21] | tert-butyl [(2R,4S)-1-{4-cyano-3-[1-(2,2-dimethylpropyl)-3-methyl-2-oxo-2,3-dihydro-1H-imidazo[4,5-b]pyridin-5-yl]benzyl}-2-(trifluoromethyl)piperidin-4-yl]carbamate | Calc'd 601.3109, found 601.3120 |

TABLE 10-continued

The following compounds were prepared from 21-1 by a reaction sequence analogous to that illustrated in Scheme 21.

| Cmpd | Structure | IUPAC Name | Exact Mass [M + H]+ |
|---|---|---|---|
| 21-86 | 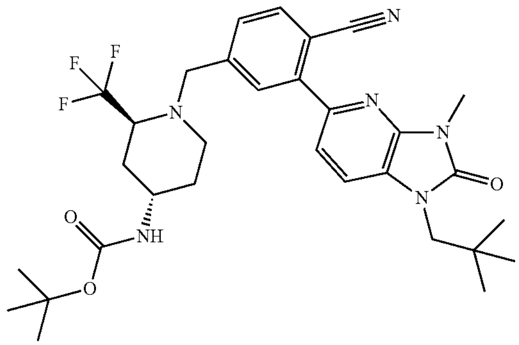 [SMILES: Cn1c(=O)n(CC(C)(C)C)c2ccc(-c3cc(CN4CC[C@H](NC(=O)OC(C)(C)C)C[C@H]4C(F)(F)F)ccc3C#N)nc21] | tert-butyl [(2S,4S)-1-{4-cyano-3-[1-(2,2-dimethylpropyl)-3-methyl-2-oxo-2,3-dihydro-1H-imidazo[4,5-b]pyridin-5-yl]benzyl}-2-(trifluoromethyl)piperidin-4-yl]carbamate | Calc'd 601.3109, found 601.31113 |
| 21-87 | 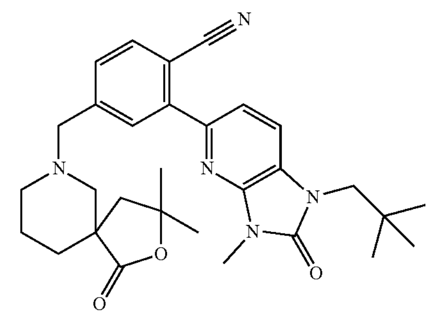 [SMILES: Cn1c(=O)n(CC(C)(C)C)c2ccc(-c3cc(CN4CCCC5(C4)CC(C)(C)OC5=O)ccc3C#N)nc21] | 4-[(3,3-dimethyl-1-oxo-2-oxa-7-azaspiro[4.5]dec-7-yl)methyl]-2-[1-(2,2-dimethylpropyl)-3-methyl-2-oxo-2,3-dihydro-1H-imidazo[4,5-b]pyridin-5-yl]benzonitrlle | Calc'd 516.2969, found 516.2973 |
| 21-88 | 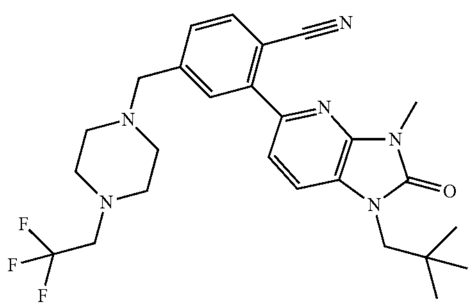 [SMILES: Cn1c(=O)n(CC(C)(C)C)c2ccc(-c3cc(CN4CCN(CC(F)(F)F)CC4)ccc3C#N)nc21] | 2-[1-(2,2-dimethylpropyl)-3-methyl-2-oxo-2,3-dihydro-1H-imidazo[4,5-b]pyridin-5-yl]-4-{[4-(2,2,2-trifluoroethyl)piperazin-1-yl]methyl}benzonitrile | Calc'd 501.2584, found 501.2588 |
| 21-89 | 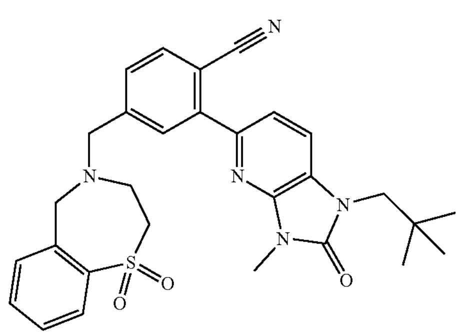 [SMILES: Cn1c(=O)n(CC(C)(C)C)c2ccc(-c3cc(CN4CCS(=O)(=O)c5ccccc5C4)ccc3C#N)nc21] | 2-[1-(2,2-dimethylpropyl)-3-methyl-2-oxo-2,3-dihydro-1H-imidazo[4,5-b]pyridin-5-yl]-4-[(1,1-dioxido-2,3-dihydro-1,4-benzothiazepin-4(5H)-yl)methyl]benzonitrile | Calc'd 530.2220, found 530.2226 |

TABLE 10-continued

The following compounds were prepared from 21-1 by a reaction sequence analogous to that illustrated in Scheme 21.

| Cmpd | Structure | IUPAC Name | Exact Mass [M + H]+ |
|---|---|---|---|
| 21-90 | 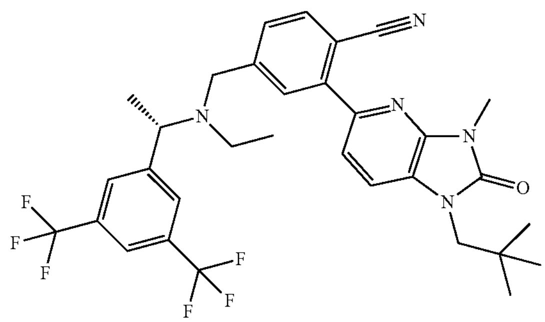 [SMILES: CCN(Cc1ccc(C#N)c(-c2ccc3c(n2)n(C)c(=O)n3CC(C)(C)C)c1)[C@@H](C)c1cc(C(F)(F)F)cc(C(F)(F)F)c1] | 4-{[{(1S)-1-[3,5-bis (trifluoromethyl)phenyl] ethyl}(ethyl)amino]methyl}- 2-[1-(2,2-dimethyl propyl)- 3-methyl-2-oxo-2,3-dihydro- 1H-imidazo[4,5-b]pyridin- 5-yl]benzonitrile | Calc'd 618.2662, found 618.2669 |
| 21-91 | 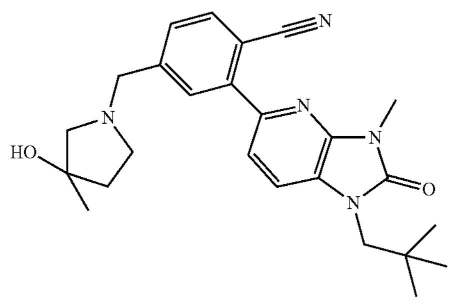 [SMILES: Cn1c(=O)n(CC(C)(C)C)c2ccc(-c3cc(CN4CCC(C)(O)C4)ccc3C#N)nc21] | 2-[1-(2,2-dimethylpropyl)- 3-methyl-2-oxo-2,3- dihydro-1H-imidazo[4,5- b]pyridin-5-yl]-4-[(3- hydroxy-3- methylpyrrolidin-1- yl)methyl]benzonitrile | Calc'd 434.2551, found 434.2555 |
| 21-92 | 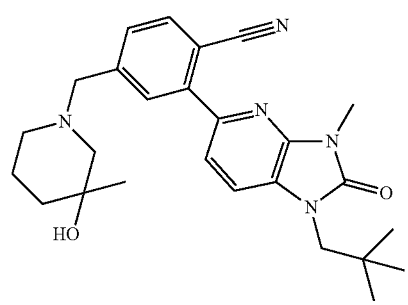 [SMILES: Cn1c(=O)n(CC(C)(C)C)c2ccc(-c3cc(CN4CCCC(C)(O)C4)ccc3C#N)nc21] | 2-[1-(2,2-dimethylpropyl)- 3-methyl-2-oxo-2,3- dihydro-1H-imidazo[4,5- b]pyridin-5-yl]-4-[(3- hydroxy-3- methylpiperidin-1- yl)methyl]benzonitrile | Calc'd 448.2707, found 448.2708 |
| 21-93 | 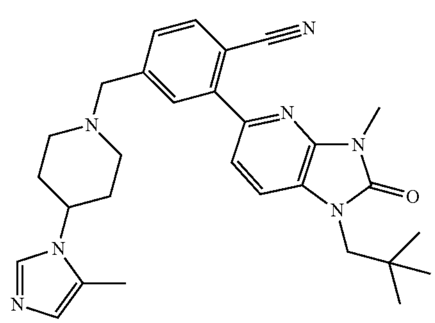 [SMILES: Cc1cncn1C1CCN(Cc2ccc(C#N)c(-c3ccc4c(n3)n(C)c(=O)n4CC(C)(C)C)c2)CC1] | 2-[1-(2,2-dimethylpropyl)- 3-methyl-2-oxo-2,3- dihydro-1H-imidazo[4,5- b]pyridin-5-yl]-4-{[4-(5- methyl-1H-imidazol-1- yl)piperidin-1- yl]methyl}benzonitrile | Calc'd 498.2976, found 498.2975 |

TABLE 10-continued

The following compounds were prepared from 21-1 by a reaction sequence analogous to that illustrated in Scheme 21.

| Cmpd | Structure | IUPAC Name | Exact Mass [M + H]+ |
|---|---|---|---|
| 21-94 | 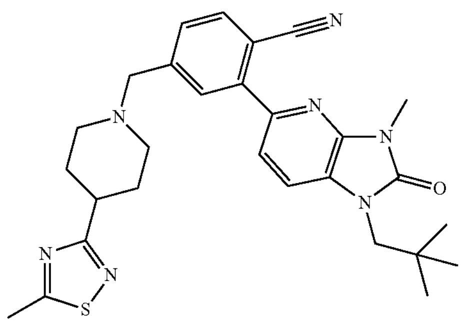 [SMILES: Cc1nc(C2CCN(Cc3ccc(C#N)c(-c4ccc5c(n4)n(C)c(=O)n5CC(C)(C)C)c3)CC2)ns1] | 2-[1-(2,2-dimethylpropyl)-3-methyl-2-oxo-2,3-dihydro-1H-imidazo[4,5-b]pyridin-5-yl]-4-{[4-(5-methyl-1,2,4-thiadiazol-3-yl)piperidin-1-yl]methyl}benzonitrile | Calc'd 516.2540, found 516.2547 |
| 21-95 | 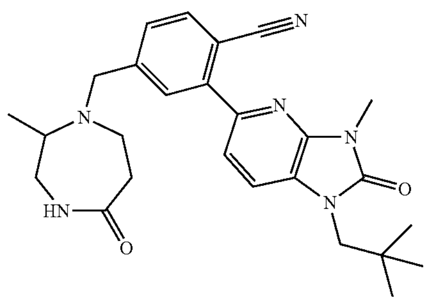 [SMILES: CC1CNC(=O)CCN1Cc1ccc(C#N)c(-c2ccc3c(n2)n(C)c(=O)n3CC(C)(C)C)c1] | 2-[1-(2,2-dimethylpropyl)-3-methyl-2-oxo-2,3-dihydro-1H-imidazo[4,5-b]pyridin-5-yl]-4-[(2-methyl-5-oxo-1,4-diazepan-1-yl)methyl]benzonitrile | Calc'd 461.2660, found 461.2662 |
| 21-96 | 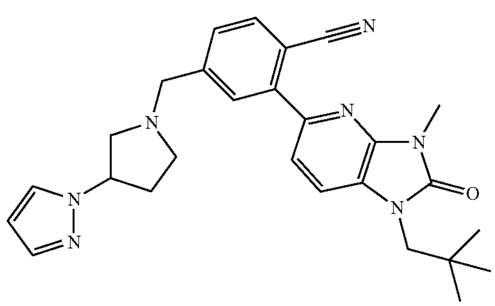 [SMILES: Cn1c(=O)n(CC(C)(C)C)c2ccc(-c3cc(CN4CCC(n5cccn5)C4)ccc3C#N)nc21] | 2-[1-(2,2-dimethylpropyl)-3-methyl-2-oxo-2,3-dihydro-1H-imidazo[4,5-b]pyridin-5-yl]-4-{[3-(1H-pyrazol-1-yl)pyrrolidin-1-yl]methyl}benzonitrile | Calc'd 470.2663, found 470.2664 |
| 21-97 | 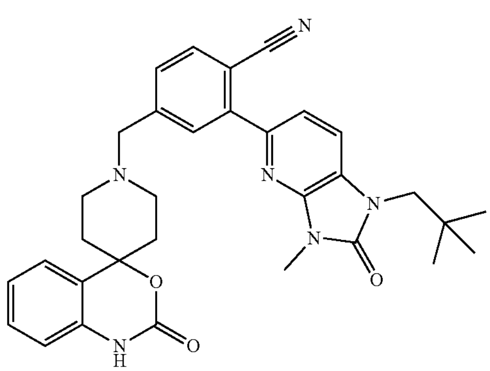 [SMILES: Cn1c(=O)n(CC(C)(C)C)c2ccc(-c3cc(CN4CCC5(CC4)OC(=O)Nc4ccccc45)ccc3C#N)nc21] | 2-[1-(2,2-dimethylpropyl)-3-methyl-2-oxo-2,3-dihydro-1H-imidazo[4,5-b]pyridin-5-yl]-4-[(2-oxo-1,2-dihydro-1'H-spiro[3,1-benzoxazine-4,4'-piperidin]-1'-yl)methyl]benzonitrile | Calc'd 551.2765, found 551.2776 |

TABLE 10-continued

The following compounds were prepared from 21-1 by a reaction sequence analogous to that illustrated in Scheme 21.

| Cmpd | Structure | IUPAC Name | Exact Mass [M + H]+ |
|---|---|---|---|
| 21-98 | 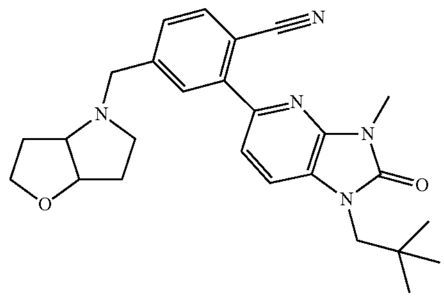 [SMILES: Cn1c(=O)n(CC(C)(C)C)c2ccc(-c3cc(CN4CCC5OCCC54)ccc3C#N)nc21] | 2-[1-(2,2-dimethylpropyl)-3-methyl-2-oxo-2,3-dihydro-1H-imidazo[4,5-b]pyridin-5-yl]-4-(hexahydro-4H-furo[3,2-b]pyrrol-4-ylmethyl)benzonitrile | Calc'd 446.2551, found 446.2550 |
| 21-99 | 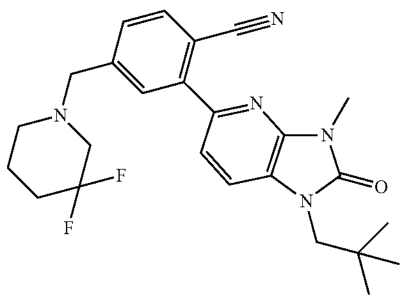 [SMILES: Cn1c(=O)n(CC(C)(C)C)c2ccc(-c3cc(CN4CCCC(F)(F)C4)ccc3C#N)nc21] | 4-[(3,3-difluoropiperidin-1-yl)methyl]-2-[1-(2,2-dimethylpropyl)-3-methyl-2-oxo-2,3-dihydro-1H-imidazo[4,5-b]pyridin-5-yl]benzonitrile | Calc'd 454.2413, found 454.2416 |
| 21-100 | 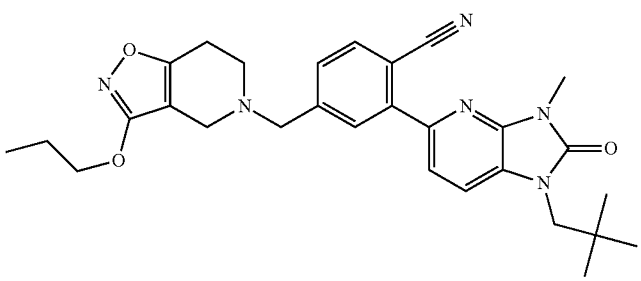 [SMILES: CCCOc1noc2c1CN(Cc1ccc(C#N)c(-c3ccc4c(n3)n(C)c(=O)n4CC(C)(C)C)c1)CC2] | 2-[1-{2,2-dimethylpropyl)-3-methyl-2-oxo-2,3-dihydro-1H-imidazo[4,5-b]pyridin-5-yl]-4-[(3-propoxy-6,7-dihydroisoxazolo[4,5-c]pyridin-5(4H)-yl)methyl]benzonitrile | Calc'd 515.2765, found 515.2758 |
| 21-101 | 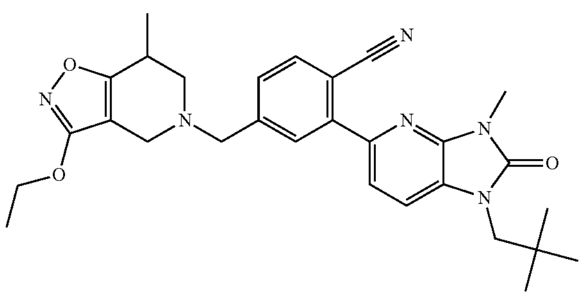 [SMILES: CCOc1noc2c1CN(Cc1ccc(C#N)c(-c3ccc4c(n3)n(C)c(=O)n4CC(C)(C)C)c1)CC2C] | 2-[1-(2,2-dimethylpropyl)-3-methyl-2-oxo-2,3-dihydro-1H-imidazo[4,5-b]pyridin-5-yl]-4-[(3-ethoxy-7-methyl-6,7-dihydroisoxazolo[4,5-c]pyridin-5(4H)-yl)methyl]benzonitrile | Calc'd 515.2765, found 515.2755 |
| 21-102 | 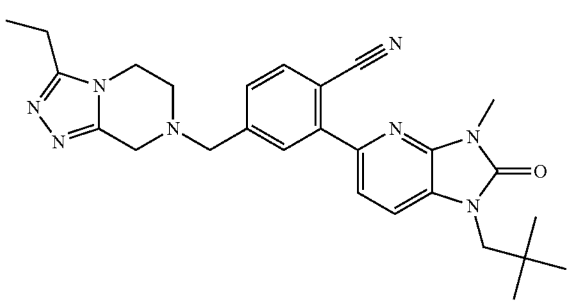 [SMILES: CCc1nnc2n1CCN(Cc1ccc(C#N)c(-c3ccc4c(n3)n(C)c(=O)n4CC(C)(C)C)c1)C2] | 2-[1-(2,2-dimethylpropyl)-3-methyl-2-oxo-2,3-dihydro-1H-imidazo[4,5-b]pyridin-5-yl]-4-[(3-ethyl-5,6-dihydro[1,2,4]triazolo[4,3-a]pyrazin-7(8H)-yl)methyl]benzonitrile | Calc'd 485.2772, found 485.2761 |

TABLE 10-continued

The following compounds were prepared from 21-1 by a reaction sequence analogous to that illustrated in Scheme 21.

| Cmpd | Structure | IUPAC Name | Exact Mass [M + H]+ |
|---|---|---|---|
| 21-103 | 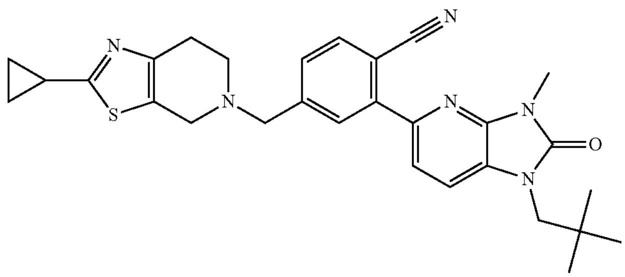 [SMILES: Cn1c(=O)n(CC(C)(C)C)c2ccc(-c3cc(CN4CCc5nc(C6CC6)sc5C4)ccc3C#N)nc21] | 4-[(2-cyclopropyl-6,7-dihydro[1,3]thiazolo[5,4-c]pyridin-5(4H)-yl)methyl]-2-[1-(2,2-dimethylpropyl)-3-methyl-2-oxo-2,3-dihydro-1H-imidazo[4,5-b]pyridin-5-yl]benzonitrile | Calc'd 513.2431, found 513.2423 |
| 21-104 | 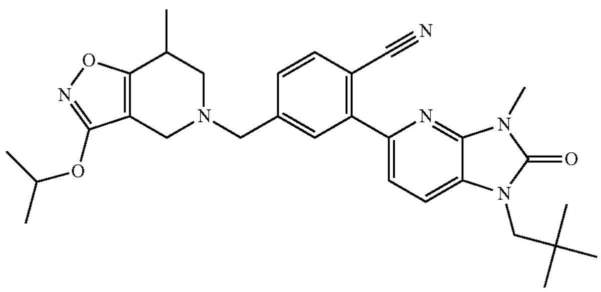 [SMILES: CC(C)Oc1noc2c1CN(Cc1ccc(C#N)c(-c3ccc4c(n3)n(C)c(=O)n4CC(C)(C)C)c1)CC2C] | 2-[1-(2,2-dimethylpropyl)-3-methyl-2-oxo-2,3-dihydro-1H-imidazo[4,5-b]pyridin-5-yl]-4-{[7-methyl-3-(1-methylethoxy)-6,7-dihydroisoxazolo[4,5-c]pyridin-5(4H)-yl]methyl}benzonitrile | Calc'd 529.2922, found 529.2909 |
| 21-105 | 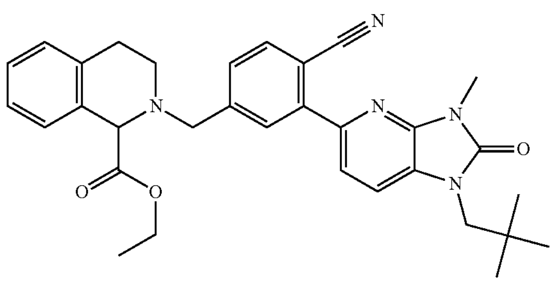 [SMILES: CCOC(=O)C1c2ccccc2CCN1Cc1ccc(C#N)c(-c2ccc3c(n2)n(C)c(=O)n3CC(C)(C)C)c1] | ethyl 2-{4-cyano-3-[1-(2,2-dimethylpropyl)-3-methyl-2-oxo-2,3-dihydro-1H-imidazo[4,5-b]pyridin-5-yl]benzyl}-1,2,3,4-tetrahydroisoquinoline-1-carboxylate | Calc'd 538.2813, found 538.2796 |
| 21-106 | 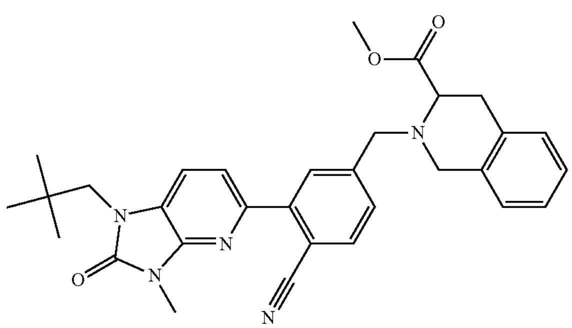 [SMILES: COC(=O)C1Cc2ccccc2CN1Cc1ccc(C#N)c(-c2ccc3c(n2)n(C)c(=O)n3CC(C)(C)C)c1] | methyl 2-{4-cyano-3-[1-(2,2-dimethylpropyl)-3-methyl-2-oxo-2,3-dihydro-1H-imidazo[4,5-b]pyridin-5-yl]benzyl}-1,2,3,4-tetrahydroisoquinoline-3-carboxylate | Calc'd 524.2656, found 524.2640 |
| 21-107 | 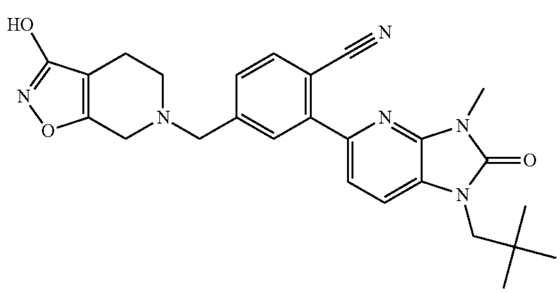 [SMILES: Cn1c(=O)n(CC(C)(C)C)c2ccc(-c3cc(CN4CCc5c(O)noc5C4)ccc3C#N)nc21] | 2-[1-(2,2-dimethylpropyl)-3-methyl-2-oxo-2,3-dihydro-1H-imidazo[4,5-b]pyridin-5-yl]-4-[(3-hydroxy-4,7-dihydroisoxazolo[5,4-c]pyridin-6(5H)-yl)methyl]benzonitrile | Calc'd 473.2296, found 473.2289 |

TABLE 10-continued

The following compounds were prepared from 21-1 by a reaction sequence analogous to that illustrated in Scheme 21.

| Cmpd | Structure | IUPAC Name | Exact Mass [M + H]+ |
|---|---|---|---|
| 21-108 | 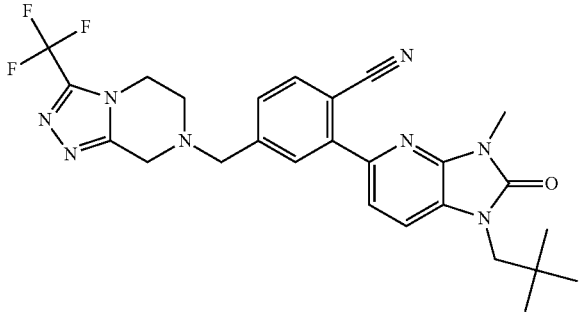 [SMILES: Cn1c(=O)n(CC(C)(C)C)c2ccc(-c3cc(CN4CCn5c(nnc5C(F)(F)F)C4)ccc3C#N)nc21] | 2-[1-(2,2-dimethylpropyl)-3-methyl-2-oxo-2,3-dihydro-1H-imidazo[4,5-b]pyridin-5-yl]-4-{[3-(trifluoromethyl)-5,6-dihydro[1,2,4]triazolo[4,3-a]pyrazin-7(8H)-yl]methyl}benzonitrile | Calc'd 525.2333, found 525.2323 |
| 21-109 | 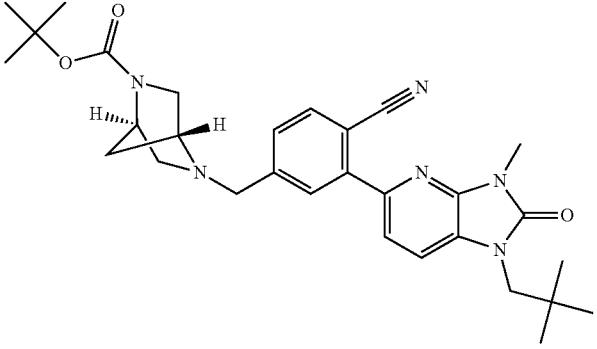 [SMILES: Cn1c(=O)n(CC(C)(C)C)c2ccc(-c3cc(CN4C[C@H]5C[C@@H]4CN5C(=O)OC(C)(C)C)ccc3C#N)nc21] | tert-butyl (1R,4R)-5-{4-cyano-3-[1-(2,2-dimethylpropyl)-3-methyl-2-oxo-2,3-dihydro-1H-imidazo[4,5-b]pyridin-5-yl]benzyl}-2,5-diazabicyclo[2.2.1]heptane-2-carboxylate | Calc'd 531.3078, found 531.3069 |
| 21-110 | 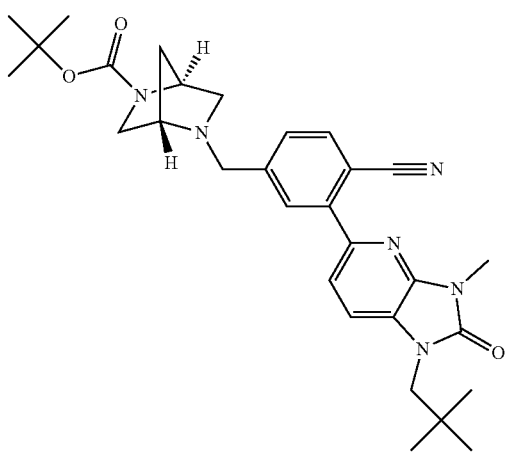 [SMILES: Cn1c(=O)n(CC(C)(C)C)c2ccc(-c3cc(CN4C[C@@H]5C[C@H]4CN5C(=O)OC(C)(C)C)ccc3C#N)nc21] | tert-butyl (1S,4S)-5-{4-cyano-3-[1-(2,2-dimethylpropyl)-3-methyl-2-oxo-2,3-dihydro-1H-imidazo[4,5-b]pyridin-5-yl]benzyl}-2,5-diazabicyclo[2.2.1]heptane-2-carboxylate | Calc'd 531.3078, found 531.3066 |

TABLE 10-continued

The following compounds were prepared from 21-1 by a reaction sequence analogous to that illustrated in Scheme 21.

| Cmpd | Structure | IUPAC Name | Exact Mass [M + H]+ |
|---|---|---|---|
| 21-111 | 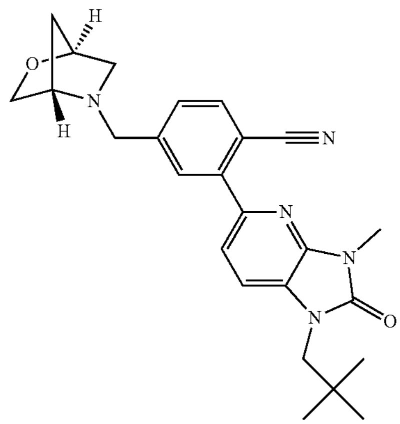 [SMILES: Cn1c(=O)n(CC(C)(C)C)c2ccc(-c3cc(CN4C[C@@H]5C[C@H]4CO5)ccc3C#N)nc21] | 2-[1-(2,2-dimethylpropyl)-3-methyl-2-oxo-2,3-dihydro-1H-imidazo[4,5-b]pyridin-5-yl]-4-[(1S,4S)-2-oxa-5-azabicyclo[2.2.1]hept-5-ylmethyl]benzonitrile | Calc'd 432.2394, found 432.2386 |
| 21-112 | 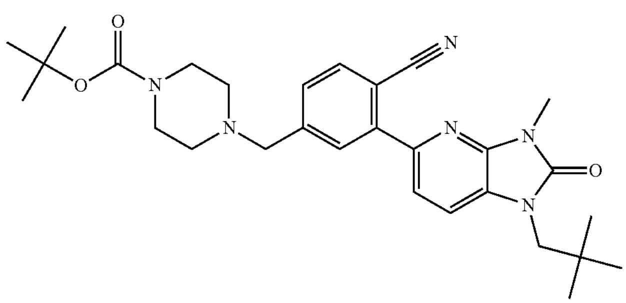 [SMILES: Cn1c(=O)n(CC(C)(C)C)c2ccc(-c3cc(CN4CCN(C(=O)OC(C)(C)C)CC4)ccc3C#N)nc21] | tert-butyl 4-{4-cyano-3-[1-(2,2-dimethylpropyl)-3-methyl-2-oxo-2,3-dihydro-1H-imidazo[4,5-b]pyridin-5-yl]benzyl}piperazine-1-carboxylate | Calc'd 519.3078, found 519.3064 |
| 21-113 | 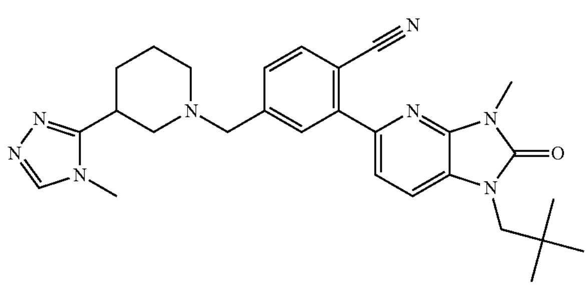 [SMILES: Cn1cnnc1C1CCCN(Cc2ccc(C#N)c(-c3ccc4c(n3)n(C)c(=O)n4CC(C)(C)C)c2)C1] | 2-[1-(2,2-dimethylpropyl)-3-methyl-2-oxo-2,3-dihydro-1H-imidazo[4,5-b]pyridin-5-yl]-4-{[3-(4-methyl-4H-1,2,4-triazol-3-yl)piperidin-1-yl]methyl}benzonitrile | Calc'd 499.2928, found 499.2932 |
| 21-114 | 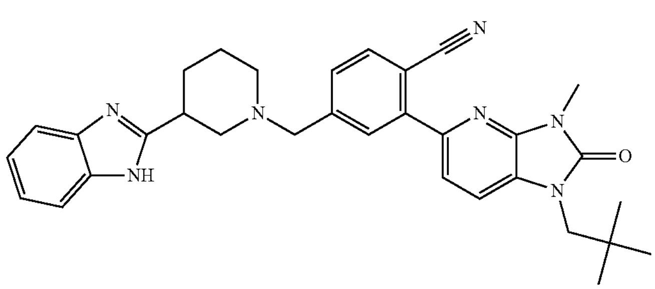 [SMILES: Cn1c(=O)n(CC(C)(C)C)c2ccc(-c3cc(CN4CCCC(c5nc6ccccc6[nH]5)C4)ccc3C#N)nc21] | 4-{[3-(1H-benzimidazol-2-yl)piperidin-1-yl]methyl}-2-[1-(2,2-dimethylpropyl)-3-methyl-2-oxo-2,3-dihydro-1H-imidazo[4,5-b]pyridin-5-yl]benzonitrile | Calc'd 534.2976, found 534.2964 |

TABLE 10-continued

The following compounds were prepared from 21-1 by a reaction sequence analogous to that illustrated in Scheme 21.

| Cmpd | Structure | IUPAC Name | Exact Mass [M + H]+ |
|---|---|---|---|
| 21-115 | 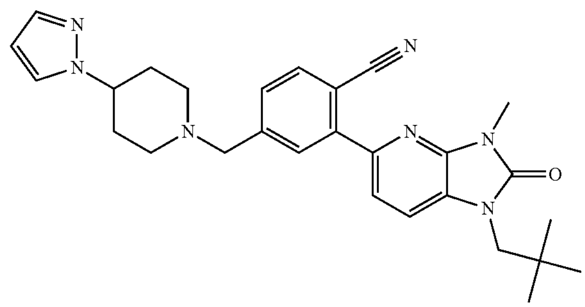 [SMILES: Cn1c(=O)n(CC(C)(C)C)c2ccc(-c3cc(CN4CCC(n5cccn5)CC4)ccc3C#N)nc21] | 2-[1-(2,2-dimethylpropyl)-3-methyl]-2-oxo-2,3-dihydro-1H-imidazo[4,5-b]pyridin-5-yl]-4-{[4-(1H-pyrazol-1-yl)piperidin-1-yl]methyl}benzonitrile | Calc'd 484.2819, found 484.2803 |
| 21-116 | 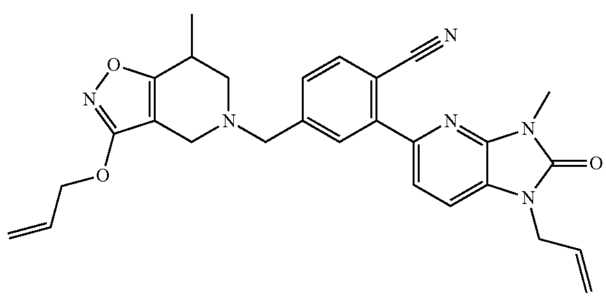 [SMILES: C=CCOc1noc2c1CN(Cc1ccc(C#N)c(-c3ccc4c(n3)n(C)c(=O)n4CC=C)c1)CC2C] | 2-(3-methyl-2-oxo-1-prop-2-en-1-yl-2,3-dihydro-1H-imidazo[4,5-b]pyridin-5-yl)-4-{[7-methyl-3-(prop-2-en-1-yloxy)-6,7-dihydroisoxazolo[4,5-c]pyridin-5(4H)-yl]methyl}benzonitrile | Calc'd 497.2296, found 497.2285 |
| 21-117 | 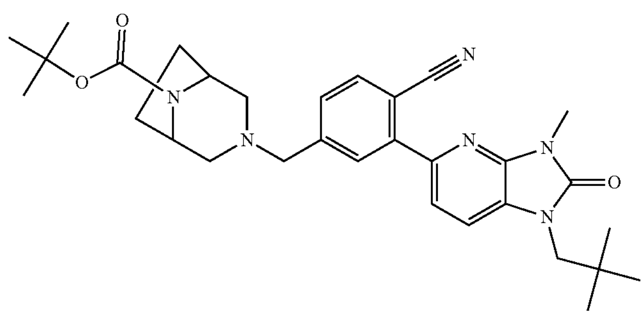 [SMILES: Cn1c(=O)n(CC(C)(C)C)c2ccc(-c3cc(CN4CC5CCC(C4)N5C(=O)OC(C)(C)C)ccc3C#N)nc21] | tert-butyl 3-{4-cyano-3-[1-(2,2-dimethylpropyl)-3-methyl-2-oxo-2,3-dihydro-1H-imidazo[4,5-b]pyridin-5-yl]benzyl}-3,8-diazabicyclo[3.2.1]octane-8-carboxylate | Calc'd 545.3235, found 545.3223 |
| 21-118 | 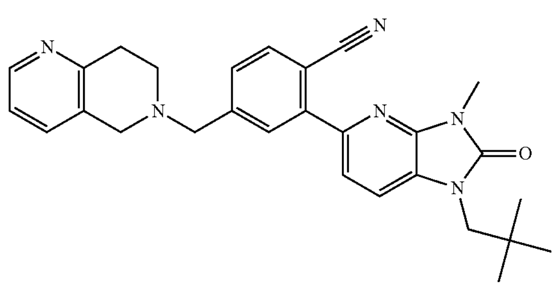 [SMILES: Cn1c(=O)n(CC(C)(C)C)c2ccc(-c3cc(CN4CCc5ncccc5C4)ccc3C#N)nc21] | 4-(7,8-dihydro-1,6-naphthyridin-6(5H)-ylmethyl)-2-[1-(2,2-dimethylpropyl)-3-methyl-2-oxo-2,3-dihydro-1H-imidazo[4,5-b]pyridin-5-yl]benzonitrile | Calc'd 467.2554, found 467.2546 |
| 21-119 | 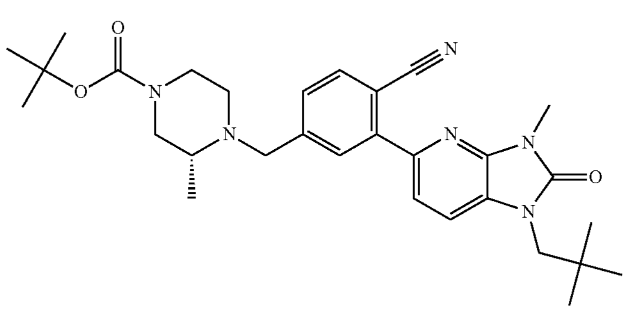 [SMILES: C[C@@H]1CN(C(=O)OC(C)(C)C)CCN1Cc1ccc(C#N)c(-c2ccc3c(n2)n(C)c(=O)n3CC(C)(C)C)c1] | tert-butyl (3R)-4-{4-cyano-3-[1-(2,2-dimethylpropyl)-3-methyl-2-oxo-2,3-dihydro-1H-imidazo[4,5-b]pyridin-5-yl]benzyl}-3-methylpiperazine-1-carboxylate | Calc'd 533.3235, found 533.3222 |

TABLE 10-continued

The following compounds were prepared from 21-1 by a reaction sequence analogous to that illustrated in Scheme 21.

| Cmpd | Structure | IUPAC Name | Exact Mass [M + H]+ |
|---|---|---|---|
| 21-120 | 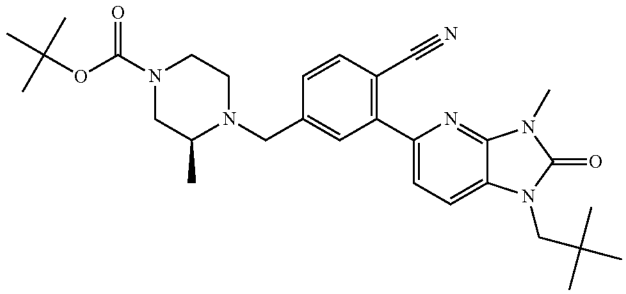 [SMILES: C[C@H]1CN(C(=O)OC(C)(C)C)CCN1Cc1ccc(C#N)c(-c2ccc3c(n2)n(C)c(=O)n3CC(C)(C)C)c1] | tert-butyl (3S)-4-{4-cyano-3-[1-(2,2-dimethylpropyl)-3-methyl-2-oxo-2,3-dihydro-1H-imidazo[4,5-b]pyridin-5-yl]benzyl}-3-methylpiperazine-1-carboxylate | Calc'd 533.3235, found 533.3221 |
| 21-121 | 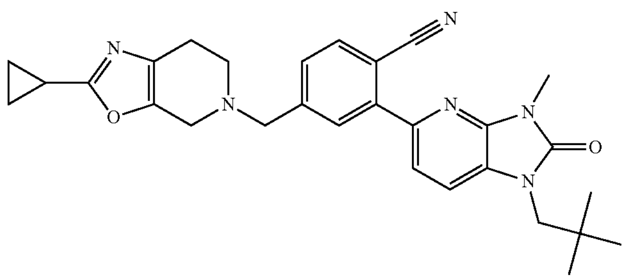 [SMILES: Cn1c(=O)n(CC(C)(C)C)c2ccc(-c3cc(CN4CCc5nc(C6CC6)oc5C4)ccc3C#N)nc21] | 4-[(2-cyclopropyl-6,7-dihydro[1,3]oxazolo[4,5-c]pyridin-5(4H)-yl)methyl]-2-[1-(2,2-dimethylpropyl)-3-methyl-2-oxo2,3-dihydro-1H-imidazo[4,5-b]pyridin-5-yl]benzonitrile | Calc'd 497.2661, found 497.2660 |
| 21-122 | 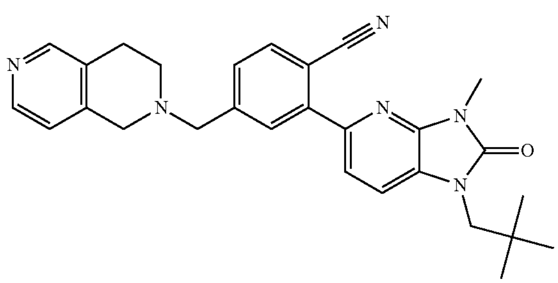 [SMILES: Cn1c(=O)n(CC(C)(C)C)c2ccc(-c3cc(CN4CCc5cnccc5C4)ccc3C#N)nc21] | 4-(3,4-dihydro-2,6-naphthyridin-2(1H)-ylmethyl)-2-[1-(2,2-dimethylpropyl)-3-methyl-2-oxo-2,3-dihydro-1H-imidazo[4,5-b]pyridin-5-yl]benzonitrile | Calc'd 467.2554, found 467.2547 |
| 21-123 | 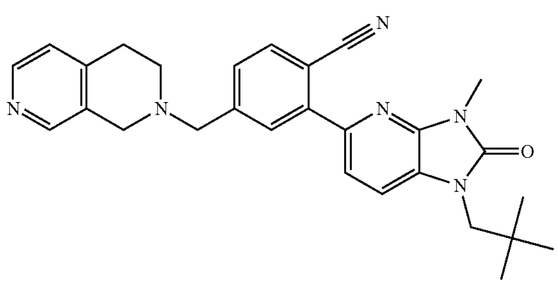 [SMILES: Cn1c(=O)n(CC(C)(C)C)c2ccc(-c3cc(CN4CCc5ccncc5C4)ccc3C#N)nc21] | 4-(3,4-dihydro-2,7-naphthyridin-2(1H)-ylmethyl)-2-[1-(2,2-dimethyl)-3-methyl-2-oxo-2,3-dihydro-1H-imidazo[4,5-b]pyridin-5-yl]benzonitrile | Calc'd 467.2554, found 467.2548 |
| 21-124 | 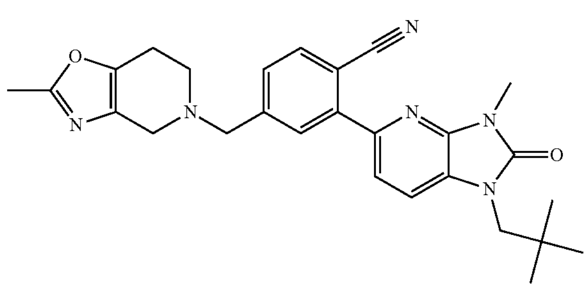 [SMILES: Cc1nc2c(o1)CCN(Cc1ccc(C#N)c(-c3ccc4c(n3)n(C)c(=O)n4CC(C)(C)C)c1)C2] | 2-[1-(2,2-dimethylpropyl)-3-methyl-2-oxo-2,3-dihydro-1H-imidazo[4,5-b]pyridin-5-yl]-4-[(2-methyl-6,7-dihydro[1,3]oxazolo[4,5-c]pyridin-5(4H)-yl)methyl]benzonitrile | Calc'd 471.2503, found 471.2501 |

TABLE 10-continued

The following compounds were prepared from 21-1 by a reaction sequence analogous to that illustrated in Scheme 21.

| Cmpd | Structure | IUPAC Name | Exact Mass [M + H]+ |
|---|---|---|---|
| 21-125 | 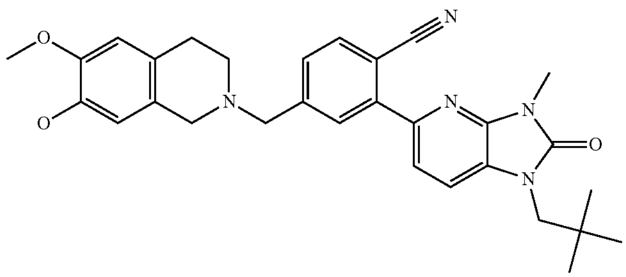 [SMILES: COc1cc2c(cc1O)CN(Cc1ccc(C#N)c(-c3ccc4c(n3)n(C)c(=O)n4CC(C)(C)C)c1)CC2] | 2-[1-(2,2-dimethylpropyl)-3-methyl-2-oxo-2,3-dihydro-1H-imidazo[4,5-b]pyridin-5-yl]-4-[(7-hydroxy-6-methoxy-3,4-dihydroisoquinolin-2(1H)-yl)methyl]benzonitrile | Calc'd 512.2656, found 512.2655 |
| 21-126 | 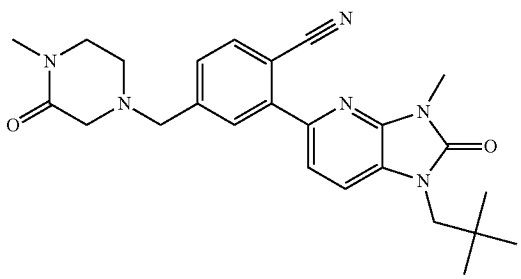 [SMILES: CN1CCN(Cc2ccc(C#N)c(-c3ccc4c(n3)n(C)c(=O)n4CC(C)(C)C)c2)CC1=O] | 2-[1-(2,2-dimethylpropyl)-3-methyl-2-oxo-2,3-dihydro-1H-imidazo[4,5-b]pyridin-5-yl]-4-[(4-methyl-3-oxopiperazin-1-yl)methyl]benzonitrile | Calc'd 447.2503, found 447.2499 |
| 21-127 | 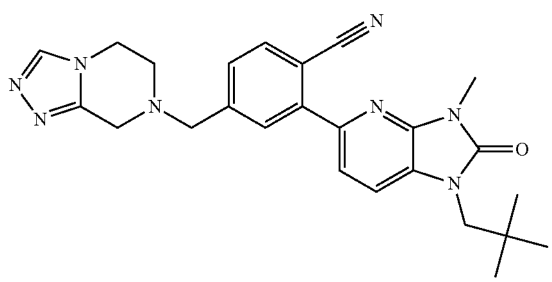 [SMILES: Cn1c(=O)n(CC(C)(C)C)c2ccc(-c3cc(CN4CCn5cnnc5C4)ccc3C#N)nc21] | 4-(5,6-dihydro[1,2,4]triazolo[4,3-a]pyrazin-7(8H)-ylmethyl)-2-[1-(2,2-dimethylpropyl)-3-methyl-2-oxo-2,3-dihydro-1H-imidazo[4,5-b]pyridin-5-yl]benzonitrile | Calc'd 457.2459, found 457.2457 |
| 21-128 | 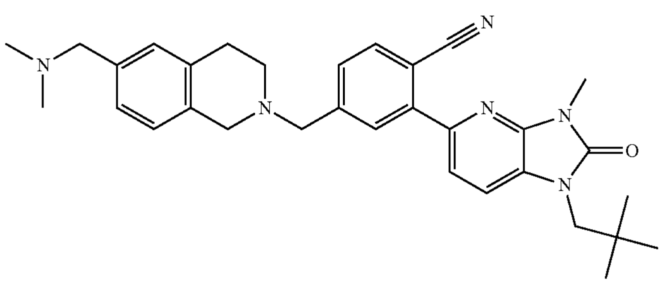 [SMILES: CN(C)Cc1ccc2c(c1)CCN(Cc1ccc(C#N)c(-c3ccc4c(n3)n(C)c(=O)n4CC(C)(C)C)c1)C2] | 4-({6-[(dimethylamino)methyl]-3,4-dihydroisoquinolin-2(1H)-yl}methyl)-2-[1-(2,2-dimethylpropyl)-3-methyl-2-oxo-2,3-dihydro-1H-imidazo[4,5-b]pyridin-5-yl]benzonitrile | Calc'd 523.3180, found 523.3173 |
| 21-129 | 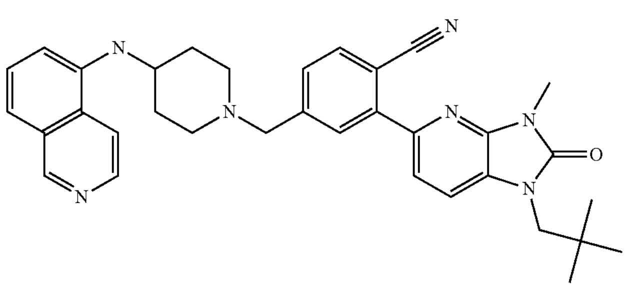 [SMILES: Cn1c(=O)n(CC(C)(C)C)c2ccc(-c3cc(CN4CCC(Nc5cccc6cnccc56)CC4)ccc3C#N)nc21] | 2-[1-(2,2-dimethylpropyl)-3-methyl-2-oxo-2,3-dihydro-1H-imidazo[4,5-b]pyridin-5-yl]-4-{[4-(isoquinolin-5-ylamino)piperidin-1-yl]methyl}benzonitrile | Calc'd 560.3132, found 560.3122 |

SCHEME 22

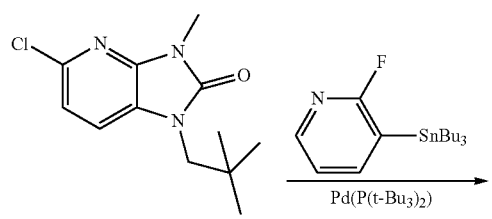

1-(2,2-dimethylpropyl)-5-(2-fluoropyridin-3-yl)-3-methyl-1,3-dihydro-2H-imidazo[4,5-b]pyridin-2-one (22-1)

To a microwave vial was added 5-chloro-1-(2,2-dimethylpropyl)-3-methyl-1,3-dihydro-2H-imidazo[4,5-b]pyridin-2-one (14-1) (25 mg, 0.1 mmol), 2-fluoro-3-(tributylstannanyl)pyridine (55 mg, 0.15 mmol), and bis(tri-t-butylphosphine)palladium(0) (10 mg, 0.02 mmol). The reagents were purged with nitrogen, dissolved in DMF (0.5 ml), and heated at 90° C. overnight. The reaction was cooled to room temperature, diluted with methanol, and passed through a syringe filter. The solution was purified using reverse phase chromatography (10-100%, 0.1% TFA in $H_2O$/Acetonitrile) and the desired fractions were collected and concentrated to produce 1-(2,2-dimethylpropyl)-5-(2-fluoropyridin-3-yl)-3-methyl-1,3-dihydro-2H-imidazo[4,5-b]pyridin-2-one (22-1). HRMS $(M+H)^+$: observed=315.1618, calculated=315.1616.

TABLE 10

The following compounds were prepared from 14-1 by a reaction sequence analogous to that illustrated in Scheme 22.

| Cmpd | Structure | IUPAC Name | Exact Mass [M + H]+ |
|---|---|---|---|
| 22-2 | 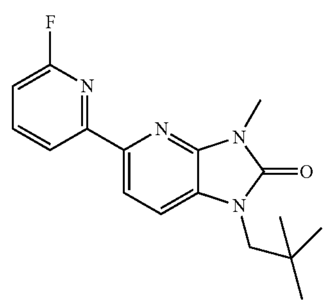 [SMILES: Cn1c(=O)n(CC(C)(C)C)c2ccc(-c3cccc(F)n3)nc21] | 1-(2,2-dimethylpropyl)-5-(6-fluoropyridin-2-yl)-3-methyl-1,3-dihydro-2H-imidazo[4,5-b]pyridin-2-one | Calc'd 315.1616, found 315.1618 |
| 22-3 | 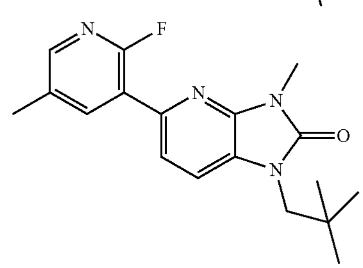 | 1-(2,2-dimethylpropyl)-5-(2-fluoro-5-methylpyridin-3-yl)-3-methyl-1,3-dihydro-2H-imidazo[4,5-b]pyridin-2-one | Calc'd 329.1772, found 329.1781 |
| 22-4 | 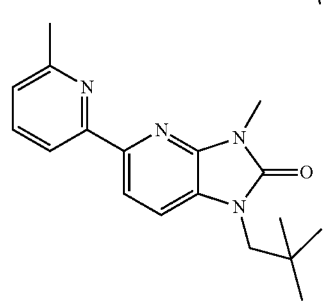 | 1-(2,2-dimethylpropyl)-3-methyl-5-(6-methylpyridin-2-yl)-1,3-dihydro-2H-imidazo[4,5-b]pyridin-2-one | Calc'd 311.1866, found 311.1866 |

TABLE 10-continued

The following compounds were prepared from 14-1 by a reaction sequence analogous to that illustrated in Scheme 22.

| Cmpd | Structure | IUPAC Name | Exact Mass [M + H]+ |
|---|---|---|---|
| 22-5 | 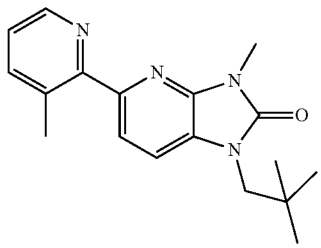 [SMILES: Cc1cccnc1-c1ccc2c(n1)n(C)c(=O)n2CC(C)(C)C] | 1-(2,2-dimethylpropyl)-3-methyl-5-(3-methylpyridin-2-yl)-1,3-dihydro-2H-imidazo[4,5-b]pyridin-2-one | Calc'd 311.1866, found 311.1866 |
| 22-6 | 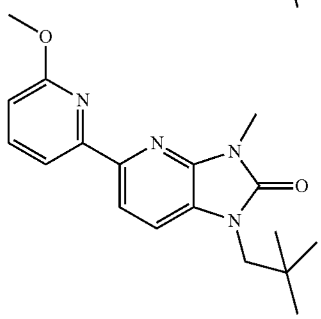 | 1-(2,2-dimethylpropyl)-5-(6-methoxypyridin-2-yl)-3-methyl-1,3-dihydro-2H-imidazo[4,5-b]pyridin-2-one | Calc'd 327.1816, found 327.1819 |
| 22-7 | 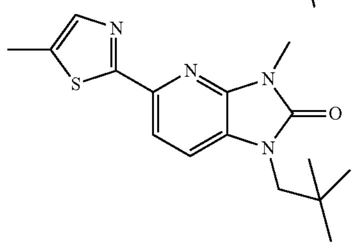 | 1-(2,2-dimethylpropyl)-3-methyl-5-(5-methyl-1,3-thiazol-2-yl)-1,3-dihydro-2H-imidazo[4,5-b]pyridin-2-one | Calc'd 317.1431, found 317.1434 |

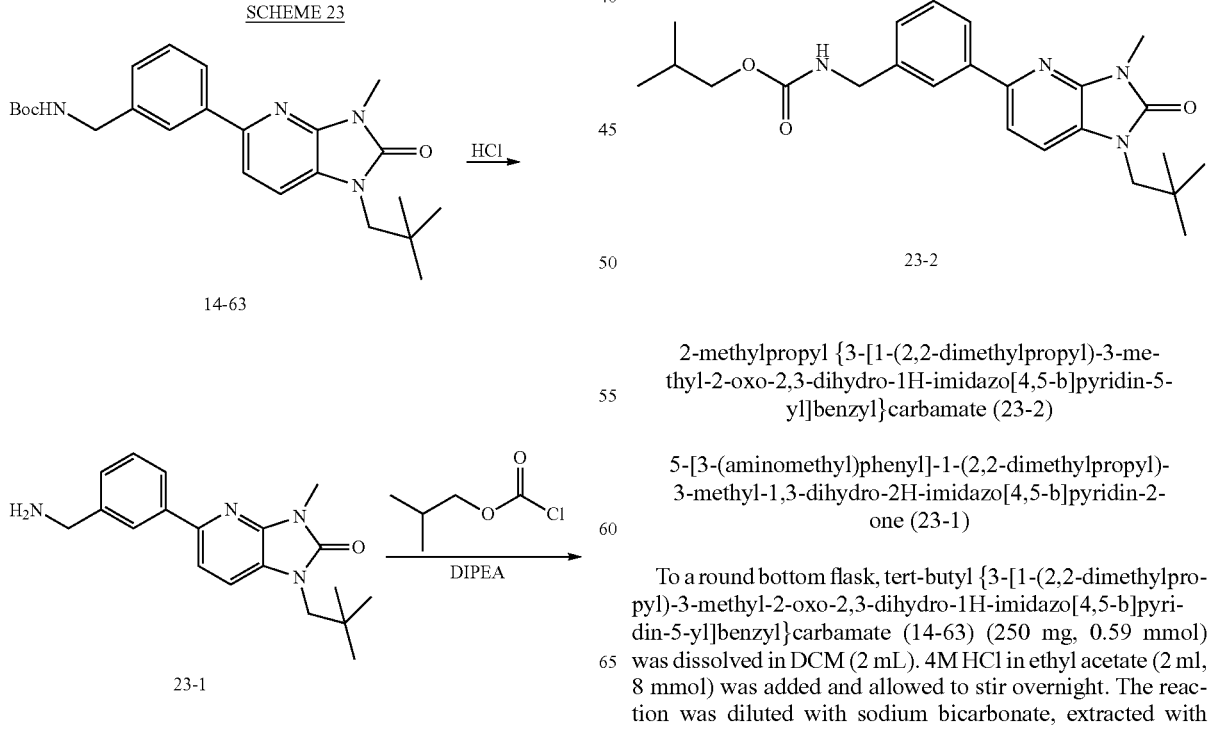

2-methylpropyl {3-[1-(2,2-dimethylpropyl)-3-methyl-2-oxo-2,3-dihydro-1H-imidazo[4,5-b]pyridin-5-yl]benzyl}carbamate (23-2)

5-[3-(aminomethyl)phenyl]-1-(2,2-dimethylpropyl)-3-methyl-1,3-dihydro-2H-imidazo[4,5-b]pyridin-2-one (23-1)

To a round bottom flask, tert-butyl {3-[1-(2,2-dimethylpropyl)-3-methyl-2-oxo-2,3-dihydro-1H-imidazo[4,5-b]pyridin-5-yl]benzyl}carbamate (14-63) (250 mg, 0.59 mmol) was dissolved in DCM (2 mL). 4M HCl in ethyl acetate (2 ml, 8 mmol) was added and allowed to stir overnight. The reaction was diluted with sodium bicarbonate, extracted with DCM (3×), and the combined organic layers were washed with brine, dried over sodium sulfate, filtered and concentrated to produce 5-[3-(aminomethyl)phenyl]-1-(2,2-dimethylpropyl)-3-methyl-1,3-dihydro-2H-imidazo[4,5-b]pyridin-2-one (23-1). MS (M+H)⁺: observed=325.2, calculated=325.4.

2-methylpropyl {3-[1-(2,2-dimethylpropyl)-3-methyl-2-oxo-2,3-dihydro-1H-imidazo[4,5-b]pyridin-5-yl]benzyl}carbamate (23-2)

To a microwave vial, 5-[3-(aminomethyl)phenyl]-1-(2,2-dimethylpropyl)-3-methyl-1,3-dihydro-2H-imidazo[4,5-b]pyridin-2-one (23-1) (15 mg, 0.05 mmol) was added under nitrogen and dissolved in THF (0.25 ml). Isobutyl chloroformate (4.4 mg, 0.055 mmol) was added followed by diisopropyl ethyl amine 9 mg, 0.07 mmol). The reaction was allowed to stir for 2 hours at room temperature. The reaction was diluted with methanol, and passed through a syringe filter. The solution was purified using reverse phase chromatography (10-100%, 0.1% TFA in H₂O/Acetonitrile) and the desired fractions were collected and concentrated to produce 2-methylpropyl {3-[1-(2,2-dimethylpropyl)-3-methyl-2-oxo-2,3-dihydro-1H-imidazo[4,5-b]pyridin-5-yl]benzyl}carbamate (23-2). HRMS (M+H)⁺: observed=425.2549, calculated=425.2547.

TABLE 11

The following compounds were prepared from 23-1 by a reaction sequence analogous to that illustrated in Scheme 23.

| Cmpd | Structure | IUPAC Name | Exact Mass [M + H]+ |
|---|---|---|---|
| 23-3 | 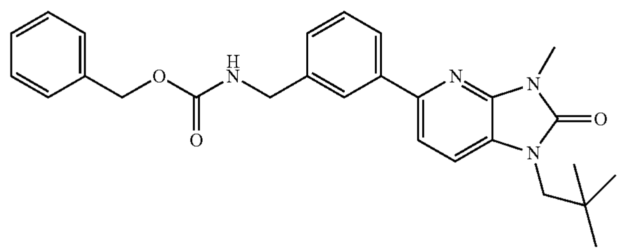 [SMILES: Cn1c(=O)n(CC(C)(C)C)c2ccc(-c3cccc(CNC(=O)OCc4ccccc4)c3)nc21] | benzyl {3-[1-(2,2-dimethylpropyl)-3-methyl-2-oxo-2,3-dihydro-1H-imidazo[4,5-b]pyridin-5-yl]benzyl}carbamate | Calc'd 459.2391, found 459.2395 |
| 23-4 | 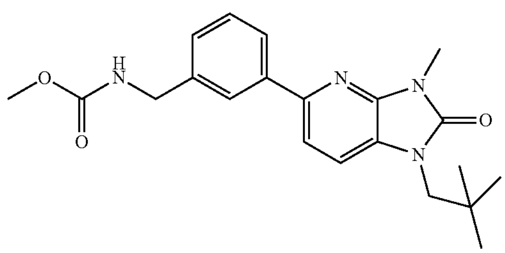 [SMILES: COC(=O)NCc1cccc(-c2ccc3c(n2)n(C)c(=O)n3CC(C)(C)C)c1] | methyl {3-[1-(2,2-dimethylpropyl)-3-methyl-2-oxo-2,3-dihydro-1H-imidazo[4,5-b]pyridin-5-yl]benzyl}carbamate | Calc'd 383.2078, found 383.2078 |
| 23-5 | 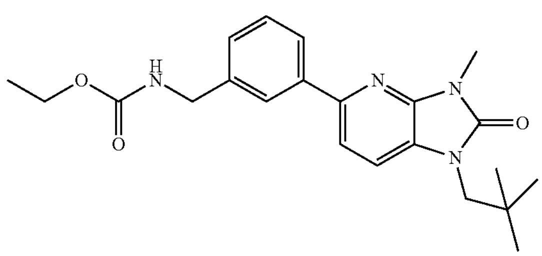 [SMILES: CCOC(=O)NCc1cccc(-c2ccc3c(n2)n(C)c(=O)n3CC(C)(C)C)c1] | ethyl {3-[1-(2,2-dimethylpropyl)-3-methyl-2-oxo-2,3-dihydro-1H-imidazo[4,5-b]pyridin-5-yl]benzyl}carbamate | Calc'd 397.2234, found 397.2233 |
| 23-6 | 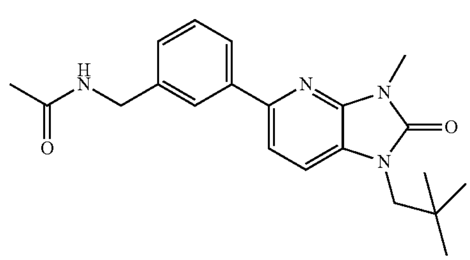 [SMILES: CC(=O)NCc1cccc(-c2ccc3c(n2)n(C)c(=O)n3CC(C)(C)C)c1] | N-{3-[1-(2,2-dimethylpropyl)-3-methyl-2-oxo-2,3-dihydro-1H-imidazo[4,5-b]pyridin-5-yl]benzyl}acetamide | Calc'd 367.2129, found 367.2129 |

TABLE 11-continued

The following compounds were prepared from 23-1 by a reaction sequence analogous to that illustrated in Scheme 23.

| Cmpd | Structure | IUPAC Name | Exact Mass [M + H]+ |
|---|---|---|---|
| 23-7 | 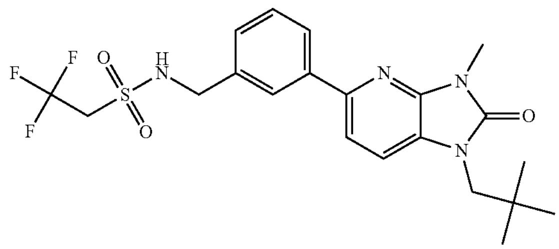 [SMILES: Cn1c(=O)n(CC(C)(C)C)c2ccc(-c3cccc(CNS(=O)(=O)CC(F)(F)F)c3)nc21] | N-{3-[1-(2,2-dimethylpropyl)-3-methyl-2-oxo-2,3-dihydro-1H-imidazo[4,5-b]pyridin-5-yl]benzyl}-2,2,2-trifluoroethanesulfonamide | Calc'd 471.2, found 471.3 |

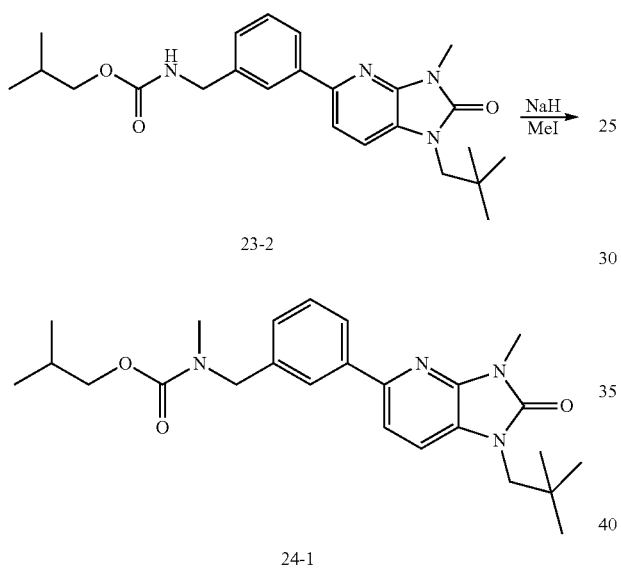

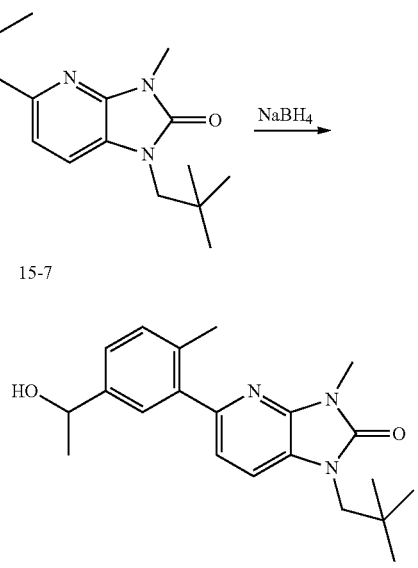

2-methylpropyl {3-[1-(2,2-dimethylpropyl)-3-methyl-2-oxo-2,3-dihydro-1H-imidazo[4,5-b]pyridin-5-yl]benzyl}methylcarbamate (24-1)

To a microwave vial, 2-methylpropyl {3-[1-(2,2-dimethylpropyl)-3-methyl-2-oxo-2,3-dihydro-1H-imidazo[4,5-b]pyridin-5-yl]benzyl}carbamate (23-2) (19 mg, 0.045 mmol) and 60% sodium hydride in mineral oil (2.2 mg, 0.054 mmol) were added under nitrogen and dissolved in THF (0.225 ml). Methyl iodide (8 mg, 0.056 mmol) was added to the solution and allowed to stir at room temperature for 2 hours. The reaction was diluted with methanol, and passed through a syringe filter. The solution was purified using reverse phase chromatography (10-100%, 0.1% TFA in H$_2$O/Acetonitrile) and the desired fractions were collected and concentrated to produce 2-methylpropyl {3-[1-(2,2-dimethylpropyl)-3-methyl-2-oxo-2,3-dihydro-1H-imidazo[4,5-b]pyridin-5-yl]benzyl}methylcarbamate (24-1). HRMS (M+H)$^+$: observed=439.2706, calculated=439.2704.

1-(2,2-dimethylpropyl)-5-{5-[(1S)-1-hydroxyethyl]-2-methylphenyl}-3-methyl-1,3-dihydro-2H-imidazo[4,5-b]pyridin-2-one (25-1)

To a microwave vial was added 5-(5-acetyl-2-methylphenyl)-1-(2,2-dimethylpropyl)-3-methyl-1,3-dihydro-2H-imidazo[4,5-b]pyridin-2-one (15-7) (15 mg, 0.043 mmol) and sodium borohydride (2.5 mg, 0.064 mmol) under nitrogen. The mixture was dissolve in methanol (0.4 ml), and allowed to stir at room temperature for 1 hour. The reaction was diluted with methanol, and passed through a syringe filter. The solution was purified using reverse phase chromatography (10-100%, 0.1% TFA in H$_2$O/Acetonitrile) and the desired fractions were collected and concentrated to produce 1-(2,2-dimethylpropyl)-5-{5-[(1S)-1-hydroxyethyl]-2-methylphenyl}-3-methyl-1,3-dihydro-2H-imidazo[4,5-b]pyridin-2-one (25-1). HRMS (M+H)$^+$: observed=354.2178, calculated=354.2176.

SCHEME 26

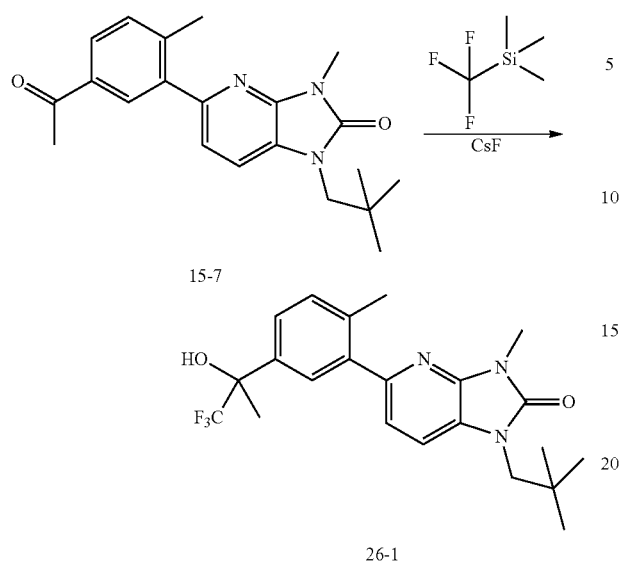

1-(2,2-dimethylpropyl)-3-methyl-5-[2-methyl-5-(1,1,1-trifluoro-2-hydroxypropan-2-yl)phenyl]1,3-dihydro-2H-imidazo[4,5-b]pyridin-2-one (26-1)

Prepared from 15-7 according to the procedures reported in Scheme 10. HRMS (M+H)$^+$: observed=422.2056, calculated=422.2050.

SCHEME 27

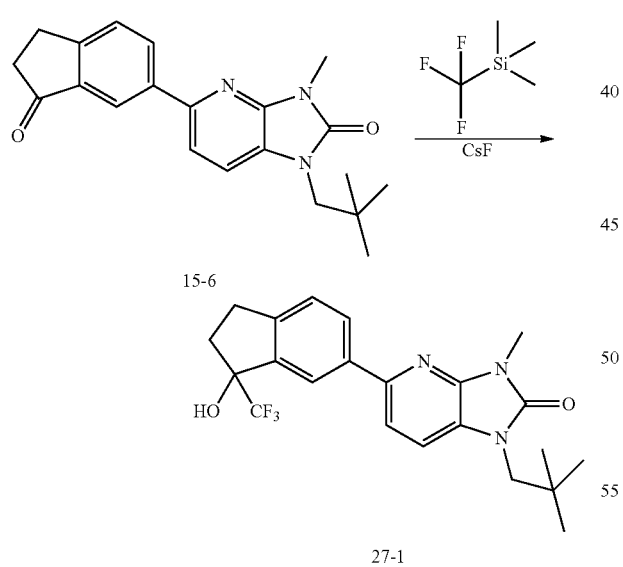

1-(2,2-dimethylpropyl)-5-[3-hydroxy-3-(trifluoromethyl)-2,3-dihydro-1H-inden-5-yl]-3-methyl-1,3-dihydro-2H-imidazo[4,5-b]pyridin-2-one (27-1)

Prepared from 15-6 according to the procedures reported in Scheme 10. HRMS (M+H)$^+$: observed=420.1896, calculated=420.1893.

SCHEME 28

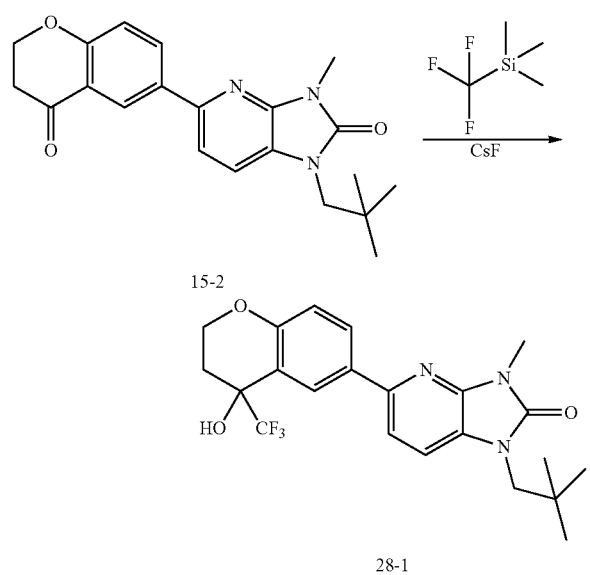

1-(2,2-dimethylpropyl)-5-[4-hydroxy-4-(trifluoromethyl)-3,4-dihydro-2H-chromen-6-yl]-3-methyl-1,3-dihydro-2H-imidazo[4,5-b]pyridin-2-one (28-1)

Prepared from 15-2 according to the procedures reported in Scheme 10. HRMS (M+H)$^+$: observed=436.1839, calculated=436.1843.

SCHEME 29

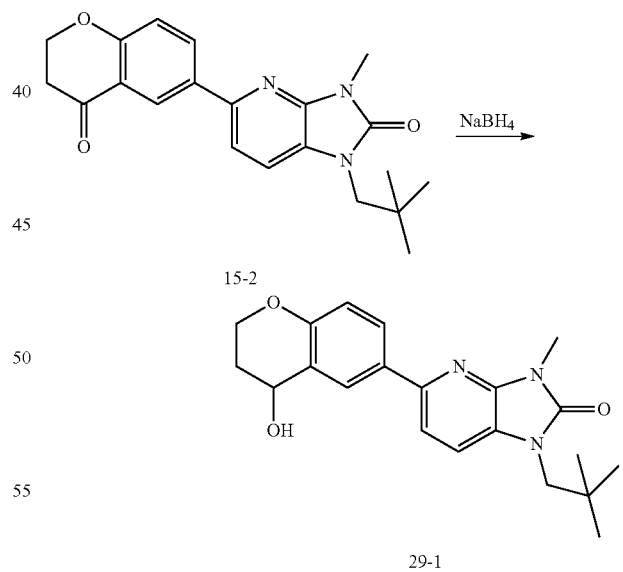

1-(2,2-dimethylpropyl)-5-[4-hydroxy-3,4-dihydro-2H-chromen-6-yl]-3-methyl-1,3-dihydro-2H-imidazo[4,5-b]pyridin-2-one (29-1)

Prepared from 15-2 according to the procedures reported in Scheme 25. HRMS (M+H)$^+$: observed=368.1965, calculated=368.1969.

SCHEME 30

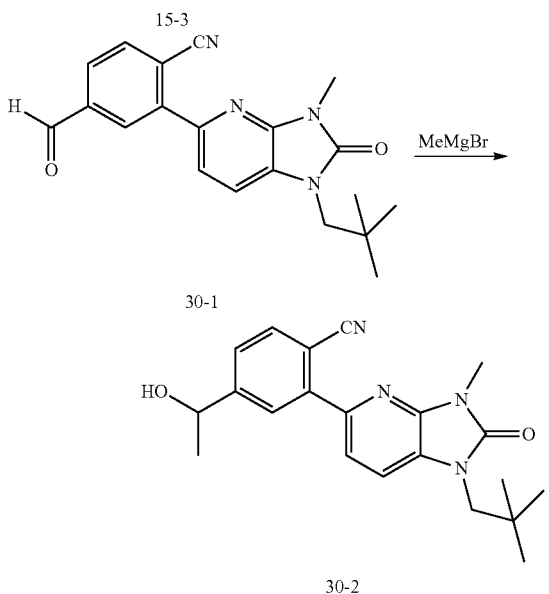

2-[1-(2,2-dimethylpropyl)-3-methyl-2-oxo-2,3-dihydro-1H-imidazo[4,5-b]pyridin-5-yl]-4-[1-hydroxyethyl]benzonitrile (30-2)

2-[1-(2,2-dimethylpropyl)-3-methyl-2-oxo-2,3-dihydro-1H-imidazo[4,5-b]pyridin-5-yl]-4-formylbenzonitrile (30-1)

To a microwave vial, 2-[1-(2,2-dimethylpropyl)-3-methyl-2-oxo-2,3-dihydro-1H-imidazo[4,5-b]pyridin-5-yl]-4-(hydroxymethyl)benzonitrile (15-3) (300 mg, 0.86 mmol) and Dess-Martin periodinane (545 mg, 1.28 mmol) was added under nitrogen and dissolved in DCM (4.3 ml). After stirring for 2 hours, the reaction was diluted with sodium thiosulfate, washed with DCM (3×), and then washed the combined organic layer with brine, dried over sodium sulfate, filtered and concentrated. The mixture was diluted with methanol, and passed through a syringe filter. The solution was purified using reverse phase chromatography (10-100%, 0.1% TFA in H$_2$O/Acetonitrile) and the desired fractions were collected and concentrated to produce 2-[1-(2,2-dimethylpropyl)-3-methyl-2-oxo-2,3-dihydro-1H-imidazo[4,5-b]pyridin-5-yl]-4-formylbenzonitrile (30-1). MS (M+H)$^+$: observed=349.2, calculated=349.4.

2-[1-(2,2-dimethylpropyl)-3-methyl-2-oxo-2,3-dihydro-1H-imidazo[4,5-b]pyridin-5-yl]-4-[(1S)-1-hydroxyethyl]benzonitrile (30-2)

To a round bottom flask, 2-[1-(2,2-dimethylpropyl)-3-methyl-2-oxo-2,3-dihydro-1H-imidazo[4,5-b]pyridin-5-yl]-4-formylbenzonitrile (30-1) (70 mg, 0.2 mmol) was added under nitrogen, dissolved in THF (1 mL), and cooled to −78° C. 3M methylmagnesium bromide (0.08 ml, 0.24 mmol) was added slowly to the cooled solution and allowed to stir for 30 minutes. The reaction was warmed to room temperature for 30 minutes until complete conversion over starting material. The mixture was diluted with methanol, and passed through a syringe filter. The solution was purified using reverse phase chromatography (10-100%, 0.1% TFA in H$_2$O/Acetonitrile) and the desired fractions were collected and concentrated to produce 2-[1-(2,2-dimethylpropyl)-3-methyl-2-oxo-2,3-dihydro-1H-imidazo[4,5-b]pyridin-5-yl]-4-[(1S)-1-hydroxyethyl]benzonitrile (30-2). HRMS (M+H)$^+$: observed=365.1976, calculated=365.1972.

SCHEME 31

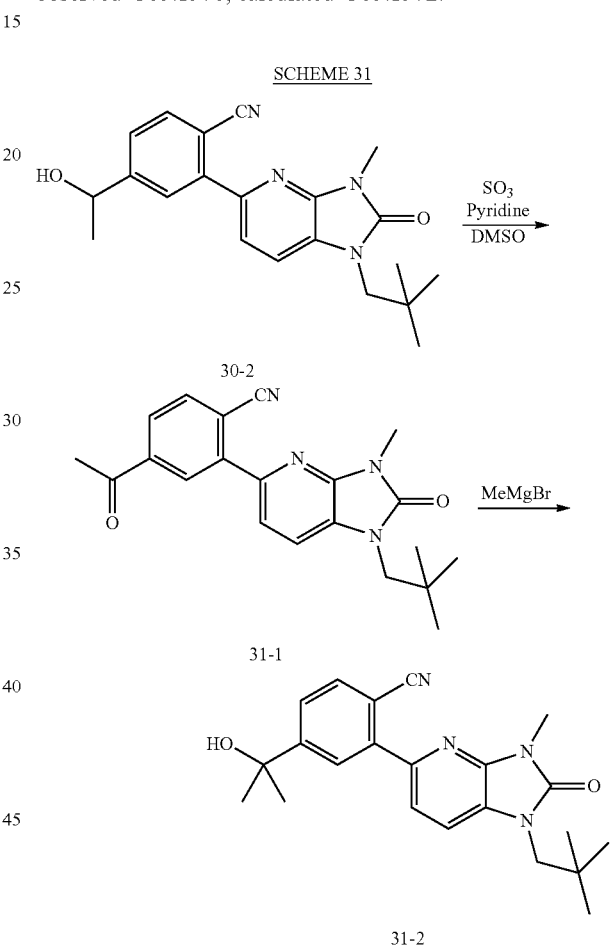

2-[1-(2,2-dimethylpropyl)-3-methyl-2-oxo-2,3-dihydro-1H-imidazo[4,5-b]pyridin-5-yl]-4-(1-hydroxy-1-methylethyl)benzonitrile (31-2)

4-acetyl-2-[1-(2,2-dimethylpropyl)-3-methyl-2-oxo-2,3-dihydro-1H-imidazo[4,5-b]pyridin-5-yl]benzonitrile (31-1)

To a microwave vial, 2-[1-(2,2-dimethylpropyl)-3-methyl-2-oxo-2,3-dihydro-1H-imidazo[4,5-b]pyridin-5-yl]-4-[1-hydroxyethyl]benzonitrile (30-2) (35 mg, 0.1 mmol) was dissolved in DCM (0.25 ml) under nitrogen, followed by the addition of Diisopropyl ethyl amine (50 mg, 0.39 mmol). In a separate vial under nitrogen, SO$_3$ Pyridine complex (61 mg, 0.39 mmol) was dissolved in DMSO (0.25 ml). The DMSO solution was then added slowly to DCM solution and allowed to stir at room temperature. After 30 minutes, the mixture was diluted with methanol, and passed through a syringe filter. The solution was purified using reverse phase chromatography (10-100%, 0.1% TFA in H$_2$O/Acetonitrile) and the desired fractions were collected and concentrated to produce 4-acetyl-2-[1-(2,2-dimethylpropyl)-3-methyl-2-oxo-2,3-dihydro-1H-imidazo[4,5-b]pyridin-5-yl]benzonitrile (31-1). HRMS (M+H)$^+$: observed=363.1832, calculated=363.1816.

2-[1-(2,2-dimethylpropyl)-3-methyl-2-oxo-2,3-dihydro-1H-imidazo[4,5-b]pyridin-5-yl]-4-(1-hydroxy-1-methylethyl)benzonitrile (31-2)

Prepared from 31-1 according to the procedures reported in Scheme 30. HRMS (M+H)$^+$: observed=379.2136, calculated=379.2129.

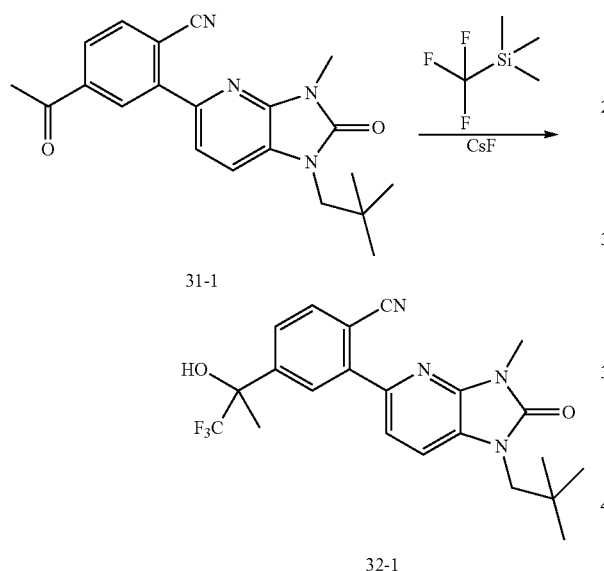

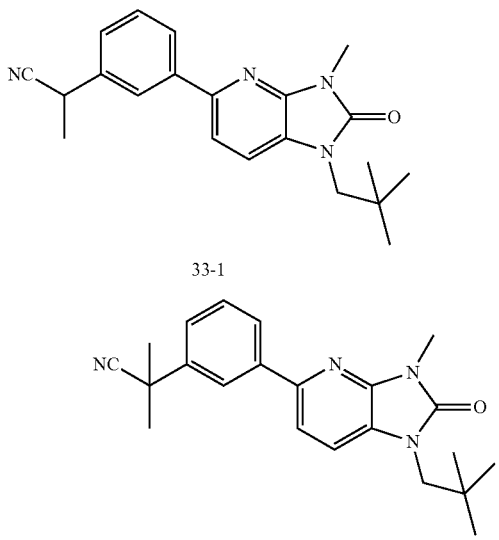

2-{3-[1-(2,2-dimethylpropyl)-3-methyl-2-oxo-2,3-dihydro-1H-imidazo[4,5-b]pyridin-5-yl]phenyl}propanenitrile (33-1) and 2-{3-[1-(2,2-dimethylpropyl)-3-methyl-2-oxo-2,3-dihydro-1H-imidazo[4,5-b]pyridin-5-yl]phenyl}-2-methylpropanenitrile (33-2)

To a round bottom flask, {3-[1-(2,2-dimethylpropyl)-3-methyl-2-oxo-2,3-dihydro-1H-imidazo[4,5-b]pyridin-5-yl]phenyl}acetonitrile (14-48) (45 mg, 0.14 mmol) was added and dissolved in THF (1.3 ml) under nitrogen and cooled to −78° C. 1 M Sodium bis(hexamethylsilyl)amide (0.18 ml, 0.18 mmol) was added slowly to the cooled solution, followed by Methyl iodide (25 mg, 0.18 mmol). The cooled solution was stirred for 30 minutes, allowed to warm to room temperature and stirred for 10 minutes. The reaction was diluted with methanol, and passed through a syringe filter. The solution was purified using reverse phase chromatography (10-100%, 0.1% TFA in H$_2$O/Acetonitrile) and the desired fractions were collected and concentrated to produce 2-{3-[1-(2,2-dimethylpropyl)-3-methyl-2-oxo-2,3-dihydro-1H-imidazo[4,5-b]pyridin-5-yl]phenyl}propanenitrile (33-1), HRMS (M+H)$^+$: observed=349.2032, calculated=349.2023 and 2-{3-[1-(2,2-dimethylpropyl)-3-methyl-2-oxo-2,3-dihydro-1H-imidazo[4,5-b]pyridin-5-yl]phenyl}-2-methylpropanenitrile (33-2); HRMS (M+H)$^+$: observed=363.2186, calculated=363.2179.

2-[1-(2,2-dimethylpropyl)-3-methyl-2-oxo-2,3-dihydro-1H-imidazo[4,5-b]pyridin-5-yl]-4-[2,2,2-trifluoro-1-hydroxy-1-methylethyl]benzonitrile (32-1)

Prepared from 31-1 according to the procedures reported in Scheme 10. HRMS (M+H)$^+$: observed=433.1852, calculated=433.1846.

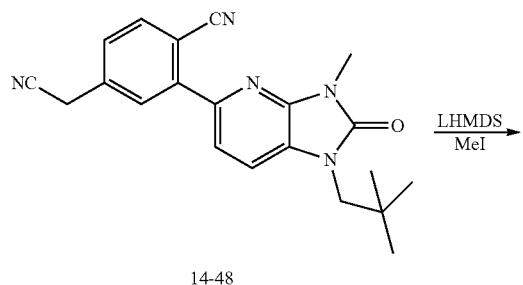

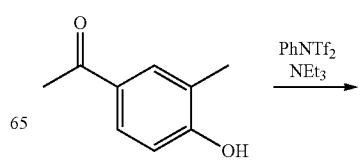

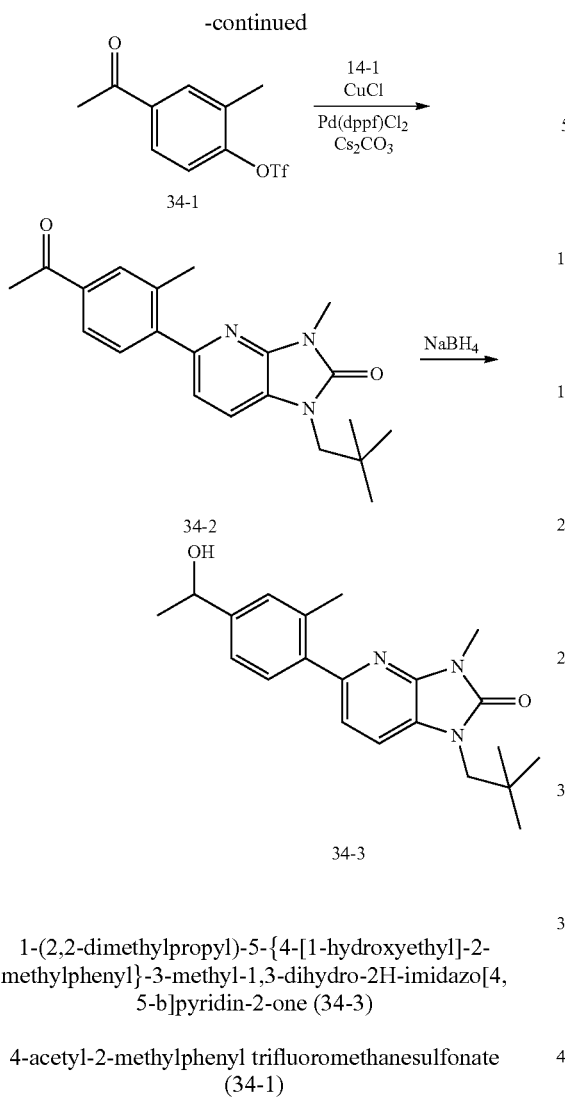

The solution was purified using reverse phase chromatography (10-100%, 0.1% TFA in H$_2$O/Acetonitrile) and the desired fractions were collected and concentrated to produce 5-(4-acetyl-2-methylphenyl)-1-(2,2-dimethylpropyl)-3-methyl-1,3-dihydro-2H-imidazo[4,5-b]pyridin-2-one (34-2). MS (M+H)$^+$: observed=352.3, calculated=352.4.

1-(2,2-dimethylpropyl)-5-{4-[1-hydroxyethyl]-2-methylphenyl}-3-methyl-1,3-dihydro-2H-imidazo[4,5-b]pyridin-2-one (34-3)

Prepared from 34-2 according to the procedures reported in Scheme 25. MS (M+H)$^+$: observed=354.3, calculated=354.5.

SCHEME 35

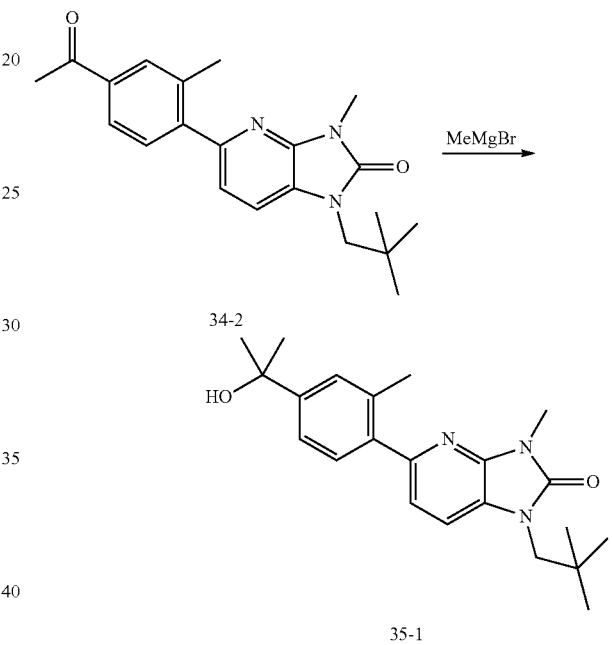

1-(2,2-dimethylpropyl)-5-[4-(1-hydroxy-1-methylethyl)-2-methylphenyl]-3-methyl-1,3-dihydro-2H-imidazo[4,5-b]pyridin-2-one (35-1)

Prepared from 34-2 according to the procedures reported in Scheme 30. HRMS (M+H)$^+$: observed=368.2336, calculated=368.2333.

SCHEME 36

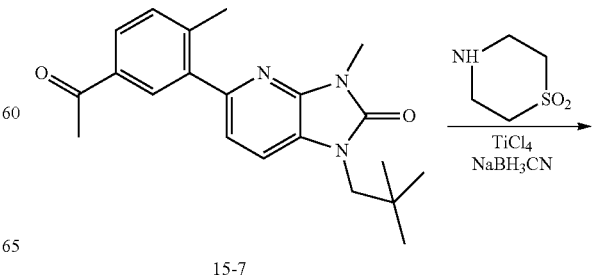

4-acetyl-2-methylphenyl trifluoromethanesulfonate (34-1)

To a microwave vial, 1-(4-hydroxy-3-methylphenyl)ethanone (200 mg, 1.3 mmol) and PhNTf2 (600 mg, 1.67 mmol) were added under nitrogen and dissolved in chloroform (6.6 ml). Triethylamine (202 mg. 2.0 mmol) was added to the solution and was heated at 50° C. for 2 hours. The solution was suspended in sodium bicarbonate, and washed with DCM. The organic layers were collected and washed with brine, dried over sodium sulfate, filtered and concentrated to produce 4-acetyl-2-methylphenyl trifluoromethanesulfonate (34-1). MS (M+H)$^+$: observed=283.0, calculated=283.2.

5-(4-acetyl-2-methylphenyl)-1-(2,2-dimethylpropyl)-3-methyl-1,3-dihydro-2H-imidazo[4,5-b]pyridin-2-one (34-2)

To a microwave vial, 4-acetyl-2-methylphenyl trifluoromethanesulfonate (34-1) (40 mg, 0.14 mmol), [1-(2,2-dimethylpropyl)-3-methyl-2-oxo-2,3-dihydro-1H-imidazo[4,5-b]pyridin-5-yl]boronic acid (14-1) (56 mg, 0.22 mmol), cesium carbonate (92 mg, 0.28 mmol), CuCl (14 mg, 0.14 mmol), and Bis(diphenylphosphino)ferrocene dicholoropalladium (8 mg, 0.015 mmol) was added under nitrogen and dissolved in DMF (0.7 ml). The suspension was heated overnight at 100° C. The reaction was cooled to room temperature, diluted with methanol, and passed through a syringe filter.

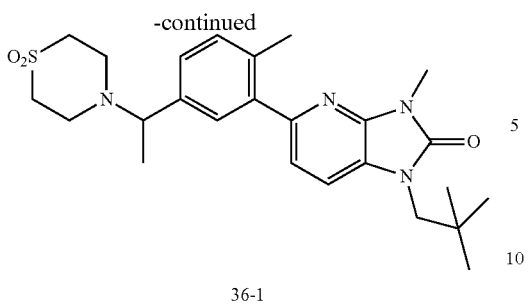

36-1

1-(2,2-dimethylpropyl)-5-{5-[1-(1,1-dioxidothiomorpholin-4-yl)ethyl]-2-methylphenyl}-3-methyl-1,3-dihydro-2H-imidazo[4,5-b]pyridin-2-one (36-1)

To a microwave vial was added 5-(5-acetyl-2-methylphenyl)-1-(2,2-dimethylpropyl)-3-methyl-1,3-dihydro-2H-imidazo[4,5-b]pyridin-2-one (15-7) (30 mg, 0.085 mmol) and thiomorpholine 1,1-dioxide (17 mg, 0.13 mmol) were added under nitrogen and dissolved in toluene (0.43 ml). Titanium (IV) chloride (10 mg, 0.05 mmol) was added to the solution and the reaction was allow to stir at room temperature overnight. Sodium cyanoborohydride (8 mg, 0.12 mmol) was then added and allowed to stir for 1 hour. The reaction was diluted with methanol, and passed through a syringe filter. The solution was purified using reverse phase chromatography (10-100%, 0.1% TFA in H₂O/Acetonitrile) and the desired fractions were collected and concentrated to produce 1-(2,2-dimethylpropyl)-5-{5-[(1R)-1-(1,1-dioxidothiomorpholin-4-yl)ethyl]-2-methylphenyl}-3-methyl-1,3-dihydro-2H-imidazo[4,5-b]pyridin-2-one (36-1). HRMS (M+H)⁺: observed=471.2421, calculated=471.2424.

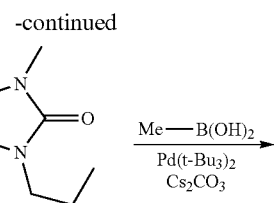

37-1

37-2

37-3

1-(2,2-dimethylpropyl)-5-[3-(2-hydroxypropan-2-yl)phenyl]-3,7-dimethyl-1,3-dihydro-2H-imidazo[4,5-b]pyridin-2-one (37-3)

5-chloro-1-(2,2-dimethylpropyl)-7-iodo-3-methyl-1,3-dihydro-2H-imidazo[4,5-b]pyridin-2-one (37-1)

To a found bottom flask, Diisopropylamine (22 ul, 0.16 mmol) was added under nitrogen, dissolved in THF (0.3 ml), and cooled to −78° C. 2.5 M n-butyl lithium (72 ul, 0.18 mmol) in hexane was added to the cooled solution and allowed to stir for 1 hour. 5-chloro-1-(2,2-dimethylpropyl)-3-methyl-1,3-dihydro-2H-imidazo[4,5-b]pyridin-2-one (14-

TABLE 12

The following compounds were prepared from 15-7 by a reaction sequence analogous to that illustrated in Scheme 36.

| Cmpd | Structure | IUPAC Name | Exact Mass [M + H]+ |
|---|---|---|---|
| 36-2 | 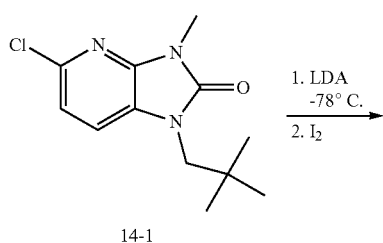 | 1-(2,2-dimethylpropyl)-5-(5-{1-[3-hydroxypyrrolidin-1-yl]ethyl}-2-methylphenyl)-3-methyl-1,3-dihydro-2H-imidazo[4,5-b]pyridin-2-one | Calc'd 423.2755, found 423.2744 |

SCHEME 37

1) (40 mg, 0.16 mmol) in THF (0.3 ml) was added to the cooled solution. After 1 hour, the solution was warmed to room temperature for 30 minutes and then cooled to −78° C. again. Iodine (48 mg, 0.19 mmol) in THF (0.2 ml) was added to the cooled solution for 1 hour and then warmed to room temperature. The reaction was diluted with methanol, and passed through a syringe filter. The solution was purified using reverse phase chromatography (10-100%, 0.1% TFA in H$_2$O/Acetonitrile) and the desired fractions were collected and concentrated to produce 5-chloro-1-(2,2-dimethylpropyl)-7-iodo-3-methyl-1,3-dihydro-2H-imidazo[4,5-b]pyridin-2-one (37-1). MS (M+H)$^+$: observed=380.1, calculated=380.6.

5-chloro-1-(2,2-dimethylpropyl)-3,7-dimethyl-1,3-dihydro-2H-imidazo[4,5-b]pyridin-2-one (37-2)

Prepared from 37-1 according to the procedures reported in Scheme 14.

1-(2,2-dimethylpropyl)-5-[3-(2-hydroxypropan-2-yl)phenyl]-3,7-dimethyl-1,3-dihydro-2H-imidazo[4,5-b]pyridin-2-one (37-3)

Prepared from 37-2 according to the procedures reported in Scheme 14. HRMS (M+H)$^+$: observed=368.2330, calculated=368.2333.

SCHEME 38

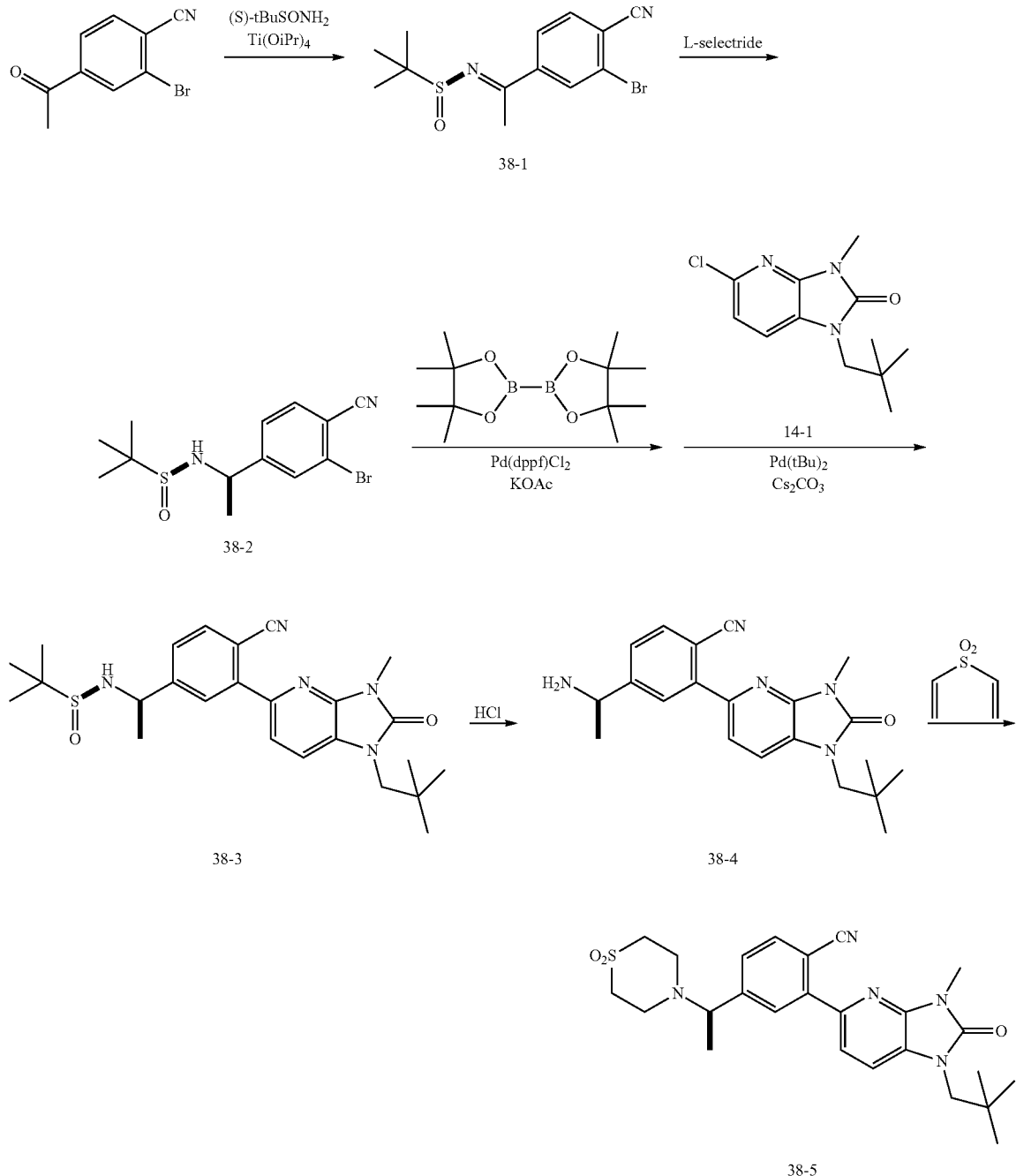

2-[1-(2,2-dimethylpropyl)-3-methyl-2-oxo-2,3-dihydro-1H-imidazo[4,5-b]pyridin-5-yl]-4-[(1R)-1-(1,1-dioxidothiomorpholin-4-yl)ethyl]benzonitrile (38-5)

N-[(1E)-1-(3-bromo-4-cyanophenyl)ethylidene]-2-methylpropane-2-sulfinamide (38-1)

To a solution of 4-acetyl-2-bromobenzonitrile (4.0 g, 18 mmol) and (S)-2-methylpropane-2-sulfinamide (2.4 g, 20 mmol) in THF (35 mL) was added titanium(IV) isopropoxide (8.1 mL, 36 mmol) and the reaction mixture was heated to 40 C under an atmosphere of nitrogen. After 2 hours, the reaction was cooled to room temperature, diluted in EtOAc, washed with saturated sodium bicarbonate, rochelle's salt, brine, dried over sodium sulfate, filtered and concentrated. Purification by silica gel chromatography gave desired product. MS (M+H)$^+$: observed=327.0/329.0, calculated=327.2/327.2.

N-[(1R)-1-(3-bromo-4-cyanophenyl)ethyl]-2-methylpropane-2-sulfinamide (38-2)

To a solution of 38-1 (500 mg, 1.5 mmol) in THF (4 mL) at −78 C was added L-Selectride (3.1 mL, 3.1 mmol, 1M). After 10 minutes, the reaction was diluted in EtOAc, washed with saturated sodium bicarbonate, dried over sodium sulfate, filtered and concentrated. Purification by reverse phase chromatography (1-100%, 0.1% TFA in H$_2$O/Acetonitrile) gave desired product. MS (M+H)$^+$: observed=329.0/331.0, calculated=329.3/331.3.

N-[(1R)-1-{4-cyano-3-[1-(2,2-dimethylpropyl)-3-methyl-2-oxo-2,3-dihydro-1H-imidazo[4,5-b]pyridin-5-yl]phenyl}ethyl]-2-methylpropane-2-sulfinamide (38-3)

Prepared from 38-2 and 14-1 according to the procedures reported in Scheme 15. MS (M+H)$^+$: observed=468.2421, calculated=468.2428.

4-[(1R)-1-aminoethyl]-2-[1-(2,2-dimethylpropyl)-3-methyl-2-oxo-2,3-dihydro-1H-imidazo[4,5-b]pyridin-5-yl]benzonitrile (38-4)

Prepared from 38-3 according to the procedures reported in Scheme 23. MS (M+H)$^+$: observed=364.2125, calculated=364.2132.

2-[1-(2,2-dimethylpropyl)-3-methyl-2-oxo-2,3-dihydro-1H-imidazo[4,5-b]pyridin-5-yl]-4-[(1R)-1-(1,1-dioxidothiomorpholin-4-yl)ethyl]benzonitrile (38-5)

To a solution of 38-4 (20 mg, 0.055 mmol) in ethanol (0.3 mL) at room temperature was added (ethenylsulfonyl)ethene (0.011 mL, 13 mg, 0.11 mmol). After 1 hour, the reaction was filtered and purified by reverse phase chromatography (1-100%, 0.1% TFA in H$_2$O/Acetonitrile) to give desired product. MS (M+H)$^+$: observed=482.2212, calculated=482.2220.

SCHEME 39

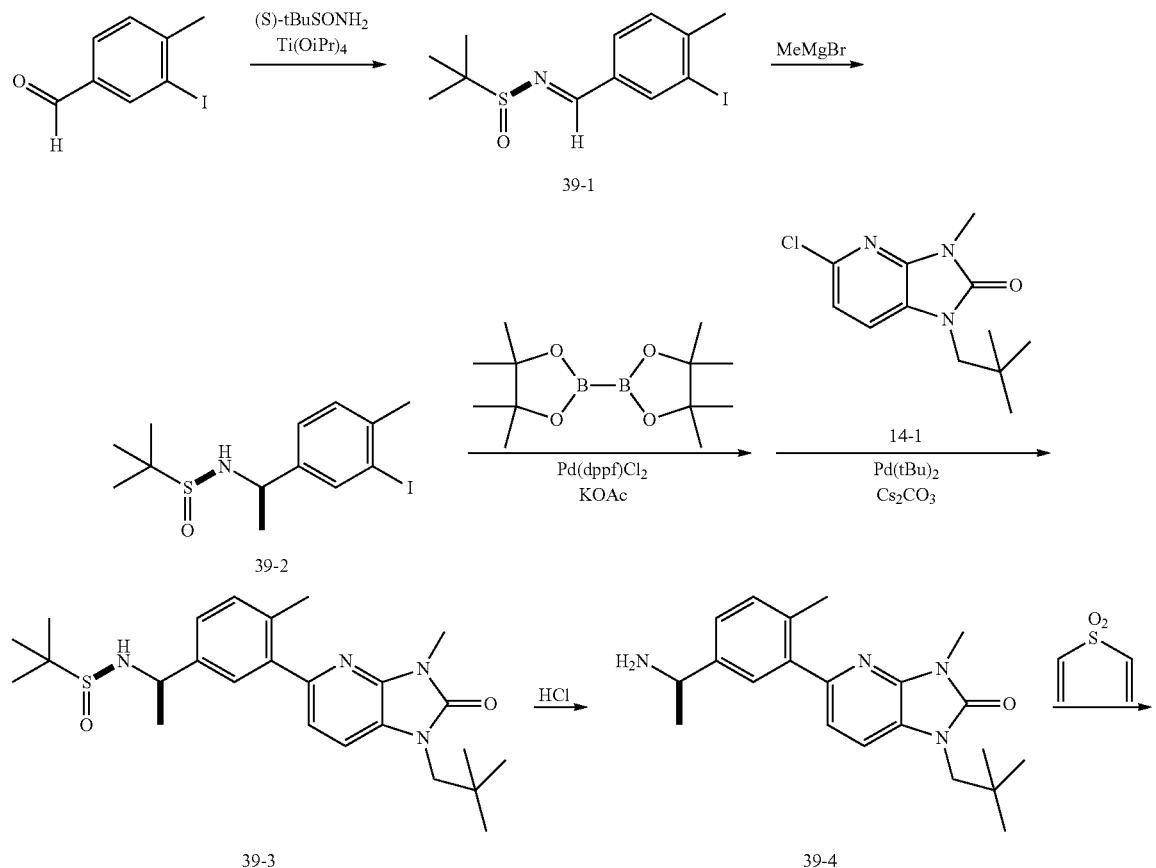

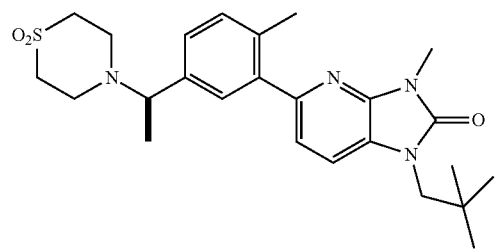
39-5

1-(2,2-dimethylpropyl)-5-{5-[(1R)-1-(1,1-dioxidothiomorpholin-4-yl)ethyl]-2-methylphenyl}-3-methyl-1,3-dihydro-2H-imidazo[4,5-b]pyridin-2-one (39-5)

N-[(E)-(3-iodo-4-methylphenyl)methylidene]-2-methylpropane-2(S)-sulfinamide (39-1)

Prepared from 3-iodo-4-methylbenzaldehyde according to the procedures reported in Scheme 38. MS (M+H)$^+$: observed=349.9, calculated=350.2.

N-[(1R)-1-(3-iodo-4-methylphenyl)ethyl]-2-methylpropane-2(S)-sulfinamide (39-2)

To a solution of 39-1 (1.5 g, 4.3 mmol) in DCM (17 mL) at −78 C was added methylmagnesium bromide (1.7 mL, 5.2 mmol, 3.0M). After 30 minutes, the reaction was quenched with saturated aqueous sodium bicarbonate and the aqueous phase was extracted with DCM. The combined organics were dried over sodium sulfate, filtered and concentrated to give the desired product. MS (M+H)$^+$: observed=366.0, calculated=366.3.

N-[(1R)-1-{3-[1-(2,2-dimethylpropyl)-3-methyl-2-oxo-2,3-dihydro-1H-imidazo[4,5-b]pyridin-5-yl]-4-methylphenyl}ethyl]-2-methylpropane-2(S)-sulfinamide (39-3)

Prepared from 39-2 and 14-1 according to the procedures reported in Scheme 38. MS (M+H)$^+$: observed=457.2620, calculated=457.2632.

5-{5-[(1R)-1-aminoethyl]-2-methylphenyl}-1-(2,2-dimethylpropyl)-3-methyl-1,3-dihydro-2H-imidazo[4,5-b]pyridin-2-one (39-4)

Prepared from 39-3 according to the procedures reported in Scheme 38. MS (M+H)$^+$: observed=353.2332, calculated=353.2336.

1-(2,2-dimethylpropyl)-5-{5-[(1R)-1-(1,1-dioxidothiomorpholin-4-yl)ethyl]-2-methylphenyl}-3-methyl-1,3-dihydro-2H-imidazo[4,5-b]pyridin-2-one (39-5)

Prepared from 1-(3-bromo-4-methylphenyl)ethanone according to the procedures reported in Scheme 38. MS (M+H)$^+$: observed=471.2418, calculated=471.2424.

SCHEME 40

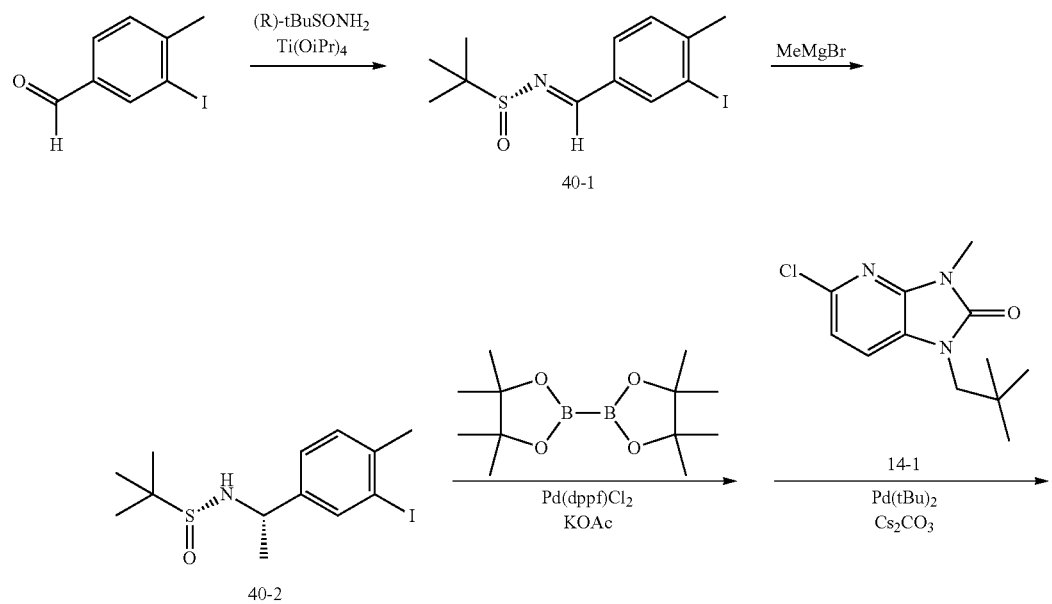

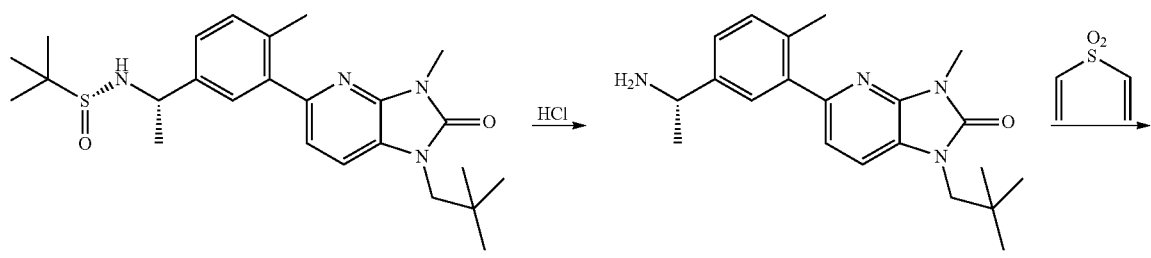

1-(2,2-dimethylpropyl)-5-{5-[(1S)-1-(1,1-dioxidot-hiomorpholin-4-yl)ethyl]-2-methylphenyl}-3-methyl-1,3-dihydro-2H-imidazo[4,5-b]pyridin-2-one (40-5)

N-[(E)-(3-iodo-4-methylphenyl)methylidene]-2-methylpropane-2(R)-sulfinamide (40-1)

Prepared from 3-iodo-4-methylbenzaldehyde according to the procedures reported in Scheme 38. MS (M+H)+: observed=349.9, calculated=350.2.

N-[(1S)-1-(3-iodo-4-methylphenyl)ethyl]-2-methylpropane-2(R)-sulfinamide (40-2)

Prepared from 40-1 according to the procedures reported in Scheme 39. MS (M+H)+: observed=366.0, calculated=366.3.

N-[(1S)-1-{3-[1-(2,2-dimethylpropyl)-3-methyl-2-oxo-2,3-dihydro-1H-imidazo[4,5-b]pyridin-5-yl]-4-methylphenyl}ethyl]-2-methylpropane-2-sulfinamide (40-3)

Prepared from 40-2 and 14-1 according to the procedures reported in Scheme 38. MS (M+H)+: observed=457.2620, calculated=457.2632.

5-{5-[(1S)-1-aminoethyl]-2-methylphenyl}-1-(2,2-dimethylpropyl)-3-methyl-1,3-dihydro-2H-imidazo[4,5-b]pyridin-2-one (40-4)

Prepared from 40-3 according to the procedures reported in Scheme 38. MS (M+H)+: observed=353.2332, calculated=353.2336.

1-(2,2-dimethylpropyl)-5-{5-[(1S)-1-(1,1-dioxidot-hiomorpholin-4-yl)ethyl]-2-methylphenyl}-3-methyl-1,3-dihydro-2H-imidazo[4,5-b]pyridin-2-one (40-5)

Prepared from 40-4 according to the procedures reported in Scheme 38. MS (M+H)+: observed=471.2412, calculated=471.2424.

SCHEME 41

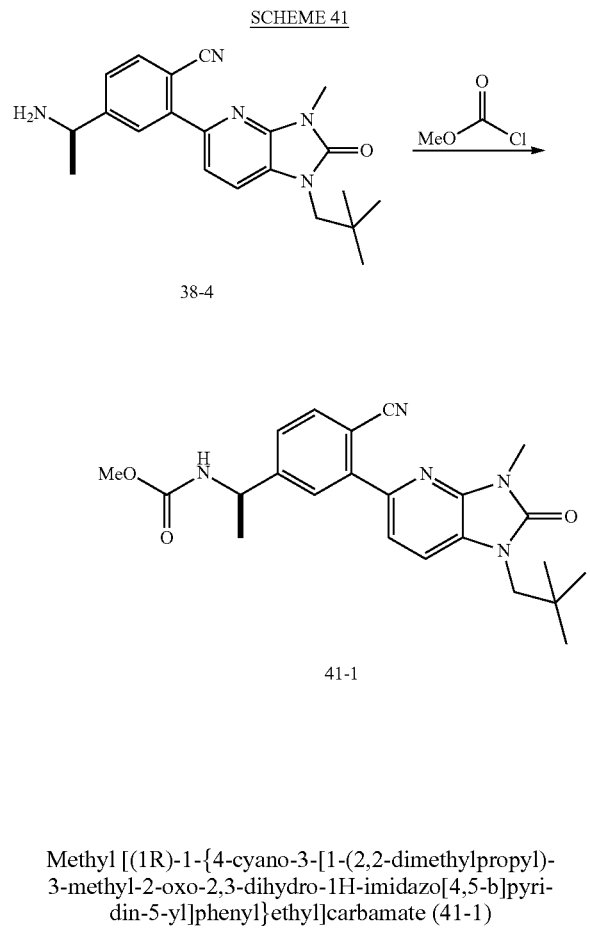

Methyl [(1R)-1-{4-cyano-3-[1-(2,2-dimethylpropyl)-3-methyl-2-oxo-2,3-dihydro-1H-imidazo[4,5-b]pyridin-5-yl]phenyl}ethyl]carbamate (41-1)

Prepared from 38-4 according to the procedures reported in Scheme 23. MS (M+H)+: observed=422.2178, calculated=422.2187.

TABLE 13

The following compounds were prepared from 38-4 by a reaction sequence analogous to that illustrated in Scheme 41.

| Cmpd | Structure | IUPAC Name | Exact Mass [M + H]+ |
|---|---|---|---|
| 41-2 | 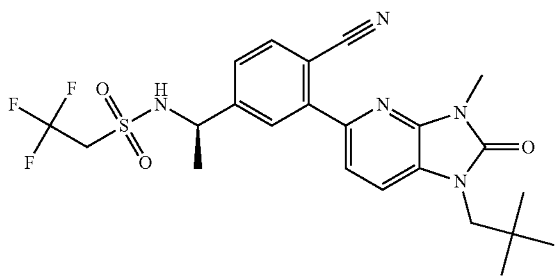 [SMILES: C[C@@H](NS(=O)(=O)CC(F)(F)F)c1ccc(C#N)c(-c2ccc3c(n2)n(C)c(=O)n3CC(C)(C)C)c1] | N-[(1R)-1-{4-cyano-3-[1-(2,2-dimethylpropyl)-3-methyl-2-oxo-2,3-dihydro-1H-imidazo[4,5-b]pyridin-5-yl]phenyl}ethyl]-2,2,2-trifluoroethanesulfonamide | Calc'd 510.1781, found 510.1773 |

SCHEME 42

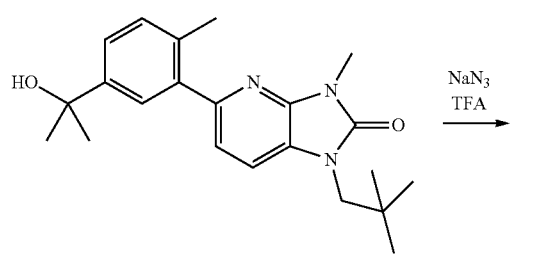

14-2

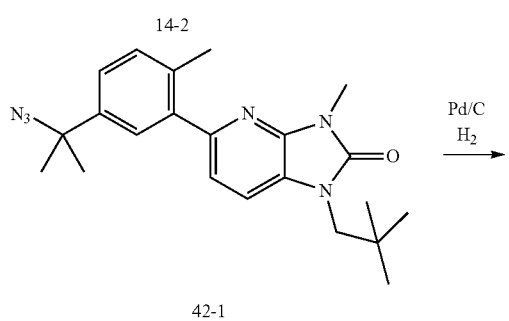

42-1

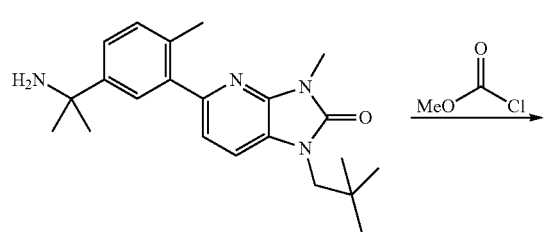

42-2

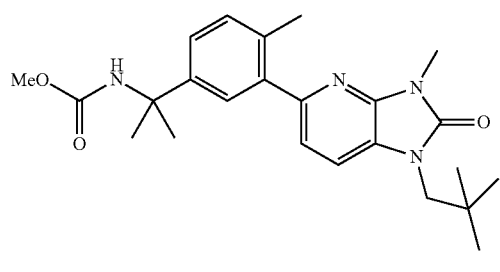

42-3

Methyl (1-{3-[1-(2,2-dimethylpropyl)-3-methyl-2-oxo-2,3-dihydro-1H-imidazo[4,5-b]pyridin-5-yl]-4-methylphenyl}-1-methylethyl)carbamate (42-3)

5-[5-(1-azido-1-methylethyl)-2-methylphenyl]-1-(2,2-dimethylpropyl)-3-methyl-1,3-dihydro-2H-imidazo[4,5-b]pyridin-2-one (42-1)

To a solution of 14-2 (1.2 g, 3.3 mmol) and sodium azide (0.42 g, 6.5 mmol) in DCM (8 mL) at −78 C was added a solution of trifluoroacetic acid (1.0 mL, 13 mmol) in DCM (0.25 mL). The reaction mixture was allowed to slowly warm to room temperature over 15 hours. The reaction was diluted in EtOAc and washed with water, brine, dried over sodium sulfate, filtered and concentrated to give product. HRMS (M+H)+: observed=393.2389, calculated=393.2397.

5-[5-(2-aminopropan-2-yl)-2-methylphenyl]-1-(2,2-dimethylpropyl)-3-methyl-1,3-dihydro-2H-imidazo[4,5-b]pyridin-2-one (42-2)

To a solution of 42-1 (1.4 g, 3.6 mmol) in EtOH (9 mL) was added 10% Pd/C (500 mg) and the flask was purged with hydrogen and fitted with a balloon filled with hydrogen gas. After 15 hours, the solution was filtered, concentrated and purified by reverse phase chromatography (1-100% Acetonitrile, 0.1% TFA in $H_2O$) and the desired fractions were concentrated to give product. MS (M+H)+: observed=367.2, calculated=367.5.

Methyl (1-{3-[1-(2,2-dimethylpropyl)-3-methyl-2-oxo-2,3-dihydro-1H-imidazo[4,5-b]pyridin-5-yl]-4-methylphenyl}-1-methylethyl)carbamate (42-3)

Prepared from 42-2 according to the procedures reported in Scheme 23. MS (M+H)+: observed=425.2539, calculated=425.2547. $^1$H NMR (400 MHz, $CD_3$ OD): δ 7.57 (d, J=8.0 Hz, 1H); 7.38 (s, 1H); 7.33 (d, J=8.2 Hz, 1H); 7.23 (d, J=8.1 Hz, 1H); 7.16 (d, J=8.0 Hz, 1H); 3.75 (s, 2H); 3.53 (s, 3H); 3.48 (s, 3H); 2.32 (s, 3H); 1.62 (s, 6H); 1.06 (s, 9H).

TABLE 14

The following compounds were prepared from 42-2 by a reaction sequence analogous to that illustrated in Scheme 42.

| Cmpd | Structure | IUPAC Name | Exact Mass [M + H]+ |
|---|---|---|---|
| 42-4 | 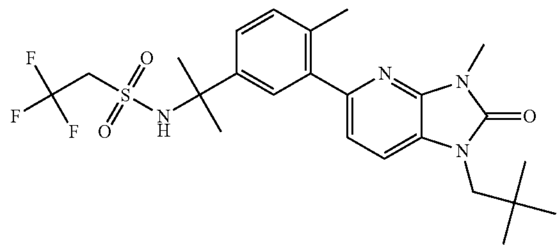 [SMILES: Cc1ccc(C(C)(C)NS(=O)(=O)CC(F)(F)F)cc1-c1ccc2c(n1)n(C)c(=O)n2CC(C)(C)C] | N-(1-{3-[1-(2,2-dimethylpropyl)-3-methyl-2-oxo-2,3-dihydro-1H-imidazo[4,5-b]pyridin-5-yl]-4-methylphenyl}-1-methylethyl)-2,2,2-trifluoroethanesulfonamide | Calc'd 513.2142, found 513.2131 |
| 42-5 | 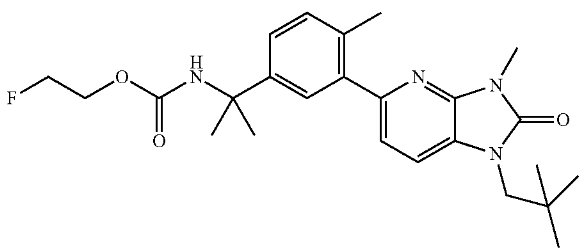 [SMILES: Cc1ccc(C(C)(C)NC(=O)OCCF)cc1-c1ccc2c(n1)n(C)c(=O)n2CC(C)(C)C] | 2-fluoroethyl (2-{3-[1-(2,2-dimethylpropyl)-3-methyl-2-oxo-2,3-dihydro-1H-imidazo[4,5-b]pyridin-5-yl]-4-methylphenyl}propan-2-yl)carbamate | Calc'd 457.2609, found 457.2610 |
| 42-6 | 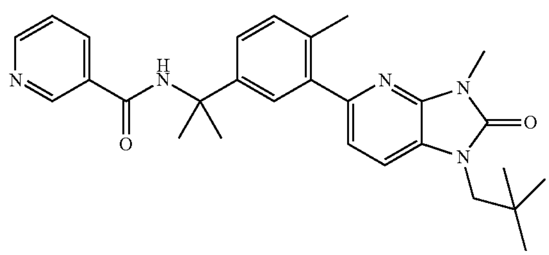 [SMILES: Cc1ccc(C(C)(C)NC(=O)c2cccnc2)cc1-c1ccc2c(n1)n(C)c(=O)n2CC(C)(C)C] | N-(2-{3-[1-(2,2-dimethylpropyl)-3-methyl-2-oxo-2,3-dihydro-1H-imidazo[4,5-b]pyridin-5-yl]-4-methylphenyl}propan-2-yl)pyridine-3-carboxamide | Calc'd 472.2707, found 472.2708 |
| 42-7 | 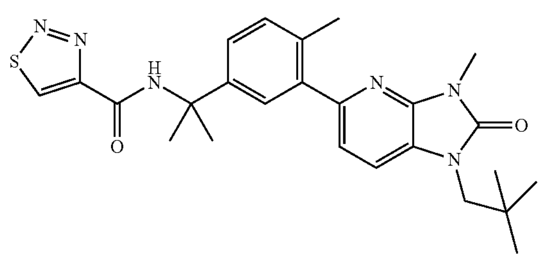 [SMILES: Cc1ccc(C(C)(C)NC(=O)c2csnn2)cc1-c1ccc2c(n1)n(C)c(=O)n2CC(C)(C)C] | N-(2-{3-[1-(2,2-dimethylpropyl)-3-methyl-2-oxo-2,3-dihydro-1H-imidazo[4,5-b]pyridin-5-yl]-4-methylphenyl}propan-2-yl)-1,2,3-thiadiazole-4-carboxamide | Calc'd 479.2224, found 479.2217 |

SCHEME 43

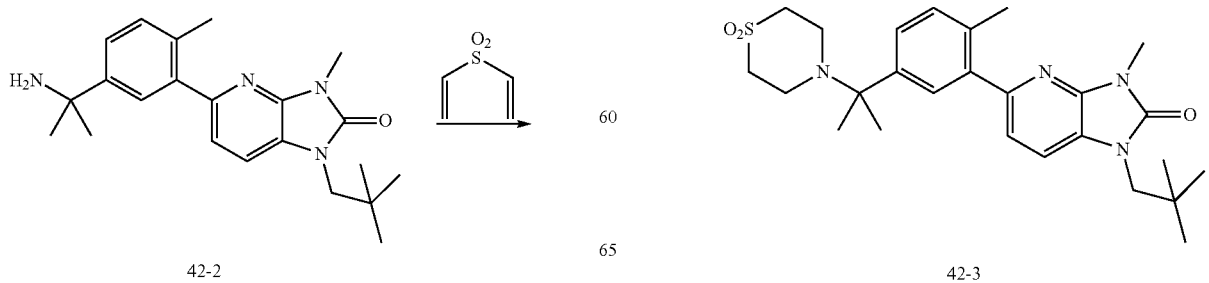

42-2

42-3

189

1-(2,2-dimethylpropyl)-5-{5-[1-(1,1-dioxidothiomorpholin-4-yl)-1-methylethyl]-2-methylphenyl}-3-methyl-1,3-dihydro-2H-imidazo[4,5-b]pyridin-2-one (43-1)

Prepared from 42-2 according to the procedures reported in Scheme 38. MS (M+H)⁺: observed=485.2571, calculated=485.2581.

SCHEME 44

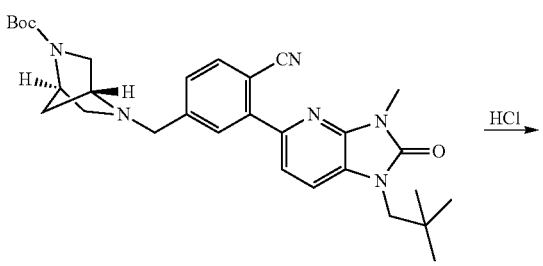

21-109

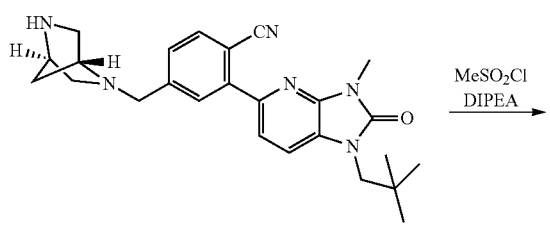

44-1

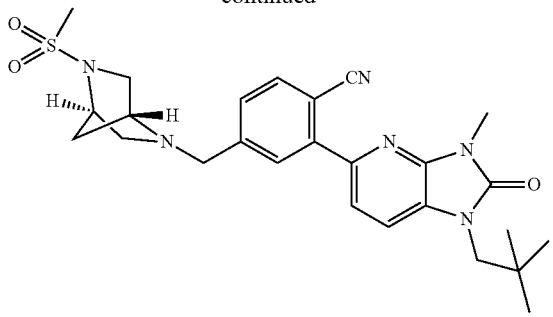

44-2

2-[1-(2,2-dimethylpropyl)-3-methyl-2-oxo-2,3-dihydro-1H-imidazo[4,5-b]pyridin-5-yl]-4-{[(1R,4R)-5-(methylsulfonyl)-2,5-diazabicyclo[2.2.1]hept-2-yl]methyl}benzonitrile (44-2)

4-[(1R,4R)-2,5-diazabicyclo[2.2.1]hept-2-ylmethyl]-2-[1-(2,2-dimethylpropyl)-3-methyl-2-oxo-2,3-dihydro-1H-imidazo[4,5-b]pyridin-5-yl]benzonitrile (44-1)

Prepared from 21-109 according to the procedures reported in Scheme 23. HRMS (M+H)⁺: observed=431.2544, calculated=431.2554.

2-[1-(2,2-dimethylpropyl)-3-methyl-2-oxo-2,3-dihydro-1H-imidazo[4,5-b]pyridin-5-yl]-4-{[(1R,4R)-5-(methylsulfonyl)-2,5-diazabicyclo[2.2.1]hept-2-yl]methyl}benzonitrile (44-2)

Prepared from 44-1 according to the procedures reported in Scheme 23. HRMS (M+H)⁺: observed=509.2317, calculated=509.2329.

TABLE 15

The following compounds were prepared by a reaction sequence analogous to that illustrated in Scheme 44.

| Cmpd | Structure | IUPAC Name | Exact Mass [M + H]+ |
|---|---|---|---|
| 44-3 | 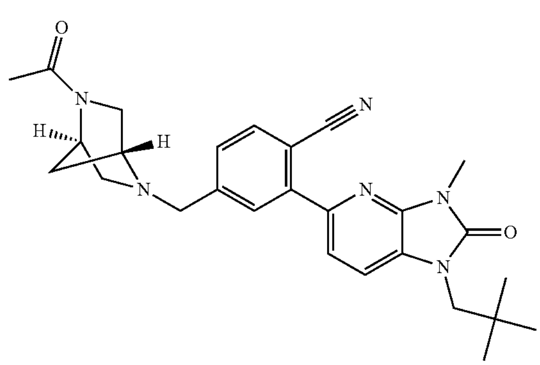 [SMILES: CC(=O)N1C[C@H]2C[C@@H]1CN2Cc1ccc(C#N)c(-c2ccc3c(n2)n(C)c(=O)n3CC(C)(C)C)c1] | 4-{[(1R,4R)-5-acetyl-2,5-diazabicyclo[2.2.1]hept-2-yl]methyl}-2-[1-(2,2-dimethylpropyl)-3-methyl-2-oxo-2,3-dihydro-1H-imidazo[4,5-b]pyridin-5-yl]benzonitrile | Calc'd 473.2660, found 473.2652 |

TABLE 15-continued

The following compounds were prepared by a reaction sequence analogous to that illustrated in Scheme 44.

| Cmpd | Structure | IUPAC Name | Exact Mass [M + H]+ |
|---|---|---|---|
| 44-4 | 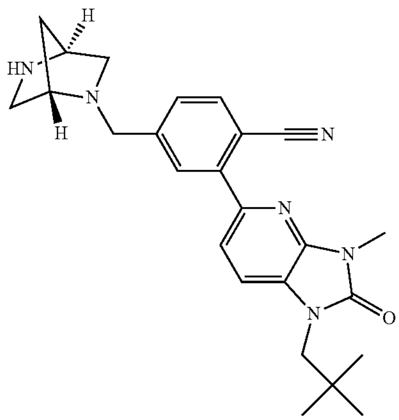 [SMILES: Cn1c(=O)n(CC(C)(C)C)c2ccc(-c3cc(CN4C[C@@H]5C[C@H]4CN5)ccc3C#N)nc21] | 4-[(1S,4S)-2,5-diazabicyclo[2.2.1]hept-2-ylmethyl]-2-[1-(2,2-dimethylpropyl)-3-methyl-2-oxo-2,3-dihydro-1H-imidazo[4,5-b]pyridin-5-yl]benzonitrile | Calc'd 431.2554, found 431.2546 |
| 44-5 | 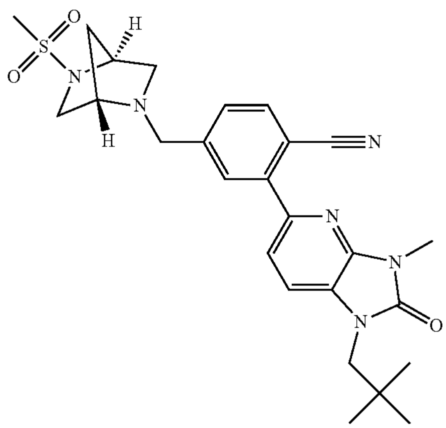 [SMILES: Cn1c(=O)n(CC(C)(C)C)c2ccc(-c3cc(CN4C[C@@H]5C[C@H]4CN5S(C)(=O)=O)ccc3C#N)nc21] | 2-[1-(2,2-dimethylpropyl)-3-methyl-2-oxo-2,3-dihydro-1H-imidazo[3,4-b]pyridin-5-yl]-4-{[(1S,4S)-5-(methylsulfonyl)-2,5-diazabicyclo[2.2.1]hept-2-yl]methyl}benzonitrile | Calc'd 509.2329, found 509.2317 |
| 44-6 | 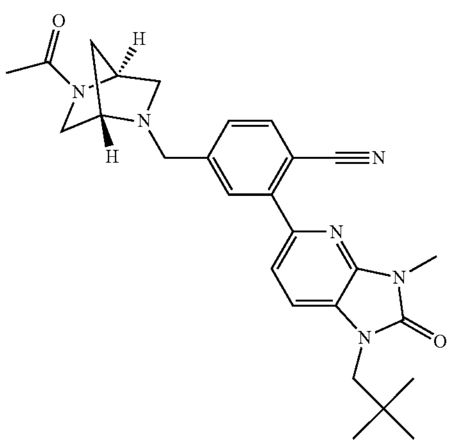 [SMILES: CC(=O)N1C[C@@H]2C[C@H]1CN2Cc1ccc(C#N)c(-c2ccc3c(n2)n(C)c(=O)n3CC(C)(C)C)c1] | 4-{[(1S,4S)-5-acetyl-2,5-diazabicyclo[2.2.1]hept-2-yl]methyl}-2-[1-(2,2-dimethylpropyl)-3-methyl-2-oxo-2,3-dihydro-1H-imidazo[4,5-b]pyridin-5-yl]benzonitrile | Calc'd 473.2660, found 473.2651 |
| 44-7 | 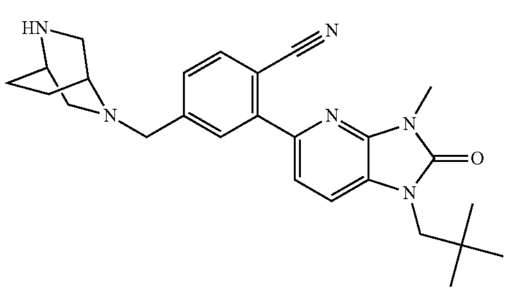 [SMILES: Cn1c(=O)n(CC(C)(C)C)c2ccc(-c3cc(CN4CC5CCC4CN5)ccc3C#N)nc21] | 4-(2,5-diazabicyclo[2.2.2]oct-2-ylmethyl)-2-[1-(2,2-dimethylpropyl)-3-methyl-2-oxo-2,3-dihydro-1H-imidazo[4,5-b]pyridin-5-yl]benzonitrile | Calc'd 445.2710, found 445.2705 |

TABLE 15-continued

The following compounds were prepared by a reaction sequence analogous to that illustrated in Scheme 44.

| Cmpd | Structure | IUPAC Name | Exact Mass [M + H]+ |
|---|---|---|---|
| 44-8 | 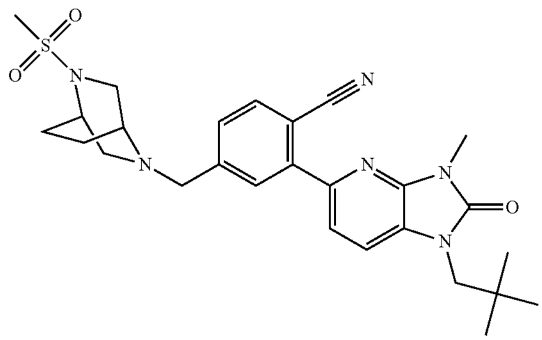 [SMILES: Cn1c(=O)n(CC(C)(C)C)c2ccc(-c3cc(CN4CC5CCC4CN5S(C)(=O)=O)ccc3C#N)nc21] | 2-[1-(2,2-dimethylpropyl)-3-methyl-2-oxo-2,3-dihydro-1H-imidazo[4,5-b]pyridin-5-yl]-4-{[5-(methylsulfonyl)-2,5-diazabicyclo[2.2.2]oct-2-yl]methyl}benzonitrile | Calc'd 523.2486, found 523.2473 |
| 44-9 | 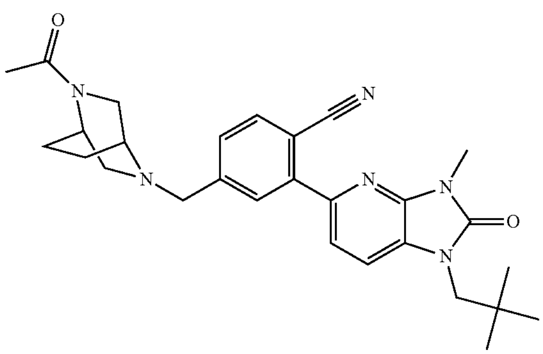 [SMILES: CC(=O)N1CC2CCC1CN2Cc1ccc(C#N)c(-c2ccc3c(n2)n(C)c(=O)n3CC(C)(C)C)c1] | 4-[(5-acetyl-2,5-diazabicyclo[2.2.2]oct-2-yl)methyl]-2-[1-(2,2-dimethylpropyl)-3-methyl-2-oxo-2,3-dihydro-1H-imidazo[4,5-b]pyridin-5-yl]benzonitrile | Calc'd 487.2816, found 487.2807 |
| 44-10 | 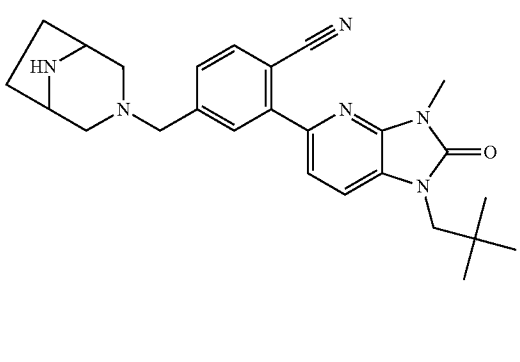 [SMILES: Cn1c(=O)n(CC(C)(C)C)c2ccc(-c3cc(CN4CC5CCC(C4)N5)ccc3C#N)nc21] | 4-(3,8-diazabicyclo[3.2.1]oct-3-ylmethyl)-2-[1-(2,2-dimethylpropyl)-3-methyl-2-oxo-2,3-dihydro-1H-imidazo[4,5-b]pyridin-5-yl]benzonitrile | Calc'd 445.2710, found 445.2705 |

TABLE 15-continued

The following compounds were prepared by a reaction sequence analogous to that illustrated in Scheme 44.

| Cmpd | Structure | IUPAC Name | Exact Mass [M + H]+ |
|---|---|---|---|
| 44-11 | 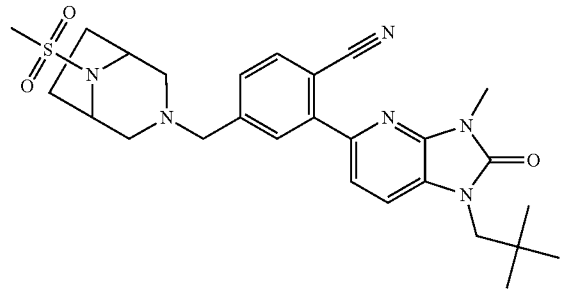 [SMILES: Cn1c(=O)n(CC(C)(C)C)c2ccc(-c3cc(CN4CC5CCC(C4)N5S(C)(=O)=O)ccc3C#N)nc21] | 2-[1-(2,2-dimethylpropyl)-3-methyl-2-oxo-2,3-dihydro-1H-imidazo[4,5-b]pyridin-5-yl]-4-{[8-(methylsulfonyl)-3,8-diazabicyclo[3.2.1]oct-3-yl]methyl}benzonitrile | Calc'd 523.2486, found 523.2473 |
| 44-12 | 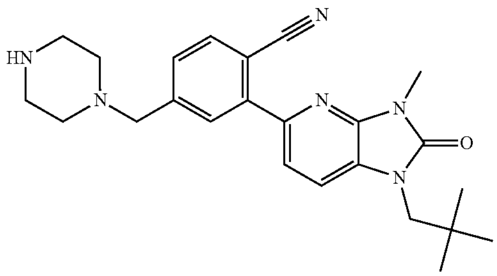 [SMILES: Cn1c(=O)n(CC(C)(C)C)c2ccc(-c3cc(CN4CCNCC4)ccc3C#N)nc21] | 2-[1-(2,2-dimethylpropyl)-3-methyl-2-oxo-2,3-dihydro-1H-imidazo[4,5-b]pyridin-5-yl]-4-(piperazin-1-ylmethyl)benzonitrile | Calc'd 419.2554, found 419.2547 |

SCHEME 45

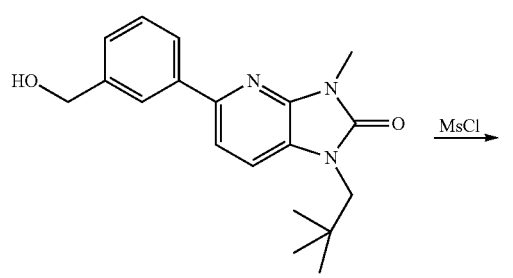

14-67

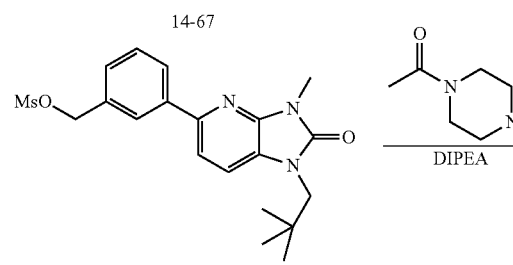

45-1

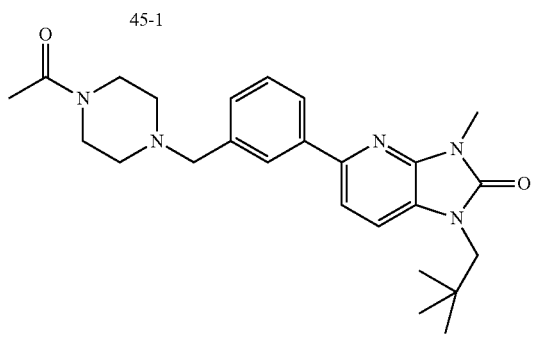

45-2

3-[1-(2,2-dimethylpropyl)-3-methyl-2-oxo-2,3-dihydro-1H-imidazo[4,5-b]pyridin-5-yl]benzyl methanesulfonate (45-1)

Prepared from 14-67 according to the procedures reported in Scheme 21. MS (M+H)$^+$: observed=404.3, calculated=404.2.

5-{3-[(4-acetylpiperazin-1-yl)methyl]phenyl}-1-(2,2-dimethylpropyl)-3-methyl-1,3-dihydro-2H-imidazo[4,5-b]pyridin-2-one (45-2)

Prepared from 45-1 according to the procedures reported in Scheme 21. MS (M+H)$^+$: observed=436.2699, calculated=436.2707.

TABLE 16

The following compounds were prepared from 45-1 by a reaction sequence analogous to that illustrated in Scheme 21.

| Cmpd | Structure | IUPAC Name | Exact Mass [M + H]+ |
|---|---|---|---|
| 45-3 | 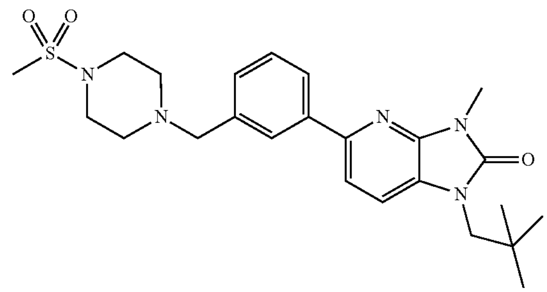 [SMILES: Cn1c(=O)n(CC(C)(C)C)c2ccc(-c3cccc(CN4CCN(S(C)(=O)=O)CC4)c3)nc21] | 1-(2,2-dimethylpropyl)-3-methyl-5-(3-{[4-(methylsulfonyl)piperazin-1-yl]methyl}phenyl)-1,3-dihydro-2H-imidazo[4,5-b]pyridin-2-one | Calc'd 472.2377, found 472.2377 |
| 45-4 | 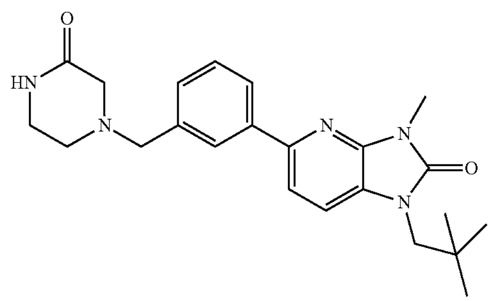 [SMILES: Cn1c(=O)n(CC(C)(C)C)c2ccc(-c3cccc(CN4CCNC(=O)C4)c3)nc21] | 1-(2,2-dimethylpropyl)-3-methyl-5-{3-[(3-oxopiperazin-1-yl)methyl]phenyl}-1,3-dihydro-2H-imidazo[4,5-b]pyridin-2-one | Calc'd 408.2394, found 408.2392 |
| 45-5 | 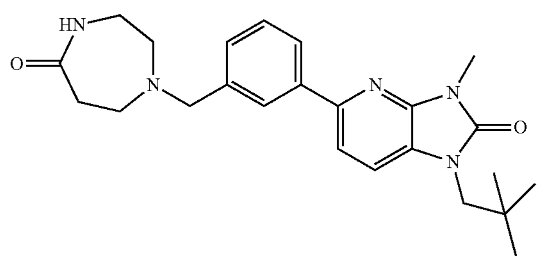 [SMILES: Cn1c(=O)n(CC(C)(C)C)c2ccc(-c3cccc(CN4CCNC(=O)CC4)c3)nc21] | 1-(2,2-dimethylpropyl)-3-methyl-5-{3-[(5-oxo-1,4-diazepan-1-yl)methyl]phenyl}-1,3-dihydro-2H-imidazo[4,5-b]pyridin-2-one | Calc'd 422.2552, found 422.2546 |
| 45-6 | 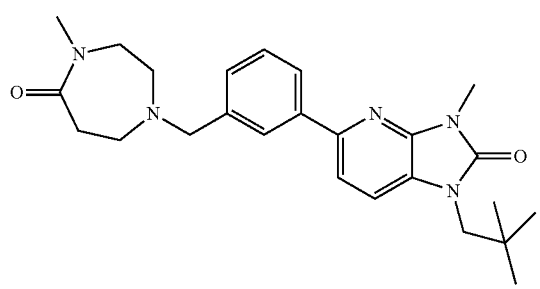 [SMILES: CN1CCN(Cc2cccc(-c3ccc4c(n3)n(C)c(=O)n4CC(C)(C)C)c2)CCC1=O] | 1-(2,2-dimethylpropyl)-3-methyl-5-{3-[(4-methyl-5-oxo-1,4-diazepan-1-yl)methyl]phenyl}-1,3-dihydro-2H-imidazo[4,5-b]pyridin-2-one | Calc'd 436.2707, found 436.2705 |
| 45-7 | 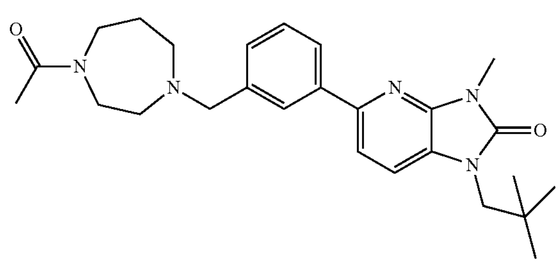 [SMILES: CC(=O)N1CCCN(Cc2cccc(-c3ccc4c(n3)n(C)c(=O)n4CC(C)(C)C)c2)CC1] | 5-{3-[(4-acetyl-1,4-diazepan-1-yl)methyl]phenyl}-1-(2,2-dimethylpropyl)-3-methyl-1,3-dihydro-2H-imidazo[4,5-b]pyridin-2-one | Calc'd 450.2864, found 450.2860 |

TABLE 16-continued

The following compounds were prepared from 45-1 by a reaction sequence analogous to that illustrated in Scheme 21.

| Cmpd | Structure | IUPAC Name | Exact Mass [M + H]+ |
|---|---|---|---|
| 45-8 | 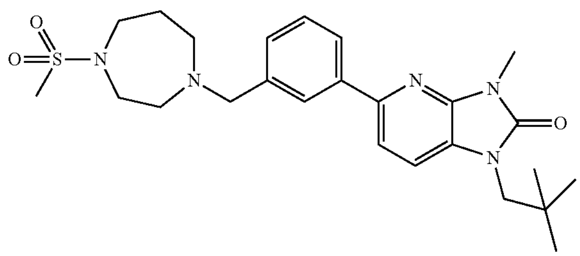 [SMILES: Cn1c(=O)n(CC(C)(C)C)c2ccc(-c3cccc(CN4CCCN(S(C)(=O)=O)CC4)c3)nc21] | 1-(2,2-dimethylpropyl)-3-methyl-5-(3-{[4-(methylsulfonyl)-1,4-diazepan-1-yl]methyl}phenyl)-1,3-dihydro-2H-imidazo[4,5-b]pyridin-2-one | Calc'd 486.2533, found 486.2531 |
| 45-9 | 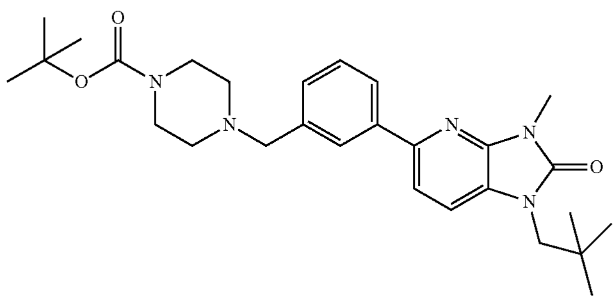 [SMILES: Cn1c(=O)n(CC(C)(C)C)c2ccc(-c3cccc(CN4CCN(C(=O)OC(C)(C)C)CC4)c3)nc21] | tert-butyl 4-{3-[1-(2,2-dimethylpropyl)-3-methyl-2-oxo-2,3-dihydro-1H-imidazo[4,5-b]pyridin-5-yl]benzyl}piperazine-1-carboxylate | Calc'd 494.3126, found 494.3127 |
| 45-10 | 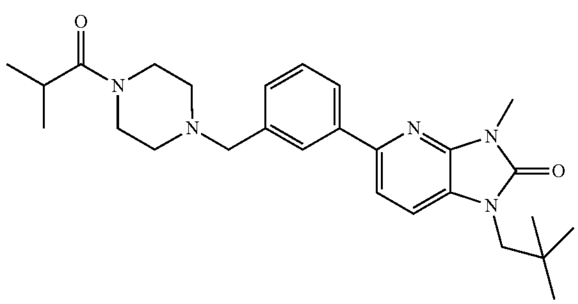 [SMILES: CC(C)C(=O)N1CCN(Cc2cccc(-c3ccc4c(n3)n(C)c(=O)n4CC(C)(C)C)c2)CC1] | 1-(2,2-dimethylpropyl)-3-methyl-5-(3-{[4-(2-methylpropanoyl)piperazin-1-yl]methyl}phenyl)-1,3-dihydro-2H-imidazo[4,5-b]pyridin-2-one | Calc'd 464.3020, found 464.3021 |
| 45-11 | 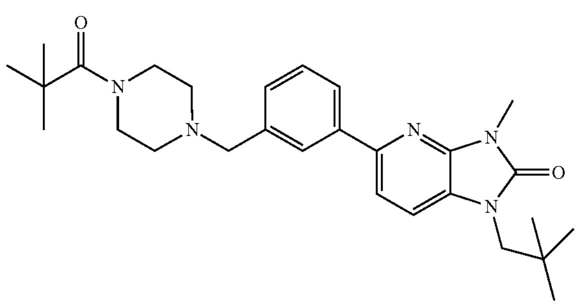 [SMILES: Cn1c(=O)n(CC(C)(C)C)c2ccc(-c3cccc(CN4CCN(C(=O)C(C)(C)C)CC4)c3)nc21] | 5-(3-{[4-(2,2-dimethylpropanoyl)piperazin-1-yl]methyl}phenyl)-1-(2,2-dimethylpropyl)-3-methyl-1,3-dihydro-2H-imidazo[4,5-b]pyridin-2-one | Calc'd 478.3177, found 478.3171 |
| 45-12 | 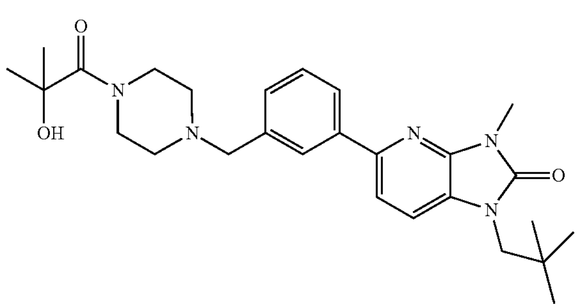 [SMILES: Cn1c(=O)n(CC(C)(C)C)c2ccc(-c3cccc(CN4CCN(C(=O)C(C)(C)O)CC4)c3)nc21] | 1-(2,2-dimethylpropyl)-5-(3-{[4-(2-hydroxy-2-methylpropanoyl)piperazin-1-yl]methyl}phenyl)-3-methyl-1,3-dihydro-2H-imidazo[4,5-b]pyridin-2-one | Calc'd 480.2969, found 480.2966 |

TABLE 16-continued

The following compounds were prepared from 45-1 by a reaction sequence analogous to that illustrated in Scheme 21.

| Cmpd | Structure | IUPAC Name | Exact Mass [M + H]+ |
|---|---|---|---|
| 45-13 | 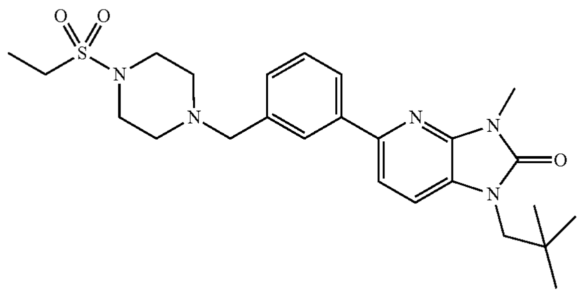 [SMILES: CCS(=O)(=O)N1CCN(Cc2cccc(-c3ccc4c(n3)n(C)c(=O)n4CC(C)(C)C)c2)CC1] | 1-(2,2-dimethylpropyl)-5-(3-{[4-(ethylsulfonyl)piperazin-1-yl]methyl}phenyl)-3-methyl-1,3-dihydro-2H-imidazo[4,5-b]pyridin-2-one | Calc'd 486.2533, found 486.2531 |
| 45-14 | 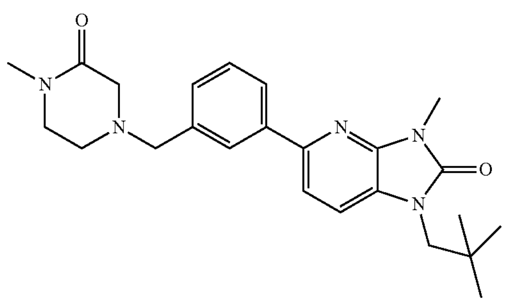 [SMILES: CN1CCN(Cc2cccc(-c3ccc4c(n3)n(C)c(=O)n4CC(C)(C)C)c2)CC1=O] | 1-(2,2-dimethylpropyl)-3-methyl-5-{3-[(4-methyl-3-oxopiperazin-1-yl)methyl]phenyl}-1,3-dihydro-2H-imidazo[4,5-b]pyridin-2-one | Calc'd 422.2551, found 422.2550 |

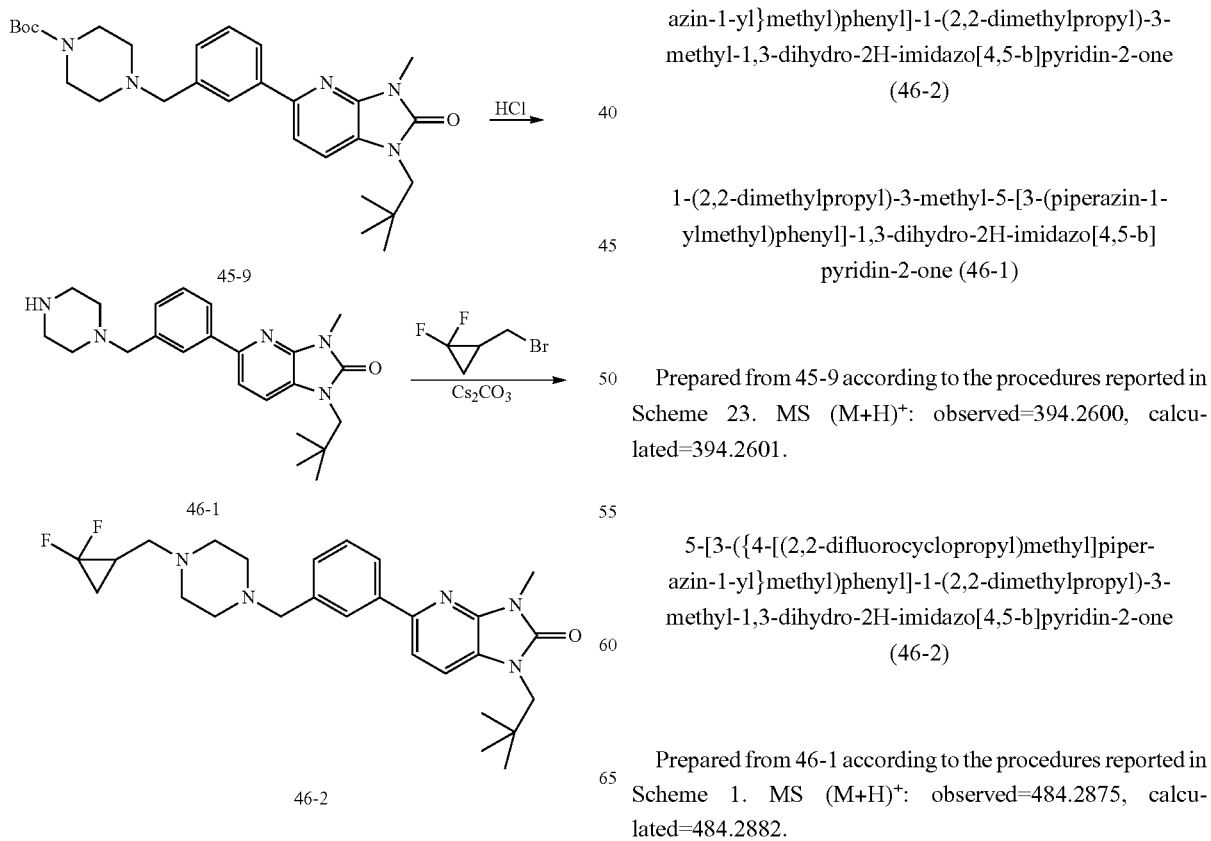

SCHEME 46

5-[3-({4-[(2,2-difluorocyclopropyl)methyl]piperazin-1-yl}methyl)phenyl]-1-(2,2-dimethylpropyl)-3-methyl-1,3-dihydro-2H-imidazo[4,5-b]pyridin-2-one (46-2)

1-(2,2-dimethylpropyl)-3-methyl-5-[3-(piperazin-1-ylmethyl)phenyl]-1,3-dihydro-2H-imidazo[4,5-b]pyridin-2-one (46-1)

Prepared from 45-9 according to the procedures reported in Scheme 23. MS (M+H)+: observed=394.2600, calculated=394.2601.

5-[3-({4-[(2,2-difluorocyclopropyl)methyl]piperazin-1-yl}methyl)phenyl]-1-(2,2-dimethylpropyl)-3-methyl-1,3-dihydro-2H-imidazo[4,5-b]pyridin-2-one (46-2)

Prepared from 46-1 according to the procedures reported in Scheme 1. MS (M+H)+: observed=484.2875, calculated=484.2882.

TABLE 17

The following compound was prepared from 46-1 by a reaction sequence analogous to that illustrated in Scheme 46.

| Cmpd | Structure | IUPAC Name | Exact Mass [M + H]+ |
|---|---|---|---|
| 46-3 | 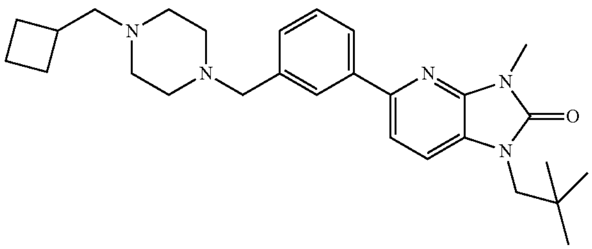 [SMILES: Cn1c(=O)n(CC(C)(C)C)c2ccc(-c3cccc(CN4CCN(CC5CCC5)CC4)c3)nc21] | 5-(3-{[4-(cyclobutylmethyl) piperazin-1-yl]methyl} phenyl)-1-(2,2-dimethyl propyl)-3-methyl-1,3-dihydro-2H-imidazo[4,5-b]pyridin-2-one | Calc'd 462.3227 found 462.3222 |

SCHEME 47

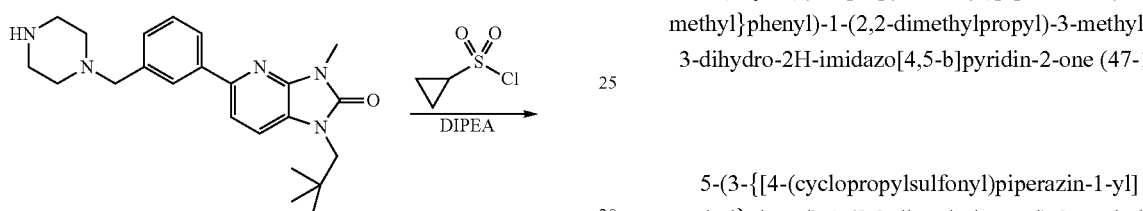

5-(3-{[4-(cyclopropylsulfonyl)piperazin-1-yl] methyl}phenyl)-1-(2,2-dimethylpropyl)-3-methyl-1, 3-dihydro-2H-imidazo[4,5-b]pyridin-2-one (47-1)

5-(3-{[4-(cyclopropylsulfonyl)piperazin-1-yl] methyl}phenyl)-1-(2,2-dimethylpropyl)-3-methyl-1, 3-dihydro-2H-imidazo[4,5-b]pyridin-2-one (47-1)

Prepared from 46-1 according to the procedures reported in Scheme 23. MS (M+H)+: observed=498.2534, calculated=498.2533.

TABLE 18

The following compound was prepared from 46-1 by a reaction sequence analogous to that illustrated in Scheme 47.

| Cmpd | Structure | IUPAC Name | Exact Mass [M + H]+ |
|---|---|---|---|
| 47-2 | 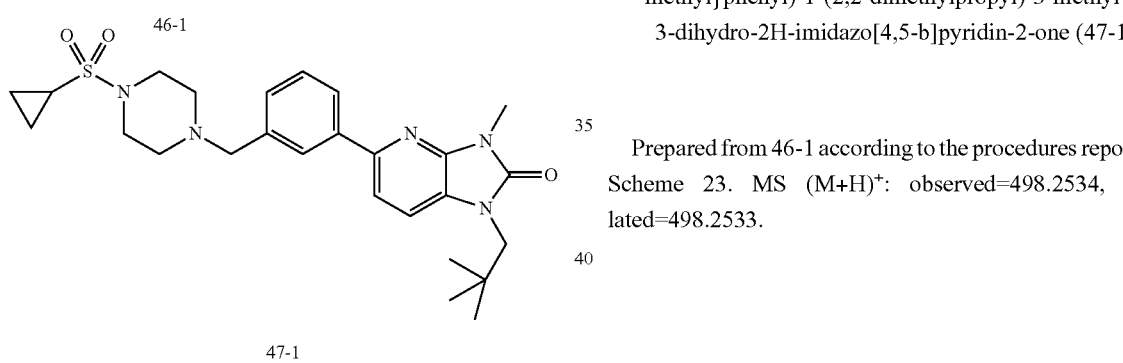 | 1-(2,2-dimethylpropyl)-3-methyl-5-[3-({4-[(1-methyl ethyl)sulfonyl]piperazin-1-yl}methyl)phenyl]-1,3-dihydro-2H-imidazo[4,5-b]pyridin-2-one | Calc'd 500.2690, found 500.2689 |

SCHEME 48

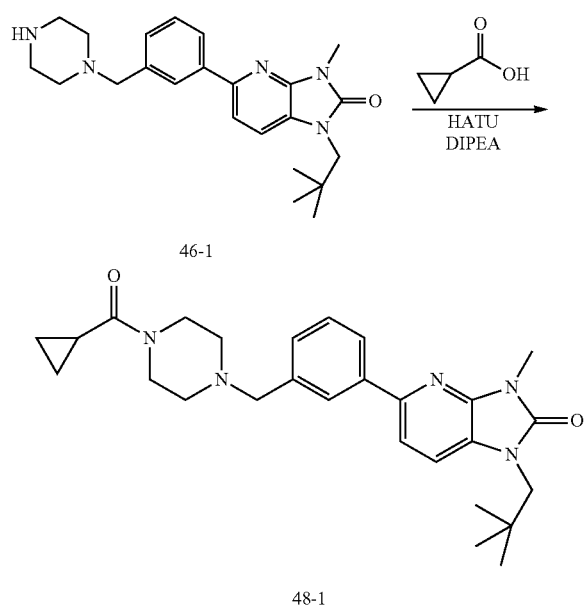

5-(3-{[4-(cyclopropylcarbonyl)piperazin-1-yl]methyl}phenyl)-1-(2,2-dimethylpropyl)-3-methyl-1,3-dihydro-2H-imidazo[4,5-b]pyridin-2-one (48-1]

1-(2,2-dimethylpropyl)-3-methyl-5-[3-(piperazin-1-ylmethyl)phenyl]-1,3-dihydro-2H-imidazo[4,5-b]pyridin-2-one (46-1) (50 mg, 0.13 mmol, 1.0 eq.) was dissolved in NMP (0.50 mL). Cyclopropanecarboxylic acid (16.4 mg, 0.19 mmol, 1.5 eq.) was added followed by N,N-diisopropylethylamine (0.07 mL, 0.38 mmol, 3.0 eq.) and HATU (72.5 mg, 0.19 mmol, 1.5 eq). The reaction stirred at ambient temperature for 5 minutes. The reaction was diluted with methanol, passed through a syringe filter and purified by reverse phase chromatography (15-95% H$_2$O/Acetonitrile with 0.1% TFA modifier over 15 minutes) to afford 2-methylpropyl 5-(3-{[4-(cyclopropylcarbonyl)piperazin-1-yl]methyl}phenyl)-1-(2,2-dimethylpropyl)-3-methyl-1,3-dihydro-2H-imidazo[4,5-b]pyridin-2-one (48-1) as a white solid. HRMS (M+H)$^+$: observed=462.2862, calculated=462.2864.

TABLE 19

The following compounds were prepared from 46-1 by a reaction sequence analogous to that illustrated in Scheme 48.

| Cmpd | Structure | IUPAC Name | Exact Mass [M + H]+ |
|---|---|---|---|
| 48-2 | 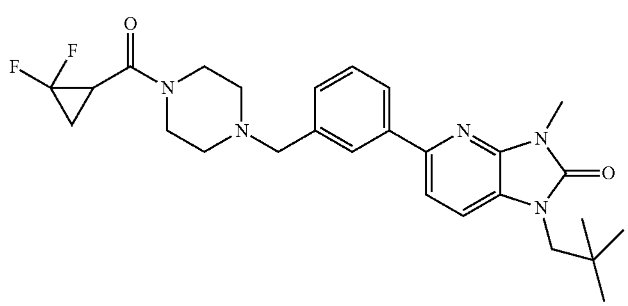 [SMILES: Cn1c(=O)n(CC(C)(C)C)c2ccc(-c3cccc(CN4CCN(C(=O)C5CC5(F)F)CC4)c3)nc21] | 5-[3-({4-[(2,2-difluorocyclopropyl)carbonyl]piperazin-1-yl}methyl)phenyl]-1-(2,2-dimethylpropyl)-3-methyl-1,3-dihydro-2H-imidazo[4,5-b]pyridin-2-one | Calc'd 498.2675, found 498.2671 |
| 48-3 | 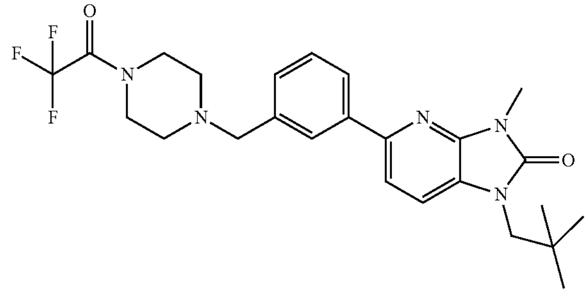 [SMILES: Cn1c(=O)n(CC(C)(C)C)c2ccc(-c3cccc(CN4CCN(C(=O)C(F)(F)F)CC4)c3)nc21] | 1-(2,2-dimethylpropyl)-3-methyl-5-(3-{[4-(trifluoroacetyl)piperazin-1-yl]methyl}phenyl)-1,3-dihydro-2H-imidazo[4,5-b]pyridin-2-one | Calc'd 490.2424, found 490.2422 |

TABLE 19-continued

The following compounds were prepared from 46-1 by a reaction sequence analogous to that illustrated in Scheme 48.

| Cmpd | Structure | IUPAC Name | Exact Mass [M + H]+ |
|---|---|---|---|
| 48-4 | 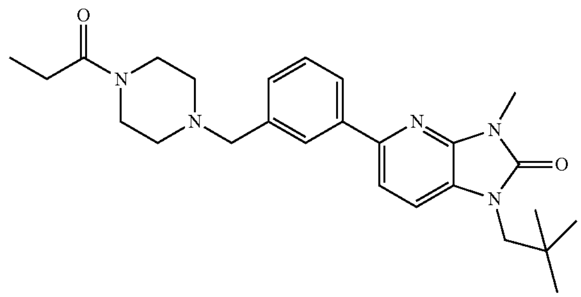 [SMILES: CCC(=O)N1CCN(Cc2cccc(-c3ccc4c(n3)n(C)c(=O)n4CC(C)(C)C)c2)CC1] | 1-(2,2-dimethylpropyl)-3-methyl-5-{3-[(4-propanoyl piperazin-1-yl)methyl] phenyl}-1,3-dihydro-2H-imidazo[4,5-b]pyridin-2-one | Calc'd 450.2864, found 450.2861 |
| 48-5 | 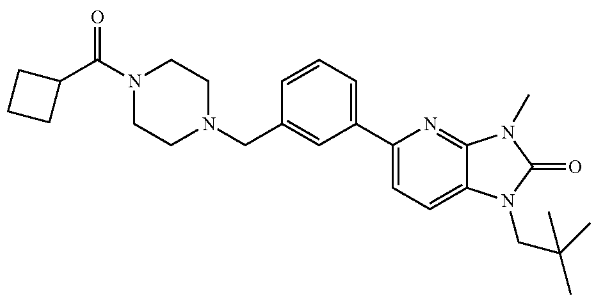 [SMILES: Cn1c(=O)n(CC(C)(C)C)c2ccc(-c3cccc(CN4CCN(C(=O)C5CCC5)CC4)c3)nc21] | 5-(3-{[4-(cyclobutyl carbonyl)piperazin-1-yl] methyl}phenyl)-1-(2,2-dimethylpropyl)-3-methyl-1,3-dihydro-2H-imidazo[4,5-b]pyridin-2-one | Calc'd 476.3020, found 476.3018 |
| 48-6 | 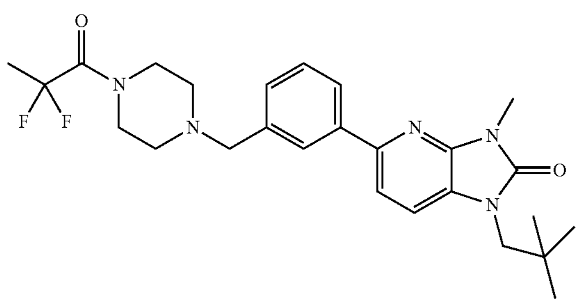 [SMILES: Cn1c(=O)n(CC(C)(C)C)c2ccc(-c3cccc(CN4CCN(C(=O)C(C)(F)F)CC4)c3)nc21] | 5-(3-{[4-(2,2-difluoropropanoyl)piperazin-1-yl]methyl}phenyl)-1-(2,2-dimethylpropyl)-3-methyl-1,3-dihydro-2H-imidazo[4,5-b]pyridin-2-one | Calc'd 486.2675, found 486.2672 |

SCHEME 49

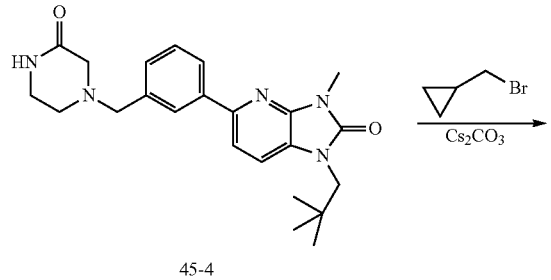

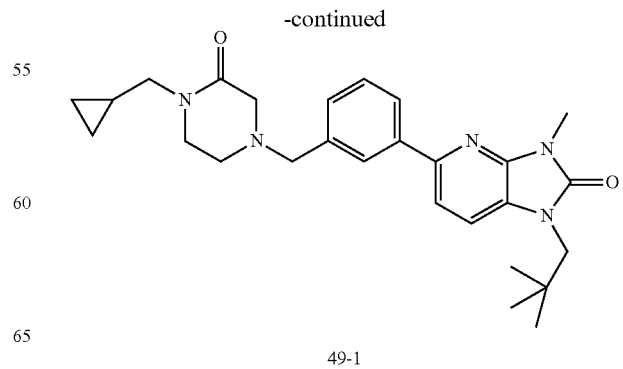

5-(3-{[4-(cyclopropylmethyl)-3-oxopiperazin-1-yl]
methyl}phenyl)-1-(2,2-dimethylpropyl)-3-methyl-1,
3-dihydro-2H-imidazo[4,5-b]pyridin-2-one (49-1)

Prepared from 45-4 according to the procedures reported in Scheme 1. MS (M+H)⁺: observed=462.4, calculated=462.3.

TABLE 20

The following compounds were prepared from 45-4 by a reaction sequence analogous to that illustrated in Scheme 49.

| Cmpd | Structure | IUPAC Name | Exact Mass [M + H]+ |
|---|---|---|---|
| 49-2 | 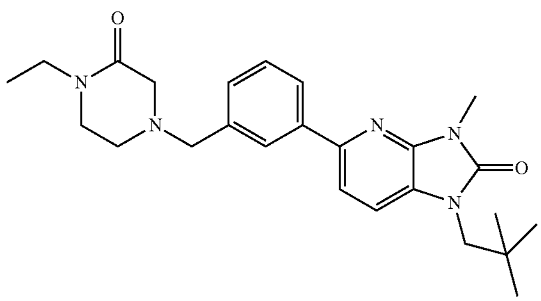 [SMILES: CCN1CCN(Cc2cccc(-c3ccc4c(n3)n(C)c(=O)n4CC(C)(C)C)c2)CC1=O] | 1-(2,2-dimethylpropyl)-5-{3-[(4-ethyl-3-oxopiperazin-1-yl)methyl]phenyl}-3-methyl-1,3-dihydro-2H-imidazo[4,5-b]pyridin-2-one | Calc'd 436.2707, found 436.2701 |
| 49-3 | 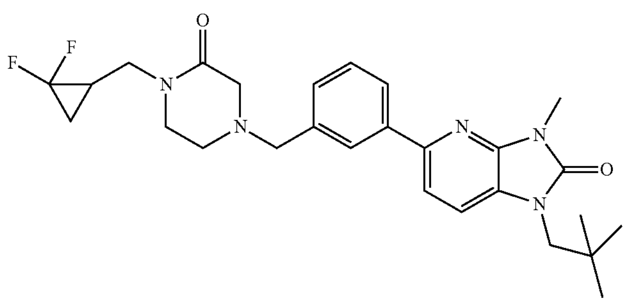 [SMILES: Cn1c(=O)n(CC(C)(C)C)c2ccc(-c3cccc(CN4CCN(CC5CC5(F)F)C(=O)C4)c3)nc21] | 5-[3-({4-[(2,2-difluorocyclopropyl)methyl]-3-oxopiperazin-1-yl}methyl)phenyl]-1-(2,2-dimethylpropyl)-3-methyl-1,3-dihydro-2H-imidazo[4,5-b]pyridin-2-one | Calc'd 498.2675, found 498.2665 |
| 49-4 | 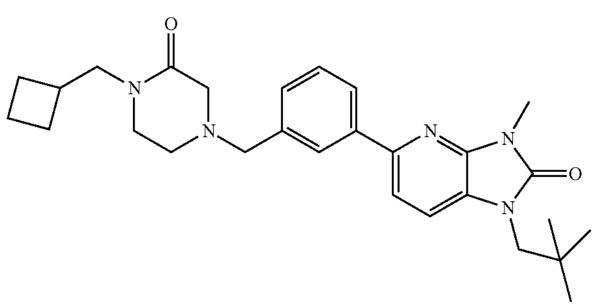 [SMILES: Cn1c(=O)n(CC(C)(C)C)c2ccc(-c3cccc(CN4CCN(CC5CCC5)C(=O)C4)c3)nc21] | 5-(3-{[4-(cyclobutylmethyl)-3-oxopiperazin-1-yl]methyl}phenyl)-1-(2,2-dimethylpropyl)-3-methyl-1,3-dihydro-2H-imidazo[4,5-b]pyridin-2-one | Calc'd 476.3020, found 476.3013 |
| 49-5 | 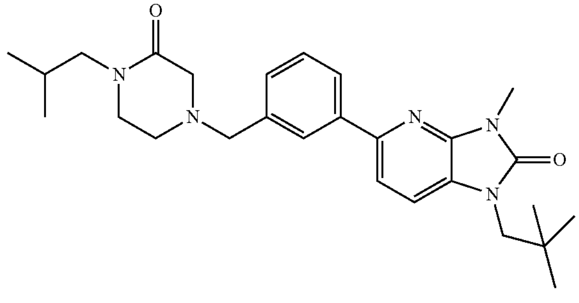 [SMILES: CC(C)CN1CCN(Cc2cccc(-c3ccc4c(n3)n(C)c(=O)n4CC(C)(C)C)c2)CC1=O] | 1-(2,2-dimethylpropyl)-3-methyl-5-(3-{[4-(2-methylpropyl)-3-oxopiperazin-1-yl]methyl}phenyl)-1,3-dihydro-2H-imidazo[4,5-b]pyridin-2-one | Calc'd 464.3020, found 464.3014 |

SCHEME 50

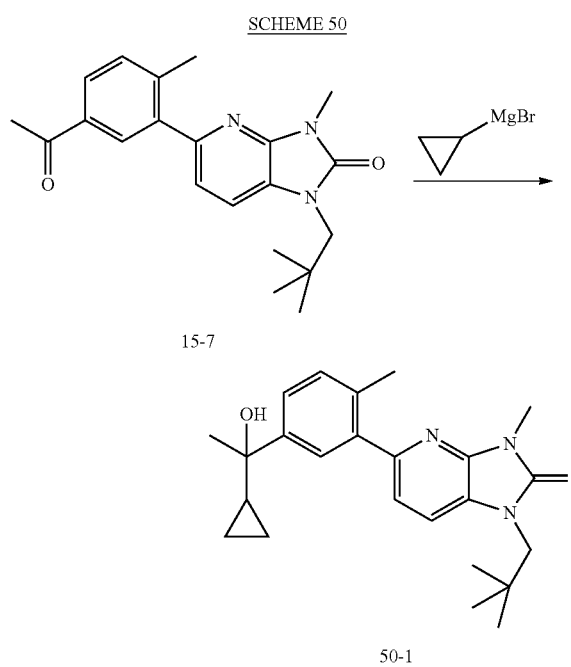

5-[5-(1-cyclopropyl-1-hydroxyethyl)-2-methylphenyl]-1-(2,2-dimethylpropyl)-3-methyl-1,3-dihydro-2H-imidazo[4,5-b]pyridin-2-one (50-1)

Prepared from 15-7 according to the procedures reported in Scheme 3. MS (M+H)+: observed=394.2484, calculated=393.2489.

SCHEME 51

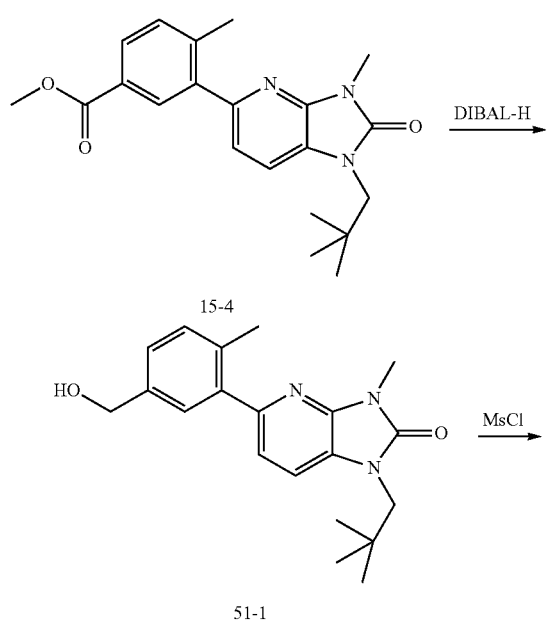

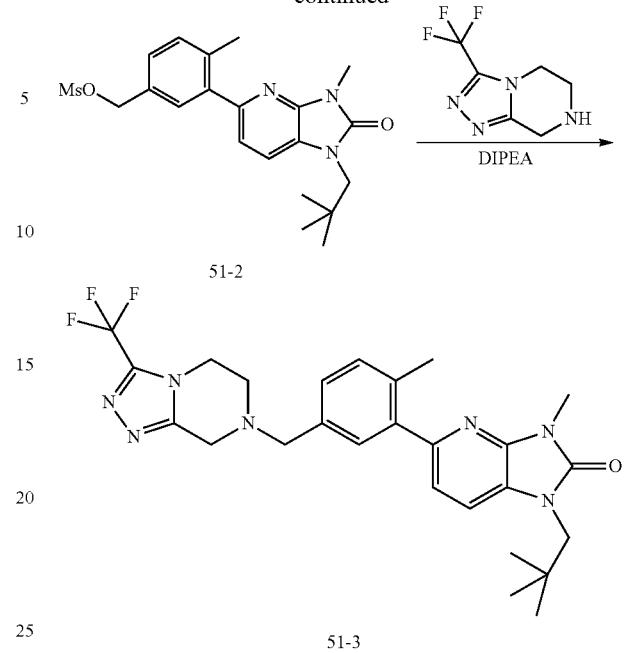

1-(2,2-dimethylpropyl)-3-methyl-5-(2-methyl-5-{[3-(trifluoromethyl)-5,6-dihydro[1,2,4]triazolo[4,3-a]pyrazin-7(8H)-yl]methyl}phenyl)-1,3-dihydro-2H-imidazo[4,5-b]pyridin-2-one (51-3)

1-(2,2-dimethylpropyl)-5-[5-(hydroxymethyl)-2-methylphenyl]-3-methyl-1,3-dihydro-2H-imidazo[4,5-b]pyridin-2-one (51-1)

Methyl 3-[1-(2,2-dimethylpropyl)-3-methyl-2-oxo-2,3-dihydro-1H-imidazo[4,5-b]pyridin-5-yl]-4-methylbenzoate (15-4) (570 mg, 1.6 mmol, 1.0 eq.) was dissolved in dry THF (6.2 mL) and cooled to −78° C. Diisobutylaluminum hydride (6.2 mL, 6.2 mmol, 4.0 eq, 1M in heptane) was carefully added under nitrogen. The resulting mixture stirred at −78° C. for 10 minutes. The reaction was warmed to 0° C. and quenched with a saturated solution of Rochelle's Salt (5 mL). The resulting mixture was warmed to ambient temperature and stirred for 2 hours. The mixture was then extracted with ethyl acetate and the combined organics were washed with water and brine, dried over magnesium sulfate, filtered and concentrated to afford 1-(2,2-dimethylpropyl)-5-[5-(hydroxymethyl)-2-methylphenyl]-3-methyl-1,3-dihydro-2H-imidazo[4,5-b]pyridin-2-one (51-1) as a white solid. MS (M+H)+: observed=340.2021, calculated=340.2020.

3-[1-(2,2-dimethylpropyl)-3-methyl-2-oxo-2,3-dihydro-1H-imidazo[4,5-b]pyridin-5-yl]-4-methylbenzyl methanesulfonate (51-2)

Prepared from 51-1 according to the procedures reported in Scheme 21. MS (M+H)+: observed=418.3, calculated=418.2.

1-(2,2-dimethylpropyl)-3-methyl-5-(2-methyl-5-{[3-(trifluoromethyl)-5,6-dihydro[1,2,4]triazolo[4,3-a]pyrazin-7(8H)-yl]methyl}phenyl)-1,3-dihydro-2H-imidazo[4,5-b]pyridin-2-one (51-3)

Prepared from 51-2 according to the procedures reported in Scheme 21. MS (M+H)+: observed=514.2531, calculated=514.2537. ¹H NMR (400 MHz, CDCl₃): δ 7.39 (d, J=1.7 Hz, 1H); 7.29-7.22 (m, 3H); 7.08 (d, J=7.9 Hz, 1H); 4.15-4.09 (m, 2H); 3.93 (s, 2H); 3.79 (s, 2H); 3.69 (s, 2H); 3.53 (s, 3H); 2.97 (t, J=5.5 Hz, 2H); 2.42 (s, 3H); 1.07 (s, 9H).

TABLE 21

The following compounds were prepared from 51-2 by a reaction sequence analogous to that illustrated in Scheme 51.

| Cmpd | Structure | IUPAC Name | Exact Mass [M + H]+ |
|---|---|---|---|
| 51-4 | 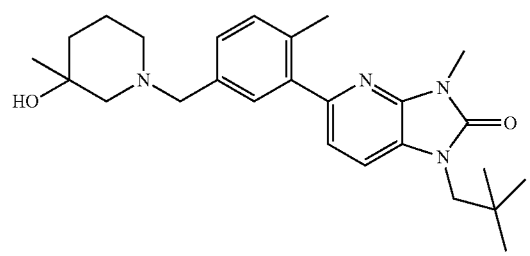 [SMILES: Cc1ccc(CN2CCCC(C)(O)C2)cc1-c1ccc2c(n1)n(C)c(=O)n2CC(C)(C)C] | 1-(2,2-dimethylpropyl)-5-{5-[(3-hydroxy-3-methylpiperidin-1-yl)methyl]-2-methylphenyl}-3-methyl-1,3-dihydro-2H-imidazo[4,5-b]pyridin-2-one | Calc'd 437.2911, found 437.2912 |
| 51-5 | 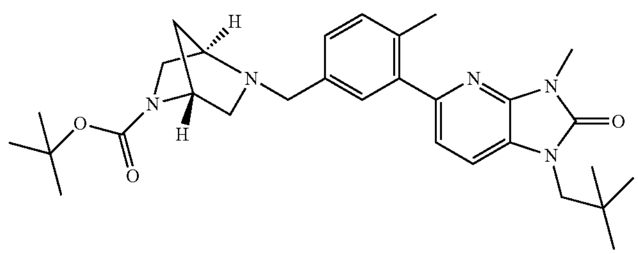 [SMILES: Cc1ccc(CN2C[C@H]3C[C@@H]2CN3C(=O)OC(C)(C)C)cc1-c1ccc2c(n1)n(C)c(=O)n2CC(C)(C)C] | tert-butyl (1R,4R)-5-{3-[1-(2,2-dimethylpropyl)-3-methyl-2-oxo-2,3-dihydro-1H-imidazo[4,5-b]pyridin-5-yl]-4-methylbenzyl}-2,5-diazabicyclo[2.2.1]heptane-2-carboxylate | Calc'd 520.3282, found 520.3281 |
| 51-6 | 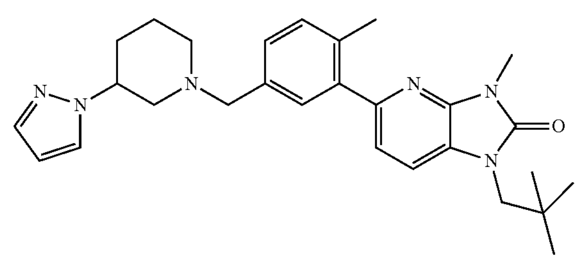 [SMILES: Cc1ccc(CN2CCCC(n3cccn3)C2)cc1-c1ccc2c(n1)n(C)c(=O)n2CC(C)(C)C] | 1-(2,2-dimethylpropyl)-3-methyl-5-(2-methyl-5-{[3-(1H-pyrazol-1-yl)piperidin-1-yl]methyl}phenyl)-1,3-dihydro-2H-imidazo[4,5-b]pyridin-2-one | Calc'd 473.3023, found 473.3024 |
| 51-7 | 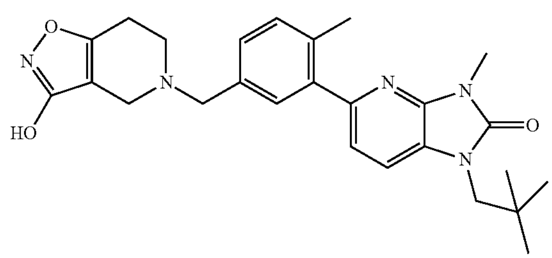 [SMILES: Cc1ccc(CN2CCc3onc(O)c3C2)cc1-c1ccc2c(n1)n(C)c(=O)n2CC(C)(C)C] | 1-(2,2-dimethylpropyl)-5-{5-[(3-hydroxy-6,7-dihydroisoxazolo[4,5-c]pyridin-5(4H)-yl)methyl]-2-methylphenyl}-3-methyl-1,3-dihydro-2H-imidazo[4,5-b]pyridin-2-one | Calc'd 462.2500, found 462.2505 |
| 51-8 | 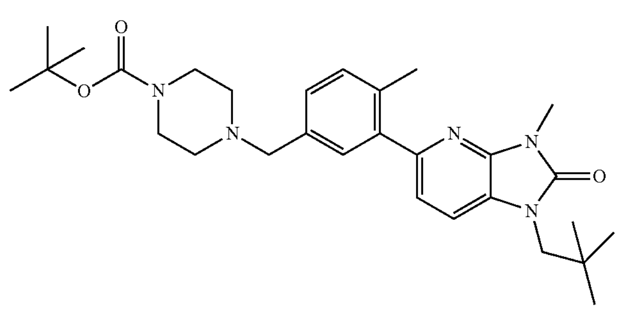 [SMILES: Cc1ccc(CN2CCN(C(=O)OC(C)(C)C)CC2)cc1-c1ccc2c(n1)n(C)c(=O)n2CC(C)(C)C] | tert-butyl 4-{3-[1-(2,2-dimethylpropyl)-3-methyl-2-oxo-2,3-dihydro-1H-imidazo[4,5-b]pyridin-5-yl]-4-methylbenzyl}piperazine-1-carboxylate | Calc'd 508.3282, found 508.3285 |

TABLE 21-continued

The following compounds were prepared from 51-2 by a reaction sequence analogous to that illustrated in Scheme 51.

| Cmpd | Structure | IUPAC Name | Exact Mass [M + H]+ |
|---|---|---|---|
| 51-9 | 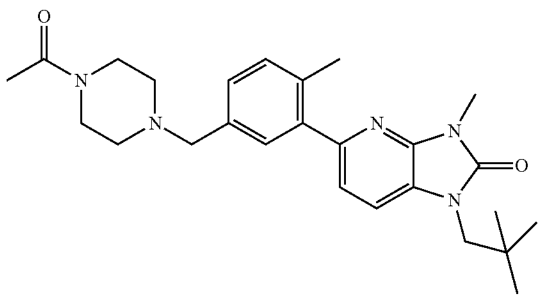 | 5-{5-[(4-acetylpiperazin-1-yl)methyl]-2-methylphenyl}-1-(2,2-dimethylpropyl)-3-methyl-1,3-dihydro-2H-imidazo[4,5-b]pyridin-2-one | Calc'd 450.2864, found 450.2854 |
| 51-10 | 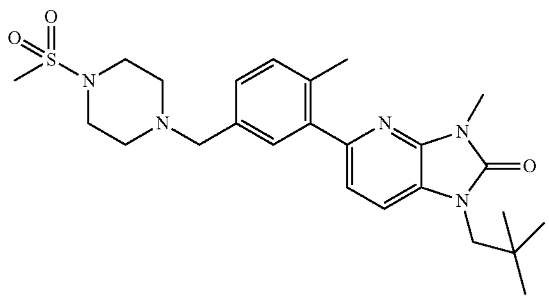 [SMILES: Cc1ccc(CN2CCN(S(C)(=O)=O)CC2)cc1-c1ccc2c(n1)n(C)c(=O)n2CC(C)(C)C] | 1-(2,2-dimethylpropyl)-3-methyl-5-(2-methyl-5-{[4-(methylsulfonyl)piperazin-1-yl]methyl}phenyl)-1,3-dihydro-2H-imidazo[4,5-b]pyridin-2-one | Calc'd 486.2533, found 486.2532 |
| 51-11 | 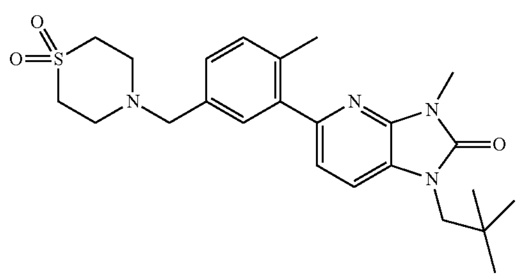 [SMILES: Cc1ccc(CN2CCS(=O)(=O)CC2)cc1-c1ccc2c(n1)n(C)c(=O)n2CC(C)(C)C] | 1-(2,2-dimethylpropyl)-5-{5-[(1,1-dioxidothiomorpholin-4-yl)methyl]-2-methylphenyl}-3-methyl-1,3-dihydro-2H-imidazo[4,5-b]pyridin-2-one | Calc'd 457.2268, found 457.2272 |
| 51-12 | 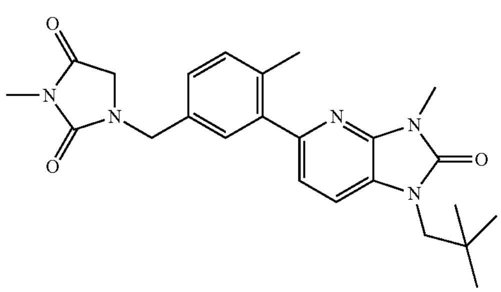 [SMILES: Cc1ccc(CN2CC(=O)N(C)C2=O)cc1-c1ccc2c(n1)n(C)c(=O)n2CC(C)(C)C] | 1-{3-[1-(2,2-dimethylpropyl)-3-methyl-2-oxo-2,3-dihydro-1H-imidazo[4,5-b]pyridin-5-yl]-4-methylbenzyl}-3-methylimidazolidine-2,4-dione | Calc'd 436.2343, found 436.2334 |

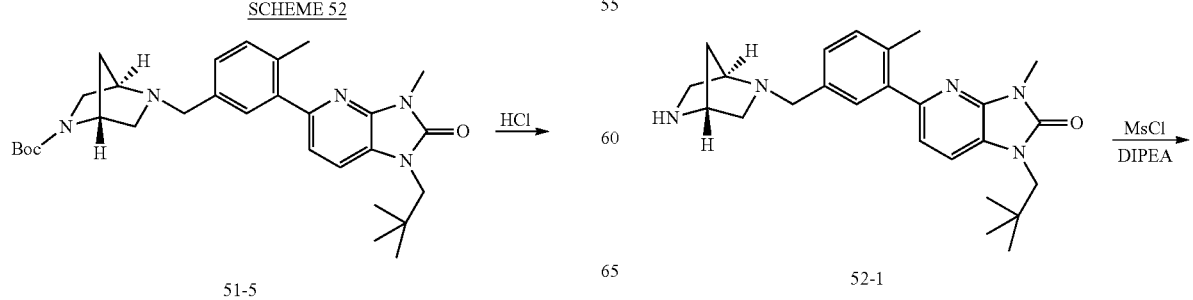

SCHEME 52

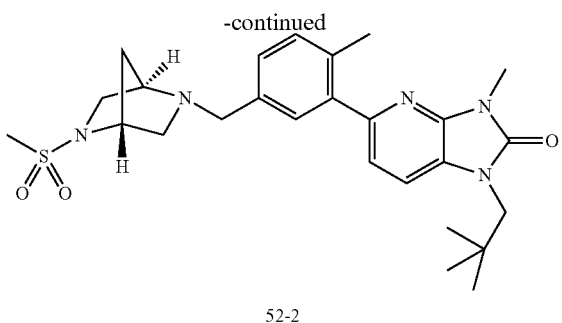

52-2

1-(2,2-dimethylpropyl)-3-methyl-5-(2-methyl-5-{[(1R,4R)-5-(methylsulfonyl)-2,5-diazabicyclo[2.2.1]hept-2-yl]methyl}phenyl)-1,3-dihydro-2H-imidazo[4,5-b]pyridin-2-one (52-2)

1-(2,2-dimethylpropyl)-3-methyl-5-[3-(piperazin-1-ylmethyl)phenyl]-1,3-dihydro-2H-imidazo[4,5-b]pyridin-2-one (52-1)

Prepared from 51-5 according to the procedures reported in Scheme 23. MS (M+H)+: observed=420.4, calculated=420.3.

1-(2,2-dimethylpropyl)-3-methyl-5-(2-methyl-5-{[(1R,4R)-5-(methylsulfonyl)-2,5-diazabicyclo[2.2.1]hept-2-yl]methyl}phenyl)-1,3-dihydro-2H-imidazo[4,5-b]pyridin-2-one (52-2)

Prepared from 52-1 according to the procedures reported in Scheme 23. MS (M+H)+: observed=498.2537, calculated=498.2533.

SCHEME 53

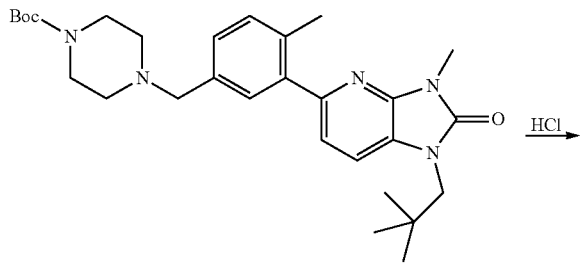

53-1

1-(2,2-dimethylpropyl)-5-(5-{[4-isoxazol-3-ylcarbonyl)piperazin-1-yl]methyl}-2-methylphenyl)-3-methyl-1,3-dihydro-2H-imidazo[4,5-b]pyridin-2-one (53-2)

1-(2,2-dimethylpropyl)-3-methyl-5-[2-methyl-5-(piperazin-1-ylmethyl)phenyl]1,3-dihydro-2H-imidazo[4,5-b]pyridin-2-one (53-1)

Prepared from 51-8 according to the procedures reported in Scheme 23. MS (M+H)+: observed=408.4, calculated=408.3.

1-(2,2-dimethylpropyl)-5-(5-{[4-(isoxazol-3-ylcarbonyl)piperazin-1-yl]methyl}-2-methylphenyl)-3-methyl-1,3-dihydro-2H-imidazo[4,5-b]pyridin-2-one (53-2)

Prepared from 53-1 according to the procedures reported in Scheme 48. MS (M+H)+: observed=503.2766, calculated=503.2765.

TABLE 22

The following compounds were prepared from 53-1 by a reaction sequence analogous to that illustrated in Scheme 53.

| Cmpd | Structure | IUPAC Name | Exact Mass [M + H]+ |
|---|---|---|---|
| 53-3 | 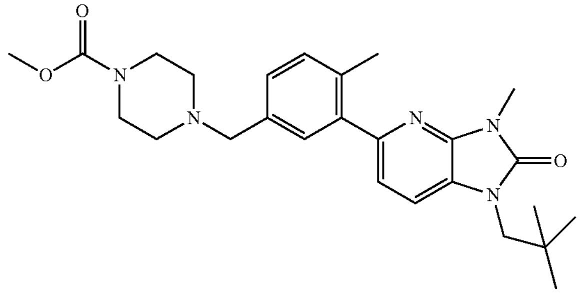 [SMILES: COC(=O)N1CCN(Cc2ccc(C)c(-c3ccc4c(n3)n(C)c(=O)n4CC(C)(C)C)c2)CC1] | methyl 4-{3-[1-(2,2-dimethylpropyl)-3-methyl-2-oxo-2,3-dihydro-1H-imidazo[4,5-b]pyridin-5-yl]-4-methylbenzyl}piperazine-1-carboxylate | Calc'd 466.2813, found 466.2802 |

TABLE 22-continued

The following compounds were prepared from 53-1 by a reaction sequence analogous to that illustrated in Scheme 53.

| Cmpd | Structure | IUPAC Name | Exact Mass [M + H]+ |
|---|---|---|---|
| 53-4 | 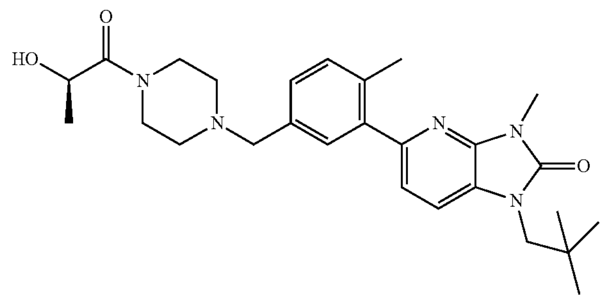 [SMILES: Cc1ccc(CN2CCN(C(=O)[C@@H](C)O)CC2)cc1-c1ccc2c(n1)n(C)c(=O)n2CC(C)(C)C] | 1-(2,2-dimethylpropyl)-5-[5-({4-[(2R)-2-hydroxy propanoyl]piperazin-1-yl}methyl)-2-methylphenyl]-3-methyl-1,3-dihydro-2H-imidazo[4,5-b]pyridin-2-one | Calc'd 480.2969, found 480.2971 |
| 53-5 | 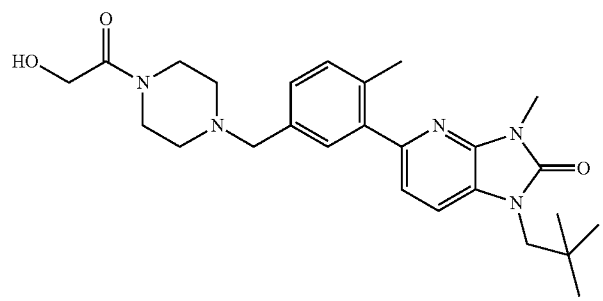 [SMILES: Cc1ccc(CN2CCN(C(=O)CO)CC2)cc1-c1ccc2c(n1)n(C)c(=O)n2CC(C)(C)C] | 1-(2,2-dimethylpropyl)-5-(5-{[4-(hydroxyacetyl) piperazin-1-yl]methyl}-2-methylphenyl)-3-methyl-1,3-dihydro-2H-imidazo[4,5-b]pyridin-2-one | Calc'd 466.2813, found 466.2817 |

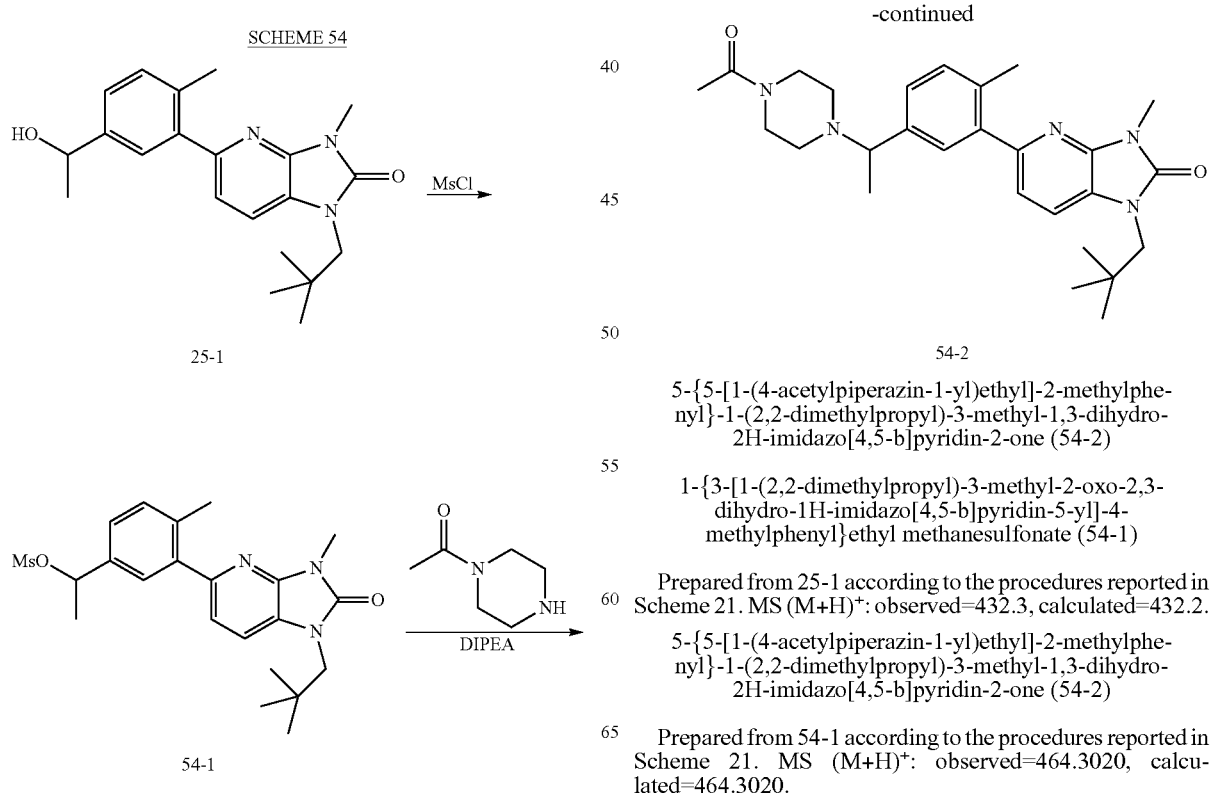

5-{5-[1-(4-acetylpiperazin-1-yl)ethyl]-2-methylphenyl}-1-(2,2-dimethylpropyl)-3-methyl-1,3-dihydro-2H-imidazo[4,5-b]pyridin-2-one (54-2)

1-{3-[1-(2,2-dimethylpropyl)-3-methyl-2-oxo-2,3-dihydro-1H-imidazo[4,5-b]pyridin-5-yl]-4-methylphenyl}ethyl methanesulfonate (54-1)

Prepared from 25-1 according to the procedures reported in Scheme 21. MS (M+H)⁺: observed=432.3, calculated=432.2.

5-{5-[1-(4-acetylpiperazin-1-yl)ethyl]-2-methylphenyl}-1-(2,2-dimethylpropyl)-3-methyl-1,3-dihydro-2H-imidazo[4,5-b]pyridin-2-one (54-2)

Prepared from 54-1 according to the procedures reported in Scheme 21. MS (M+H)⁺: observed=464.3020, calculated=464.3020.

TABLE 23

The following compound was prepared from 54-1 by a reaction sequence analogous to that illustrated in Scheme 54.

| Cmpd | Structure | IUPAC Name | Exact Mass [M + H]+ |
|---|---|---|---|
| 54-3 | 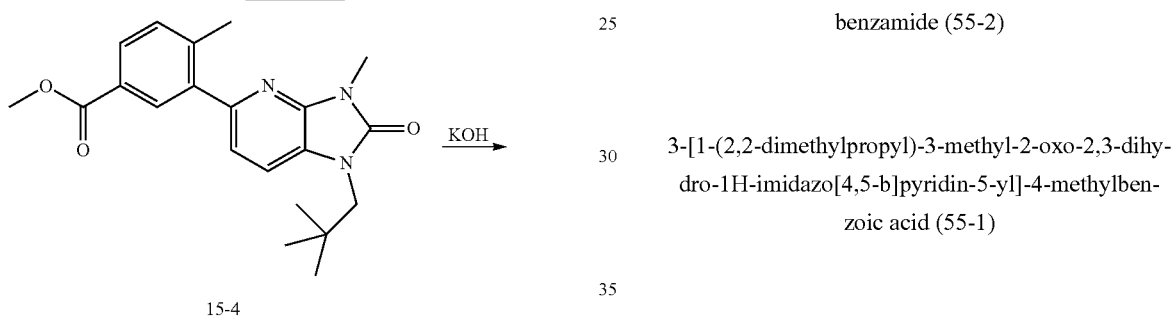 | 1-(2,2-dimethylpropyl)-3-methyl-5-(2-methyl-5-{1-[4-(methylsulfonyl)piperazin-1-yl]ethyl}phenyl)-1,3-dihydro-2H-imidazo[4,5-b]pyridin-2-one | Calc'd 500.2690, found 500.2692 |

SCHEME 55

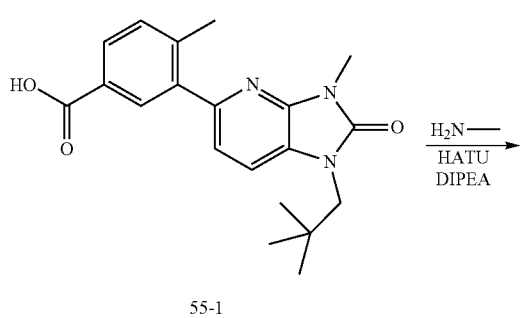

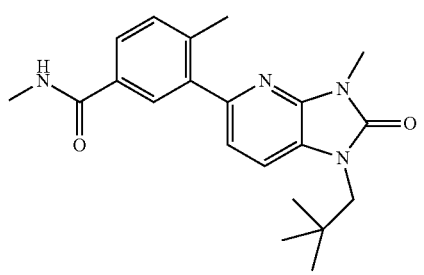

3-[1-(2,2-dimethylpropyl)-3-methyl-2-oxo-2,3-dihydro-1H-imidazo[4,5-b]pyridin-5-yl]-N,4-dimethylbenzamide (55-2)

3-[1-(2,2-dimethylpropyl)-3-methyl-2-oxo-2,3-dihydro-1H-imidazo[4,5-b]pyridin-5-yl]-4-methylbenzoic acid (55-1)

Methyl 3-[1-(2,2-dimethylpropyl)-3-methyl-2-oxo-2,3-dihydro-1H-imidazo[4,5-b]pyridin-5-yl]-4-methylbenzoate (15-4) (550 mg, 1.5 mmol, 1.0 eq.) was dissolved in THF (2.5 mL)/MeOH (2.5 mL) and potassium hydroxide (340 mg, 6.0 mmol, 4.0 eq.) was added. The mixture stirred overnight at ambient temperature. Upon completion, the reaction mixture was concentrated and 1N HCl was added. The mixture was then extracted with ethyl acetate and the combined organics were dried over magnesium sulfate, filtered and concentrated to afford 3-[1-(2,2-dimethylpropyl)-3-methyl-2-oxo-2,3-dihydro-1H-imidazo[4,5-b]pyridin-5-yl]-4-methylbenzoic acid (55-1) as a white solid. MS (M+H)+: observed=354.0, calculated=354.2.

3-[1-(2,2-dimethylpropyl)-3-methyl-2-oxo-2,3-dihydro-1H-imidazo[4,5-b]pyridin-5-yl]-N,4-dimethylbenzamide (55-2)

Prepared from 55-1 according to the procedures reported in Scheme 48. MS (M+H)+: observed=367.2132, calculated=367.2129.

TABLE 24

The following compounds were prepared from 55-1 by a reaction sequence analogous to that illustrated in Scheme 55.

| Cmpd | Structure | IUPAC Name | Exact Mass [M + H]+ |
|---|---|---|---|
| 55-2 | 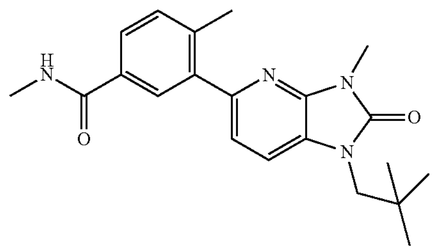 [SMILES: CNC(=O)c1ccc(C)c(-c2ccc3c(n2)n(C)c(=O)n3CC(C)(C)C)c1] | 3-[1-(2,2-dimethylpropyl)-3-methyl-2-oxo-2,3-dihydro-1H-imidazo[4,5-b]pyridin-5-yl]-N,4-dimethylbenzamide | Calc'd 367.2129, found 367.2132 |
| 55-3 | 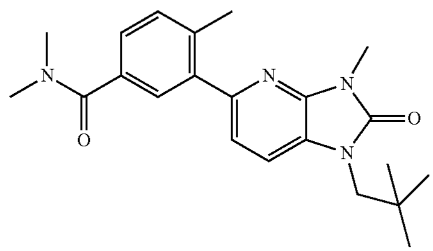 [SMILES: Cc1ccc(C(=O)N(C)C)cc1-c1ccc2c(n1)n(C)c(=O)n2CC(C)(C)C] | 3-[1-(2,2-dimethylpropyl)-3-methyl-2-oxo-2,3-dihydro-1H-imidazo[4,5-b]pyridin-5-yl]-N,N,4-trimethylbenzamide | Calc'd 381.2285, found 381.2294 |
| 55-4 | 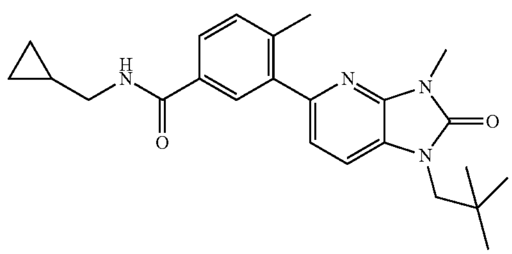 [SMILES: Cc1ccc(C(=O)NCC2CC2)cc1-c1ccc2c(n1)n(C)c(=O)n2CC(C)(C)C] | N-(cyclopropylmethyl)-3-[1-(2,2-dimethylpropyl)-3-methyl-2-oxo-2,3-dihydro-1H-imidazo[4,5-b]pyridin-5-yl]-4-methylbenzamide | Calc'd 407.2442, found 407.2448 |
| 55-5 | 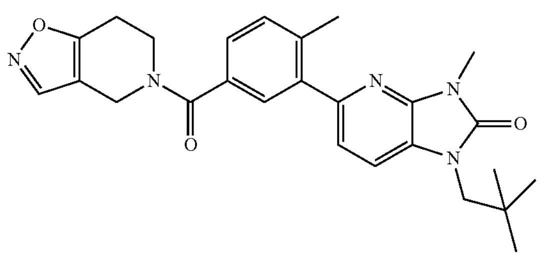 [SMILES: Cc1ccc(C(=O)N2CCc3oncc3C2)cc1-c1ccc2c(n1)n(C)c(=O)n2CC(C)(C)C] | 5-[5-(6,7-dihydroisoxazolo[4,5-c]pyridin-5(4H)-ylcarbonyl)-2-methylphenyl]-1-(2,2-dimethylpropyl)-3-methyl-1,3-dihydro-2H-imidazo[4,5-b]pyridin-2-one | Calc'd 460.2343, found 460.2349 |
| 55-6 | 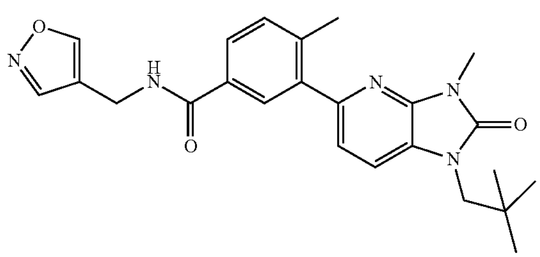 [SMILES: Cc1ccc(C(=O)NCc2cnoc2)cc1-c1ccc2c(n1)n(C)c(=O)n2CC(C)(C)C] | 3-[1-(2,2-dimethylpropyl)-3-methyl-2-oxo-2,3-dihydro-1H-imidazo[4,5-b]pyridin-5-yl]-N-(isoxazol-4-ylmethyl)-4-methylbenzamide | Calc'd 434.2187, found 434.2193 |
| 55-7 | 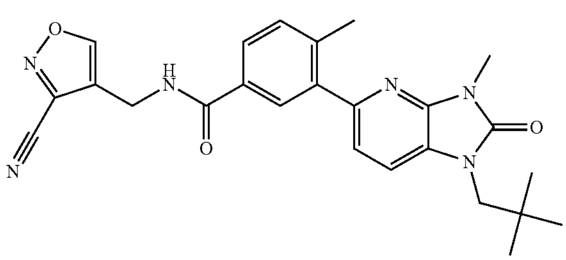 [SMILES: Cc1ccc(C(=O)NCc2conc2C#N)cc1-c1ccc2c(n1)n(C)c(=O)n2CC(C)(C)C] | N-[(3-cyanoisoxazol-4-yl)methyl]-3-[1-(2,2-dimethylpropyl)-3-methyl-2-oxo-2,3-dihydro-1H-imidazo[4,5-b]pyridin-5-yl]-4-methylbenzamide | Calc'd 459.2139, found 459.2140 |

TABLE 24-continued

The following compounds were prepared from 55-1 by a reaction sequence analogous to that illustrated in Scheme 55.

| Cmpd | Structure | IUPAC Name | Exact Mass [M + H]+ |
|---|---|---|---|
| 55-8 | 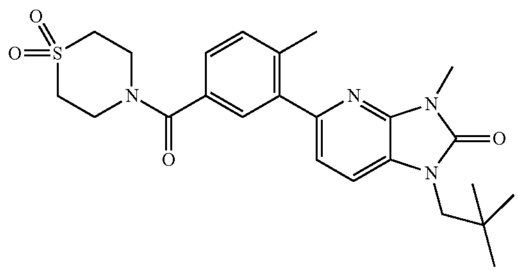 [SMILES: Cc1ccc(C(=O)N2CCS(=O)(=O)CC2)cc1-c1ccc2c(n1)n(C)c(=O)n2CC(C)(C)C] | 1-(2,2-dimethylpropyl)-5-{5-[(1,1-dioxidothiomorpholin-4-yl)carbonyl]-2-methylphenyl}-3-methyl-1,3-dihydro-2H-imidazo[4,5-b]pyridin-2-one | Calc'd 471.2061, found 471.2071 |
| 55-9 | 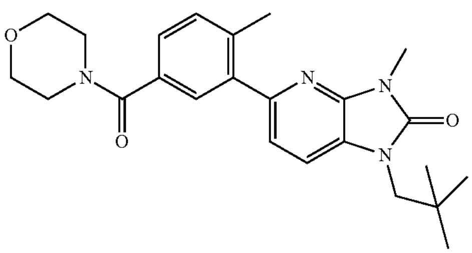 [SMILES: Cc1ccc(C(=O)N2CCOCC2)cc1-c1ccc2c(n1)n(C)c(=O)n2CC(C)(C)C] | 1-(2,2-dimethylpropyl)-3-methyl-5-[2-methyl-5-(morpholin-4-ylcarbonyl)phenyl]-1,3-dihydro-2H-imidazo[4,5-b]pyridin-2-one | Calc'd 423.2391, found 423.2398 |
| 55-10 | 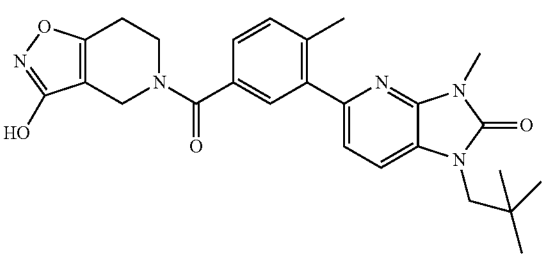 [SMILES: Cc1ccc(C(=O)N2CCc3onc(O)c3C2)cc1-c1ccc2c(n1)n(C)c(=O)n2CC(C)(C)C] | 1-(2,2-dimethylpropyl)-5-{5-[(3-hydroxy-6,7-dihydroisoxazolo[4,5-c]pyridin-5(4H)-yl)carbonyl]-2-methylphenyl}-3-methyl-1,3-dehydro-2H-imidazo[4,5-b]pyridin-2-one | Calc'd 476.2292, found 476.2301 |

SCHEME 56

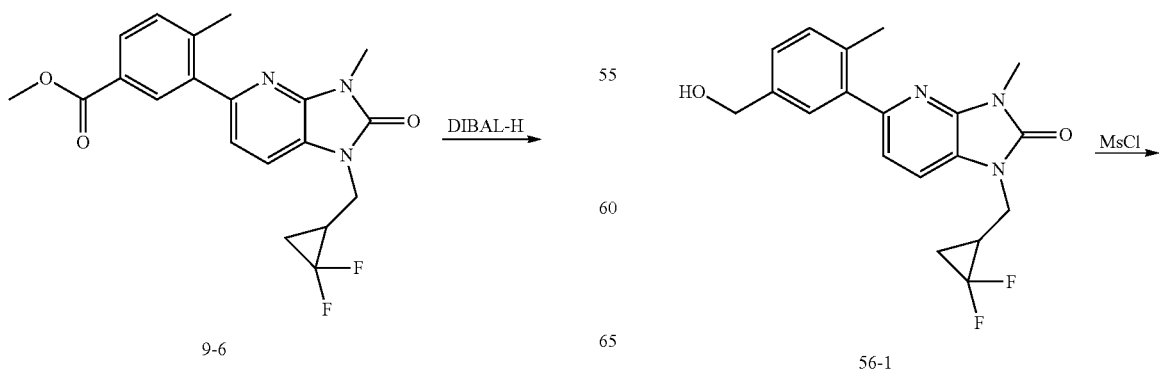

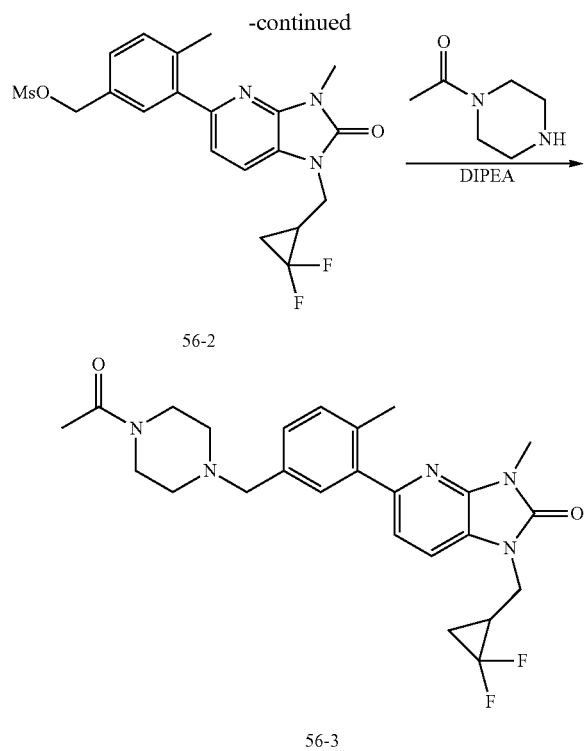

5-{5-[(4-acetylpiperazin-1-yl)methyl]-2-methylphenyl}-1-[(2,2-difluorocyclopropyl)methyl]-3-methyl-1,3-dihydro-2H-imidazo[4,5-b]pyridin-2-one (56-3)

1-[(2,2-difluorocyclopropyl)methyl]-5-[5-(hydroxymethyl)-2-methylphenyl]-3-methyl-1,3-dihydro-2H-imidazo[4,5-b]pyridin-2-one (56-1)

Prepared from 9-6 according to the procedures reported in Scheme 51. MS (M+H)+: observed=360.2, calculated=360.2.

3-{1-[(2,2-difluorocyclopropyl)methyl]-3-methyl-2-oxo-2,3-dihydro-1H-imidazo[4,5-b]pyridin-5-yl}-4-methylbenzyl methanesulfonate (56-2)

Prepared from 56-1 according to the procedures reported in Scheme 21. MS (M+H)+: observed=437.2, calculated=437.1.

5-{5-[(4-acetylpiperazin-1-yl)methyl]-2-methylphenyl}-1-[(2,2-difluoro cyclopropyl)methyl]-3-methyl-1,3-dihydro-2H-imidazo[4,5-b]pyridin-2-one (56-3)

Prepared from 51-2 according to the procedures reported in Scheme 21. MS (M+H)+: observed=470.2358, calculated=470.2362. $^1$H NMR (400 MHz, CD$_3$ OD): δ 7.64 (d, J=8.0 Hz, 1H); 7.59 (s, 1H); 7.47 (s, 2H); 7.28 (d, J=8.0 Hz, 1H); 4.67 (m, 2H); 4.41 (s, 2H); 4.28-4.12 (m, 2H); 4.03 (m, 2H); 3.53-3.44 (m, 5H); 3.22-2.96 (m, 2H); 2.42 (s, 3H); 2.23-2.15 (m, 1H); 2.14 (s, 3H); 1.64-1.55 (m, 1H); 1.50-1.38 (m, 1H).

TABLE 25

The following compounds were prepared from 56-2 by a reaction sequence analogous to that illustrated in Scheme 56.

| Cmpd | Structure | IUPAC Name | Exact Mass [M + H]+ |
|---|---|---|---|
| 56-4 | 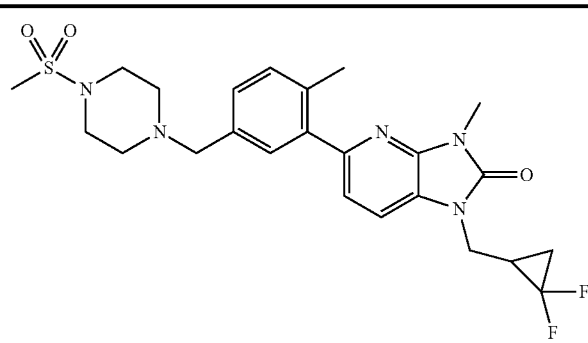 | 1-[(2,2-difluorocyclopropyl)methyl]-3-methyl-5-(2-methyl-5-{[4-(methylsulfonyl)piperazin-1-yl]methyl}phenyl)-1,3-dihydro-2H-imidazo[4,5-b]pyridin-2-one | Calc'd 506.2032, found 506.2027 |
| 56-5 | 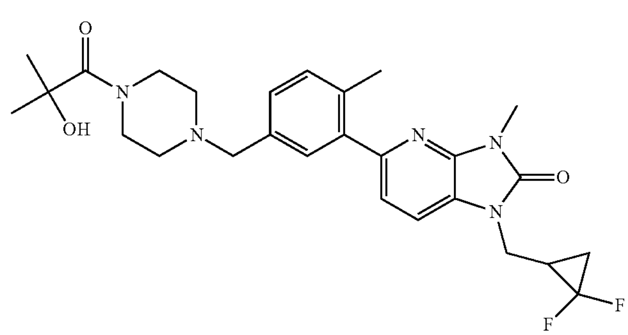 [SMILES: Cc1ccc(CN2CCN(C(=O)C(C)(C)O)CC2)cc1-c1ccc2c(n1)n(C)c(=O)n2CC1CC1(F)F] | 1-[(2,2-difluorocyclopropyl)methyl]-5-(5-{[4-(2-hydroxy-2-methylpropanoyl)piperazin-1-yl]methyl}-2-methylphenyl)-3-methyl-1,3-dihydro-2H-imidazo[4,5-b]pyridin-2-one | Calc'd 514.2624, found 514.2625 |

SCHEME 57

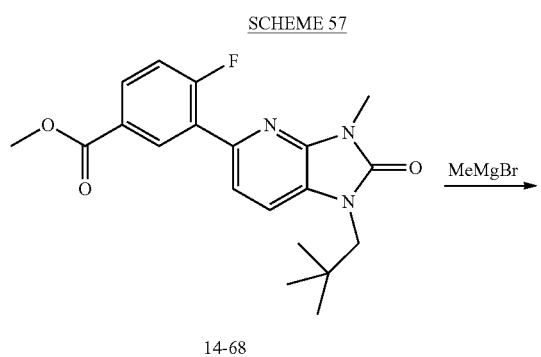

14-68

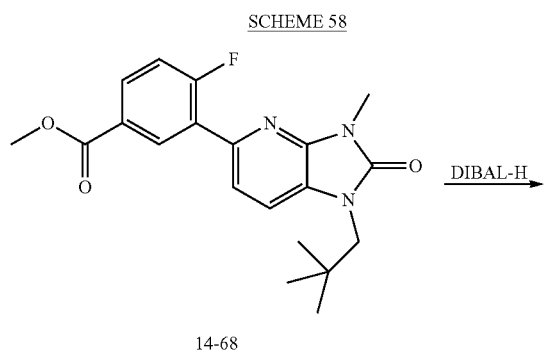

57-1

1-(2,2-dimethylpropyl)-5-[2-fluoro-5-(1-hydroxy-1-methylethyl)phenyl]-3-methyl-1,3-dihydro-2H-imidazo[4,5-b]pyridin-2-one (57-1)

Prepared from 14-68 according to the procedures reported in Scheme 3. MS (M+H)+: observed=372.2082, calculated=372.2085.

SCHEME 58

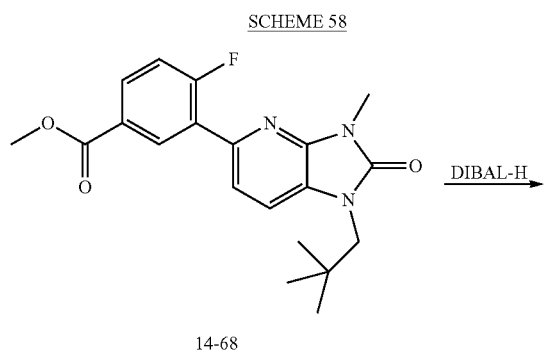

14-68

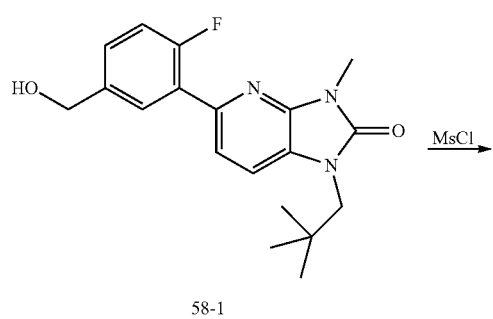

58-1

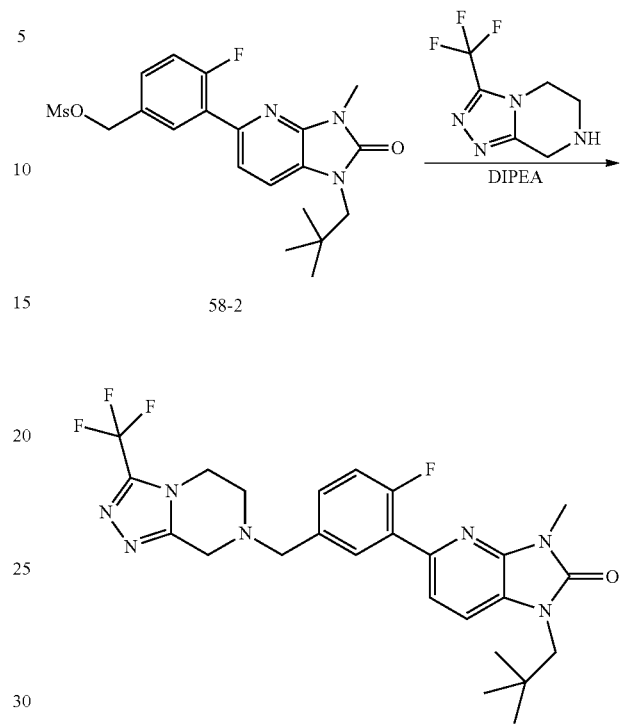

58-2

58-3

1-(2,2-dimethylpropyl)-5-(2-fluoro-5-{[3-(trifluoromethyl)-5,6-dihydro[1,2,4]triazolo[4,3-a]pyrazin-7(8H)-yl]methyl}phenyl)-3-methyl-1,3-dihydro-2H-imidazo[4,5-b]pyridin-2-one (58-3)

1-(2,2-dimethylpropyl)-5-[2-fluoro-5-(hydroxymethyl)phenyl]-3-methyl-1,3-dihydro-2H-imidazo[4,5-b]pyridin-2-one (58-1)

Prepared from 14-68 according to the procedures reported in Scheme 51. MS (M+H)+: observed=344.1770, calculated=344.1769.

3-[1-(2,2-dimethylpropyl)-3-methyl-2-oxo-2,3-dihydro-1H-imidazo[4,5-b]pyridin-5-yl]-4-fluorobenzyl methanesulfonate (58-2)

Prepared from 58-1 according to the procedures reported in Scheme 21. MS (M+H)+: observed=422.3, calculated=422.2.

1-(2,2-dimethylpropyl)-5-(2-fluoro-5-{[3-(trifluoromethyl)-5,6-dihydro[1,2,4]triazolo[4,3-a]pyrazin-7(8H)-yl]methyl}phenyl)-3-methyl-1,3-dihydro-2H-imidazo[4,5-b]pyridin-2-one (58-3)

Prepared from 58-2 according to the procedures reported in Scheme 21. MS (M+H)+: observed=518.2288, calculated=518.2286.

TABLE 26

The following compounds were prepared from 58-2 by a reaction sequence analogous to that illustrated in Scheme 58.

| Cmpd | Structure | IUPAC Name | Exact Mass (M + H)+ |
|---|---|---|---|
| 58-4 | 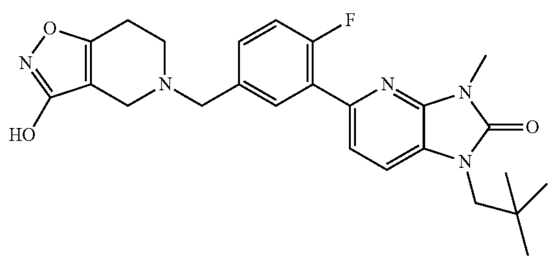 [SMILES: Cn1c(=O)n(CC(C)(C)C)c2ccc(-c3cc(CN4CCc5onc(O)c5C4)ccc3F)nc21] | 1-(2,2-dimethylpropyl)-5-{2-fluoro-5-[(3-hydroxy-6,7-dihydroisoxazolo[4,5-c]pyridin-5(4H)-yl)methyl]phenyl}-3-methyl-1,3-dihydro-2H-imidazo[4,5-b]pyridin-2-one | Calc'd 466.2249, found 466.2253 |
| 58-5 | 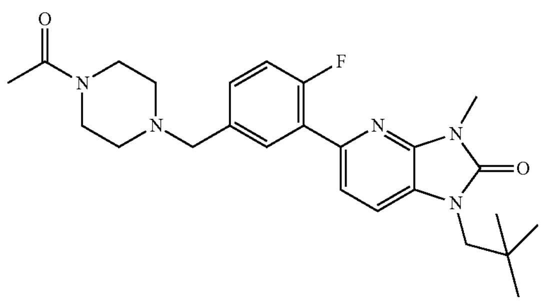 [SMILES: CC(=O)N1CCN(Cc2ccc(F)c(-c3ccc4c(n3)n(C)c(=O)n4CC(C)(C)C)c2)CC1] | 5-{5-[(4-acetylpiperazin-1-yl)methyl]-2-fluorophenyl}-1-(2,2-dimethylpropyl)-3-methyl-1,3-dihydro-2H-imidazo[4,5-b]pyridin-2-one | Calc'd 454.2613, found 454.2616 |
| 58-6 | 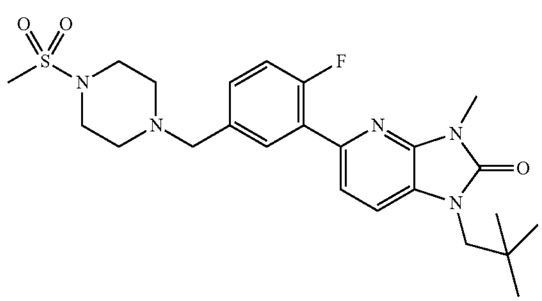 [SMILES: Cn1c(=O)n(CC(C)(C)C)c2ccc(-c3cc(CN4CCN(S(C)(=O)=O)CC4)ccc3F)nc21] | 1-(2,2-dimethylpropyl)-5-(2-fluoro-5-{[4-(methylsulfonyl)piperazin-1-yl]methyl}phenyl)-3-methyl-1,3-dihydro-2H-imidazo[4,5-b]pyridin-2-one | Calc'd 490.2283, found 490.2279 |
| 58-7 | 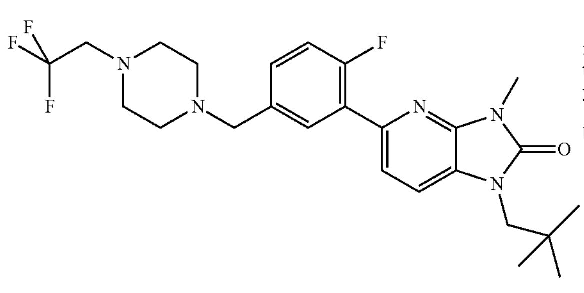 | 1-(2,2-dimethylpropyl)-5-(2-fluoro-5-{[4-(2,2,2-trifluoroethyl)piperazin-1-yl]methyl}phenyl)-3-methyl-1,3-dihydro-2H-imidazo[4,5-b]pyridin-2-one | Calc'd 494.2538, found 494.2539 |

SCHEME 59

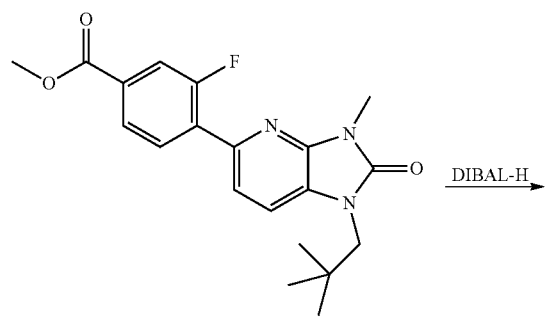

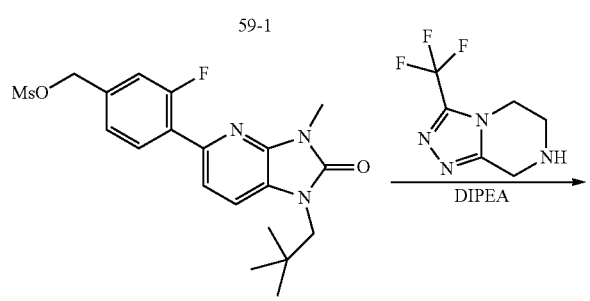

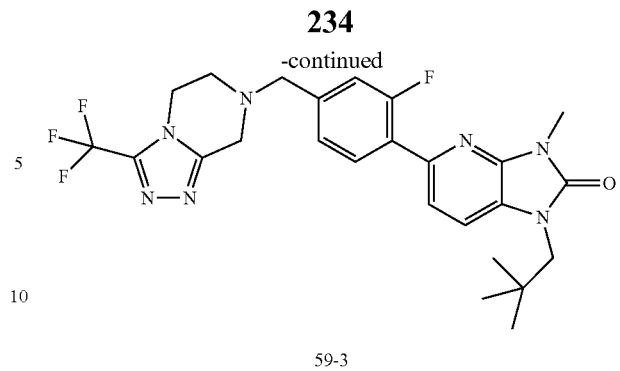

1-(2,2-dimethylpropyl)-5-(2-fluoro-4-{[3-(trifluoromethyl)-5,6-dihydro[1,2,4]triazolo[4,3-a]pyrazin-7(8H)-yl]methyl}phenyl)-3-methyl-1,3-dihydro-2H-imidazo[4,5-b]pyridin-2-one (59-3)

1-(2,2-dimethylpropyl)-5-[2-fluoro-4-(hydroxymethyl)phenyl]-3-methyl-1,3-dihydro-2H-imidazo pyridin-2-one (59-1)

Prepared from 14-69 according to the procedures reported in Scheme 51. MS (M+H)+: observed=344.1764, calculated=344.1769.

4-[1-(2,2-dimethylpropyl)-3-methyl-2-oxo-2,3-dihydro-1H-imidazo[4,5-b]pyridin-5-yl]-3-fluorobenzyl methanesulfonate (59-2)

Prepared from 59-1 according to the procedures reported in Scheme 21. MS (M+H)+: observed=422.3, calculated=422.2.

1-(2,2-dimethylpropyl)-5-(2-fluoro-4-{[3-(trifluoromethyl)-5,6-dihydro[1,2,4]triazolo[4,3-a]pyrazin-7(8H)-yl]methyl}phenyl)-3-methyl-1,3-dihydro-2H-imidazo[4,5-b]pyridin-2-one (59-3)

Prepared from 59-2 according to the procedures reported in Scheme 21. MS (M+H)+: observed=518.2277, calculated=518.2286.

TABLE 27

The following compounds were prepared from 59-2 by a reaction sequence analogous to that illustrated in Scheme 59.

| Cmpd | Structure | IUPAC Name Exact Mass [M + H]+ | Exact Mass [M + H]+ |
|---|---|---|---|
| 59-4 | 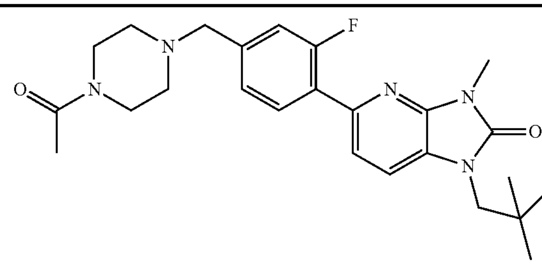 | 5-{4-[(4-acetylpiperazin-1-yl)methyl]-2-fluorophenyl}-1-(2,2-dimethylpropyl)-3-methyl-1,3-dihydro-2H-imidazo[4,5-b]pyridin-2-one | Calc'd 454.2613, found 454.2609 |
| 59-5 | 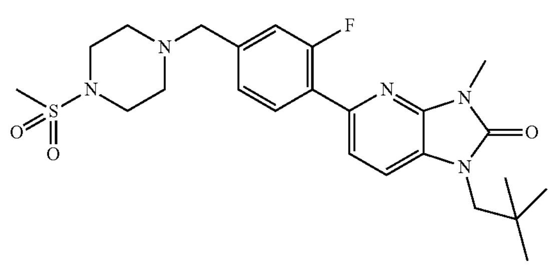 [SMILES: Cn1c(=O)n(CC(C)(C)C)c2ccc(-c3ccc(CN4CCN(S(C)(=O)=O)CC4)cc3F)nc21] | 1-(2,2-dimethylpropyl)-5-(2-fluoro-4-{[4-(methylsulfonyl)piperazin-1-yl]methyl}phenyl)-3-methyl-1,3-dihydro-2H-imidazo[4,5-b]pyridin-2-one | Calc'd 490.2283, found 490.2275 |

SCHEME 60

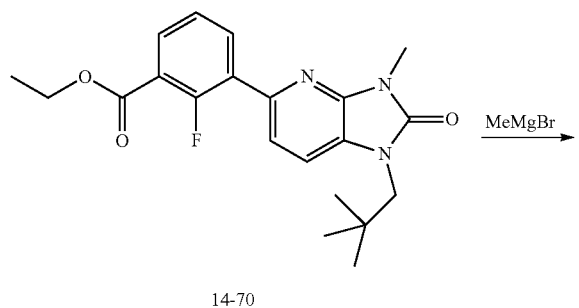

14-70

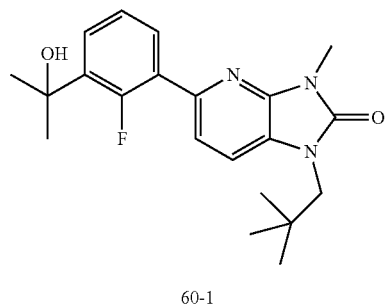

60-1

1-(2,2-dimethylpropyl)-5-[2-fluoro-3-(1-hydroxy-1-methylethyl)phenyl]-3-methyl-1,3-dihydro-2H-imidazo[4,5-b]pyridin-2-one (60-1)

Prepared from 14-70 according to the procedures reported in Scheme 3. MS (M+H)⁺: observed=372.2080, calculated=372.2082. ¹H NMR (400 MHz, CDCl₃): δ 7.84 (td, J=7.5, 1.9 Hz, 1H); 7.58 (td, J=7.7, 1.9 Hz, 1H); 7.47 (dd, J=8.1, 2.3 Hz, 1H); 725-7.21 (m, 2H); 3.69 (s, 2H); 3.55 (s, 3H); 2.17 (d, J=3.6 Hz, 1H); 1.70 (d, J=1.1 Hz, 6H); 1.07 (s, 9H).

SCHEME 61

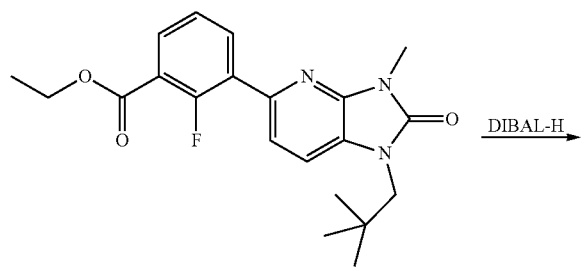

14-70

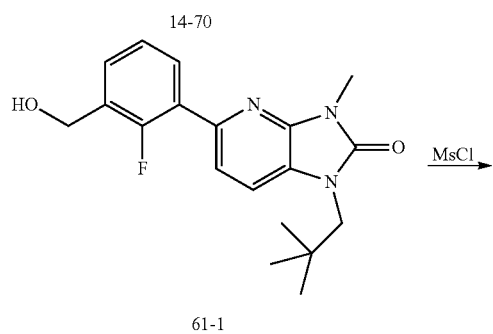

61-1

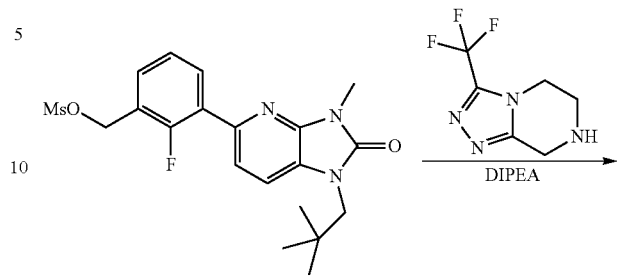

61-2

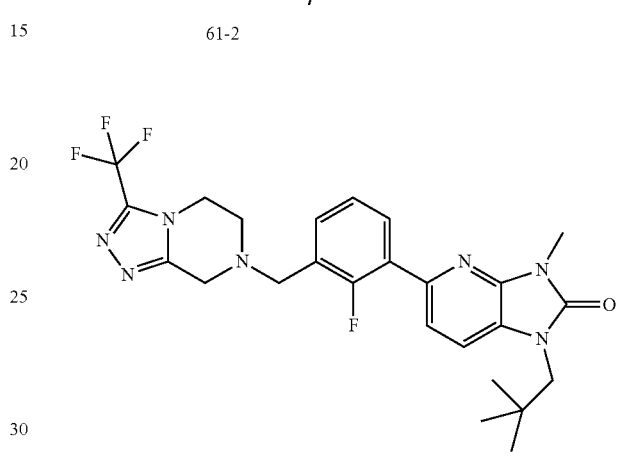

61-3

1-(2,2-dimethylpropyl)-5-(2-fluoro-3-{[3-(trifluoromethyl)-5,6-dihydro[1,2,4]triazolo[4,3-a]pyrazin-7(8H)-yl]methyl}phenyl)-3-methyl-1,3-dihydro-2H-imidazo[4,5-b]pyridin-2-one (61-3)

1-(2,2-dimethylpropyl)-5-[2-fluoro-3-(hydroxymethyl)phenyl]-3-methyl-1,3-dihydro-2H-imidazo[4,5-b]pyridin-2-one (61-1)

Prepared from 14-70 according to the procedures reported in Scheme 51. MS (M+H)⁺: observed=344.1769, calculated=344.1769.

3-[1-(2,2-dimethylpropyl)-3-methyl-2-oxo-2,3-dihydro-1H-imidazo[4,5-b]pyridin-5-yl]-2-fluorobenzyl methanesulfonate (61-2)

Prepared from 61-1 according to the procedures reported in Scheme 21. MS (M+H)⁺: observed=422.3, calculated=422.2.

1-(2,2-dimethylpropyl)-5-(2-fluoro-3-{[3-(trifluoromethyl)-5,6-dihydro[1,2,4]triazolo[4,3-a]pyrazin-7(8H)-yl]methyl}phenyl)-3-methyl-1,3-dihydro-2H-imidazo[4,5-b]pyridin-2-one (61-3)

Prepared from 61-2 according to the procedures reported in Scheme 21. MS (M+H)⁺: observed=518.2286, calculated=518.2286.

TABLE 28

The following compounds were prepared from 61-2 by a reaction sequence analogous to that illustrated in Scheme 61.

| Cmpd | Structure | IUPAC Name | Exact Mass (M + H)+ |
| --- | --- | --- | --- |
| 61-4 | 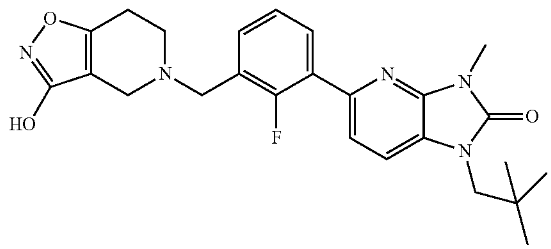 [SMILES: Cn1c(=O)n(CC(C)(C)C)c2ccc(-c3cccc(CN4CCc5onc(O)c5C4)c3F)nc21] | 1-(2,2-dimethylpropyl)-5-{2-fluoro-3-[(3-hydroxy-6,7-dihydroisoxazolo[4,5-c]pyridin-5(4H)-yl)methyl]phenyl}-3-methyl-1,3-dihydro-2H-imidazo[4,5-b]pyridin-2-one | Calc'd 466.2249, found 466.2250 |
| 61-5 | 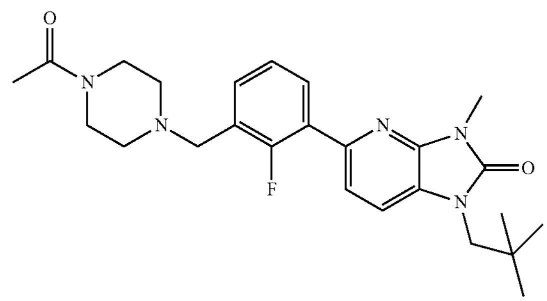 [SMILES: CC(=O)N1CCN(Cc2cccc(-c3ccc4c(n3)n(C)c(=O)n4CC(C)(C)C)c2F)CC1] | 5-{3-[(4-acetylpiperazin-1-yl)methyl]-2-fluorophenyl}-1-(2,2-dimethylpropyl)-3-methyl-1,3-dihydro-2H-imidazo[4,5-b]pyridin-2-one | Calc'd 454.2613, found 454.2612 |
| 61-6 | 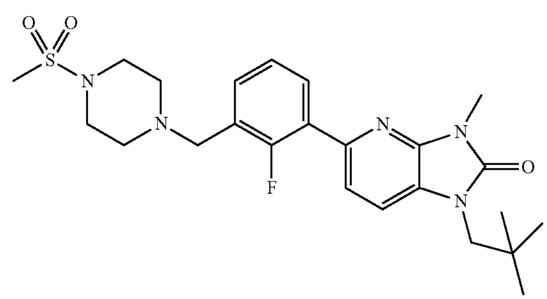 [SMILES: Cn1c(=O)n(CC(C)(C)C)c2ccc(-c3cccc(CN4CCN(S(C)(=O)=O)CC4)c3F)nc21] | 1-(2,2-dimethylpropyl)-5-(2-fluoro-3-{[4-(methylsulfonyl)piperazin-1-yl]methyl}phenyl)-3-imidazo[4,5-b]pyridin-2-one | Calc'd 490.2283, found 490.2282 |
| 61-7 | 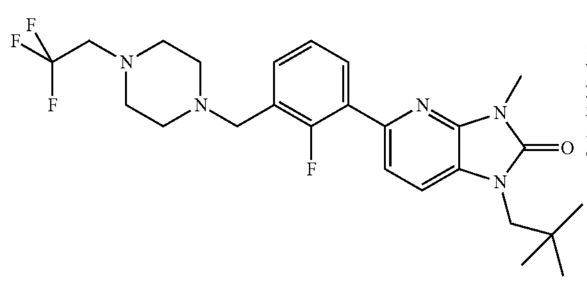 | 1-(2,2-dimethylpropyl)-5-(2-fluoro-3-{[4-(2,2,2-trifluoroethyl)piperazin-1-yl]methyl}phenyl)-3-methyl-1,3-dihydro-2H-imidazo[4,5-b]pyridin-2-one | Calc'd 494.2538, found 494.2535 |

SCHEME 62

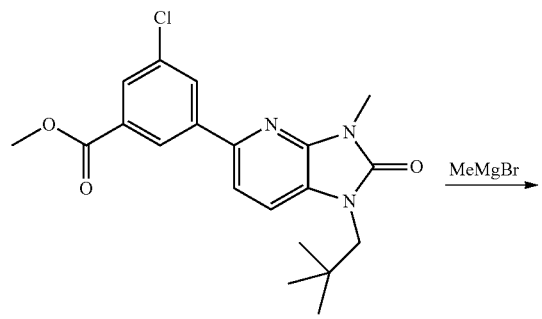

14-71

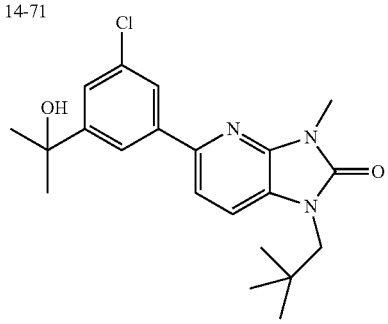

62-1

5-[3-chloro-5-(1-hydroxy-1-methylethyl)phenyl]-1-(2,2-dimethylpropyl)-3-methyl-1,3-dihydro-2H-imidazo[4,5-b]pyridin-2-one (62-1)

5-[3-chloro-5-(1-hydroxy-1-methylethyl)phenyl]-1-(2,2-dimethylpropyl)-3-methyl-1,3-dihydro-2H-imidazo[4,5-b]pyridin-2-one (62-1)

Prepared from 14-71 according to the procedures reported in Scheme 3. MS (M+H)⁺: observed=388.1780, calculated=388.1786.

SCHEME 63

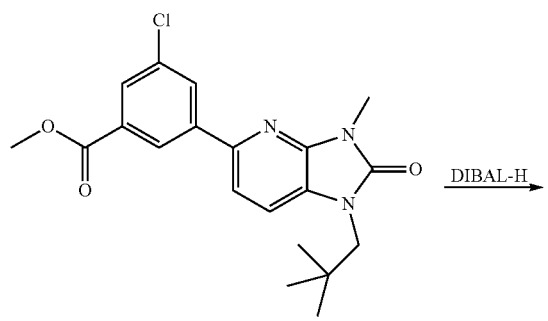

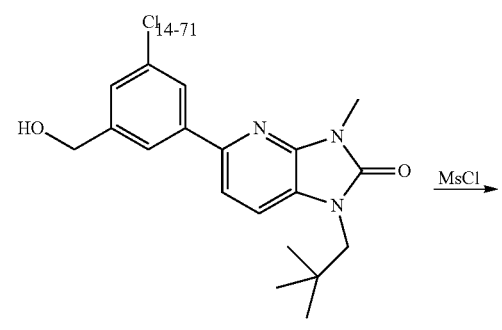

63-1

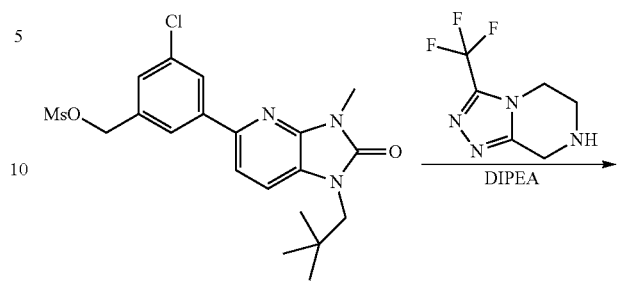

63-2

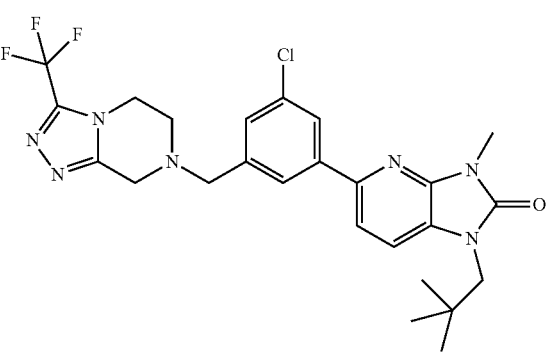

63-3

5-(3-chloro-5-{[3-(trifluoromethyl)-5,6-dihydro[1,2,4]triazolo[4,3-a]pyrazin-7(8H)-yl]methyl}phenyl)-1-(2,2-dimethylpropyl)-3-methyl-1,3-dihydro-2H-imidazo[4,5-b]pyridin-2-one (63-3)

5-[3-chloro-5-(hydroxymethyl)phenyl]-1-(2,2-dimethylpropyl)-3-methyl-1,3-dihydro-2H-imidazo[4,5-b]pyridin-2-one (63-1)

Prepared from 14-71 according to the procedures reported in Scheme 51. MS (M+H)⁺: observed=360.1466, calculated=360.1473.

3-chloro-5-[1-(2,2-dimethylpropyl)-3-methyl-2-oxo-2,3-dihydro-1H-imidazo[4,5-b]pyridin-5-yl]benzyl methanesulfonate (63-2)

Prepared from 63-1 according to the procedures reported in Scheme 21. MS (M+H)⁺: observed=437.9, calculated=438.1.

5-(3-chloro-5-{[3-(trifluoromethyl)-5,6-dihydro[1,2,4]triazolo[4,3-a]pyrazin-7(8H)-yl]methyl}phenyl)-1-(2,2-dimethylpropyl)-3-methyl-1,3-dihydro-2H-imidazo[4,5-b]pyridin-2-one (63-3)

Prepared from 63-2 according to the procedures reported in Scheme 21. MS (M+H)⁺: observed=534.1983, calculated=534.1990.

TABLE 29

The following compounds were prepared from 63-2 by a reaction sequence analogous to that illustrated in Scheme 63.

| Cmpd | Structure | IUPAC Name | |
|---|---|---|---|
| 63-4 | 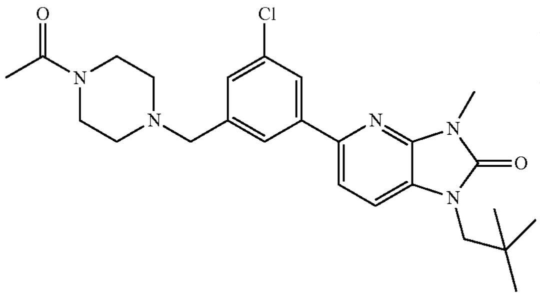 [SMILES: CC(=O)N1CCN(Cc2cc(Cl)cc(-c3ccc4c(n3)n(C)c(=O)n4CC(C)(C)C)c2)CC1] | 5-{3-[(4-acetylpiperazin-1-yl)methyl]-5-chlorophenyl}-1-(2,2-dimethylpropyl)-3-methyl-1,3-dihydro-2H-imidazo[4,5-b]pyridin-2-one | Calc'd 470.2317, found 470.2310 |
| 63-5 | 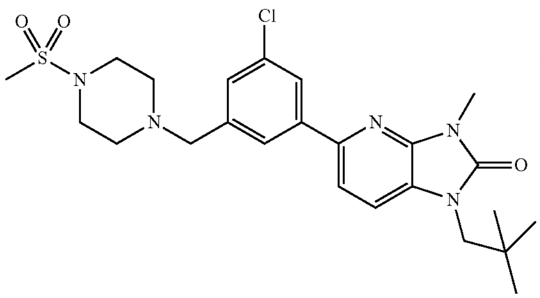 [SMILES: Cn1c(=O)n(CC(C)(C)C)c2ccc(-c3cc(Cl)cc(CN4CCN(S(C)(=O)=O)CC4)c3)nc21] | 5-(3-chloro-5-{[4-(methylsulfonyl)piperazin-1-yl]methyl}phenyl)-1-(2,2-dimethylpropyl)-3-methyl-1,3-dihydro-2H-imidazo[4,5-b]pyridin-2-one | Calc'd 506.1987, found 506.1978 |

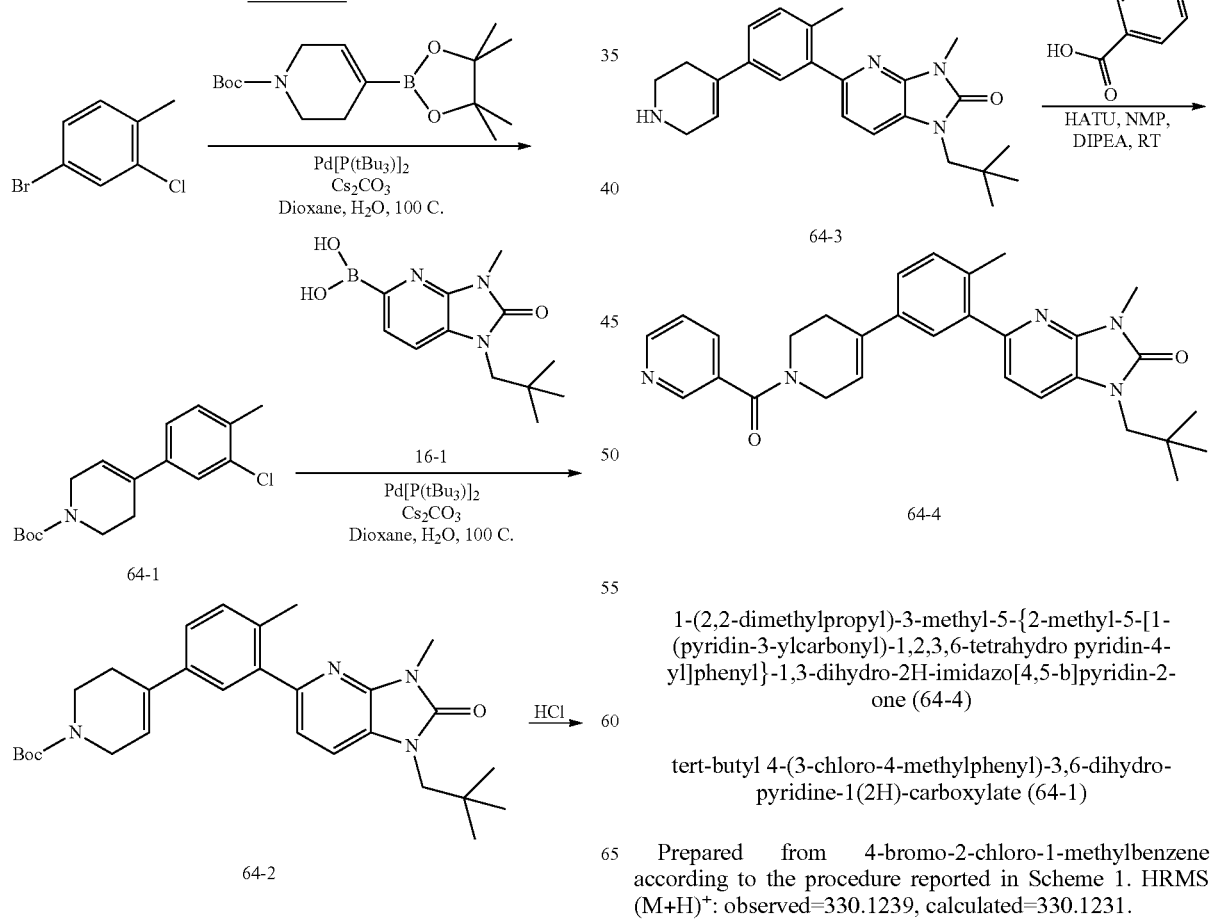

SCHEME 64

1-(2,2-dimethylpropyl)-3-methyl-5-{2-methyl-5-[1-(pyridin-3-ylcarbonyl)-1,2,3,6-tetrahydro pyridin-4-yl]phenyl}-1,3-dihydro-2H-imidazo[4,5-b]pyridin-2-one (64-4)

tert-butyl 4-(3-chloro-4-methylphenyl)-3,6-dihydro-pyridine-1(2H)-carboxylate (64-1)

Prepared from 4-bromo-2-chloro-1-methylbenzene according to the procedure reported in Scheme 1. HRMS (M+H)$^+$: observed=330.1239, calculated=330.1231.

tert-butyl 4-{3-[1-(2,2-dimethylpropyl)-3-methyl-2-oxo-2,3-dihydro-1H-imidazo[4,5-b]pyridin-5-yl]-4-methylphenyl}-3,6-dihydropyridine-1(2H)-carboxylate (64-2)

Prepared from 16-1 and 64-1 according to the procedure reported in Scheme 1. HRMS (M+H)+: observed=491.3026, calculated=491.3017.

1-(2,2-dimethylpropyl)-3-methyl-5-[2-methyl-5-(1,2,3,6-tetrahydropyridin-4-yl)phenyl]-1,3-dihydro-2H-imidazo[4,5-b]pyridin-2-one (64-3)

Prepared from 64-2 according to the procedure reported in Scheme 23. HRMS (M+H)+: observed=391.2492, calculated=391.2502.

1-(2,2-dimethylpropyl)-3-methyl-5-{2-methyl-5-[1-(pyridin-3-ylcarbonyl)-1,2,3,6-tetrahydropyridin-4-yl]phenyl}-1,3-dihydro-2H-imidazo[4,5-b]pyridin-2-one (64-4)

Prepared from 64-3 according to the procedure reported in Scheme 48. HRMS (M+H)+: observed=496.2711, calculated=496.2707.

SCHEME 65

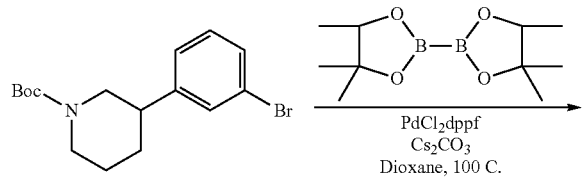

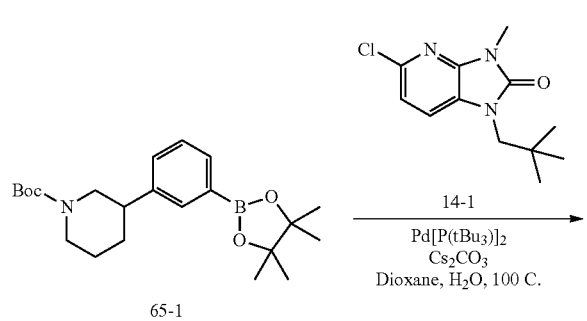

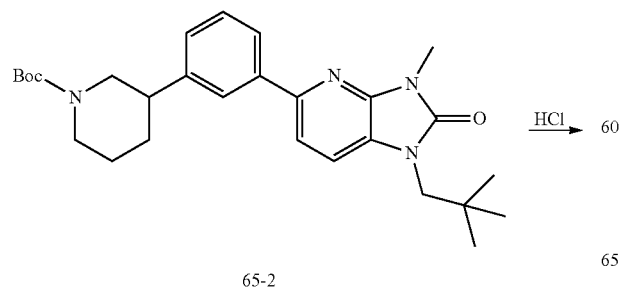

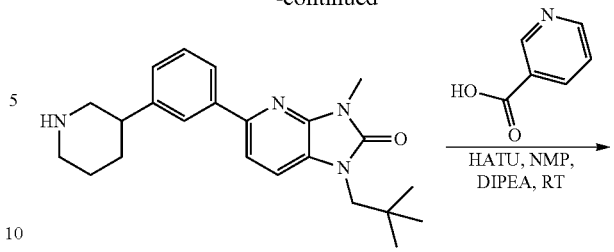

65-3

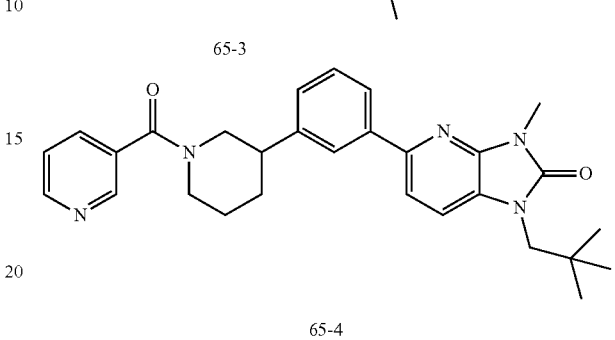

65-4

1-(2,2-dimethylpropyl)-3-methyl-5-{3-[1-(pyridin-3-ylcarbonyl)piperidin-3-yl]phenyl}-1,3-dihydro-2H-imidazo[4,5-b]pyridin-2-one (65-4)

tert-butyl 3-[3-(4,4,5,5-tetramethyl-1,3,2-dioxaborolan-2-yl)phenyl]piperidine-1-carboxylate (65-1)

Prepared from tert-butyl 3-(3-bromophenyl)piperidine-1-carboxylate according to the procedures reported in Scheme 3. MS (M−55)+: observed=332.1, calculated=332.3.

tert-butyl 3-{3-[1-(2,2-dimethylpropyl)-3-methyl-2-oxo-2,3-dihydro-1H-imidazo[4,5-b]pyridin-5-yl]phenyl}piperidine-1-carboxylate (65-2)

Prepared from 14-1 and 65-1 according to the procedures reported in Scheme 1. HRMS (M+H)+: observed=479.3018, calculated=479.3017.

1-(2,2-dimethylpropyl)-3-methyl-5-(3-piperidin-3-ylphenyl)-1,3-dihydro-2H-imidazo[4,5-b]pyridin-2-one (65-3)

Prepared from 65-2 according to the procedure reported in Scheme 23. HRMS (M+H)+: observed=379.2496, calculated=379.2492.

1-(2,2-dimethylpropyl)-3-methyl-5-{3-[1-(pyridin-3-ylcarbonyl)piperidin-3-yl]phenyl}-1,3-dihydro-2H-imidazo[4,5-b]pyridin-2-one (65-4)

Prepared from 65-3 according to the procedure reported in Scheme 48. HRMS (M+H)+: observed=484.2706, calculated=484.2707. 1H NMR (400 MHz, CD3 OD): δ 9.12-8.82 (m, 2H); 8.69 (d, J=7.6 Hz, 1H); 8.20-7.80 (m, 3H); 7.71-7.26 (m, 4H); 3.74 (s, 3H); 3.58-3.44 (m, 4H); 3.32 (s, 3H); 3.13-3.04 (m, 1H); 2.99 (t, J=11.6 Hz, 1H); 2.20-1.75 (m, 2H); 1.05 (s, 9H).

TABLE 30

The following compounds were prepared from 65-3 by a reaction sequence analogous to that illustrated in Scheme 65.

| Cmpd | Structure | IUPAC Name | Exact Mass [M + H]+ |
|---|---|---|---|
| 65-5 | 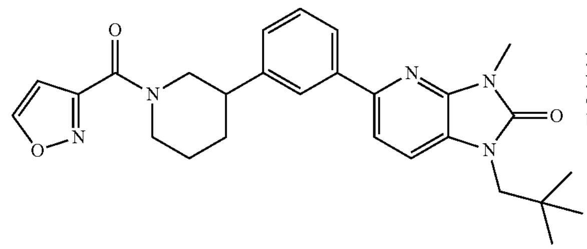 [SMILES: Cn1c(=O)n(CC(C)(C)C)c2ccc(-c3cccc(C4CCCN(C(=O)c5ccon5)C4)c3)nc21] | 1-(2,2-dimethylpropyl)-5-{3-[1-(isoxazol-3-ylcarbonyl)piperidin-3-yl]phenyl}-3-methyl-1,3-dihydro-2H-imidazo[4,5-b]pyridin-2-one | Calc'd 474.2500, found 474.2494 |
| 65-6 | 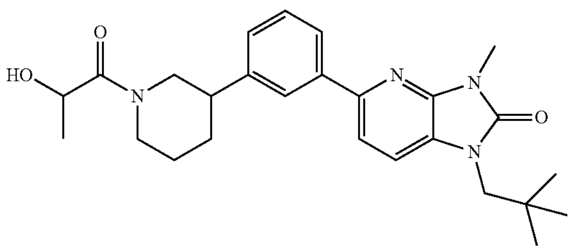 [SMILES: CC(O)C(=O)N1CCCC(c2cccc(-c3ccc4c(n3)n(C)c(=O)n4CC(C)(C)C)c2)C1] | 1-(2,2-dimethylpropyl)-5-{3-[1-(2-hydroxy propanoyl)piperidin-3-yl]phenyl}-3-methyl-1,3-dihydro-2H-imidazo[4,5-b]pyridin-2-one | Calc'd 451.2704, found 451.2705 |

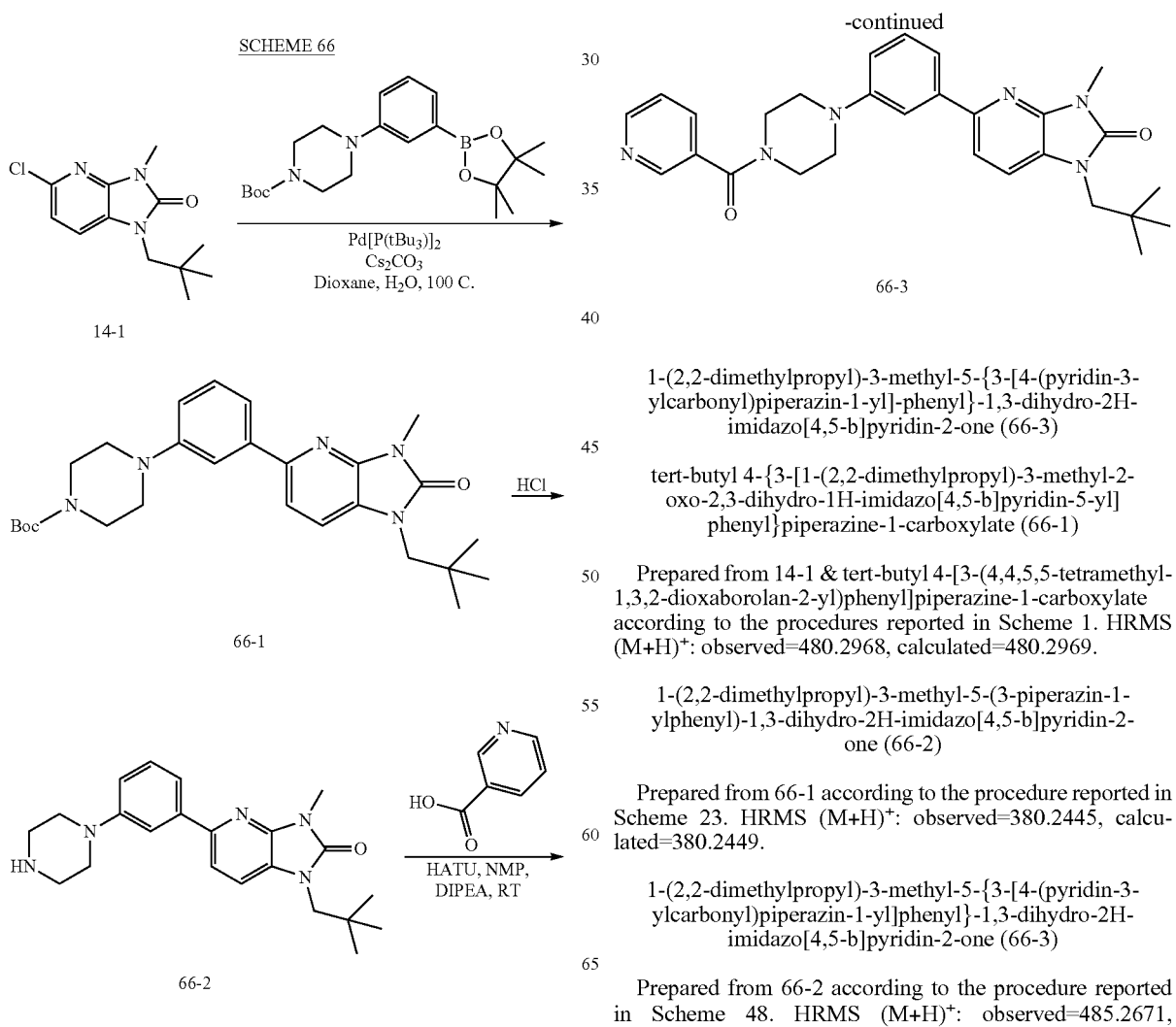

SCHEME 66

1-(2,2-dimethylpropyl)-3-methyl-5-{3-[4-(pyridin-3-ylcarbonyl)piperazin-1-yl]-phenyl}-1,3-dihydro-2H-imidazo[4,5-b]pyridin-2-one (66-3)

tert-butyl 4-{3-[1-(2,2-dimethylpropyl)-3-methyl-2-oxo-2,3-dihydro-1H-imidazo[4,5-b]pyridin-5-yl]phenyl}piperazine-1-carboxylate (66-1)

Prepared from 14-1 & tert-butyl 4-[3-(4,4,5,5-tetramethyl-1,3,2-dioxaborolan-2-yl)phenyl]piperazine-1-carboxylate according to the procedures reported in Scheme 1. HRMS (M+H)+: observed=480.2968, calculated=480.2969.

1-(2,2-dimethylpropyl)-3-methyl-5-(3-piperazin-1-ylphenyl)-1,3-dihydro-2H-imidazo[4,5-b]pyridin-2-one (66-2)

Prepared from 66-1 according to the procedure reported in Scheme 23. HRMS (M+H)+: observed=380.2445, calculated=380.2449.

1-(2,2-dimethylpropyl)-3-methyl-5-{3-[4-(pyridin-3-ylcarbonyl)piperazin-1-yl]phenyl}-1,3-dihydro-2H-imidazo[4,5-b]pyridin-2-one (66-3)

Prepared from 66-2 according to the procedure reported in Scheme 48. HRMS (M+H)+: observed=485.2671, calculated=485.2660. ¹H NMR (400 MHz, CD₃ OD): δ 9.16 (s, 1H); 8.99 (d, J=5.8 Hz, 1H); 8.81 (d, J=8.1 Hz, 1H); 8.26-8.17 (m, 2H); 7.99 (d, J=7.8 Hz, 1H); 7.69 (d, J=8.2 Hz, 1H); 7.62-7.55 (m, 2H); 7.51 (d, J=8.3 Hz, 1H); 3.75 (s, 2H); 3.55 (s, 4H); 3.32-3.30 (m, 7H); 1.05 (s, 9H).

TABLE 31

The following compounds were prepared from 66-2 by a reaction sequence analogous to that illustrated in Scheme 66.

| Cmpd | Structure | IUPAC Name | Exact Mass [M + H]+ |
|---|---|---|---|
| 66-4 | 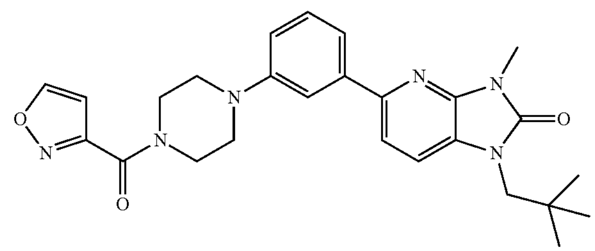 [SMILES: Cn1c(=O)n(CC(C)(C)C)c2ccc(-c3cccc(N4CCN(C(=O)c5ccon5)CC4)c3)nc21] | 1-(2,2-dimethylpropyl)-5-{3-[4-(isoxazol-3-ylcarbonyl)piperazin-1-yl]phenyl}-3-methyl-1,3-dihydro-2H-imidazo[4,5-b]pyridin-2-one | Calc'd 475.2452, found 475.2447 |
| 66-5 | 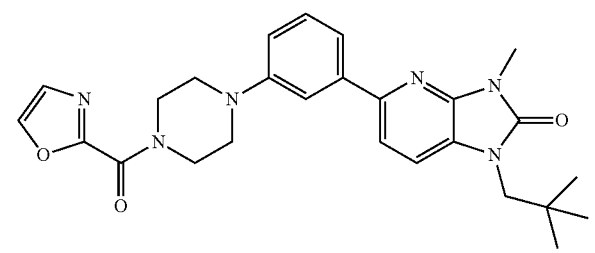 [SMILES: Cn1c(=O)n(CC(C)(C)C)c2ccc(-c3cccc(N4CCN(C(=O)c5ncco5)CC4)c3)nc21] | 1-(2,2-dimethylpropyl)-3-methyl-5-{3-[4-(1,3-oxazol-2-ylcarbonyl)piperazin-1-yl]phenyl}-1,3-dihydro-2H-imidazo[4,5-b]pyridin-2-one | Calc'd 475.2452, found 475.2463 |
| 66-6 | 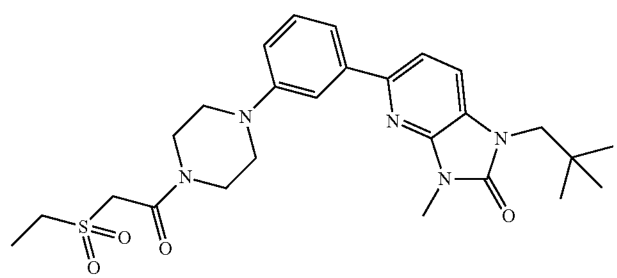 [SMILES: CCS(=O)(=O)CC(=O)N1CCN(c2cccc(-c3ccc4c(n3)n(C)c(=O)n4CC(C)(C)C)c2)CC1] | 1-(2,2-dimethylpropyl)-5-(3-{4-[(ethylsulfonyl)acetyl]piperazin-1-yl}phenyl)-3-methyl-1,3-dihydro-2H-imidazo[4,5-b]pyridin-2-one | Calc'd 514.2483, found 514.2475 |
| 66-7 | 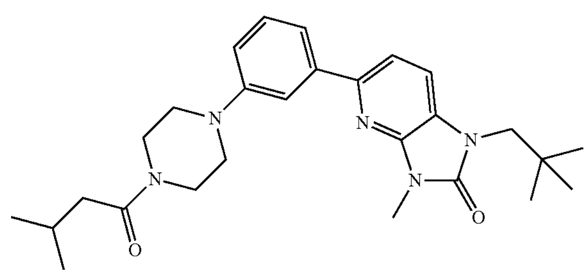 [SMILES: CC(C)CC(=O)N1CCN(c2cccc(-c3ccc4c(n3)n(C)c(=O)n4CC(C)(C)C)c2)CC1] | 1-(2,2-dimethylpropyl)-3-methyl-5-{3-[4-(3-methylbutanoyl)piperazin-1-yl]phenyl}-1,3-dihydro-2H-imidazo[4,5-b]pyridin-2-one | Calc'd 464.3020, found 464.3023 |
| 66-8 | 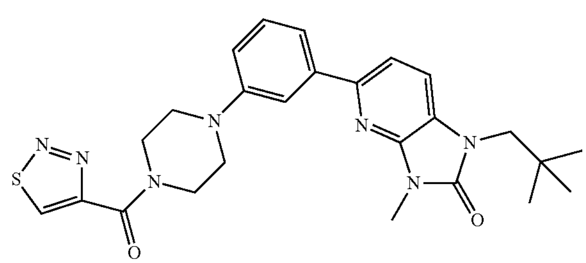 [SMILES: Cn1c(=O)n(CC(C)(C)C)c2ccc(-c3cccc(N4CCN(C(=O)c5csnn5)CC4)c3)nc21] | 1-(2,2-dimethylpropyl)-3-methyl-5-{3-[4-(1,2,3-thiadiazol-4-ylcarbonyl)piperazin-1-yl]phenyl}-1,3-dihydro-2H-imidazo[4,5-b]pyridin-2-one | Calc'd 492.2176, found 492.2173 |

TABLE 31-continued

The following compounds were prepared from 66-2 by a reaction sequence analogous to that illustrated in Scheme 66.

| Cmpd | Structure | IUPAC Name | Exact Mass [M + H]+ |
|---|---|---|---|
| 66-9 | 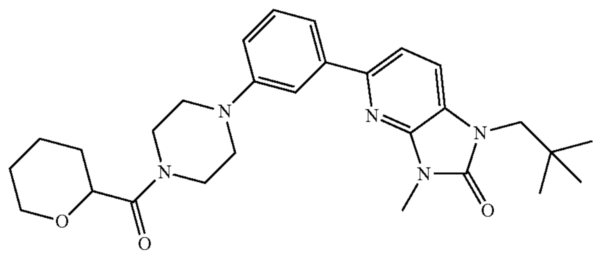 [SMILES: Cn1c(=O)n(CC(C)(C)C)c2ccc(-c3cccc(N4CCN(C(=O)C5CCCCO5)CC4)c3)nc21] | 1-(2,2-dimethylpropyl)-3-methyl-5-{3-[4-(tetrahydro-2H-pyran-2-ylcarbonyl)piperazin-1-yl]phenyl}-1,3-dihydro-2H-imidazo[4,5-b]pyridin-2-one | Calc'd 492.2969, found 492.2965 |
| 66-10 | 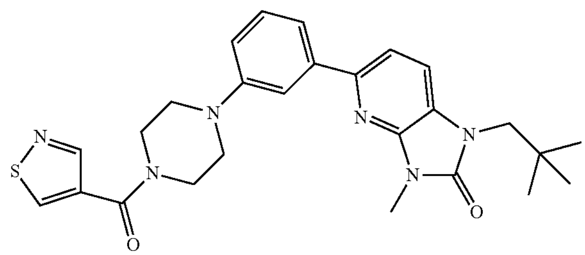 | 1-(2,2-dimethylpropyl)-5-{3-[4-(isothiazol-4-ylcarbonyl)piperazin-1-yl]phenyl}-3-methyl-1,3-dihydro-2H-imidazo[4,5-b]pyridin-2-one | Calc'd 491.2224, found 491.2215 |
| 66-11 | 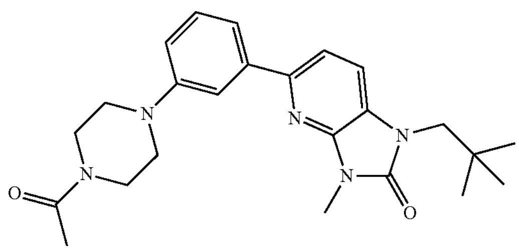 [SMILES: CC(=O)N1CCN(c2cccc(-c3ccc4c(n3)n(C)c(=O)n4CC(C)(C)C)c2)CC1] | 5-[3-(4-acetylpiperazin-1-yl)phenyl]-1-(2,2-dimethylpropyl)-3-methyl-1,3-dihydro-2H-imidazo[4,5-b]pyridin-2-one | Calc'd 422.2551, found 422.2544 |
| 66-12 | 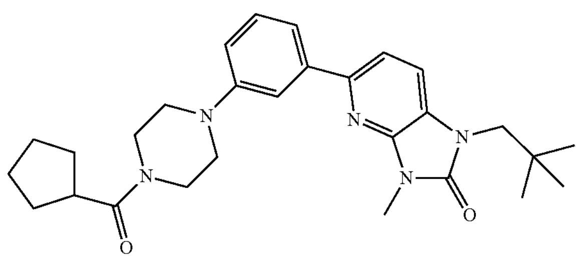 [SMILES: Cn1c(=O)n(CC(C)(C)C)c2ccc(-c3cccc(N4CCN(C(=O)C5CCCC5)CC4)c3)nc21] | 5-{3-[4-(cyclopentylcarbonyl)piperazin-1-yl]phenyl}-1-(2,2-dimethylpropyl)-3-methyl-1,3-dihydro-2H-imidazo[4,5-b]pyridin-2-one | Calc'd 476.3020, found 476.3014 |
| 66-13 | 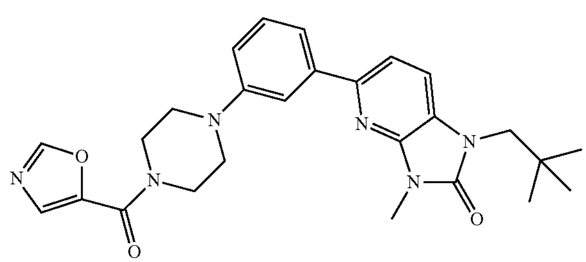 [SMILES: Cn1c(=O)n(CC(C)(C)C)c2ccc(-c3cccc(N4CCN(C(=O)c5cnco5)CC4)c3)nc21] | 1-(2,2-dimethylpropyl)-3-methyl-5-{3-[4-(1,3-oxazol-5-ylcarbonyl)piperazin-1-yl]phenyl}-1,3-dihydro-2H-imidazo[4,5-b]pyridin-2-one | Calc'd 475.2452, found 475.2445 |
| 66-14 | 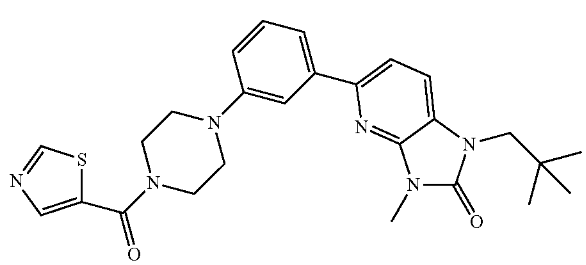 [SMILES: Cn1c(=O)n(CC(C)(C)C)c2ccc(-c3cccc(N4CCN(C(=O)c5cncs5)CC4)c3)nc21] | 1-(2,2-dimethylpropyl)-3-methyl-5-{3-[4-(1,3-thiazol-5-ylcarbonyl)piperazin-1-yl]phenyl}-1,3-dihydro-2H-imidazo[4,5-b]pyridin-2-one | Calc'd 491.2224, found 491.2215 |

TABLE 31-continued

The following compounds were prepared from 66-2 by a reaction sequence analogous to that illustrated in Scheme 66.

| Cmpd | Structure | IUPAC Name | Exact Mass [M + H]+ |
|---|---|---|---|
| 66-15 | 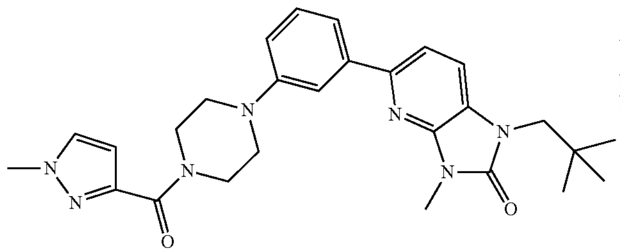 [SMILES: Cn1ccc(C(=O)N2CCN(c3cccc(-c4ccc5c(n4)n(C)c(=O)n5CC(C)(C)C)c3)CC2)n1] | 1-(2,2-dimethylpropyl)-3-methyl-5-(3-{4-[(1-methyl-1H-pyrazol-3-yl)carbonyl]piperazin-1-yl}phenyl)-1,3-dihydro-2H-imidazo[4,5-b]pyridin-2-one | Calc'd 488.2769, found 488.2763 |
| 66-16 | 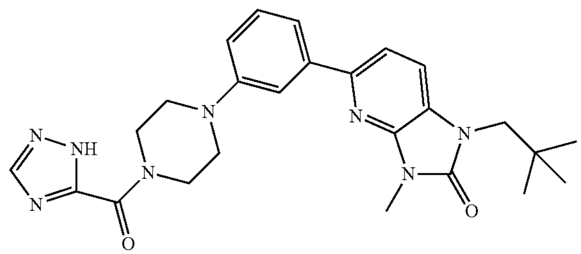 [SMILES: Cn1c(=O)n(CC(C)(C)C)c2ccc(-c3cccc(N4CCN(C(=O)c5ncn[nH]5)CC4)c3)nc21] | 1-(2,2-dimethylpropyl)-3-methyl-5-{3-[4-(1H-1,2,4-triazol-5-ylcarbonyl)piperazin-1-yl]phenyl}-1,3-dihydro-2H-imidazo[4,5-b]pyridin-2-one | Calc'd 475.2564, found 475.2557 |
| 66-17 | 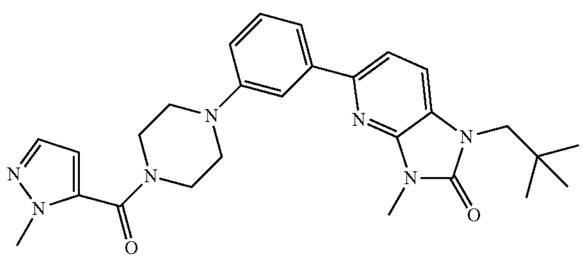 [SMILES: Cn1nccc1C(=O)N1CCN(c2cccc(-c3ccc4c(n3)n(C)c(=O)n4CC(C)(C)C)c2)CC1] | 1-(2,2-dimethylpropyl)-3-methyl-5-(3-{4-[(1-methyl-1H-pyrazol-5-yl)carbonyl]piperazin-1-yl}phenyl)-1,3-dihydro-2H-imidazo[4,5-b]pyridin-2-one | Calc'd 488.2769, found 488.2761 |
| 66-18 | 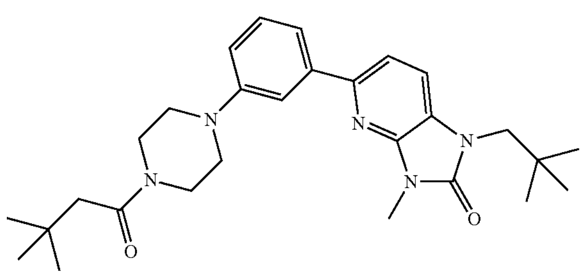 [SMILES: Cn1c(=O)n(CC(C)(C)C)c2ccc(-c3cccc(N4CCN(C(=O)CC(C)(C)C)CC4)c3)nc21] | 5-{3-[4-(3,3-dimethylbutanoyl)piperazin-1-yl]phenyl}-1-(2,2-dimethylpropyl)-3-methyl-1,3-dihydro-2H-imidazo[4,5-b]pyridin-2-one | Calc'd 478.3177, found 478.3174 |
| 66-19 | 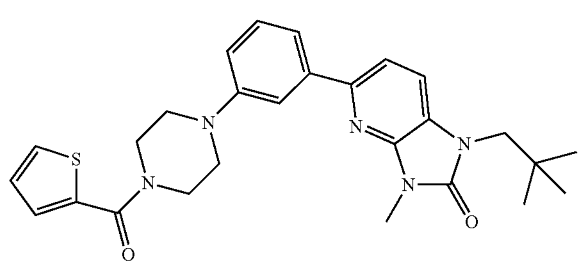 [SMILES: Cn1c(=O)n(CC(C)(C)C)c2ccc(-c3cccc(N4CCN(C(=O)c5cccs5)CC4)c3)nc21] | 1-(2,2-dimethylpropyl)-3-methyl-5-{3-[4-(thiophen-2-ylcarbonyl)piperazin-1-yl]phenyl}-1,3-dihydro-2H-imidazo[4,5-b]pyridin-2-one | Calc'd 490.2271, found 490.2266 |

TABLE 31-continued

The following compounds were prepared from 66-2 by a reaction sequence analogous to that illustrated in Scheme 66.

| Cmpd | Structure | IUPAC Name | Exact Mass [M + H]+ |
|---|---|---|---|
| 66-20 | 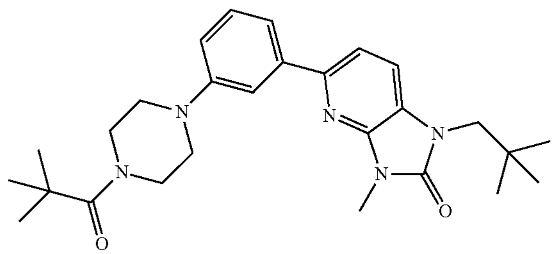 [SMILES: Cn1c(=O)n(CC(C)(C)C)c2ccc(-c3cccc(N4CCN(C(=O)C(C)(C)C)CC4)c3)nc21] | 5-{3-[4-(2,2-dimethylpropanoyl)piperazin-1-yl]phenyl}-1-(2,2-dimethylpropyl)-3-methyl-1,3-dihydro-2H-imidazo[4,5-b]pyridin-2-one | Calc'd 464.3020, found 464.3015 |
| 66-21 | 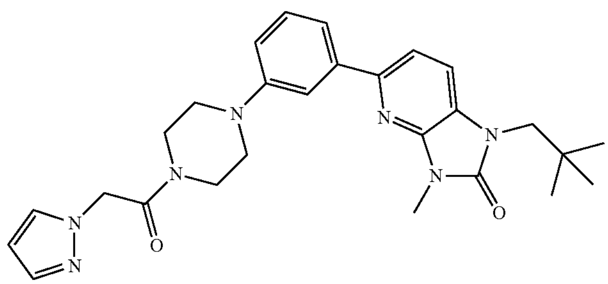 [SMILES: Cn1c(=O)n(CC(C)(C)C)c2ccc(-c3cccc(N4CCN(C(=O)Cn5cccn5)CC4)c3)nc21] | 1-(2,2-dimethylpropyl)-3-methyl-5-{3-[4-(1H-pyrazol-1-ylacetyl)piperazin-1-yl]phenyl}-1,3-dihydro-2H-imidazo[4,5-b]pyridin-2-one | Calc'd 488.2769, found 488.2762 |
| 66-22 | 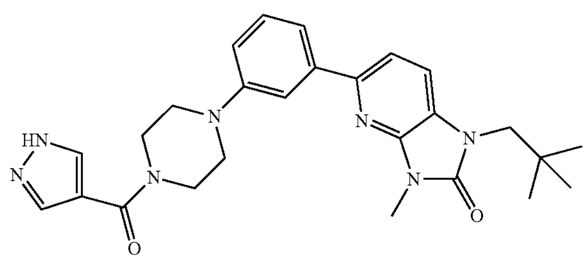 | 1-(2,2-dimethylpropyl)-3-methyl-5-{3-[4-(1H-pyrazol-4-ylcarbonyl)piperazin-1-yl]phenyl}-1,3-dihydro-2H-imidazo[4,5-b]pyridin-2-one | Calc'd 474.2612, found 474.2608 |
| 66-23 | 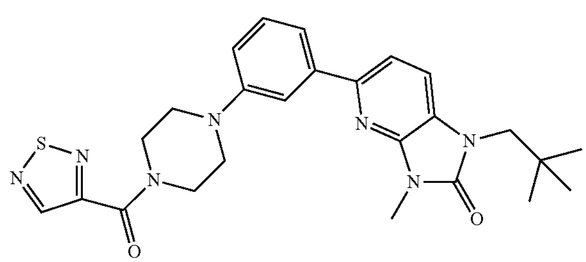 [SMILES: Cn1c(=O)n(CC(C)(C)C)c2ccc(-c3cccc(N4CCN(C(=O)c5cnsn5)CC4)c3)nc21] | 1-(2,2-dimethylpropyl)-3-methyl-5-{3-[4-(1,2,5-thiadiazol-3-ylcarbonyl)piperazin-1-yl]phenyl}-1,3-dihydro-2H-imidazo[4,5-b]pyridin-2-one | Calc'd 492.2176, found 492.2172 |
| 66-24 | 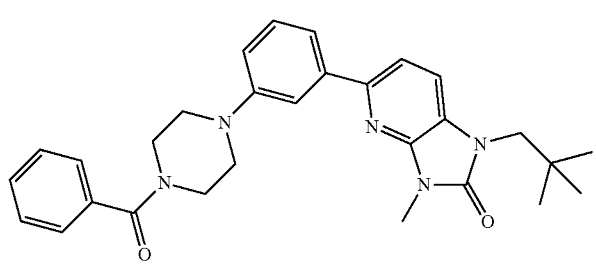 [SMILES: Cn1c(=O)n(CC(C)(C)C)c2ccc(-c3cccc(N4CCN(C(=O)c5ccccc5)CC4)c3)nc21] | 1-(2,2-dimethylpropyl)-3-methyl-5-{3-[4-(phenylcarbonyl)piperazin-1-yl]phenyl}-1,3-dihydro-2H-imidazo[4,5-b]pyridin-2-one | Calc'd 484.2707, found 484.2702 |

TABLE 31-continued

The following compounds were prepared from 66-2 by a reaction sequence analogous to that illustrated in Scheme 66.

| Cmpd | Structure | IUPAC Name | Exact Mass [M + H]+ |
|---|---|---|---|
| 66-25 | 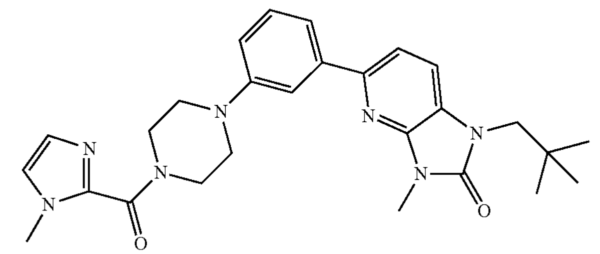 [SMILES: Cn1ccnc1C(=O)N1CCN(c2cccc(-c3ccc4c(n3)n(C)c(=O)n4CC(C)(C)C)c2)CC1] | 1-(2,2-dimethylpropyl)-3-methyl-5-(3-{4-[(1-methyl-1H-imidazol-2-yl)carbonyl]piperazin-1-yl}phenyl)-1,3-dihydro-2H-imidazo[4,5-b]pyridin-2-one | Calc'd 488.2769, found 488.2758 |
| 66-26 | 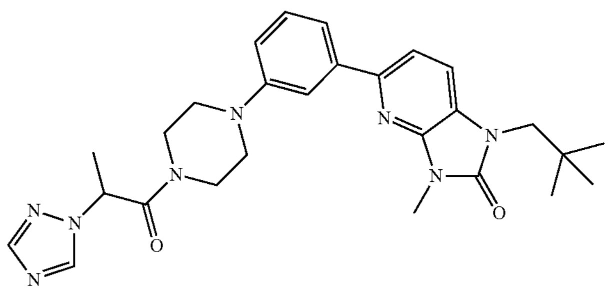 [SMILES: CC(C(=O)N1CCN(c2cccc(-c3ccc4c(n3)n(C)c(=O)n4CC(C)(C)C)c2)CC1)n1cncn1] | 1-(2,2-dimethylpropyl)-3-methyl-5-(3-{4-[2-(1H-1,2,4-triazol-1-yl)propanoyl]piperazin-1-yl}phenyl)-1,3-dihydro-2H-imidazo[4,5-b]pyridin-2-one | Calc'd 503.2877, found 503.2868 |
| 66-27 | 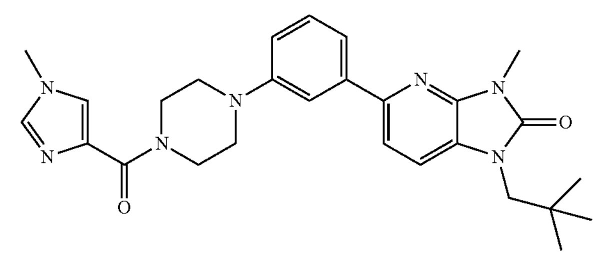 [SMILES: Cn1cnc(C(=O)N2CCN(c3cccc(-c4ccc5c(n4)n(C)c(=O)n5CC(C)(C)C)c3)CC2)c1] | 1-(2,2-dimethylpropyl)-3-methyl-5-(3-{4-[(1-methyl-1H-imidazol-4-yl)carbonyl]piperazin-1-yl}phenyl)-1,3-dihydro-2H-imidazo[4,5-b]pyridin-2-one | Calc'd 488.2769, found 488.2780 |
| 66-28 | 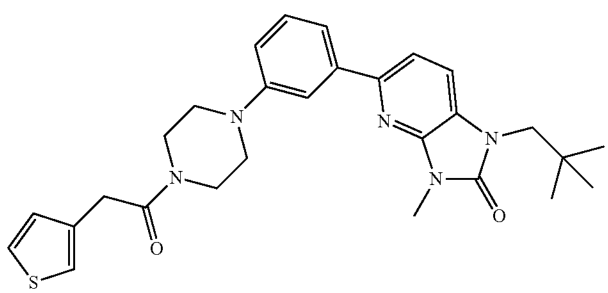 [SMILES: Cn1c(=O)n(CC(C)(C)C)c2ccc(-c3cccc(N4CCN(C(=O)Cc5ccsc5)CC4)c3)nc21] | 1-(2,2-dimethylpropyl)-3-methyl-5-{3-[4-(thiophen-3-ylacetyl)piperazin-1-yl]phenyl}-1,3-dihydro-2H-imidazo[4,5-b]pyridin-2-one | Calc'd 504.2428, found 504.2421 |
| 66-29 | 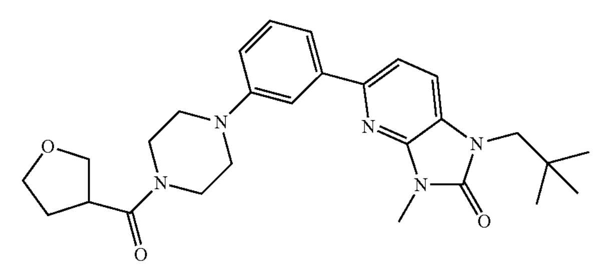 | 1-(2,2-dimethylpropyl)-3-methyl-5-{3-[4-(tetrahydrofuran-3-ylcarbonyl)piperazin-1-yl]phenyl}-1,3-dihydro-2H-imidazo[4,5-b]pyridin-2-one | Calc'd 478.2813, found 478.2809 |

TABLE 31-continued

The following compounds were prepared from 66-2 by a reaction sequence analogous to that illustrated in Scheme 66.

| Cmpd | Structure | IUPAC Name | Exact Mass [M + H]+ |
|---|---|---|---|
| 66-30 | 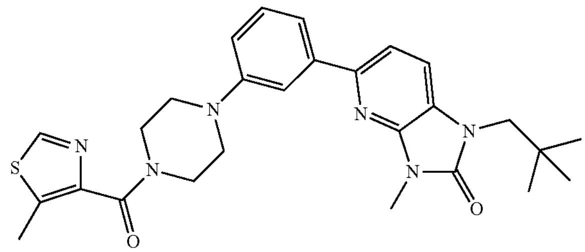 [SMILES: Cc1scnc1C(=O)N1CCN(c2cccc(-c3ccc4c(n3)n(C)c(=O)n4CC(C)(C)C)c2)CC1] | 1-(2,2-dimethylpropyl)-3-methyl-5-(3-{4-[(5-methyl-1,3-thiazol-4-yl)carbonyl]piperazin-1-yl}phenyl)-1,3-dihydro-2H-imidazo[4,5-b]pyridin-2-one | Calc'd 505.2380, found 505.2374 |
| 66-31 | 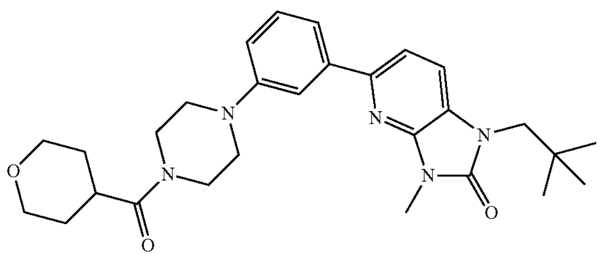 [SMILES: Cn1c(=O)n(CC(C)(C)C)c2ccc(-c3cccc(N4CCN(C(=O)C5CCOCC5)CC4)c3)nc21] | 1-(2,2-dimethylpropyl)-3-methyl-5-{3-[4-(tetrahydro-2H-pyran-4-ylcarbonyl)piperazin-1-yl]phenyl}-1,3-dihydro-2H-imidazo[4,5-b]pyridin-2-one | Calc'd 492.2969, found 492.2964 |
| 66-32 | 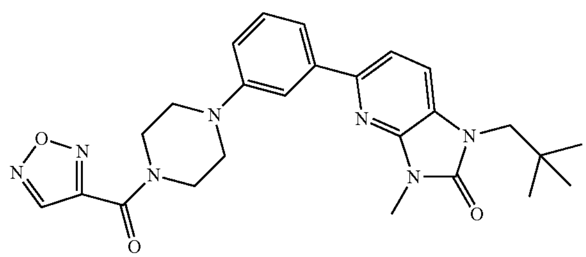 | 1-(2,2-dimethylpropyl)-3-methyl-5-{3-[4-(1,2,5-oxadiazol-3-ylcarbonyl)piperazin-1-yl]phenyl}-1,3-dihydro-2H-imidazo[4,5-b]pyridin-2-one | Calc'd 476.2405, found 476.2398 |
| 66-33 | 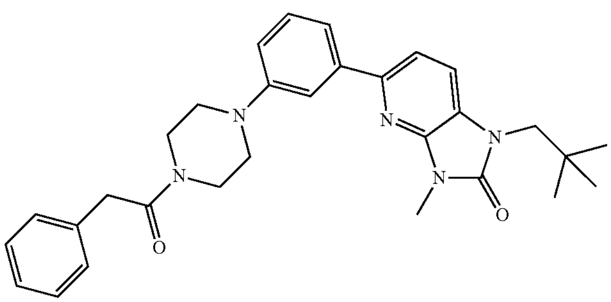 [SMILES: Cn1c(=O)n(CC(C)(C)C)c2ccc(-c3cccc(N4CCN(C(=O)Cc5ccccc5)CC4)c3)nc21] | 1-(2,2-dimethylpropyl)-3-methyl-5-{3-[4-(phenylacetyl)piperazin-1-yl]phenyl}-1,3-dihydro-2H-imidazo[4,5-b]pyridin-2-one | Calc'd 498.2864, found 498.2858 |

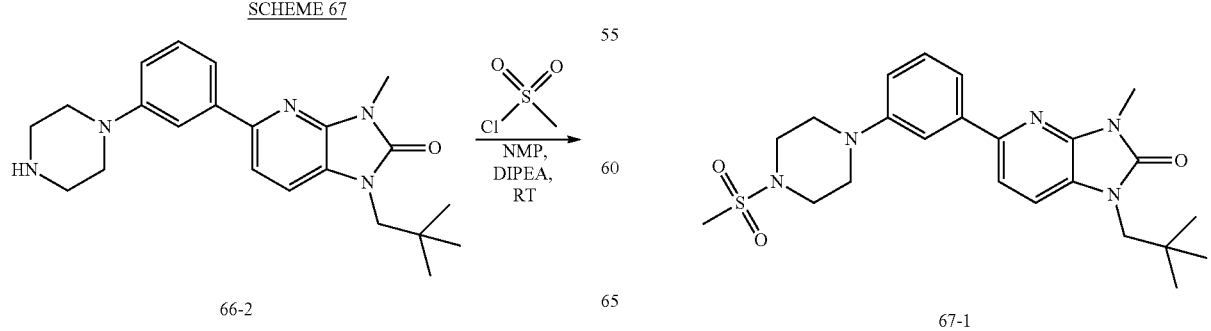

SCHEME 67

1-(2,2-dimethylpropyl)-3-methyl-5-{3-[4-(methyl-sulfonyl)piperazin-1-yl]phenyl}-1,3-dihydro-2H-imidazo[4,5-b]pyridin-2-one (67-1)

Prepared from 66-2 according to the procedure reported in Scheme 21. HRMS (M+H)+: observed=458.2219, calculated=458.2220.

2-fluoroethyl 4-{3-[1-(2,2-dimethylpropyl)-3-methyl-2-oxo-2,3-dihydro-1H-imidazo[4,5-b]pyridin-5-yl]phenyl}piperazine-1-carboxylate (68-1)

Prepared from 66-2 according to the procedure reported in Scheme 23. HRMS (M+H)+: observed=470.2573, calculated=470.2562.

TABLE 32

The following compounds were prepared from 69-2 by a reaction sequence analogous to that illustrated in Scheme 67.

| Cmpd | Structure | IUPAC Name | Exact Mass [M + H]+ |
|---|---|---|---|
| 67-2 | 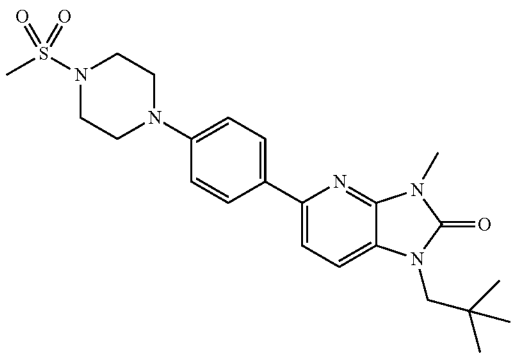 [SMILES: Cn1c(=O)n(CC(C)(C)C)c2ccc(-c3ccc(N4CCN(S(C)(=O)=O)CC4)cc3)nc21] | 1-(2,2-dimethylpropyl)-3-methyl-5-{4-[4-(methylsulfonyl)piperazin-1-yl]phenyl}-1,3-dihydro-2H-imidazo[4,5-b]pyridin-2-one | Calc'd 458.2220, found 458.2218 |

SCHEME 68

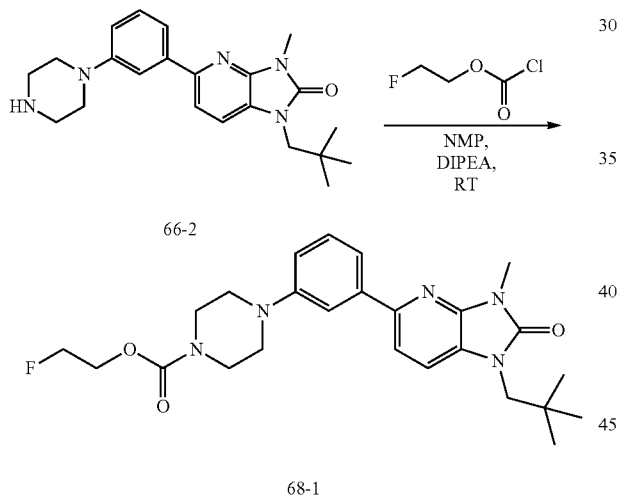

TABLE 33

The following compounds were prepared from 66-2 by a reaction sequence analogous to that illustrated in Scheme 68.

| Cmpd | Structure | IUPAC Name | Exact Mass [M + H]+ |
|---|---|---|---|
| 68-2 | 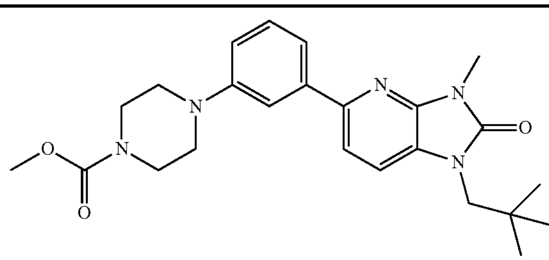 | methyl 4-{3-[1-(2,2-dimethylpropyl)-3-methyl-2-oxo-2,3-dihydro-1H-imidazo[4,5-b]pyridin-5-yl]phenyl}piperazine-1-carboxylate | Calc'd 438.2500, found 438.2493 |

SCHEME 69
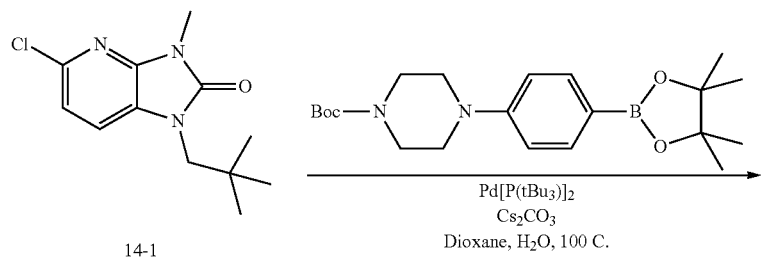
14-1
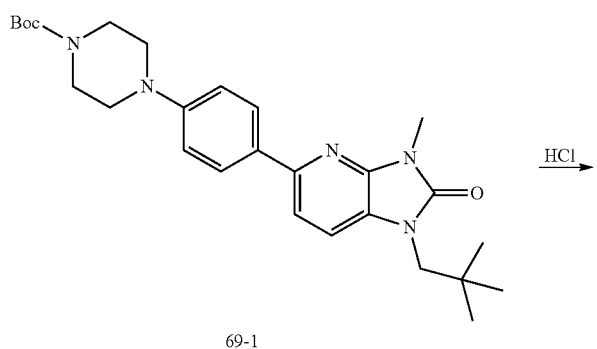
69-1
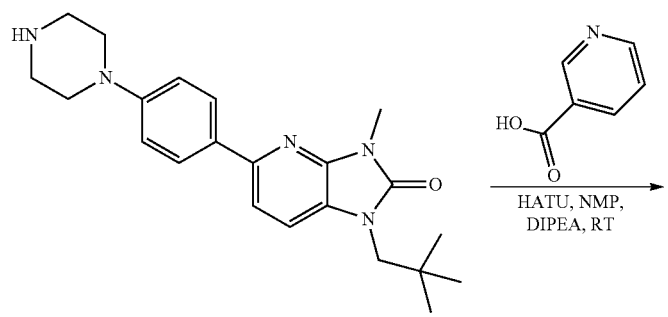
69-2
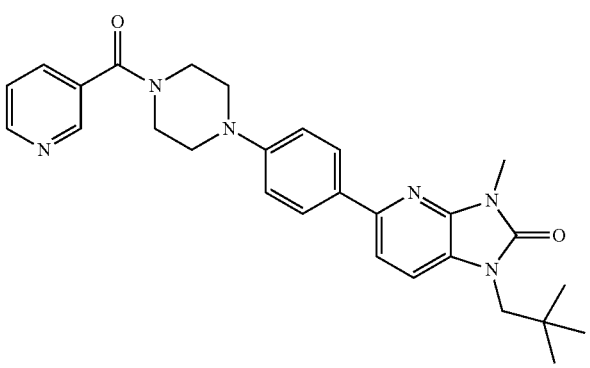
69-3

1-(2,2-dimethylpropyl)-3-methyl-5-{4-[4-(pyridin-3-ylcarbonyl)piperazin-1-yl]phenyl}-1,3-dihydro-2H-imidazo[4,5-b]pyridin-2-one (69-3)

Prepared from 69-2 according to the procedures reported in Scheme 3. HRMS (M+H)+: observed=485.2652, calculated=485.2660.

TABLE 34

The following compounds were prepared from 69-2 by a reaction sequence analogous to that illustrated in Scheme 69.

| Cmpd | Structure | IUPAC Name | Exact Mass [M + H]+ |
|---|---|---|---|
| 69-4 | 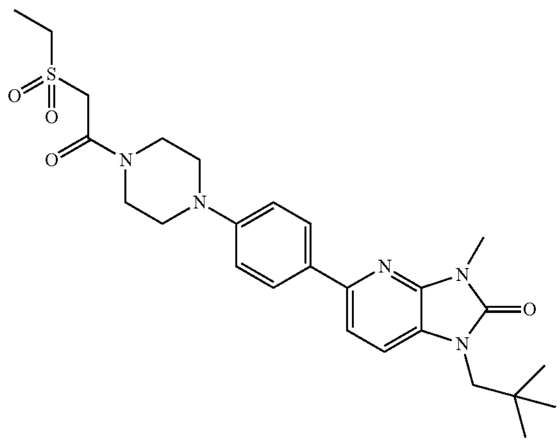 [SMILES: CCS(=O)(=O)CC(=O)N1CCN(c2ccc(-c3ccc4c(n3)n(C)c(=O)n4CC(C)(C)C)cc2)CC1] | 1-(2,2-dimethylpropyl)-5-(4-{4-[(ethylsulfonyl)acetyl]piperazin-1-yl}phenyl)-3-methyl-1,3-dihydro-2H-imidazo[4,5-b]pyridin-2-one | Calc'd 514.2483, found 514.2470 |
| 69-5 | 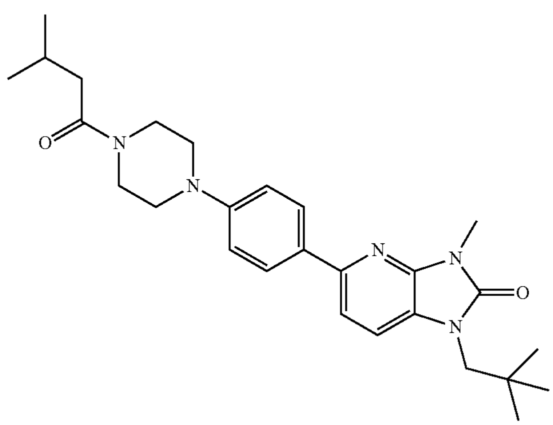 [SMILES: CC(C)CC(=O)N1CCN(c2ccc(-c3ccc4c(n3)n(C)c(=O)n4CC(C)(C)C)cc2)CC1] | 1-(2,2-dimethylpropyl)-3-methyl-5-{4-[4-(3-methylbutanoyl)piperazin-1-yl]phenyl}-1,3-dihydro-2H-imidazo[4,5-b]pyridin-2-one | Calc'd 464.3020, found 464.3014 |
| 69-6 | 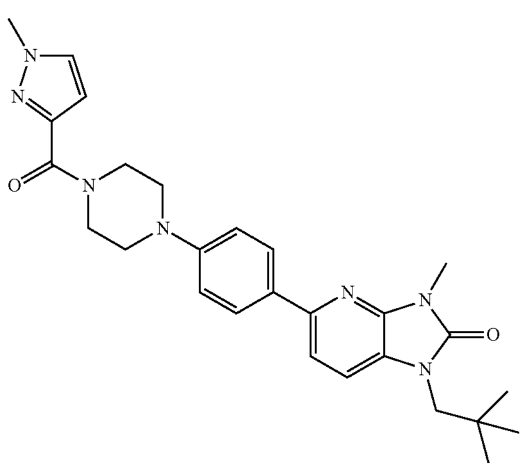 [SMILES: Cn1ccc(C(=O)N2CCN(c3ccc(-c4ccc5c(n4)n(C)c(=O)n5CC(C)(C)C)cc3)CC2)n1] | 1-(2,2-dimethylpropyl)-3-methyl-5-(4-{4-[(1-methyl-1H-pyrazol-3-yl)carbonyl]piperazin-1-yl}phenyl)-1,3-dihydro-2H-imidazo[4,5-b]pyridin-2-one | Calc'd 488.2769, found 488.2773 |

TABLE 34-continued

The following compounds were prepared from 69-2 by a reaction sequence analogous to that illustrated in Scheme 69.

| Cmpd | Structure | IUPAC Name | Exact Mass [M + H]+ |
|---|---|---|---|
| 69-7 | 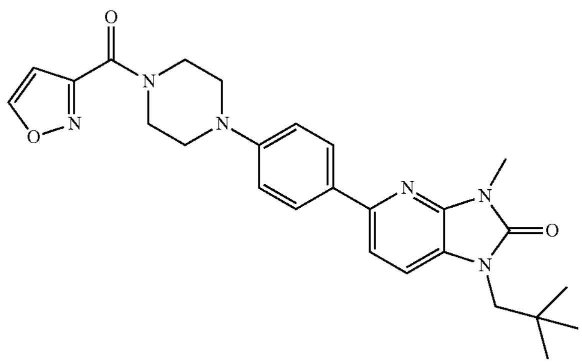 [SMILES: Cn1c(=O)n(CC(C)(C)C)c2ccc(-c3ccc(N4CCN(C(=O)c5ccon5)CC4)cc3)nc21] | 1-(2,2-dimethylpropyl)-5-{4-[4-(isoxazol-3-ylcarbonyl)piperazin-1-yl]phenyl}-3-methyl-1,3-dihydro-2H-imidazo[4,5-b]pyridin-2-one | Calc'd 475.2452, found 475.2447 |
| 69-8 | 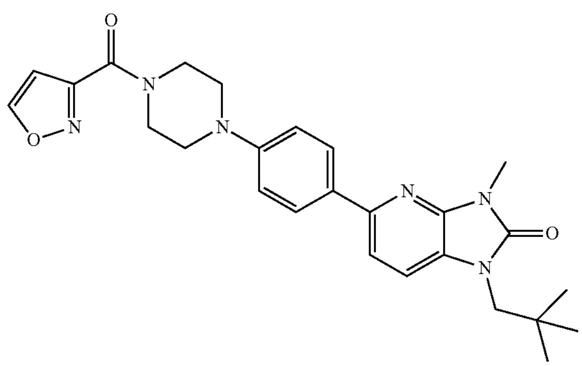 [SMILES: Cn1c(=O)n(CC(C)(C)C)c2ccc(-c3ccc(N4CCN(C(=O)c5ccon5)CC4)cc3)nc21] | 1-(2,2-dimethylpropyl)-5-{4-[4-(isoxazol-3-ylcarbonyl)piperazin-1-yl]phenyl}-3-methyl-1,3-dihydro-2H-imidazo[4,5-b]pyridin-2-one | Calc'd 475.2452, found 475.2444 |
| 69-9 | 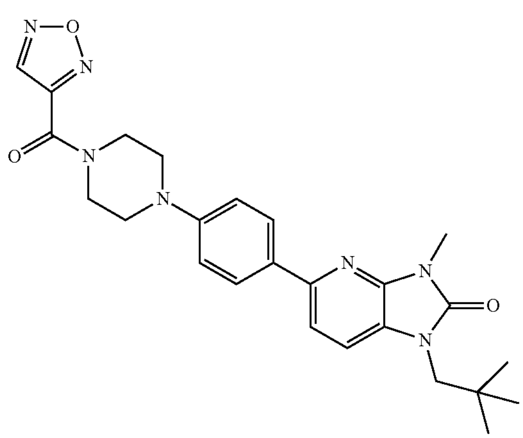 [SMILES: Cn1c(=O)n(CC(C)(C)C)c2ccc(-c3ccc(N4CCN(C(=O)c5cnon5)CC4)cc3)nc21] | 1-(2,2-dimethylpropyl)-3-methyl-5-{4-[4-(1,2,5-oxadiazol-3-ylcarbonyl)piperazin-1-yl]phenyl}-1,3-dihydro-2H-imidazo[4,5-b]pyridin-2-one | Calc'd 476.2405, found 476.2393 |

TABLE 34-continued

The following compounds were prepared from 69-2 by a reaction sequence analogous to that illustrated in Scheme 69.

| Cmpd | Structure | IUPAC Name | Exact Mass [M + H]+ |
|---|---|---|---|
| 69-10 | 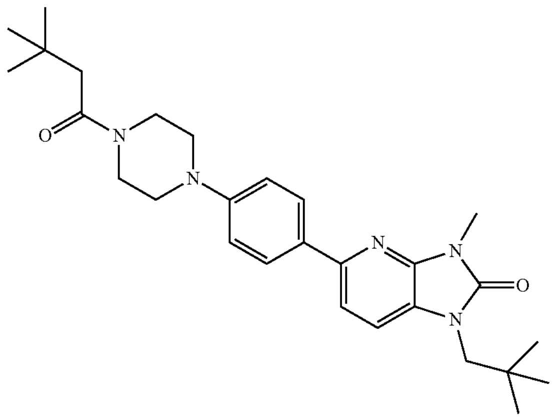 [SMILES: Cn1c(=O)n(CC(C)(C)C)c2ccc(-c3ccc(N4CCN(C(=O)CC(C)(C)C)CC4)cc3)nc21] | 5-{4-[4-(3,3-dimethylbutanoyl)piperazin-1-yl]phenyl}-1-(2,2-dimethylpropyl)-3-methyl-1,3-dihydro-2H-imidazo[4,5-b]pyridin-2-one | Calc'd 478.3177, found 478.3172 |
| 69-11 | 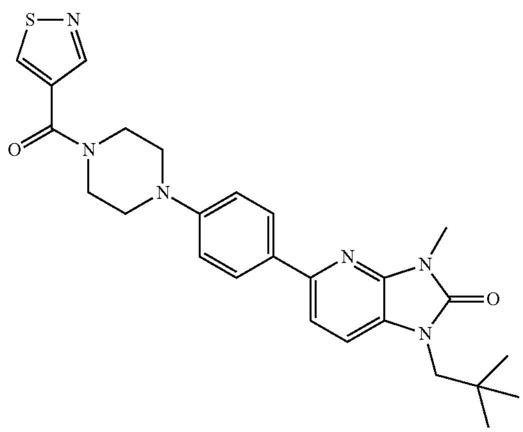 | 1-(2,2-dimethylpropyl)-5-{4-[4-(isothiazol-4-ylcarbonyl)piperazin-1-yl]phenyl}-3-methyl-1,3-dihydro-2H-imidazo[4,5-b]pyridin-2-one | Calc'd 491.2224, found 491.2215 |
| 69-12 | 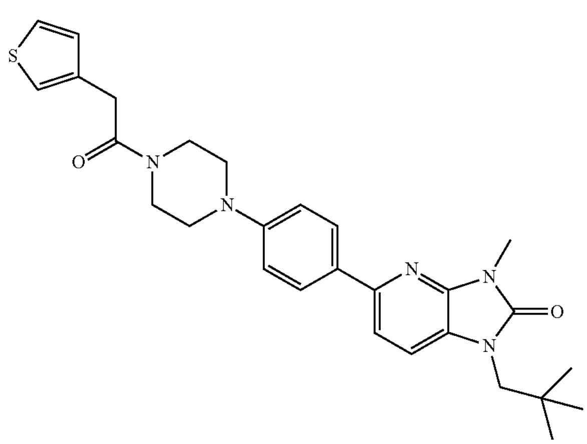 [SMILES: Cn1c(=O)n(CC(C)(C)C)c2ccc(-c3ccc(N4CCN(C(=O)Cc5ccsc5)CC4)cc3)nc21] | 1-(2,2-dimethylpropyl)-3-methyl-5-{4-[4-(thiophen-3-ylacetyl)piperazin-1-yl]phenyl}-1,3-dihydro-2H-imidazo[4,5-b]pyridin-2-one | Calc'd 504.2428, found 504.2428 |

TABLE 34-continued

The following compounds were prepared from 69-2 by a reaction sequence analogous to that illustrated in Scheme 69.

| Cmpd | Structure | IUPAC Name | Exact Mass [M + H]+ |
|---|---|---|---|
| 69-13 | 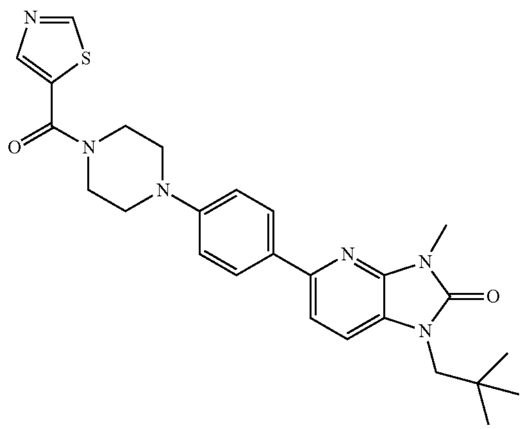 | 1-(2,2-dimethylpropyl)-3-methyl-5-{4-[4-(1,3-thiazol-5-ylcarbonyl)piperazin-1-yl]phenyl}-1,3-dihydro-2H-imidazo[4,5-b]pyridin-2-one | Calc'd 491.2224, found 491.2214 |
| 69-14 | 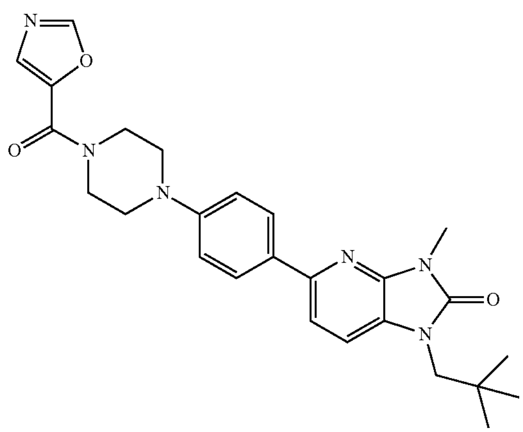 [SMILES: Cn1c(=O)n(CC(C)(C)C)c2ccc(-c3ccc(N4CCN(C(=O)c5cnco5)CC4)cc3)nc21] | 1-(2,2-dimethylpropyl)-3-methyl-5-{4-[4-(1,3-oxazol-5-ylcarbonyl)piperazin-1-yl]phenyl}-1,3-dihydro-2H-imidazo[4,5-b]pyridin-2-one | Calc'd 475.2452, found 475.2445 |
| 69-15 | 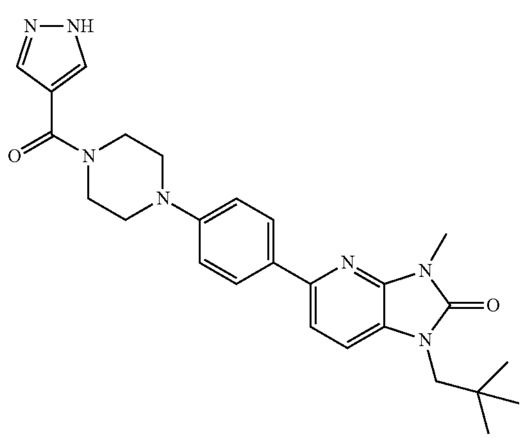 [SMILES: Cn1c(=O)n(CC(C)(C)C)c2ccc(-c3ccc(N4CCN(C(=O)c5cn[nH]c5)CC4)cc3)nc21] | 1-(2,2-dimethylpropyl)-3-methyl-5-{4-[4-(1H-pyrazol-4-ylcarbonyl)piperazin-1-yl]phenyl}-1,3-dihydro-2H-imidazo[4,5-b]pyridin-2-one | Calc'd 474.2612, found 474.2617 |

TABLE 34-continued

The following compounds were prepared from 69-2 by a reaction sequence analogous to that illustrated in Scheme 69.

| Cmpd | Structure | IUPAC Name | Exact Mass [M + H]+ |
|---|---|---|---|
| 69-16 | 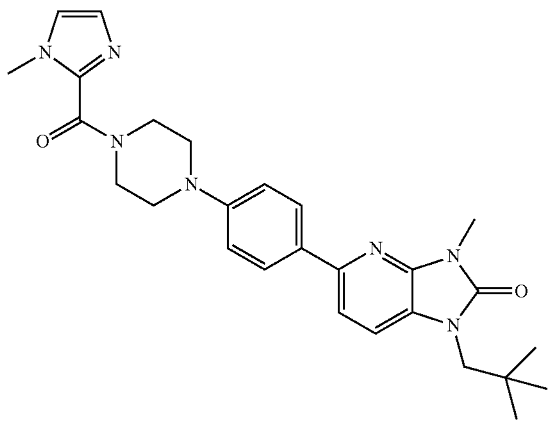 [SMILES: Cn1ccnc1C(=O)N1CCN(c2ccc(-c3ccc4c(n3)n(C)c(=O)n4CC(C)(C)C)cc2)CC1] | 1-(2,2-dimethylpropyl)-3-methyl-5-(4-{4-[(1-methyl-1H-imidazol-2-yl)carbonyl]piperazin-1-yl}phenyl)-1,3-dihydro-2H-imidazo[4,5-b]pyridin-2-one | Calc'd 488.2769, found 488.2761 |
| 69-17 | 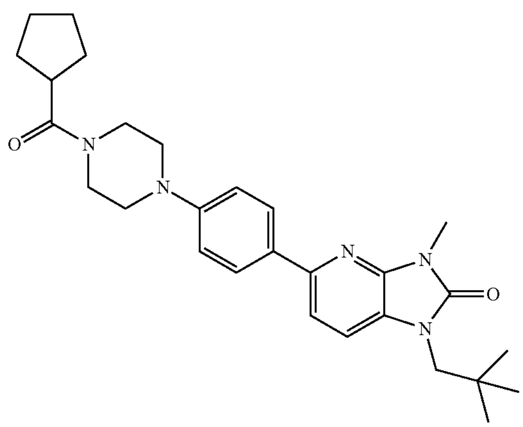 [SMILES: Cn1c(=O)n(CC(C)(C)C)c2ccc(-c3ccc(N4CCN(C(=O)C5CCCC5)CC4)cc3)nc21] | 5-{4-[4-(cyclopentylcarbonyl)piperazin-1-yl]phenyl}-1-(2,2-dimethylpropyl)-3-methyl-1,3-dihydro-2H-imidazo[4,5-b]pyridin-2-one | Calc'd 476.3020, found 476.3014 |
| 69-18 | 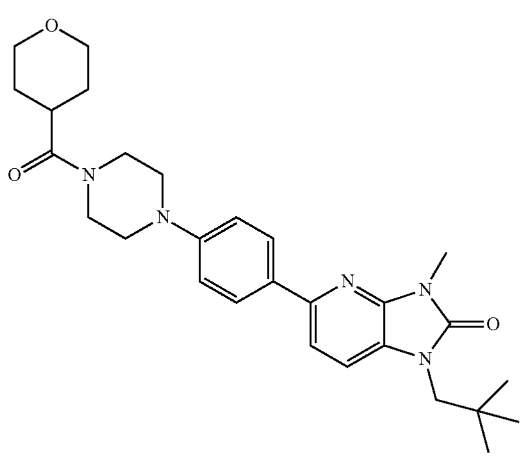 [SMILES: Cn1c(=O)n(CC(C)(C)C)c2ccc(-c3ccc(N4CCN(C(=O)C5CCOCC5)CC4)cc3)nc21] | 1-(2,2-dimethylpropyl)-3-methyl-5-{4-[4-(tetrahydro-2H-pyran-4-ylcarbonyl)piperazin-1-yl]phenyl}-1,3-dihydro-2H-imidazo[4,5-b]pyridin-2-one | Calc'd 492.2969, found 492.2966 |

TABLE 34-continued

The following compounds were prepared from 69-2 by a reaction sequence
analogous to that illustrated in Scheme 69.

| Cmpd | Structure | IUPAC Name | Exact Mass [M + H]+ |
|---|---|---|---|
| 69-19 | 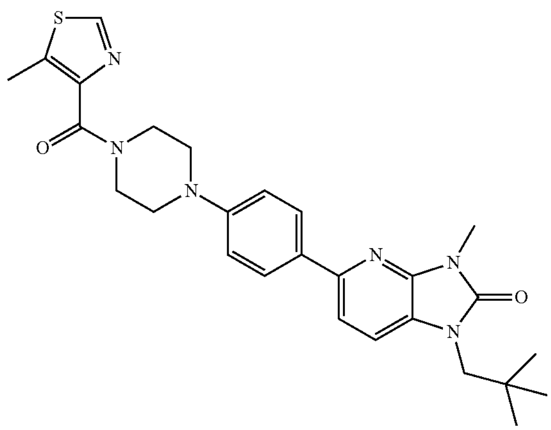 [SMILES: Cc1scnc1C(=O)N1CCN(c2ccc(-c3ccc4c(n3)n(C)c(=O)n4CC(C)(C)C)cc2)CC1] | 1-(2,2-dimethylpropyl)-3-methyl-5-(4-{4-[(5-methyl-1,3-thiazol-4-yl)carbonyl]piperazin-1-yl}phenyl)-1,3-dihydro-2H-imidazo[4,5-b]pyridin-2-one | Calc'd 505.2380, found 505.2376 |
| 69-20 | 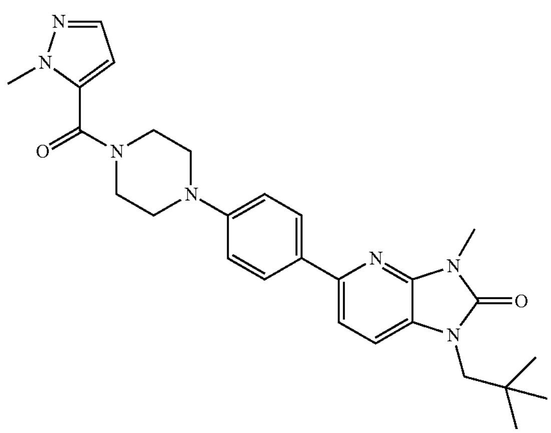 [SMILES: Cn1nccc1C(=O)N1CCN(c2ccc(-c3ccc4c(n3)n(C)c(=O)n4CC(C)(C)C)cc2)CC1] | 1-(2,2-dimethylpropyl)-3-methyl-5-(4-{4-[(1-methyl-1H-pyrazol-5-yl)carbonyl]piperazin-1-yl}phenyl)-1,3-dihydro-2H-imidazo[4,5-b]pyridin-2-one | Calc'd 488.2769, found 488.2758 |
| 69-21 | 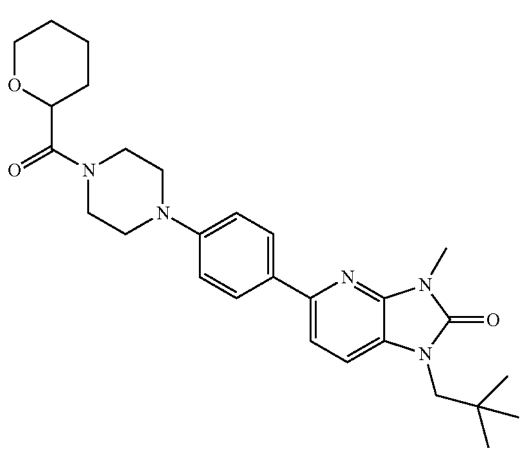 [SMILES: Cn1c(=O)n(CC(C)(C)C)c2ccc(-c3ccc(N4CCN(C(=O)C5CCCCO5)CC4)cc3)nc21] | 1-(2,2-dimethylpropyl)-3-methyl-5-{4-[4-(tetrahydro-2H-pyran-2-ylcarbonyl)piperazin-1-yl]phenyl}-1,3-dihydro-2H-imidazo[4,5-b]pyridin-2-one | Calc'd 492.2969, found 492.2969 |

TABLE 34-continued

The following compounds were prepared from 69-2 by a reaction sequence analogous to that illustrated in Scheme 69.

| Cmpd | Structure | IUPAC Name | Exact Mass [M + H]+ |
|---|---|---|---|
| 69-22 | 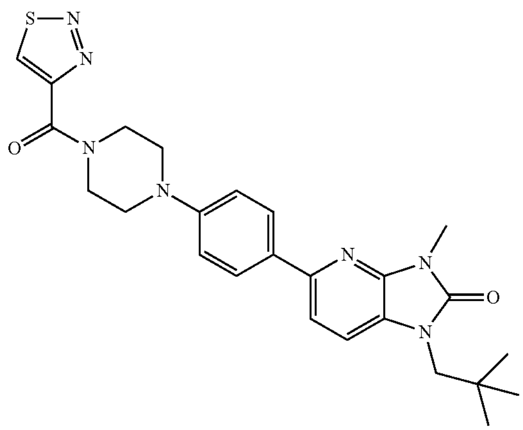 [SMILES: Cn1c(=O)n(CC(C)(C)C)c2ccc(-c3ccc(N4CCN(C(=O)c5csnn5)CC4)cc3)nc21] | 1-(2,2-dimethylpropyl)-3-methyl-5-{4-[4-(1,2,3-thiadiazol-4-ylcarbonyl)piperazin-1-yl]phenyl}-1,3-dihydro-2H-imidazo[4,5-b]pyridin-2-one | Calc'd 492.2176, found 492.2175 |
| 69-23 | 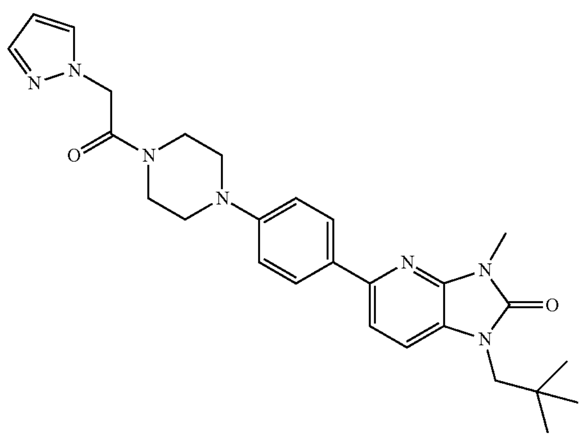 [SMILES: Cn1c(=O)n(CC(C)(C)C)c2ccc(-c3ccc(N4CCN(C(=O)Cn5cccn5)CC4)cc3)nc21] | 1-(2,2-dimethylpropyl)-3-methyl-5-{4-[4-(1H-pyrazol-1-ylacetyl)piperazin-1-yl]phenyl}-1,3-dihydro-2H-imidazo[4,5-b]pyridin-2-one | Calc'd 488.2769, found 488.2761 |
| 69-24 | 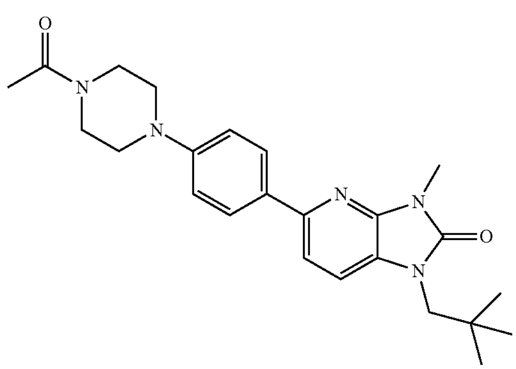 [SMILES: CC(=O)N1CCN(c2ccc(-c3ccc4c(n3)n(C)c(=O)n4CC(C)(C)C)cc2)CC1] | 5-[4-(4-acetylpiperazin-1-yl)phenyl]-1-(2,2-dimethylpropyl)-3-methyl-1,3-dihydro-2H-imidazo[4,5-b]pyridin-2-one | Calc'd 422.2551, found 422.2543 |

TABLE 34-continued

The following compounds were prepared from 69-2 by a reaction sequence analogous to that illustrated in Scheme 69.

| Cmpd | Structure | IUPAC Name | Exact Mass [M + H]+ |
|---|---|---|---|
| 69-25 | 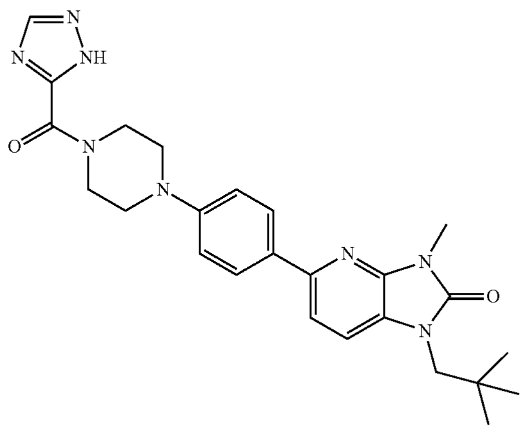 [SMILES: Cn1c(=O)n(CC(C)(C)C)c2ccc(-c3ccc(N4CCN(C(=O)c5ncn[nH]5)CC4)cc3)nc21] | 1-(2,2-dimethylpropyl)-3-methyl-5-{4-[4-(1H-1,2,4-triazol-5-ylcarbonyl)piperazin-1-yl]phenyl}-1,3-dihydro-2H-imidazo[4,5-b]pyridin-2-one | Calc'd 475.2564, found 475.2559 |
| 69-26 | 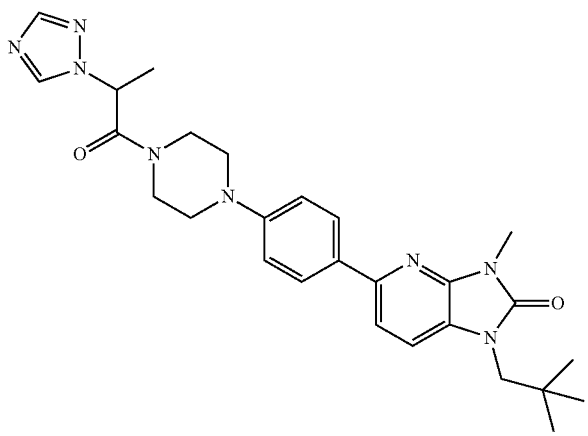 [SMILES: CC(C(=O)N1CCN(c2ccc(-c3ccc4c(n3)n(C)c(=O)n4CC(C)(C)C)cc2)CC1)n1cncn1] | 1-(2,2-dimethylpropyl)-3-methyl-5-(4-{4-[2-(1H-1,2,4-triazol-1-yl)propanoyl]piperazin-1-yl}phenyl)-1,3-dihydro-2H-imidazo[4,5-b]pyridin-2-one | Calc'd 503.2877, found 503.2869 |
| 69-27 | 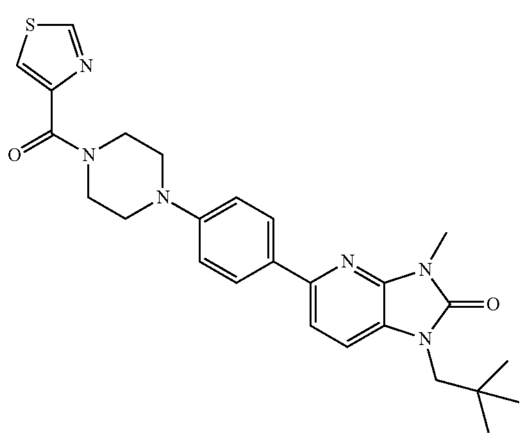 [SMILES: Cn1c(=O)n(CC(C)(C)C)c2ccc(-c3ccc(N4CCN(C(=O)c5cscn5)CC4)cc3)nc21] | 1-(2,2-dimethylpropyl)-3-methyl-5-{4-[4(1,3-thiazol-4-ylcarbonyl)piperazin-1-yl]phenyl}-1,3-dihydro-2H-imidazo[4,5-b]pyridin-2-one | Calc'd 491.2224, found 491.2217 |

TABLE 34-continued

The following compounds were prepared from 69-2 by a reaction sequence analogous to that illustrated in Scheme 69.

| Cmpd | Structure | IUPAC Name | Exact Mass [M + H]+ |
|---|---|---|---|
| 69-28 | 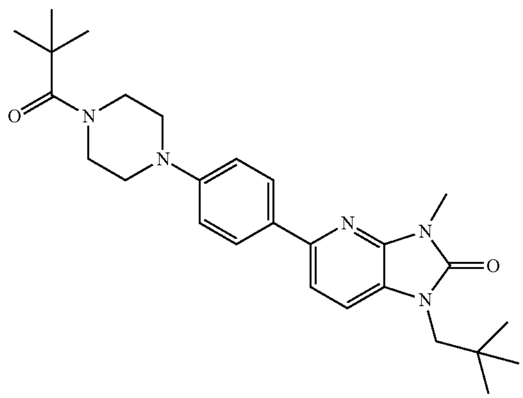 [SMILES: Cn1c(=O)n(CC(C)(C)C)c2ccc(-c3ccc(N4CCN(C(=O)C(C)(C)C)CC4)cc3)nc21] | 5-{4-[4-(2,2-dimethylpropanoyl)piperazin-1-yl]phenyl}-1-(2,2-dimethylpropyl)-3-methyl-1,3-dihydro-2H-imidazo[4,5-b]pyridin-2-one | Calc'd 464.3020, found 464.3013 |
| 69-29 | 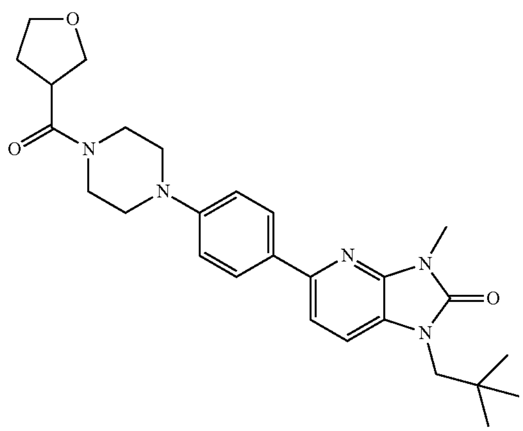 [SMILES: Cn1c(=O)n(CC(C)(C)C)c2ccc(-c3ccc(N4CCN(C(=O)C5CCOC5)CC4)cc3)nc21] | 1-(2,2-dimethylpropyl)-3-methyl-5-{4-[4-(tetrahydrofuran-3-ylcarbonyl)piperazin-1-yl]phenyl}-1,3-dihydro-2H-imidazo[4,5-b]pyridin-2-one | Calc'd 478.2813, found 478.2809 |
| 69-30 | 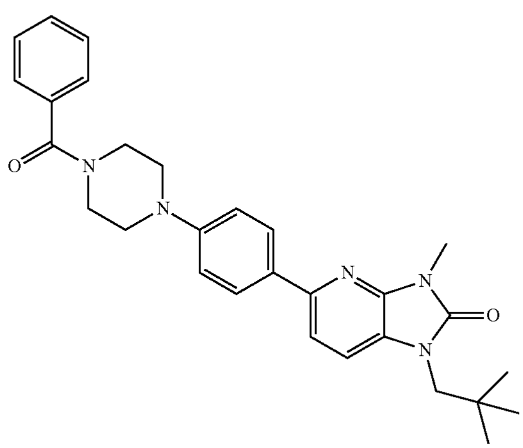 [SMILES: Cn1c(=O)n(CC(C)(C)C)c2ccc(-c3ccc(N4CCN(C(=O)c5ccccc5)CC4)cc3)nc21] | 1-(2,2-dimethylpropyl)-3-methyl-5-{4-[4-(phenylcarbonyl)piperazin-1-yl]phenyl}-1,3-dihydro-2H-imidazo[4,5-b]pyridin-2-one | Calc'd 484.2707, found 484.2695 |

TABLE 34-continued

The following compounds were prepared from 69-2 by a reaction sequence analogous to that illustrated in Scheme 69.

| Cmpd | Structure | IUPAC Name | Exact Mass [M + H]+ |
|---|---|---|---|
| 69-31 | 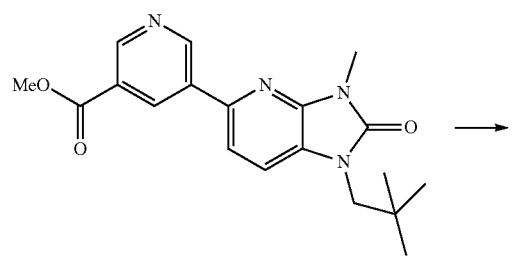 | 1-(2,2-dimethylpropyl)-3-methyl-5-{4-[4-(thiophen-2-ylcarbonyl)piperazin-1-yl]phenyl}-1,3-dihydro-2H-imidazo[4,5-b]pyridin-2-one | Calc'd 490.2271, found 490.2258 |

SCHEME 70

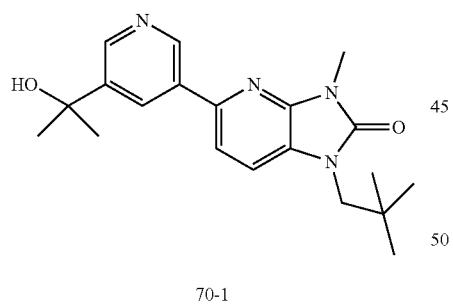

14-43

↓

70-1

1-(2,2-dimethylpropyl)-5-[5-(1-hydroxy-1-methylethyl)pyridin-3-yl]-3-methyl-1,3-dihydro-2H-imidazo[4,5-b]pyridin-2-one (70-1)

Prepared from 14-43 according to the procedures reported in Scheme 3. HRMS (M+H)+: observed=355.2128, calculated=355.2129.

SCHEME 71

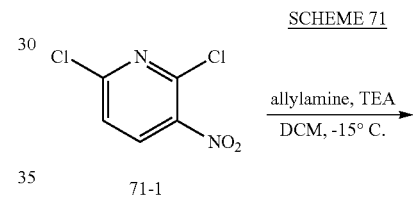

71-1

$\xrightarrow{\text{allylamine, TEA}}{\text{DCM, -15° C.}}$

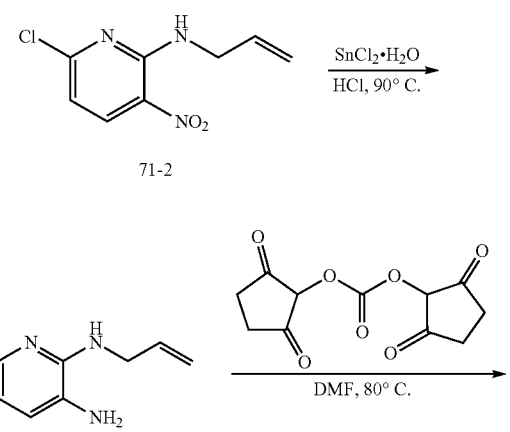

71-2

$\xrightarrow{\text{SnCl}_2\cdot\text{H}_2\text{O}}{\text{HCl, 90° C.}}$ 71-3

$\xrightarrow{\text{DMF, 80° C.}}$

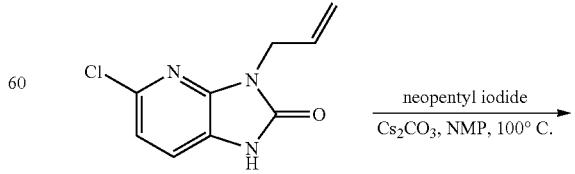

71-4

$\xrightarrow{\text{neopentyl iodide}}{\text{Cs}_2\text{CO}_3, \text{NMP, 100° C.}}$

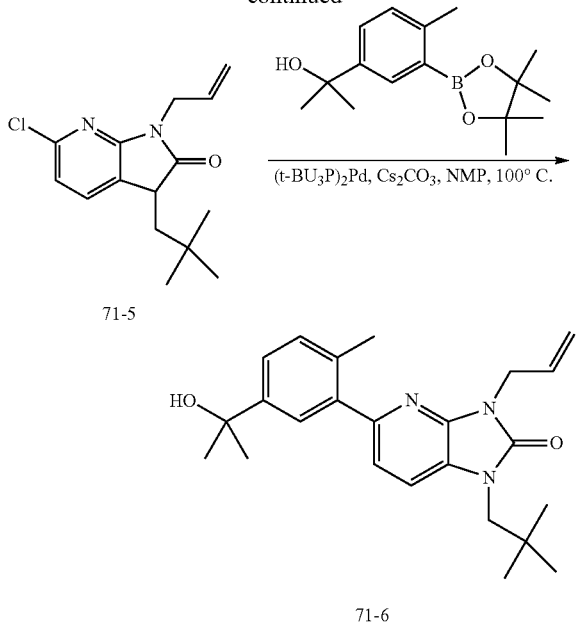

1-(2,2-Dimethylpropyl)-5-[5-(1-hydroxy-1-methylethyl)-2-methylphenyl]-3-prop-2-en-1-yl-1,3-dihydro-2H-imidazo[4,5-b]pyridin-2-one (71-6)

6-Chloro-3-nitro-N-(prop-2-en-1-yl)pyridin-2-amine (71-2)

2,6-Dichloro-3-nitropyridine (71-1, 10 g, 51.8 mmol, 1.0 equiv) was added to anhydrous DCM (207 mL) and cooled to −15° C. TEA (7.57 mL, 53.9 mmol, 1.04 equiv) was then added followed by allyl amine (4.05 mL, 53.9 mmol, 1.04 equiv) over 12 h via syringe pump. Following this duration, the reaction vessel was removed from the −15° C. bath and allowed to gradually warm to RT. After 18 h, the reaction was quenched with 0.2M citric acid (100 mL) and diluted with $CH_2Cl_2$ (40 mL). The layers were separated and the organics were washed an additional time with 1×100 mL 0.2M citric acid. Washed combined organics with 2×100 mL sat. $NaHCO_3$, dried over $Na_2SO_4$, filtered and concentrated to give an orange oil. The crude material was carried onward without further purification. LRMS (M+H)$^+$: observed=214.0, calculated=213.6.

6-Chloro-N-(prop-2-en-1-yl)pyridine-2,3-diamine (71-3)

6-Chloro-3-nitro-N-(prop-2-en-1-yl)pyridin-2-amine (71-2, 11.07 g, 51.8 mmol, 1.0 equiv) was added to concentrated HCl (106 mL) to give a suspension. The resulting reaction contents were cooled to −5° C. Tin(II) chloride dehydrate (70.2 g, 311 mmol, 6.0 equiv) was then added in seven 10-g portions while maintaining an internal temperature below 0° C. Following the addition, the reaction mixture was then transferred to a 90° C. bath. After 1 h at 90° C., the reaction contents were cooled to RT and added dropwise to 10N NaOH (300 mL) at 0° C. with vigorous stirring. Following the addition, the mixture was warmed to RT and stirred for 10 min. The aqueous layer was then extracted with 3×100 mL EtOAc and the combined organics were dried over $Na_2SO_4$, filtered and concentrated to give a thick, purple oil. The crude material was carried onward without further purification. LRMS (M+H)$^+$: observed=189.0, calculated=183.6.

5-Chloro-3-(prop-2-en-1-yl)-1,3-dihydro-2H-imidazo[4,5-b]pyridin-2-one (71-4)

6-Chloro-N-(prop-2-en-1-yl)pyridine-2,3-diamine (71-3, 9.52 g, 51.8 mmol, 1.0 equiv) was added to anhydrous DMF (55 mL) to give a dark purple solution. Bis(2,5-dioxocyclopentyl)carbonate (13.18 g, 51.8 mmol, 1.0 equiv) was added in one portion to give a dark green solution. The resulting reaction mixture was then heated to 80° C. After 18 h, the reaction contents were cooled to RT, diluted with EtOAc (100 mL) and added slowly to saturated aqueous $NaHCO_3$ (200 mL). The layers were separated and the aqueous layer was back-extracted with 3×100 mL EtOAc. The combined organics were dried over $Na_2SO_4$, filtered and concentrated to give a dark purple residue. Purification by normal-phase HPLC provided 5-chloro-3-(prop-2-en-1-yl)-1,3-dihydro-2H-imidazo[4,5-b]pyridin-2-one (71-4) as a tan solid. LRMS (M+H)$^+$: observed=210.0, calculated=209.6.

5-Chloro-1-(2,2-dimethylpropyl)-3-(prop-2-en-1-yl)-1,3-dihydro-2H-imidazo[4,5-b]pyridin-2-one (71-5)

5-Chloro-3-(prop-2-en-1-yl)-1,3-dihydro-2H-imidazo[4,5-b]pyridin-2-one (71-4, 2.37 g, 11.31 mmol, 1.0 equiv) and $Cs_2CO_3$ (18.42 g, 56.6 mmol, 5.0 equiv) were added sequentially to anhydrous NMP (18.6 mL). Neopentyl iodide (2.70 mL, 20.35 mmol, 1.8 equiv) was added dropwise and the resulting mixture was heated to 100° C. for 24 h. Following this duration, the contents were cooled to RT and diluted with EtOAc (50 mL) and saturated aqueous $NaHCO_3$ (50 mL). The layers were separated and the aqueous layer was back-extracted with 3×50 mL EtOAc. The combined organics were dried over $Na_2SO_4$, filtered and concentrated to give a brown semi-solid. Purification by normal-phase HPLC provided 5-chloro-1-(2,2-dimethylpropyl)-3-(prop-2-en-1-yl)-1,3-dihydro-2H-imidazo[4,5-b]pyridin-2-one (71-5) as a white solid. HRMS (M+H)$^+$: observed=280.1207, calculated=280.1211.

1-(2,2-Dimethylpropyl)-5-[5-(1-hydroxy-1-methylethyl)-2-methylphenyl]-3-prop-2-en-1-yl-1,3-dihydro-2H-imidazo[4,5-b]pyridin-2-one (71-6)

5-Chloro-1-(2,2-dimethylpropyl)-3-(prop-2-en-1-yl)-1,3-dihydro-2H-imidazo[4,5-b]pyridin-2-one (71-5, 100 mg, 0.36 mmol, 1.0 equiv), $Cs_2CO_3$ (1.17 g, 3.57 mmol, 10.0 equiv), 2-[4-methyl-3-(4,4,5,5-tetramethyl-1,3,2-dioxaborolan-2-yl)phenyl]propan-2-ol (225 mg, 0.82 mmol, 2.3 equiv), and bis(tri-t-butyl-phosphino)palladium (18.3 mg, 0.04 mmol, 0.1 equiv) were added to anhydrous NMP (4 mL). The resulting suspension was warmed to 100° C. for 20 min in a microwave emitter. Following this duration, the reaction contents were filtered through Celite® and washed with EtOAc (5 mL). The filtrate was then diluted with saturated aqueous $NaHCO_3$ (5 mL). The layers were separated and the aqueous layer was back-extracted with 3×5 mL EtOAc. The combined organics were dried over $Na_2SO_4$, filtered and concentrated to give a brown semi-solid. Purification by reverse-phase HPLC afforded 1-(2,2-dimethylpropyl)-5-[5-(1-hydroxy-1-methylethyl)-2-methylphenyl]-3-prop-2-en-1-yl-1,3-dihydro-2H-imidazo[4,5-b]pyridin-2-one (71-6) as a white solid. HRMS (M+H)$^+$: observed=394.2490, calculated=394.2489.

TABLE 35

The following compounds were prepared from 71-5 by a reaction sequence analogous to that illustrated in Scheme 71.

| Cmpd | Structure | IUPAC Name | Exact Mass [M + H]+ |
|---|---|---|---|
| 71-7 | 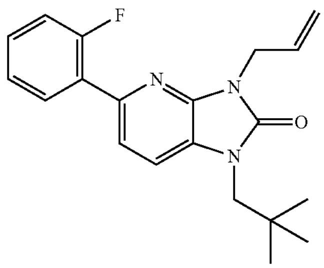 [SMILES: C=CCn1c(=O)n(CC(C)(C)C)c2ccc(-c3ccccc3F)nc21] | 1-(2,2-dimethylpropyl)-5-(2-fluorophenyl)-3-prop-2-en-1-yl-1,3-dihydro-2H-imidazo[4,5-b]pyridin-2-one | Calc'd 340.1820, found 340.1812 |
| 71-8 | 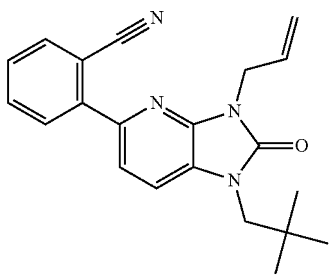 [SMILES: C=CCn1c(=O)n(CC(C)(C)C)c2ccc(-c3ccccc3C#N)nc21] | 2-[1-(2,2-dimethylpropyl)-2-oxo-3-prop-2-en-1-yl-2,3-dihydro-1H-imidazo[4,5-b]pyridin-5-yl]benzonitrile | Calc'd 347.1866, found 347.1858 |
| 871-9 | 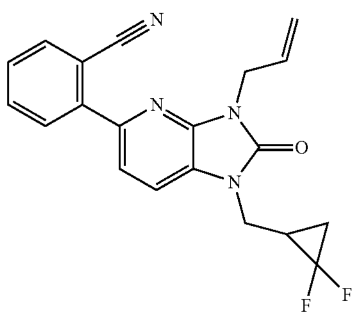 [SMILES: C=CCn1c(=O)n(CC2CC2(F)F)c2ccc(-c3ccccc3C#N)nc21] | 2-{1-[(2,2-difluorocyclopropyl)methyl]-2-oxo-3-prop-2-en-1-yl-2,3-dihydro-1H-imidazo[4,5-b]pyridin-5-yl}benzonitrile | Calc'd 367.1365, found 367.1357 |
| 71-10 | 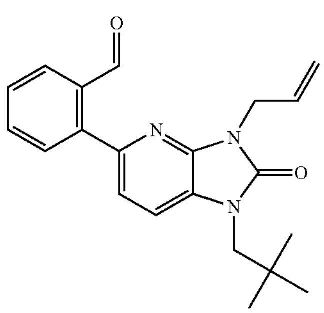 [SMILES: C=CCn1c(=O)n(CC(C)(C)C)c2ccc(-c3ccccc3C=O)nc21] | 2-[1-(2,2-dimethylpropyl)-2-oxo-3-prop-2-en-1-yl-2,3-dihydro-1H-imidazo[4,5-b]pyridin-5-yl]benzaldehyde | Calc'd 350.1863, found 350.1867 |
| 71-11 | 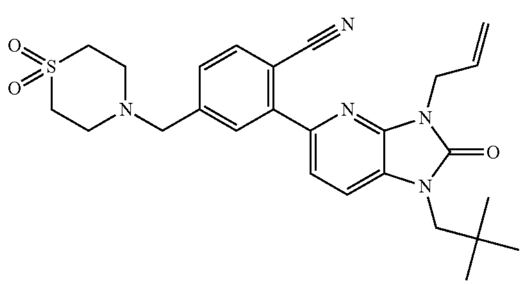 [SMILES: C=CCn1c(=O)n(CC(C)(C)C)c2ccc(-c3cc(CN4CCS(=O)(=O)CC4)ccc3C#N)nc21] | 2-[1-(2,2-dimethylpropyl)-2-oxo-3-prop-2-en-1-yl-2,3-dihydro-1H-imidazo[4,5-b]pyridin-5-yl]-[(1,1-dioxidothiomorpholin-4-yl)methyl]benzonitrile | Calc'd 494.2220, found 494.2210 |

SCHEME 72

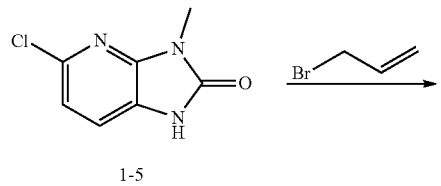

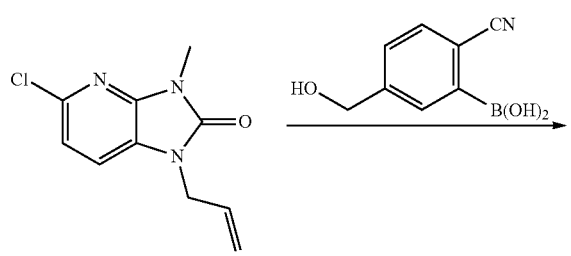

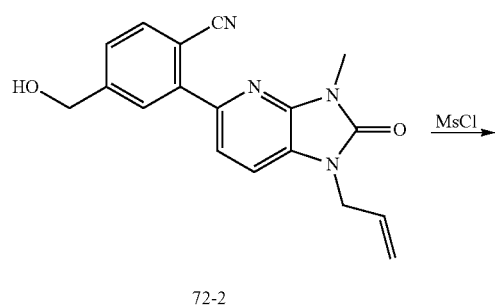

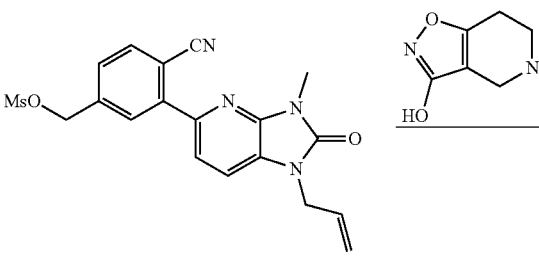

4-[(3-hydroxy-6,7-dihydroisoxazolo[4,5-c]pyridin-5(4H)-yl)methyl]-2-(3-methyl-2-oxo-1-prop-2-en-1-yl-2,3-dihydro-1H-imidazo[4,5-b]pyridin-5-yl)benzonitrile (72-4)

4-[(3-hydroxy-6,7-dihydroisoxazolo[4,5-c]pyridin-5(4H)-yl)methyl]-2-(3-methyl-2-oxo-1-prop-2-en-1-yl-2,3-dihydro-1H-imidazo[4,5-b]pyridin-5-yl)benzonitrile (72-3)

Prepared from 72-1 and 72-2 according to the procedures reported in Scheme 21. HRMS (M+H)$^+$: observed=443.1818, calculated=443.1826.

SCHEME 73

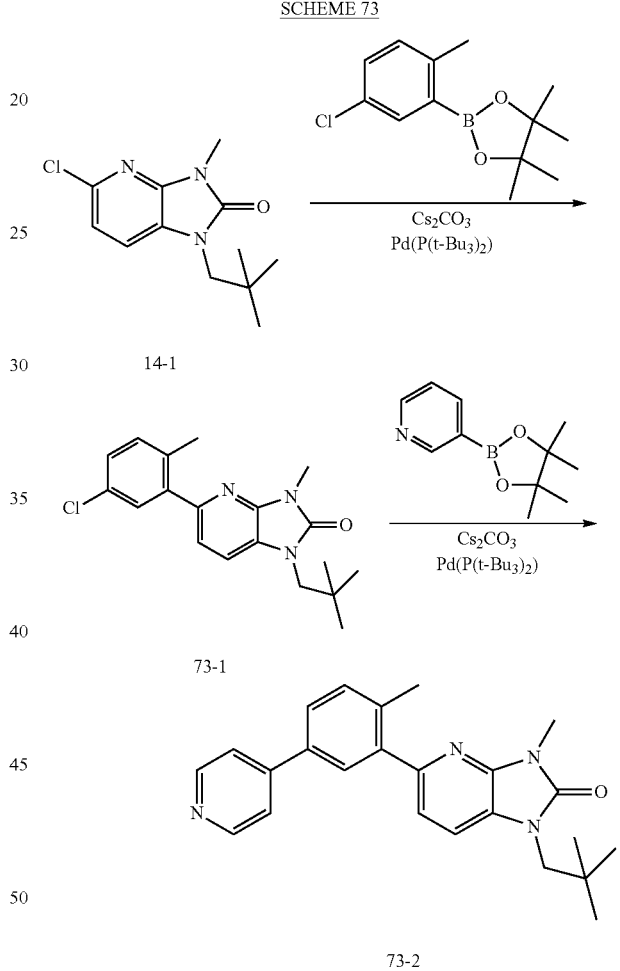

1-(2,2-dimethylpropyl)-3-methyl-5-[2-methyl-5-(pyridin-4-yl)phenyl]-1,3-dihydro-2H-imidazo[4,5-b]pyridin-2-one (73-2)

5-(5-chloro-2-methylphenyl)-1-(2,2-dimethylpropyl)-3-methyl-1,3-dihydro-2H-imidazo[4,5-b]pyridin-2-one (73-1)

Prepared from 14-1 according to the procedures reported in Scheme 14. HRMS (M+H)$^+$: observed=344.8581, calculated=344.8583.

1-(2,2-dimethylpropyl)-3-methyl-5-[2-methyl-5-(pyridin-4-yl)phenyl]-1,3-dihydro-2H-imidazo[4,5-b]pyridin-2-one (73-2)

Prepared from 40-2 according to the procedures reported in Scheme 14. HRMS (M+H)+: observed=387.4971, calculated=387.4972.

TABLE 36

The following compounds were prepared from 73-1 by a reaction sequence analogous to that illustrated in Scheme 73.

| Cmpd | Structure | IUPAC Name | Exact Mass [M + H]+ |
|---|---|---|---|
| 73-4 | 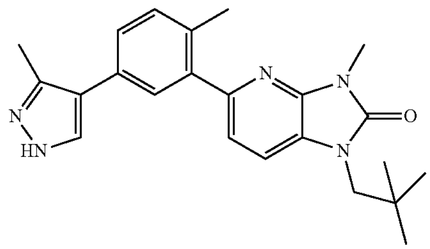 [SMILES: Cc1ccc(-c2c[nH]nc2C)cc1-c1ccc2c(n1)n(C)c(=O)n2CC(C)(C)C] | 1-(2,2-dimethylpropyl)-3-methyl-5-[2-methyl-5-(3-methyl-1H-pyrazol-4-yl)phenyl]-1,3-dihydro-2H-imidazo[4,5-b]pyridin-2-one | Calc'd 390.2118, found 390.2114 |
| 73-5 | 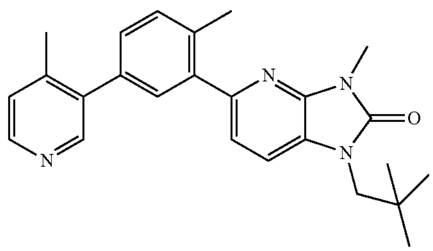 [SMILES: Cc1ccncc1-c1ccc(C)c(-c2ccc3c(n2)n(C)c(=O)n3CC(C)(C)C)c1] | 1-(2,2-dimethylpropyl)-3-methyl-5-[2-methyl-5-(4-methylpyridin-3-yl)phenyl]-1,3-dihydro-2H-imidazo[4,5-b]pyridin-2-one | Calc'd 401.1721, found 401.1717 |
| 73-6 | 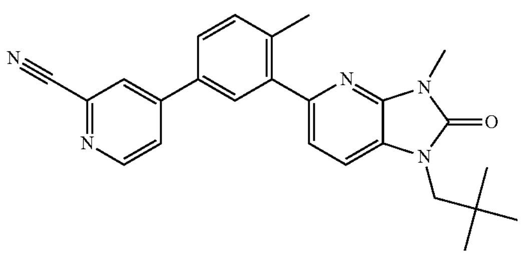 [SMILES: Cc1ccc(-c2ccnc(C#N)c2)cc1-c1ccc2c(n1)n(C)c(=O)n2CC(C)(C)C] | 4-{3-[1-(2,2-dimethylpropyl)-3-methyl-2-oxo-2,3-dihydro-1H-imidazo[4,5-b]pyridin-5-yl]-4-methylphenyl}pyridine-2-carbonitrile | Calc'd 412.1834, found 412.1838 |
| 73-7 | 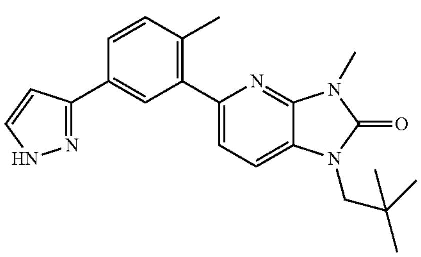 [SMILES: Cc1ccc(-c2cc[nH]n2)cc1-c1ccc2c(n1)n(C)c(=O)n2CC(C)(C)C] | 1-(2,2-dimethylpropyl)-3-methyl-5-[2-methyl-5-(1H-pyrazol-3-yl)phenyl]-1,3-dihydro-2H-imidazo[4,5-b]pyridin-2-one | Calc'd 376.067, found 376.0664 |
| 73-8 | 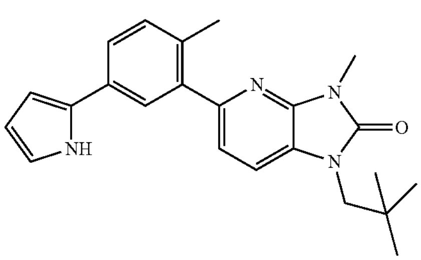 [SMILES: Cc1ccc(-c2ccc[nH]2)cc1-c1ccc2c(n1)n(C)c(=O)n2CC(C)(C)C] | 1-(2,2-dimethylpropyl)-3-methyl-5-[2-methyl-5-(1H-pyrrol-2-yl)phenyl]-1,3-dihydro-2H-imidazo[4,5-b]pyridin-2-one | Calc'd 375.1615, found 375.1599 |

TABLE 36-continued

The following compounds were prepared from 73-1 by a reaction sequence analogous to that illustrated in Scheme 73.

| Cmpd | Structure | IUPAC Name | Exact Mass [M + H]+ |
|---|---|---|---|
| 73-9 | 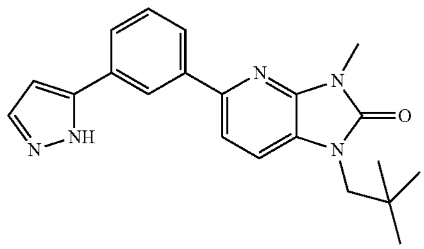 [SMILES: Cn1c(=O)n(CC(C)(C)C)c2ccc(-c3cccc(-c4ccn[nH]4)c3)nc21] | 1-(2,2-dimethylpropyl)-3-methyl-5-[3-(1H-pyrazol-5-yl)phenyl]-1,3-dihydro-2H-imidazo[4,5-b]pridin-2-one | Calc'd 362.0817, found 362.0821 |
| 73-10 | 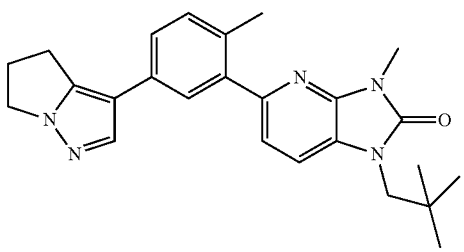 [SMILES: Cc1ccc(-c2cnn3c2CCC3)cc1-c1ccc2c(n1)n(C)c(=O)n2CC(C)(C)C] | 5-[5-(5,6-dihydro-4H-pyrrolo[1,2-b]pyrazol-3-yl)-2-methylphenyl]-1-(2,2-dimethylpropyl)-3-methyl-1,3-dihydro-2H-imidazo[4,5-b]pyridin-2-one | Calc'd 416.2196, found 416.2195 |
| 73-11 | 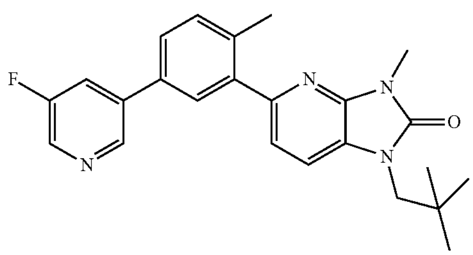 [SMILES: Cc1ccc(-c2cncc(F)c2)cc1-c1ccc2c(n1)n(C)c(=O)n2CC(C)(C)C] | 1-(2,2-dimethylpropyl)-5-[5-(5-fluoropyridin-3-yl)-2-methylphenyl]-3-methyl-1,3-dihydro-2H-imidazo[4,5-b]pyridin-2-one | Calc'd 405.0823, found. 405.0812 |
| 73-12 | 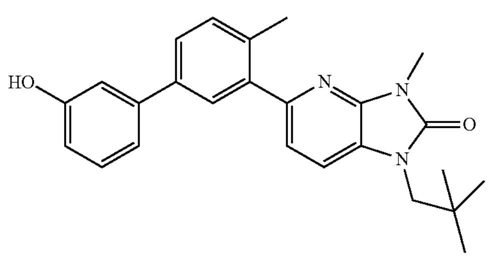 [SMILES: Cc1ccc(-c2cccc(O)c2)cc1-c1ccc2c(n1)n(C)c(=O)n2CC(C)(C)C] | 1-(2,2-dimethylpropyl)-5-(3'-hydroxy-4-methylbiphenyl-3-yl)-3-methyl-1,3-dihydro-2H-imidazo[4,5-b]pyridin-2-one | Calc'd 402.0496, found 402.0496 |
| 73-13 | 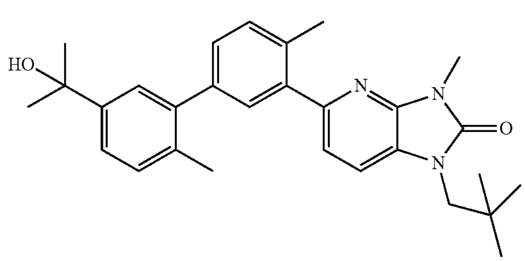 [SMILES: Cc1ccc(C(C)(C)O)cc1-c1ccc(C)c(-c2ccc3c(n2)n(C)c(=O)n3CC(C)(C)C)c1] | 1-(2,2-dimethylpropyl)-5-[5'-(1-hydroxy-1-methylethyl)-2',4-dimethylbiphenyl-3-yl]-3-methyl-1,3-dihydro-2H-imidazo[4,5-b]pyridin-2-one | Calc'd 458.2192, found 458.219 |

SCHEME 74

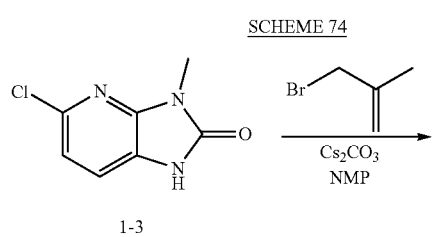

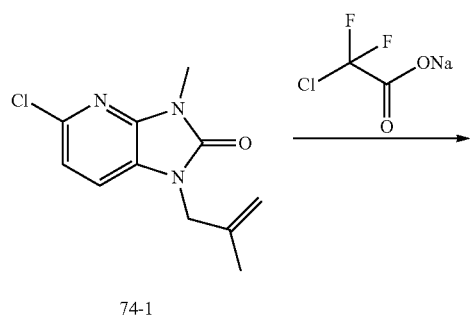

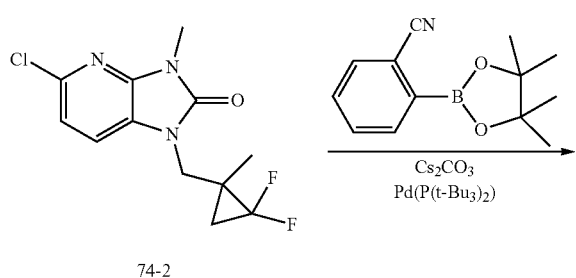

2-{1-[(2,2-difluoro-1-methylcyclopropyl)methyl]-3-methyl-2-oxo-2,3-dihydro-1H-imidazo[4,5-b]pyridin-5-yl}benzonitrile (74-3)

5-chloro-3-methyl-1-(2-methylprop-2-en-1-yl)-1,3-dihydro-2H-imidazo[4,5-b]pyridin-2-one (74-1)

5-chloro-3-methyl-1,3-dihydro-2H-imidazo[4,5-b]pyridin-2-one (1-3) (1.852 g, 8.16 mmol) and cesium carbonate (7.97 g, 24.47 mmol) were added to a round bottom flask and suspended in NMP (25 mL) under nitrogen. 3-bromo-2-methylprop-1-ene (1.101 g, 8.16 mmol) was added to the suspension and then refluxed at 90° C. overnight. The reaction was then cooled to room temperature and suspended in ethyl acetate and sodium bicarbonate. The suspension was washed with sodium bicarbonate, brine (×5), dried over sodium sulfate, filtered, and concentrated. The mixture was purified using normal phase chromatography (0-60% Ethyl Acetate/Hexanes), and the desired fractions were collected to produce the tan solid 5-chloro-3-methyl-1-(2-methylprop-2-en-1-yl)-1,3-dihydro-2H-imidazo[4,5-b]pyridin-2-one (74-1). MS (M+H)$^+$: observed=238.59, calculated=238.69.

5-chloro-1-[(2,2-difluoro-1-methylcyclopropyl)methyl]-3-methyl-1,3-dihydro-2H-imidazo[4,5-b]pyridin-2-one (74-2)

5-chloro-3-methyl-1-(2-methylprop-2-en-1-yl)-1,3-dihydro-2H-imidazo[4,5-b]pyridin-2-one (74-1) (6 g, 25.2 mmol) was added to a round bottom flask along with chloro(difluoro)acetic acid-sodium (1:1) (38.42 g, 252 mmol) this was mixed together with a spatula then heated to 200° C. for one hour. The reaction was then cooled to room temperature and suspended in ethyl acetate and sodium bicarbonate. The suspension was washed with sodium bicarbonate, brine (×5), dried over sodium sulfate, filtered, and concentrated. The mixture was purified using normal phase chromatography (0-60% Ethyl Acetate/Hexanes), and the desired fractions were collected to produce the solid 5-chloro-1-[(2,2-difluoro-1-methylcyclopropyl)methyl]-3-methyl-1,3-dihydro-2H-imidazo[4,5-b]pyridin-2-one (74-2). HRMS (M+H)$^+$: observed=288.0713, calculated=288.0715.

2-{1-[(2,2-difluoro-1-methylcyclopropyl)methyl]-3-methyl-2-oxo-2,3-dihydro 1H-imidazo[4,5-b]pyridin-5-yl}benzonitrile (74-3)

Prepared from 74-2 according to the procedures reported in Scheme 14 MS (M+H)$^+$: observed=355.1369, calculated=355.1370.

TABLE 37

The following compounds were prepared from 74-2 by a reaction sequence analogous to that illustrated in Scheme 74.

| Cmpd | Structure | IUPAC Name | Exact Mass [M + H]+ |
|---|---|---|---|
| 74-4 | 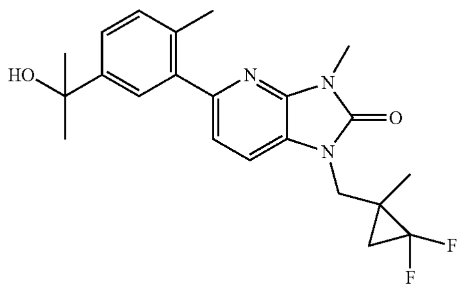 [SMILES: Cc1ccc(C(C)(C)O)cc1-c1ccc2c(n1)n(C)c(=O)n2CC1(C)CC1(F)F] | 1-[(2,2-difluoro-1-methylcyclopropyl)methyl]-5-[5-(1-hydroxy-1-methylethyl)-2-methylphenyl]-3-methyl-1,3-dihydro-2H-imidazo[4,5-b]pyridin-2-one | Calc'd 402.1993, found 402.1992 |
| 74-5 | 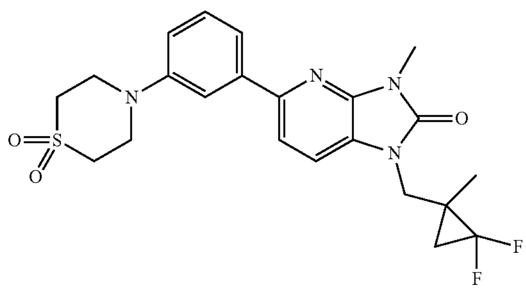 [SMILES: Cn1c(=O)n(CC2(C)CC2(F)F)c2ccc(-c3cccc(N4CCS(=O)(=O)CC4)c3)nc21] | 1-[(2,2-difluoro-1-methylcyclopropyl)methyl]-5-[3-(1,1-dioxidothiomorpholin-4-yl)phenyl]-3-methyl-1,3-dihydro-2H-imidazo[4,5-b]pyridin-2-one | Calc'd 463.2605, found 463.2603 |
| 74-6 | 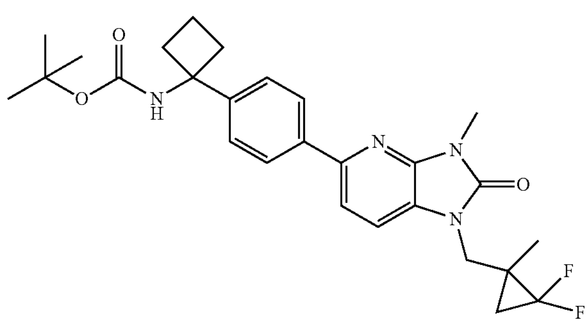 [SMILES: Cn1c(=O)n(CC2(C)CC2(F)F)c2ccc(-c3ccc(C4(NC(=O)OC(C)(C)C)CCC4)cc3)nc21] | tert-butyl [1-(4-{1-[(2,2-difluoro-1-methylcyclopropyl)methyl]-3-methyl-2-oxo-2,3-dihydro-1H-imidazo[4,5-b]pyridin-5-yl}phenyl)cyclobutyl]carbamate | Calc'd 492.2394, found 492.2383 |
| 74-7 | 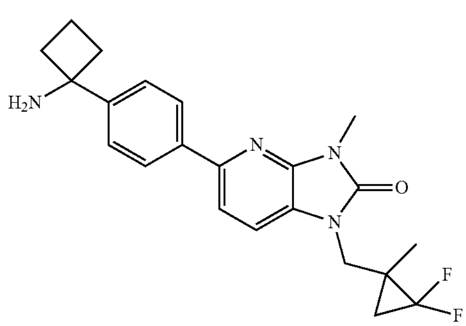 [SMILES: Cn1c(=O)n(CC2(C)CC2(F)F)c2ccc(-c3ccc(C4(N)CCC4)cc3)nc21] | 5-[4-(1-aminocyclobutyl)phenyl]-1-[(2,2-difluoro-1-methylcyclopropyl)methyl]-3-methyl-1,3-dihydro-2H-imidazo[4,5-b]pyridin-2-one | Calc'd 399.1996, found 399.1994 |

TABLE 37-continued

The following compounds were prepared from 74-2 by a reaction sequence analogous to that illustrated in Scheme 74.

| Cmpd | Structure | IUPAC Name | Exact Mass [M + H]+ |
|---|---|---|---|
| 74-8 | 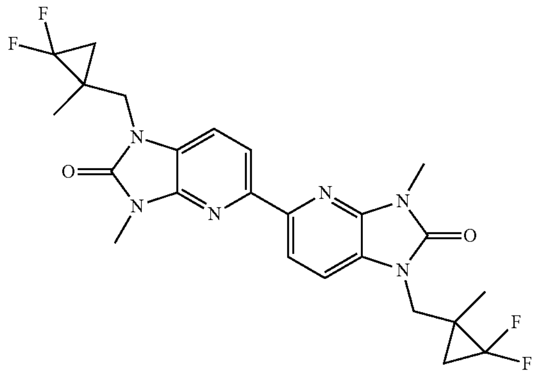 [SMILES: Cn1c(=O)n(CC2(C)CC2(F)F)c2ccc(-c3ccc4c(n3)n(C)c(=O)n4CC3(C)CC3(F)F)nc21] | 1,1'-bis[(2,2-difluoro-1-methylcyclopropyl)methyl]-3,3'-dimethyl-1,1',3,3'-tetrahydro-2H,2'H-5,5'-biimidazo[4,5-b]pyridine-2,2'-dione | Calc'd 505.1975, found 505.1973 |
| 74-9 | 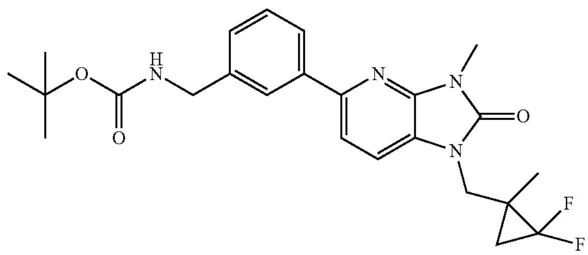 [SMILES: Cn1c(=O)n(CC2(C)CC2(F)F)c2ccc(-c3cccc(CNC(=O)OC(C)(C)C)c3)nc21] | tert-butyl [3-(1-{[(1S)-2,2-difluoro-1-methylcyclopropyl]methyl}-3-methyl-2-oxo-2,3-dihydro-1H-imidazo[4,5-b]pyridin-5-yl)benzyl]carbamate | Calc'd 402.4496, found 402.4496 |
| 74-10 | 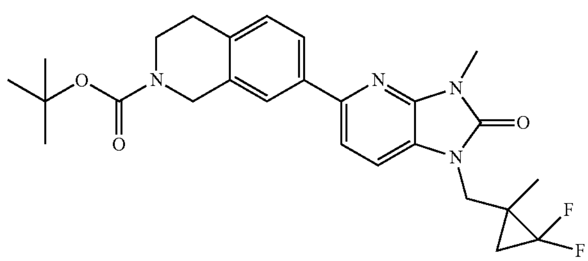 [SMILES: Cn1c(=O)n(CC2(C)CC2(F)F)c2ccc(-c3ccc4c(c3)CN(C(=O)OC(C)(C)C)CC4)nc21] | tert-butyl 7-(1-{[(1S)-2,2-difluoro-1-methylcyclopropyl]methyl}-3-methyl-2-oxo-2,3-dihydro-1H-imidazo[4,5-b]pyridin-5-yl)-3,4-dihydroisoquinoline-2(1H)-carboxylate | Calc'd 485.2359, found 485.2368 |
| 74-11 | 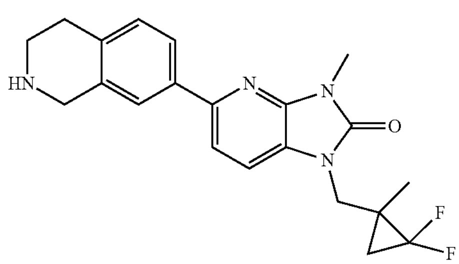 [SMILES: Cn1c(=O)n(CC2(C)CC2(F)F)c2ccc(-c3ccc4c(c3)CNCC4)nc21] | 1-{[(1S)-2,2-difluoro-1-methylcyclopropyl]methyl}-5-[5-(1-hydroxy-1-methylethyl)-2-methylphenyl]-3-methyl-1,3-dihydro-2H-imidazo[4,5-b]pyridin-2-one | Calc'd 385.1471, found 385.1469 |
| 74-12 | 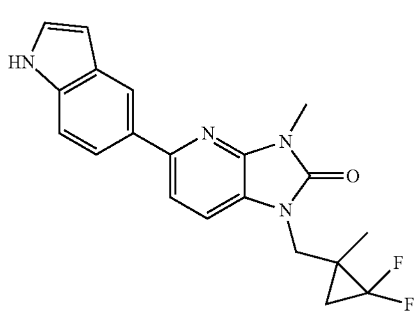 [SMILES: Cn1c(=O)n(CC2(C)CC2(F)F)c2ccc(-c3ccc4[nH]ccc4c3)nc21] | 1-[(2,2-difluoro-1-methylcyclopropyl)methyl]-5-(1H-indol-5-yl)-3-methyl-1,3-dihydro-2H-imidazo[4,5-b]pyridin-2-one | Calc'd 369.1521, found 369.1519 |

TABLE 37-continued

The following compounds were prepared from 74-2 by a reaction sequence analogous to that illustrated in Scheme 74.

| Cmpd | Structure | IUPAC Name | Exact Mass [M + H]+ |
|---|---|---|---|
| 74-13 | 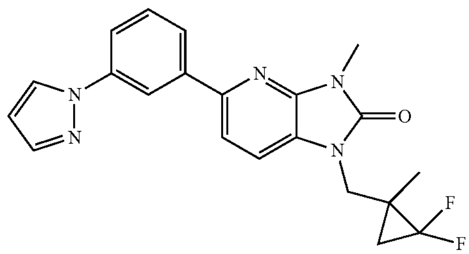 [SMILES: Cn1c(=O)n(CC2(C)CC2(F)F)c2ccc(-c3cccc(-n4cccn4)c3)nc21] | 1-[(2,2-difluoro-1-methylcyclopropyl)methyl]-3-methyl-5-[3-(1H-pyrazol-1-yl)phenyl]-1,3-dihydro-2H-imidazo[4,5-b]pyridin-2-one | Calc'd 396.2071, found 396.2058 |
| 74-14 | 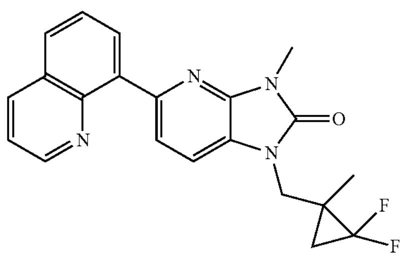 [SMILES: Cn1c(=O)n(CC2(C)CC2(F)F)c2ccc(-c3cccc4cccnc34)nc21] | 1-[(2,2-difluoro-1-methylcyclopropyl)methyl]-3-methyl-5-quinolin-8-yl-1,3-dihydro-2H-imidazo[4,5-b]pyridin-2-one | Calc'd 381.1878, found 381.1882 |
| 74-15 | 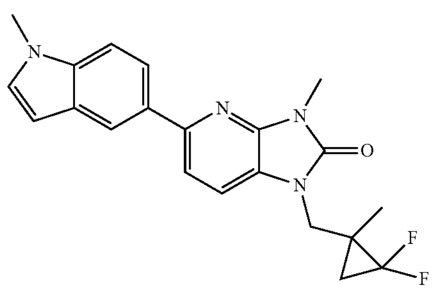 [SMILES: Cn1ccc2cc(-c3ccc4c(n3)n(C)c(=O)n4CC3(C)CC3(F)F)ccc21] | 1-[(2,2-difluoro-1-methylcyclopropyl)methyl]-3-methyl-5-(1-methyl-1H-indol-5-yl)-1,3-dihydro-2H-imidazo[4,5-b]pyridin-2-one | Calc'd 383.1868, found 383.1862 |
| 74-16 | 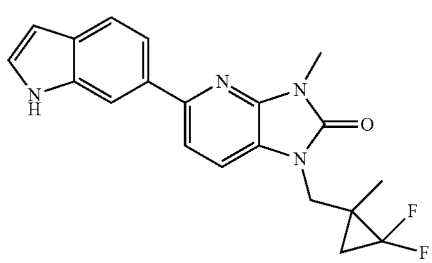 [SMILES: Cn1c(=O)n(CC2(C)CC2(F)F)c2ccc(-c3ccc4cc[nH]c4c3)nc21] | 1-[(2,2-difluoro-1-methylcyclopropyl)methyl]-5-(1H-indol-6-yl)-3-methyl-1,3-dihydro-2H-imidazo[4,5-b]pyridin-2-one | Calc'd 369.1521, found 369.1519 |
| 74-17 | 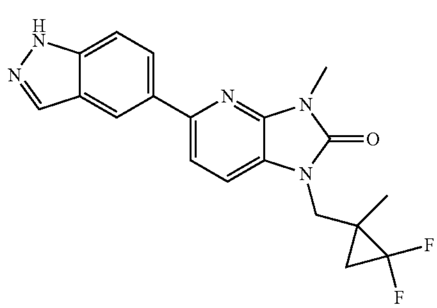 [SMILES: Cn1c(=O)n(CC2(C)CC2(F)F)c2ccc(-c3ccc4[nH]ncc4c3)nc21] | 1-[(2,2-difluoro-1-methylcyclopropyl)methyl]-5-(1H-indazol-5-yl)-3-methyl-1,3-dihydro-2H-imidazo[4,5-b]pyridin-2-one | Calc'd 370.1474, found 370.1472 |

TABLE 37-continued

The following compounds were prepared from 74-2 by a reaction sequence analogous to that illustrated in Scheme 74.

| Cmpd | Structure | IUPAC Name | Exact Mass [M + H]+ |
|---|---|---|---|
| 74-18 | 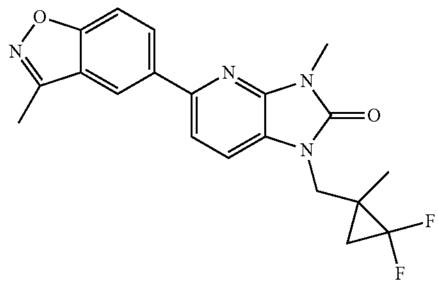 [SMILES: Cc1noc2ccc(-c3ccc4c(n3)n(C)c(=O)n4CC3(C)CC3(F)F)cc12] | 1-[(2,2-difluoro-1-methylcyclopropyl)methyl]-3-methyl-5-(3-methyl-1,2-benzisoxazol-5-yl)-1,3-dihydro-2H-imidazo[4,5-b]pyridin-2-one | Calc'd 385.1834, found 385.1842 |
| 74-19 | 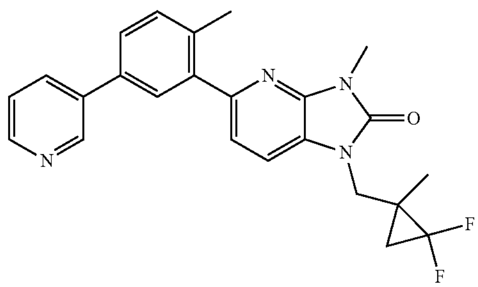 [SMILES: Cc1ccc(-c2cccnc2)cc1-c1ccc2c(n1)n(C)c(=O)n2CC1(C)CC1(F)F] | 1-[(2,2-difluoro-1-methylcyclopropyl)methyl]-3-methyl-5-(2-methyl-5-pyridin-3-ylphenyl)-1,3-dihydro-2H-imidazo[4,5-b]pyridin-2-one | Calc'd 421.2135, found 421.213 |
| 74-20 | 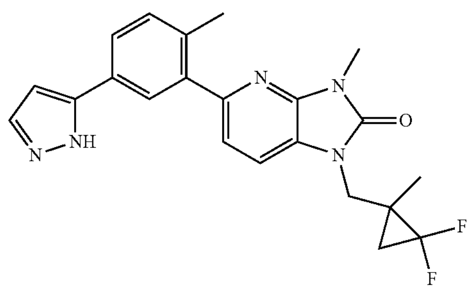 [SMILES: Cc1ccc(-c2ccn[nH]2)cc1-c1ccc2c(n1)n(C)c(=O)n2CC1(C)CC1(F)F] | 1-{[(1R)-2,2-difluoro-1-methylcyclopropyl]methyl}-3-methyl-5-[2-methyl-5-(1H pyrazol-5-yl)phenyl]-1,3-dihydro-2H-imidazo[4,5-b]pyridin-2-one | Calc'd 410.2351, found 410.2352 |
| 74-21 | 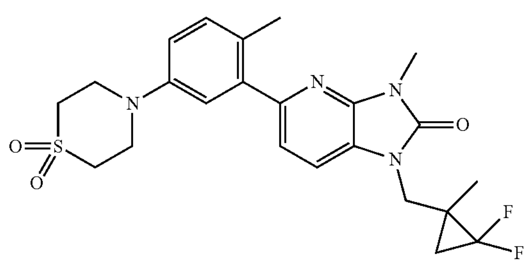 [SMILES: Cc1ccc(N2CCS(=O)(=O)CC2)cc1-c1ccc2c(n1)n(C)c(=O)n2CC1(C)CC1(F)F] | 1-{[(1R)-2,2-difluoro-1-methylcyclopropyl]methyl}-5-[5-(1,1-dioxidothiomorpholin-4-yl)-2-methylphenyl]-3-methyl-1,3-dihydro-2H-imidazo[4,5-b]pyridin-2-one | Calc'd 477.1926, found 477.1932 |
| 74-22 | 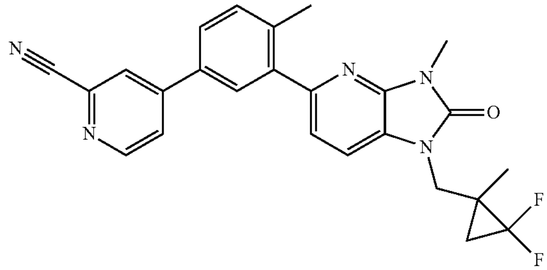 [SMILES: Cc1ccc(-c2ccnc(C#N)c2)cc1-c1ccc2c(n1)n(C)c(=O)n2CC1(C)CC1(F)F] | 4-(3-{1-[(2,2-difluoro-1-methylcyclopropyl)methyl]-3-methyl-2-oxo-2,3-dihydro-1H-imidazo[4,5-b]pyridin-5-yl}-4-methylphenyl)pyridine-2-carbonitrile | Calc'd 446.2359, found 446.235 |

SCHEME 75

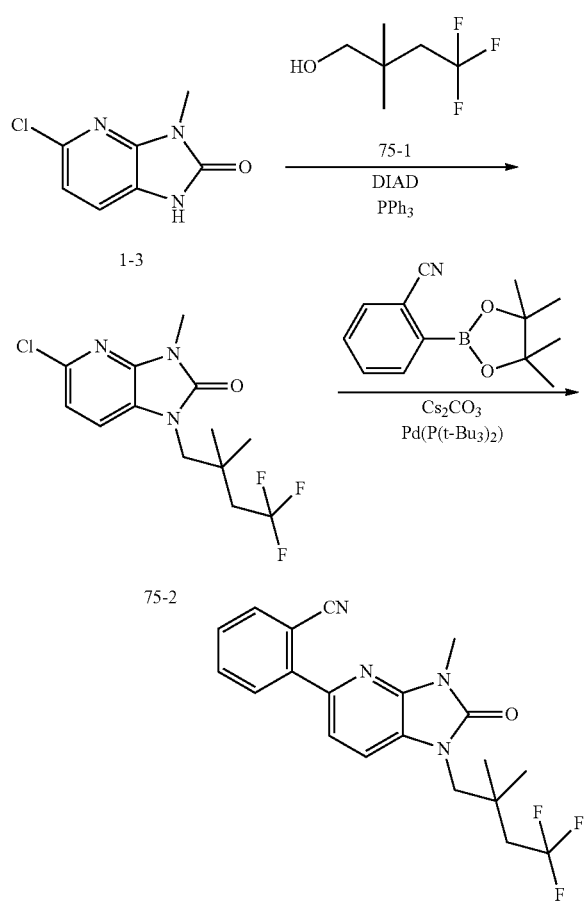

2-[3-methyl-2-oxo-1-(4,4,4-trifluoro-2,2-dimethylbutyl)-2,3-dihydro-1H-imidazo[4,5-b]pyridin-5-yl]benzonitrile (75-3)

4,4,4-trifluoro-2,2-dimethylbutan-1-ol (75-1)

To a solution of ethyl 4,4,4-trifluoro-2,2-dimethylbutanoate (1 g, 5.05 mmol) in ether (25 ml) under nitrogen was added LAH (1M solution in ether, 20.2 mmol) and allowed to stir at room temperature for one hour. Methanol was slowly added to Rxn until bubbling stopped. The reaction was then suspended in ether and Water. The suspension was washed with Water, dried over sodium sulfate, filtered, and concentrated without heat to produce an oil 4,4,4-trifluoro-2,2-dimethylbutan-1-ol (75-1). $^1$H NMR (500 MHz, CDCl$_3$) δ 3.4 (s, 2H), 2.20-2.01 (m, 2H), 1.05 (s, 6H). (M+H)$^+$: observed=157.16, calculated=157.15

5-chloro-3-methyl-1-(4,4,4-trifluoro-2,2-dimethylbutyl)-1,3-dihydro-2H-imidazo[4,5-b]pyridin-2-one (75-2)

Prepared from 75-1 according to the procedures reported in Scheme 4. HRMS (M+H)$^+$: observed=322.1105, calculated=322.1103.

2-[3-methyl-2-oxo-1-(4,4,4-trifluoro-2,2-dimethylbutyl)-2,3-dihydro-1H imidazo[4,5-b]pyridin-5-yl]benzonitrile (75-3)

Prepared from 75-2 according to the procedures reported in Scheme 14. HRMS (M+H)$^+$: observed=332.2036, calculated=332.2034.

TABLE 38

The following compounds were prepared from 75-2 by a reaction sequence analogous to that illustrated in Scheme 75.

| Cmpd | Structure | IUPAC Name | Exact Mass [M + H]+ |
|---|---|---|---|
| 75-4 | 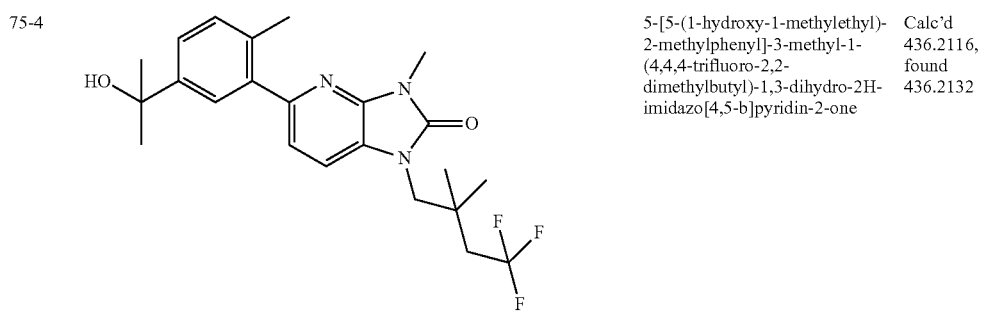 | 5-[5-(1-hydroxy-1-methylethyl)-2-methylphenyl]-3-methyl-1-(4,4,4-trifluoro-2,2-dimethylbutyl)-1,3-dihydro-2H-imidazo[4,5-b]pyridin-2-one | Calc'd 436.2116, found 436.2132 |

TABLE 38-continued

The following compounds were prepared from 75-2 by a reaction sequence analogous to that illustrated in Scheme 75.

| Cmpd | Structure | IUPAC Name | Exact Mass [M + H]+ |
| --- | --- | --- | --- |
| 75-5 | 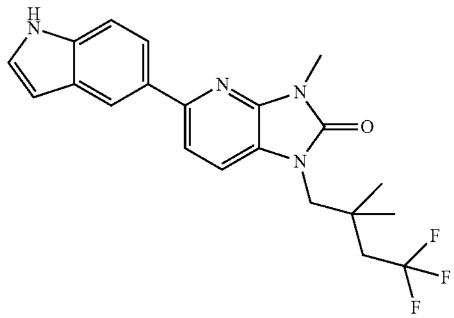 [SMILES: Cn1c(=O)n(CC(C)(C)CC(F)(F)F)c2ccc(-c3ccc4[nH]ccc4c3)nc21] | 5-(1H-indol-5-yl)-3-methyl-1-(4,4,4-trifluoro-2,2-dimethylbutyl)-1,3-dihydro-2H-imidazo[4,5-b]pyridin-2-one | Calc'd 403.4128, found 403.4129 |
| 75-6 | 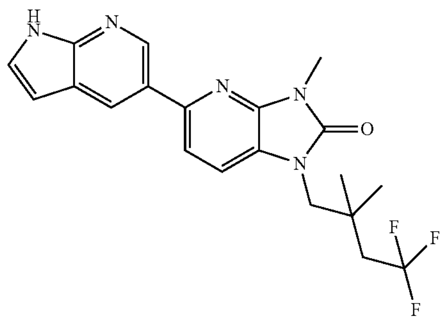 [SMILES: Cn1c(=O)n(CC(C)(C)CC(F)(F)F)c2ccc(-c3cnc4[nH]ccc4c3)nc21] | 3-methyl-5-(1H-pyrrolo[2,3-b]pyridin-5-yl)-1-(4,4,4-trifluoro-2,2-dimethylbutyl)-1,3-dihydro-2H-imidazo[4,5-b]pyridin-2-one | Calc'd 404.1693, found 404.1697 |
| 75-7 | 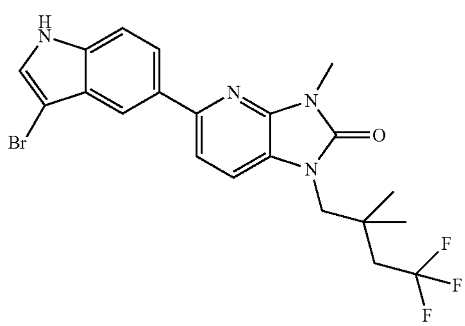 [SMILES: Cn1c(=O)n(CC(C)(C)CC(F)(F)F)c2ccc(-c3ccc4[nH]cc(Br)c4c3)nc21] | 5-(3-bromo-1H-indol-5-yl)-3-methyl-1-(4,4,4-trifluoro-2,2-dimethylbutyl)-1,3-dihydro-2H-imidazo[4,5-b]pyridin-2-one | Calc'd 481.0845, found 481.0859 |
| 75-8 | 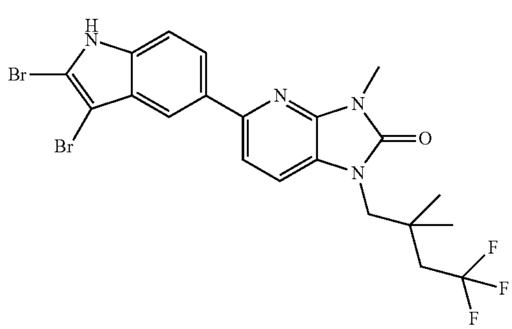 [SMILES: Cn1c(=O)n(CC(C)(C)CC(F)(F)F)c2ccc(-c3ccc4[nH]c(Br)c(Br)c4c3)nc21] | 5-(2,3-dibromo-1H-indol-5-yl)-3-methyl-1-(4,4,4-trifluoro-2,2-dimethylbutyl)-1,3-dihydro-2H-imidazo[4,5-b]pyridin-2-one | Calc'd 558.995, found 558.9967 |

TABLE 38-continued

The following compounds were prepared from 75-2 by a reaction sequence analogous to that illustrated in Scheme 75.

| Cmpd | Structure | IUPAC Name | Exact Mass [M + H]+ |
|---|---|---|---|
| 75-9 | 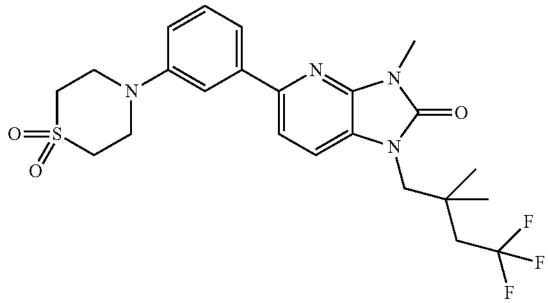 [SMILES: Cn1c(=O)n(CC(C)(C)CC(F)(F)F)c2ccc(-c3cccc(N4CCS(=O)(=O)CC4)c3)nc21] | 5-[3-(1,1-dioxidothiomorpholin-4-yl)phenyl]-3-methyl-1-(4,4,4-trifluoro-2,2-dimethylbutyl)-1,3-dihydro-2H-imidazo[4,5-b]pyridin-2-one | Calc'd 497.1829, found 497.1831 |
| 75-10 | 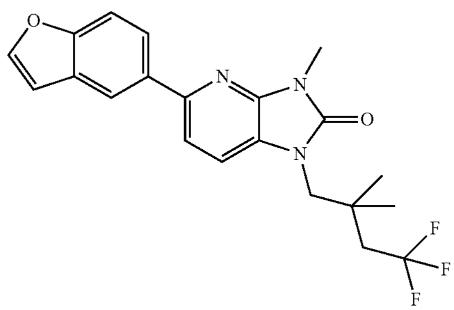 [SMILES: Cn1c(=O)n(CC(C)(C)CC(F)(F)F)c2ccc(-c3ccc4occc4c3)nc21] | 5-(1-benzofuran-5-yl)-3-methyl-1-(4,4,4-trifluoro-2,2-dimethylbutyl)-1,3-dihydro-2H-imidazo[4,5-b]pyridin-2-one | Calc'd 404.158, found 404.1576 |
| 75-11 | 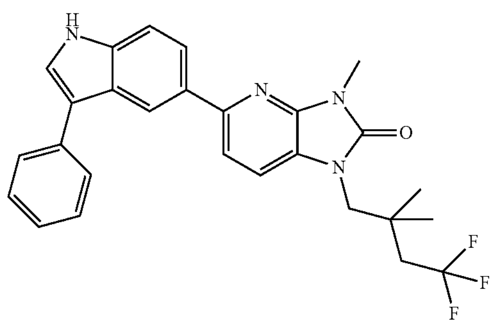 [SMILES: Cn1c(=O)n(CC(C)(C)CC(F)(F)F)c2ccc(-c3ccc4[nH]cc(-c5ccccc5)c4c3)nc21] | 3-methyl-5-(3-phenyl-1H-indol-5-yl)-1-(4,4,4-trifluoro-2,2-dimethylbutyl)-1,3-dihydro-2H-imidazo[4,5-b]pyridin-2-one | Calc'd 479.2053, found 479.2056 |

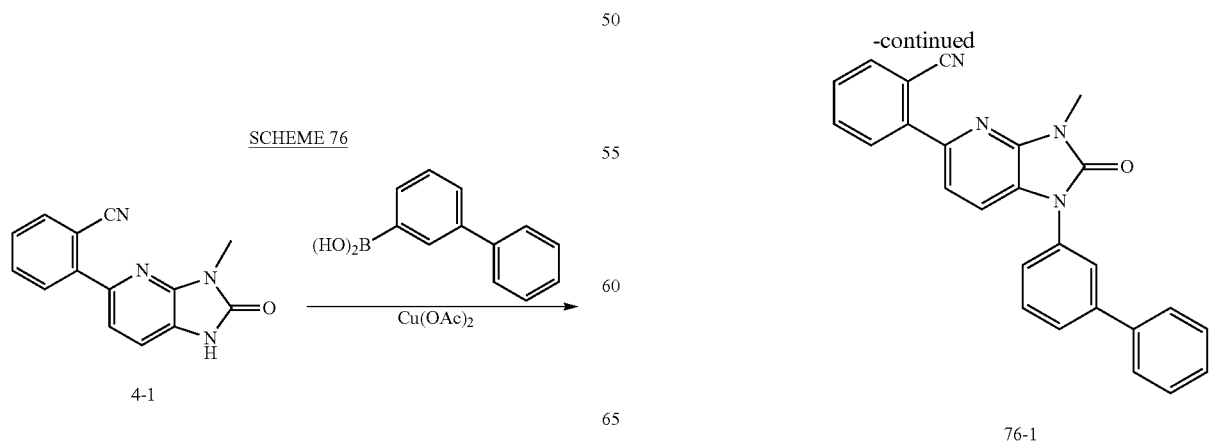

2-(1-biphenyl-3-yl-3-methyl-2-oxo-2,3-dihydro-1H-imidazo[4,5-b]pyridin-5-yl)benzonitrile (76-1)

To a solution of 4-1 (13 mg, 0.052 mmol) in DCM (0.25 mL) was added copper (II) acetate, biphenyl-3-ylboronic acid (30 mg, 0.16 mmol) and triethylamine (0.022 mL, 16 mg, 0.16 mmol) at room temperature. After 4 days, the crude mixture was diluted in DCM (4 mL), filtered, concentrated and purified via reverse phase chromatography (1-100% Acetonitrile, 0.1% TFA in H$_2$O) and the desired fractions were concentrated to give 76-1. MS (M+H)$^+$: observed=403.0, calculated=403.2.

SCHEME 77

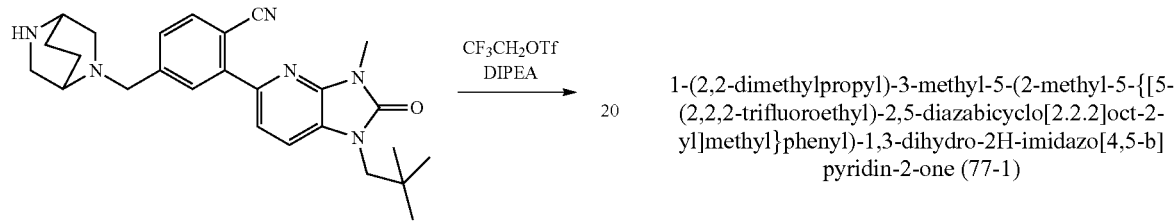

44-7

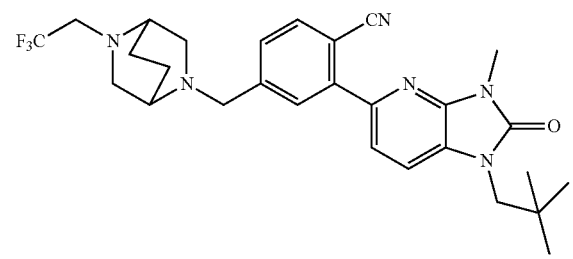

77-1

1-(2,2-dimethylpropyl)-3-methyl-5-(2-methyl-5-{[5-(2,2,2-trifluoroethyl)-2,5-diazabicyclo[2.2.2]oct-2-yl]methyl}phenyl)-1,3-dihydro-2H-imidazo[4,5-b]pyridin-2-one (77-1)

Prepared from 44-7 according to the procedures reported in Scheme 44. HRMS (M+H)$^+$: observed=527.2747, calculated=527.2741

SCHEME 78

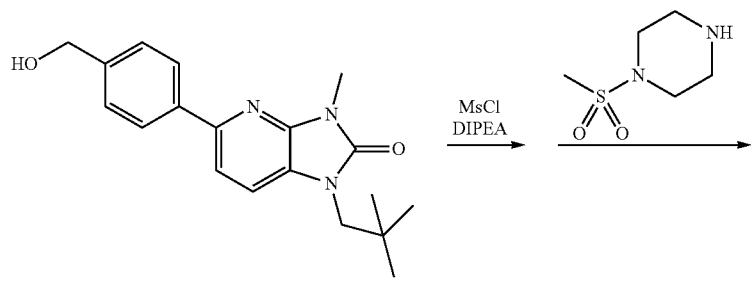

14-95

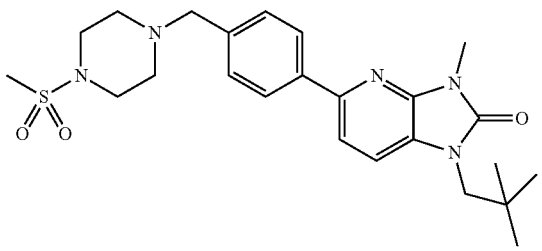

78-1

311

1-(2,2-dimethylpropyl)-3-methyl-5-(4-{[4-(methyl-sulfonyl)piperazin-1-yl]methyl}phenyl)-1,3-dihydro-2H-imidazo[4,5-b]pyridin-2-one (78-1)

Prepared from 14-95 according to the procedures reported in Scheme 21. HRMS (M+H)$^+$: observed=472.2377, calculated=472.2382.

312

5-{3-[cyclopropyl(hydroxy)methyl]phenyl}-1-(2,2-dimethylpropyl)-3-methyl-1,3-dihydro-2H-imidazo[4,5-b]pyridin-2-one (79-2)

Prepared from 14-67 according to the procedures reported in Scheme 30. HRMS (M+H)$^+$: observed=366.2177, calculated=366.2176.

TABLE 39

The following compounds were prepared from 79-1 by a reaction sequence analogous to that illustrated in Scheme 79.

| Cmpd | Structure | IUPAC Name | Exact Mass [M + H]+ |
|---|---|---|---|
| 79-3 | 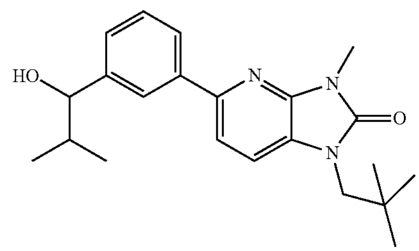 [SMILES: CC(C)C(O)c1cccc(-c2ccc3c(n2)n(C)c(=O)n3CC(C)(C)C)c1] | 1-(2,2-dimethylpropyl)-5-[3-(1-hydroxy-2-methylpropyl)phenyl]-3-methyl-1,3-dihydro-2H-imidazo[4,5-b]pyridin-2-one | Calc'd 368.2333, found 368.2333 |

SCHEME 79

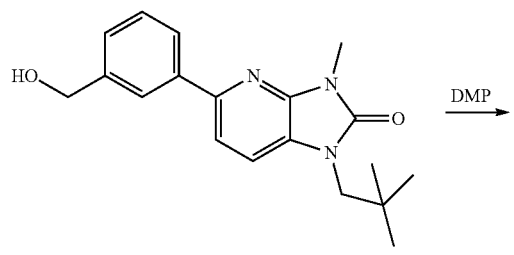

14-67

↓ DMP 79-1

↓ cPrMgBr 79-2

SCHEME 80

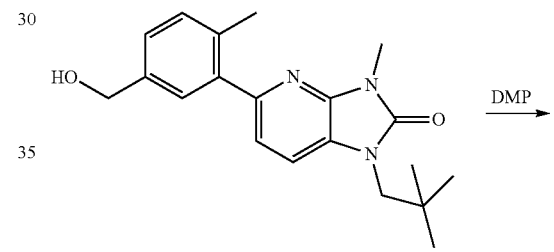

51-1

↓ DMP 80-1

↓ cPrMgBr 80-2

313

5-{5-[cyclopropyl(hydroxy)methyl]-2-methylphenyl}-1-(2,2-dimethylpropyl)-3-methyl-1,3-dihydro-2H-imidazo[4,5-b]pyridin-2-one (79-2)

Prepared from 14-67 according to the procedures reported in Scheme 30. HRMS (M+H)⁺: observed=380.2335, calculated=380.2333.

314

1-(2,2-dimethylpropyl)-5-[5-(2-hydroxy-2-methylpropyl)-2-methylphenyl]-3-methyl-1,3-dihydro-2H-imidazo[4,5-b]pyridin-2-one (81-3)

Prepared from methyl(3-chloro-4-methylphenyl)acetate according to the procedures reported in Scheme 3. HRMS (M+H)⁺: observed=382.2494, calculated=382.2489. ¹H NMR (499 MHz, DMSO): δ 7.59 (d, J=8.0 Hz, 1H); 7.22 (s, 1H); 7.18-7.09 (m, 3H); 4.27 (s, 1H); 3.67 (s, 2H); 3.36 (s, 3H); 2.66 (s, 2H); 2.33 (s, 3H); 1.07 (s, 6H); 0.99 (s, 9H).

TABLE 40

The following compounds were prepared from 80-1 by a reaction sequence analogous to that illustrated in Scheme 80.

| Cmpd | Structure | IUPAC Name | Exact Mass [M + H]+ |
|---|---|---|---|
| 80-3 | 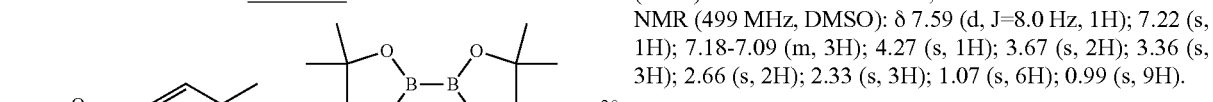 | 1-(2,2-dimethylpropyl)-5-[5-(1-hydroxy-2-methylpropyl)-2-methylphenyl]-3-methyl-1,3-dihydro-2H-imidazo[4,5-b]pyridin-2-one | Calc'd 382.2489, found 382.2493 |

SCHEME 81

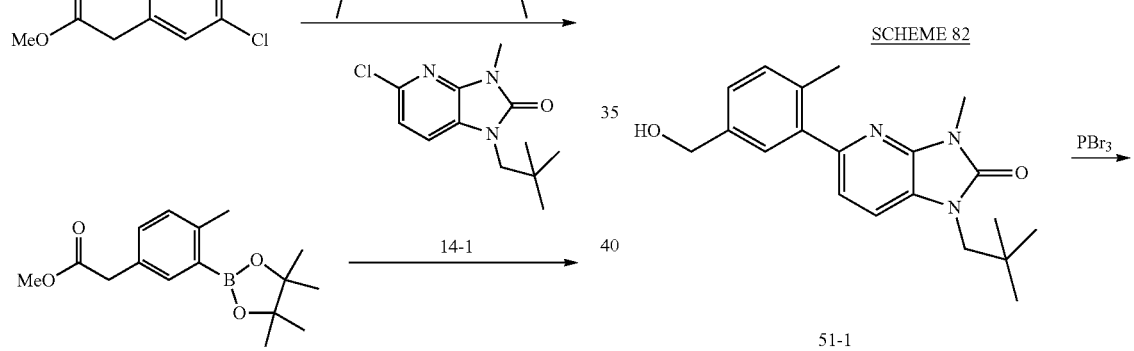

SCHEME 82

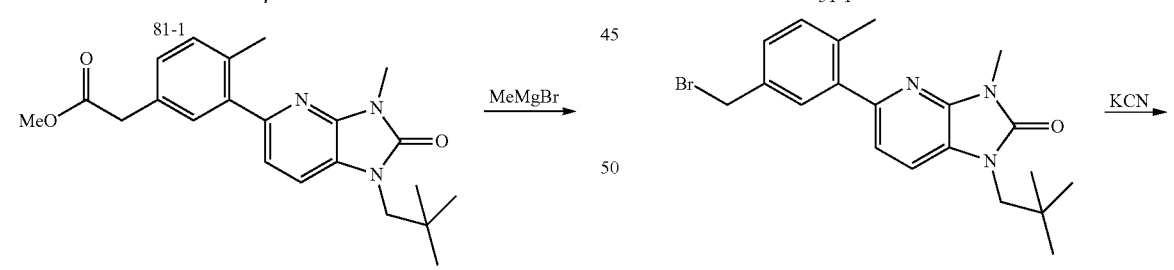

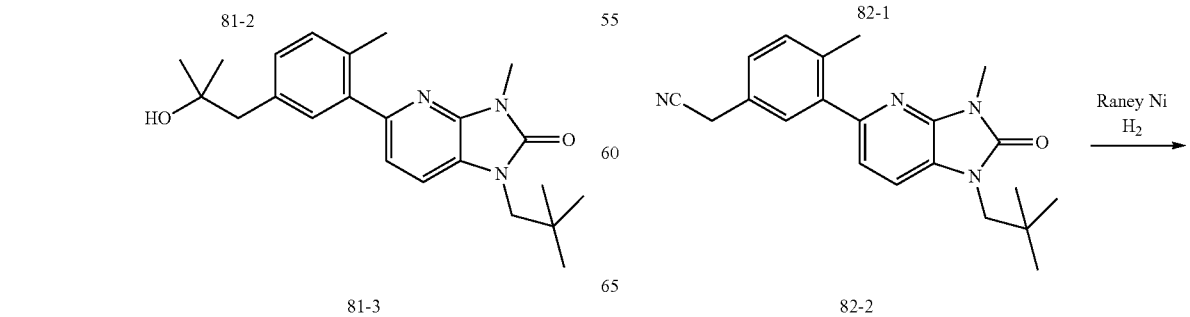

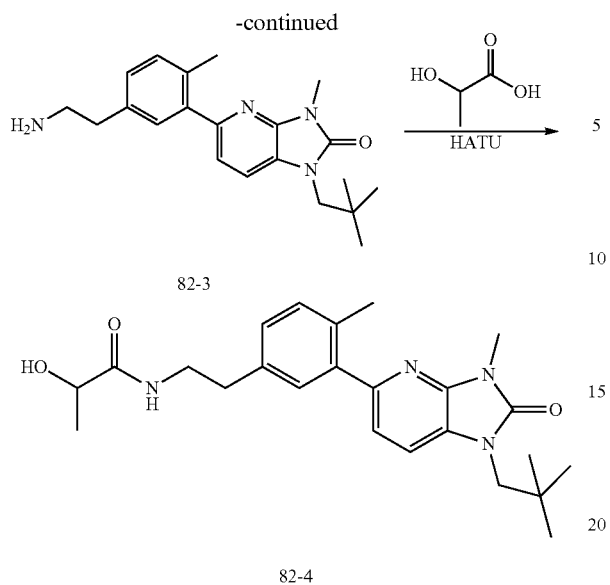

82-3

82-4

N-(2-{3-[1-(2,2-dimethylpropyl)-3-methyl-2-oxo-2, 3-dihydro-1H-imidazo[4,5-b]pyridin-5-yl]-4-methylphenyl}ethyl)-2-hydroxypropanamide (82-4)

5-[5-(bromomethyl)-2-methylphenyl]-1-(2,2-dimethylpropyl)-3-methyl-1,3-dihydro-2H-imidazo[4,5-b]pyridin-2-one (82-1)

To a solution of 51-1 (150 mg, 0.44 mmol) in DCM (2 mL) at 0° C. was added phosphorus oxybromide (126 mg, 0.46 mmol). After 4 hours, the reaction was diluted with EtOAc, and washed with water, saturated aqueous sodium bicarbonate and brine. The organic layer was dried over Na2SO4, filtered and concentrated to give product as a white foam. MS (M+H)$^+$: observed=402.0/404.0, calculated=402.3/404.3.

{3-[1-(2,2-dimethylpropyl)-3-methyl-2-oxo-2,3-dihydro-1H-imidazo[4,5-b]pyridin-5-yl]-4-methylphenyl}acetonitrile (82-2)

To a solution of 82-1 (180 mg, 0.45 mmol) in NMP was added potassium cyanide (32 mg, 0.49 mmol), the vessel was sealed and heated to 120 C. After 15 hours, the reaction was purified by reverse phase chromatography (Sunfire C18, 40-95% CH3CN/0.1% TFA/water). Fractions containing product were partially concentrated, quenched with aqueous sodium bicarbonate and extracted with ethyl acetate. The combined organics were washed with brine, dried over Na2SO4, filtered and concentrated to give 82-2 as an oil. HRMS (M+H)$^+$: observed=349.1, calculated=349.4.

5-[5-(2-aminoethyl)-2-methylphenyl]-1-(2,2-dimethylpropyl)-3-methyl-1,3-dihydro-2H-imidazo[4,5-b]pyridin-2-one (82-3)

Raney 2800 Nickel (30 mg, suspended in water) was added to a 25 mL receiver flask. The black solid was rinsed with EtOH and a solution of 82-2 (38 mg, 0.11 mmol) dissolved in 2M ammonia in EtOH (2 mL) was added. The flask was purged with hydrogen and the reaction was stirred at room temperature under a balloon of hydrogen. After 3 hours, the flask was purged with nitrogen and the mixture was filtered, rinsed with EtOH and concentrated. Purified by reverse phase (Sunfire C18, 25-85% CH3CN/0.1% TFA in water) and the fractions containing product were passed through an SCX cation exchange column, washed with acetonitrile, and eluted with 2M ammonia in EtOH to give 82-3 as a colorless oil. HRMS (M+H)$^+$: observed=353.2, calculated=353.5.

N-(2-{3-[1-(2,2-dimethylpropyl)-3-methyl-2-oxo-2, 3-dihydro-1H-imidazo[4,5-b]pyridin-5-yl]-4-methylphenyl}ethyl)-2-hydroxypropanamide (82-4)

Prepared from 82-3 according to the procedures reported in Scheme 48. HRMS (M+H)$^+$: observed=425.2559, calculated=425.2547.

What is claimed is:

1. A compound according to Formula I

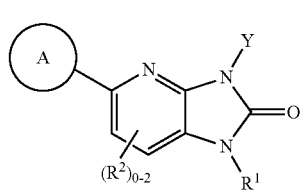

I wherein:
Y is H, $C_{1-6}$alkyl or $C_{2-6}$alkenyl, said $C_{1-6}$alkyl and $C_{2-6}$alkenyl optionally substituted with 1 to 3 groups selected from: halo and $C_{1-4}$alkoxy;

$R^1$ is selected from the group consisting of:
(1) $C_{2-8}$alkyl,
(2) $C_{2-8}$alkenyl,
(3) $C_{2-8}$alkynyl,
(4) $C_{3-6}$cycloalkyl-$(CH_2)_p$—, wherein p is 1, 2, 3 or 4,
(5) benzyl,
(6) biphenyl, and
(7) 1-phenyl-1H-pyrazol-4-yl, wherein groups (1) to (7) above are optionally substituted with 1 to 3 $R^2$ groups;

each $R^2$ is independently selected from the group consisting of: halo, OH, $C_{1-4}$alkyl, $C_{1-4}$alkoxy, $CF_3$, —$OCF_3$ and —CN;

ring A is selected from aryl, heteroaryl and heterocycle, wherein said heterocycle is fused to an aryl group or a heteroaryl group, and wherein said aryl, heteroaryl and heterocycle are optionally substituted with one or more $R^3$ groups up to the maximum number of substitutable positions;

each $R^3$ is independently selected from the group consisting of: halo, —CN, —NO$_2$, X, —C(R$^4$)$_2$—N(R)—X, —C(R$^4$)$_2$—N(R)C(O)—X, —C(R$^4$)$_2$—N(R)S(O)$_k$—X, —C(R$^4$)$_2$—N(R)C(O)—O—X, —C(O)—X, —C(O)—O—X, —C(O)—N(R)—X, —S(O)$_k$—X, —S(O)$_k$N(R)—X, —N(R)—X, —O—X, —N(R)C(O)—X, —N(R)S(O)$_k$—X, —N(R)C(O)—O—X, —N(R)C(O)N(R)—X and —N(R)SO$_2$N(R)—X;

each X is independently selected from the group consisting of: H, $C_{1-8}$alkyl, $C_{2-6}$alkenyl, $C_{2-6}$alkynyl, $C_{3-6}$cycloalkyl, aryl, heteroaryl, heterocycle, $C_{3-6}$cycloalkyl-C(R$^4$)$_2$—, aryl-C(R$^4$)$_2$—, heteroaryl-C(R$^4$)$_2$— and heterocycle-C(R$^4$)$_2$—, wherein each member of the group excluding hydrogen is optionally substituted from one up to the maximum number of substitutable positions with one or more substituents independently selected from the group consisting of: CN, halo, $R^5$, —O—$R^5$, —N(R)—$R^5$, —N(R)C(O)—$R^5$, —N(R)S(O)$_2$—$R^5$, —N(R)—C(O)—O—$R^5$, —C(O)—N(R)—$R^5$, —C(O)—O—$R^5$, —C(O)—$R^5$, —C(O)—C(R$^4$)$_2$—$R^5$, —C(O)—C(R$^4$)$_2$—S(O)$_2$—R$^5$, —C(R$^4$)$_2$—N(R)—R$^5$, —SO$_2$—N(R)—R$^5$, —Si(CH$_3$)$_2$(R$^5$), —C(R$^4$)$_2$—R$^5$ and —SO$_2$—R$^5$;

each k is independently 0, 1 or 2;

each R is independently selected from the group consisting of: H and C$_{1-4}$alkyl;

each R$^4$ is independently selected from the group consisting of: H, OH and C$_{1-4}$alkyl;

each R$^5$ is independently selected from the group consisting of: H, C$_{1-4}$-alkyl, C$_{2-4}$alkenyl, C$_{2-4}$alkynyl, C$_{3-6}$cycloalkyl, phenyl, heterocycle and heteroaryl, wherein each member of the group excluding hydrogen is optionally substituted with 1 to 3 substituents independently selected from: halogen, cyano, hydroxy and methyl;

aryl at each occurrence is independently selected from the group consisting of: phenyl, naphthyl, anthryl and phenanthryl;

heteroaryl at each occurrence independently means a 5-membered monocyclic aromatic selected from the group consisting of isoxazolyl, isothiazolyl, pyrazolyl, oxazolyl, oxadiazolyl, thiadiazolyl, thiazolyl, imidazolyl, triazolyl, tetrazolyl, furanyl, triazinyl and thienyl, a 6-membered monocyclic aromatic or 9- or 10-membered bicyclic aromatic, wherein at least one atom in the aromatic is selected from N(R), O and S, the sulfur optionally oxidized to sulfone or sulfoxide, and the remaining atoms are selected from C, N(R), O and S, the sulfur optionally oxidized to sulfone or sulfoxide;

heterocycle at each occurrence independently means a 4- to 7-membered monocyclic non-aromatic ring, an 8- to 11-membered bi-cyclic non-aromatic ring or a 12- to 20-membered tri-cyclic, non-aromatic ring, each optionally substituted with 1 to 2 oxo groups, wherein at least one atom is selected from N(R), O and S, the sulfur optionally oxidized to sulfone or sulfoxide, and the remaining atoms are selected from C, N(R), O and S, the sulfur optionally oxidized to sulfone or sulfoxide;

or a pharmaceutically acceptable salt thereof.

2. The compound according to claim 1 or a pharmaceutically acceptable salt thereof, wherein Y is methyl.

3. The compound according to claim 1 or a pharmaceutically acceptable salt thereof, wherein R$^1$ is selected from the group consisting of: cyclopropylmethyl, 2,2-difluorocyclopropylmethyl, 2,2-difluoro-1-methylcyclopropylmethyl, 1-(trifluoromethyl)cyclopropylmethyl, 4,4,4-trifluoro-2,2-dimethylbutyl, cyclobutylmethyl, 2,2-dimethylpropyl, prop-2-enyl, biphenyl and benzyl, optionally substituted with methoxy or —OCF$_3$.

4. The compound according to claim 1 of Formula Ia

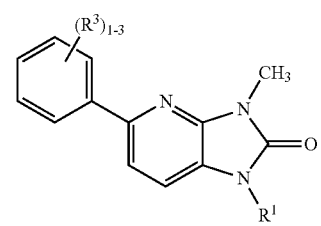

Ia or a pharmaceutically acceptable salt thereof.

5. The compound according to claim 4 or a pharmaceutically acceptable salt thereof, wherein R$^3$ is selected from the group consisting of: halo, —CN, —N(O)$_2$, amino, —N(C$_{1-4}$alkyl)$_2$, —C(O)—O—C$_{1-4}$alkyl, —C(O)—C$_{1-4}$alkyl, —S(O)$_2$—C$_{1-4}$alkyl, C$_{3-6}$cycloalkyl, —C(C$_{1-4}$alkyl)$_2$-NHC(O)—O—C$_{1-4}$alkyl and C$_{1-8}$alkyl optionally substituted with 1 to 4 substituents independently selected from hydroxy and halo.

6. The compound according to claim 1 of Formula Ib

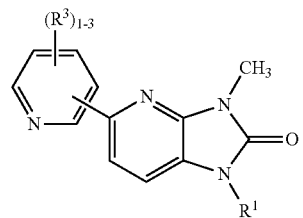

Ib or a pharmaceutically acceptable salt thereof.

7. The compound according to claim 6 or a pharmaceutically acceptable salt thereof, wherein R$^3$ is selected from the group consisting of: halo, —CN, —N(O)$_2$, amino, —N(C$_{1-4}$alkyl)$_2$, —C(O)—O—C$_{1-4}$alkyl, —C(O)—C$_{1-4}$alkyl, —S(O)$_2$—C$_{1-4}$alkyl, C$_{3-6}$cycloalkyl and C$_{1-8}$alkyl optionally substituted with 1 to 4 substituents independently selected from hydroxy and halo.

8. The compound according to claim 1 of Formula Ic

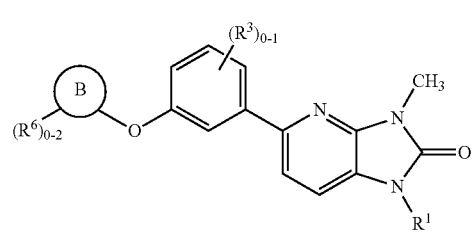

Ic or a pharmaceutically acceptable salt thereof, wherein:

ring B is heteroaryl;

R$^3$ is CN, halo or C$_{1-4}$alkyl, optionally substituted with 1-5 halo atoms; and each R$^6$ is independently selected from the group consisting of: —CN, halo, —N(R)$_2$, C$_{1-44}$alkoxy, —C(O)—O—C$_{1-4}$alkyl, and C$_{1-4}$alkyl, optionally substituted with hydroxy.

9. The compound according to claim 8 or a pharmaceutically acceptable salt thereof, wherein ring B is pyridyl.

10. The compound according to claim 1 of Formula Id

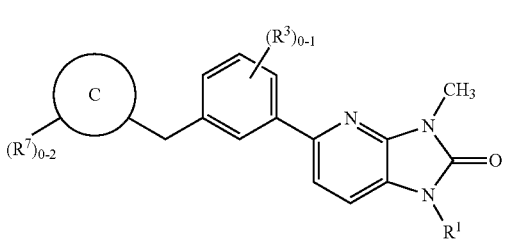

Id or a pharmaceutically acceptable salt thereof, wherein:

ring C is heterocycle;

R$^3$ is CN, halo or C$_{1-4}$alkyl, optionally substituted with 1-5 halo atoms; and each R⁷ is independently selected from the group consisting of: OH, acetyl, methylsulfonyl, acetylamino, —C(O)—O—C₁₋₄alkyl and C₁₋₄alkyl, optionally substituted with 1-3 halo atoms or hydroxy.

11. The compound according to claim 10 or a pharmaceutically acceptable salt thereof, wherein ring C is dioxidothiomorpholin-4-yl.

12. The compound according to claim 10 or a pharmaceutically acceptable salt thereof, wherein ring C is 6,7-dihydroisoxazolo[4,5-c]pyridine-5(4H)-yl.

13. The compound according to claim 1 of Formula Ie

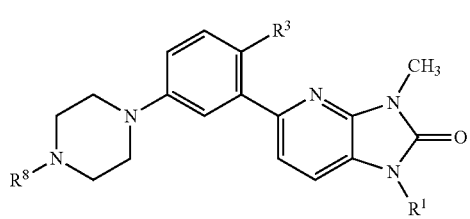

Ie or a pharmaceutically acceptable salt thereof, wherein:
R³ is CN, halo or C₁₋₄alkyl, optionally substituted with 1-5 halo atoms; and
R⁸ is selected from the group consisting of: heteroaryl, heteroarylcarbonyl, methylsulfonyl and C₁₋₆alkyl-C(O)—, optionally substituted with 1 to 3 substituents independently selected from halo or hydroxy.

14. The compound according to claim 1 of Formula If

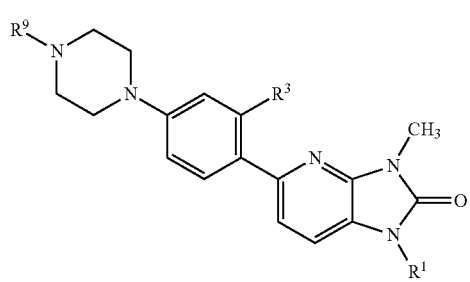

If or a pharmaceutically acceptable salt thereof, wherein:
R³ is CN, halo or C₁₋₄alkyl, optionally substituted with 1-5 halo atoms; and
R⁹ is selected from the group consisting of: heteroaryl, heteroarylcarbonyl, methylsulfonyl and C₁₋₆alkyl-C(O)—, optionally substituted with 1 to 3 substituents independently selected from halo or hydroxy.

15. The compound according to claim 1 of Formula Ih

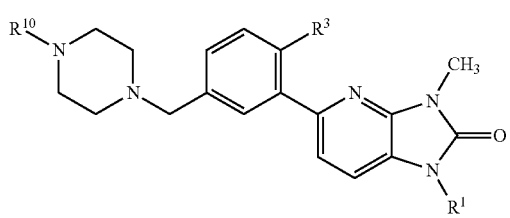

Ih or a pharmaceutically acceptable salt thereof, wherein:
R³ is CN, halo or C₁₋₄alkyl, optionally substituted with 1-5 halo atoms; and R¹⁰ is selected from the group consisting of: heteroaryl, heteroarylcarbonyl, methylsulfonyl and C₁₋₆alkyl-C(O)—, optionally substituted with 1 to 3 substituents independently selected from halo or hydroxy.

16. The compound according to claim 1 of Formula Ii

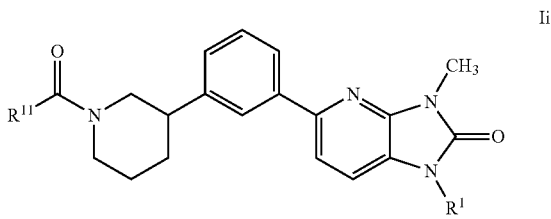

Ii or a pharmaceutically acceptable salt thereof, wherein:
R¹¹ is selected from the group consisting of: heteroaryl and C₁₋₆alkyl, optionally substituted with 1 to 3 substituents independently selected from halo or hydroxy.

17. A compound according to claim 1 selected from the following group:
2-[1-(cyclopropylmethyl)-3-methyl-2-oxo-2,3-dihydro-1H-imidazo[4,5b]pyridin-5-yl]benzonitrile;
1-(cyclopropylmethyl)-3-methyl-5-thiophen-2-yl-1,3-dihydro-2H-imidazo[4,5-b]pyridin-2-one;
3-[1-(cyclopropylmethyl)-3-methyl-2-oxo-2,3-dihydro-1H-imidazo[4,5-b]pyridin-5-yl]benzonitrile;
1-(cyclopropylmethyl)-5-(2-fluorophenyl)-3-methyl-1,3-dihydro-2H-imidazo[4,5-b]pyridin-2-one;
2-[1-(cyclopropylmethyl)-3-methyl-2-oxo-2,3-dihydro-1H-imidazo[4,5-b]pyridin-5-yl]-5-fluorobenzonitrile;
1-(cyclopropylmethyl)-5-[3-(1-hydroxy-1-methylethyl)phenyl]-3-methyl-1,3-dihydro-2H-imidazo[4,5-b]pyridin-2-one;
3-[1-(cyclopropylmethyl)-3-methyl-2-oxo-2,3-dihydro-1H-imidazo[4,5-b]pyridin-5-yl]pyridine-4-carbonitrile;
1-(cyclopropylmethyl)-5-(2,4-difluorophenyl)-3-methyl-1,3-dihydro-2H-imidazo[4,5-b]pyridin-2-one;
1-(cyclopropylmethyl)-5-(4-fluorophenyl)-3-methyl-1,3-dihydro-2H-imidazo[4,5-b]pyridin-2-one;
5-[1-(cyclopropylmethyl)-3-methyl-2-oxo-2,3-dihydro-1H-imidazo[4,5-b]pyridin-5-yl]-2-fluorobenzonitrile;
1-(cyclopropylmethyl)-5-(4-fluoro-2-methylphenyl)-3-methyl-1,3-dihydro-2H-imidazo[4,5-b]pyridin-2-one;
4-[1-(cyclopropylmethyl)-3-methyl-2-oxo-2,3-dihydro-1H-imidazo[4,5-b]pyridin-5-yl]benzonitrile;
5-(2-chlorophenyl)-1-(cyclopropylmethyl)-3-methyl-1,3-dihydro-2H-imidazo[4,5-b]pyridin-2-one;
1-(cyclopropylmethyl)-5-(3,5-dichlorophenyl)-3-methyl-1,3-dihydro-2H-imidazo[4,5-b]pyridin-2-one;
1-(cyclopropylmethyl)-3-methyl-5-(3-nitrophenyl)-1,3-dihydro-2H-imidazo[4,5-b]pyridin-2-one;
1-(cyclopropylmethyl)-3-methyl-5-thiophen-3-yl-1,3-dihydro-2H-imidazo[4,5-b]pyridin-2-one;
1-(cyclopropylmethyl)-5-[2-(dimethylamino)phenyl]-3-methyl-1,3-dihydro-2H-imidazo[4,5-b]pyridin-2-one;
5-(4-fluoro-2-methylphenyl)-3-methyl-1-(4,4,4-trifluorobutyl)-1,3-dihydro-2H-imidazo[4,5-b]pyridin-2-one;
2-[3-methyl-2-oxo-1-(4,4,4-trifluorobutyl)-2,3-dihydro-1H-imidazo[4,5-b]pyridin-5-yl]benzonitrile;
5-[3-(1-hydroxy-1-methylethyl)phenyl]-3-methyl-1-(4,4,4-trifluorobutyl)-1,3-dihydro-2H-imidazo[4,5-b]pyridin-2-one;

5-[5-(1-hydroxy-1-methylethyl)-2-methylphenyl]-3-methyl-1-(4,4,4-trifluorobutyl)-1,3-dihydro-2H-imidazo[4,5-b]pyridin-2-one;
2-{3-methyl-1-[(1-methylcyclopropyl)methyl]-2-oxo-2,3-dihydro-1H-imidazo[4,5-b]pyridin-5-yl}benzonitrile;
2-[1-(2-cyclopropylethyl)-3-methyl-2-oxo-2,3-dihydro-1H-imidazo[4,5-b]pyridin-5-yl]benzonitrile;
2-{1-[2-fluoro-5-(trifluoromethyl)benzyl]-3-methyl-2-oxo-2,3-dihydro1H-imidazo[4,5-b]pyridin-5-yl}benzonitrile;
2-[1-(4-methoxybenzyl)-3-methyl-2-oxo-2,3-dihydro-1H-imidazo[4,5-b]pyridin-5-yl]benzonitrile;
5-[3-(1-hydroxy-1-methylethyl)phenyl]-3-methyl-1-{[1-(trifluoromethyl)cyclopropyl]methyl}-1,3-dihydro-2H-imidazo[4,5-b]pyridin-2-one;
5-[5-(1-hydroxy-1-methylethyl)-2-methylphenyl]-3-methyl-1-{[1-(trifluoromethyl)cyclopropyl]methyl}-1,3-dihydro-2H-imidazo[4,5-b]pyridin-2-one;
5-(4-fluoro-2-methylphenyl)-3-methyl-1-{[1-(trifluoromethyl)cyclopropyl]methyl}-1,3-dihydro-2H-imidazo[4,5-b]pyridin-2-one;
2-(3-methyl-2-oxo-1-{[1-(trifluoromethyl)cyclopropyl]methyl}-2,3-dihydro-1H-imidazo[4,5-b]pyridin-5-yl)benzonitrile;
3-(3-methyl-2-oxo-1-{[1-(trifluoromethyl)cyclopropyl]methyl}-2,3-dihydro-1H-imidazo[4,5-b]pyridin-5-yl)pyridine-4-carbonitrile;
2-(1-{[2,2-difluorocyclopropyl]methyl}-3-methyl-2-oxo-2,3-dihydro-1H-imidazo[4,5-b]pyridin-5-yl)benzonitrile;
1-[(2,2-difluorocyclopropyl)methyl]-5-[5-(1-hydroxy-1-methylethyl)-2-methylphenyl]-3-methyl-1,3-dihydro-2H-imidazo[4,5-b]pyridin-2-one;
5-(5-acetyl-2-methylphenyl)-1-[(2,2-difluorocyclopropyl)methyl]-3-methyl-1,3-dihydro-2H-imidazo[4,5-b]pyridin-2-one;
1-[(2,2-difluorocyclopropyl)methyl]-5-[3-(1-hydroxy-1-methylethyl)phenyl]-3-methyl-1,3-dihydro-2H-imidazo[4,5-b]pyridin-2-one;
methyl-3-{1-[(2,2-difluorocyclopropyl)methyl]-3-methyl-2-oxo-2,3-dihydro-1H-imidazo[4,5-b]pyridin-5-yl}-4-methylbenzoate;
1-[(2,2-difluorocyclopropyl)methyl]-3-methyl-5-[2-methylthyl-5-(1,1,1-trifluoro-2-hydroxypropan-2-yl)phenyl]-1,3-dihydro-2H-imidazo[4,5-b]pyridin-2-one;
2-(1-{[1-(4-fluorophenyl)-1H-pyrazol-4-yl]methyl}-3-methyl-2-oxo-2,3-dihydro-1H-imidazo[4,5-b]pyridin-5-yl)benzonitrile;
5-chloro-1-{[1-(4-fluorophenyl)-1H-pyrazol-4-yl]methyl}-3-methyl-1,3-dihydro-2H-imidazo[4,5-b]pyridin-2-one;
1-{[1-(4-fluorophenyl)-1H-pyrazol-4-yl]methyl}-5-[3-(1-hydroxy-1-methylethyl)phenyl]-3-methyl-1,3-dihydro-2H-imidazo[4,5-b]pyridin-2-one;
3-[1-(2-fluoro-2-methylpropyl)-3-methyl-2-oxo-2,3-dihydro-1H-imidazo[4,5-b]pyridin-5-yl]pyridine-4-carbonitrile;
1-(2,2-dimethylpropyl)-5-[5-(1-hydroxy-1-methylethyl)-2-methylphenyl]-3-methyl-1,3-dihydro-2H-imidazo[4,5-b]pyridin-2-one;
1-(2,2-dimethylpropyl)-3-methyl-5-[4-(methylsulfonyl)phenyl]-1,3-dihydro-2H-imidazo[4,5-b]pyridin-2-one;
1-(2,2-dimethylpropyl)-3-methyl-5-[2-(trifluoromethyl)phenyl]-1,3-dihydro-2H-imidazo[4,5-b]pyridin-2-one;
5-(3-chlorophenyl)-1-(2,2-dimethylpropyl)-3-methyl-1,3-dihydro-2H-imidazo[4,5-b]pyridin-2-one;
1-(2,2-dimethylpropyl)-5-(4-fluoropyridin-3-yl)-3-methyl-1,3-dihydro-2H-imidazo[4,5-b]pyridin-2-one;
1-(2,2-dimethylpropyl)-5-(4-fluoro-2-methylphenyl)-3-methyl-1,3-dihydro-2H-imidazo[4,5-b]pyridin-2-one;
5-(5,6-dihydro-4H-pyrrolo[1,2-b]pyrazol-3-yl)-1-(2,2-dimethylpropyl)-3-methyl-1,3-dihydro-2H-imidazo[4,5-b]pyridin-2-one;
1-(2,2-dimethylpropyl)-3-methyl-5-(4,5,6,7-tetrahydropyrazlo[1,5-a]pyridin-3-yl)-1,3-dihydro-2H-imidazo[4,5-b]pyridin-2-one;
5-(1,3-dimethyl-2-oxo-2,3-dihydro-1H-benzimidazol-5-yl)-1-(2,2-dimethylpropyl)-3-methyl-1,3-dihydro-2H-imidazo[4,5-b]pyridin-2-one;
1-(2,2-dimethylpropyl)-3-methyl-5-[1-methyl-3-(trifluoromethyl)-1H-pyrazol-5-yl]-1,3-dihydro-2H-imidazo[4,5-b]pyridin-2-one;
1-(2,2-dimethylpropyl)-3-methyl-5-(1-methyl-1H-pyrazol-5-yl)-1,3-dihydro-2H-imidazo[4,5-b]pyridin-2-one;
3-[1-(2,2-dimethylpropyl)-3-methyl-2-oxo-2,3-dihydro-1H-imidazo[4,5-b]pyridin-5-yl]pyridine-4-carbonitrile;
5-(2,3-dihydro-1-benzofuran-5-yl)-1-(2,2-dimethylpropyl)-3-methyl-1,3-dihydro-2H-imidazo[4,5-b]pyridin-2-one;
1-(2,2-dimethylpropyl)-3-methyl-5-[1,2,4]triazolo[4,3-a]pyridin-6-yl-1,3-dihydro-2H-imidazo[4,5-b]pyridin-2-one;
1-(2,2-dimethylpropyl)-3-methyl-5-[1,2,4]triazolo[1,5-a]pyridin-7-yl-1,3-dihydro-2H-imidazo[4,5-b]pyridin-2-one;
1-(2,2-dimethylpropyl)-3-methyl-5-[1,2,4]triazolo[1,5-a]pyridin-6-yl-1,3-dihydro-2H-imidazo[4,5-b]pyridin-2-one;
1-(2,2-dimethylpropyl)-3-methyl-5-(1-methyl-1H-benzotriazol-6-yl)-1,3-dihydro-2H-imidazo[4,5-b]pyridin-2-one;
5-(2-cyclopropylphenyl)-1-(2,2-dimethylpropyl)-3-methyl-1,3-dihydro-2H-imidazo[4,5-b]pyridin-2-one;
5-(3-cyclopropylphenyl)-1-(2,2-dimethylpropyl)-3-methyl-1,3-dihydro-2H-imidazo[4,5-b]pyridin-2-one;
2-[1-(2,2-dimethylpropyl)-3-methyl-2-oxo-2,3-dihydro-1H-imidazo[4,5-b]pyridin-5-yl]-5-methylbenzonitrile;
1-(2,2-dimethylpropyl)-5-[5-(hydroxymethyl)pyridin-3-yl]-3-methyl-1,3-dihydro-2H-imidazo[4,5-b]pyridin-2-one;
1-(2,2-dimethylpropyl)-5-[2-(hydroxymethyl)pyridin-4-yl]-3-methyl-1,3-dihydro-2H-imidazo[4,5-b]pyridin-2-one;
1-(2,2-dimethylpropyl)-3-methyl-5-quinolin-6-yl-1,3-dihydro-2H-imidazo[4,5-b]pyridin-2-one;
1-(2,2-dimethylpropyl)-5-[2-(3-hydroxy-3-methylbutyl)phenyl]-3-methyl-1,3-dihydro-2H-imidazo[4,5-b]pyridin-2-one;
1-(2,2-dimethylpropyl)-3-methyl-5-[3-(1-pyrrolidin-1-ylethyl)phenyl]-1,3-dihydro-2H-imidazo[4,5-b]pyridin-2-one;
1-(2,2-dimethylpropyl)-3-methyl-5-[4-(1-morpholin-4-ylethyl)phenyl]-1,3-dihydro-2H-imidazo[4,5-b]pyridin-2-one;
1-(2,2-dimethylpropyl)-3-methyl-5-[3-(1,1-dioxidothiomorpholin-4-yl)phenyl]-3-methyl-1,3-dihydro-2H-imidazo[4,5-b]pyridin-2-one;
5-(1-benzyl-1H-pyrazol-5-yl)-1-(2,2-dimethylpropyl)-3-methyl-1,3-dihydro-2H-imidazo[4,5-b]pyridin-2-one;

4-[1-(2,2-dimethylpropyl)-3-methyl-2-oxo-2,3-dihydro-1H-imidazo[4,5-b]pyridin-5-yl]thiophene-3-carbonitrile;
5-(1-benzyl-1H-pyrazol-4-yl)-1-(2,2-dimethylpropyl)-3-methyl-1,3-dihydro-2H-imidazo[4,5-b]pyridin-2-one;
1-(2,2-dimethylpropyl)-3-methyl-5-[1-(2-methylpropyl)-1H-pyrazol-4-yl]-1,3-dihydro-2H-imidazo[4,5-b]pyridin-2-one;
1-(2,2-dimethylpropyl)-3-methyl-5-(1-methyl-1H-pyrrol-2-yl)-1,3-dihydro-2H-imidazo[4,5-b]pyridin-2-one;
1-(2,2-dimethylpropyl)-3-methyl-5-(5-methyl-1-phenyl-1H-pyrazol-4-yl)-1,3-dihydro-2H-imidazo[4,5-b]pyridin-2-one;
1-(2,2-dimethylpropyl)-3-methyl-5-quinolin-8-yl-1,3-dihydro-2H-imidazo[4,5-b]pyridin-2-one;
1-(2,2-dimethylpropyl)-3-methyl-5-[3-(morpholin-4-ylmethyl)phenyl]-1,3-dihydro-2H-imidazo[4,5-b]pyridin-2-one;
5-(3-chloro-4-fluorophenyl)-1-(2,2-dimethylpropyl)-3-methyl-1,3-dihydro-2H-imidazo[4,5-b]pyridin-2-one;
1-(2,2-dimethylpropyl)-3-methyl-5-[2-(1H-pyrazol-1-yl)phenyl]-1,3-dihydro-2H-imidazo[4,5-b]pyridin-2-one;
1-(2,2-dimethylpropyl)-3-methyl-5-[3-(1H-pyrazol-1-yl)phenyl]-1,3-dihydro-2H-imidazo[4,5-b]pyridin-2-one;
1-(2,2-dimethylpropyl)-3-methyl-5-[3-(4-methylpiperazin-1-yl)phenyl]-1,3-dihydro-2H-imidazo[4,5-b]pyridin-2-one;
1-(2,2-dimethylpropyl)-3-methyl-5-quinolin-5-yl-1,3-dihydro-2H-imidazo[4,5-b]pyridin-2-one;
1-(2,2-dimethylpropyl)-5-[4-(1,1-dioxidothiomorpholin-4-yl)phenyl]-3-methyl-1,3-dihydro-2H-imidazo[4,5-b]pyridin-2-one;
ethyl 5-[1-(2,2-dimethylpropyl)-3-methyl-2-oxo-2,3-dihydro-1H-imidazo[4,5-b]pyridin-5-yl]pyridine-3-carboxylate;
1-(2,2-dimethylpropyl)-3-methyl-5-[4-(trifluoromethyl)pyridin-3-yl]-1,3-dihydro-2H-imidazo[4,5-b]pyridin-2-one;
1-(2,2-dimethylpropyl)-5-(4-methoxy-3-methylphenyl)-3-methyl-1,3-dihydro-2H-imidazo[4,5-b]pyridin-2-one;
1-(2,2-dimethylpropyl)-3-methyl-5-[5-(morpholin-4-ylcarbonyl)pyridin-3-yl]-1,3-dihydro-2H-imidazo[4,5-b]pyridin-2-one;
1-(2,2-dimethylpropyl)-5-(3-fluoro-2-morpholin-4-ylpyridin-4-yl)-3-methyl-1,3-dihydro-2H-imidazo[4,5-b]pyridin-2-one;
{3-[1-(2,2-dimethylpropyl)-3-methyl-2-oxo-2,3-dihydro-1H-imidazo[4,5-b]pyridin-5-yl]phenyl}acetonitrile;
3-[1-(2,2-dimethylpropyl)-3-methyl-2-oxo-2,3-dihydro-1H-imidazo[4,5-b]pyridin-5-yl]-N,N-dimethylbenzenesulfonamide;
5-[6-(dimethylamino)pyridin-3-yl]-1-(2,2-dimethylpropyl)-3-methyl-1,3-dihydro-2H-imidazo[4,5-b]pyridin-2-one;
tert-butyl ({5-[1-(2,2-dimethylpropyl)-3-methyl-2-oxo-2,3-dihydro-1H-imidazo[4,5-b]pyridin-5-yl]pyridin-3-yl}methyl)carbamate;
tert-butyl 4-{3-[1-(2,2-dimethylpropyl)-3-methyl-2-oxo-2,3-dihydro-1H-imidazo[4,5-b]pyridin-5-yl]phenyl}piperazine-1-carboxylate;
5-(3-aminophenyl)-1-(2,2-dimethylpropyl)-3-methyl-1,3-dihydro-2H-imidazo[4,5-b]pyridin-2-one;
5-(4-chloro-2-methylphenyl)-1-(2,2-dimethylpropyl)-3-methyl-1,3-dihydro-2H-imidazo[4,5-b]pyridin-2-one;
1-(2,2-dimethylpropyl)-3-methyl-5-(3-morpholin-4-ylphenyl)-1,3-dihydro-2H-imidazo[4,5-b]pyridin-2-one;
tert-butyl 4-{2-[1-(2,2-dimethylpropyl)-3-methyl-2-oxo-2,3-dihydro-1H-imidazo[4,5-b]pyridin-5-yl]phenyl}piperazine-1-carboxylate;
3-[1-(2,2-dimethylpropyl)-3-methyl-2-oxo-2,3-dihydro-1H-imidazo[4,5-b]pyridin-5-yl]-4-methoxybenzonitrile;
3-[1-(2,2-dimethylpropyl)-3-methyl-2-oxo-2,3-dihydro-1H-imidazo[4,5-b]pyridin-5-yl]pyridine-2-carbonitrile;
1-(2,2-dimethylpropyl)-5-(2,4-dimethyl-1,3-thiazol-5-yl)-3-methyl-1,3-dihydro-2H-imidazo[4,5-b]pyridin-2-one;
3-[1-(2,2-dimethylpropyl)-3-methyl-2-oxo-2,3-dihydro-1H-imidazo[4,5-b]pyridin-5-yl]-N,N-dimethylbenzamide;
methyl 3-[1-(2,2-dimethylpropyl)-3-methyl-2-oxo-2,3-dihydro-1H-imidazo[4,5-b]pyridin-5-yl]benzoate;
tert-butyl {3-[1-(2,2-dimethylpropyl)-3-methyl-2-oxo-2,3-dihydro-1H-imidazo[4,5-b]pyridin-5-yl]benzyl}carbamate;
2-[1-(2,2-dimethylpropyl)-3-methyl-2-oxo-2,3-dihydro-1H-imidazo[4,5-b]pyridin-5-yl]-4-methylbenzonitrile;
1-(2,2-dimethylpropyl)-5-(2-fluoro-6-methylpyridin-3-yl)-3-methyl-1,3-dihydro-2H-imidazo[4,5-b]pyridin-2-one;
1-(2,2-dimethylpropyl)-5-(6-fluoro-2-methylpyridin-3-yl)-3-methyl-1,3-dihydro-2H-imidazo[4,5-b]pyridin-2-one;
1-(2,2-dimethylpropyl)-3-methyl-5-(4-methyl-2-phenyl-1,3-thiazol-5-yl)-1,3-dihydro-2H-imidazo[4,5-b]pyridin-2-one;
1-(2,2-dimethylpropyl)-5-[3-(hydroxymethyl)phenyl]-3-methyl-1,3-dihydro-2H-imidazo[4,5-b]pyridin-2-one;
methyl 3-[1-(2,2-dimethylpropyl)-3-methyl-2-oxo-2,3-dihydro-1H-imidazo[4,5-b]pyridin-5-yl]-4-fluorobenzoate;
methyl 4-[1-(2,2-dimethylpropyl)-3-methyl-2-oxo-2,3-dihydro-1H-imidazo[4,5-b]pyridin-5-yl]-3-fluorobenzoate;
ethyl 3-[1-(2,2-dimethylpropyl)-3-methyl-2-oxo-2,3-dihydro-1H-imidazo[4,5-b]pyridin-5-yl]-2-fluorobenzoate;
methyl 3-chloro-5-[1-(2,2-dimethylpropyl)-3-methyl-2-oxo-2,3-dihydro-1H-imidazo[4,5-b]pyridin-5-yl]benzoate;
1-(2,2-dimethylpropyl)-3-methyl-5-phenyl-1,3-dihydro-2H-imidazo[4,5-b]pyridin-2-one;
2-[1-(2,2-dimethylpropyl)-3-methyl-2-oxo-2,3-dihydro-1H-imidazo[4,5-b]pyridin-5-yl]benzonitrile;
1-(2,2-dimethylpropyl)-5-[3-(1-hydroxy-1-methylethyl)phenyl]-3-methyl-1,3-dihydro-2H-imidazo[4,5-b]pyridin-2-one;
1-{4-[1-(2,2-dimethylpropyl)-3-methyl-2-oxo-2,3-dihydro-1H-imidazo[4,5-b]pyridin-5-yl]benzyl}-3-methylimidazolidine-2,4-dione;
2-[1-(2,2-dimethylpropyl)-3-methyl-2-oxo-2,3-dihydro-1H-imidazo[4,5-b]pyridin-5-yl]-6-(trifluoromethyl)benzonitrile;
2-[1-(2,2-dimethylpropyl)-3-methyl-2-oxo-2,3-dihydro-1H-imidazo[4,5-b]pyridin-5-yl]-5-fluorobenzonitrile;
1-(2,2-dimethylpropyl)-5-(3-fluoro-4-methylphenyl)-3-methyl-1,3-dihydro-2H-imidazo[4,5-b]pyridin-2-one;
1-(2,2-dimethylpropyl)-3-methyl-5-pyridin-3-yl-1,3-dihydro-2H-imidazo[4,5-b]pyridin-2-one;

2-[1-(2,2-dimethylpropyl)-3-methyl-2-oxo-2,3-dihydro-1H-imidazo[4,5-b]pyridin-5-yl]-3-methoxybenzonitrile;
5-[4-(aminomethyl)phenyl]-1-(2,2-dimethylpropyl)-3-methyl-1,3-dihydro-2H-imidazo[4,5-b]pyridin-2-one;
2-[1-(2,2-dimethylpropyl)-3-methyl-2-oxo-2,3-dihydro-1H-imidazo[4,5-b]pyridin-5-yl]-5-(trifluoromethyl)benzonitrile;
2-[1-(2,2-dimethylpropyl)-3-methyl-2-oxo-2,3-dihydro-1H-imidazo[4,5-b]pyridin-5-yl]-6-methoxybenzonitrile;
3-[1-(2,2-dimethylpropyl)-3-methyl-2-oxo-2,3-dihydro-1H-imidazo[4,5-b]pyridin-5-yl]benzonitrile;
5-(2,4-difluorophenyl)-1-(2,2-dimethylpropyl)-3-methyl-1,3-dihydro-2H-imidazo[4,5-b]pyridin-2-one;
1-(2,2-dimethylpropyl)-5-(2-fluorophenyl)-3-methyl-1,3-dihydro-2H-imidazo[4,5-b]pyridin-2-one;
4-[1-(2,2-dimethylpropyl)-3-methyl-2-oxo-2,3-dihydro-1H-imidazo[4,5-b]pyridin-5-yl]benzonitrile;
1-(2,2-dimethylpropyl)-3-methyl-5-(4-methylphenyl)-1,3-dihydro-2H-imidazo[4,5-b]pyridin-2-one;
1-(2,2-dimethylpropyl)-5-(4-fluorophenyl)-3-methyl-1,3-dihydro-2H-imidazo[4,5-b]pyridin-2-one;
1-(2,2-dimethylpropyl)-5-(3-methoxyphenyl)-3-methyl-1,3-dihydro-2H-imidazo[4,5-b]pyridin-2-one;
1-(2,2-dimethylpropyl)-5-(2-methoxyphenyl)-3-methyl-1,3-dihydro-2H-imidazo[4,5-b]pyridin-2-one;
1-(2,2-dimethylpropyl)-3-methyl-5-(2-methylphenyl)-1,3-dihydro-2H-imidazo[4,5-b]pyridin-2-one;
1-(2,2-dimethylpropyl)-3-methyl-5-naphthalen-2-yl-1,3-dihydro-2H-imidazo[4,5-b]pyridin-2-one;
1-(2,2-dimethylpropyl)-3-methyl-5-(3-methylphenyl)-1,3-dihydro-2H-imidazo[4,5-b]pyridin-2-one;
1-(2,2-dimethylpropyl)-5-[4-(hydroxymethyl)phenyl]-3-methyl-1,3-dihydro-2H-imidazo[4,5-b]pyridin-2-one;
5-(3-acetylphenyl)-1-(2,2-dimethylpropyl)-3-methyl-1,3-dihydro-2H-imidazo[4,5-b]pyridin-2-one;
3-[1-(2,2-dimethylpropyl)-3-methyl-2-oxo-2,3-dihydro-1H-imidazo[4,5-b]pyridin-5-yl]-4-methylbenzonitrile;
1-(2,2-dimethylpropyl)-3-methyl-5-(4-oxo-3,4-dihydro-2H-chromen-6-yl)-1,3-dihydro-2H-imidazo[4,5-b]pyridin-2-one;
2-[1-(2,2-dimethylpropyl)-3-methyl-2-oxo-2,3-dihydro-1H-imidazo[4,5-b]pyridin-5-yl]-4-(hydroxylmethyl)benzonitrile;
methyl 3-[1-(2,2-dimethylpropyl)-3-methyl-2-oxo-2,3-dihydro-1H-imidazo[4,5-b]pyridin-5-yl]-4-methylbenzoate;
1-(2,2-dimethylpropyl)-5-[2-fluoro-3-(1H-pyrazol-5-yl)phenyl]-3-methyl-1,3-dihydro-2H-imidazo[4,5-b]pyridin-2-one;
1-(2,2-dimethylpropyl)-3-methyl-5-(3-oxo-2,3-dihydro-1H-inden-5-yl)-1,3-dihydro-2H-imidazo[4,5-b]pyridin-2-one;
5-(5-acetyl-2-methylphenyl)-1-(2,2-dimethylpropyl)-3-methyl-1,3-dihydro-2H-imidazo[4,5-b]pyridin-2-one;
4-{4-cyano-3-[1-(2,2-dimethylpropyl)-3-methyl-2-oxo-2,3-dihydro-1H-imidazo[4,5-b]pyridin-5-yl]phenoxy}pyridine-2-carbonitrile;
6-{4-cyano-3-[1-(2,2-dimethylpropyl)-3-methyl-2-oxo-2,3-dihydro-1H-imidazo[4,5-b]pyridin-5-yl]phenoxy}pyridine-3-carbonitrile;
6-{4-cyano-3-[1-(2,2-dimethylpropyl)-3-methyl-2-oxo-2,3-dihydro-1H-imidazo[4,5-b]pyridin-5-yl]phenoxy}pyridine-2-carbonitrile;
4-{4-cyano-3-[1-(cyclopropylmethyl)-3-methyl-2-oxo-2,3-dihydro-1H-imidazo[4,5-b]pyridin-5-yl]phenoxy}pyridine-2-carbonitrile;
4-{3-[1-(2,2-dimethylpropyl)-3-methyl-2-oxo-2,3-dihydro-1H-imidazo[4,5-b]pyridin-5-yl]phenoxy}pyridine-2-carbonitrile;
1-(2,2-dimethylpropyl)-3-methyl-5-[3-(pyridin-2-yloxy)phenyl]-1,3-dihydro-2H-imidazo[4,5-b]pyridin-2-one;
6-{3-[1-(2,2-dimethylpropyl)-3-methyl-2-oxo-2,3-dihydro-1H-imidazo[4,5-b]pyridin-5-yl]phenoxy}pyridine-3-carbonitrile;
4-{3-[1-(2,2-dimethylpropyl)-3-methyl-2-oxo-2,3-dihydro-1H-imidazo[4,5-b]pyridin-5-yl]phenoxy}pyridine-3-carbonitrile;
6-{3-[1-(2,2-dimethylpropyl)-3-methyl-2-oxo-2,3-dihydro-1H-imidazo[4,5-b]pyridin-5-yl]phenoxy}pyridine-3-carbonitrile;
6-{3-[1-(2,2-dimethylpropyl)-3-methyl-2-oxo-2,3-dihydro-1H-imidazo[4,5-b]pyridin-5-yl]phenoxy}pyridine-2-carbonitrile;
2-{3-[1-(2,2-dimethylpropyl)-3-methyl-2-oxo-2,3-dihydro-1H-imidazo[4,5-b]pyridin-5-yl]phenoxy}pyridine-4-carbonitrile;
2-{3-[1-(2,2-dimethylpropyl)-3-methyl-2-oxo-2,3-dihydro-1H-imidazo[4,5-b]pyridin-5-yl]phenoxy}pyridine-3-carbonitrile;
4-{3-[1-(2,2-dimethylpropyl)-3-methyl-2-oxo-2,3-dihydro-1H-imidazo[4,5-b]pyridin-5-yl]-4-methylphenoxy}pyridine-2-carbonitrile;
6-{3-[1-(2,2-dimethylpropyl)-3-methyl-2-oxo-2,3-dihydro-1H-imidazo[4,5-b]pyridin-5-yl]-4-methylphenoxy}pyridine-3-carbonitrile;
4-{3-[1-(2,2-dimethylpropyl)-3-methyl-2-oxo-2,3-dihydro-1H-imidazo[4,5-b]pyridin-5-yl]-4-methylphenoxy}pyridine-3-carbonitrile;
1-(2,2-dimethylpropyl)-5-[3-(1-hydroxy-1-phenylethyl)phenyl]-3-methyl-1,3-dihydro-2H-imidazo[4,5-b]pyridin-2-one;
2-[1-(2,2-dimethylpropyl)-3-methyl-2-oxo-2,3-dihydro-1H-imidazo[4,5-b]pyridin-5-yl]-4-(pyrrolidin-1-ylmethyl)benzonitrile;
2-[1-(2,2-dimethylpropyl)-3-methyl-2-oxo-2,3-dihydro-1H-imidazo[4,5-b]pyridin-5-yl]-4-(morpholin-4-ylmethyl)benzonitrile;
2-[1-(2,2-dimethylpropyl)-3-methyl-2-oxo-2,3-dihydro-1H-imidazo[4,5-b]pyridin-5-yl]-4-[(2-oxo-1,3-oxazolidin-3-yl)methyl]benzonitrile;
4-({[2-(dimethylamino)ethyl]amino}methyl)-2-[1-(2,2-dimethylpropyl)-3-methyl-2-oxo-2,3-dihydro-1H-imidazo[4,5-b]pyridin-5-yl]benzonitrile;
2-[1-(2,2-dimethylpropyl)-3-methyl-2-oxo-2,3-dihydro-1H-imidazo[4,5-b]pyridin-5-yl]-4-[(4-hydroxypiperidin-1-yl)methyl]benzonitrile;
2-[1-(2,2-dimethylpropyl)-3-methyl-2-oxo-2,3-dihydro-1H-imidazo[4,5-b]pyridin-5-yl]-4-{[(2-hydroxyethyl)amino]methyl}benzonitrile;
2-[1-(2,2-dimethylpropyl)-3-methyl-2-oxo-2,3-dihydro-1H-imidazo[4,5-b]pyridin-5-yl]-4-[(3-hydroxypiperidin-1-yl)methyl]benzonitrile;
2-[1-(2,2-dimethylpropyl)-3-methyl-2-oxo-2,3-dihydro-1H-imidazo[4,5-b]pyridin-5-yl]-4-{[(3-hydroxy-2,2-dimethylpropyl)amino]methyl}benzonitrile;
2-[1-(2,2-dimethylpropyl)-3-methyl-2-oxo-2,3-dihydro-1H-imidazo[4,5-b]pyridin-5-yl]-4-[(4-methylpiperazin-1-yl)methyl]benzonitrile;

2-[1-(2,2-dimethylpropyl)-3-methyl-2-oxo-2,3-dihydro-1H-imidazo[4,5-b]pyridin-5-yl]-4-[(1,1-dioxidothiomorpholin-4-yl)methyl]benzonitrile;

2-[1-(2,2-dimethylpropyl)-3-methyl-2-oxo-2,3-dihydro-1H-imidazo[4,5-b]pyridin-5-yl]-4-[(3-hydroxypyrrolidin-1-yl)methyl]benzonitrile;

2-[1-(2,2-dimethylpropyl)-3-methyl-2-oxo-2,3-dihydro-1H-imidazo[4,5-b]pyridin-5-yl]-4-[(2-methyl-1-oxo-2,8-diazaspiro[4.5]dec-8-yl)methyl]benzonitrile;

2-[1-(2,2-dimethylpropyl)-3-methyl-2-oxo-2,3-dihydro-1H-imidazo[4,5-b]pyridin-5-yl]-4-{[8-methyl-3-(trifluoromethyl)-5,6-dihydroimidazo[1,2-a]pyrazin-7(8H)-yl]methyl}benzonitrile;

2-[1-(2,2-dimethylpropyl)-3-methyl-2-oxo-2,3-dihydro-1H-imidazo[4,5-b]pyridin-5-yl]-4-[(1-oxidothiomorpholin-4-yl)methyl]benzonitrile;

2-[1-(2,2-dimethylpropyl)-3-methyl-2-oxo-2,3-dihydro-1H-imidazo[4,5-b]pyridin-5-yl]-4-{[(2R,4R)-4-hydroxy-2-methylpyrrolidin-1-yl]methyl}benzonitrile;

4-(8-azabicyclo[3.2.1]oct-8-ylmethyl)-2-[1-(2,2-dimethylpropyl)-3-methyl-2-oxo-2,3-dihydro-1H-imidazo[4,5-b]pyridin-5-yl]benzonitrile;

2-[1-(2,2-dimethylpropyl)-3-methyl-2-oxo-2,3-dihydro-1H-imidazo[4,5-b]pyridin-5-yl]-4-[(1R,4R)-2-oxa-5-azabicyclo[2.2.1]hept-5-ylmethyl]benzonitrile;

2-[1-(2,2-dimethylpropyl)-3-methyl-2-oxo-2,3-dihydro-1H-imidazo[4,5-b]pyridin-5-yl]-4-{[2-(trifluoromethyl)piperidin-1-yl]methyl}benzonitrile;

2-[1-(2,2-dimethylpropyl)-3-methyl-2-oxo-2,3-dihydro-1H-imidazo[4,5-b]pyridin-5-yl]-4-({[3-(3,5-dimethyl-1H-pyrazol-1-yl)benzyl](methyl)amino}methyl)benzonitrile;

2-[1-(2,2-dimethylpropyl)-3-methyl-2-oxo-2,3-dihydro-1H-imidazo[4,5-b]pyridin-5-yl]-4-({methyl[2-(4-methylpiperazin-1-yl)ethyl]amino}methyl)benzonitrile;

2-[1-(2,2-dimethylpropyl)-3-methyl-2-oxo-2,3-dihydro-1H-imidazo[4,5-b]pyridin-5-yl]-4-{[3-(trifluoromethyl)-1,5,6,7-tetrahydro-4H-pyrazolo[4,3-b]pyridin-4-yl]methyl}benzonitrile;

4-(6,7-dihydroisoxazolo[4,5-c]pyridin-5(4H)-ylmethyl)-2-[1-(2,2-dimethylpropyl)-3-methyl-2-oxo-2,3-dihydro-1H-imidazo[4,5-b]pyridin-5-yl]benzonitrile;

2-[1-(2,2-dimethylpropyl)-3-methyl-2-oxo-2,3-dihydro-1H-imidazo[4,5-b]pyridin-5-yl]-4-{[3-(trifluoromethyl)-1,4,6,7-tetrahydro-5H-pyrazolo[4,3-c]pyridin-5-yl]methyl}benzonitrile;

2-[1-(2,2-dimethylpropyl)-3-methyl-2-oxo-2,3-dihydro-1H-imidazo[4,5-b]pyridin-5-yl]-4-{[3-(trifluoromethyl)-1,4,5,7-tetrahydro-6H-pyrazolo[3,4-c]pyridin-6-yl]methyl}benzonitrile;

2-[1-(2,2-dimethylpropyl)-3-methyl-2-oxo-2,3-dihydro-1H-imidazo[4,5-b]pyridin-5-yl]-4-({[1-(methylsulfonyl)piperidin-4-yl]amino}methyl)benzonitrile;

2-[1-(2,2-dimethylpropyl)-3-methyl-2-oxo-2,3-dihydro-1H-imidazo[4,5-b]pyridin-5-yl]-4-[(3-hydroxy-3-phenylpyrrolidin-1-yl)methyl]benzonitrile;

2-({4-cyano-3-[1-(2,2-dimethylpropyl)-3-methyl-2-oxo-2,3-dihydro-1H-imidazo[4,5-b]pyridin-5-yl]benzyl}amino)-N,N-dimethylethanesulfonamide;

2-[1-(2,2-dimethylpropyl)-3-methyl-2-oxo-2,3-dihydro-1H-imidazo[4,5-b]pyridin-5-yl]-4-{[2-(trifluoromethyl)morpholin-4-yl]methyl}benzonitrile;

4-{[(3S,4S)-3,4-difluoropyrrolidin-1-yl]methyl}-2-[1-(2,2-dimethylpropyl)-3-methyl-2-oxo-2,3-dihydro-1H-imidazo[4,5-b]pyridin-5-yl]benzonitrile;

2-[1-(2,2-dimethylpropyl)-3-methyl-2-oxo-2,3-dihydro-1H-imidazo[4,5-b]pyridin-5-yl]-4-{[(2R)-2-(trifluoromethyl)pyrrolidin-1-yl]methyl}benzonitrile;

tert-butyl (3-{4-cyano-3-[1-(2,2-dimethylpropyl)-3-methyl-2-oxo-2,3-dihydro-1H-imidazo[4,5-b]pyridin-5-yl]benzyl}-3-azabicyclo[3.1.0]hex-6-yl)carbamate;

2-[1-(2,2-dimethylpropyl)-3-methyl-2-oxo-2,3-dihydro-1H-imidazo[4,5-b]pyridin-5-yl]-4-[(3-oxo-1,4-diazepan-1-yl)methyl]benzonitrile;

2-[1-(2,2-dimethylpropyl)-3-methyl-2-oxo-2,3-dihydro-1H-imidazo[4,5-b]pyridin-5-yl]-4-{[4-(methylsulfonyl)piperidin-1-yl]methyl}benzonitrile;

4-({4-[dimethyl(phenyl)silyl]piperidin-1-yl}methyl)-2-[1-(2,2-dimethylpropyl)-3-methyl-2-oxo-2,3-dihydro-1H-imidazo[4,5-b]pyridin-5-yl]benzonitrile;

4-[(3,3-difluoropyrrolidin-1-yl)methyl]-2-[1-(2,2-dimethylpropyl)-3-methyl-2-oxo-2,3-dihydro-1H-imidazo[4,5-b]pyridin-5-yl]benzonitrile;

4-[(3,3-difluoroazetidin-1-yl)methyl]-2-[1-(2,2-dimethylpropyl)-3-methyl-2-oxo-2,3-dihydro-1H-imidazo[4,5-b]pyridin-5-yl]benzonitrile;

4-[(3,3-dimethoxypyrrolidin-1-yl)methyl]-2-[1-(2,2-dimethylpropyl)-3-methyl-2-oxo-2,3-dihydro-1H-imidazo[4,5-b]pyridin-5-yl]benzonitrile;

4-(6,7-dihydrothieno[3,2-c]pyridin-5(4H)-ylmethyl)-2-[1-(2,2-dimethylpropyl)-3-methyl-2-oxo-2,3-dihydro-1H-imidazo[4,5-b]pyridin-5-yl]benzonitrile;

2-[1-(2,2-dimethylpropyl)-3-methyl-2-oxo-2,3-dihydro-1H-imidazo[4,5-b]pyridin-5-yl]-4-{[(2S)-2-(trifluoromethyl)pyrrolidin-1-yl]methyl}benzonitrile;

2-[1-(2,2-dimethylpropyl)-3-methyl-2-oxo-2,3-dihydro-1H-imidazo[4,5-b]pyridin-5-yl]-4-({4-[hydroxy(pyridin-3-yl)methyl]piperidin-1-yl}methyl)benzonitrile;

2-[1-(2,2-dimethylpropyl)-3-methyl-2-oxo-2,3-dihydro-1H-imidazo[4,5-b]pyridin-5-yl]-4-({4-[(3-hydroxyphenyl)sulfonyl]piperazin-1-yl}methyl)benzonitrile;

2-[1-(2,2-dimethylpropyl)-3-methyl-2-oxo-2,3-dihydro-1H-imidazo[4,5-b]pyridin-5-yl]-4-{[4-(1,1-dioxidotetrahydrothiophen-3-yl)piperazin-1-yl]methyl}benzonitrile;

2-[1-(2,2-dimethylpropyl)-3-methyl-2-oxo-2,3-dihydro-1H-imidazo[4,5-b]pyridin-5-yl]-4-{[3-(trifluoromethyl)piperidin-1-yl]methyl}benzonitrile;

2-[1-(2,2-dimethylpropyl)-3-methyl-2-oxo-2,3-dihydro-1H-imidazo[4,5-b]pyridin-5-yl]-4-{[4-(methylsulfonyl)piperazin-1-yl]methyl}benzonitrile;

tert-butyl 5-{4-cyano-3-[1-(2,2-dimethylpropyl)-3-methyl-2-oxo-2,3-dihydro-1H-imidazo[4,5-b]pyridin-5-yl]benzyl}-2,5-diazabicyclo[2.2.2]octane-2-carboxylate;

4-[(4-acetylpiperazin-1-yl)methyl]-2-[1-(2,2-dimethylpropyl)-3-methyl-2-oxo-2,3-dihydro-1H-imidazo[4,5-b]pyridin-5-yl]benzonitrile;

1-{4-cyano-3-[1-(2,2-dimethylpropyl)-3-methyl-2-oxo-2,3-dihydro-1H-imidazo[4,5-b]pyridin-5-yl]benzyl}piperidine-4-carboxamide;

2-[1-(2,2-dimethylpropyl)-3-methyl-2-oxo-2,3-dihydro-1H-imidazo[4,5-b]pyridin-5-yl]-4-[(4-hydroxy-4-phenylpiperidin-1-yl)methyl]benzonitrile;

ethyl 4-({4-cyano-3-[1-(2,2-dimethylpropyl)-3-methyl-2-oxo-2,3-dihydro-1H-imidazo[4,5-b]pyridin-5-yl]benzyl}amino)piperidine-1-carboxylate;

2-[1-(2,2-dimethylpropyl)-3-methyl-2-oxo-2,3-dihydro-1H-imidazo[4,5-b]pyridin-5-yl]-4-{[4-(4-methyl-4H-1,2,4-triazol-3-yl)piperidin-1-yl]methyl}benzonitrile;

2-[1-(2,2-dimethylpropyl)-3-methyl-2-oxo-2,3-dihydro-1H-imidazo[4,5-b]pyridin-5-yl]-4-[(5-oxo-1,4-diazepan-1-yl)methyl]benzonitrile;

4-(3,4-dihydroisoquinolin-2(1H)-ylmethyl)-2-[1-(2,2-dimethylpropyl)-3-methyl-2-oxo-2,3-dihydro-1H-imidazo[4,5-b]pyridin-5-yl]benzonitrile;

4-(3,4-dihydroquinolin-1(2H)-ylmethyl)-2-[1-(2,2-dimethylpropyl)-3-methyl-2-oxo-2,3-dihydro-1H-imidazo[4,5-b]pyridin-5-yl]benzonitrile;

2-[1-(2,2-dimethylpropyl)-3-methyl-2-oxo-2,3-dihydro-1H-imidazo[4,5-b]pyridin-5-yl]-4-{[1-methyl-3-(trifluoromethyl)-1,5,6,7-tetrahydro-4H-pyrazolo[4,3-b]pyridin-4-yl]methyl}benzonitrile;

4-[(2-cyclopropyl-6,7-dihydro[1,3]oxazolo[4,5-c]pyridin-5(4H)-yl)methyl]-2-[1-(2,2-dimethylpropyl)-3-methyl-2-oxo-2,3-dihydro-1H-imidazo[4,5-b]pyridin-5-yl]benzonitrile;

2-[1-(2,2-dimethylpropyl)-3-methyl-2-oxo-2,3-dihydro-1H-imidazo[4,5-b]pyridin-5-yl]-4-{[2-(trifluoromethyl)-1,4,6,7-tetrahydro-5H-imidazo[4,5-c]pyridin-5-yl]methyl}benzonitrile;

2-[1-(2,2-dimethylpropyl)-3-methyl-2-oxo-2,3-dihydro-1H-imidazo[4,5-b]pyridin-5-yl]-4-{[5,5-dimethyl-3-(trifluoromethyl)-5,6-dihydro[1,2,4]triazolo[4,3-a]pyrazin-7(8H)-yl]methyl}benzonitrile;

2-[1-(2,2-dimethylpropyl)-3-methyl-2-oxo-2,3-dihydro-1H-imidazo[4,5-b]pyridin-5-yl]-4-{[2-(trifluoromethyl)-6,7-dihydro[1,3]thiazolo[4,5-c]pyridin-5(4H)-yl]methyl}benzonitrile;

2-[1-(2,2-dimethylpropyl)-3-methyl-2-oxo-2,3-dihydro-1H-imidazo[4,5-b]pyridin-5-yl]-4-[(2-phenyl-3,4,6,7-tetrahydro-5H-imidazo[4,5-c]pyridin-5-yl)methyl]benzonitrile;

2-[1-(2,2-dimethylpropyl)-3-methyl-2-oxo-2,3-dihydro-1H-imidazo[4,5-b]pyridin-5-yl]-4-[(2-methyl-6,7-dihydro[1,3]oxazolo[5,4-c]pyridin-5(4H)-yl)methyl]benzonitrile;

2-[1-(2,2-dimethylpropyl)-3-methyl-2-oxo-2,3-dihydro-1H-imidazo[4,5-b]pyridin-5-yl]-4-[(2-methyl-6,7-dihydro[1,3]thiazolo[5,4-c]pyridin-5(4H)-yl)methyl]benzonitrile;

2-[1-(2,2-dimethylpropyl)-3-methyl-2-oxo-2,3-dihydro-1H-imidazo[4,5-b]pyridin-5-yl]-4-(1,4,6,7-tetrahydro-5H-pyrazolo[4,3-c]pyridin-5-ylmethyl)benzonitrile;

2-[1-(2,2-dimethylpropyl)-3-methyl-2-oxo-2,3-dihydro-1H-imidazo[4,5-b]pyridin-5-yl]-4-[(3-methyl-1,4,6,7-tetrahydro-5H-pyrazolo[4,3-c]pyridin-5-yl)methyl]benzonitrile;

2-[1-(2,2-dimethylpropyl)-3-methyl-2-oxo-2,3-dihydro-1H-imidazo[4,5-b]pyridin-5-yl]-4-{[3-(4-fluorophenyl)-1,4,6,7-tetrahydro-5H-pyrazolo[4,3-c]pyridin-5-yl]methyl}benzonitrile;

2-[1-(2,2-dimethylpropyl)-3-methyl-2-oxo-2,3-dihydro-1H-imidazo[4,5-b]pyridin-5-yl]-4-[(3-methoxy-5,6-dihydro[1,2,4]triazolo[4,3-a]pyrazin-7(8H)-yl)methyl]benzonitrile;

2-[1-(2,2-dimethylpropyl)-3-methyl-2-oxo-2,3-dihydro-1H-imidazo[4,5-b]pyridin-5-yl]-4-{[8-methyl-2-(trifluoromethyl)-5,6-dihydroimidazo[1,2-a]pyrazin-7(8H)-yl]methyl}benzonitrile;

2-[1-(2,2-dimethylpropyl)-3-methyl-2-oxo-2,3-dihydro-1H-imidazo[4,5-b]pyridin-5-yl]-4-{[5,8-dimethyl-3-(trifluoromethyl)-5,6-dihydro[1,2,4]triazolo[4,3-a]pyrazin-7(8H)-yl]methyl}benzonitrile;

ethyl 7-{4-cyano-3-[1-(2,2-dimethylpropyl)-3-methyl-2-oxo-2,3-dihydro-1H-imidazo[4,5-b]pyridin-5-yl]benzyl}-5,6,7,8-tetrahydro[1,2,4]triazolo[4,3-a]pyrazine-3-carboxylate;

ethyl 7-{4-cyano-3-[1-(2,2-dimethylpropyl)-3-methyl-2-oxo-2,3-dihydro-1H-imidazo[4,5-b]pyridin-5-yl]benzyl}-5,6,7,8-tetrahydroimidazo[1,2-a]pyrazine-2-carboxylate;

2-[1-(2,2-dimethylpropyl)-3-methyl-2-oxo-2,3-dihydro-1H-imidazo[4,5-b]pyridin-5-yl]-4-{[1-methyl-3-(trifluoromethyl)-1,4,6,7-tetrahydro-5H-pyrazolo[4,3-c]pyridin-5-yl]methyl}benzonitrile;

4-(5,6-dihydroimidazo[1,2-a]pyrazin-7(8H)-ylmethyl)-2-[1-(2,2-dimethylpropyl)-3-methyl-2-oxo-2,3-dihydro-1H-imidazo[4,5-b]pyridin-5-yl]benzonitrile;

2-[1-(2,2-dimethylpropyl)-3-methyl-2-oxo-2,3-dihydro-1H-imidazo[4,5-b]pyridin-5-yl]-4-{[1-methyl-3-(trifluoromethyl)-1,4,5,7-tetrahydro-6H-pyrazolo[3,4-c]pyridin-6-yl]methyl}benzonitrile;

2-[1-(2,2-dimethylpropyl)-3-methyl-2-oxo-2,3-dihydro-1H-imidazo[4,5-b]pyridin-5-yl]-4-{[8-methyl-2-(trifluoromethyl)-5,6-dihydro[1,2,4]triazolo[1,5-a]pyrazin-7(8H)-yl]methyl}benzonitrile;

4-[(3-cyclopropyl-1,4,5,7-tetrahydro-6H-pyrazolo[3,4-c]pyridin-6-yl)methyl]-2-[1-(2,2-dimethylpropyl)-3-methyl-2-oxo-2,3-dihydro-1H-imidazo[4,5-b]pyridin-5-yl]benzonitrile;

4-[(2-cyclopropyl-5,6-dihydro[1,2,4]triazolo[1,5-a]pyrazin-7(8H)-yl)methyl]-2-[1-(2,2-dimethylpropyl)-3-methyl-2-oxo-2,3-dihydro-1H-imidazo[4,5-b]pyridin-5-yl]benzonitrile;

2-[1-(2,2-dimethylpropyl)-3-methyl-2-oxo-2,3-dihydro-1H-imidazo[4,5-b]pyridin-5-yl]-4-{[2-(trifluoromethyl)-5,6-dihydro[1,2,4]triazolo[1,5-a]pyrazin-7(8H)-yl]methyl}benzonitrile;

2-[1-(2,2-dimethylpropyl)-3-methyl-2-oxo-2,3-dihydro-1H-imidazo[4,5-b]pyridin-5-yl]-4-[(3-hydroxy-6,7-dihydroisoxazolo[4,5-c]pyridin-5(4H)-yl)methyl]benzonitrile;

2-[1-(2,2-dimethylpropyl)-3-methyl-2-oxo-2,3-dihydro-1H-imidazo[4,5-b]pyridin-5-yl]-4-{[2-(trifluoromethyl)-5,6-dihydroimidazo[1,2-a]pyrazin-7(8H)-yl]methyl}benzonitrile;

2-[1-(2,2-dimethylpropyl)-3-methyl-2-oxo-2,3-dihydro-1H-imidazo[4,5-b]pyridin-5-yl]-4-[(1-methyl-3,4-dihydropyrrolo[1,2-a]pyrazin-2(1H)-yl)methyl]benzonitrile;

2-[1-(2,2-dimethylpropyl)-3-methyl-2-oxo-2,3-dihydro-1H-imidazo[4,5-b]pyridin-5-yl]-4-[(3-phenyl-5,6-dihydroimidazo[1,2-a]pyrazin-7(8H)-yl)methyl]benzonitrile;

4-[(3-benzyl-5,6-dihydroimidazo[1,2-a]pyrazin-7(8H)-yl)methyl]-2-[1-(2,2-dimethylpropyl)-3-methyl-2-oxo-2,3-dihydro-1H-imidazo[4,5-b]pyridin-5-yl]benzonitrile;

2-[1-(2,2-dimethylpropyl)-3-methyl-2-oxo-2,3-dihydro-1H-imidazo[4,5-b]pyridin-5-yl]-4-[(1-phenyl-3,4-dihydropyrrolo[1,2-a]pyrazin-2(1H)-yl)methyl]benzonitrile;

2-[1-(2,2-dimethylpropyl)-3-methyl-2-oxo-2,3-dihydro-1H-imidazo[4,5-b]pyridin-5-yl]-4-[(1,1-dioxido-1,4-thiazepan-4-yl)methyl]benzonitrile;

tert-butyl [(2R,4S)-1-{4-cyano-3-[1-(2,2-dimethylpropyl)-3-methyl-2-oxo-2,3-dihydro-1H-imidazo[4,5-b]pyridin-5-yl]benzyl}-2-(trifluoromethyl)piperidin-4-yl]carbamate;

tert-butyl [(2S,4S)-1-{4-cyano-3-[1-(2,2-dimethylpropyl)-3-methyl-2-oxo-2,3-dihydro-1H-imidazo[4,5-b]pyridin-5-yl]benzyl}-2-(trifluoromethyl)piperidin-4-yl]carbamate;

4-[(3,3-dimethyl-1-oxo-2-oxa-7-azaspiro[4.5]dec-7-yl)methyl]-2-[1-(2,2-dimethylpropyl)-3-methyl-2-oxo-2,3-dihydro-1H-imidazo[4,5-b]pyridin-5-yl]benzonitrile;

2-[1-(2,2-dimethylpropyl)-3-methyl-2-oxo-2,3-dihydro-1H-imidazo[4,5-b]pyridin-5-yl]-4-{[4-(2,2,2-trifluoroethyl)piperazin-1-yl]methyl}benzonitrile;

2-[1-(2,2-dimethylpropyl)-3-methyl-2-oxo-2,3-dihydro-1H-imidazo[4,5-b]pyridin-5-yl]-4-[(1,1-dioxido-2,3-dihydro-1,4-benzothiazepin-4(5H)-yl)methyl]benzonitrile;

4-{[{(1S)-1-[3,5-bis(trifluoromethyl)phenyl]ethyl}(ethyl)amino]methyl}-2-[1-(2,2-dimethylpropyl)-3-methyl-2-oxo-2,3-dihydro-1H-imidazo[4,5-b]pyridin-5-yl]benzonitrile;

2-[1-(2,2-dimethylpropyl)-3-methyl-2-oxo-2,3-dihydro-1H-imidazo[4,5-b]pyridin-5-yl]-4-[(3-hydroxy-3-methylpyrrolidin-1-yl)methyl]benzonitrile;

2-[1-(2,2-dimethylpropyl)-3-methyl-2-oxo-2,3-dihydro-1H-imidazo[4,5-b]pyridin-5-yl]-4-[(3-hydroxy-3-methylpiperidin-1-yl)methyl]benzonitrile;

2-[1-(2,2-dimethylpropyl)-3-methyl-2-oxo-2,3-dihydro-1H-imidazo[4,5-b]pyridin-5-yl]-4-{[4-(5-methyl-1H-imidazol-1-yl)piperidin-1-yl]methyl}benzonitrile;

2-[1-(2,2-dimethylpropyl)-3-methyl-2-oxo-2,3-dihydro-1H-imidazo[4,5-b]pyridin-5-yl]-4-{[4-(5-methyl-1,2,4-thiadiazol-3-yl)piperidin-1-yl]methyl}benzonitrile;

2-[1-(2,2-dimethylpropyl)-3-methyl-2-oxo-2,3-dihydro-1H-imidazo[4,5-b]pyridin-5-yl]-4-[(2-methyl-5-oxo-1,4-diazepan-1-yl)methyl]benzonitrile;

2-[1-(2,2-dimethylpropyl)-3-methyl-2-oxo-2,3-dihydro-1H-imidazo[4,5-b]pyridin-5-yl]-4-{[3-(1H-pyrazol-1-yl)pyrrolidin-1-yl]methyl}benzonitrile;

2-[1-(2,2-dimethylpropyl)-3-methyl-2-oxo-2,3-dihydro-1H-imidazo[4,5-b]pyridin-5-yl]-4-[(2-oxo-1,2-dihydro-1'H-spiro[3,1-benzoxazine-4,4'-piperidin]-1'-yl)methyl]benzonitrile;

2-[1-(2,2-dimethylpropyl)-3-methyl-2-oxo-2,3-dihydro-1H-imidazo[4,5-b]pyridin-5-yl]-4-(hexahydro-4H-furo[3,2-b]pyrrol-4-ylmethyl)benzonitrile;

4-[(3,3-difluoropiperidin-1-yl)methyl]-2-[1-(2,2-dimethylpropyl)-3-methyl-2-oxo-2,3-dihydro-1H-imidazo[4,5-b]pyridin-5-yl]benzonitrile;

2-[1-(2,2-dimethylpropyl)-3-methyl-2-oxo-2,3-dihydro-1H-imidazo[4,5-b]pyridin-5-yl]-4-[(3-propoxy-6,7-dihydroisoxazolo[4,5-c]pyridin-5(4H)-yl)methyl]benzonitrile;

2-[1-(2,2-dimethylpropyl)-3-methyl-2-oxo-2,3-dihydro-1H-imidazo[4,5-b]pyridin-5-yl]-4-[(3-ethoxy-7-methyl-6,7-dihydroisoxazolo[4,5-c]pyridin-5(4H)-yl)methyl]benzonitrile;

2-[1-(2,2-dimethylpropyl)-3-methyl-2-oxo-2,3-dihydro-1H-imidazo[4,5-b]pyridin-5-yl]-4-[(3-ethyl-5,6-dihydro[1,2,4]triazolo[4,3-a]pyrazin-7(8H)-yl)methyl]benzonitrile;

4-[(2-cyclopropyl-6,7-dihydro[1,3]thiazolo[5,4-c]pyridin-5(4H)-yl)methyl]-2-[1-(2,2-dimethylpropyl)-3-methyl-2-oxo-2,3-dihydro-1H-imidazo[4,5-b]pyridin-5-yl]benzonitrile;

2-[1-(2,2-dimethylpropyl)-3-methyl-2-oxo-2,3-dihydro-1H-imidazo[4,5-b]pyridin-5-yl]-4-{[7-methyl-3-(1-methylethoxy)-6,7-dihydroisoxazolo[4,5-c]pyridin-5(4H)-yl]methyl}benzonitrile;

ethyl 2-{4-cyano-3-[1-(2,2-dimethylpropyl)-3-methyl-2-oxo-2,3-dihydro-1H-imidazo[4,5-b]pyridin-5-yl]benzyl}-1,2,3,4-tetrahydroisoquinoline-1-carboxylate;

methyl 2-{4-cyano-3-[1-(2,2-dimethylpropyl)-3-methyl-2-oxo-2,3-dihydro-1H-imidazo[4,5-b]pyridin-5-yl]benzyl}-1,2,3,4-tetrahydroisoquinoline-3-carboxylate;

2-[1-(2,2-dimethylpropyl)-3-methyl-2-oxo-2,3-dihydro-1H-imidazo[4,5-b]pyridin-5-yl]-4-[(3-hydroxy-4,7-dihydroisoxazolo[5,4-c]pyridin-6(5H)-yl)methyl]benzonitrile;

2-[1-(2,2-dimethylpropyl)-3-methyl-2-oxo-2,3-dihydro-1H-imidazo[4,5-b]pyridin-5-yl]-4-{[3-(trifluoromethyl)-5,6-dihydro[1,2,4]triazolo[4,3-a]pyrazin-7(8H)-yl]methyl}benzonitrile;

tert-butyl (1R,4R)-5-{4-cyano-3-[1-(2,2-dimethylpropyl)-3-methyl-2-oxo-2,3-dihydro-1H-imidazo[4,5-b]pyridin-5-yl]benzyl}-2,5-diazabicyclo[2.2.1]heptane-2-carboxylate;

tert-butyl (1S,4S)-5-{4-cyano-3-[1-(2,2-dimethylpropyl)-3-methyl-2-oxo-2,3-dihydro-1H-imidazo[4,5-b]pyridin-5-yl]benzyl}-2,5-diazabicyclo[2.2.1]heptane-2-carboxylate;

2-[1-(2,2-dimethylpropyl)-3-methyl-2-oxo-2,3-dihydro-1H-imidazo[4,5-b]pyridin-5-yl]-4-[(1S,4S)-2-oxa-5-azabicyclo[2.2.1]hept-5-ylmethyl]benzonitrile;

tert-butyl 4-{4-cyano-3-[1-(2,2-dimethylpropyl)-3-methyl-2-oxo-2,3-dihydro-1H-imidazo[4,5-b]pyridin-5-yl]benzyl}piperazine-1-carboxylate;

2-[1-(2,2-dimethylpropyl)-3-methyl-2-oxo-2,3-dihydro-1H-imidazo[4,5-b]pyridin-5-yl]-4-{[3-(4-methyl-4H-1,2,4-triazol-3-yl)piperidin-1-yl]methyl}benzonitrile;

4-{[3-(1H-benzimidazol-2-yl)piperidin-1-yl]methyl}-2-[1-(2,2-dimethylpropyl)-3-methyl-2-oxo-2,3-dihydro-1H-imidazo[4,5-b]pyridin-5-yl]benzonitrile;

2-[1-(2,2-dimethylpropyl)-3-methyl-2-oxo-2,3-dihydro-1H-imidazo[4,5-b]pyridin-5-yl]-4-{[4-(1H-pyrazol-1-yl)piperidin-1-yl]methyl}benzonitrile;

2-(3-methyl-2-oxo-1-prop-2-en-1-yl-2,3-dihydro-1H-imidazo[4,5-b]pyridin-5-yl)-4-{[7-methyl-3-(prop-2-en-1-yloxy)-6,7-dihydroisoxazolo[4,5-c]pyridin-5(4H)-yl]methyl}benzonitrile;

tert-butyl 3-{4-cyano-3-[1-(2,2-dimethylpropyl)-3-methyl-2-oxo-2,3-dihydro-1H-imidazo[4,5-b]pyridin-5-yl]benzyl}-3,8-diazabicyclo[3.2.1]octane-8-carboxylate;

4-(7,8-dihydro-1,6-naphthyridin-6(5H)-ylmethyl)-2-[1-(2,2-dimethylpropyl)-3-methyl-2-oxo-2,3-dihydro-1H-imidazo[4,5-b]pyridin-5-yl]benzonitrile;

tert-butyl (3R)-4-{4-cyano-3-[1-(2,2-dimethylpropyl)-3-methyl-2-oxo-2,3-dihydro-1H-imidazo[4,5-b]pyridin-5-yl]benzyl}-3-methylpiperazine-1-carboxylate;

tert-butyl (3S)-4-{4-cyano-3-[1-(2,2-dimethylpropyl)-3-methyl-2-oxo-2,3-dihydro-1H-imidazo[4,5-b]pyridin-5-yl]benzyl}-3-methylpiperazine-1-carboxylate;

4-[(2-cyclopropyl-6,7-dihydro[1,3]oxazolo[4,5-c]pyridin-5(4H)-yl)methyl]-2-[1-(2,2-dimethylpropyl)-3-methyl-2-oxo-2,3-dihydro-1H-imidazo[4,5-b]pyridin-5-yl]benzonitrile;

4-(3,4-dihydro-2,6-naphthyridin-2(1H)-ylmethyl)-2-[1-(2,2-dimethylpropyl)-3-methyl-2-oxo-2,3-dihydro-1H-imidazo[4,5-b]pyridin-5-yl]benzonitrile;

4-(3,4-dihydro-2,7-naphthyridin-2(1H)-ylmethyl)-2-[1-(2,2-dimethylpropyl)-3-methyl-2-oxo-2,3-dihydro-1H-imidazo[4,5-b]pyridin-5-yl]benzonitrile;

2-[1-(2,2-dimethylpropyl)-3-methyl-2-oxo-2,3-dihydro-1H-imidazo[4,5-b]pyridin-5-yl]-4-[(2-methyl-6,7-dihydro[1,3]oxazolo[4,5-c]pyridin-5(4H)-yl)methyl]benzonitrile;
2-[1-(2,2-dimethylpropyl)-3-methyl-2-oxo-2,3-dihydro-1H-imidazo[4,5-b]pyridin-5-yl]-4-[(7-hydroxy-6-methoxy-3,4-dihydroisoquinolin-2(1H)-yl)methyl]benzonitrile;
2-[1-(2,2-dimethylpropyl)-3-methyl-2-oxo-2,3-dihydro-1H-imidazo[4,5-b]pyridin-5-yl]-4-[(4-methyl-3-oxopiperazin-1-yl)methyl]benzonitrile;
4-(5,6-dihydro[1,2,4]triazolo[4,3-a]pyrazin-7(8H)-ylmethyl)-2-[1-(2,2-dimethylpropyl)-3-methyl-2-oxo-2,3-dihydro-1H-imidazo[4,5-b]pyridin-5-yl]benzonitrile;
4-({6-[(dimethylamino)methyl]-3,4-dihydroisoquinolin-2(1H)-yl}methyl)-2-[1-(2,2-dimethylpropyl)-3-methyl-2-oxo-2,3-dihydro-1H-imidazo[4,5-b]pyridin-5-yl]benzonitrile;
2-[1-(2,2-dimethylpropyl)-3-methyl-2-oxo-2,3-dihydro-1H-imidazo[4,5-b]pyridin-5-yl]-4-{[4-(isoquinolin-5-ylamino)piperidin-1-yl]methyl}benzonitrile;
1-(2,2-dimethylpropyl)-5-(2-fluoropyridin-3-yl)-3-methyl-1,3-dihydro-2H-imidazo[4,5-b]pyridin-2-one;
1-(2,2-dimethylpropyl)-5-(6-fluoropyridin-2-yl)-3-methyl-1,3-dihydro-2H-imidazo[4,5-b]pyridin-2-one;
1-(2,2-dimethylpropyl)-5-(2-fluoro-5-methylpyridin-3-yl)-3-methyl-1,3-dihydro-2H-imidazo[4,5-b]pyridin-2-one;
1-(2,2-dimethylpropyl)-3-methyl-5-(6-methylpyridin-2-yl)-1,3-dihydro-2H-imidazo[4,5-b]pyridin-2-one;
1-(2,2-dimethylpropyl)-3-methyl-5-(3-methylpyridin-2-yl)-1,3-dihydro-2H-imidazo[4,5-b]pyridin-2-one;
1-(2,2-dimethylpropyl)-5-(6-methoxypyridin-2-yl)-3-methyl-1,3-dihydro-2H-imidazo[4,5-b]pyridin-2-one;
1-(2,2-dimethylpropyl)-3-methyl-5-(5-methyl-1,3-thiazol-2-yl)-1,3-dihydro-2H-imidazo[4,5-b]pyridin-2-one;
2-methylpropyl {3-[1-(2,2-dimethylpropyl)-3-methyl-2-oxo-2,3-dihydro-1H-imidazo[4,5-b]pyridin-5-yl]benzyl}carbamate;
benzyl {3-[1-(2,2-dimethylpropyl)-3-methyl-2-oxo-2,3-dihydro-1H-imidazo[4,5-b]pyridin-5-yl]benzyl}carbamate;
methyl {3-[1-(2,2-dimethylpropyl)-3-methyl-2-oxo-2,3-dihydro-1H-imidazo[4,5-b]pyridin-5-yl]benzyl}carbamate;
ethyl {3-[1-(2,2-dimethylpropyl)-3-methyl-2-oxo-2,3-dihydro-1H-imidazo[4,5-b]pyridin-5-yl]benzyl}carbamate;
N-{3-[1-(2,2-dimethylpropyl)-3-methyl-2-oxo-2,3-dihydro-1H-imidazo[4,5-b]pyridin-5-yl]benzyl}acetamide;
N-{3-[1-(2,2-dimethylpropyl)-3-methyl-2-oxo-2,3-dihydro-1H-imidazo[4,5-b]pyridin-5-yl]benzyl}-2,2,2-trifluoroethanesulfonamide;
2-methylpropyl {3-[1-(2,2-dimethylpropyl)-3-methyl-2-oxo-2,3-dihydro-1H-imidazo[4,5-b]pyridin-5-yl]benzyl}methylcarbamate;
1-(2,2-dimethylpropyl)-5-{5-[(1S)-1-hydroxyethyl]-2-methylphenyl}-3-methyl-1,3-dihydro-2H-imidazo[4,5-b]pyridin-2-one;
1-(2,2-dimethylpropyl)-3-methyl-5-[2-methyl-5-(1,1,1-trifluoro-2-hydroxypropan-2-yl)phenyl]-1,3-dihydro-2H-imidazo[4,5-b]pyridin-2-one;
1-(2,2-dimethylpropyl)-5-[3-hydroxy-3-(trifluoromethyl)-2,3-dihydro-1H-inden-5-yl]-3-methyl-1,3-dihydro-2H-imidazo[4,5-b]pyridin-2-one;
1-(2,2-dimethylpropyl)-5-[4-hydroxy-4-(trifluoromethyl)-3,4-dihydro-2H-chromen-6-yl]-3-methyl-1,3-dihydro-2H-imidazo[4,5-b]pyridin-2-one;
1-(2,2-dimethylpropyl)-5-[4-hydroxy-3,4-dihydro-2H-chromen-6-yl]-3-methyl-1,3-dihydro-2H-imidazo[4,5-b]pyridin-2-one;
2-[1-(2,2-dimethylpropyl)-3-methyl-2-oxo-2,3-dihydro-1H-imidazo[4,5-b]pyridin-5-yl]-4-[1-hydroxyethyl]benzonitrile;
2-[1-(2,2-dimethylpropyl)-3-methyl-2-oxo-2,3-dihydro-1H-imidazo[4,5-b]pyridin-5-yl]-4-(1-hydroxy-1-methylethyl)benzonitrile;
2-[1-(2,2-dimethylpropyl)-3-methyl-2-oxo-2,3-dihydro-1H-imidazo[4,5-b]pyridin-5-yl]-4-[2,2,2-trifluoro-1-hydroxy-1-methylethyl]benzonitrile;
2-{3-[1-(2,2-dimethylpropyl)-3-methyl-2-oxo-2,3-dihydro-1H-imidazo[4,5-b]pyridin-5-yl]phenyl}propanenitrile;
2-{3-[1-(2,2-dimethylpropyl)-3-methyl-2-oxo-2,3-dihydro-1H-imidazo[4,5-b]pyridin-5-yl]phenyl}-2-methylpropanenitrile;
1-(2,2-dimethylpropyl)-5-{4-[1-hydroxyethyl]-2-methylphenyl}-3-methyl-1,3-dihydro-2H-imidazo[4,5-b]pyridin-2-one;
1-(2,2-dimethylpropyl)-5-[4-(1-hydroxy-1-methylethyl)-2-methylphenyl]-3-methyl-1,3-dihydro-2H-imidazo[4,5-b]pyridin-2-one;
1-(2,2-dimethylpropyl)-5-{5-[1-(1,1-dioxidothiomorpholin-4-yl)ethyl]-2-methylphenyl}-3-methyl-1,3-dihydro-2H-imidazo[4,5-b]pyridin-2-one;
1-(2,2-dimethylpropyl)-5-(5-{1-[3-hydroxypyrrolidin-1-yl]ethyl}-2-methylphenyl)-3-methyl-1,3-dihydro-2H-imidazo[4,5-b]pyridin-2-one;
1-(2,2-dimethylpropyl)-5-[3-(2-hydroxypropan-2-yl)phenyl]-3,7-dimethyl-1,3-dihydro-2H-imidazo[4,5-b]pyridin-2-one;
2-[1-(2,2-dimethylpropyl)-3-methyl-2-oxo-2,3-dihydro-1H-imidazo[4,5-b]pyridin-5-yl]-4-[(1R)-1-(1,1-dioxidothiomorpholin-4-yl)ethyl]benzonitrile;
1-(2,2-dimethylpropyl)-5-{5-[(1R)-1-(1,1-dioxidothiomorpholin-4-yl)ethyl]-2-methylphenyl}-3-methyl-1,3-dihydro-2H-imidazo[4,5-b]pyridin-2-one;
1-(2,2-dimethylpropyl)-5-{5-[(1S)-1-(1,1-dioxidothiomorpholin-4-yl)ethyl]-2-methylphenyl}-3-methyl-1,3-dihydro-2H-imidazo[4,5-b]pyridin-2-one;
Methyl [(1R)-1-{4-cyano-3-[1-(2,2-dimethylpropyl)-3-methyl-2-oxo-2,3-dihydro-1H-imidazo[4,5-b]pyridin-5-yl]phenyl}ethyl]carbamate;
N-[(1R)-1-{4-cyano-3-[1-(2,2-dimethylpropyl)-3-methyl-2-oxo-2,3-dihydro-1H-imidazo[4,5-b]pyridin-5-yl]phenyl}ethyl]-2,2,2-trifluoroethanesulfonamide;
Methyl (1-{3-[1-(2,2-dimethylpropyl)-3-methyl-2-oxo-2,3-dihydro-1H-imidazo[4,5-b]pyridin-5-yl]-4-methylphenyl}-1-methylethyl)carbamate;
N-(1-{3-[1-(2,2-dimethylpropyl)-3-methyl-2-oxo-2,3-dihydro-1H-imidazo[4,5-b]pyridin-5-yl]-4-methylphenyl}-1-methylethyl)-2,2,2-trifluoroethanesulfonamide;
2-fluoroethyl (2-{3-[1-(2,2-dimethylpropyl)-3-methyl-2-oxo-2,3-dihydro-1H-imidazo[4,5-b]pyridin-5-yl]-4-methylphenyl}propan-2-yl)carbamate;
N-(2-{3-[1-(2,2-dimethylpropyl)-3-methyl-2-oxo-2,3-dihydro-1H-imidazo[4,5-b]pyridin-5-yl]-4-methylphenyl}propan-2-yl)pyridine-3-carboxamide;
N-(2-{3-[1-(2,2-dimethylpropyl)-3-methyl-2-oxo-2,3-dihydro-1H-imidazo[4,5-b]pyridin-5-yl]-4-methylphenyl}propan-2-yl)-1,2,3-thiadiazole-4-carboxamide;

1-(2,2-dimethylpropyl)-5-{5-[1-(1,1-dioxidothiomorpholin-4-yl)-1-methylethyl]-2-methylphenyl}-3-methyl-1,3-dihydro-2H-imidazo[4,5-b]pyridin-2-one;

2-[1-(2,2-dimethylpropyl)-3-methyl-2-oxo-2,3-dihydro-1H-imidazo[4,5-b]pyridin-5-yl]-4-{[(1R,4R)-5-(methylsulfonyl)-2,5-diazabicyclo[2.2.1]hept-2-yl]methyl}benzonitrile;

4-{[(1R,4R)-5-acetyl-2,5-diazabicyclo[2.2.1]hept-2-yl]methyl}-2-[1-(2,2-dimethylpropyl)-3-methyl-2-oxo-2,3-dihydro-1H-imidazo[4,5-b]pyridin-5-yl]benzonitrile;

4-[(1S,4S)-2,5-diazabicyclo[2.2.1]hept-2-ylmethyl]-2-[1-(2,2-dimethylpropyl)-3-methyl-2-oxo-2,3-dihydro-1H-imidazo[4,5-b]pyridin-5-yl]benzonitrile;

2-[1-(2,2-dimethylpropyl)-3-methyl-2-oxo-2,3-dihydro-1H-imidazo[4,5-b]pyridin-5-yl]-4-{[(1S,4S)-5-(methylsulfonyl)-2,5-diazabicyclo[2.2.1]hept-2-yl]methyl}benzonitrile;

4-{[(1S,4S)-5-acetyl-2,5-diazabicyclo[2.2.1]hept-2-yl]methyl}-2-[1-(2,2-dimethylpropyl)-3-methyl-2-oxo-2,3-dihydro-1H-imidazo[4,5-b]pyridin-5-yl]benzonitrile;

4-(2,5-diazabicyclo[2.2.2]oct-2-ylmethyl)-2-[1-(2,2-dimethylpropyl)-3-methyl-2-oxo-2,3-dihydro-1H-imidazo[4,5-b]pyridin-5-yl]benzonitrile;

2-[1-(2,2-dimethylpropyl)-3-methyl-2-oxo-2,3-dihydro-1H-imidazo[4,5-b]pyridin-5-yl]-4-{[5-(methylsulfonyl)-2,5-diazabicyclo[2.2.2]oct-2-yl]methyl}benzonitrile;

4-[(5-acetyl-2,5-diazabicyclo[2.2.2]oct-2-yl)methyl]-2-[1-(2,2-dimethylpropyl)-3-methyl-2-oxo-2,3-dihydro-1H-imidazo[4,5-b]pyridin-5-yl]benzonitrile;

4-(3,8-diazabicyclo[3.2.1]oct-3-ylmethyl)-2-[1-(2,2-dimethylpropyl)-3-methyl-2-oxo-2,3-dihydro-1H-imidazo[4,5-b]pyridin-5-yl]benzonitrile;

2-[1-(2,2-dimethylpropyl)-3-methyl-2-oxo-2,3-dihydro-1H-imidazo[4,5-b]pyridin-5-yl]-4-{[8-(methylsulfonyl)-3,8-diazabicyclo[3.2.1]oct-3-yl]methyl}benzonitrile;

2-[1-(2,2-dimethylpropyl)-3-methyl-2-oxo-2,3-dihydro-1H-imidazo[4,5-b]pyridin-5-yl]-4-(piperazin-1-ylmethyl)benzonitrile;

5-{3-[(4-acetylpiperazin-1-yl)methyl]phenyl}-1-(2,2-dimethylpropyl)-3-methyl-1,3-dihydro-2H-imidazo[4,5-b]pyridin-2-one;

1-(2,2-dimethylpropyl)-3-methyl-5-(3-{[4-(methylsulfonyl)piperazin-1-yl]methyl}phenyl)-1,3-dihydro-2H-imidazo[4,5-b]pyridin-2-one;

1-(2,2-dimethylpropyl)-3-methyl-5-{3-[(3-oxopiperazin-1-yl)methyl]phenyl}-1,3-dihydro-2H-imidazo[4,5-b]pyridin-2-one;

1-(2,2-dimethylpropyl)-3-methyl-{3-[(5-oxo-1,4-diazepan-1-yl)methyl]phenyl}-1,3-dihydro-2H-imidazo[4,5-b]pyridin-2-one;

1-(2,2-dimethylpropyl)-3-methyl-5-{3-[(4-methyl-5-oxo-1,4-diazepan-1-yl)methyl]phenyl}-1,3-dihydro-2H-imidazo[4,5-b]pyridin-2-one;

5-{3-[(4-acetyl-1,4-diazepan-1-yl)methyl]phenyl}-1-(2,2-dimethylpropyl)-3-methyl-1,3-dihydro-2H-imidazo[4,5-b]pyridin-2-one;

1-(2,2-dimethylpropyl)-3-methyl-5-(3-{[4-(methylsulfonyl)-1,4-diazepan-1-yl]methyl}phenyl)-1,3-dihydro-2H-imidazo[4,5-b]pyridin-2-one;

tert-butyl 4-{3-[1-(2,2-dimethylpropyl)-3-methyl-2-oxo-2,3-dihydro-1H-imidazo[4,5-b]pyridin-5-yl]benzyl}piperazine-1-carboxylate;

1-(2,2-dimethylpropyl)-3-methyl-5-(3-{[4-(2-methylpropanoyl)piperazin-1-yl]methyl}phenyl)-1,3-dihydro-2H-imidazo[4,5-b]pyridin-2-one;

5-(3-{[4-(2,2-dimethylpropanoyl)piperazin-1-yl]methyl}phenyl)-1-(2,2-dimethylpropyl)-3-methyl-1,3-dihydro-2H-imidazo[4,5-b]pyridin-2-one;

1-(2,2-dimethylpropyl)-5-(3-{[4-(2-hydroxy-2-methylpropanoyl)piperazin-1-yl]methyl}phenyl)-3-methyl-1,3-dihydro-2H-imidazo[4,5-b]pyridin-2-one;

1-(2,2-dimethylpropyl)-5-(3-{[4-(ethylsulfonyl)piperazin-1-yl]methyl}phenyl)-3-methyl-1,3-dihydro-2H-imidazo[4,5-b]pyridin-2-one;

1-(2,2-dimethylpropyl)-3-methyl-5-{3-[(4-methyl-3-oxopiperazin-1-yl)methyl]phenyl}-1,3-dihydro-2H-imidazo[4,5-b]pyridin-2-one;

5-[3-({4-[(2,2-difluorocyclopropyl)methyl]piperazin-1-yl}methyl)phenyl]-1-(2,2-dimethylpropyl)-3-methyl-1,3-dihydro-2H-imidazo[4,5-b]pyridin-2-one;

5-(3-{[4-(cyclobutylmethyl)piperazin-1-yl]methyl}phenyl)-1-(2,2-dimethylpropyl)-3-methyl-1,3-dihydro-2H-imidazo[4,5-b]pyridin-2-one;

5-(3-{[4-(cyclopropylsulfonyl)piperazin-1-yl]methyl}phenyl)-1-(2,2-dimethylpropyl)-3-methyl-1,3-dihydro-2H-imidazo[4,5-b]pyridin-2-one;

1-(2,2-dimethylpropyl)-3-methyl-5-[3-({4-[(1-methylethyl)sulfonyl]piperazin-1-yl}methyl)phenyl]-1,3-dihydro-2H-imidazo[4,5-b]pyridin-2-one;

5-(3-{[4-(cyclopropylcarbonyl)piperazin-1-yl]methyl}phenyl)-1-(2,2-dimethylpropyl)-3-methyl-1,3-dihydro-2H-imidazo[4,5-b]pyridin-2-one;

5-[3-({4-[(2,2-difluorocyclopropyl)carbonyl]piperazin-1-yl}methyl)phenyl]-1-(2,2-dimethylpropyl)-3-methyl-1,3-dihydro-2H-imidazo[4,5-b]pyridin-2-one;

1-(2,2-dimethylpropyl)-3-methyl-5-(3-{[4-(trifluoroacetyl)piperazin-1-yl]methyl}phenyl)-1,3-dihydro-2H-imidazo[4,5-b]pyridin-2-one;

1-(2,2-dimethylpropyl)-3-methyl-5-{3-[(4-propanoylpiperazin-1-yl)methyl]phenyl}-1,3-dihydro-2H-imidazo[4,5-b]pyridin-2-one;

5-(3-{[4-(cyclobutylcarbonyl)piperazin-1-yl]methyl}phenyl)-1-(2,2-dimethylpropyl)-3-methyl-1,3-dihydro-2H-imidazo[4,5-b]pyridin-2-one;

5-(3-{[4-(2,2-difluoropropanoyl)piperazin-1-yl]methyl}phenyl)-1-(2,2-dimethylpropyl)-3-methyl-1,3-dihydro-2H-imidazo[4,5-b]pyridin-2-one;

5-(3-{[4-(cyclopropylmethyl)-3-oxopiperazin-1-yl]methyl}phenyl)-1-(2,2-dimethylpropyl)-3-methyl-1,3-dihydro-2H-imidazo[4,5-b]pyridin-2-one;

1-(2,2-dimethylpropyl)-5-{3-[(4-ethyl-3-oxopiperazin-1-yl)methyl]phenyl}-3-methyl-1,3-dihydro-2H-imidazo[4,5-b]pyridin-2-one;

5-[3-({4-[(2,2-difluorocyclopropyl)methyl]-3-oxopiperazin-1-yl}methyl)phenyl]-1-(2,2-dimethylpropyl)-3-methyl-1,3-dihydro-2H-imidazo[4,5-b]pyridin-2-one;

5-(3-{[4-(cyclobutylmethyl)-3-oxopiperazin-1-yl]methyl}phenyl)-1-(2,2-dimethylpropyl)-3-methyl-1,3-dihydro-2H-imidazo[4,5-b]pyridin-2-one;

1-(2,2-dimethylpropyl)-3-methyl-5-(3-{[4-(2-methylpropyl)-3-oxopiperazin-1-yl]methyl}phenyl)-1,3-dihydro-2H-imidazo[4,5-b]pyridin-2-one;

5-[5-(1-cyclopropyl-1-hydroxyethyl)-2-methylphenyl]-1-(2,2-dimethylpropyl)-3-methyl-1,3-dihydro-2H-imidazo[4,5-b]pyridin-2-one;

1-(2,2-dimethylpropyl)-3-methyl-5-(2-methyl-5-{[3-(trifluoromethyl)-5,6-dihydro[1,2,4]triazolo[4,3-a]pyrazin-7(8H)-yl]methyl}phenyl)-1,3-dihydro-2H-imidazo[4,5-b]pyridin-2-one;

1-(2,2-dimethylpropyl)-5-{5-[(3-hydroxy-3-methylpiperidin-1-yl)methyl]-2-methylphenyl}-3-methyl-1,3-dihydro-2H-imidazo[4,5-b]pyridin-2-one;
tert-butyl (1R,4R)-5-{3-[1-(2,2-dimethylpropyl)-3-methyl-2-oxo-2,3-dihydro-1H-imidazo[4,5-b]pyridin-5-yl]-4-methylbenzyl}-2,5-diazabicyclo[2.2.1]heptane-2-carboxylate;
1-(2,2-dimethylpropyl)-3-methyl-5-(2-methyl-5-{[3-(1H-pyrazol-1-yl)piperidin-1-yl]methyl}phenyl)-1,3-dihydro-2H-imidazo[4,5-b]pyridin-2-one;
1-(2,2-dimethylpropyl)-5-{5-[(3-hydroxy-6,7-dihydroisoxazolo[4,5-c]pyridin-5(4H)-yl)methyl]-2-methylphenyl}-3-methyl-1,3-dihydro-2H-imidazo[4,5-b]pyridin-2-one;
tert-butyl 4-{3-[1-(2,2-dimethylpropyl)-3-methyl-2-oxo-2,3-dihydro-1H-imidazo[4,5-b]pyridin-5-yl]-4-methylbenzyl}piperazine-1-carboxylate;
5-{5-[(4-acetylpiperazin-1-yl)methyl]-2-methylphenyl}-1-(2,2-dimethylpropyl)-3-methyl-1,3-dihydro-2H-imidazo[4,5-b]pyridin-2-one;
1-(2,2-dimethylpropyl)-3-methyl-5-(2-methyl-5-{[4-(methylsulfonyl)piperazin-1-yl]methyl}phenyl)-1,3-dihydro-2H-imidazo[4,5-b]pyridin-2-one;
1-(2,2-dimethylpropyl)-5-{5-[(1,1-dioxidothiomorpholin-4-yl)methyl]-2-methylphenyl}-3-methyl-1,3-dihydro-2H-imidazo[4,5-b]pyridin-2-one;
1-{3-[1-(2,2-dimethylpropyl)-3-methyl-2-oxo-2,3-dihydro-1H-imidazo[4,5-b]pyridin-5-yl]-4-methylbenzyl}-3-methylimidazolidine-2,4-dione;
1-(2,2-dimethylpropyl)-3-methyl-5-(2-methyl-5-{[(1R,4R)-5-(methylsulfonyl)-2,5-diazabicyclo[2.2.1]hept-2-yl]methyl}phenyl)-1,3-dihydro-2H-imidazo[4,5-b]pyridin-2-one;
1-(2,2-dimethylpropyl)-5-(5-{[4-(isoxazol-3-ylcarbonyl)piperazin-1-yl]methyl}-2-methylphenyl)-3-methyl-1,3-dihydro-2H-imidazo[4,5-b]pyridin-2-one;
methyl 4-{3-[1-(2,2-dimethylpropyl)-3-methyl-2-oxo-2,3-dihydro-1H-imidazo[4,5-b]pyridin-5-yl]-4-methylbenzyl}piperazine-1-carboxylate;
1-(2,2-dimethylpropyl)-5-[5-({4-[(2R)-2-hydroxypropanoyl]piperazin-1-yl}methyl)-2-methylphenyl]-3-methyl-1,3-dihydro-2H-imidazo[4,5-b]pyridin-2-one;
1-(2,2-dimethylpropyl)-5-(5-{[4-(hydroxyacetyl)piperazin-1-yl]methyl}-2-methylphenyl)-3-methyl-1,3-dihydro-2H-imidazo[4,5-b]pyridin-2-one;
5-{5-[1-(4-acetylpiperazin-1-yl)ethyl]-2-methylphenyl}-1-(2,2-dimethylpropyl)-3-methyl-1,3-dihydro-2H-imidazo[4,5-b]pyridin-2-one;
1-(2,2-dimethylpropyl)-3-methyl-5-(2-methyl-5-{1-[4-(methylsulfonyl)piperazin-1-yl]ethyl}phenyl)-1,3-dihydro-2H-imidazo[4,5-b]pyridin-2-one;
3-[1-(2,2-dimethylpropyl)-3-methyl-2-oxo-2,3-dihydro-1H-imidazo[4,5-b]pyridin-5-yl]-N,4-dimethylbenzamide;
3-[1-(2,2-dimethylpropyl)-3-methyl-2-oxo-2,3-dihydro-1H-imidazo[4,5-b]pyridin-5-yl]-N,4-dimethylbenzamide;
3-[1-(2,2-dimethylpropyl)-3-methyl-2-oxo-2,3-dihydro-1H-imidazo[4,5-b]pyridin-5-yl]-N,N,4-trimethylbenzamide;
N-(cyclopropylmethyl)-3-[1-(2,2-dimethylpropyl)-3-methyl-2-oxo-2,3-dihydro-1H-imidazo[4,5-b]pyridin-5-yl]-4-methylbenzamide;
5-[5-(6,7-dihydroisoxazolo[4,5-c]pyridin-5(4H)-ylcarbonyl)-2-methylphenyl]-1-(2,2-dimethylpropyl)-3-methyl-1,3-dihydro-2H-imidazo[4,5-b]pyridin-2-one;
3-[1-(2,2-dimethylpropyl)-3-methyl-2-oxo-2,3-dihydro-1H-imidazo[4,5-b]pyridin-5-yl]-N-(isoxazol-4-ylmethyl)-4-methylbenzamide;
N-[(3-cyanoisoxazol-4-yl)methyl]-3-[1-(2,2-dimethylpropyl)-3-methyl-2-oxo-2,3-dihydro-1H-imidazo[4,5-b]pyridin-5-yl]-4-methylbenzamide;
1-(2,2-dimethylpropyl)-5-{5-[(1,1-dioxidothiomorpholin-4-yl)carbonyl]-2-methylphenyl}-3-methyl-1,3-dihydro-2H-imidazo[4,5-b]pyridin-2-one;
1-(2,2-dimethylpropyl)-3-methyl-5-[2-methyl-5-(morpholin-4-ylcarbonyl)phenyl]-1,3-dihydro-2H-imidazo[4,5-b]pyridin-2-one;
1-(2,2-dimethylpropyl)-5-{5-[(3-hydroxy-6,7-dihydroisoxazolo[4,5-c]pyridin-5(4H)-yl)carbonyl]-2-methylphenyl}-3-methyl-1,3-dihydro-2H-imidazo[4,5-b]pyridin-2-one;
5-{5-[(4-acetylpiperazin-1-yl)methyl]-2-methylphenyl}-1-[(2,2-difluorocyclopropyl)methyl]-3-methyl-1,3-dihydro-2H-imidazo[4,5-b]pyridin-2-one;
1-[(2,2-difluorocyclopropyl)methyl]-3-methyl-5-(2-methyl-5-{[4-(methylsulfonyl)piperazin-1-yl]methyl}phenyl)-1,3-dihydro-2H-imidazo[4,5-b]pyridin-2-one;
1-[(2,2-difluorocyclopropyl)methyl]-5-(5-{[4-(2-hydroxy-2-methylpropanoyl)piperazin-1-yl]methyl}-2-methylphenyl)-3-methyl-1,3-dihydro-2H-imidazo[4,5-b]pyridin-2-one;
1-(2,2-dimethylpropyl)-5-[2-fluoro-5-(1-hydroxy-1-methylethyl)phenyl]-3-methyl-1,3-dihydro-2H-imidazo[4,5-b]pyridin-2-one;
1-(2,2-dimethylpropyl)-5-(2-fluoro-5-{[3-(trifluoromethyl)-5,6-dihydro[1,2,4]triazolo[4,3-a]pyrazin-7(8H)-yl]methyl}phenyl)-3-methyl-1,3-dihydro-2H-imidazo[4,5-b]pyridin-2-one;
1-(2,2-dimethylpropyl)-5-{2-fluoro-5-[(3-hydroxy-6,7-dihydroisoxazolo[4,5-c]pyridin-5(4H) yl)methyl]phenyl}-3-methyl-1,3-dihydro-2H-imidazo[4,5-b]pyridin-2-one
5-{5-[(4-acetylpiperazin-1-yl)methyl]-2-fluorophenyl}-1-(2,2-dimethylpropyl)-3-methyl-1,3-dihydro-2H-imidazo[4,5-b]pyridin-2-one;
1-(2,2-dimethylpropyl)-5-(2-fluoro-5-{[4-(methylsulfonyl)piperazin-1-yl]methyl}phenyl)-3-methyl-1,3-dihydro-2H-imidazo[4,5-b]pyridin-2-one;
1-(2,2-dimethylpropyl)-5-(2-fluoro-5-{[4-(2,2,2-trifluoroethyl)piperazin-1-yl]methyl}phenyl)-3-methyl-1,3-dihydro-2H-imidazo[4,5-b]pyridin-2-one;
1-(2,2-dimethylpropyl)-5-(2-fluoro-4-{[3-(trifluoromethyl)-5,6-dihydro[1,2,4]triazoio[4,3-a]pyrazin-7(8H)-yl]methyl}phenyl)-3-methyl-1,3-dihydro-2H-imidazo[4,5-b]pyridin-2-one;
5-{4-[(4-acetylpiperazin-1-yl)methyl]-2-fluorophenyl}-1-(2,2-dimethylpropyl)-3-methyl-1,3-dihydro-2H-imidazo[4,5-b]pyridin-2-one;
1-(2,2-dimethylpropyl)-5-(2-fluoro-4-{[4-(methylsulfonyl)piperazin-1-yl]methyl}phenyl)-3-methyl-1,3-dihydro-2H-imidazo[4,5-b]pyridin-2-one;
1-(2,2-dimethylpropyl)-5-[2-fluoro-3-(1-hydroxy-1-methylethyl)phenyl]-3-methyl-1,3-dihydro-2H-imidazo[4,5-b]pyridin-2-one;
1-(2,2-dimethylpropyl)-5-(2-fluoro-3-{[3-(trifluoromethyl)-5,6-dihydro[1,2,4]triazolo[4,3-a]pyrazin-7(8H)-yl]methyl}phenyl)-3-methyl-1,3-dihydro-2H-imidazo[4,5-b]pyridin-2-one;

1-(2,2-dimethylpropyl)-5-{2-fluoro-3-[(3-hydroxy-6,7-dihydroisoxazolo[4,5-c]pyridin-5(4H)-yl)methyl]phenyl}-3-methyl-1,3-dihydro-2H-imidazo[4,5-b]pyridin-2-one;

5-{3-[(4-acetylpiperazin-1-yl)methyl]-2-fluorophenyl}-1-(2,2-dimethylpropyl)-3-methyl-1,3-dihydro-2H-imidazo[4,5-b]pyridin-2-one;

1-(2,2-dimethylpropyl)-5-(2-fluoro-3-{[4-(methylsulfonyl)piperazin-1-yl]methyl}phenyl)-3-methyl-1,3-dihydro-2H-imidazo[4,5-b]pyridin-2-one;

1-(2,2-dimethylpropyl)-5-(2-fluoro-3-{[4-(2,2,2-trifluoroethyl)piperazin-1-yl]methyl}phenyl)-3-methyl-1,3-dihydro-2H-imidazo[4,5-b]pyridin-2-one;

5-[3-chloro-5-(1-hydroxy-1-methylethyl)phenyl]-1-(2,2-dimethylpropyl)-3-methyl-1,3-dihydro-2H-imidazo[4,5-b]pyridin-2-one;

5-(3-chloro-5-{[3-(trifluoromethyl)-5,6-dihydro[1,2,4]triazolo[4,3-a]pyrazin-7(8H)-yl]methyl}phenyl)-1-(2,2-dimethylpropyl)-3-methyl-1,3-dihydro-2H-imidazo[4,5-b]pyridin-2-one;

5-{3-[(4-acetylpiperazin-1-yl)methyl]-5-chlorophenyl}-1-(2,2-dimethylpropyl)-3-methyl-1,3-dihydro-2H-imidazo[4,5-b]pyridin-2-one;

5-(3-chloro-5-{[4-(methylsulfonyl)piperazin-1-yl]methyl}phenyl)-1-(2,2-dimethylpropyl)-3-methyl-1,3-dihydro-2H-imidazo[4,5-b]pyridin-2-one;

1-(2,2-dimethylpropyl)-3-methyl-5-{2-methyl-5-[1-(pyridin-3-ylcarbonyl)-1,2,3,6-tetrahydropyridin-4-yl]phenyl}-1,3-dihydro-2H-imidazo[4,5-b]pyridin-2-one;

1-(2,2-dimethylpropyl)-3-methyl-5-{3-[1-(pyridin-3-ylcarbonyl)piperidin-3-yl]phenyl}-1,3-dihydro-2H-imidazo[4,5-b]pyridin-2-one;

1-(2,2-dimethylpropyl)-5-{3-[1-(isoxazol-3-ylcarbonyl)piperidin-3-yl]phenyl}-3-methyl-1,3-dihydro-2H-imidazo[4,5-b]pyridin-2-one;

1-(2,2-dimethylpropyl)-5-{3-[1-(2-hydroxypropanoyl)piperidin-3-yl]phenyl}-3-methyl-1,3-dihydro-2H-imidazo[4,5-b]pyridin-2-one;

1-(2,2-dimethylpropyl)-3-methyl-5-{3-[4-(pyridin-3-ylcarbonyl)piperazin-1-yl]phenyl}-1,3-dihydro-2H-imidazo[4,5-b]pyridin-2-one;

1-(2,2-dimethylpropyl)-5-{3-[4-(isoxazol-3-ylcarbonyl)piperazin-1-yl]phenyl}-3-methyl-1,3-dihydro-2H-imidazo[4,5-b]pyridin-2-one;

1-(2,2-dimethylpropyl)-3-methyl-5-{3-[4-(1,3-oxazol-2-ylcarbonyl)piperazin-1-yl]phenyl}-1,3-dihydro-2H-imidazo[4,5-b]pyridin-2-one;

1-(2,2-dimethylpropyl)-5-(3-{4-[(ethylsulfonyl)acetyl]piperazin-1-yl}phenyl)-3-methyl-1,3-dihydro-2H-imidazo[4,5-b]pyridin-2-one;

1-(2,2-dimethylpropyl)-3-methyl-5-{3-[4-(3-methylbutanoyl)piperazin-1-yl]phenyl}-1,3-dihydro-2H-imidazo[4,5-b]pyridin-2-one;

1-(2,2-dimethylpropyl)-3-methyl-5-{3-[4-(1,2,3-thiadiazol-4-ylcarbonyl)piperazin-1-yl]phenyl}-1,3-dihydro-2H-imidazo[4,5-b]pyridin-2-one;

1-(2,2-dimethylpropyl)-3-methyl-5-{3-[4-(tetrahydro-2H-pyran-2-ylcarbonyl)piperazin-1-yl]phenyl}-1,3-dihydro-2H-imidazo[4,5-b]pyridin-2-one;

1-(2,2-dimethylpropyl)-5-{3-[4-(isothiazol-4-ylcarbonyl)piperazin-1-yl]phenyl}-3-methyl-1,3-dihydro-2H-imidazo[4,5-b]pyridin-2-one;

5-[3-(4-acetylpiperazin-1-yl)phenyl]-1-(2,2-dimethylpropyl)-3-methyl-1,3-dihydro-2H-imidazo[4,5-b]pyridin-2-one;

5-{3-[4-(cyclopentylcarbonyl)piperazin-1-yl]phenyl}-1-(2,2-dimethylpropyl)-3-methyl-1,3-dihydro-2H-imidazo[4,5-b]pyridin-2-one;

1-(2,2-dimethylpropyl)-3-methyl-5-{3-[4-(1,3-oxazol-5-ylcarbonyl)piperazin-1-yl]phenyl}-1,3-dihydro-2H-imidazo[4,5-b]pyridin-2-one;

1-(2,2-dimethylpropyl)-3-methyl-5-{3-[4-(1,3-thiazol-5-ylcarbonyl)piperazin-1-yl]phenyl}-1,3-dihydro-2H-imidazo[4,5-b]pyridin-2-one;

1-(2,2-dimethylpropyl)-3-methyl-5-(3-{4-[(1-methyl-1H-pyrazol-3-yl)carbonyl]piperazin-1-yl}phenyl)-1,3-dihydro-2H-imidazo[4,5-b]pyridin-2-one;

1-(2,2-dimethylpropyl)-3-methyl-5-{3-[4-(1H-1,2,4-triazol-5-ylcarbonyl)piperazin-1-yl]phenyl}-1,3-dihydro-2H-imidazo[4,5-b]pyridin-2-one;

1-(2,2-dimethylpropyl)-3-methyl-5-(3-{4-[(1-methyl-1H-pyrazol-5-yl)carbonyl]piperazin-1-yl}phenyl)-1,3-dihydro-2H-imidazo[4,5-b]pyridin-2-one;

5-{3-[4-(3,3-dimethylbutanoyl)piperazin-1-yl]phenyl}-1-(2,2-dimethylpropyl)-3-methyl-1,3-dihydro-2H-imidazo[4,5-b]pyridin-2-one;

1-(2,2-dimethylpropyl)-3-methyl-5-{3-[4-(thiophen-2-ylcarbonyl)piperazin-1-yl]phenyl}-1,3-dihydro-2H-imidazo[4,5-b]pyridin-2-one;

5-{3-[4-(2,2-dimethylpropanoyl)piperazin-1-yl]phenyl}-1-(2,2-dimethylpropyl)-3-methyl-1,3-dihydro-2H-imidazo[4,5-b]pyridin-2-one;

1-(2,2-dimethylpropyl)-3-methyl-5-{3-[4-(1H-pyrazol-1-ylacetyl)piperazin-1-yl]phenyl}-1,3-dihydro-2H-imidazo[4,5-b]pyridin-2-one;

1-(2,2-dimethylpropyl)-3-methyl-5-{3-[4-(1H-pyrazol-4-ylcarbonyl)piperazin-1-yl]phenyl}-1,3-dihydro-2H-imidazo[4,5-b]pyridin-2-one;

1-(2,2-dimethylpropyl)-3-methyl-5-{3-[4-(1,2,5-thiadiazol-3-ylcarbonyl)piperazin-1-yl]phenyl}-1,3-dihydro-2H-imidazo[4,5-b]pyridin-2-one;

1-(2,2-dimethylpropyl)-3-methyl-5-{3-[4-(phenylcarbonyl)piperazin-1-yl]phenyl}-1,3-dihydro-2H-imidazo[4,5-b]pyridin-2-one;

1-(2,2-dimethylpropyl)-3-methyl-5-(3-{4-[(1-methyl-1H-imidazol-2-yl)carbonyl]piperazin-1-yl}phenyl)-1,3-dihydro-2H-imidazo[4,5-b]pyridin-2-one;

1-(2,2-dimethylpropyl)-3-methyl-5-(3-{4-[2-(1H-1,2,4-triazol-1-yl)propanoyl]piperazin-1-yl}phenyl)-1,3-dihydro-2H-imidazo[4,5-b]pyridin-2-one;

1-(2,2-dimethylpropyl)-3-methyl-5-(3-{4-[(1-methyl-1H-imidazol-4-yl)carbonyl]piperazin-1-yl}phenyl)-1,3-dihydro-2H-imidazo[4,5-b]pyridin-2-one;

1-(2,2-dimethylpropyl)-3-methyl-5-{3-[4-(thiophen-3-ylacetyl)piperazin-1-yl]phenyl}-1,3-dihydro-2H-imidazo[4,5-b]pyridin-2-one;

1-(2,2-dimethylpropyl)-3-methyl-5-{3-[4-(tetrahydrofuran-3-ylcarbonyl)piperazin-1-yl]phenyl}-1,3-dihydro-2H-imidazo[4,5-b]pyridin-2-one;

1-(2,2-dimethylpropyl)-3-methyl-5-(3-{4-[(5-methyl-1,3-thiazol-4-yl)carbonyl]piperazin-1-yl}phenyl)-1,3-dihydro-2H-imidazo[4,5-b]pyridin-2-one;

1-(2,2-dimethylpropyl)-3-methyl-5-{3-[4-(tetrahydro-2H-pyran-4-ylcarbonyl)piperazin-1-yl]phenyl}-1,3-dihydro-2H-imidazo[4,5-b]pyridin-2-one;

1-(2,2-dimethylpropyl)-3-methyl-5-{3-[4-(1,2,5-oxadiazol-3-ylcarbonyl)piperazin-1-yl]phenyl}-1,3-dihydro-2H-imidazo[4,5-b]pyridin-2-one;

1-(2,2-dimethylpropyl)-3-methyl-5-{3-[4-(phenylacetyl)piperazin-1-yl]phenyl}-1,3-dihydro-2H-imidazo[4,5-b]pyridin-2-one;

1-(2,2-dimethylpropyl)-3-methyl-5-{3-[4-(methylsulfonyl)piperazin-1-yl]phenyl}-1,3-dihydro-2H-imidazo[4,5-b]pyridin-2-one;

1-(2,2-dimethylpropyl)-3-methyl-5-{4-[4-(methylsulfonyl)piperazin-1-yl]phenyl}-1,3-dihydro-2H-imidazo[4,5-b]pyridin-2-one;

2-fluoroethyl 4-{3-[1-(2,2-dimethylpropyl)-3-methyl-2-oxo-2,3-dihydro-1H-imidazo[4,5-b]pyridin-5-yl]phenyl}piperazine-1-carboxylate;

methyl 4-{3-[1-(2,2-dimethylpropyl)-3-methyl-2-oxo-2,3-dihydro-1H-imidazo[4,5-b]pyridin-5-yl]phenyl}piperazine-1-carboxylate;

1-(2,2-dimethylpropyl)-3-methyl-5-{4-[4-(pyridin-3-ylcarbonyl)piperazin-1-yl]phenyl}-1,3-dihydro-2H-imidazo[4,5-b]pyridin-2-one;

1-(2,2-dimethylpropyl)-5-(4-{4-[(ethylsulfonyl)acetyl]piperazin-1-yl}phenyl)-3-methyl-1,3-dihydro-2H-imidazo[4,5-b]pyridin-2-one;

1-(2,2-dimethylpropyl)-3-methyl-5-{4-[4-(3-methylbutanoyl)piperazin-1-yl]phenyl}-1,3-dihydro-2H-imidazo[4,5-b]pyridin-2-one;

1-(2,2-dimethylpropyl)-3-methyl-5-(4-{4-[(1-methyl-1H-pyrazol-3-yl)carbonyl]piperazin-1-yl}phenyl)-1,3-dihydro-2H-imidazo[4,5-b]pyridin-2-one;

1-(2,2-dimethylpropyl)-5-{4-[4-(isoxazol-3-ylcarbonyl)piperazin-1-yl]phenyl}-3-methyl-1,3-dihydro-2H-imidazo[4,5-b]pyridin-2-one;

1-(2,2-dimethylpropyl)-5-{4-[4-(isoxazol-3-ylcarbonyl)piperazin-1-yl]phenyl}-3-methyl-1,3-dihydro-2H-imidazo[4,5-b]pyridin-2-one;

1-(2,2-dimethylpropyl)-3-methyl-5-{4-[4-(1,2,5-oxadiazol-3-ylcarbonyl)piperazin-1-yl]phenyl}-1,3-dihydro-2H-imidazo[4,5-b]pyridin-2-one;

5-{4-[4-(3,3-dimethylbutanoyl)piperazin-1-yl]phenyl}-1-(2,2-dimethylpropyl)-3-methyl-1,3-dihydro-2H-imidazo[4,5-b]pyridin-2-one;

1-(2,2-dimethylpropyl)-5-{4-[4-(isothiazol-4-ylcarbonyl)piperazin-1-yl]phenyl}-3-methyl-1,3-dihydro-2H-imidazo[4,5-b]pyridin-2-one;

1-(2,2-dimethylpropyl)-3-methyl-5-{4-[4-(thiophen-3-ylacetyl)piperazin-1-yl]phenyl}-1,3-dihydro-2H-imidazo[4,5-b]pyridin-2-one;

1-(2,2-dimethylpropyl)-3-methyl-5-{4-[4-(1,3-thiazol-5-ylcarbonyl)piperazin-1-yl]phenyl}-1,3-dihydro-2H-imidazo[4,5-b]pyridin-2-one;

1-(2,2-dimethylpropyl)-3-methyl-5-{4-[4-(1,3-oxazol-5-ylcarbonyl)piperazin-1-yl]phenyl}-1,3-dihydro-2H-imidazo[4,5-b]pyridin-2-one;

1-(2,2-dimethylpropyl)-3-methyl-5-{4-[4-(1H-pyrazol-4-ylcarbonyl)piperazin-1-yl]phenyl}-1,3-dihydro-2H-imidazo[4,5-b]pyridin-2-one;

1-(2,2-dimethylpropyl)-3-methyl-5-(4-{4-[(1-methyl-1H-imidazol-2-yl)carbonyl]piperazin-1-yl}phenyl)-1,3-dihydro-2H-imidazo[4,5-b]pyridin-2-one;

5-{4-[4-(cyclopentylcarbonyl)piperazin-1-yl]phenyl}-1-(2,2-dimethylpropyl)-3-methyl-1,3-dihydro-2H-imidazo[4,5-b]pyridin-2-one;

1-(2,2-dimethylpropyl)-3-methyl-5-{4-[4-(tetrahydro-2H-pyran-4-ylcarbonyl)piperazin-1-yl]phenyl}-1,3-dihydro-2H-imidazo[4,5-b]pyridin-2-one;

1-(2,2-dimethylpropyl)-3-methyl-5-(4-{4-[(5-methyl-1,3-thiazol-4-yl)carbonyl]piperazin-1-yl}phenyl)-1,3-dihydro-2H-imidazo[4,5-b]pyridin-2-one;

1-(2,2-dimethylpropyl)-3-methyl-5-(4-{4-[(1-methyl-1H-pyrazol-5-yl)carbonyl]piperazin-1-yl}phenyl)-1,3-dihydro-2H-imidazo[4,5-b]pyridin-2-one;

1-(2,2-dimethylpropyl)-3-methyl-5-{4-[4-(tetrahydro-2H-pyran-2-ylcarbonyl)piperazin-1-yl]phenyl}-1,3-dihydro-2H-imidazo[4,5-b]pyridin-2-one;

1-(2,2-dimethylpropyl)-3-methyl-5-{4-[4-(1,2,3-thiadiazol-4-ylcarbonyl)piperazin-1-yl]phenyl}-1,3-dihydro-2H-imidazo[4,5-b]pyridin-2-one;

1-(2,2-dimethylpropyl)-3-methyl-5-{4-[4-(1H-pyrazol-1-ylacetyl)piperazin-1-yl]phenyl}-1,3-dihydro-2H-imidazo[4,5-b]pyridin-2-one;

5-[4-(4-acetylpiperazin-1-yl)phenyl]-1-(2,2-dimethylpropyl)-3-methyl-1,3-dihydro-2H-imidazo[4,5-b]pyridin-2-one;

1-(2,2-dimethylpropyl)-3-methyl-5-{4-[4-(1H-1,2,4-triazol-5-ylcarbonyl)piperazin-1-yl]phenyl}-1,3-dihydro-2H-imidazo[4,5-b]pyridin-2-one;

1-(2,2-dimethylpropyl)-3-methyl-5-(4-{4-[2-(1H-1,2,4-triazol-1-yl)propanoyl]piperazin-1-yl}phenyl)-1,3-dihydro-2H-imidazo[4,5-b]pyridin-2-one;

1-(2,2-dimethylpropyl)-3-methyl-5-{4-[4-(1,3-thiazol-4-ylcarbonyl)piperazin-1-yl]phenyl}-1,3-dihydro-2H-imidazo[4,5-b]pyridin-2-one;

5-{4-[4-(2,2-dimethylpropanoyl)piperazin-1-yl]phenyl}-1-(2,2-dimethylpropyl)-3-methyl-1,3-dihydro-2H-imidazo[4,5-b]pyridin-2-one;

1-(2,2-dimethylpropyl)-3-methyl-5-{4-[4-(tetrahydrofuran-3-ylcarbonyl)piperazin-1-yl]phenyl}-1,3-dihydro-2H-imidazo[4,5-b]pyridin-2-one;

1-(2,2-dimethylpropyl)-3-methyl-5-{4-[4-(phenylcarbonyl)piperazin-1-yl]phenyl}-1,3-dihydro-2H-imidazo[4,5-b]pyridin-2-one;

1-(2,2-dimethylpropyl)-3-methyl-5-{4-[4-(thiophen-2-ylcarbonyl)piperazin-1-yl]phenyl}-1,3-dihydro-2H-imidazo[4,5-b]pyridin-2-one;

1-(2,2-dimethylpropyl)-5-[5-(1-hydroxy-1-methylethyl)pyridin-3-yl]-3-methyl-1,3-dihydro-2H-imidazo[4,5-b]pyridin-2-one;

1-(2,2-Dimethylpropyl)-5-[5-(1-hydroxy-1-methylethyl)-2-methylphenyl]-3-prop-2-en-1-yl-1,3-dihydro-2H-imidazo[4,5-b]pyridin-2-one;

1-(2,2-dimethylpropyl)-5-(2-fluorophenyl)-3-prop-2-en-1-yl-1,3-dihydro-2H-imidazo[4,5-b]pyridin-2-one;

2-[1-(2,2-dimethylpropyl)-2-oxo-3-prop-2-en-1-yl-2,3-dihydro-1H-imidazo[4,5-b]pyridin-5-yl]benzonitrile;

2-{1-[(2,2-difluorocyclopropyl)methyl]-2-oxo-3-prop-2-en-1-yl-2,3-dihydro-1H-imidazo[4,5-b]pyridin-5-yl}benzonitrile;

2-[1-(2,2-dimethylpropyl)-2-oxo-3-prop-2-en-1-yl-2,3-dihydro-1H-imidazo[4,5-b]pyridin-5-yl]benzaldehyde;

2-[1-(2,2-dimethylpropyl)-2-oxo-3-prop-2-en-1-yl-2,3-dihydro-1H-imidazo[4,5-b]pyridin-5-yl]-4-[(1,1-dioxidothiomorpholin-4-yl)methyl]benzonitrile;

4-[(3-hydroxy-6,7-dihydroisoxazolo[4,5-c]pyridin-5(4H)-yl)methyl]-2-(3-methyl-2-oxo-1-prop-2-en-1-yl-2,3-dihydro-1H-imidazo[4,5-b]pyridin-5-yl)benzonitrile;

1-(2,2-dimethylpropyl)-3-methyl-5-[2-methyl-5-(pyridin-4-yl)phenyl]-1,3-dihydro-2H-imidazo[4,5-b]pyridin-2-one;

1-(2,2-dimethylpropyl)-3-methyl-5-[2-methyl-5-(3-methyl-1H-pyrazol-4-yl)phenyl]-1,3-dihydro-2H-imidazo[4,5-b]pyridin-2-one;

1-(2,2-dimethylpropyl)-3-methyl-5-[2-methyl-5-(4-methylpyridin-3-yl)phenyl]-1,3-dihydro-2H-imidazo[4,5-b]pyridin-2-one;

4-{3-[1-(2,2-dimethylpropyl)-3-methyl-2-oxo-2,3-dihydro-1H-imidazo[4,5-b]pyridin-5-yl]-4-methylphenyl}pyridine-2-carbonitrile;

1-(2,2-dimethylpropyl)-3-methyl-5-[2-methyl-5-(1H-pyrazol-3-yl)phenyl]-1,3-dihydro-2H-imidazo[4,5-b]pyridin-2-one;

1-(2,2-dimethylpropyl)-3-methyl-5-[2-methyl-5-(1H-pyrrol-2-yl)phenyl]-1,3-dihydro-2H-imidazo[4,5-b]pyridin-2-one;

1-(2,2-dimethylpropyl)-3-methyl-5-[3-(1H-pyrazol-5-yl)phenyl]-1,3-dihydro-2H-imidazo[4,5-b]pyridin-2-one;

5-[5-(5,6-dihydro-4H-pyrrolo[1,2-b]pyrazol-3-yl)-2-methylphenyl]-1-(2,2-dimethylpropyl)-3-methyl-1,3-dihydro-2H-imidazo[4,5-b]pyridin-2-one;

1-(2,2-dimethylpropyl)-5-[5-(5-fluoropyridin-3-yl)-2-methylphenyl]-3-methyl-1,3-dihydro-2H-imidazo[4,5-b]pyridin-2-one;

1-(2,2-dimethylpropyl)-5-(3'-hydroxy-4-methylbiphenyl-3-yl)-3-methyl-1,3-dihydro-2H-imidazo[4,5-b]pyridin-2-one;

1-(2,2-dimethylpropyl)-5-[5'-(1-hydroxy-1-methylethyl)-2',4-dimethylbiphenyl-3-yl]-3-methyl-1,3-dihydro-2H-imidazo[4,5-b]pyridin-2-one;

2-{1-[(2,2-difluoro-1-methylcyclopropyl)methyl]-3-methyl-2-oxo-2,3-dihydro-1H-imidazo[4,5-b]pyridin-5-yl}benzonitrile;

1-[(2,2-difluoro-1-methylcyclopropyl)methyl]-5-[5-(1-hydroxy-1-methylethyl)-2-methylphenyl]-3-methyl-1,3-dihydro-2H-imidazo[4,5-b]pyridin-2-one;

1-[(2,2-difluoro-1-methylcyclopropyl)methyl]-5-[3-(1,1-dioxidothiomorpholin-4-yl)phenyl]-3-methyl 1,3-dihydro-2H-imidazo[4,5-b]pyridin-2-one;

tert-butyl [1-(4-{1-[(2,2-difluoro-1-methylcyclopropyl)methyl]-3-methyl-2-oxo-2,3-dihydro-1H-imidazo[4,5-b]pyridin-5-yl}phenyl)cyclobutyl]carbamate;

5-[4-(1-aminocyclobutyl)phenyl]-1-[(2,2-difluoro-1-methylcyclopropyl)methyl]-3-methyl-1,3-dihydro-2H-imidazo[4,5-b]pyridin-2-one;

1,1'-bis[(2,2-difluoro-1-methylcyclopropyl)methyl]-3,3'-dimethyl-1,1',3,3'-tetrahydro-2H,2'H-5,5'-biimidazo[4,5-b]pyridine-2,2'-dione;

tert-butyl [3-(1-{[(1S)-2,2-difluoro-1-methylcyclopropyl]methyl}-3-methyl-2-oxo-2,3-dihydro-1H-imidazo[4,5-b]pyridin-5-yl)benzyl]carbamate;

tert-butyl 7-(1-{[(1S)-2,2-difluoro-1-methylcyclopropyl]methyl}-3-methyl-2-oxo-2,3-dihydro-1H-imidazo[4,5-b]pyridin-5-yl)-3,4-dihydroisoquinoline-2(1H)-carboxylate;

1-{[(1S)-2,2-difluoro-1-methylcyclopropyl]methyl}-5-[5-(1-hydroxy-1-methylethyl)-2-methylphenyl]-3-methyl-1,3-dihydro-2H-imidazo[4,5-b]pyridin-2-one;

1-[(2,2-difluoro-1-methylcyclopropyl)methyl]-5-(1H-indol-5-yl)-3-methyl-1,3-dihydro-2H-imidazo[4,5-b]pyridin-2-one;

1-[(2,2-difluoro-1-methylcyclopropyl)methyl]-3-methyl-5-[3-(1H-pyrazol-1-yl)phenyl]-1,3-dihydro-2H-imidazo[4,5-b]pyridin-2-one;

1-[(2,2-difluoro-1-methylcyclopropyl)methyl]-3-methyl-5-quinolin-8-yl-1,3-dihydro-2H-imidazo[4,5-b]pyridin-2-one;

1-[(2,2-difluoro-1-methylcyclopropyl)methyl]-3-methyl-5-(1-methyl-1H-indol-5-yl)-1,3-dihydro-2H-imidazo[4,5-b]pyridin-2-one;

1-[(2,2-difluoro-1-methylcyclopropyl)methyl]-5-(1H-indol-6-yl)-3-methyl-1,3-dihydro-2H-imidazo[4,5-b]pyridin-2-one;

1-[(2,2-difluoro-1-methylcyclopropyl)methyl]-5-(1H-indazol-5-yl)-3-methyl-1,3-dihydro-2H-imidazo[4,5-b]pyridin-2-one;

1-[(2,2-difluoro-1-methylcyclopropyl)methyl]-3-methyl-5-(3-methyl-1,2-benzisoxazol-5-yl)-1,3-dihydro-2H-imidazo[4,5-b]pyridin-2-one;

1-[(2,2-difluoro-1-methylcyclopropyl)methyl]-3-methyl-5-(2-methyl-5-pyridin-3-ylphenyl)-1,3-dihydro-2H-imidazo[4,5-b]pyridin-2-one;

1-{[(1R)-2,2-difluoro-1-methylcyclopropyl]methyl}3-methyl-5-[2-methyl-5-(1H-pyrazol-5-yl)phenyl]-1,3-dihydro-2H-imidazo[4,5-b]pyridin-2-one;

1-{[(1R)-2,2-difluoro-1-methylcyclopropyl]methyl}-5-[5-(1,1-dioxidothiomorpholin-4-yl)-2-methylphenyl]-3-methyl-1,3-dihydro-2H-imidazo[4,5-b]pyridin-2-one;

4-(3-{1-[(2,2-difluoro-1-methylcyclopropyl)methyl]-3-methyl-2-oxo-2,3-dihydro-1H-imidazo[4,5-b]pyridin-5-yl}-4-methylphenyl)pyridine-2-carbonitrile;

2-[3-methyl-2-oxo-1-(4,4,4-trifluoro-2,2-dimethylbutyl)-2,3-dihydro-1H-imidazo[4,5-b]pyridin-5-yl]benzonitrile;

5-[5-(1-hydroxy-1-methylethyl)-2-methylphenyl]-3-methyl-1-(4,4,4-trifluoro-2,2-dimethylbutyl)-1,3-dihydro-2H-imidazo[4,5-b]pyridin-2-one;

5-(1H-indol-5-yl)-3-methyl-1-(4,4,4-trifluoro-2,2-dimethylbutyl)-1,3-dihydro-2H-imidazo[4,5-b]pyridin-2-one;

3-methyl-5-(1H-pyrrolo[2,3-b]pyridin-5-yl)-1-(4,4,4-trifluoro-2,2-dimethylbutyl)-1,3-dihydro-2H-imidazo[4,5-b]pyridin-2-one;

5-(3-bromo-1H-indol-5-yl)-3-methyl-1-(4,4,4-trifluoro-2,2-dimethylbutyl)-1,3-dihydro-2H-imidazo[4,5-b]pyridin-2-one;

5-(2,3-dibromo-1H-indol-5-yl)-3-methyl-1-(4,4,4-trifluoro-2,2-dimethylbutyl)-1,3-dihydro-2H-imidazo[4,5-b]pyridin-2-one;

5-[3-(1,1-dioxidothiomorpholin-4-yl)phenyl]-3-methyl-1-(4,4,4-trifluoro-2,2-dimethylbutyl)-1,3-dihydro-2H-imidazo[4,5-b]pyridin-2-one;

5-(1-benzofuran-5-yl)-3-methyl-1-(4,4,4-trifluoro-2,2-dimethylbutyl)-1,3-dihydro-2H-imidazo[4,5-b]pyridin-2-one;

3-methyl-5-(3-phenyl-1H-indol-5-yl)-1-(4,4,4-trifluoro-2,2-dimethylbutyl)-1,3-dihydro-2H-imidazo[4,5-b]pyridin-2-one;

2-(1-biphenyl-3-yl-3-methyl-2-oxo-2,3-dihydro-1H-imidazo[4,5-b]pyridin-5-yl)benzonitrile;

1-(2,2-dimethylpropyl)-3-methyl-5-(2-methyl-5-{[5-(2,2,2-trifluoroethyl)-2,5-diazabicyclo[2.2.2]oct-2-yl]methyl}phenyl)-1,3-dihydro-2H-imidazo[4,5-b]pyridin-2-one;

1-(2,2-dimethylpropyl)-3-methyl-5-(4-{[4-(methylsulfonyl)piperazin-1-yl]methyl}phenyl)-1,3-dihydro-2H-imidazo[4,5-b]pyridin-2-one;

5-{3-[cyclopropyl(hydroxy)methyl]phenyl}-1-(2,2-dimethylpropyl)-3-methyl-1,3-dihydro-2H-imidazo[4,5-b]pyridin-2-one;

1-(2,2-dimethylpropyl)-5-[3-(1-hydroxy-2-methylpropyl)phenyl]-3-methyl-1,3-dihydro-2H-imidazo[4,5-b]pyridin-2-one;

5-{5-[cyclopropyl(hydroxy)methyl]-2-methylphenyl}-1-(2,2-dimethylpropyl)-3-methyl-1,3-dihydro-2H-imidazo[4,5-b]pyridin-2-one;

1-(2,2-dimethylpropyl)-5-[5-(1-hydroxy-2-methylpropyl)-2-methylphenyl]-3-methyl-1,3-dihydro-2H-imidazo[4,5-b]pyridin-2-one;

1-(2,2-dimethylpropyl)-5-[5-(2-hydroxy-2-methylpropyl)-2-methylphenyl]-3-methyl-1,3-dihydro-2H-imidazo[4,5-b]pyridin-2-one; and N-(2-{3-[1-(2,2-dimethylpropyl)-3-methyl-2-oxo-2,3-dihydro-1H-imidazo[4,5-b]pyridin-5-yl]-4-methylphenyl}ethyl)-2-hydroxypropanamide;

or a pharmaceutically acceptable salt thereof.

18. A pharmaceutical composition comprising a compound according to claim 1 or a pharmaceutically acceptable salt thereof in combination with a pharmaceutically acceptable carrier.

19. A method for treating a neurological or psychiatric disorder associated with glutamate dysfunction in a patient in need thereof, wherein the neurological or psychiatric disorder associated with glutamate dysfunction is schizophrenia, the method comprising administering to the patient a therapeutically effective amount of a compound according to claim 1 or a pharmaceutically acceptable salt thereof.

* * * * *